US007691867B2

(12) United States Patent
Heron et al.

(10) Patent No.: US 7,691,867 B2
(45) Date of Patent: Apr. 6, 2010

(54) CHEMICAL COMPOUNDS

(75) Inventors: Nicola Murdoch Heron, Macclesfield (GB); Georges Rene Pasquet, Reims Cedex 2 (FR); Andrew Austen Mortlock, Macclesfield (GB); Frederic Henri Jung, Reims Cedex 2 (FR)

(73) Assignee: AstraZeneca AB, Sodertalje (SE)

( * ) Notice: Subject to any disclaimer, the term of this patent is extended or adjusted under 35 U.S.C. 154(b) by 1078 days.

(21) Appl. No.: 10/552,425

(22) PCT Filed: Apr. 14, 2004

(86) PCT No.: PCT/GB2004/001614

§ 371 (c)(1),
(2), (4) Date: Oct. 7, 2005

(87) PCT Pub. No.: WO2004/094410

PCT Pub. Date: Nov. 4, 2004

(65) Prior Publication Data

US 2006/0270692 A1 Nov. 30, 2006

(30) Foreign Application Priority Data

Apr. 16, 2003 (EP) .................................. 03290951

(51) Int. Cl.
*A61K 31/517* (2006.01)
*C07D 403/12* (2006.01)
*C07F 9/6512* (2006.01)

(52) U.S. Cl. ................... 514/266.24; 544/284; 544/232

(58) Field of Classification Search .............. 514/266.2, 514/266.24; 544/284, 232
See application file for complete search history.

(56) References Cited

U.S. PATENT DOCUMENTS 6,919,338 B2 * 7/2005 Mortlock et al. ......... 514/234.5
7,407,946 B2 * 8/2008 Mortlock ..................... 514/80
7,528,121 B2 * 5/2009 Heron et al. .................. 514/81

FOREIGN PATENT DOCUMENTS

| | | |
|---|---|---|
| WO | WO 95/15758 | 6/1995 |
| WO | WO 01/21597 | 3/2001 |
| WO | WO 02/00649 | 1/2002 |
| WO | WO 03/055491 | 7/2003 |
| WO | WO 2004/058752 | 7/2004 |
| WO | WO 2004/058781 | 7/2004 |
| WO | WO2004/058782 | 7/2004 |
| WO | WO 2004/058782 | 7/2004 |

OTHER PUBLICATIONS

Voskoglou-Nomikos et. al., Clin. Can. Res., vol. 9, Sep. 15, 2003, pp. 4227-4239.*

M.D. Anderson, The Aurora Kinases: Role in cell transformation and tumorigenesis, Cancer and Metastasis Reviews vol. 22, 2003, p. 451-64, Baylor College of Medicine, Texas.

Mahadevan, Daruka, Structure-Based Design of Novel Anti-Cancer Agents Targeting Aurora Kinases, Current Medicinal Chemistry, Anti Cancer Agents vol. 3, 2003, pp. 25-34, Bentham Science Publishers Ltd.

* cited by examiner

*Primary Examiner*—James O Wilson
*Assistant Examiner*—Tamthom N Truong

(57) ABSTRACT

Quinazoline derivatives of formula (I); for use in the treatment of proliferative diseases such as cancer and in the preparation of medicaments for use in the treatment of proliferative diseases, and to process for their preparation, as well as pharmaceutical compositions containing them as active ingredient.

(I)

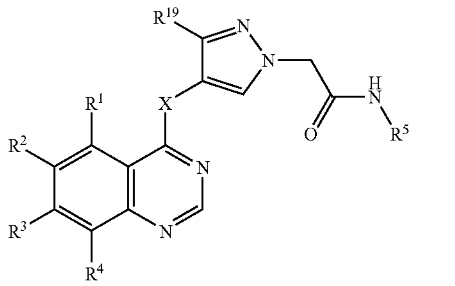

21 Claims, No Drawings

CHEMICAL COMPOUNDS

CROSS-REFERENCE TO RELATED APPLICATIONS

This application is a U.S. National State under 35 U.S.C. §371 of International Application No. PCT/GB2004/001614 (filed Apr. 14, 2004) which claims priority under 35 U.S.C. §119(a)-(d) to Application No. EP 03290951.7 filed on Apr. 16, 2003.

The present invention relates to quinazoline derivatives for use in the treatment of disease in particular proliferative diseases such as cancer and in the preparation of medicaments for the treatment of proliferative diseases, and to processes for their preparation, as well as pharmaceutical compositions containing them as active ingredient.

Cancer (and other hyperproliferative diseases) are characterised by uncontrolled cellular proliferation. The loss of the normal regulation of cell proliferation often appears to occur as the result of genetic damage to cellular pathways that control progress through the cell cycle.

In eukaryotes, an ordered cascade of protein phosphorylation is thought to control the cell cycle. Several families of protein kinases that play critical roles in this cascade have now been identified. The activity of many of these kinases is increased in human tumours when compared to normal tissue. This can occur by either increased levels of expression of the protein (as a result of gene amplification for example), or by changes in expression of co activators or inhibitory proteins.

The first identified, and most widely studied of these cell cycle regulators have been the cyclin dependent kinases (or CDKs). Activity of specific CDKs at specific times is essential for both initiation and coordinated progress through the cell cycle. For example, the CDK4 protein appears to control entry into the cell cycle (the G0-G1-S transition) by phosphorylating the retinoblastoma gene product pRb. This stimulates the release of the transcription factor E2F from pRb, which then acts to increase the transcription of genes necessary for entry into S phase. The catalytic activity of CDK4 is stimulated by binding to a partner protein, Cyclin D. One of the first demonstrations of a direct link between cancer and the cell cycle was made with the observation that the Cyclin D1 gene was amplified and cyclin D protein levels increased (and hence the activity of CDK4 increased) in many human tumours (Reviewed in Sherr, 1996, Science 274: 1672-1677; Pines, 1995, Seminars in Cancer Biology 6: 63-72). Other studies (Loda et al., 1997, Nature Medicine 3(2): 231-234; Gemma et al., 1996, International Journal of Cancer 68(5): 605-11; Elledge et al. 1996, Trends in Cell Biology 6; 388-392) have shown that negative regulators of CDK function are frequently down regulated or deleted in human tumours again leading to inappropriate activation of these kinases.

More recently, protein kinases that are structurally distinct from the CDK family have been identified which play critical roles in regulating the cell cycle and which also appear to be important in oncogenesis. These include the newly identified human homologues of the *Drosophila aurora* and *S. cerevisiae* Ipl1 proteins. The three human homologues of these genes Aurora-A, Aurora-B and Aurora-C (also known as aurora2, aurora1 and aurora3 respectively) encode cell cycle regulated serine-threonine protein kinases (summarised in Adams et al., 2001, Trends in Cell Biology. 11(2): 49-54). They show a peak of expression and kinase activity through G2 and mitosis. Several observations implicate the involvement of human aurora proteins in cancer. This evidence is strong for Aurora-A. The Aurora-A gene maps to chromosome 20q13, a region that is frequently amplified in human tumours including both breast and colon tumours. Aurora-A may be the major target gene of this amplicon, since Aurora-A DNA is amplified and mRNA overexpressed in greater than 50% of primary human colorectal cancers. In these tumours Aurora-A protein levels appear greatly elevated compared to adjacent normal tissue. In addition, transfection of rodent fibroblasts with human Aurora-A leads to transformation, conferring the ability to grow in soft agar and form tumours in nude mice (Bischoff et al., 1998, The EMBO Journal. 17(11): 3052-3065). Other work (Zhou et al., 1998, Nature Genetics. 20(2): 189-93) has shown that artificial overexpression of Aurora-A leads to an increase in centrosome number and an increase in aneuploidy, a known event in the development of cancer. Further work has shown an increase in expression of Aurora-B (Adams et al., 2001, Chromsoma. 110(2):65-74) and Aurora-C (Kimura et al., 1999, Journal of Biological Chemistry, 274(11): 7334-40) in tumour cells when compared to normal cells.

Importantly, it has also been demonstrated that abrogation of Aurora-A expression and function by antisense oligonucleotide treatment of human tumour cell lines (WO97/22702 and WO99/37788) leads to cell cycle arrest and exerts an antiproliferative effect in these tumour cell lines. Additionally, small molecule inhibitors of Aurora-A and Aurora-B have been demonstrated to have an antiproliferative effect in human tumour cells (Keen et al. 2001, Poster #2455, American Association of Cancer research annual meeting), as has selective abrogation of Aurora-B expression alone by siRNA treatment (Ditchfield et al., 2003, Journal of Cell Biology, 161(2): 267-280). This indicates that inhibition of the function of Aurora-A and/or Aurora-B will have an antiproliferative effect that may be useful in the treatment of human tumours and other hyperproliferative diseases. Inhibition of Aurora kinases as a therapeutic approach to these diseases may have significant advantages over targeting signalling pathways upstream of the cell cycle (e.g. those activated by growth factor receptor tyrosine kinases such as epidermal growth factor receptor (EGFR) or other receptors). Since the cell cycle is ultimately downstream of all of these diverse signalling events, cell cycle directed therapies such as inhibition of Aurora kinases would be predicted to be active across all proliferating tumour cells, whilst approaches directed at specific signalling molecules (e.g. EGFR) would be predicted to be active only in the subset of tumour cells which express those receptors. It is also believed that significant "cross talk" exists between these signalling pathways meaning that inhibition of one component may be compensated for by another.

A number of quinazoline derivatives have been proposed hitherto for use in the inhibition of Aurora kinases. For example, WO01/21594, WO01/21595 and WO01/215968 describe the use of certain phenyl-quinazoline compounds as Aurora-A kinase inhibitors, which may be useful in the treatment of proliferative diseases and WO01/21597 discloses other quinazoline derivatives as inhibitors of Aurora-A kinase. Additionally, WO02/00649 discloses quinazoline derivative bearing a 5-membered heteroaromatic ring where the ring is, in particular, substituted thiazole or substituted thiophene. However despite the compounds of WO02/00649 there still exists a need for further compounds having Aurora kinase inhibitory properties. In addition inhibitors are required which have physical and pharmacological properties suitable for use in the treatment of disease.

The applicants have been successful in finding a novel series of compounds which inhibit the effects of the Aurora kinases and in particular Aurora-A kinase and/or Aurora-B kinase which are thus of use in the treatment of proliferative diseases such as cancer. The cancer may occur as either solid or haematological tumours, and in particular includes colorectal, breast, lung, prostate, bladder, renal or pancreatic cancer or leukaemia or lymphoma. In addition certain aspects of the invention provide compounds that have favourable solubility properties that make them useful in the formulation of medicaments for the treatment of disease.

According to one aspect of the invention there is provided a compound of formula (I)

formula (I)

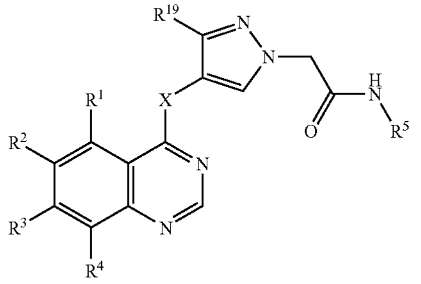

or a salt, ester or prodrug thereof;

where:

X is O or $NR^6$;

$R^6$ is hydrogen or $C_{1-4}$alkyl;

$R^1$ is hydrogen, halo, or —$X^1R^{11}$;

$X^1$ is a direct bond, —$CH_2$═$CH_2$—, —O—, —NH—, —N($C_{1-6}$alkyl)-, —C(O)—, —C(O)O—, —OC(O)—, —NHC(O)—, —N($C_{1-6}$alkyl)C(O)—, —C(O)NH— or —C(O)N($C_{1-6}$alkyl)-;

$R^{11}$ is hydrogen, or a group selected from $C_{1-6}$alkyl, $C_{2-6}$alkenyl, $C_{2-6}$alkynyl, $C_{3-6}$cycloalkyl, $C_{3-6}$cycloalkenyl, heterocyclyl, heterocyclyl$C_{1-4}$alkyl, heterocyclyl$C_{2-4}$alkenyl and heterocyclyl$C_{2-4}$alkyl which group is optionally substituted by 1 or 2 substituents independently selected from halo, hydroxy, $C_{1-4}$-alkoxy, hydroxy$C_{1-4}$alkyl, —$NR^9R^{10}$, —C(O)$R^9$, —C(O)$NR^9R^{10}$ and —C(O)O$R^9$;

$R^2$ is hydrogen, halo, nitro, cyano or —$X^2R^{12}$;

$X^2$ is a direct bond, —O—, —NH—, —N($C_{1-6}$alkyl)-, —OC(O)— or —C(O)O—;

$R^{12}$ is hydrogen, or a group selected from $C_{1-6}$alkyl, $C_{2-6}$alkenyl, $C_{2-6}$alkyl, $C_{3-6}$cycloalkyl, $C_{3-6}$cycloalkenyl, aryl, aryl$C_{1-4}$alkyl, aryl$C_{2-4}$alkenyl, aryl$C_{2-4}$alkynyl, heterocyclyl, heterocyclyl$C_{1-4}$alkyl, heterocyclyl$C_{2-4}$alkenyl and heterocyclyl$C_{2-4}$alkynyl, which group is optionally substituted by 1, 2 or 3 substituents selected from halo, hydroxy, $C_{1-4}$-alkyl, $C_{1-4}$alkoxy, —$NR^{15}R^{16}$, —NHC(O)$NR^{15}R^{16}$, —C(O)$R^{15}$ and —C(O)O$R^{15}$;

$R^3$ is hydrogen, halo or —$X^3R^{13}$;

$X^3$ is a direct bond, —$CH_2$═$CH_2$—, —O—, —NH—, —N($C_{1-6}$alkyl)-, —C(O)—, —C(O)O—, —OC(O)—, —NHC(O)—, —N($C_{1-6}$alkyl)C(O)—, —C(O)NH— or —C(O)N($C_{1-6}$alkyl)-;

$R^{13}$ is hydrogen or a group selected from $C_{1-6}$alkyl, $C_{2-6}$alkenyl, $C_{2-6}$alkynyl, $C_{3-6}$cycloalkyl, $C_{3-6}$cycloalkenyl, aryl, aryl$C_{1-4}$alkyl, aryl$C_{2-4}$alkenyl, aryl$C_{2-4}$alkynyl, heterocyclyl, heterocyclyl$C_{1-4}$alkyl, heterocyclyl$C_{2-4}$alkenyl and heterocyclyl$C_{2-4}$alkynyl which group is optionally substituted by 1 or 2 substituents independently selected from —$NR^7R^8$, —C(O)$NR^7R^8$, halo, hydroxy, $C_{1-4}$alkyl, $C_{1-4}$alkoxy, hydroxy$C_{1-4}$alkyl, hydroxy$C_{1-4}$alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$ alkylcarbonyl;

$R^7$ and $R^8$ are independently selected from hydrogen, heterocyclyl, heterocyclyl$C_{1-4}$alkyl, $C_{1-4}$alkylheterocyclyl$C_{1-4}$ alkyl, $C_{1-6}$alkyl, hydroxy$C_{1-6}$alkyl, $C_{1-4}$alkoxy$C_{1-6}$alkyl, $C_{3-6}$cycloalkyl, $C_{3-6}$cycloalkyl$C_{1-4}$alkyl, hydroxy$C_{3-6}$cycloalkyl, hydroxy$C_{1-4}$alkyl$C_{3-6}$cycloalkyl, hydroxy$C_{1-4}$ alkyl$C_{3-6}$cycloalkyl$C_{1-4}$alkyl, hydroxy$C_{3-6}$cycloalkyl$C_{1-4}$ alkyl, $C_{1-4}$alkoxy$C_{3-6}$cycloalkyl, $C_{1-4}$alkoxy$C_{3-6}$ cycloalkyl$C_{1-4}$alkyl, halo$C_{1-6}$alkyl, halo$C_{3-6}$cycloalkyl, halo$C_{3-6}$cycloalkyl$C_{1-4}$alkyl, $C_{2-6}$alkenyl, $C_{2-6}$alkynyl, cyano$C_{1-4}$alkyl, amino$C_{1-6}$alkyl, $C_{1-4}$alkylamino$C_{1-6}$ alkyl, bis($C_{1-4}$alkyl)amino$C_{1-6}$alkyl, hydroxy$C_{1-4}$ alkoxy$C_{1-4}$alkyl, hydroxy$C_{1-4}$alkylcarbonyl, $C_{1-4}$alkylcarbonyl, amino$C_{1-4}$alkylcarbonyl, $C_{1-4}$alkylamino$C_{1-4}$ alkylcarbonyl and bis($C_{1-4}$alkyl)amino$C_{1-4}$ alkylcarbonyl;

or $R^7$ and $R^8$ together with the nitrogen to which they are attached form a heterocyclic ring which ring is monocyclic or bicyclic and comprises 4 to 7 ring atoms of which one is nitrogen and of which another is optionally selected from N, NH, O, S, SO and $SO_2$, and which ring is optionally substituted on carbon or nitrogen by 1 or 2 substituents independently selected from $C_{1-4}$alkyl, hydroxy, $C_{1-4}$alkoxy, hydroxy$C_{1-4}$alkyl, $C_{1-4}$alkoxy$C_{1-4}$alkyl, hydroxy$C_{1-4}$alkoxy$C_{1-4}$alkyl, $C_{1-4}$alkoxy$C_{1-4}$alkoxy, hydroxy$C_{1-4}$alkylcarbonyl, $C_{1-4}$alkylcarbonyl, amino$C_{1-4}$ alkylcarbonyl, $C_{1-4}$alkylamino$C_{1-4}$alkylcarbonyl and bis ($C_{1-4}$alkyl)amino$C_{1-4}$alkylcarbonyl, and where a ring —$CH_2$— is optionally replaced with —C(O)—;

$R^4$ is selected from hydrogen, halo or —$X^4R^{14}$;

$X^4$ is a direct bond, —O—, —NH— or —N($C_{1-6}$alkyl)-;

$R^{14}$ is selected from hydrogen, $C_{1-6}$alkyl, $C_{2-6}$alkenyl and $C_{2-6}$alkynyl;

$R^5$ is aryl or heteroaryl optionally substituted by 1, 2 or 3 substituents independently selected from halo, hydroxy, cyano, nitro, amino, $C_{1-4}$alkylamino, bis($C_{1-4}$alkyl)amino, $C_{1-4}$alkyl, $C_{2-4}$alkenyl, $C_{2-4}$alkynyl, $C_{1-4}$alkoxy, —C(O)NH$R^{17}$, —NHC(O)$R^{18}$—S$R^{17}$, —S(O)$R^{17}$ and —S(O)O$R^{17}$;

$R^9$, $R^{10}$, $R^{15}$ and $R^{16}$ are independently selected from hydrogen, $C_{1-6}$alkyl, $C_{3-6}$cycloalkyl, $C_{3-6}$cycloalkyl$C_{1-4}$yl, hydroxy$C_{1-6}$alkyl, halo$C_{1-6}$alkyl, amino$C_{1-6}$alkyl, $C_{1-4}$alkylamino$C_{1-6}$alkyl and bis($C_{1-4}$alkyl)amino$C_{1-6}$ alkyl;

or $R^9$ and $R^{10}$ together with the nitrogen to which they are attached form a heterocyclic ring which ring is monocyclic or bicyclic and comprises 4 to 7 ring atoms of which one is nitrogen and of which another is optionally selected from N, NH, O, S, SO and $SO_2$, and which ring is optionally substituted on carbon or nitrogen by 1 or 2 substituents independently selected from $C_{1-4}$alkyl, hydroxy, $C_{1-4}$alkoxy, hydroxy$C_{1-4}$alkyl, $C_{1-4}$alkoxy$C_{1-4}$alkyl, hydroxy$C_{1-4}$alkoxy$C_{1-4}$alkyl, $C_{1-4}$alkoxy$C_{1-4}$alkoxy, hydroxy$C_{1-4}$alkylcarbonyl, $C_{1-4}$alkylcarbonyl, amino$C_{1-4}$ alkylcarbonyl, $C_{1-4}$alkylamino$C_{1-4}$alkylcarbonyl and bis ($C_{1-4}$alkyl)amino$C_{1-4}$alkylcarbonyl, and where a ring —$CH_2$— is optionally replaced with —C(O)—;

$R^{17}$ and $R^{18}$ are independently selected from hydrogen, $C_{1-4}$alkyl, $C_{3-6}$cycloalkyl, $C_{2-4}$alkenyl and $C_{2-4}$alkynyl;

$R^{19}$ is hydrogen, hydroxy$C_{1-4}$alkyl, —C(O)$R^{20}$, —C(O)O$R^{20}$, —C(O)$NR^{20}R^{21}$, —NHC(O)$R^{20}$ or —NHC(O)O$R^{20}$;

$R^{20}$ are $R^{21}$ are independently selected from hydrogen, $C_{1-4}$alkyl and aryl.

As a further aspect a compound of formula (I) or a pharmaceutically acceptable salt thereof is provided.

In a further aspect the invention provides a compound of formula (IA)

formula (IA)

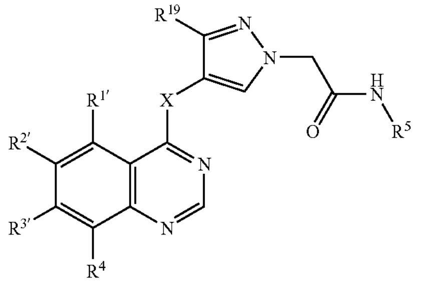

or salt or ester thereof where X, $X^1$, $X^2$, $X^3$, $R^4$, $R^5$ and $R^{19}$ are as defined in relation to formula (I) and $R^{1'}$ is hydrogen, halo, or —$X^1R^{11'}$;

$R^{11'}$ is hydrogen, phosphonooxy or a group selected from $C_{1-6}$alkyl, $C_{2-6}$alkenyl, $C_{2-6}$alkynyl; $C_{3-6}$cycloalkyl, $C_{3-6}$cycloalkenyl, heterocyclyl, heterocyclyl$C_{1-4}$alkyl, heterocyclyl$C_{2-4}$alkenyl and heterocyclyl$C_{2-4}$alkynyl which group is optionally substituted by a substituent selected from halo, hydroxy, phosphonooxy, $C_{1-4}$alkoxy, hydroxy$C_{1-4}$alkyl, phosphonooxy$C_{1-4}$alkyl, —$NR^{9'}R^{10'}$, —$C(O)R^{9'}$, —$C(O)NR^{9'}R^{10'}$ and —$C(O)OR^{9'}$;

$R^{2'}$ is hydrogen, halo, nitro, cyano or —$X^2R^{12'}$;

$R^{12'}$ is hydrogen, phosphonooxy or a group selected from $C_{1-6}$alkyl, $C_{2-6}$alkenyl, $C_{2-6}$alkynyl, $C_{3-6}$cycloalkyl, $C_{3-6}$cycloalkenyl, aryl, aryl$C_{1-4}$alkyl, aryl$C_{2-4}$alkenyl, aryl$C_{2-4}$alkynyl, heterocyclyl, heterocyclyl$C_{1-4}$alkyl, heterocyclyl$C_{2-4}$alkenyl and heterocyclyl$C_{2-4}$alkynyl, which group is optionally substituted by 1, 2 or 3 substituents selected from halo, hydroxy, phosphonooxy, $C_{1-4}$alkyl, $C_{1-4}$alkoxy, —$NR^{15}R^{16}$, —$NHC(O)NR^{15}R^{16}$, —$C(O)R^{15}$ and —$C(O)OR^{15}$;

$R^{3'}$ is hydrogen, halo or —$X^3R^{13'}$;

$R^{13'}$ is hydrogen, phosphonooxy or a group selected from $C_{1-6}$alkyl, $C_{2-6}$alkenyl, $C_{2-6}$alkynyl, $C_{3-6}$cycloalkyl, $C_{3-6}$cycloalkenyl, aryl, aryl$C_{1-4}$alkyl, aryl$C_{2-4}$alkenyl, aryl$C_{2-4}$alkynyl, heterocyclyl, heterocyclyl$C_{1-4}$alkyl, heterocyclyl$C_{2-4}$alkenyl and heterocyclyl$C_{2-4}$alkynyl which group is optionally substituted by 1 or 2 substituents independently selected from —$NR^{7'}R^{8'}$, —$C(O)NR^{7'}R^{8'}$, halo, hydroxy, phosphonooxy, $C_{1-4}$alkyl, $C_{1-4}$alkoxy, hydroxy$C_{1-4}$alkyl, phosponooxy$C_{1-4}$alkyl, hydroxy$C_{1-4}$ alkylcarbonyl, phosphonooxy$C_{1-4}$alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$ alkylcarbonyl;

$R^{7'}$ and $R^{8'}$ are independently selected from hydrogen, heterocyclyl, heterocyclyl$C_{1-4}$alkyl, $C_{1-4}$alkylheterocyclyl$C_{1-4}$alkyl, $C_{1-6}$alkyl, hydroxy$C_{1-6}$alkyl, phosphonooxy$C_{1-6}$alkyl, $C_{1-4}$alkoxy$C_{1-6}$alkyl, $C_{3-6}$cycloalkyl, $C_{3-6}$cycloalkyl$C_{1-4}$alkyl, hydroxy$C_{3-6}$cycloalkyl, phosphonooxy$C_{3-6}$cycloalkyl, hydroxy$C_{1-4}$alkyl$C_{3-6}$cycloalkyl, phosphonooxy$C_{1-4}$alkyl$C_{3-6}$cycloalkyl, hydroxy$C_{3-6}$cycloalkyl$C_{1-4}$alkyl, phosphonooxy$C_{3-6}$cycloalkyl$C_{1-4}$-alkyl, hydroxy$C_{1-4}$alkyl$C_{3-6}$cycloalkyl$C_{1-4}$ alkyl, phosphonooxy$C_{1-4}$alkyl$C_{3-6}$cycloalkyl$C_{1-4}$alkyl, $C_{1-4}$alkoxy$C_{3-6}$cycloalkyl, $C_{1-4}$alkoxy$C_{3-6}$cycloalkyl$C_{1-4}$ alkyl, halo$C_{1-6}$alkyl, halo$C_{3-6}$cycloalkyl, halo$C_{3-6}$cycloalkyl$C_{1-4}$alkyl, $C_{2-6}$alkenyl, $C_{2-6}$alkynyl, cyano$C_{1-4}$ alkyl, amino$C_{1-6}$alkyl, $C_{1-4}$alkylamino$C_{1-6}$alkyl, bis($C_{1-4}$ alkyl)amino$C_{1-6}$alkyl, hydroxy$C_{1-4}$alkoxy$C_{1-4}$alkyl, phosphonooxy$C_{1-4}$alkoxy$C_{1-4}$alkyl, hydroxy$C_{1-4}$alkylcarbonyl, phosphonooxy$C_{1-4}$alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$alkylcarbonyl; or $R^{7'}$ and $R^{8'}$ together with the nitrogen to which they are attached form a heterocyclic ring which ring is monocyclic or bicyclic and comprises 4 to 7 ring atoms of which one is nitrogen and of which another is optionally selected from N, NH, O, S, SO and $SO_2$, and which ring is optionally substituted on carbon or nitrogen by 1 or 2 substituents independently selected from $C_{1-4}$alkyl, hydroxy, phosphonooxy, $C_{1-4}$alkoxy, hydroxy$C_{1-4}$alkyl, phosphonooxy$C_{1-4}$ alkyl, $C_{1-4}$alkoxy$C_{1-4}$alkyl, hydroxy$C_{1-4}$alkoxy$C_{1-4}$alkyl, phosphonooxy$C_{1-4}$alkoxy$C_{1-4}$alkyl, $C_{1-4}$alkoxy$C_{1-4}$ alkoxy, hydroxy$C_{1-4}$alkylcarbonyl, phosphonooxy$C_{1-4}$ alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl) amino$C_{1-4}$alkylcarbonyl, and where a ring —$CH_2$— is optionally replaced with —C(O)—;

$R^{9'}$, $R^{10'}$, $R^{15'}$ and $R^{16'}$ are independently selected from hydrogen, $C_{1-6}$alkyl, $C_{3-6}$cycloalkyl, $C_{3-6}$cycloalkyl$C_{1-3}$alkyl, hydroxy$C_{1-6}$alkyl, phosphonooxy$C_{1-6}$alkyl, halo$C_{1-6}$ alkyl, amino$C_{1-6}$alkyl, $C_{1-6}$ alkylamino$C_{1-6}$alkyl and bis ($C_{1-6}$alkyl)amino$C_{1-6}$alkyl;

or $R^{9'}$ and $R^{10'}$ together with the nitrogen to which they are attached form a heterocyclic ring which ring is monocyclic or bicyclic and comprises 4 to 7 ring atoms of which one is nitrogen and of which another is optionally selected from N, NH, O, S, SO and $SO_2$, and which ring is optionally substituted on carbon or nitrogen by 1 or 2 substituents independently selected from $C_{1-4}$alkyl, hydroxy, phosphonooxy, $C_{1-4}$alkoxy, hydroxy$C_{1-4}$alkyl, phosphonooxy$C_{1-4}$ alkyl, $C_{1-4}$alkoxy$C_{1-4}$alkyl, hydroxy$C_{1-4}$alkoxy$C_{1-4}$alkyl, phosphonooxy$C_{1-4}$alkoxy$C_{1-4}$alkyl, $C_{1-4}$alkoxy$C_{1-4}$ alkoxy, hydroxy$C_{1-4}$alkylcarbonyl, phosphonooxy$C_{1-4}$ alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl) amino$C_{1-4}$alkylcarbonyl, and where a ring —$CH_2$— is optionally replaced with —C(O)—;

provided that a compound of formula (IA) contains at least one phosphonooxy group.

In a preferred embodiment a compound of formula (IA) contains only one phosphonooxy group.

In further aspects of the invention there is also provided a compound of formula (I) or a salt ester or prodrug thereof or a compound of formula (IA) or a salt, ester or prodrug thereof as described below.

A compound of formula (I) comprises formula (I)

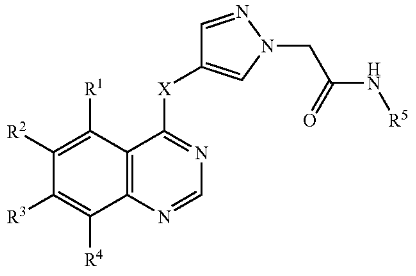

or a salt, ester or prodrug thereof;

where:

X is O or $NR^6$;

$R^6$ is hydrogen or $C_{1-4}$alkyl;

$R^1$ is hydrogen, halo, or —$X^1R^{11}$;

$X^1$ is a direct bond, —O—, —NH— or —N($C_{1-6}$alkyl)-;

$R^{11}$ is hydrogen, heterocyclyl or a group selected from $C_{1-6}$alkyl, $C_{2-6}$alkenyl, $C_{2-6}$alkynyl, $C_{3-6}$cycloalkyl and $C_{3-6}$cycloalkenyl where the group is optionally substituted by heterocyclyl, halo, hydroxy, $C_{1-4}$alkoxy or —$NR^9R^{10}$;

$R^2$ is hydrogen, halo, nitro, cyano or —$X^2R^{12}$;

$X^2$ is a direct bond, —O—, —NH— or —N($C_{1-6}$alkyl)-;

$R^{12}$ is hydrogen, heterocyclyl or a group selected from aryl, $C_{1-6}$alkyl, $C_{2-6}$alkenyl, $C_{2-6}$alkynyl, $C_{3-6}$cycloalkyl and $C_{3-6}$cycloalkenyl where the group is optionally substituted by aryl, heterocyclyl, halo, hydroxy or —$NR^{15}R^{16}$;

$R^3$ is hydrogen, halo or —$X^3R^{13}$;

$X^3$ is a direct bond, —$CH_2$═$CH_2$—, —O—, —NH— or —N($C_{1-6}$alkyl)-;

$R^{13}$ is hydrogen, heterocyclyl or a group selected from $C_{1-6}$alkyl, $C_{2-6}$alkenyl, $C_{2-6}$alkynyl, $C_{3-6}$cycloalkyl and $C_{3-6}$cycloalkenyl where the group is optionally substituted by —$NR^7R^8$, heterocyclyl, halo, hydroxy or $C_{1-4}$-alkoxy;

$R^7$ and $R^8$ are independently selected from hydrogen, heterocyclyl, $C_{1-6}$alkyl, hydroxy$C_{1-6}$alkyl, $C_{1-3}$alkoxy$C_{1-6}$alkyl, $C_{3-6}$cycloalkyl, $C_{3-6}$cycloalkyl$C_{1-3}$alkyl, hydroxy$C_{3-6}$cycloalkyl, hydroxy$C_{1-4}$alkyl$C_{3-6}$cycloalkyl, hydroxy$C_{3-6}$cycloalkyl$C_{1-3}$alkyl, $C_{1-3}$alkoxy$C_{3-6}$cycloalkyl, $C_{1-3}$alkoxy$C_{3-6}$cycloalkyl$C_{1-3}$alkyl, halo$C_{1-6}$alkyl, halo$C_{3-6}$cycloalkyl, halo$C_{3-6}$cycloalkyl$C_{1-3}$alkyl, $C_{2-6}$alkenyl, $C_{2-6}$alkynyl, cyano$C_{1-4}$alkyl, amino$C_{1-6}$alkyl, $C_{1-3}$alkylamino$C_{1-6}$alkyl and di($C_{1-3}$alkyl)amino$C_{1-6}$alkyl;

or $R^7$ and $R^8$ together with the nitrogen to which they are attached form a heterocyclic ring which ring comprises 4 to 7 ring atoms of which one is nitrogen and of which another is optionally selected from N, NH, O, S, SO and $SO_2$, and which ring is optionally substituted on carbon or nitrogen by 1 or 2 groups independently selected from $C_{1-4}$alkyl, hydroxy, $C_{1-4}$alkoxy, hydroxy$C_{1-4}$alkyl, hydroxy$C_{1-4}$alkoxy$C_{1-4}$alkyl and $C_{1-4}$alkoxy$C_{1-4}$alkoxy, and where a ring —$CH_2$— is optionally replaced with —C(O)—;

$R^4$ is selected from hydrogen, halo or —$X^4R^{14}$;

$X^4$ is a direct bond, —O—, —NH— or —N($C_{1-6}$alkyl)-;

$R^{14}$ is selected from hydrogen, $C_{1-6}$alkyl, $C_{2-6}$alkenyl and $C_{2-6}$alkynyl;

$R^5$ is aryl or heteroaryl optionally substituted by 1, 2 or 3 substituents independently selected from halo, hydroxy, cyano, nitro, amino, $C_{1-4}$alkylamino, di($C_{1-4}$alkyl)amino, $C_{1-4}$alkyl, $C_{2-4}$alkenyl, $C_{2-4}$alkynyl, $C_{1-4}$alkoxy, C(O)$NHR^{17}$, NHC(O)$R^{18}$ and S(O)$_pR^{19}$ where p is 0, 1 or 2;

$R^9$, $R^{10}$, $R^{15}$ and $R^{16}$ are independently selected from hydrogen, $C_{1-6}$alkyl, $C_{3-6}$cycloalkyl, $C_{3-6}$cycloalkyl$C_{1-3}$alkyl, hydroxy$C_{1-6}$alkyl, halo$C_{1-6}$alkyl, amino$C_{1-6}$alkyl, $C_{1-6}$alkylamino$C_{1-6}$alkyl and di($C_{1-6}$alkyl)amino$C_{1-6}$alkyl;

$R^{17}$, $R^{18}$ and $R^{19}$ are independently selected from hydrogen, $C_{1-4}$alkyl, $C_{3-6}$cycloalkyl, $C_{2-4}$alkenyl and $C_{2-4}$alkynyl.

A compound of formula (IA) comprises:

formula (IA)

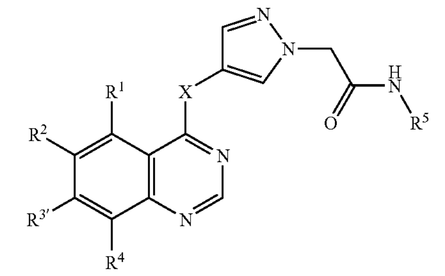

where X, $R^1$, $R^2$, $R^4$ and $R^5$ are as defined in relation to formula (I) and $R^{3'}$ is hydrogen, halo or —$X^{3'}R^{13'}$;

$X^{3'}$ is a direct bond, —$CH_2$═$CH_2$—, —O—, —NH— or —N($C_{1-6}$alkyl)-;

$R^{13'}$ is a group selected from $C_{1-6}$alkyl, $C_{2-6}$alkenyl, $C_{2-6}$alkynyl, $C_{3-6}$cycloalkyl and $C_{3-6}$cycloalkenyl where the group is substituted by —$NR^{7'}R^{8'}$;

$R^{7'}$ and $R^{8'}$ are independently selected from hydrogen, heterocyclyl, $C_{1-6}$alkyl, phosphonooxy$C_{1-6}$alkyl, $C_{1-3}$alkoxy$C_{1-6}$alkyl, phosphonooxy$C_{1-4}$alkoxy$C_{1-4}$alkyl, $C_{3-6}$cycloalkyl, $C_{3-6}$cycloalkyl$C_{1-3}$alkyl, phosphonooxy$C_{3-6}$cycloalkyl, phosphonooxy$C_{1-4}$alkyl$C_{3-6}$cycloalkyl, phosphonooxy$C_{3-6}$cycloalkyl$C_{1-3}$alkyl, $C_{1-3}$alkoxy$C_{3-6}$cycloalkyl, $C_{1-3}$alkoxy$C_{3-6}$cycloalkyl$C_{1-3}$alkyl, halo$C_{1-6}$alkyl, halo$C_{3-6}$cycloalkyl, halo$C_{3-6}$cycloalkyl$C_{1-3}$alkyl, $C_{2-6}$alkenyl, $C_{2-6}$alkynyl, cyano$C_{1-4}$alkyl, amino$C_{1-6}$alkyl, $C_{1-3}$alkylamino$C_{1-6}$alkyl and di($C_{1-3}$alkyl)amino$C_{1-6}$alkyl; provided that at least one of $R^{7'}$ and $R^{8'}$ contains a phosphonooxy substituent;

or $R^{7'}$ and $R^{8'}$ together with the nitrogen to which they are attached form a heterocyclic ring which ring comprises 4 to 7 ring atoms of which one is nitrogen and of which another is optionally selected from N, NH, O, S, SO and $SO_2$, and which ring is substituted on carbon or nitrogen by 1 or 2 groups independently selected from phosphonooxy, phosphonooxy$C_{1-4}$alkyl and phosphonooxy$C_{1-4}$alkoxy$C_{1-4}$alkyl, and where a ring —$CH_2$— is optionally replaced with a —C(O)—.

In this specification the term alkyl when used either alone or as a suffix or prefix includes straight-chain and branched-chain saturated structures comprising carbon and hydrogen atoms. References to individual alkyl groups such as propyl are specific for the straight-chain version only and references to individual branched-chain alkyl groups such as tert-butyl are specific for the branched chain version only. An analogous convention applies to other generic terms such as alkenyl and alkynyl.

Cycloalkyl is a monocyclic alkyl group, and cycloalkenyl and cycloalkynyl are monocyclic alkenyl and alkynyl groups respectively.

The prefix $C_{m-n}$ in $C_{m-n}$alkyl and other terms (where m and n are integers) indicates the range of carbon atoms that are present in the group, for example $C_{1-3}$alkyl includes $C_1$alkyl (methyl), $C_2$alkyl (ethyl) and $C_3$alkyl (propyl or isopropyl).

The terms $C_{m-n}$alkoxy comprise —O—$C_{m-n}$alkyl groups.

The term halo includes fluoro, chloro, bromo and iodo.

Aryl groups are aromatic carbocyclic rings which may be monocyclic or bicyclic.

Unless otherwise stated heteroaryl groups are monocyclic or bicyclic aromatic rings containing 5 to 10 ring atoms of which 1, 2, 3 or 4 ring atoms are chosen from nitrogen, sulphur or oxygen where a ring nitrogen or sulphur may be oxidised.

Heterocyclyl is a saturated, unsaturated or partially saturated, monocyclic or bicyclic ring containing 4 to 7 ring atoms of which 1, 2 or 3 ring atoms are selected from nitrogen, sulphur or oxygen, which ring may be carbon or nitrogen linked, wherein a ring —$CH_2$— group is optionally replaced by a —C(O) group; wherein a ring nitrogen or sulphur atom is optionally oxidised to form the N-oxide or S-oxide(s); wherein a ring —NH— is optionally substituted by acetyl, formyl, methyl or mesyl; and which ring is optionally substituted by 1 or 2 groups selected from $C_{1-4}$alkyl, $C_{1-4}$alkoxy, hydroxy$C_{1-4}$alkyl, hydroxy and halo$C_{1-4}$alkyl. In one aspect of the invention when used within the definition of $R^1$, $R^2$ or $R^3$ heterocyclyl is a saturated monocyclic ring containing 4 to 7 ring atoms of which 1 ring atom is nitrogen and another ring atom is optionally nitrogen or oxygen which ring is optionally substituted by $C_{1-4}$alkyl, hydroxy$C_{1-4}$alkyl and hydroxy.

Phosphonooxy is in one aspect a group of formula —OP(O)$(OH)_2$. However the term phosphonooxy also includes salts such as those formed with alkali metal ions such as sodium or potassium ions or alkaline earth metal ions, for example calcium or magnesium ions.

This specification also makes use of several composite terms to describe groups comprising more than one functionality. Such terms are to be interpreted as is understood in the art. For example $C_{m-n}$cycloalkyl$C_{m-n}$alkyl comprises $C_{m-n}$alkyl substituted by $C_{m-n}$cycloalkyl, and heterocyclyl$C_{m-n}$alkyl comprises $C_{m-n}$alkyl substituted by heterocyclyl.

Halo$C_{m-n}$alkyl is a $C_{m-n}$alkyl group that is substituted by 1, 2 or 3 halo substituents. Similarly, halo$C_{m-n}$cycloalkyl and halo$C_{m-n}$cycloalkyl$C_{m-n}$alkyl groups may contain 1, 2 or 3 halo substituents.

Hydroxy$C_{m-n}$alkyl is a $C_{m-n}$alkyl group that is substituted by 1, 2 or 3 hydroxy substituents. Similarly, hydroxy$C_{m-n}$ cycloalkyl and hydroxy$C_{m-n}$cycloalkyl$C_{m-n}$alkyl groups may contain 1, 2 or 3 hydroxy substituents.

$C_{m-n}$alkoxy$C_{m-n}$alkyl is a $C_{m-n}$alkyl group that is substituted by 1, 2 or 3 $C_{m-n}$alkoxy substituents. Similarly, $C_{m-n}$ alkoxy$C_{m-n}$cycloalkyl and $C_{m-n}$alkoxy$C_{m-n}$cycloalkyl$C_{m-n}$ alkyl groups may contain 1, 2 or 3 $C_{m-n}$alkoxy substituents.

Where optional substituents are chosen from 1 or 2 or from 1, 2, or 3 groups or substituents it is to be understood that this definition includes all substituents being chosen from one of the specified groups i.e. all substituents being the same or the substituents being chosen from two or more of the specified groups i.e. the substituents not being the same.

Unless specifically stated the bonding atom of a group may be any atom of that group so for example propyl includes prop-1-yl and prop-2-yl.

Compounds of the present invention have been named with the aid of computer software (ACD/Name version 6.6 or ACD Name Batch version 6.0).

Suitable values for any R group or any part or substituent for such groups include examples selected from:

for $C_{1-4}$alkyl: methyl, ethyl, propyl, isopropyl, butyl, isobutyl and tert-butyl;

for $C_{1-6}$alkyl: $C_{1-4}$alkyl, pentyl, neopentyl, 1,3-dimethylbutyl and hexyl;

for $C_{2-4}$alkenyl: vinyl, allyl and but-2-enyl;

for $C_{2-6}$alkenyl: $C_{2-4}$alkenyl, 3-methylbut-2-enyl and 3-methylpent-2-enyl;

for $C_{2-4}$alkynyl: ethynyl, propargyl and prop-1-ynyl;

for $C_{2-6}$alkynyl: $C_{2-4}$alkynyl, pent-4-ynyl and 2-methylpent-4-ynyl;

for $C_{3-6}$cycloalkyl: cyclopropyl, cyclobutyl, cyclopentyl and cyclohexyl;

for $C_{3-6}$cycloalkenyl: cyclobutenyl, cyclopentenyl, cyclohexenyl and cyclohex-1,4-dienyl;

for $C_{3-6}$cycloalkyl$C_{1-4}$alkyl: cyclopropylmethyl, cyclobutylmethyl, cyclopentylmethyl, cyclopropylethyl and cyclobutylethyl;

for $C_{1-4}$alkoxy: methoxy, ethoxy, propoxy, isopropoxy, butoxy and tert-butoxy;

for $C_{1-4}$alkoxy$C_{1-4}$alkyl: methoxymethyl, 2-methoxyethyl, 3-methoxypropyl and 2-ethoxyethyl;

for $C_{1-4}$alkoxy$C_{1-6}$alkyl: $C_{1-4}$alkoxy$C_{1-4}$alkyl, 4-methoxybutyl and 2-ethoxybutyl;

for $C_{1-4}$alkoxy$C_{3-6}$cycloalkyl: methoxycyclobutyl, methoxycyclopentyl and ethoxycyclopentyl;

for $C_{1-4}$alkoxy$C_{3-6}$cycloalkyl$C_{1-4}$alkyl: methoxycyclobutylmethyl and methoxycyclopentylmethyl;

for $C_{1-4}$alkoxy$C_{1-4}$alkoxy: methoxymethoxy, 2-methoxyethoxy and 2-ethoxyethoxy;

for hydroxy$C_{1-4}$alkyl: hydroxymethyl, 2-hydroxyethyl, 3-hydroxypropoxy, 2-hydroxypropyl, 2-hydroxy-1-methylethyl, 2,3-dihydroxypropyl, 2-hydroxy-1,1-dimethylethyl;

for hydroxy$C_{1-6}$alkyl: hydroxy$C_{1-4}$alkyl, 3-hydroxypentyl, 3-hydroxy-2,2-dimethylpropyl, 3-hydroxy-1,1-dimethylpropyl, 1-hydroxymethyl-2-methylpropyl and 6-hydroxyhexyl;

for hydroxy$C_{3-6}$cycloalkyl: 2-hydroxycyclopropyl, 2-hydroxycyclobutyl, 2-hydroxycyclopentyl and 4-hydroxycyclohexyl;

for hydroxy$C_{3-6}$cycloalkyl$C_{1-4}$alkyl: 2-hydroxycyclopropylmethyl and 2-hydroxycyclobutylmethyl;

for hydroxy$C_{1-4}$alkyl$C_{3-6}$cycloalkyl: 1-(hydroxymethyl)cyclopentyl and 2-(hydroxymethyl)cyclohexyl;

for hydroxy$C_{1-4}$alkyl$C_{3-6}$cycloalkyl$C_{1-4}$alkyl: 1-(hydroxymethyl)cyclopropylmethyl;

for hydroxy$C_{1-4}$alkoxy$C_{1-4}$alkyl: 2-(2-hydroxyethoxy)ethyl;

for $C_{1-4}$alkylcarbonyl: acetyl, ethylcarbonyl and isopropylcarbonyl;

for $C_{1-4}$alkoxycarbonyl; methoxycarbonyl, ethoxycarbonyl and tert-butoxycarbonyl;

for $C_{1-4}$alkoxy$C_{1-4}$alkylcarbonyl: methoxymethylcarbonyl and tert-butylmethylcarbonyl;

for hydroxy$C_{1-4}$alkylcarbonyl: glycoloyl(hydroxymethylcarbonyl);

for halo$C_{1-6}$alkyl: chloromethyl, 2-chloroethyl, 3-chloropropyl, trifluoromethyl and 3,3,3-trifluoropropyl;

for halo$C_{3-6}$cycloalkyl: 2-chlorocyclopropyl and 2-chlorocyclobutyl;

for halo$C_{3-6}$cycloalkyl$C_{1-4}$alkyl: 2-chlorocyclopropylmethyl and 2-chlorocyclobutylmethyl;

for cyano$C_{1-4}$alkyl: cyanomethyl and 2-cyanoethyl;

for amino$C_{1-4}$alkyl: aminomethyl, 2-aminoethyl, 2-aminopropyl and 4-aminobutyl;

for amino$C_{1-6}$alkyl: amino$C_{1-4}$alkyl and 6-aminohexyl;

for $C_{1-4}$alkylamino$C_{1-4}$alkyl: 2-(methylamino)ethyl and 3-(ethylaminopropyl);

for $C_{1-4}$alkylamino$C_{1-6}$alkyl: $C_{1-4}$alkylamino$C_{1-4}$alkyl and 2-(methylamino)hexyl;

for bis($C_{1-4}$alkyl)amino$C_{1-4}$alkyl: 2-(dimethylamino)ethyl, 2-[methyl(ethyl)amino]ethyl and 2-(diethylamino)ethyl;

for bis($C_{1-4}$alkyl)amino$C_{1-6}$alkyl: bis($C_{1-4}$alkyl)amino$C_{1-4}$ alkyl and 2-[methyl(ethyl)amino]pentyl;

for $C_{1-4}$alkylamino: methylamino, ethylamino, propylamino and isopropylamino;

for bis($C_{1-4}$alkyl)amino: dimethylamine, methyl(ethyl) amino and diethylamino;

for amino$C_{1-4}$alkylcarbonyl: glycyl(aminomethylcarbonyl);

for $C_{1-4}$alkylamino$C_{1-4}$alkylcarbonyl: N-methylglycyl;

for bis($C_{1-4}$alkyl)amino$C_{1-4}$alkylcarbonyl: N,N-dimethylglycyl;

for $C_{1-4}$alkanoylamino: acetylamino for aryl: phenyl and naphthyl;

for aryl$C_{1-4}$alkyl: benzyl, 2-phenylethyl;

for aryl$C_{2-4}$alkenyl: 3-phenylallyl;

for aryl$C_{2-4}$alkynyl: 3-phenylprop-2-ynyl;

for heteroaryl: furyl, thienyl, pyrrolyl, pyrazolyl, pyridyl, pyrazinyl, pyridazinyl, pyrimidinyl, quinazolinyl and quinolinyl for heterocyclyl: azetidinyl, pyrrolidinyl, imidazolidinyl, piperidinyl, piperazinyl, azepanyl, diazepanyl, pyridyl, imidazolyl, tetrahydrofuranyl, tetrahydropyranyl, furanyl, pyranyl, tetrahydrothienyl, thienyl, isoxazolyl, tetrahydro-2H-pyranyl, morpholinyl, 2-oxopyrrolidinyl, 3-oxopiperazinyl and 4-oxopiperdinyl;

for heterocyclyl$C_{1-4}$alkyl: pyrrolidinylmethyl, 2-pyrrolidinylethyl, 2-morpholinylethyl, 3-morpholinylpropyl, tetrahydrofuranylmethyl, 2-(2-oxopyrrolidinyl)ethyl and 3-(3-oxopiperazinyl)propyl;

for heterocyclyl$C_{2-4}$alkenyl: 3-pyrrolidinylallyl;

for heterocyclyl$C_{2-4}$alkynyl: 3-pyrrolidinylprop-2-ynyl;

for $C_{1-4}$alkylheterocyclyl$C_{1-4}$alkyl: 5-methylisoxazol-3-ylmethyl;

for phosphonooxy$C_{1-4}$alkyl: phosphonooxymethyl, 2-phosphonooxyethyl and 3-phosphonooxypropyl, 2-phosphonooxypropyl, 2-phosphonooxy- 1-methylethyl, 2-hydroxy-3-hydroxypropyl, 2-phosphonooxy-3-hydroxypropyl and 2-phosphonooxy-1,1-dimethylethyl;

for phosphonooxy$C_{1-6}$alkyl: phosphonooxy$C_{1-4}$alkyl and 3-phosphonooxy-1,1-dimethylpropyl, 3-phosphonooxy, 3-phosphonooxy-2,2-dimethylpropyl, 1-phosphonooxymethyl-2-methylpropyl and 6-phosphonooxyhexyl;

for phosphonooxy$C_{3-6}$cycloalkyl: 2-phosphonooxycyclopropyl, 2-phosphonooxycyclobutyl, 2-phosphonooxycyclopentyl and 4-phosphonooxycyclohexyl;

for phosphonooxy$C_{3-6}$cycloalkyl$C_{1-4}$alkyl: 2-phosphonooxycyclopropylmethyl and 2-phosphonooxycyclobutylmethyl;

for phosphonooxy$C_{1-4}$alkyl$C_{3-6}$cycloalkyl: 1-(phosphonooxymethyl)cyclopentyl and 2-(hydroxymethyl)cyclohexyl;

for phosphonooxy$_{1-4}$alkoxy$C_{1-4}$alkyl: 2-(2-phosphonooxyethoxy)ethyl;

for phosphonooxy$C_{1-4}$alkylcarbonyl: phosphonooxymethylcarbonyl;

Within the present invention, it is to be understood that, insofar as certain of compounds of formula (I) or formula (IA) herein defined may exist in optically active or racemic forms by virtue of one or more asymmetric carbon or sulphur atoms, the invention includes in its definition any such optically active or racemic form which possesses aurora kinase inhibitory activity and in particular Aurora-A and/or Aurora-B kinase inhibitory activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to herein.

Within the present invention it is to be understood that a compound of formula (I) or formula (IA) or a salt thereof may exhibit the phenomenon of tautomerism and that the formulae drawings within this specification can represent only one of the possible tautomeric forms. It is to be understood that the invention encompasses any tautomeric form which has Aurora kinase inhibitory activity and in particular Aurora-A and/or Aurora-B kinase inhibitory activity and is not to be limited merely to any one tautomeric form utilised within the formulae drawings.

It is also to be understood that certain compounds of formula (I) or formula (IA) and salts thereof can exist in solvated as well as unsolvated forms such as, for example, hydrated forms. It is to be understood that the invention encompasses all such solvated forms which have Aurora kinase inhibitory activity and in particular Aurora-A and/or Aurora-B kinase inhibitory activity.

The present invention relates to the compounds of formula (I) or formula (IA) as herein defined as well as to the salts thereof. Salts for use in pharmaceutical compositions will be pharmaceutically acceptable salts, but other salts may be useful in the production of the compounds of formula (I) or formula (IA) and their pharmaceutically acceptable salts. Pharmaceutically acceptable salts of the invention may, for example, include acid addition salts of compounds of formula (I) or formula (IA) as herein defined which are sufficiently basic to form such salts. Such acid addition salts include but are not limited to, furmarate, methanesulphonate, hydrochloride, hydrobromide, citrate and maleate salts and salts formed with phosphoric and sulphuric acid. In addition where compounds of formula (I) or formula (IA) are sufficiently acidic, salts are base salts and examples include but are not limited to, an alkali metal salt for example sodium or potassium, an alkaline earth metal salt for example calcium or magnesium, or organic amine salt for example triethylamine, ethanolamine, diethanolamine, triethanolamine, morpholine, N-methylpiperidine, N-ethylpiperidine, dibenzylamine or amino acids such as lysine.

The compounds of formula (I) or formula (IA) may also be provided as esters and in particular in vivo hydrolysable esters. An in vivo hydrolysable ester of a compound of formula (I) or formula (II) containing carboxy or hydroxy group is, for example a pharmaceutically acceptable ester which is cleaved in the human or animal body to produce the parent acid or alcohol. Such esters can be identified by administering, for example, intravenously to a test animal, the compound under test and subsequently examining the test animal's body fluid.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

Suitable pharmaceutically-acceptable esters for hydroxy include inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include $C_{1-10}$alkanoyl, for example formyl, acetyl; benzoyl; phenylacetyl; substituted benzoyl and phenylacetyl, $C_{1-10}$alkoxycarbonyl (to give alkyl carbonate esters), for example ethoxycarbonyl; di-$C_{1-4}$alkylcarbamoyl and N-(di-$C_{1-4}$ alkylaminoethyl)-N-$C_{1-4}$alkylcarbamoyl (to give carbamates); di-$C_{1-4}$alkylaminoacetyl and carboxyacetyl. Examples of ring substituents on phenylacetyl and benzoyl include aminomethyl, $C_{1-4}$alkylaminomethyl and di-($C_{1-4}$ alkyl)aminomethyl, and morpholino or piperazino linked from a ring nitrogen atom via a methylene linking group to the 3- or 4-position of the benzoyl ring. Other interesting in vivo hydrolysable esters include, for example, $R^AC(O)OC_{1-6}$ alkyl-CO—, wherein $R^A$ is for example, benzyloxy-$C_{1-4}$ alkyl, or phenyl). Suitable substituents on a phenyl group in such esters include, for example, 4-$C_{1-4}$piperazino-$C_{1-4}$alkyl, piperazino-$C_{1-4}$alkyl and morpholino-$C_{1-4}$alkyl.

The compounds of the formula (I) may be also be administered in the form of a prodrug which is broken down in the human or animal body to give a compound of the formula (I). Examples of prodrugs include in vivo hydrolysable esters of a compound of the formula (I). Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, Advanced Drug Delivery Reviews, 8, 1-38 (1992);
d) H. Bundgaard, et al., Journal of Pharmaceutical Sciences, 77, 285 (1988); and
e) N. Kakeya, et al., Chem Pharm Bull, 32, 692 (1984).

Preferred values of X, $R^1$, $R^2$, $R^3$, $R^4$, $R^5$ and $R^{19}$ for a compound of formula (I) are as follows. Such values may be used where appropriate with any of the definitions, claims or embodiments defined herein.

In one aspect of the invention X is $NR^6$. In another aspect X is NH.

In one aspect of the invention $R^6$ is hydrogen or methyl. In another aspect $R^6$ is hydrogen.

In one aspect of the invention $R^1$ is hydrogen, halo or —$OR^{11}$. In a further aspect $R^1$ is hydrogen or —$OR^{11}$. In another aspect $R^1$ is hydrogen, fluoro, hydroxy, methoxy, isopropoxy, pyrrolidin-2-ylmethoxy, 1-(2-hydroxyethyl)pyrrolidin-2-ylmethoxy, 1-glycoloylpyrrolidin-2-ylmethoxy, 1-(N,N-dimethylglycyl)pyrrolidin-2-ylmethoxy, 2-(5-hydroxymethyl-2-oxo-pyrrolidin-1-yl)ethoxy, 3-(5-hydroxymethyl-2-oxo-pyrrolidin-1-yl)propoxy, 2-(6-hydroxymethyl-2-oxo-piperazin-1-yl)ethoxy, 3-(6-hydroxymethyl-2-oxo-piperazin-1-yl)propoxy, 2-(5-hydroxymethyl-3-oxo-piperazin-1-yl)ethoxy or 3-(5-hydroxymethyl-3-oxo-piperazin-1-yl)propoxy. In yet a further aspect $R^1$ is hydrogen, fluoro, hydroxy, methoxy, isopropoxy, pyrrolidin-2-ylmethoxy, 1-(2-hydroxyethyl)pyrrolidin-2-ylmethoxy, 1-glycoloylpyrrolidin-2-ylmethoxy or 1-(N,N-dimethylglycyl)pyrrolidin-2-ylmethoxy. In another aspect $R^1$ is hydrogen.

In one aspect of the invention $X^1$ is a direct bond, —O—, —NH— or —N($C_{1-4}$alkyl)-. In a further aspect $X^1$ is a direct bond or —O—. In another aspect $X^1$ is a direct bond. In yet another aspect $X^1$ is —O—.

In one aspect of the invention $R^{11}$ is hydrogen or a group selected from $C_{1-6}$alkyl, heterocyclyl, heterocyclyl$C_{1-4}$alkyl, heterocyclyl$C_{2-4}$alkenyl and heterocyclyl$C_{2-4}$alkynyl which group is optionally substituted by a substituent selected from hydroxy, $C_{1-4}$alkoxy, hydroxy$C_{1-4}$alkyl, amino, $C_{1-4}$alkylamino, bis($C_{1-4}$alkyl)amino, hydroxycarbonyl, $C_{1-4}$alkoxycarbonyl, hydroxy$C_{1-4}$alkylcarbonyl, $C_{1-4}$alkoxy$C_{1-4}$alkylcarbonyl, amino$C_{1-4}$alkylcarbonyl, $C_{1-4}$alkylamino$C_{1-4}$ alkylcarbonyl and bis($C_{1-4}$alkyl)amino$C_{1-4}$alkylcarbonyl. In a further aspect $R^{11}$ is hydrogen or a group selected from $C_{1-6}$alkyl, heterocyclyl and heterocyclyl$C_{1-4}$alkyl, which group is optionally substituted by a substituent selected from hydroxy, $C_{1-4}$alkoxy, hydroxy$C_{1-4}$alkyl, hydroxy$C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$alkylcarbonyl. In another aspect $R^{11}$ is hydrogen, methyl, ethyl, propyl, isopropyl or a group selected from pyrrolidinylmethyl, pyrrolidinylethyl, pyrrolidinylpropyl, 2-oxopyrrolidin-1-ylmethyl, 2-oxopyrrolidin-1-ylethyl, 2-oxopyrrolidin-1-ylpropyl, 3-oxopyrrolidin-1-ylmethyl, 3-oxopyrrolidin-1-ylethyl, 3-oxopyrrolidin-1-ylpropyl, piperidinylmethyl, piperidinylethyl, piperidinylpropyl, 2-oxopiperidinylmethyl, 2-oxopiperidinylethyl, 2-oxopiperidinylpropyl, 3-oxopiperidinylmethyl, 3-oxopiperidinylethyl, 3-oxopiperidinylpropyl, 4-oxopiperidinylmethyl, 4oxopiperidinylethyl, 4-oxopiperidinylpropyl, piperazinylmethyl, piperazinylethyl, piperazinylpropyl, 2-oxopiperazinylmethyl, 2-oxopiperazinylethyl, 2-oxopiperazinylpropyl, 3-oxopiperazinylmethyl, 3-oxopiperazinylethyl and 3-oxopiperazinylpropyl, which group is optionally substituted by hydroxy, hydroxymethyl, 2-hydroxyethyl, tert-butoxycarbonyl, glycoloyl, glycyl, N-methylglycyl or N,N-dimethylglycyl. In a further aspect $R^{11}$ is hydrogen, methyl, ethyl, propyl, isopropyl, pyrrolidinylmethyl which pyrrolidinylmethyl is optionally substituted by 2-hydroxyethyl, glycoloyl or N,N-dimethylglycyl or $R^{11}$ is 2-(2-oxopyrrolidin-1-yl)ethyl, 3-(2-oxopyrrolidin-1-yl)propyl, 2-(2-oxopiperazin-1-yl)ethyl, 3-(2-oxopiperazin-1-yl)propyl, 2-(3-oxopiperazin-1-yl)ethyl or 3-(3-oxopiperazin-1-yl)propyl optionally substituted by hydroxymethyl or 2-hydroxyethyl. In yet a further aspect $R^{11}$ is hydrogen, methyl, ethyl, propyl, isopropyl or pyrrolidinylmethyl which pyrrolidinylmethyl is optionally substituted by 2-hydroxyethyl, glycoloyl or N,N-dimethylglycyl. In yet another aspect $R^{11}$ is hydrogen, $C_{1-4}$alkyl or $C_{1-4}$alkoxy. In a further aspect $R^{11}$ is hydrogen.

In one aspect of the invention $R^2$ is hydrogen, halo, —$OR^{12}$ or —$C(O)R^{12}$. In a further aspect $R^2$ is hydrogen, fluoro, hydroxy, methoxy, 2-methoxyethoxy, benzoyloxy, 2-morpholin-4-ylethoxy, 3-morpholin-4-ylpropoxy or 1-methylpyrrolidin-2-yloxy. In another aspect $R^2$ is hydrogen or methoxy. In a further aspect $R^2$ is hydrogen. In yet a further aspect $R^2$ is methoxy.

In one aspect of the invention $X^2$ is a direct bond, —O— or —OC(O)—. In another aspect of the invention $X^2$ is a direct bond or —O—.

In one aspect of the invention $R^{12}$ is hydrogen or a group selected from $C_{1-6}$alkyl, $C_{2-6}$alkenyl, $C_{2-6}$alkynyl, $C_{3-6}$cycloalkyl, aryl, aryl$C_{1-4}$alkyl, heterocyclyl and heterocyclyl$C_{1-4}$alkyl, which group is optionally substituted by 1, 2 or 3 substituents selected from halo, hydroxy, $C_{1-4}$alkyl, $C_{1-4}$alkoxy, —$NR^{15}R^{16}$, —$NHC(O)NR^{15}R^{16}$, —$C(O)R^{15}$. In a further aspect $R^{12}$ is hydrogen or a group selected from $C_{1-4}$alkyl, aryl, heterocyclyl and heterocyclyl$C_{1-4}$alkyl which group is optionally substituted by a substituent selected from $C_{1-4}$alkyl and $C_{1-4}$alkoxy. In yet another aspect $R^{12}$ is hydrogen or group selected from methyl, 2-morpholinylethyl, 3-morpholinylpropyl, 2-methoxyethyl and pyrrolidinyl which group is optionally substituted by methyl. In another aspect $R^{12}$ is hydrogen or $C_{1-4}$alkyl. In another aspect of the invention $R^{12}$ is hydrogen. In a further aspect of the invention $R^{12}$ is methyl.

In one aspect of the invention $R^3$ is hydrogen or —$X^3R^{13}$. In another aspect $R^3$ is hydrogen, hydroxy, methoxy, 3-chloropropoxy, 2-chloroethoxy, 2,2-dimethoxyethoxy, 3-[2-(hydroxymethyl)pyrrolidin-1-yl]propoxy, 3-[(2-hydroxyethyl)(isobutyl)amino]propoxy, 3-[(2-hydroxyethyl)(propyl)amino]propoxy, 3-piperidin-1-ylpropoxy, 3-pyrrolidin-1- ylpropoxy, 3-(diethylamino)propoxy, 3-piperazin-1-ylpropoxy, 3-[(2-hydroxyethyl)(methyl)amino]propoxy, 3-(cyclopropylamino)propoxy, 3-{[2-(dimethylamino)ethyl](methyl)amino}propoxy, 3-(4-methylpiperazin-1-yl)propoxy, 3-(4-hydroxypiperidin-1-yl)propoxy, 3-[bis(2-hydroxyethyl)amino]propoxy, 3-[ethyl(methyl)amino]propoxy, 3-[ethyl(2-hydroxyethyl)amino]propoxy, 3-{[2-(dimethylamino)ethyl](ethyl)amino}propoxy, 3-[2-(2-hydroxyethyl)piperidin-1-yl]propoxy, 3-[4-(2-hydroxyethyl)piperazin-1-yl]propoxy, 3-[(cyclopropylmethyl)amino]propoxy, 3-[4-(2-hydroxyethyl)piperidin-1-yl]propoxy, 3-[methyl(prop-2-yn-1-yl)amino]propoxy, 3-[allyl(methyl)amino]propoxy, 3-[isobutyl(methyl)amino]propoxy, 3-(3-hydroxypiperidin-1-yl)propoxy, 3-[4-(hydroxymethyl)piperidin-1-yl]propoxy, 3-[methyl(propyl)amino]propoxy, 3-[cyclopropylmethyl(propyl)amino]propoxy, 3-{[2-(diethylamino)ethyl](methyl)amino}propoxy, 3-{[2-(diethylamino)ethyl](ethyl)amino}propoxy, 3-(4-methyl-1,4-diazepan-1-yl)propoxy, 3-[(2-hydroxyethyl)(isopropyl)amino]propoxy, 3-[cyclopropyl(2-hydroxyethyl)amino]propoxy, 3-[(2-hydroxyethyl)(2-methoxyethyl)amino]propoxy, 3-[cyclobutyl(2-hydroxyethyl)amino]propoxy, 3-[cyclopropylmethyl(2-hydroxyethyl)amino]propoxy, 3-[cyclobutylmethyl(2-hydroxyethyl)amino]propoxy, 3-[(2-hydroxy)prop-2-yn-1-lyamino]propoxy, 3-[allyl(2-hydroxyethyl)amino]propoxy, 3-[(2,2-dimethylpropyl(2-hydroxyethyl)amino]propoxy, 3-[(2-hydroxyethyl)(3,3,3-trifluoropropyl)amino]propoxy, 3-azetidin-1-ylpropoxy, 3-(dimethylamino)propoxy, 2-[(2-hydroxymethyl)pyrrolidin-1-yl]ethoxy, 2-{4-[2-(2-hydroxyethoxy)ethyl]piperazin-1-yl}ethoxy, 2-[2-(2-hydroxyethyl)piperidin-1-yl]ethoxy, 2-[2-(hydroxymethyl)piperidin-1-yl]ethoxy, 2-[(2-hydroxy-1,1-dimethylethyl)amino]ethoxy, 2-[4-(2-hydroxyethyl)piperazin-1-yl]ethoxy, 2-[(4-hydroxycyclohexyl)amino]ethoxy, 2-[3-(hydroxymethyl)piperidin-1-yl]ethoxy, 2-{[1-(hydroxymethyl)cyclopentyl]amino}ethoxy, 2-[4-(3-hydroxypropyl)piperazin-1-yl]ethoxy, 2-[cyclohexyl(2-hydroxyethyl)amino]ethoxy, 2-[(2-hydroxyethyl)(propyl)amino]ethoxy, 2-[(3-hydroxy-2,2-dimethylpropyl)amino]ethoxy, 2-tetrahydro-2H-pyran-4-ylamino)ethoxy, 2-[cyclobutyl(2-hydroxyethyl)amino]ethoxy, 2-[(2-hydroxyethyl)(tetrahydro-2H-pyran-4-yl)amino]ethoxy, 3-[cyclopentyl(2-hydroxyethyl)amino]propoxy, 3-[(3-hydroxy-1,1-dimethylpropyl)amino]propoxy, 3-[(2-cyanoethyl)(2-hydroxyethyl)amino]propoxy, 3-morpholin-4-ylpropoxy, 3-[(3-hydroxy-2,2-dimethylpropyl)amino]propoxy, 3-[(3-hydroxypropyl)amino]propoxy, 3-[(3-hydroxypropyl)(propyl)amino]propoxy, 3-[(3-hydroxypropyl)(ethyl)amino]propoxy, 3-[4-(2-hydroxyethyl)-3-oxopiperazin-1-yl]propoxy, 3-(propylamino)propoxy, 3-[glycoloyl(propyl)amino]propoxy, 3-(4-glycoloylpiperazin-1-yl)propoxy, 3-{[2-(hydroxymethyl)cyclohexyl]amino}propoxy, 3-[{1α,5α,6α)-6-(hydroxymethyl)-3-azabicyclo[3.1.0]hex-3-yl]propoxy, 3-{[2-hydroxypropyl]amino}propoxy, 3-{[2-hydroxy-1-methylethyl]amino}propoxy, 3-[(2-hydroxy-1,1-dimethylethyl)amino]propoxy, 3-[(2,3-dihydroxypropyl)amino]propoxy, 3-{[2-(2-hydroxyethoxy)ethyl]amino}propoxy, 3-(4-acetylpiperazin-1-yl)propoxy, 3-[(tetrahydrofuran-2-ylmethyl)amino]propoxy, 3-(allylamino)propoxy, 3-{[1-(hydroxymethyl)-2-methylpropyl]amino}propoxy, 3-{[(5-methylisoxazol-3-yl)methyl]amino}propoxy, 3-(tetrahydro-2H-pyran-4-ylamino)propoxy, 3-[3-hydroxymethyl)pyrrolidin-1-yl]propoxy, 3-aminopropoxy, 3-[-4-hydroxy-2-(hydroxymethyl)pyrrolidin-1-yl]propoxy, 2-(cyclopropylamino)ethoxy, 2-(cyclobutylamino)ethoxy, 2-(cyclopentylamino)ethoxy, 2-[{2-hydroxyethyl)(tetrahydro-2H-pyran-4-yl)amino]ethoxy, 2-[cyclopentyl(2-hydroxyethyl)amino]ethoxy, 2-[cyclopropyl(2-hydroxyethyl)amino]ethoxy, 2-[cyclopentyl(3-hydroxypropyl)amino]ethoxy, 2-[cyclopentyl(glycoloyl)amino]ethoxy, 2-[3-(hydroxymethyl)-4-methylpiperazin-1-yl]ethoxy, 2-[2-(hydroxymethyl)-4-methylpiperazin-1-yl]ethoxy, 2-[4-(hydroxymethyl)piperidin-1-yl]ethoxy, 2-[4-(2-hydroxyethyl)piperidin-1-yl]ethoxy, 2-[(2-hydroxyethyl)amino]ethoxy, 2-{[2-(hydroxymethyl)cyclohexyl]amino}ethoxy, 3-[(2-hydroxyethyl)amino]propoxy, 3-[(2-hydroxyethyl)(tetrahydrofuran-3-yl)amino]propoxy, pyrrolidin-2-ylmethoxy, [1-(2-hydroxyethyl)pyrrolidin-2-yl]methoxy, [1-glycoloyopyrrolidin-2-yl]methoxy, pyrrolidin-3-ylmethoxy, [1-(2-hydroxyethyl)pyrrolidin-3-yl]methoxy, (1-glycoloylpyrrolidin-3-yl)methoxy, 3-[(2-hydroxyethyl)(2-methoxyethyl)amino]propoxy, (2-hydroxyethyl)amino]propoxy, 2-(5-hydroxymethyl-2-oxo-pyrrolidin-1-yl)ethoxy, 3-(5-hydroxymethyl-2-oxo-pyrrolidin-1-yl)propoxy, 2-(6-hydroxymethyl-2-oxo-piperazin-1-yl)ethoxy, 3-(6-hydroxymethyl-2-oxo-piperazin-1-yl)propoxy, 2-(5-hydroxymethyl-3-oxo-piperazin-1-yl)ethoxy, 3-(5-hydroxymethyl-3-oxo-piperazin-1-yl)propoxy, 3-(3-hydroxymethyl-4-methylpiperazin-1yl)propoxy, 3-(2-hydroxymethylmorpholin-4-yl)propoxy, 3-(glycoloylamino)propoxy or 3-(4-hydroxymethylpiperazin-1-yl)propoxy. In a further aspect $R^3$ is selected from 3-chloropropoxy, 3-[2-(hydroxymethyl)pyrrolidin-1-yl]propoxy, 3-[(2-hydroxyethyl)(isobutyl)amino]propoxy, 3-[(2-hydroxyethyl)(propyl)amino]propoxy, 3-piperidin-1-ylpropoxy, 3-pyrrolidin-1-ylpropoxy, 3-(diethylamino)propoxy, 3-piperazin-1-ylpropoxy, 3-[(2-hydroxyethyl)(methyl)amino]propoxy, 3-(cyclopropylamino)propoxy, 3-{[2-(dimethylamino)ethyl](methyl)amino}propoxy, 3-(4-methylpiperazin-1-yl)propoxy, 3-(4-hydroxypiperidin-1-yl)propoxy, 3-[bis(2-hydroxyethyl)amino]propoxy, 3-[ethyl(methyl)amino]propoxy, 3-[ethyl(2-hydroxyethyl)amino]propoxy, 3-{[2-(dimethylamino)ethyl](ethyl)amino}propoxy, 3-[2-(2-hydroxyethyl)piperidin-1-yl]propoxy, 3-[4-(2-hydroxyethyl)piperazin-1-yl]propoxy, 3-[(cyclopropylmethyl)amino]propoxy, 3-[4-(2-hydroxyethyl)piperidin-1-yl]propoxy, 3-[methyl(propargyl)amino]propoxy, 3-[allyl(methyl)amino]propoxy, 3-[isobutyl(methyl)amino]propoxy, 3-(3-hydroxypiperidin-1-yl)propoxy, 3-[4-(hydroxymethyl)piperidin-1-yl]propoxy, 3-[methyl(propyl)amino]propoxy, 3-[cyclopropylmethyl(propyl)amino]propoxy, 3-{[2-(diethylamino)ethyl](methyl)amino}propoxy, 3-{[2-(diethylamino)ethyl](ethyl)amino}propoxy, 3-(4-methyl-1,4-diazepan-1-yl)propoxy, 3-[(2-hydroxyethyl)(isopropyl)amino]propoxy, 3-[cyclopropyl(2-hydroxyethyl)amino]propoxy, 3-[(2-hydroxyethyl)(2-methoxyethyl)amino]propoxy, 3-[cyclobutyl(2-hydroxyethyl)amino]propoxy, 3-[cyclopropylmethyl(2-hydroxyethyl)amino]propoxy, 3-[cyclobutylmethyl(2-hydroxyethyl)amino]propoxy, 3-[(2-hydroxy)propargylamino]propoxy, 3-[allyl(2-hydroxyethyl)amino]propoxy, 3-[(2-hydroxyethyl)neopentylamino]propoxy, 3-[(2-hydroxyethyl)(3,3,3-trifluoropropyl)amino]propoxy, 3-azetidin-1-ylpropoxy, 3-[cyclopentyl(2-hydroxyethyl)amino]propoxy, 3-[(3-hydroxy-1,1-dimethylpropyl)amino]propoxy, 3-[(2-cyanoethyl)(2-hydroxyethyl)amino]propoxy and 3-(dimethylamino)propoxy. In another aspect $R^3$ is selected from 3-[2-(hydroxymethyl)pyrrolidin-1-yl]propoxy, 3-[(2-hydroxyethyl)(isobutyl)amino]propoxy, 3-[(2-hydroxyethyl)(propyl)amino]propoxy, 3-[ethyl(2-hydroxyethyl)amino]propoxy, 3-[4-(2-hydroxyethyl)piperazin-1-yl]propoxy, 3-[4-(2-hydroxyethyl)piperidin-1-yl]propoxy, 3-[(2-hydroxyethyl)(2-methoxyethyl)amino]propoxy, 3-[cyclobutyl(2-hydroxyethyl)amino]propoxy, 3-[cyclopropylmethyl(2-hydroxyethyl)amino]propoxy and 3-[(3-hydroxy-1,1-dimethylpropyl)amino]propoxy.

In one aspect of the invention $X^3$ is a direct bond, —$CH_2$═$CH_2$—, —O—, —NH— or —N($C_{1-6}$alkyl)-. In a further aspect $X^3$ is —$CH_2$═$CH_2$—, —O— or —NH—. In another aspect $X^3$ is a direct bond or —O—. In yet another aspect $X^3$ is —O—.

In one aspect of the invention $R^{13}$ is hydrogen or a group selected from $C_{1-6}$alkyl, aryl, aryl$C_{1-4}$alkyl, heterocyclyl and heterocyclyl$C_{1-4}$alkyl, which group is optionally substituted by 1 or 2 substituents independently selected from —$NR^7R^8$, —C(O)$NR^7R^8$, halo, hydroxy, $C_{1-4}$alkyl, $C_{1-4}$alkoxy, hydroxy$C_{1-4}$alkyl, hydroxy$C_{1-4}$alkylcarbonyl and $C_{1-4}$alkylcarbonyl. In another aspect $R^{13}$ is hydrogen, methyl, ethyl, propyl, heterocyclyl, heterocyclylmethyl, heterocyclylethyl or heterocyclylpropyl which methyl, ethyl or propyl are optionally substituted by —$NR^7R^8$, —C(O)$NR^7R^8$ or 1 or 2 halo, hydroxy or $C_{1-4}$alkoxy substituents and which heterocyclylmethyl, heterocyclylethyl or heterocyclylpropyl are optionally substituted on heterocyclyl by hydroxy, $C_{1-4}$alkyl, hydroxy$C_{1-4}$alkyl or hydroxy$C_{1-4}$alkylcarbonyl. In a further aspect $R^{13}$ is hydrogen, methyl, ethyl, propyl or piperidinyl which methyl, ethyl or propyl are substituted by chloro, 1 or 2 hydroxy, 1 or 2 methoxy, —$NR^7R^8$ or a heterocyclyl selected from pyrrolidinyl and piperidinyl which heterocyclyl is optionally substituted by hydroxy, methyl, hydroxymethyl, 2-hydroxyethyl or glycoloyl. In a further aspect $R^{13}$ is ethyl or propyl, both of which are substituted by —$NR^7R^8$, heterocyclyl or halo. In yet a further aspect $R^{13}$ is propyl substituted by chloro, —$NR^7R^8$ or a heterocyclyl selected from pyrrolidinyl, piperidinyl, piperazinyl, diazepanyl and azetidinyl which heterocyclyl is optionally substituted by hydroxy, methyl, hydroxymethyl or 2-hydroxyethyl. In another aspect $R^{13}$ is ethyl or propyl substituted by chloro or —$NR^7R^8$. In yet another aspect $R^{13}$ is ethyl or propyl substituted by —$NR^7R^8$. In a further aspect $R^{13}$ is propyl substituted by —$NR^7R^8$.

In one aspect of the invention $R^7$ and $R^8$ are independently selected from hydrogen, heterocyclyl, heterocyclyl$C_{1-4}$alkyl, $C_{1-4}$alkylheterocyclyl$C_{1-4}$alkyl, $C_{1-6}$alkyl, hydroxy$C_{1-6}$alkyl, $C_{1-4}$alkoxy$C_{1-4}$alkyl, $C_{3-6}$cycloalkyl, $C_{3-6}$cycloalkyl$C_{1-4}$alkyl, hydroxy$C_{3-6}$cycloalkyl, hydroxy$C_{1-4}$alkyl$C_{3-6}$cycloalkyl, halo$C_{1-6}$alkyl, $C_{2-4}$alkenyl, $C_{2-4}$alkynyl, cyano$C_{1-4}$alkyl, amino$C_{1-4}$alkyl, $C_{1-4}$alkylamino$C_{1-4}$alkyl, bis($C_{1-4}$alkyl)amino$C_{1-4}$alkyl, hydroxy$C_{1-4}$ alkoxy$C_{1-4}$alkyl and hydroxy$C_{1-4}$alkylcarbonyl; or $R^7$ and $R^8$ together with the nitrogen to which they are attached form a heterocyclic ring selected from azetidine, pyrrolidine, piperidine, morpholine, piperazine, diazepane, 1,4-diazepane and azabicyclo[3.1.0]hexane which ring is optionally substituted on carbon or nitrogen by 1 or 2 substituents independently selected from $C_{1-4}$alkyl, hydroxy, hydroxy$C_{1-4}$alkyl, $C_{1-4}$alkoxy$C_{1-4}$alkyl, hydroxy$C_{1-4}$alkoxy$C_{1-4}$alkyl, $C_{1-4}$alkylcarbonyl and hydroxy$C_{1-4}$alkylcarbonyl, and where a ring —$CH_2$— is optionally replaced with —C(O)—. In another aspect $R^7$ and $R^8$ are independently selected from hydrogen, heterocyclyl, $C_{1-6}$alkyl, hydroxy$C_{1-6}$alkyl, hydroxy$C_{1-4}$alkyl$C_{3-6}$cycloalkyl, $C_{1-4}$alkoxy$C_{1-4}$alkyl, $C_{3-6}$cycloalkyl, $C_{3-6}$cycloalkyl$C_{1-4}$alkyl, halo$C_{1-6}$alkyl, $C_{2-6}$alkenyl, $C_{2-6}$alkyl, cyano$C_{1-4}$alkyl, and bis($C_{1-4}$alkyl)amino$C_{1-6}$alkyl; or $R^7$ and $R^8$ together with the nitrogen to which they are attached form a heterocyclic ring which ring comprises 4 to 7 ring atoms of which one is nitrogen and of which another is optionally NH and which ring is optionally substituted on carbon or nitrogen by a group selected from $C_{1-4}$alkyl, hydroxy, hydroxy$C_{1-4}$ alkyl and hydroxy$C_{1-4}$ alkoxy$C_{1-4}$alkyl, and where a ring —$CH_2$— is optionally replaced with —C(O)—. In a further aspect $R^7$ and $R^8$ are independently selected from hydrogen, methyl, ethyl, propyl, isopropyl, butyl, isobutyl, tert-butyl, pentyl, neopentyl, hydroxymethyl, 2-hydroxyethyl, 2-hydroxy-1-methylethyl, 2-hydroxy-1,1-dimethylethyl, 3-hydroxypropyl, 3-hydroxy-2,2-dimethylpropyl, 3-hydroxy-1,1-dimethylpropyl, 2-hydroxypropyl, 2,3-dihydroxypropyl, 1-hydroxymethyl-2-methylpropyl, cyclopropyl, cyclobutyl, cyclopentyl, cyclohexyl, 4-hydroxycyclohexyl, 1-hydroxymethylcyclopentyl, 2-hydroxymethylcyclohexyl, cyclopropylmethyl, cyclobutylmethyl, tetrahydro-2H-pyran-4-yl, tetrahydrofuran-3-yl, tetrahydrofuran-2-ylmethyl, 5-methylisoxazol-3-yl, 2-cyanoethyl, allyl, prop-2-ynyl, 2-methoxyethyl, 3,3,3-trifluoropropyl, 2-(2-hydroxyethoxy)ethyl, 2-(dimethylamino)ethyl, 2-(diethylamino)ethyl, 3-aminopropyl, 3-(propylamino)propyl and glycoloyl; or $R^7$ and $R^8$ together with the nitrogen to which they are attached form a heterocyclic ring selected from azetidine, pyrrolidine, piperidine, morpholine, piperazine, diazepane or 1,4-diazepane which ring is optionally substituted by 1 or 2 substituents independently selected from methyl, hydroxy, hydroxymethyl, 2-hydroxyethyl, 3-hydroxypropyl, 2-(2-hydroxyethoxy)ethyl, glycoloyl, acetyl, methoxymethyl and oxo. In a further aspect $R^7$ and $R^8$ are independently selected from hydrogen, methyl, ethyl, propyl, isopropyl, butyl, isobutyl, tert-butyl, pentyl, neopentyl, hydroxymethyl, 2-hydroxyethyl, 2-hydroxy-1-methylethyl, 2-hydroxy-1,1-dimethylethyl, 3-hydroxypropyl, 3-hydroxy-2,2-dimethylpropyl, 3-hydroxy-1,1-dimethylpropyl, 2-hydroxypropyl, 2,3-dihydroxypropyl, 1-hydroxymethyl-2-methylpropyl, cyclopropyl, cyclobutyl, cyclopentyl, cyclohexyl, 4-hydroxycyclohexyl, 1-hydroxymethylcyclopentyl, 2-hydroxymethylcyclohexyl, cyclopropylmethyl, cyclobutylmethyl, tetrahydro-2H-pyranyl, tetrahydrofuran-3-yl, tetrahydrofuran-2-ylmethyl, 5-methylisoxazol-3-yl, 2-cyanoethyl, allyl, prop-2-ynyl, 2-methoxyethyl, methoxymethyl, 3,3,3-trifluoropropyl, 2-(2-hydroxyethoxy)ethyl, 2-(dimethylamino)ethyl, 2-(diethylamino)ethyl, 3-aminopropyl, 3-(propylamino)propyl and glycoloyl. In yet another aspect $R^7$ and $R^8$ together with the nitrogen to which they are attached form azetidine, pyrrolidine, piperidine, morpholine, piperazine, diazepane, 1,4-diazepane, azabicyclo[3.1.0]hexane 4-methylpiperazine, 4-methyl-1,4-diazepane, 4-hydroxypiperidine, 3-hydroxypiperidine, 2-hydroxymethylpyrrolidine, 3-hydroxymethylpyrrolidine, 2-hydroxymethylpiperidine, 3-hydroxymethylpiperidine, 4-hydroxymethylpiperidine, 2-(2-hydroxyethyl)piperidine, 4-(2-hydroxyethyl)piperidine, 4-(2-hydroxyethyl)piperazine, 4-(3-hydroxypropyl)piperazine, 4-[2-(2-hydroxyethoxy)ethyl]piperazine, 4-glycoloylpiperazine, 4-acylpiperazine, 3-hydroxymethyl-4-methylpiperazine, 2-hydroxymethylmorphine 3-hydroxymethyl-4-methylpiperazine, 3-methoxymethyl-4-methylpiperazine, 4-(2-hydroxyethyl)-3-oxopiperazine or (1α,5α,6α)-6-(hydroxymethyl)-3-azobicyclo[3.1.0]hexane, 4-hydroxy-2-hydroxymethylpyrrolidine, 5-hydroxymethyl-2-oxopyrrolidine, 6-hydroxymethyl-2-oxopiperazine or 5-hydroxymethyl-3-oxopiperazine. In a further aspect $R^7$ and $R^8$ are independently selected from hydrogen, methyl, ethyl, propyl, isopropyl, butyl, isobutyl, tert-butyl, pentyl, neopentyl, hydroxymethyl, 2-hydroxyethyl, 3-hydroxy-1,1-dimethylpropyl, methoxymethyl, 2-methoxyethyl, 2-ethoxyethyl, cyclopropyl, cyclobutyl, cyclopentyl, cyclopropylmethyl, cyclobutylmethyl, cyclopentylmethyl, trifluoromethyl, 2,2,2-trifluoroethyl, 3,3,3-trifluoropropyl, allyl, propargyl, 2-(dimethylamino)ethyl and 2-(diethylamino)ethyl; or $R^7$ and $R^8$ together with the nitrogen to which they are attached form a heterocyclic ring selected from pyrrolidinyl, piperidinyl, piperazinyl, diazepanyl and azetidinyl where the ring is optionally substituted by hydroxy, methyl, hydroxymethyl or 2-hydroxyethyl. In yet another aspect $R^7$ and $R^8$ are independently selected from hydrogen, ethyl, propyl, isobutyl, 3-hydroxy-1,1-dimethyl, 2-methoxyethyl, cyclobutyl and cyclopropylmethyl; or $R^7$ and $R^8$ together with the nitrogen to which they are attached form a heterocyclic ring selected from pyrrolidinyl, piperidinyl and piperazinyl, where the ring is optionally substituted by hydroxymethyl or 2-hydroxyethyl.

In one aspect of the invention $R^4$ is hydrogen.

In one aspect of the invention $R^5$ is aryl optionally substituted by 1 or 2 halo. In another aspect $R^5$ is phenyl optionally substituted by 1 or 2 fluoro or chloro. In a further aspect $R^5$ is phenyl optionally substituted by 1 or 2 fluoro. In yet another aspect $R^5$ is 2,3-difluorophenyl, 3-fluorophenyl, 2-fluorophenyl or 2,6-difluorophenyl. In yet another aspect $R^5$ is 2,3-difluorophenyl or 3-fluorophenyl.

In one aspect of the invention $R^9$ is hydrogen, $C_{1-4}$alkyl, hydroxy$C_{1-4}$alkyl, amino$C_{1-4}$alkyl, $C_{1-4}$alkylamino$C_{1-4}$alkyl or bis($C_{1-4}$alkyl)amino$C_{1-4}$alkyl. In a further aspect $R^9$ is hydroxy$C_{1-4}$alkyl or bis($C_{1-4}$alkyl)amino$C_{1-4}$alkyl.

In one aspect of the invention $R^{19}$ is hydrogen, hydroxycarbonyl, $C_{1-4}$alkoxycarbonyl, aminocarbonyl or $C_{1-4}$alkanoylamino. In another aspect $R^{19}$ is hydrogen, hydroxycarbonyl, ethoxycarbonyl, aminocarbonyl and acetylamino. In yet another aspect $R^{19}$ is hydrogen.

In one aspect of the invention $R^{10}$, $R^{15}$, $R^{16}$, $R^{17}$, $R^{18}$, $R^{20}$ and $R^{21}$ are each independently hydrogen, methyl or ethyl.

Preferred values of $R^{1'}$, $R^{2'}$ and $R^{3'}$ for a compound of formula (IA) are as follows and preferred values of X, $X^1$, $X^2$, $X^3$, $R^4$, $R^5$ and $R^{19}$ for a compound of formula (IA) are as defined for a compound of formula (I). Such values may be used where appropriate with any of the definitions, claims or embodiments defined herein.

In one aspect of the invention $R^1$ is hydrogen, halo or —$OR^{11'}$. In a further aspect $R^{1'}$ is hydrogen or —$OR^{11'}$. In another aspect $R^{1'}$ is hydrogen, fluoro, hydroxy, phosphonooxy, methoxy, isopropoxy, pyrrolidin-2-ylmethoxy, 1-(2-hydroxyethyl)pyrrolidin-2-ylmethoxy, -(2-phosphonooxyethyl)pyrrolidin-2-ylmethoxy, 1-glycoloylpyrrolidin-2-ylmethoxy, 1-phosponooxymethylcarbonylpyrrolidin-2-ylmethoxy, 1-(N,N-dimethylglycyl)pyrrolidin-2-ylmethoxy, 2-(5-hydroxymethyl-2-oxo-pyrrolidin-1-yl)ethoxy, 2-(5-phosphonooxymethyl-2-oxo-pyrrolidin-1-yl)ethoxy, 3-(5-hydroxymethyl-2-oxo-pyrrolidin-1-yl)propoxy, 3-(5-phosphonooxymethyl-2-oxo-pyrrolidin-1-yl)propoxy, 2-(6-hydroxymethyl-2-oxo-piperazin-1-yl)ethoxy, 2-(6-phosphonooxymethyl-2-oxo-piperazin-1-yl)ethoxy, 3-(6-hydroxymethyl-2-oxo-piperazin-1-yl)propoxy, 3-(6-phosphonooxymethyl-2-oxo-piperazin-1-yl)propoxy, 2-(5-hydroxymethyl-3-oxo-piperazin-1-yl)ethoxy, 2-(5-phosphonooxymethyl-3-oxo-piperazin-1-yl)ethoxy, 3-(5-hydroxymethyl-3-oxo-piperazin-1-yl)propoxy or 3-(5-phosphonooxymethyl-3-oxo-piperazin-1-yl)propoxy. In yet a further aspect $R^{1'}$ is hydrogen, fluoro, methoxy, isopropoxy, pyrrolidin-2-ylmethoxy, 1-(2-hydroxyethyl)pyrrolidin-2-ylmethoxy, 1-(2-phosphonooxyethyl)pyrrolidin-2-ylmethoxy, 1-glycoloylpyrrolidin-2-ylmethoxy, 1-phosponooxymethylcarbonylpyrrolidin-2-ylmethoxy or 1-(N,N-dimethylglycyl) pyrrolidin-2-ylmethoxy. In another aspect $R^{1'}$ is hydrogen.

In one aspect of the invention $R^{11'}$ is hydrogen, phosponooxy or a group selected from $C_{1-6}$alkyl, heterocyclyl, heterocyclyl$C_{1-4}$alkyl, heterocyclyl$C_{2-4}$alkenyl and heterocyclyl$C_{2-4}$alkynyl which group is optionally substituted by a substituent selected from hydroxy, phosphonooxy, $C_{1-4}$alkoxy, hydroxy$C_{1-4}$alkyl, phosphonooxy$C_{1-4}$alkyl, amino, $C_{1-4}$alkylamino, bis($C_{1-4}$alkyl)amino, hydroxycarbonyl, $C_{1-4}$alkoxycarbonyl, hydroxy$C_{1-4}$alkylcarbonyl, phosphonooxy$C_{1-4}$alkylcarbonyl, $C_{1-4}$alkoxy$C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$alkylcarbonyl. In a further aspect $R^{11'}$ is hydrogen, phosphonooxy or a group selected from $C_{1-6}$alkyl, heterocyclyl and heterocyclyl$C_{1-4}$ alkyl, which group is optionally substituted by a substituent selected from hydroxy, phosphonooxy, $C_{1-4}$alkoxy, hydroxy$C_{1-4}$alkyl, phosphonooxy$C_{1-4}$alkyl, hydroxy$C_{1-4}$alkylcarbonyl, phosphonooxy$C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$alkylcarbonyl. In another aspect $R^{11'}$ is hydrogen, methyl, ethyl, propyl, isopropyl or a group selected from pyrrolidinylmethyl, pyrrolidinylethyl, pyrrolidinylpropyl, 2-oxopyrrolidin-1-ylmethyl, 2-oxopyrrolidin-1-ylethyl, 2-oxopyrrolidin-1-ylpropyl, 3-oxopyrrolidin-1-ylmethyl, 3-oxopyrrolidin-1-ylethyl, 3-oxopyrrolidin-1-ylpropyl, piperidinylmethyl, piperidinylethyl, piperidinylpropyl, 2-oxopiperidinylmethyl, 2-oxopiperidinylethyl, 2-oxopiperidinylpropyl, 3-oxopiperidinylmethyl, 3-oxopiperidinylethyl, 3-oxopiperidinylpropyl, 4-oxopiperidinylmethyl, 4-oxopiperidinylethyl, 4-oxopiperidinylpropyl, piperazinylmethyl, piperazinylethyl, piperazinylpropyl, 2-oxopiperazinylmethyl, 2-oxopiperazinylethyl, 2-oxopiperazinylpropyl, 3-oxopiperazinylmethyl, 3-oxopiperazinylethyl and 3-oxopiperazinylpropyl, which group is optionally substituted by hydroxy, phosphonooxy, hydroxymethyl, phosphonooxymethyl, 2-hydroxyethyl, 2-phosphonooxyethyl, tert-butoxycarbonyl, glycoloyl, phosphonooxymethylcarbonyl, glycyl, N-methylglycyl or N,N-dimethylglycyl. In a further aspect $R^{11}$ is hydrogen, methyl, ethyl, propyl, isopropyl, pyrrolidinylmethyl which pyrrolidinylmethyl is optionally substituted by 2-hydroxyethyl, 2-phosphonooxyethyl, glycoloyl, phosphonooxymethylcarbonyl or N,N-dimethylglycyl or $R^{11}$ is 2-(2-oxopyrrolidin-1-yl)ethyl, 3-(2-oxopyrrolidin-1-yl) propyl, 2-(2-oxopiperazin-1-yl)ethyl, 3-(2-oxopiperazin-1-yl)propyl, 2-(3-oxopiperazin-1-yl)ethyl or 3-(3-oxopiperazin-1-yl)propyl optionally substituted by hydroxymethyl, phosphonooxymethyl, 2-hydroxyethyl or 2-phosphonooxyethyl. In another aspect $R^{11'}$ is hydrogen, methyl, ethyl, propyl, isopropyl or a group selected from pyrrolidinylmethyl, pyrrolidinylethyl, piperidinylmethyl and piperidinylethyl which group is optionally substituted by hydroxy, phosphonooxy, hydroxymethyl, phosphonooxymethyl, 2-hydroxyethyl, 2-phosphonooxyethyl, tert-butoxycarbonyl, glycoloyl, phosphonooxymethylcarbonyl, glycyl, N-methylglycyl or N,N-dimethylglycyl. In a further aspect $R^{11'}$ is hydrogen, methyl, ethyl, propyl, isopropyl or pyrrolidinylmethyl which pyrrolidinylmethyl is optionally substituted by 2-hydroxyethyl, 2-phosphonooxyethyl, glycoloyl, phosphonooxymethylcarbonyl or N,N-dimethylglycyl. In yet another aspect $R^{11'}$ is hydrogen, $C_{1-4}$alkyl or $C_{1-4}$alkoxy. In a further aspect $R^{11'}$ is hydrogen.

In one aspect of the invention $R^{2'}$ is hydrogen, halo, —$OR^{12'}$ or —OC(O)$R^{12'}$. In a further aspect $R^{2'}$ is hydrogen, fluoro, hydroxy, phosphonooxy, methoxy, 2-methoxyethoxy, benzoyloxy, 2-morpholin-4-ylethoxy, 3-morpholin-4-ylpropoxy or 1-methylpyrrolidin-2-yloxy. In yet a further aspect $R^{2'}$ is hydrogen, methoxy, phosphonooxy or fluoro. In another aspect $R^{2'}$ is hydrogen or methoxy. In a further aspect $R^{2'}$ is hydrogen. In yet a further aspect $R^{2'}$ is methoxy.

In one aspect of the invention $R^{12'}$ is hydrogen, phosphonooxy or a group selected from $C_{1-6}$alkyl, $C_{2-6}$alkenyl, $C_{2-6}$alkynyl, $C_{3-6}$cycloalkyl, aryl, aryl$C_{1-4}$alkyl, heterocyclyl and heterocyclyl$C_{1-4}$alkyl, which group is optionally substituted by 1, 2 or 3 substituents selected from halo, hydroxy, phosphonooxy, $C_{1-4}$alkyl, $C_{1-4}$alkoxy, —$NR^{15'}R^{16'}$, —NHC (O)$NR^{15'}R^{16'}$, —C(O)$R^{15'}$ and —C(O)$OR^{15'}$. In a further aspect $R^{12'}$ is hydrogen, phosphonooxy or a group selected from $C_{1-4}$alkyl, aryl, heterocyclyl and heterocyclyl$C_{1-4}$alkyl which group is optionally substituted by a substituent selected from $C_{1-4}$alkyl and $C_{1-4}$alkoxy. In yet another aspect $R^{12'}$ is hydrogen or group selected from methyl, 2-morpholinylethyl, 3-morpholinylpropoxy, 2-methoxyethyl and pyrrolidinyl which group is optionally substituted by methyl. In another aspect $R^{12'}$ is hydrogen or $C_{1-4}$alkyl. In another aspect of the invention $R^{12'}$ is hydrogen. In a further aspect of the invention $R^{12'}$ is methyl.

In one aspect of the invention $R^{3'}$ is hydrogen, phosponooxy or —$X^3R^{13'}$.

In another aspect $R^{3'}$ is hydrogen, hydroxy, phosphonooxy, methoxy, 3-chloropropoxy, 2-chloroethoxy, 2,2-dimethoxyethoxy, 3-[2-(hydroxymethyl)pyrrolidin-1-yl]propoxy, 3-[2-(phosphonooxymethyl)pyrrolidin-1-yl]propoxy, 3-[(2-hydroxyethyl)(isobutyl)amino]propoxy, 3-[2-phosphonooxyethyl)(isobutyl)amino]propoxy, 3-[(2-hydroxyethyl)(propyl)amino]propoxy, 3-[(2-phosphonooxyethyl)(propyl)amino]propoxy, 3-piperidin-1-ylpropoxy, 3-pyrrolidin-1-ylpropoxy, 3-(diethylamino)propoxy, 3-piperazin-1-ylpropoxy, 3-[(2-hydroxyethyl)(methyl)amino]propoxy, 3-[(2-phosphonooxyethyl)(methyl)amino]propoxy, 3-(cyclopropylamino)propoxy, 3-{[2-(dimethylamino)ethyl](methyl)amino}propoxy, 3-(4-methylpiperazin-1-yl)propoxy, 3-(4-hydroxypiperidin-1-yl)propoxy, 3-(4-phosphonooxypiperidin-1-yl)propoxy, 3-[bis(2-hydroxyethyl)amino]propoxy, 3-[(2-hydroxyethyl)(2-phosphonooxyethyl)amino]propoxy, 3-[ethyl(methyl)amino]propoxy, 3-[ethyl(2-hydroxyethyl)amino]propoxy, 3-[ethyl(2-phosphonooxyethyl)amino]propoxy, 3-{[2-(dimethylamino)ethyl](ethyl)amino}propoxy, 3-[2-(2-hydroxyethyl)piperidin-1-yl]propoxy, 3-[2-(2-phosphonooxyethyl)piperidin-1-yl]propoxy, 3-[4-(2-hydroxyethyl)piperazin-1-yl]propoxy, 3-[4-(2-phosponooxyethyl)piperazin-1-yl]propoxy, 3-[(cyclopropylmethyl)amino]propoxy, 3-[4-(2-hydroxyethyl)piperidin-1-yl]propoxy, 3-[4-(2-phosphonooxyethyl)piperidin-1-yl]propoxy, 3-[methyl(prop-2-yn-1-yl)amino]propoxy, 3-[allyl(methyl)amino]propoxy, 3-[isobutyl(methyl)amino]propoxy, 3-(3-hydroxypiperidin-1-yl)propoxy, 3-(3-phosphonooxypiperidin-1-yl)propoxy, 3-[4-(hydroxymethyl)piperidin-1-yl]propoxy, 3-[4-(phosphonooxymethyl)piperidin-1-yl]propoxy, 3-[methyl(propyl)amino]propoxy, 3-[cyclopropylmethyl(propyl)amino]propoxy, 3-{[2-(diethylamino)ethyl](methyl)amino}propoxy, 3-{[2-(diethylamino)ethyl](ethyl)amino}propoxy, 3-(4-methyl-1,4-diazepan-1-yl)propoxy, 3-[(2-hydroxyethyl)(isopropyl)amino]propoxy, 3-[(2-phosphonooxyethyl)(isopropyl)amino]propoxy, 3-[cyclopropyl(2-hydroxyethyl)amino]propoxy, 3-[cyclopropyl(2-phosphonooxyethyl)amino]propoxy, 3-[(2-hydroxyethyl)(2-methoxyethyl)amino]propoxy, 3-[(2-phosphonooxyethyl)(2-methoxyethyl)amino]propoxy, 3-[cyclobutyl(2-hydroxyethyl)amino]propoxy, 3-[cyclobutyl(2-phosphonooxyethyl)amino]propoxy, 3-[cyclopropylmethyl(2-hydroxyethyl)amino]propoxy, 3-[cyclopropylmethyl(2-phosphonooxyethyl)amino]propoxy, 3-[cyclobutylmethyl(2-hydroxyethyl)amino]propoxy, 3-[cyclobutylmethyl(2-phosphonooxyethyl)amino]propoxy, 3-[(2-hydroxyethyl)prop-2-yn-1-ylamino]propoxy, 3-[(2-phosphonooxyethyl)prop-2-yn-1-ylamino]propoxy, 3-[allyl(2-hydroxyethyl)amino]propoxy, 3-[allyl(2-phosphonooxyethyl)amino]propoxy, 3-[(2,2-dimethylpropyl(2-hydroxyethyl)amino]propoxy, 3-[(2,2-dimethylpropyl(2-phosphonooxyethyl)amino]propoxy, 3-[(2-hydroxyethyl)(3,3,3-trifluoropropyl)amino]propoxy, 3-[(2-phosphonooxyethyl)(3,3,3-trifluoropropyl)amino]propoxy, 3-azetidin-1-ylpropoxy, 3-(dimethylamino)propoxy, 2-[(2-hydroxymethyl)pyrrolidin-1-yl]ethoxy, 2-[(2-phosphonooxymethyl)pyrrolidin-1-yl]ethoxy, 2-{4-[2-(2-hydroxyethoxy)ethyl]piperazin-1-yl}ethoxy, 2-{4-[2-(2-phosphonooxyethoxy)ethyl]piperazin-1-yl}ethoxy, 2-[2-(2-hydroxyethyl)piperidin-1-yl]ethoxy, 2-[2-(2-phosphonooxyethyl)piperidin-1-yl]ethoxy, 2-[2-(hydroxymethyl)piperidin-1-yl]ethoxy, 2-[2-(phosphonooxymethyl)piperidin-1-yl]ethoxy, 2-[(2-hydroxy-1,1-dimethylethyl)amino]ethoxy, 2-[(2-phosphonooxy-1,1-dimethylethyl)amino]ethoxy, 2-[4-(2-hydroxyethyl)piperazin-1-yl]ethoxy, 2-[4-(2-phosphonooxyethyl)piperazin-1-yl]ethoxy, 2-[(4-hydroxycyclohexyl)amino]ethoxy, 2-[(4-phosphonooxycyclohexyl)amino]ethoxy, 2-[3-(hydroxymethyl)piperidin-1-yl]ethoxy, 2-[3-(phosphonooxymethyl)piperidin-1-yl]ethoxy, 2-{[1-(hydroxymethyl)cyclopentyl]amino)}ethoxy, 2-{[1-{phosphonooxymethyl)cyclopentyl]amino}ethoxy, 2-[4-(3-hydroxypropyl)piperazin-1-yl]ethoxy, 2-[4-(3-phosphonooxypropyl)piperazin-1-yl]ethoxy, 2-[cyclohexyl(2-hydroxyethyl)amino]ethoxy, 2-[cyclohexyl(2-phosphonooxyethyl)amino]ethoxy, 2-[(2-hydroxyethyl)(propyl)amino]ethoxy, 2-[(2-phosphonooxyethyl)(propyl)amino]ethoxy, 2-[(3-hydroxy-2,2-dimethylpropyl)amino]ethoxy, 2-[(3-phosphonooxy-2,2-dimethylpropyl)amino]ethoxy, 2-(tetrahydro-2H-pyran-4-ylamino)ethoxy, 2-[cyclobutyl(2-hydroxyethyl)amino]ethoxy, 2-[cyclobutyl(2-phosphonooxyethyl)amino]ethoxy, 2-[(2-hydroxyethyl)(tetrahydro-2H-pyranyl)amino]ethoxy, 2-[(2-phosphonooxyethyl)(tetrahydro-2H-pyran-4-yl)amino]ethoxy, 3-[cyclopentyl(2-hydroxyethyl)amino]propoxy, 3-[cyclopentyl(2-phosphonooxyethyl)amino]propoxy, 3-[(3-hydroxy-1,1-dimethylpropyl)amino]propoxy, 3-[(3-phosphonooxy-1,1-dimethylpropyl)amino]propoxy, 3-[(2-cyanoethyl)(2-hydroxyethyl)amino]propoxy, 3-[(2-cyanoethyl)(2-phosphonooxyethyl)amino]propoxy, 3-morpholin-4-ylpropoxy, 3-[(3-hydroxy-2,2-dimethylpropyl)amino]propoxy, 3-[(3-phosphonooxy-2,2-dimethylpropyl)amino]propoxy, 3-[(3-hydroxypropyl)amino]propoxy, 3-[(3-phosphonooxypropyl)amino]propoxy, 3-[(3-hydroxypropyl)(propyl)amino]propoxy, 3-[(3-phosphonooxypropyl)(propyl)amino]propoxy, 3-[(3-hydroxypropyl)(ethyl)amino]propoxy, 3-[(3-phosphomooxypropyl)(ethyl)amino]propoxy, 3-[4-(2-hydroxyethyl)-3-oxopiperazin-1-yl]propoxy, 3-[4-(2-phosphonooxyethyl)-3-oxopiperazin-1-yl]propoxy, 3-(propylamino)propoxy, 3-[glycoloyl(propyl)amino]propoxy, 3-[phosphonooxymethylcarbonyl(propyl)amino]propoxy, 3-(4-glycoloylpiperazin-1-yl)propoxy, 3-(4-phosphonooxymethylcarbonylpiperazin-1-yl)propoxy, 3-{[2-(hydroxymethyl)cyclohexyl]amino}propoxy, 3-{[2-(phosphonooxymethyl)cyclohexyl]amino}propoxy, 3-[{1α,5α,6α)-6-(hydroxymethyl)-3-azabicyclo[3.1.0]hex-3-yl]propoxy, 3-[{1α,5α,6α)-6-(phosphonooxymethyl)-3-azabicyclo[3.1.0]hex-3-yl]propoxy, 3-{[2-hydroxypropyl]amino}propoxy, 3-{[2-phosphonooxypropyl]amino}propoxy, 3-{[2-hydroxy-1-methylethyl]amino}propoxy, 3-{[2-phosphonooxy-1-methylethyl]amino}propoxy, 3-[(2-hydroxy-1,1-dimethylethyl)amino]propoxy, 3-[(2-phosphonooxy-1,1-dimethylethyl)amino]propoxy, 3-[(2,3-dihydroxypropyl)amino]propoxy, 3-[(2-phosphonoxy-3-hydroxypropyl)amino]propoxy, 3-[(2-hydroxy-3-phosphonooxypropyl)amino]propoxy, 3-{[2-(2-hydroxyethoxy)ethyl]amino}propoxy, 3-{[2-(2-phosphonooxyethoxy)ethyl]amino}propoxy, 3-(4-acetylpiperazin-1-yl)propoxy, 3-[(tetrahydrofuran-2-ylmethyl)amino]propoxy, 3-(allylamino)propoxy, 3-{[1-

(hydroxymethyl)-2-methylpropyl]amino}propoxy, 3-{[1-(phosphonooxymethyl)-2-methylpropyl]amino}propoxy, 3-{[(5-methylisoxazol-3-yl)methyl]amino}propoxy, 3-(tetrahydro-2H-pyran-4-ylamino)propoxy, 3-[3-(hydroxymethyl)pyrrolidin-1-yl]propoxy, 3-[3-(phosphonooxymethyl) pyrrolidin-1-yl]propoxy, 3-aminopropoxy, 3-[-4-hydroxy-2-(hydroxymethyl)pyrrolidin-1-yl]propoxy, 3-[-4-phosphonooxy-2-(hydroxymethyl)pyrrolidin-1-yl]propoxy, 3-[-4-hydroxy-2-(phosphonooxymethyl)pyrrolidin-1-yl] propoxy, 2-(cyclopropylamino)ethoxy, 2-(cyclobutylamino) ethoxy, 2-(cyclopentylamino)ethoxy, 2-[{2-hydroxyethyl) (tetrahydro-2H-pyran-4-yl)amino]ethoxy, 2-[{2-phosphonooxyethyl)(tetrahydro-2H-pyran-4-yl)amino] ethoxy, 2-[cyclopentyl(2-hydroxyethyl)amino]ethoxy, 2-[cyclopentyl(2-phosphonooxyethyl)amino]ethoxy, 2-[cyclopropyl(2-hydroxyethyl)amino]ethoxy, 2-[cyclopropyl(2-phosphonooxyethyl)amino]ethoxy, 2-[cyclopentyl(3-hydroxypropyl)amino]ethoxy, 2-[cyclopentyl(3-phosphonooxypropyl)amino]ethoxy, 2-[cyclopentyl (glycoloyl)amino]ethoxy, 2-[cyclopentyl (phosphonooxymethylcarbonyl)amino]ethoxy, 2-[3-(hydroxymethyl)-4-methylpiperazin-1-yl]ethoxy, 2-[3-(phosphonooxymethyl)-4-methylpiperazin-1-yl]ethoxy, 2-[2-(hydroxymethyl)-4-methylpiperazin-1-yl]ethoxy, 2-[2-(phosphonooxymethyl)-4-methylpiperazin-1-yl]ethoxy, 2-[4-(hydroxymethyl)piperidin-1-yl]ethoxy, 2-[4-(phosphonooxymethyl)piperidin-1-yl]ethoxy, 2-[4-(2-hydroxyethyl) piperidin-1-yl]ethoxy, 2-[4-(2-phosphonooxyethyl)piperidin-1-yl]ethoxy, 2-[(2-hydroxyethyl)amino]ethoxy, 2-[(2-phosphonooxyethyl)amino]ethoxy, 2-{[2-(hydroxymethyl) cyclohexyl]amino}ethoxy, 2-{[2-(phosphonooxymethyl) cyclohexyl]amino}ethoxy, 3-[(2-hydroxyethyl)amino] propoxy, 3-[(2-phosphonooxyethyl)amino]propoxy, 3-[(2-hydroxyethyl)(tetrahydrofuran-3-yl)amino]propoxy, 3-[(2-phosphonooxyethyl)(tetrahydrofuran-3-yl)amino]propoxy, pyrrolidin-2-ylmethoxy, [1-(2-hydroxyethyl)pyrrolidin-2-yl]methoxy, [1-(2-phosphonooxyethyl)pyrrolidin-2-yl] methoxy, [1-glycoloylpyrrolidin-2-yl]methoxy, [1-phosphonooxymethylcarbonylpyrrolidin-2-yl]methoxy, pyrrolidin-3-ylmethoxy, [1-(2-hydroxyethyl)pyrrolidin-3-yl]methoxy, [1-(2-phosphonooxyethyl)pyrrolidin-3-yl]methoxy, (1-glycoloylpyrrolidin-3-yl)methoxy, (1-phoshonooxymethylcarbonylpyrrolidin-3-yl)methoxy, 3-[(2-hydroxyethyl)(2-methoxyethyl)amino]propoxy, 3-[(2-phosphonooxyethyl)(2-methoxyethyl)amino]propoxy, (2-hydroxyethyl)amino] propoxy, (2-phosphonooxyethyl)amino]propoxy, 2-(5-hydroxymethyl-2-oxo-pyrrolidin-1-yl)ethoxy, 2-(5-phosphonooxymethyl-2-oxo-pyrrolidin-1-yl)ethoxy, 3-(5-hydroxymethyl-2-oxo-pyrrolidin-1-yl)propoxy, 3-(5-phosphonooxymethyl-2-oxo-pyrrolidin-1-yl)propoxy, 2-(6-hydroxymethyl-2-oxo-piperazin-1-yl)ethoxy, 2-(6-phosphonooxymethyl-2-oxo-piperazin-1-yl)ethoxy, 3-(6-hydroxymethyl-2-oxo-piperazin-1-yl)propoxy, 3-(6-phosphonooxymethyl-2-oxo-piperazin-1-yl)propoxy, 2-(5-hydroxymethyl-3-oxo-piperazin-1-yl)ethoxy, 2-(5-phosphonooxymethyl-3-oxo-piperazin-1-yl)ethoxy, 3-(5-hydroxymethyl-3-oxo-piperazin-1-yl)propoxy, 3-(5-phosphonooxymethyl-3-oxo-piperazin-1-yl)propoxy, 3-(3-hydroxymethyl-4-methylpiperazin-1yl)propoxy, 3-(3-phosphonooxymethyl-4-methylpiperazin-1yl)propoxy, 3-(2-hydroxymethylmorpholin-4-yl)propoxy, 3-(2-phosphonooxymorpholin-4-yl)propoxy, 3-(glycoloylamino) propoxy, 3-(phosphonooxymethylcarbonylamino)propoxy, 3-(4-hydroxymethylpiperazin-1-yl)propoxy or 3-(4-phosphonooxymethylpiperazin-1-yl)propoxy.

In one aspect of the invention $R^{13'}$ is hydrogen or a group selected from $C_{1-6}$alkyl, aryl, aryl$C_{1-4}$alkyl, heterocyclyl and heterocyclyl$C_{1-4}$alkyl, which group is optionally substituted by 1 or 2 substituents independently selected from —$NR^{7'}R^{8'}$, —C(O)$NR^{7'}R^{8'}$, halo, hydroxy, phosphonooxy, $C_{1-4}$alkyl, $C_{1-4}$alkoxy, hydroxy$C_{1-4}$alkyl, phosphonooxy$C_{1-4}$alkyl, hydroxy$C_{1-4}$alkylcarbonyl, phosphonooxy$C_{1-4}$alkylcarbonyl and $C_{1-4}$alkylcarbonyl. In another aspect $R^{13'}$ is hydrogen, methyl, ethyl or propyl, which methyl, ethyl or propyl are optionally substituted by —$NR^{7'}R^{8'}$, —C(O)$NR^{7'}R^{8'}$, heterocyclyl or 1 or 2 halo, hydroxy, phosphonooxy or $C_{1-4}$alkoxy substituents and which heterocyclyl is optionally substituted by hydroxy, phosphonooxy, $C_{1-4}$alkyl, hydroxy$C_{1-4}$alkyl, phosphonooxy$C_{1-4}$alkyl, hydroxy$C_{1-4}$alkylcarbonyl or phosphonooxy$C_{1-4}$alkylcarbonyl. In a further aspect $R^{13'}$ is methyl, ethyl or propyl substituted by chloro, 1 or 2 hydroxy, 1 phosphonooxy, 1 or 2 methoxy, —$NR^{7'}R^{8'}$ or a heterocyclyl selected from pyrrolidinyl and piperidinyl which heterocyclyl is optionally substituted by hydroxy, phosphonooxy, methyl, hydroxymethyl, phosphonooxymethyl, 2-hydroxyethyl, 2-phosphonooxyethyl, glycoloyl or phosphonooxymethylcarbonyl. In a further aspect of the invention $R^{13'}$ is ethyl or propyl, both of which are substituted by —$NR^{7'}R^{8'}$, heterocyclyl or halo. In yet a further aspect of the invention $R^{13'}$ is propyl substituted by chloro, —$NR^{7'}R^{8'}$ or a heterocyclyl selected from pyrrolidinyl, piperidinyl, piperazinyl, diazepanyl and azetidinyl where the heterocyclyl is optionally substituted by hydroxy, phosphonooxy, methyl, hydroxymethyl, phosphonooxymethyl, 2-hydroxyethyl or 2-phosphonooxyethyl. In another aspect $R^{13'}$ is ethyl or propyl substituted by chloro or —$NR^{7'}R^{8'}$. In yet another aspect $R^{13'}$ is ethyl or propyl substituted by —$NR^{7'}R^{8'}$. In a further aspect $R^{13'}$ is propyl substituted by —$NR^{7'}R^{8'}$.

In one aspect of the invention $R^{7'}$ and $R^{8'}$ are independently selected from hydrogen, heterocyclyl, heterocyclyl$C_{1-4}$alkyl, $C_{1-4}$alkylheterocyclyl$C_{1-4}$alkyl, $C_{1-6}$alkyl, hydroxy$C_{1-6}$ alkyl, phosphonooxy$C_{1-6}$alkyl, $C_{1-4}$alkoxy$C_{1-4}$alkyl, $C_{3-6}$cycloalkyl, $C_{3-6}$cycloalkyl$C_{1-4}$alkyl, hydroxy$C_{3-6}$cycloalkyl, phosphonooxy$C_{3-6}$cycloalkyl, hydroxy$C_{1-4}$alkyl$C_{3-6}$cycloalkyl, phosphonooxy$C_{1-4}$alkyl$C_{3-6}$cycloalkyl, halo$C_{1-6}$ alkyl, $C_{2-4}$alkenyl, $C_{2-4}$alkynyl, cyano$C_{1-4}$alkyl, amino$C_{1-4}$ alkyl, bis($C_{1-4}$alkyl)amino$C_{1-4}$alkyl, hydroxy$C_{1-4}$alkoxy$C_{1-4}$ alkyl, phosphonooxy$C_{1-4}$alkoxy$C_{1-4}$alkyl, hydroxy$C_{1-4}$alkylcarbonyl and phosphonooxy$C_{1-4}$alkylcarbonyl; or $R^{7'}$ and $R^{8'}$ together with the nitrogen to which they are attached form a heterocyclic ring selected from azetidine, pyrrolidine, piperidine, morpholine, piperazine, diazepane, 1,4-diazepane and azabicyclo[3.1.0]hexane which ring is optionally substituted on carbon or nitrogen by 1 or 2 substituents independently selected from $C_{1-4}$alkyl, hydroxy, phosphonooxy, hydroxy$C_{1-4}$alkyl, phosphonooxy$C_{1-4}$alkyl, $C_{1-4}$alkoxy$C_{1-4}$ alkyl, hydroxy$C_{1-4}$alkoxy$C_{1-4}$alkyl, phosphonooxy$C_{1-4}$ alkoxy$C_{1-4}$alkyl, $C_{1-4}$alkylcarbonyl, hydroxy$C_{1-4}$alkylcarbonyl and phosphonooxy$C_{1-4}$alkylcarbonyl, and where a ring —$CH_2$— is optionally replaced with —C(O)—. In another aspect $R^{7'}$ and $R^{8'}$ are independently selected from hydrogen, heterocyclyl, $C_{1-6}$alkyl, hydroxy$C_{1-6}$alkyl, phosphonooxy$C_{1-6}$alkyl, hydroxy$C_{1-4}$alkyl$C_{3-6}$cycloalkyl, phosphonooxy$C_{1-4}$alkyl$C_{3-6}$cycloalkyl, $C_{1-4}$alkoxy$C_{1-4}$alkyl, $C_{3-6}$cycloalkyl, $C_{3-6}$cycloalkyl$C_{1-4}$alkyl, halo$C_{1-6}$alkyl, $C_{2-6}$alkenyl, $C_{2-6}$alkynyl, cyano$C_{1-4}$alkyl, amino$C_{1-6}$alkyl, $C_{1-4}$alkylamino$C_{1-6}$alkyl and bis($C_{1-4}$alkyl)amino$C_{1-6}$alkyl; or $R^{7'}$ and $R^{8'}$ together with the nitrogen to which they are attached form a heterocyclic ring which ring comprises 4 to 7 ring atoms of which one is nitrogen and of which another is optionally NH and which ring is optionally substituted on carbon or nitrogen by a group selected from $C_{1-4}$alkyl, hydroxy, phosphonooxy, hydroxy$C_{1-4}$alkyl, phosphonooxy$C_{1-4}$alkyl, hydroxy$C_{1-4}$alkoxy$C_{1-4}$alkyl, and phosphonooxy$C_{1-4}$alkoxy$C_{1-4}$alkyl, and where a ring —$CH_2$— is optionally replaced with —C(O). In a further aspect $R^{7'}$ and $R^{8'}$ are independently selected from hydrogen, methyl, ethyl, propyl, isopropyl, butyl, isobutyl, tert-butyl, pentyl, neopentyl, hydroxymethyl, phosphonooxymethyl, 2-hydroxyethyl, 2-phosphonooxyethyl, 2-hydroxy-1,1-dimethylethyl, 2-phosphonooxy-1,1-dimethylethyl, 3-hydroxypropyl, 3-phosphonooxypropyl, 3-hydroxy-2,2-dimethylpropyl, 3-phosphonooxy-2,2-dimethylpropyl, 3-hydroxy-1,1-dimethylpropyl, 3-phosphonooxy-1,1-dimethylpropyl, 2-hydroxypropyl, 2-phosphonooxypropyl, 2,3-dihydroxypropyl, 2-hydroxy-3-phosphonooxypropyl, 2-phosphonooxy-3-hydroxypropyl, 1-hydroxymethyl-2-methylpropyl, 1-phosphonooxymethyl-2-methylpropyl, cyclopropyl, cyclobutyl, cyclopentyl, cyclohexyl, 4-hydroxycyclohexyl, 4-phosphonooxycyclohexyl, 1-hydroxymethylcyclopentyl, 1-phosphonooxymethylcyclopentyl, 2-hydroxymethylcyclohexyl, 2-phosphonooxymethylcyclohexyl, cyclopropylmethyl, cyclobutylmethyl, tetrahydro-2H-pyran-4-yl, tetrahydrofuran-3-yl, tetrahydrofuran-2-ylmethyl, 5-methylisoxazol-3-yl, 2-cyanoethyl, allyl, prop-2-ynyl, 2-methoxyethyl, methoxymethyl, 3,3,3-trifluoropropyl, 2-(2-hydroxyethoxy)ethyl, 2-(2-phosphonooxyethoxy)ethyl, 2-(dimethylamino)ethyl, 2-(diethylamino)ethyl, 3-aminopropyl, 3-(propylamino)propyl, glycoloyl and phosphonooxymethylcarbonyl; or $R^{7'}$ and $R^{8'}$ together with the nitrogen to which they are attached form a heterocyclic ring selected from azetidine, pyrrolidine, piperidine, morpholine, piperazine, diazepane or 1,4-diazepane which ring is optionally substituted by 1 or 2 substituents independently selected from methyl, hydroxy, phosphonooxy, hydroxymethyl, phosphonooxymethyl, 2-hydroxyethyl, 2-phosphonooxyethyl, 3-hydroxypropyl, 3-phosphonooxypropyl, 2-(2-hydroxyethoxy)ethyl, 2-(2-phosphonooxyethyl)ethyl, glycoloyl, phosphonooxymethylcarbonyl, acetyl, methoxymethyl and oxo. In a further aspect $R^{7'}$ and $R^{8'}$ are independently selected from hydrogen, methyl, ethyl, propyl, isopropyl, butyl, isobutyl, tert-butyl, pentyl, neopentyl, hydroxymethyl, phosphonooxymethyl, 2-hydroxyethyl, 2-phosphonooxyethyl, 2-hydroxy-1,1-dimethylethyl, 2-phosphonooxy-1,1-dimethylethyl, 3-hydroxypropyl, 3-phosphonooxypropyl, 3-hydroxy-2,2-dimethylpropyl, 3-phosphonooxy-2,2-dimethylpropyl, 3-hydroxy-1,1-dimethylpropyl, 3-phosphonooxy-1,1-dimethylpropyl, 2-hydroxypropyl, 2-phosphonooxypropyl, 2,3-dihydroxypropyl, 2-hydroxy-3-phosphonooxypropyl, 2-phosphonooxy-3-hydroxypropyl, 1-hydroxymethyl-2-methylpropyl, 1-phosphonooxymethyl-2-methylpropyl, cyclopropyl, cyclobutyl, cyclopentyl, cyclohexyl, 4-hydroxycyclohexyl, 4-phosphonooxycyclohexyl, 1-hydroxymethylcyclopentyl, 1-phosphonooxymethylcyclopentyl, 2-hydroxymethylcyclohexyl, 2-phosphonooxymethylcyclohexyl, cyclopropylmethyl, cyclobutylmethyl, tetrahydro-2H-pyran-4-yl, tetrahydrofuran-3-yl, tetrahydrofuran-2-ylmethyl, 5-methylisoxazol-3-yl, 2-cyanoethyl, allyl, prop-2-ynyl, 2-methoxyethyl, methoxymethyl, 3,3,3-trifluoropropyl, 2-(2-hydroxyethoxy)ethyl, 2-(2-phosphonooxyethoxy)ethyl, 2-(dimethylamino)ethyl, 2-(diethylamino)ethyl, 3-aminopropyl, 3-(propylamino)propyl, glycoloyl and phosphonooxymethylcarbonyl. In yet another aspect $R^{7'}$ and $R^{8'}$ together with the nitrogen to which they are attached form 4-methylpiperazine, 4-methyl-1,4-diazepane, 4-hydroxypiperidine, 4-phosphonooxypiperidine, 3-hydroxypiperidine, 3-phosphonooxypiperidine, 2-hydroxymethylpyrrolidine, 2-phosphonooxymethylpyrrolidine, 3-hydroxymethylpyrrolidine, 3-phosphonooxymethylpyrrolidine, 2-hydroxymethylpiperidine, 2-phosphonooxymethylpiperidine, 3-hydroxymethylpiperidine, 3-phosphonooxymethylpiperidine, 4-hydroxymethylpiperidine, 4-phosphonooxymethylpiperidine, 2-(2-hydroxyethyl)piperidine, 2-(2-phosphonooxyethyl)piperidine, 4-(2-hydroxyethyl)piperidine, 4-(2-phosphonooxyethyl)piperidine, 4-(2-hydroxyethyl)piperazine, 4-(2-phosphonooxyethyl)piperazine, 4-(3-hydroxypropyl)piperazine, 4-(3-phosphonooxypropyl)piperazine, 4-[2-(2-hydroxyethoxy)ethyl]piperazine, 4-[2-(2-phosphonooxyethoxy)ethyl]piperazine, 4-glycoloylpiperazine, 4-phosphonooxymethylcarbonylpiperazine, 4-acylpiperazine, 3-hydroxymethyl-4-methylpiperazine, 3-phosphonooxymethyl-4-methylpiperazine, 2-hydroxymethylmorphine, 2-phosphonooxy methylmorphine, 3-hydroxymethyl-4-methylpiperazine, 3-methoxymethyl-4-methylpiperazine, 4-(2-hydroxyethyl)-3-oxopiperazine, 4-(2-phosphonooxyethyl)-3-oxopiperazine, (1α,5α,6α)-6-(hydroxymethyl)-3-azobicyclo[3.1.0]hexane, (1α,5α,6α)-6-(phosphonooxymethyl)-3-azobicyclo[3.1.0]hexane, 4-hydroxy-2-hydroxymethylpyrrolidine, 4-phosphonooxy-2-hydroxymethylpyrrolidine, 4-hydroxy-2-phosphonooxymethylpyrrolidine, 5-hydroxymethyl-2-oxopyrrolidine, 6-hydroxymethyl-2-oxopiperazine or 5-hydroxymethyl-3-oxopiperazine. In yet another aspect $R^{7'}$ and $R^{8'}$ are independently selected from hydrogen, methyl, ethyl, propyl, cyclopropyl, cyclobutyl, cyclopentyl, 2-phosphonooxyethyl, 2-phosphonooxypropyl, 3-phosphonooxy-1,1-dimethylpropyl, 2-methoxyethyl, phosphonooxymethylcarbonyl and tetrahydro-2H-furan-4-yl; or $R^{7'}$ and $R^{8'}$ together with the nitrogen to which they are attached form 2-phosphonooxymethylpyrrolidine, 4-(2-phosphonooxyethyl)piperazine or 4-(phosphonooxymethylcarbonyl)piperazine.

In one aspect of the invention $R^{9'}$ is hydrogen, $C_{1-4}$alkyl, hydroxy$C_{1-4}$alkyl, phosphonooxy$C_{1-4}$alkyl, amino$C_{1-4}$alkyl, $C_{1-4}$alkylamino$C_{1-4}$alkyl or bis($C_{1-4}$alkyl)amino$C_{1-4}$alkyl. In a further aspect $R^{9'}$ is hydroxy$C_{1-4}$alkyl, phosphonooxy$C_{1-4}$ alkyl or bis($C_{1-4}$alkyl)amino$C_{1-4}$alkyl.

In one aspect of the invention $R^{10'}$, $R^{15'}$ and $R^{16}$ are each independently hydrogen, methyl or ethyl.

A preferred class of compounds is of formula (I) wherein:

X is $NR^6$;

$R^6$ is hydrogen or methyl;

$R^1$ is hydrogen, halo, or —$X^1R^{11}$;

$X^1$ is a direct bond, —O—, —NH— or —N($C_{1-4}$alkyl)-;

$R^{11}$ is hydrogen or a group selected from $C_{1-6}$alkyl, heterocyclyl, heterocyclyl$C_{1-4}$alkyl, heterocyclyl$C_{2-4}$alkenyl and heterocyclyl$C_{2-4}$alkynyl which group is optionally substituted by a substituent selected from hydroxy, $C_{1-4}$alkoxy, hydroxy$C_{1-4}$alkyl, amino, $C_{1-4}$alkylamino, bis($C_{1-4}$alkyl)amino, hydroxycarbonyl, $C_{1-4}$alkoxycarbonyl, hydroxy$C_{1-4}$alkylcarbonyl, $C_{1-4}$alkoxy$C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$alkylcarbonyl;

$R^2$ is hydrogen, halo, nitro, cyano or —$X^2R^{12}$;

$X^2$ is a direct bond, —O— or —C(O)—;

$R^{12}$ is hydrogen or a group selected from $C_{1-6}$alkyl, $C_{2-6}$alkenyl, $C_{2-6}$alkynyl, $C_{3-6}$cycloalkyl, aryl, aryl$C_{1-4}$alkyl, heterocyclyl and heterocyclyl$C_{1-4}$alkyl, which group is optionally substituted by 1, 2 or 3 substituents selected from halo, hydroxy, $C_{1-4}$alkyl, $C_{1-4}$alkoxy, —$NR^{15}R^{16}$, —NHC(O)$NR^{15}R^{16}$, —C(O)$R^{15}$ and —C(O)O$R^{15}$;

$R^3$ is hydrogen or —$X^3R^{13}$;

$X^3$ is a direct bond, —$CH_2$═$CH_2$—, —O—, —NH— or —N($C_{1-6}$alkyl)-;

$R^{13}$ is hydrogen or a group selected from $C_{1-6}$alkyl, aryl, aryl$C_{1-4}$alkyl, heterocyclyl and heterocyclyl$C_{1-4}$alkyl, which group is optionally substituted by 1 or 2 substituents independently selected from —$NR^7R^8$, —$C(O)NR^7R^8$, halo, hydroxy, $C_{1-4}$alkyl, $C_{1-4}$alkoxy, hydroxy$C_{1-4}$alkyl, hydroxy$C_{1-4}$alkylcarbonyl and $C_{1-4}$alkylcarbonyl;

$R^7$ and $R^8$ are independently selected from hydrogen, heterocyclyl, heterocyclyl$C_{1-4}$alkyl, $C_{1-4}$alkylheterocyclyl$C_{1-4}$ alkyl, $C_{1-6}$alkyl, hydroxy$C_{1-6}$alkyl, $C_{1-4}$alkoxy$C_{1-4}$alkyl, $C_{3-6}$cycloalkyl, $C_{3-6}$cycloalkyl$C_{1-4}$alkyl, hydroxy$C_{3-6}$cycloalkyl, hydroxy$C_{1-4}$alkyl$C_{3-6}$cycloalkyl, halo$C_{1-6}$alkyl, $C_{2-4}$alkenyl, $C_{2-4}$alkynyl, cyano$C_{1-4}$alkyl, amino$C_{-1-4}$ alkyl, $C_{1-4}$alkylamino$C_{1-4}$alkyl, bis($C_{1-4}$alkyl)amino$C_{1-4}$ alkyl, hydroxy$C_{1-4}$alkoxy$C_{1-4}$alkyl and hydroxy$C_{1-4}$ alkylcarbonyl; or $R^7$ and $R^8$ together with the nitrogen to which they are attached form a heterocyclic ring selected from azetidine, pyrrolidine, piperidine, morpholine, piperazine, diazepane, 1,4-diazepane and azabicyclo[3.1.0]hexane which ring is optionally substituted on carbon or nitrogen by 1 or 2 substituents independently selected from $C_{1-4}$alkyl, hydroxy, hydroxy$C_{1-4}$alkyl, $C_{1-4}$alkoxy$C_{1-4}$ alkyl, hydroxy$C_{1-4}$alkoxy$C_{1-4}$alkyl, $C_{1-4}$alkylcarbonyl and hydroxy$C_{1-4}$alkylcarbonyl, and where a ring —$CH_2$— is optionally replaced with —C(O)—;

$R^4$ is hydrogen;

$R^5$ is aryl optionally substituted by 1 or 2 halo;

$R^{15}$ and $R^{16}$ are each independently hydrogen, methyl or ethyl; and $R^{19}$ is hydrogen, hydroxycarbonyl, $C_{1-4}$alkoxycarbonyl, aminocarbonyl or $C_{1-4}$alkanoylamino.

Another preferred class of compounds is of formula (I) wherein:

X is NH;

$R^1$ is hydrogen, halo or —$OR^{11}$;

$R^{11}$ is hydrogen or a group selected from $C_{1-6}$alkyl, heterocyclyl and heterocyclyl$C_{1-4}$alkyl, which group is optionally substituted by a substituent selected from hydroxy, $C_{1-4}$alkoxy, hydroxy$C_{1-4}$alkyl, hydroxy$C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$alkylcarbonyl;

$R^2$ is hydrogen, halo, —$OR^{12}$ or —$OC(O)R^{12}$;

$R^{12}$ is hydrogen or a group selected from $C_{1-4}$alkyl, aryl, heterocyclyl and heterocyclyl$C_{1-4}$alkyl which group is optionally substituted by a substituent selected from $C_{1-4}$alkyl and $C_{1-4}$alkoxy;

$R^3$ is hydrogen or —$X^3R^{13}$;

$X^3$ is a direct bond or —O—;

$R^{13}$ is hydrogen, methyl, ethyl, propyl or piperidinyl which methyl, ethyl or propyl are substituted by chloro, 1 or 2 hydroxy, 1 or 2 methoxy, —$NR^7R^8$ or a heterocyclyl selected from pyrrolidinyl and piperidinyl which heterocyclyl is optionally substituted by hydroxy, methyl, hydroxymethyl, 2-hydroxyethyl or glycoloyl;

$R^7$ and $R^8$ are independently selected from hydrogen, heterocyclyl, $C_{1-6}$alkyl, hydroxy$C_{1-6}$alkyl, hydroxy$C_{1-4}$ alkyl$C_{3-6}$ cycloalkyl, $C_{1-4}$alkoxy$C_{1-4}$alkyl, $C_{3-6}$cycloalkyl, $C_{3-6}$cycloalkyl$C_{1-4}$alkyl, halo$C_{1-6}$alkyl, $C_{2-6}$alkenyl, $C_{2-6}$alkynyl, cyano$C_{1-4}$alkyl and bis($C_{1-4}$ alkyl)amino$C_{1-6}$ alkyl; or $R^7$ and $R^8$ together with the nitrogen to which they are attached form a heterocyclic ring which ring comprises 4 to 7 ring atoms of which one is nitrogen and of which another is optionally NH and which ring is optionally substituted on carbon or nitrogen by a group selected from $C_{1-4}$alkyl, hydroxy, hydroxy$C_{1-4}$alkyl hydroxy$C_{1-4}$ alkoxy$C_{1-4}$alkyl and where a ring —$CH_2$— is optionally replaced with —C(O)—;

$R^4$ is hydrogen;

$R^5$ is phenyl optionally substituted by 1 or 2 fluoro; and $R^{19}$ is hydrogen, hydroxycarbonyl, ethoxycarbonyl, aminocarbonyl and acetylamino.

A further preferred class of compounds is of formula (I) wherein:

X is NH;

$R^1$ is hydrogen, fluoro, hydroxy, methoxy, isopropoxy, pyrrolidin-2-ylmethoxy, 1-(2-hydroxyethyl)pyrrolidin-2-ylmethoxy, 1-glycoloylpyrrolidin-2-ylmethoxy, 1-(N,N-dimethylglycyl)pyrrolidin-2-ylmethoxy, 2-(5-hydroxymethyl-2-oxo-pyrrolidin-1-yl)ethoxy, 3-(5-hydroxymethyl-2-oxo-pyrrolidin-1-yl)propoxy, 2-(6-hydroxymethyl-2-oxo-piperazin-1-yl)ethoxy, 3-(6-hydroxymethyl-2-oxo-piperazin-1-yl)propoxy, 2-(5-hydroxymethyl-3-oxo-piperazin-1-yl)ethoxy or 3-(5-hydroxymethyl-3-oxo-piperazin-1-yl)propoxy;

$R^2$ is hydrogen, fluoro, hydroxy, methoxy, 2-methoxyethoxy, benzoyloxy, 2-morpholin-4-ylethoxy, 3-morpholin-4-ylpropoxy or 1-methylpyrrolidin-2-yloxy;

$R^3$ is hydrogen, hydroxy, methoxy, 3-chloropropoxy, 2-chloroethoxy, 2,2-dimethoxyethoxy, 3-[2-(hydroxymethyl)pyrrolidin-1-yl]propoxy, 3-[(2-hydroxyethyl)(isobutyl)amino]propoxy, 3-[(2-hydroxyethyl)(propyl)amino]propoxy, 3-piperidin-1-ylpropoxy, 3-pyrrolidin-1-ylpropoxy, 3-(diethylamino)propoxy, 3-piperazin-1-ylpropoxy, 3-[(2-hydroxyethyl)(methyl)amino]propoxy, 3-(cyclopropylamino)propoxy, 3-{[2-(dimethylamino)ethyl](methyl)amino}propoxy, 3-(4-methylpiperazin-1-yl)propoxy, 3-(4-hydroxypiperidin-1-yl)propoxy, 3-[bis(2-hydroxyethyl)amino]propoxy, 3-[ethyl(methyl)amino]propoxy, 3-[ethyl(2-hydroxyethyl)amino]propoxy, 3-{[2-(dimethylamino)ethyl](ethyl)amino}propoxy, 3-[2-(2-hydroxyethyl)piperidin-1-yl]propoxy, 3-[4-(2-hydroxyethyl)piperazin-1-yl]propoxy, 3-[(cyclopropylmethyl)amino]propoxy, 3-[4-(2-hydroxyethyl)piperidin-1-yl]propoxy, 3-[methyl(prop-2-yn-1-yl)amino]propoxy, 3-[allyl(methyl)amino]propoxy, 3-[isobutyl(methyl)amino]propoxy, 3-(3-hydroxypiperidin-1-yl)propoxy, 3-[4-(hydroxymethyl)piperidin-1-yl]propoxy, 3-[methyl(propyl)amino]propoxy, 3-[cyclopropylmethyl(propyl)amino]propoxy, 3-{[2-(diethylamino)ethyl](methyl)amino}propoxy, 3-{[2-(diethylamino)ethyl](ethyl)amino}propoxy, 3-(4-methyl-1,4-diazepan-1-yl)propoxy, 3-[(2-hydroxyethyl)(isopropyl)amino]propoxy, 3-[cyclopropyl(2-hydroxyethyl)amino]propoxy, 3-[(2-hydroxyethyl)(2-methoxyethyl)amino]propoxy, 3-[cyclobutyl(2-hydroxyethyl)amino]propoxy, 3-[cyclopropylmethyl(2-hydroxyethyl)amino]propoxy, 3-[cyclobutylmethyl(2-hydroxyethyl)amino]propoxy, 3-[(2-hydroxy)prop-2-yn-1-lyamino]propoxy, 3-[allyl(2-hydroxyethyl)amino]propoxy, 3-[(2,2-dimethylpropyl(2-hydroxyethyl)amino]propoxy, 3-[(2-hydroxyethyl)(3,3,3-trifluoropropyl)amino]propoxy, 3-azetidin-1-ylpropoxy, 3-(dimethylamino)propoxy, 2-[(2-hydroxymethyl)pyrrolidin-1-yl]ethoxy, 2-{4-[2-(2-hydroxyethoxy)ethyl]piperazin-1-yl}ethoxy, 2-[2-(2-hydroxyethyl)piperidin-1-yl]ethoxy, 2-[2-(hydroxymethyl)piperidin-1-yl]ethoxy, 2-[(2-hydroxy-1,1-dimethylethyl)amino]ethoxy, 2-[4-(2-hydroxyethyl)piperazin-1yl]ethoxy, 2-[(4-hydroxycyclohexyl)amino]ethoxy, 2-[3-(hydroxymethyl)piperidin-1-yl]ethoxy, 2-{[1-(hydroxymethyl)cyclopentyl]amino}ethoxy, 2-[4-(3-hydroxypropyl)piperazin- 1-yl]ethoxy, 2-[cyclohexyl(2-hydroxyethyl)amino]ethoxy, 2-[(2-hydroxyethyl)(propyl)amino]ethoxy, 2-[(3-hydroxy-2,2-dimethylpropyl)amino]ethoxy, 2-tetrahydro-2H-pyran-4-ylamino)ethoxy, 2-[cyclobutyl(2-hydroxyethyl)amino]ethoxy, 2-[(2-hydroxyethyl)(tetrahydro-2H-pyran-4-yl)amino]ethoxy, 3-[cyclopentyl(2-hydroxyethyl)amino]propoxy, 3-[(3-hydroxy-1,1-dimethylpropyl)amino]propoxy, 3-[(2-cyanoethyl)(2- hydroxyethyl)amino]propoxy, 3-morpholin-4-ylpropoxy, 3-[(3-hydroxy-2,2-dimethylpropyl)amino]propoxy, 3-[(3-hydroxypropyl)amino]propoxy, 3-[(3-hydroxypropyl)(propyl)amino]propoxy, 3-[(3-hydroxypropyl)(ethyl)amino]propoxy, 3-[4-(2-hydroxyethyl)-3-oxopiperazin-1-yl]propoxy, 3-(propylamino)propoxy, 3-[glycoloyl(propyl)amino]propoxy, 3-(4-glycoloylpiperazin-1-yl)propoxy, 3-{[2-(hydroxymethyl)cyclohexyl]amino}propoxy, 3-[{1α,5α,6α)-6-(hydroxymethyl)-3-azabicyclo[3.1.0]hex-3-yl]propoxy, 3-{[2-hydroxypropyl]amino}propoxy, 3-{[2-hydroxy-1-methylethyl]amino}propoxy, 3-[(2-hydroxy-1,1-dimethylethyl)amino]propoxy, 3-[(2,3-dihydroxypropyl)amino]propoxy, 3-{[2-(2-hydroxyethoxy)ethyl]amino}propoxy, 3-(4-acetylpiperazin-1-yl)propoxy, 3-[(tetrahydrofuran-2-ylmethyl)amino]propoxy, 3-(allylamino)propoxy, 3-{[1-(hydroxymethyl)-2-methylpropyl]amino}propoxy, 3-{[(5-methylisoxazol-3-yl)methyl]amino}propoxy, 3-(tetrahydro-2H-pyran-4-ylamino)propoxy, 3-[3-(hydroxymethyl)pyrrolidin-1-yl]propoxy, 3-aminopropoxy, 3-[4-hydroxy-2-(hydroxymethyl)pyrrolidin-1-yl]propoxy, 2-(cyclopropylamino)ethoxy, 2-(cyclobutylamino)ethoxy, 2-(cyclopentylamino)ethoxy, 2-[{2-hydroxyethyl)(tetrahydro-2H-pyran-4-yl)amino]ethoxy, 2-[cyclopentyl(2-hydroxyethyl)amino]ethoxy, 2-[cyclopropyl(2-hydroxyethyl)amino]ethoxy, 2-[cyclopentyl(3-hydroxypropyl)amino]ethoxy, 2-[cyclopentyl(glycoloyl)amino]ethoxy, 2-[3-hydroxymethyl)-4-methylpiperazin-1-yl]ethoxy, 2-[2-(hydroxymethyl)-4-methylpiperazin-1-yl]ethoxy, 2-[4-(hydroxymethyl)piperidin-1-yl]ethoxy, 2-[4-(2-hydroxyethyl)piperidin-1-yl]ethoxy, 2-[(2-hydroxyethyl)amino]ethoxy, 2-{[2-(hydroxymethyl)cyclohexyl]amino}ethoxy, 3-[(2-hydroxyethyl)amino]propoxy, 3-[(2-hydroxyethyl)(tetrahydrofuran-3-yl)amino]propoxy, pyrrolidin-2-ylmethoxy, [1-(2-hydroxyethyl)pyrrolidin-2-yl]methoxy, [1-glycoloyopyrrolidin-2-yl]methoxy, pyrrolidin-3-ylmethoxy, [1-(2-hydroxyethyl)pyrrolidin-3-yl]methoxy, (1-glycoloylpyrrolidin-3-yl)methoxy, 3-[(2-hydroxyethyl)(2-methoxyethyl)amino]propoxy, (2-hydroxyethyl)amino]propoxy, 2-(5-hydroxymethyl-2-oxo-pyrrolidin-1-yl)ethoxy, 3-(5-hydroxymethyl-2-oxo-pyrrolidin-1-yl)propoxy, 2-(6-hydroxymethyl-2-oxo-piperazin-1-yl)ethoxy, 3-(6-hydroxymethyl-2-oxo-piperazin-1-yl)propoxy, 2-(5-hydroxymethyl-3-oxo-piperazin-1-yl)ethoxy, 3-(5-hydroxymethyl-3-oxo-piperazin-1-yl)propoxy, 3-(3-hydroxymethyl-4-methylpiperazin-1yl)propoxy, 3-(2-hydroxymethylmorpholin-4-yl)propoxy, 3-(glycoloylamino)propoxy or 3-(4hydroxymethylpiperazin-1-yl)propoxy;

$R^4$ is hydrogen;

$R^5$ is 2,3-difluorophenyl, 3-fluorophenyl, 2-fluorophenyl or 2,6-difluorophenyl; and $R^{19}$ is hydrogen, hydroxycarbonyl, ethoxycarbonyl, aminocarbonyl and acetylamino.

A preferred class of compounds is of formula (I) wherein:

X is $NR^6$;

$R^6$ is hydrogen or methyl;

$R^1$ is hydrogen, halo or —$OR^{11}$;

$R^{11}$ is hydrogen, heterocyclyl selected from piperidinyl or pyrrolidinyl, $C_{1-4}$alkyl optionally substituted by hydroxy, $C_{1-4}$alkoxy, amino, $C_{1-4}$alkylamino or bis($C_{1-4}$alkyl)amino;

$R^2$ is hydrogen or —$OR^{12}$;

$R^{12}$ is hydrogen, $C_{1-4}$alkyl (optionally substituted by heterocyclyl) or heterocyclyl;

$R^3$ is —$X^3R^{13}$;

$X^3$ is —$CH_2$═$CH_2$—, —O— or —NH—;

$R^{13}$ is $C_{1-6}$alkyl substituted by —$NR^7R^8$, heterocyclyl or halo;

$R^7$ and $R^8$ are independently selected from hydrogen, heterocyclyl, $C_{1-6}$alkyl, hydroxy$C_{1-6}$alkyl, hydroxy$C_{1-4}$alkyl$C_{3-6}$cycloalkyl, $C_{1-3}$alkoxy$C_{1-4}$alkyl, $C_{3-6}$cycloalkyl, $C_{3-6}$cycloalkyl$C_{1-3}$alkyl, halo$C_{1-6}$alkyl, $C_{2-6}$alkenyl, $C_{2-6}$alkynyl, cyano$C_{1-4}$alkyl and bis($C_{1-3}$ alkyl)amino$C_{1-6}$alkyl; or $R^7$ and $R^8$ together with the nitrogen to which they are attached form a heterocyclic ring which ring comprises 4 to 7 ring atoms of which one is nitrogen and of which another is optionally NH and which ring is optionally substituted on carbon or nitrogen by a group selected from $C_{1-4}$alkyl, hydroxy, hydroxy$C_{1-4}$alkyl and hydroxy$C_{1-4}$alkoxy$C_{1-4}$alkyl, and where a ring —$CH_2$— is optionally replaced with —C(O)—;

$R^4$ is hydrogen; and $R^5$ is aryl optionally substituted by 1 or 2 halo.

A further preferred class of compounds is of formula (I) wherein:

X is NH;

$R^1$ is hydrogen;

$R^2$ is hydrogen or methoxy;

$R^3$ is —$X^3R^{13}$;

$X^3$ is —O—;

$R^{13}$ is propyl substituted by chloro or —$NR^7R^8$;

$R^7$ and $R^8$ are independently selected from hydrogen, methyl, ethyl, propyl, isopropyl, butyl, isobutyl, tert-butyl, pentyl, neopentyl, hydroxymethyl, 2-hydroxyethyl, 3-hydroxy-1,1-dimethylpropyl, methoxymethyl, 2-methoxyethyl, 2-ethoxyethyl, cyclopropyl, cyclobutyl, cyclopentyl, cyclopropylmethyl, cyclobutylmethyl, cyclopentylmethyl, trifluoromethyl, 2,2,2-trifluoroethyl, 3,3,3-trifluoropropyl, allyl, propargyl, 2-(dimethylamino)ethyl and 2-(diethylamino)ethyl; or $R^7$ and $R^8$ together with the nitrogen to which they are attached form a heterocyclic ring selected from pyrrolidinyl, piperidinyl, piperazinyl, diazepanyl and azetidinyl where the ring is optionally substituted by hydroxy, methyl, hydroxymethyl or 2-hydroxyethyl;

$R^4$ is hydrogen; and $R^5$ is 2,3-difluorophenyl or 3-fluorophenyl.

A preferred class of compounds is of formula (IA) wherein:

X is $NR^6$;

$R^6$ is hydrogen or methyl;

$R^{1'}$ is hydrogen, halo, or —$X^1R^{11'}$;

$X^1$ is a direct bond, —O—, —NH— or —N($C_{1-4}$alkyl)-;

$R^{11'}$ is hydrogen, phosphonooxy or a group selected from $C_{1-6}$alkyl, heterocyclyl, heterocyclyl$C_{1-4}$alkyl, heterocyclyl$C_{2-4}$alkenyl and heterocyclyl$C_{2-4}$alkynyl which group is optionally substituted by a substituent selected from hydroxy, phosphonooxy, $C_{1-4}$alkoxy, hydroxy$C_{1-4}$alkyl, phosphonooxy$C_{1-4}$alkyl, amino, $C_{1-4}$alkylamino, bis($C_{1-4}$alkyl)amino, hydroxycarbonyl, $C_{1-4}$alkoxycarbonyl, hydroxy$C_{1-4}$alkylcarbonyl, phosphonooxy$C_{1-4}$alkylcarbonyl, $C_{1-4}$alkoxy$C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$alkylcarbonyl;

$R^{2'}$ is hydrogen, halo, nitro, cyano or —$X^2R^{12'}$;

$X^2$ is a direct bond, —O— or —OC(O)—;

$R^{12'}$ is hydrogen, phosphonooxy or a group selected from $C_{1-6}$alkyl, $C_{2-6}$alkenyl, $C_{2-6}$alkynyl, $C_{3-6}$cycloalkyl, aryl, aryl$C_{1-4}$alkyl, heterocyclyl and heterocyclyl$C_{1-4}$alkyl, which group is optionally substituted by 1, 2 or 3 substituents selected from halo, hydroxy, phosphonooxy, $C_{1-4}$alkyl, $C_{1-4}$alkoxy, —$NR^{15'}R^{16'}$, —NHC(O)$NR^{15'}R^{16'}$, —C(O)$R^{15'}$ and —C(O)$OR^{15'}$;

$R^{3'}$ is hydrogen, phosponooxy or —$X^3R^{13'}$;

$X^3$ is a direct bond, —$CH_2$=$CH_2$—, —O—, —NH— or —N($C_{1-6}$alkyl)-;

$R^{13'}$ is hydrogen or a group selected from $C_{1-6}$alkyl, aryl, aryl$C_{1-4}$alkyl, heterocyclyl and heterocyclyl$C_{1-4}$alkyl, which group is optionally substituted by 1 or 2 substituents independently selected from —$NR^{7'}R^{8'}$, —C(O)$NR^{7'}R^{8'}$, halo, hydroxy, phosphonooxy, $C_{1-4}$alkyl, $C_{1-4}$alkoxy, hydroxy$C_{1-4}$alkyl, phosphonooxy$C_{1-4}$alkyl, hydroxy$C_{1-4}$alkylcarbonyl, phosphonooxy$C_{1-4}$alkylcarbonyl and $C_{1-4}$alkylcarbonyl;

$R^{7'}$ and $R^{8'}$ are independently selected from hydrogen, heterocyclyl, heterocyclyl$C_{1-4}$alkyl, $C_{1-4}$alkylheterocyclyl$C_{1-4}$alkyl, $C_{1-6}$alkyl, hydroxy$C_{1-6}$alkyl, phosphonooxy$C_{1-6}$alkyl, $C_{1-4}$alkoxy$C_{1-4}$alkyl, $C_{3-6}$cycloalkyl, $C_{3-6}$cycloalkyl$C_{1-4}$alkyl, hydroxy$C_{3-6}$cycloalkyl, phosphonooxy$C_{3-6}$cycloalkyl, hydroxy$C_{1-4}$alkyl$C_{3-6}$cycloalkyl, phosphonooxy$C_{1-4}$alkyl$C_{3-6}$cycloalkyl, halo$C_{1-6}$ alkyl, $C_{2-4}$alkenyl, $C_{2-4}$alkynyl, cyano$C_{1-4}$alkyl, amino$C_{1-4}$ alkyl, bis($C_{1-4}$alkyl)amino$C_{1-4}$alkyl, hydroxy$C_{1-4}$ alkoxy$C_{1-4}$alkyl, phosphonooxy$C_{1-4}$alkoxy$C_{1-4}$alkyl, hydroxy$C_{1-4}$alkylcarbonyl and phosphonooxy$C_{1-4}$alkylcarbonyl; or $R^{7'}$ and $R^{8'}$ together with the nitrogen to which they are attached form a heterocyclic ring selected from azetidine, pyrrolidine, piperidine, morpholine, piperazine, diazepane, 1,4-diazepane and azabicyclo[3.1.0]hexane which ring is optionally substituted on carbon or nitrogen by 1 or 2 substituents independently selected from $C_{1-4}$alkyl, hydroxy, phosphonooxy, hydroxy$C_{1-4}$alkyl, phosphonooxy$C_{1-4}$alkyl, $C_{1-4}$alkoxy$C_{1-4}$alkyl, hydroxy$C_{1-4}$alkoxy$C_{1-4}$alkyl, phosphonooxy$C_{1-4}$ alkoxy$C_{1-4}$alkyl, $C_{1-4}$alkylcarbonyl, hydroxy$C_{1-4}$alkylcarbonyl and phosphonooxy$C_{1-4}$alkylcarbonyl, and where a ring —$CH_2$— is optionally replaced with —C(O)—;

$R^4$ is hydrogen;

$R^5$ is aryl optionally substituted by 1 or 2 halo;

$R^{15'}$ and $R^{16'}$ are each independently hydrogen, methyl or ethyl; and $R^{19}$ is hydrogen, hydroxycarbonyl, $C_{1-4}$alkoxycarbonyl, aminocarbonyl or $C_{1-4}$alkanoylamino; provided that a compound of formula (IA) contains one phosponooxy group.

Another preferred class of compounds is of formula (IA) wherein:

X is NH;

$R^{1'}$ is hydrogen, halo or —$OR^{11'}$;

$R^{11'}$ is hydrogen, phosphonooxy or a group selected from $C_{1-6}$alkyl, heterocyclyl and heterocyclyl$C_{1-4}$alkyl, which group is optionally substituted by a substituent selected from hydroxy, phosphonooxy, $C_{1-4}$alkoxy, hydroxy$C_{1-4}$ alkyl, phosphonooxy$C_{1-4}$alkyl, hydroxy$C_{1-4}$alkylcarbonyl, phosphonooxy$C_{1-4}$alkylcarbonyl, amino$C_{1-4}$alkylcarbonyl, $C_{1-4}$alkylamino$C_{1-4}$alkylcarbonyl and bis($C_{1-4}$ alkyl)amino$C_{1-4}$alkylcarbonyl;

$R^{2'}$ is hydrogen, halo, —$OR^{12'}$ or —OC(O)$R^{12'}$;

$R^{12'}$ is hydrogen, phosphonooxy or a group selected from $C_{1-4}$alkyl, aryl, heterocyclyl and heterocyclyl$C_{1-4}$alkyl which group is optionally substituted by a substituent selected from $C_{1-4}$alkyl and $C_{1-4}$alkoxy;

$R^{3'}$ is hydrogen, phosponooxy or —$X^3R^{13'}$;

$X^3$ is a direct bond or —O—;

$R^{13'}$ is methyl, ethyl or propyl substituted by chloro, 1 or 2 hydroxy, 1 phosphonooxy, 1 or 2 methoxy, —$NR^{7'}R^{8'}$ or a heterocyclyl selected from pyrrolidinyl and piperidinyl which heterocyclyl is optionally substituted by hydroxy, phosphonooxy, methyl, hydroxymethyl, phosphonooxymethyl, 2-hydroxyethyl, 2-phosphonooxyethyl, glycoloyl or phosphonooxymethylcarbonyl;

$R^{7'}$ and $R^{8'}$ are independently selected from hydrogen, heterocyclyl, $C_{1-6}$alkyl, hydroxy$C_{1-6}$alkyl, phosphonooxy$C_{1-6}$ alkyl, hydroxy$C_{1-4}$alkyl$C_{3-6}$cycloalkyl, phosphonooxy$C_{1-4}$alkyl$C_{3-6}$cycloalkyl, $C_{1-4}$alkoxy$C_{1-4}$ alkyl, $C_{3-6}$cycloalkyl, $C_{3-6}$cycloalkyl$C_{1-4}$alkyl, halo$C_{1-6}$ alkyl, $C_{2-6}$alkenyl, $C_{2-6}$alkynyl, cyano$C_{1-4}$alkyl, amino$C_{1-6}$ alkyl, $C_{1-4}$alkylamino$C_{1-6}$alkyl and bis($C_{1-4}$alkyl)amino$C_{1-6}$ alkyl; or $R^{7'}$ and $R^{8'}$ together with the nitrogen to which they are attached form a heterocyclic ring which ring comprises 4 to 7 ring atoms of which one is nitrogen and of which another is optionally NH and which ring is optionally substituted on carbon or nitrogen by a group 1 or 2 substituents independently selected from $C_{1-4}$alkyl, hydroxy, phosphonooxy, hydroxy$C_{1-4}$alkyl, phosphonooxy$C_{1-4}$alkyl, hydroxy$C_{1-4}$alkoxy$C_{1-4}$alkyl and phosphonooxy$C_{1-4}$alkoxy$C_{1-4}$alkyl, and where a ring —$CH_2$— is optionally replaced with —C(O);

$R^4$ is hydrogen;

$R^5$ is phenyl optionally substituted by 1 or 2 fluoro; and $R^{19}$ is hydrogen, hydroxycarbonyl, ethoxycarbonyl, aminocarbonyl and acetylamino; provided that a compound of formula (IA) contains one phosponooxy group.

A further preferred class of compounds is of formula (IA) wherein:

X is NH;

$R^{1'}$ is hydrogen, fluoro, hydroxy, phosphonooxy, methoxy, isopropoxy, pyrrolidin-2-ylmethoxy, 1-(2-hydroxyethyl)pyrrolidin-2-ylmethoxy, 1-(2-phosphonooxyethyl)pyrrolidin-2-ylmethoxy, 1-glycoloylpyrrolidin-2-ylmethoxy, 1-phosponooxymethylcarbonylpyrrolidin-2-ylmethoxy, 1-(N,N-dimethylglycyl)pyrrolidin-2-ylmethoxy, 2-(5-hydroxymethyl-2-oxo-pyrrolidin-1-yl)ethoxy, 2-(5-phosphonooxymethyl-2-oxo-pyrrolidin-1-yl)ethoxy, 3-(5-hydroxymethyl-2-oxo-pyrrolidin-1-yl)propoxy, 3-(5-phosphonooxymethyl-2-oxo-pyrrolidin-1-yl)propoxy, 2-(6-hydroxymethyl-2-oxo-piperazin-1-yl)ethoxy, 2-(6-phosphonooxymethyl-2-oxo-piperazin-1-yl)ethoxy, 3-(6-hydroxymethyl-2-oxo-piperazin-1-yl)propoxy, 3-(6-phosphonooxymethyl-2-oxo-piperazin-1-yl)propoxy, 2-(5-hydroxymethyl-3-oxo-piperazin-1-yl)ethoxy, 2-(5-phosphonooxymethyl-3-oxo-piperazin-1-yl)ethoxy, 3-(5-hydroxymethyl-3-oxo-piperazin-1-yl)propoxy or 3-(5-phosphonooxymethyl-3-oxo-piperazin-1-yl)propoxy;

$R^{2'}$ is hydrogen, fluoro, hydroxy, phosphonooxy, methoxy, 2-methoxyethoxy, benzoyloxy, 2-morpholin-4-ylethoxy, 3-morpholin-4-ylpropoxy or 1-methylpyrrolidin-2-yloxy.

$R^{3'}$ is hydrogen, phosponooxy or —$X^3R^{13'}$;

$X^3$ is a direct bond or —O—;

$R^{13'}$ is methyl, ethyl or propyl substituted by chloro, 1 or 2 hydroxy, 1 phosphonooxy, 1 or 2 methoxy, —$NR^{7'}R^{8'}$ or a heterocyclyl selected from pyrrolidinyl and piperidinyl which heterocyclyl is optionally substituted by hydroxy, phosphonooxy, methyl, hydroxymethyl, phosphonooxymethyl, 2-hydroxyethyl, 2-phosphonooxyethyl, glycoloyl or phosphonooxymethylcarbonyl;

$R^{7'}$ and $R^{8'}$ are independently selected from hydrogen, methyl, ethyl, propyl, isopropyl, butyl, isobutyl, tert-butyl, pentyl, neopentyl, hydroxymethyl, phosphonooxymethyl, 2-hydroxyethyl, 2-phosphonooxyethyl, 2-hydroxy-1,1-dimethylethyl, 2-phosphonooxy-1,1-dimethylethyl, 3-hydroxypropyl, 3-phosphonooxypropyl, 3-hydroxy-2,2-dimethylpropyl, 3-phosphonooxy-2,2-dimethylpropyl, 3-hydroxy-1,1-dimethylpropyl, 3-phosphonooxy-1,1-dimethylpropyl, 2-hydroxypropyl, 2-phosphonooxypropyl, 2,3-dihydroxypropyl, 2-hydroxy-3-phosphonooxypropyl, 2-phosphonooxy-3-hydroxypropyl, 1-hydroxymethyl-2-methylpropyl, 1-phosphonooxymethyl-2-methylpropyl, cyclopropyl, cyclobutyl, cyclopentyl, cyclohexyl, 4-hydroxycyclohexyl, 4-phosphonooxycyclohexyl, 1-hydroxymethylcyclopentyl, 1-phosphonooxymethylcyclopentyl, 2-hydroxymethylcyclohexyl, 2-phosphonooxymethylcyclohexyl, cyclopropylmethyl, cyclobutylmethyl, tetrahydro-2H-pyran-4-yl, tetrahydrofuran-3-yl, tetrahydrofuran-2-ylmethyl, 5-methylisoxazol-3-yl, 2-cyanoethyl, allyl, prop-2-ynyl, 2-methoxyethyl, methoxymethyl, 3,3,3-trifluoropropyl, 2-(2-hydroxyethoxy)ethyl, 2-(2-phosphonooxyethoxy)ethyl, 2-(dimethylamino)ethyl, 2-(diethylamino)ethyl, 3-aminopropyl, 3-(propylamino)propyl, glycoloyl and phosphonooxymethylcarbonyl; or $R^{7'}$ and $R^{8'}$ together with the nitrogen to which they are attached form a heterocyclic ring selected from azetidine, pyrrolidine, piperidine, morpholine, piperazine, diazepane or 1,4-diazepane which ring is optionally substituted by 1 or 2 substituents independently selected from methyl, hydroxy, phosphonooxy, hydroxymethyl, phosphonooxymethyl, 2-hydroxyethyl, 2-phosphonooxyethyl, 3-hydroxypropyl, 3-phosphonooxypropyl, 2-(2-hydroxyethoxy)ethyl, 2-(2-phosphonooxyethyl)ethyl, glycoloyl, phosphonooxymethylcarbonyl, acetyl, methoxymethyl and oxo.

$R^4$ is hydrogen;

$R^5$ is 2,3-difluorophenyl, 3-fluorophenyl, 2-fluorophenyl or 2,6-difluorophenyl; and $R^{19}$ is hydrogen, hydroxycarbonyl, ethoxycarbonyl, aminocarbonyl and acetylamino; provided that a compound of formula (IA) contains one phosponooxy group.

A preferred class of compounds is of formula (IA) wherein:

X is $NR^6$;

$R^6$ is hydrogen or methyl;

$R^1$ is hydrogen or —$OR^{11}$;

$R^{11}$ is hydrogen, heterocyclyl selected from piperidinyl or pyrrolidinyl, $C_{1-4}$alkyl optionally substituted by hydroxy, $C_{1-4}$alkoxy, amino, $C_{1-4}$alkylamino or bis($C_{1-4}$alkyl)amino;

$R^2$ is hydrogen or —$OR^{12}$;

$R^{12}$ is hydrogen, $C_{1-4}$alkyl (optionally substituted with heterocyclyl) or heterocyclyl;

$R^{3'}$ is —$X^{3'}R^{13'}$;

$X^{3'}$ is —$CH_2$=$CH_2$—, —O— or —NH—;

$R^{13'}$ is $C_{1-6}$alkyl substituted by —$NR^{7'}R^{8'}$;

$R^{7'}$ is selected from hydrogen, heterocyclyl, $C_{1-6}$alkyl, $C_{1-3}$alkoxy$C_{1-6}$alkyl, cyano$C_{1-4}$alkyl and $C_{3-6}$cycloalkyl;

$R^{8'}$ is phosphonooxy$C_{1-4}$alkyl or phosphonooxy$C_{1-4}$alkyl$C_{3-6}$cycloalkyl;

or $R^{7'}$ and $R^{8'}$ together with the nitrogen to which they are attached form a heterocyclic ring selected from pyrrolidinyl, piperidinyl and piperazinyl which ring is substituted on carbon or nitrogen by a group selected from phosphonooxy, phosponooxymethyl and 2-phoshonooxyethyl;

$R^4$ is hydrogen; and $R^5$ is aryl optionally substituted by 1 or 2 halo.

A further preferred class of compounds is of formula (IA) wherein:

X is NH;

$R^1$ is hydrogen;

$R^2$ is hydrogen or methoxy;

$R^{3'}$ is —$X^{3'}R^{13'}$;

$X^{3'}$ is —O—;

$R^{13'}$ is propyl substituted by —$NR^{7'}R^{8'}$;

$R^{7'}$ is ethyl, propyl, cyclobutyl or 2-methoxyethyl;

$R^{8'}$ is 2-phosphonooxyethyl or 1,1-dimethyl-3-phosphonooxypropyl;

or $R^{7'}$ and $R^{8'}$ together with the nitrogen to which they are attached form a heterocyclic ring selected from pyrrolidinyl, piperidinyl and piperazinyl which ring is substituted on carbon or nitrogen by a group selected from phosphonooxy, phosponooxymethyl and 2-phoshonooxyethyl;

$R^4$ is hydrogen; and $R^5$ is 2,3-difluorophenyl or 3-fluorophenyl.

A particular compound of formula (I) is any one of:

2-(4-{[7-(3-chloropropoxy)-6-methoxyquinazolin-4-yl]amino}-1H-pyrazol-1-yl)-N-(3-fluorophenyl)acetamide;

2-(4-{[7-(3-chloropropoxy)quinazolin-4-yl]amino}-1H-pyrazol-1-yl)-N-(2,3-difluorophenyl)acetamide;

2-(4-{[7-(3-chloropropoxy)-6-methoxyquinazolin-4-yl]amino}-1H-pyrazol-1-yl)-N-(2,3-difluorophenyl)acetamide;

2-(4-{[7-(3-chloropropoxy)quinazolin-4-yl]amino}-1H-pyrazol-1-yl)-N-(3-fluorophenyl)acetamide;

2-(4-{[7-(2-chloroethoxy)quinazolin-4-yl]amino}-1H-pyrazol-1-yl)-N-(2,3-difluorophenyl)acetamide;

2-(4-{[7-(2-chloroethoxy)-6-methoxyquinazolin-4-yl]amino}-1H-pyrazol-1-yl)-N-(2,3-difluorophenyl)acetamide;

N-(2,3-difluorophenyl)-2-(4-{[7-(2,2-dimethoxyethoxy)quinazolin-4-yl]amino}-1H-pyrazol-1-yl)acetamide;

4-{[7-(3-chloropropoxy)-6-methoxyquinazolin-4-yl]amino}-1-{2-[(3-fluorophenyl)amino]-2-oxoethyl}-1H-pyrazole-3-carboxamide;

ethyl 4-{[7-(3-chloropropoxy)quinazolin-4-yl]amino}-1-{2-[(3-fluorophenyl)amino]-2-oxoethyl}-1H-pyrazole-3-carboxylate;

2-(3-(acetylamino)-1-{[7-(3-chloropropoxy)quinazolin-4-yl]amino}-1H-pyrazol-1-yl)-N-(3-fluorophenyl)acetamide;

N-(2,3-difluorophenyl)-2-[4-(quinazolin-4-ylamino)-1H-pyrazol-1-yl]acetamide;

2-(4-{[7-(3-chloropropoxy)-5-isopropoxyquinazolin-4-yl]amino}-1H-pyrazol-1-yl)-N-(2,3-difluorophenyl)acetamide;

2-(4-{[7-(3 -chloropropoxy)-5-methoxyquinazolin-4-yl]amino}-1H-pyrazol-1-yl)-N-(2,3-difluorophenyl)acetamide;

2-(4-{[7-(3-chloropropoxy)-6-fluoroquinazolin-4-yl]amino}-1H-pyrazol-1-yl)-N-(2,3-difluorophenyl)acetamide;

2-(4-{[7-(3-chloropropoxy)-6-fluoroquinazolin-4-yl]amino}-1H-pyrazol-1-yl)-N-(3-fluorophenyl)acetamide;

N-(3-fluorophenyl)-2-{4-[(7-{3-[(2S)-2-(hydroxymethyl)pyrrolidin-1-yl]propoxy}-6-methoxyquinazolin-4-yl)amino]-1H-pyrazol-1-yl}acetamide;

N-(3-fluorophenyl)-2-{4-[(7-{3-[(2-hydroxyethyl)(isobutyl)amino]propoxy}-6-methoxyquinazolin-4-yl)amino]-1H-pyrazol-1-yl}acetamide;

N-(3-fluorophenyl)-2-{4-[(7-{3-[(2-hydroxyethyl)(propyl)amino]propoxy}-6-methoxyquinazolin-4-yl)amino]-1H-pyrazol-1-yl}acetamide;

N-(3-fluorophenyl)-2-(4-{[6-methoxy-7-(3-piperidin-1-ylpropoxy)quinazolin-4-yl]amino}-1H-pyrazol-1-yl)acetamide;

N-(3-fluorophenyl)-2-(4-{[6-methoxy-7-(3-pyrrolidin-1-ylpropoxy)quinazolin-4-yl]amino}-1H-pyrazol-1-yl)acetamide;

2-[4-({7-[3-(diethylamino)propoxy]-6-methoxyquinazolin-4-yl}amino)-1H-pyrazol-1-yl]-N-(3-fluorophenyl)acetamide;

N-(3-fluorophenyl)-2-(4-{[6-methoxy-7-(3-piperazin-1-yl-propoxy)quinazolin-4-yl]amino}-1H-pyrazol-1-yl)acetamide;

N-(3-fluorophenyl)-2-{4-[(7-{3-[(2-hydroxyethyl)(methyl)amino]propoxy}-6-methoxyquinazolin-4-yl)amino]-1H-pyrazol-1-yl}acetamide;

2-[4-({7-[3-(cyclopropylamino)propoxy]-6-methoxyquinazolin-4-yl}amino)-1H-pyrazol-1-yl]-N-(3-fluorophenyl)acetamide;

2-{4-[(7-{3-[[2-(dimethylamino)ethyl](methyl)amino]propoxy}-6-methoxyquinazolin-4-yl)amino]-1H-pyrazol-1-yl}-N-(3-fluorophenyl)acetamide;

N-(3-fluorophenyl)-2-[4-({6-methoxy-7-[3-(4-methylpiperazin-1-yl)propoxy]quinazolin-4-yl}amino)-1H-pyrazol-1-yl]acetamide;

N-(3-fluorophenyl)-2-{4-[(7-{3-[(2R)-2-(hydroxymethyl)pyrrolidin-1-yl]propoxy}-6-methoxyquinazolin-4-yl)amino]-1H-pyrazol-1-yl}acetamide;

N-(3-fluorophenyl)-2-[4-({7-[3-(4-hydroxypiperidin-1-yl)propoxy]-6-methoxyquinazolin-4-yl}amino)-1H-pyrazol-1-yl]acetamide;

2-{4-[(7-{3-[bis(2-hydroxyethyl)amino]propoxy}-6-methoxyquinazolin-4-yl)amino]-1H-pyrazol-1-yl}-N-(3-fluorophenyl)acetamide;

2-{4-[(7-{3-[ethyl(methyl)amino]propoxy}-6-methoxyquinazolin-4-yl)amino]-1H-pyrazol-1-yl}-N-(3-fluorophenyl)acetamide;

2-{4-[(7-{3-[ethyl(2-hydroxyethyl)amino]propoxy}-6-methoxyquinazolin-4-yl)amino]-1H-pyrazol-1-yl}-N-(3-fluorophenyl)acetamide;

2-{4-[(7-{3-[[2-(dimethylamino)ethyl](ethyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[2-(2-hydroxyethyl)piperidin-1-yl]propoxy}-6-methoxyquinazolin-4-yl)amino]-1H-pyrazol-1-yl}acetamide;

N-(3-fluorophenyl)-2-{4-[(7-{3-[4-(2-hydroxyethyl)piperazin-1-yl]propoxy}-6-methoxyquinazolin-4-yl)amino]-1H-pyrazol-1-yl}acetamide;

2-{4-[(7-{3-[(cyclopropylmethyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[4-(2-hydroxyethyl)piperidin-1-yl]propoxy}-6-methoxyquinazolin-4-yl)amino]-1H-pyrazol-1-yl}acetamide;

N-(3-fluorophenyl)-2-{4-[(6-methoxy-7-{3-[methyl(prop-2-yn-1-yl)amino]propoxy}quinazolin-4-yl)amino]-1H-pyrazol-1-yl}acetamide;

2-{4-[(7-{3-[allyl(methyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[isobutyl(methyl)amino]propoxy}-6-methoxyquinazolin-4-yl)amino]-1H-pyrazol-1-yl}acetamide;

N-(3-fluorophenyl)-2-[4-({7-[3-(3-hydroxypiperidin-1-yl)propoxy]-6-methoxyquinazolin-4-yl}amino)-1H-pyrazol-1-yl]acetamide;

N-(3-fluorophenyl)-2-{4-[(7-{3-[4-(hydroxymethyl)piperidin-1-yl]propoxy}-6-methoxyquinazolin-4-yl)amino]-1H-pyrazol-1-yl}acetamide;

N-(3-fluorophenyl)-2-{4-[(6-methoxy-7-{3-[methyl(propyl)amino]propoxy}quinazolin-4-yl)amino]-1H-pyrazol-1-yl}acetamide;

2-{4-[(7-{3-[(cyclopropylmethyl)(propyl)amino]propoxy}-6-methoxyquinazolin-4-yl)amino]-1H-pyrazol-1-yl}-N-(3-fluorophenyl)acetamide;

2-{4-[(7-{3-[[2-(diethylamino)ethyl](methyl)amino]propoxy}-6-methoxyquinazolin-4-yl)amino]-1H-pyrazol-1-yl}-N-(3-fluorophenyl)acetamide;

2-{4-[(7-{3-[[2-(diethylamino)ethyl](ethyl)amino]propoxy}-6-methoxyquinazolin-4-yl)amino]-1H-pyrazol-1-yl}-N-(3-fluorophenyl)acetamide;

N-(3-fluorophenyl)-2-[4-({6-methoxy-7-[3-(4-methyl-1,4-diazepan-1-yl)propoxy]quinazolin-4-yl}amino)-1H-pyrazol-1-yl]acetamide;

N-(3-fluorophenyl)-2-{4-[(7-{3-[(2-hydroxyethyl)(isopropyl)amino]propoxy}-6-methoxyquinazolin-4-yl)amino]-1H-pyrazol-1-yl}acetamide;

2-{4-[(7-{3-[cyclopropyl(2-hydroxyethyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[(2-hydroxyethyl)(2-methoxyethyl)amino]propoxy}-6-methoxyquinazolin-4-yl)amino]-1H-pyrazol-1-yl}acetamide;

2-{4-[(7-{3-[cyclobutyl(2-hydroxyethyl)amino]propoxy}-6-methoxyquinazolin-4-yl)amino]-1H-pyrazol-1-yl}-N-(3-fluorophenyl)acetamide;

-2-{4-[(7-{3-[(cyclopropylmethyl)(2-hydroxyethyl)amino]propoxy}-6-methoxyquinazolin-4-yl)amino]-1H-pyrazol-1-yl}-N-(3-fluorophenyl)acetamide;

2-{4-[(7-{3-[(cyclobutylmethyl)(2-hydroxyethyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[(2-hydroxyethyl)(prop-2-yn-1-yl)amino]propoxy}-6-methoxyquinazolin-4-yl)amino]-1H-pyrazol-1-yl}acetamide;

2-{4-[(7-{3-[allyl(2-hydroxyethyl)amino]propoxy}-6-methoxyquinazolin-4-yl)amino]-1H-pyrazol-1-yl}-N-(3-fluorophenyl)acetamide;

2-{4-[(7-{3-[(2,2-dimethylpropyl)(2-hydroxyethyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[(2-hydroxyethyl)(3,3,3-trifluoropropyl)amino]propoxy}-6-methoxyquinazolin-4-yl)amino]-1H-pyrazol-1-yl}acetamide;

2-(4-{[7-(3-azetidin-1-ylpropoxy)-6-methoxyquinazolin-4-yl]amino}-1H-pyrazol-1-yl)-N-(3-fluorophenyl)acetamide;

2-{4-[(6,7-dimethoxyquinazolin-4-yl)amino]-1H-pyrazol-1-yl}-N-(3-fluorophenyl)acetamide;

N-(3-fluorophenyl)-2-{4-[(7-hydroxy-6-methoxyquinazolin4-yl)amino]-1H-pyrazol-1-yl}acetamide;

N-(2,3-difluorophenyl)-2-{4-[(7-{3-[(2-hydroxyethyl)(isobutyl)amino]propoxy}-6-methoxyquinazolin-4-yl)amino]-1H-pyrazol-1-yl}acetamide;

N-(2,3-difluorophenyl)-2-{4-[(7-{3-[(2S)-2-(hydroxymethyl)pyrrolidin-1-yl]propoxy}-6-methoxyquinazolin-4-yl)amino]-1H-pyrazol-1-yl}acetamide;

N-(2,3-difluorophenyl)-2-{4-[(7-{3-[(2-hydroxyethyl)(propyl)amino]propoxy}-6-methoxyquinazolin-4-yl)amino]-1H-pyrazol-1-yl}acetamide;

N-(2,3-difluorophenyl)-2-[4-({7-[3-(dimethylamino)propoxy]-6-methoxyquinazolin-4-yl}amino)-1H-pyrazol-1-yl]acetamide;

N-(2,3-difluorophenyl)-2-(4-{[6-methoxy-7-(3-piperidin-1-ylpropoxy)quinazolin-4-yl]amino}-1H-pyrazol-1-yl)acetamide;

N-(2,3-difluorophenyl)-2-(4-{[6-methoxy-7-(3-pyrrolidin-1-ylpropoxy)quinazolin-4-yl]amino}-1H-pyrazol-1-yl)acetamide;

N-(2,3-difluorophenyl)-2-(4-{[6-methoxy-7-(3-piperazin-1-ylpropoxy)quinazolin-4-yl]amino}-1H-pyrazol-1-yl)acetamide;

N-(2,3-difluorophenyl)-2-{4-[(7-{3-[(2-hydroxyethyl)(methyl)amino]propoxy}-6-methoxyquinazolin-4-yl)amino]-1H-pyrazol-1-yl}acetamide;

2-[4-({7-[3-(cyclopropylamino)propoxy]-6-methoxyquinazolin-4-yl}amino)-1H-pyrazol-1-yl]-N-(2,3-difluorophenyl)acetamide;

N-(2,3-difluorophenyl)-2-{4-[(7-{3-[[2-(dimethylamino)ethyl](methyl)amino]propoxy}-6-methoxyquinazolin-4-yl)amino]-1H-pyrazol-1-yl}acetamide;

N-(2,3-difluorophenyl)-2-[4-({6-methoxy-7-[3-(4-methylpiperazin-1-yl)propoxy]quinazolin-4-yl}amino)-1H-pyrazol-1-yl]acetamide;

N-(2,3-difluorophenyl)-2-{4-[(7-{3-[(2R)-2-(hydroxymethyl)pyrrolidin-1-yl]propoxy}-6-methoxyquinazolin-4-yl)amino]-1H-pyrazol-1-yl}acetamide;

N-(2,3-difluorophenyl)-2-[4-({7-[3-(4-hydroxypiperidin-1-yl)propoxy]-6-methoxyquinazolin-4-yl}amino)-1H-pyrazol-1-yl]acetamide;

2-{4-[(7-{3-[bis(2-hydroxyethyl)amino]propoxy}-6-methoxyquinazolin-4-yl)amino]-1H-pyrazol-1-yl}-N-(2,3-difluorophenyl)acetamide;

N-(2,3-difluorophenyl)-2-{4-[(7-{3-[ethyl(methyl)amino]propoxy}-6-methoxyquinazolin-4-yl)amino]-1H-pyrazol-1-yl}acetamide;

N-(2,3-difluorophenyl)-2-{4-[(7-{3-[ethyl(2-hydroxyethyl)amino]propoxy}-6-methoxyquinazolin-4-yl)amino]-1H-pyrazol-1-yl}acetamide;

N-(2,3-difluorophenyl)-2-{4-[(7-{3-[[2-(dimethylamino)ethyl](ethyl)amino]propoxy}-6-methoxyquinazolin-4-yl)amino]-1H-pyrazol-1-yl}acetamide;

N-(2,3-difluorophenyl)-2-{4-[(7-{3-[2-(2-hydroxyethyl)piperidin-1-yl]propoxy}-6-methoxyquinazolin-4-yl)amino]-1H-pyrazol-1-yl}acetamide;

N-(2,3-difluorophenyl)-2-{4-[(7-{3-[4-(2-hydroxyethyl)piperazin-1-yl]propoxy}-6-methoxyquinazolin-4-yl)amino]-1H-pyrazol-1-yl}acetamide;

2-{4-[(7-{3-[(cyclopropylmethyl)amino]propoxy}-6-methoxyquinazolin-4-yl)amino]-1H -pyrazol-1-yl}-N-(2,3-difluorophenyl)acetamide;

N-(2,3-difluorophenyl)-2-{4-[(7-{3-[4-(2-hydroxyethyl)piperidin-1-yl]propoxy}-6-methoxyquinazolin-4-yl)amino]-1H-pyrazol-1-yl}acetamide;

N-(2,3-difluorophenyl)-2-{4-[(6-methoxy-7-{3-[methyl(prop-2-yn-1-yl)amino]propoxy}quinazolin-4-yl)amino]-1H-pyrazol-1-yl}acetamide;

N-(2,3-difluorophenyl)-2-{4-[(7-{3-[isobutyl(methyl)amino]propoxy}-6-methoxyquinazolin-4-yl)amino]-1H-pyrazol-1-yl}acetamide;

N-(2,3-difluorophenyl)-2-[4-({7-[3-(3-hydroxypiperidin-1-yl)propoxy]-6-methoxyquinazolin-4-yl}amino)-1H-pyrazol-1-yl]acetamide;

N-(2,3-difluorophenyl)-2-{4-[(7-{3-[4-(hydroxymethyl)piperidin-1-yl]propoxy}-6-methoxyquinazolin-4-yl)amino]-1H-pyrazol-1-yl}acetamide;

N-(2,3-difluorophenyl)-2-{4-[(6-methoxy-7-{3-[methyl(propyl)amino]propoxy}quinazolin-4-yl)amino]-1H-pyrazol-1-yl}acetamide;

2-{4-[(7-{3-[(cyclopropylmethyl)(propyl)amino]propoxy}-6-methoxyquinazolin-4-yl)amino]-1H-pyrazol-1-yl}-N-(2,3-difluorophenyl)acetamide;

2-{4-[(7-{3-[[2-(diethylamino)ethyl](methyl)amino]propoxy}-6-methoxyquinazolin-4-yl)amino]-1H-pyrazol-1-yl}-N-(2,3-difluorophenyl)acetamide;

2-{4-[(7-{3-[[2-(diethylamino)ethyl](ethyl)amino]propoxy}-6-methoxyquinazolin-4-yl)amino]-1H-pyrazol-1-yl}-N-(2,3-difluorophenyl)acetamide;

N-(2,3-difluorophenyl)-2-[4-({6-methoxy-7-[3-(4-methyl-1,4-diazepan-1-yl)propoxy]quinazolin-4-yl}amino)-1H-pyrazol-1-yl]acetamide;

N-(2,3-difluorophenyl)-2-{4-[(7-{3-[(2-hydroxyethyl)(isopropyl)amino]propoxy}-6-methoxyquinazolin-4-yl)amino]-1H-pyrazol-1-yl}acetamide;

2-{4-[(7-{3-[cyclopropyl(2-hydroxyethyl)amino]propoxy}-6-methoxyquinazolin-4-yl)amino]-1H-pyrazol-1-yl}-N-(2,3-difluorophenyl)acetamide;

N-(2,3-difluorophenyl)-2-{4-[(7-{3-[(2-hydroxyethyl)(2-methoxyethyl)amino]propoxy}-6-methoxyquinazolin-4-yl)amino]-1H-pyrazol-1-yl}acetamide;

2-{4-[(7-{3-[cyclobutyl(2-hydroxyethyl)amino]propoxy}-6-methoxyquinazolin-4-yl)amino]-1H-pyrazol-1-yl}-N-(2,3-difluorophenyl)acetamide;

2-{4-[(7-{3-[(cyclopropylmethyl)(2-hydroxyethyl)amino]propoxy}-6-methoxyquinazolin-4-yl)amino]-1H-pyrazol-1-yl}-N-(2,3-difluorophenyl)acetamide;

2-{4-[(7-{3-[(cyclobutylmethyl)(2-hydroxyethyl)amino]propoxy}-6-methoxyquinazolin-4-yl)amino]-1H-pyrazol-1-yl}-N-(2,3-difluorophenyl)acetamide;

N-(2,3-difluorophenyl)-2-{4-[(7-{3-[(2-hydroxyethyl)(prop-2-yn-1-yl)amino]propoxy}-6-methoxyquinazolin-4-yl)amino]-1H-pyrazol-1-yl}acetamide;

2-{4-[(7-{3-[allyl(2-hydroxyethyl)amino]propoxy}-6-methoxyquinazolin-4-yl)amino]-1H-pyrazol-1-yl}-N-(2,3-difluorophenyl)acetamide;

N-(2,3-difluorophenyl)-2-{4-[(7-{3-[(2,2-dimethylpropyl)(2-hydroxyethyl)amino]propoxy}-6-methoxyquinazolin-4-yl)amino]-1H-pyrazol-1-yl}acetamide;

N-(2,3-difluorophenyl)-2-{4-[(7-{3-[(2-hydroxyethyl)(3,3,3-trifluoropropyl)amino]propoxy}-6-methoxyquinazolin-4-yl)amino]-1H-pyrazol-1-yl}acetamide;

N-(2,3-difluorophenyl)-2-{4-[(7-{2-[(2R)-2-(hydroxymethyl)pyrrolidin-1-yl]ethoxy}-6-methoxyquinazolin-4-yl)amino]-1H-pyrazol-1-yl}acetamide;

N-(2,3-difluorophenyl)-2-(4-{[7-(2-{4-[2-(2-hydroxyethoxy)ethyl]piperazin-1-yl}ethoxy)-6-methoxyquinazolin-4-yl]amino}-1H-pyrazol-1-yl)acetamide;

N-(2,3-difluorophenyl)-2-{4-[(7-{2-[2-(hydroxymethyl)piperidin-1-yl]ethoxy}-6-methoxyquinazolin-4-yl)amino]-1H-pyrazol-1-yl}acetamide;

N-(2,3-difluorophenyl)-2-{4-[(7-{2-[(2-hydroxy-1,1-dimethylethyl)amino]ethoxy}-6-methoxyquinazolin-4-yl)amino]-1H-pyrazol-1-yl}acetamide;

N-(2,3-difluorophenyl)-2-{4-[(7-{2-[4-(2-hydroxyethyl)piperazin-1-yl]ethoxy}-6-methoxyquinazolin-4-yl)amino]-1H-pyrazol-1-yl}acetamide;

N-(2,3-difluorophenyl)-2-{4-[(7-{2-[(trans-4-hydroxycyclohexyl)amino]ethoxy}-6-methoxyquinazolin-4-yl)amino]-1H-pyrazol-1-yl}acetamide;

N-(2,3-difluorophenyl)-2-{4-[(7-{2-[3-(hydroxymethyl)piperidin-1-yl]ethoxy}-6-methoxyquinazolin-4-yl)amino]-1H-pyrazol-1-yl}acetamide;

N-(2,3-difluorophenyl)-2-(4-{[7-(2-{[1-(hydroxymethyl)cyclopentyl]amino}ethoxy)-6-methoxyquinazolin-4-yl]amino}-1H-pyrazol-1-yl)acetamide;

N-(2,3-difluorophenyl)-2-{4-[(7-{2-[4-(3-hydroxypropyl)piperazin-1-yl]ethoxy}-6-methoxyquinazolin-4-yl)amino]-1H-pyrazol-1-yl}acetamide;

2-{4-[(7-{2-[cyclohexyl(2-hydroxyethyl)amino]ethoxy}-6-methoxyquinazolin-4-yl)amino]-1H-pyrazol-1-yl}-N-(2,3-difluorophenyl)acetamide;

N-(2,3-difluorophenyl)-2-{4-[(7-{2-[(2-hydroxyethyl)(propyl)amino]ethoxy}-6-methoxyquinazolin-4-yl)amino]-1H-pyrazol-1-yl}acetamide;

N-(2,3-difluorophenyl)-2-{4-[(7-{2-[(3-hydroxy-2,2-dimethylpropyl)amino]ethoxy}-6-methoxyquinazolin-4-yl)amino]-1H-pyrazol-1-yl}acetamide;

N-(2,3-difluorophenyl)-2-[4-({6-methoxy-7-[2-(tetrahydro-2H-pyran-4-ylamino)ethoxy]quinazolin-4-yl}amino)-1H-pyrazol-1-yl]acetamide;

2-{4-[(7-{2-[cyclobutyl(2-hydroxyethyl)amino]ethoxy}-6-methoxyquinazolin-4-yl)amino]-1H-pyrazol-1-yl}-N-(2,3-difluorophenyl)acetamide;

N-(2,3-difluorophenyl)-2-{4-[(7-{2-[(2-hydroxyethyl)(tetrahydro-2H-pyran-4-yl)amino]ethoxy}-6-methoxyquinazolin-4-yl)amino]-1H-pyrazol-1-yl}acetamide;

N-(2,3-difluorophenyl)-2-{4-[(7-{2-[(2S)-2-(hydroxymethyl)pyrrolidin-1-yl]ethoxy}-6-methoxyquinazolin-4-yl)amino]-1H-pyrazol-1-yl}acetamide;

N-(2,3-difluorophenyl)-2-{4-[(7-{2-[(2R)-2-(2-hydroxyethyl)piperidin-1-yl]ethoxy}-6-methoxyquinazolin-4-yl)amino]-1H-pyrazol-1-yl}acetamide;

N-(2,3-difluorophenyl)-2-{4-[(7-{2-[(2S)-2-(2-hydroxyethyl)piperidin-1-yl]ethoxy}-6-methoxyquinazolin-4-yl)amino]-1H-pyrazol-1-yl}acetamide;

N-(2,3-difluorophenyl)-2-{4-[(7-{3-[(2-hydroxyethyl)(propyl)amino]propoxy}quinazolin-4-yl)amino]-1H-pyrazol-1-yl}acetamide;

N-(2,3-difluorophenyl)-2-{4-[(7-{3-[(2-hydroxyethyl)(isobutyl)amino]propoxy}quinazolin-4-yl)amino]-1H-pyrazol-1-yl}acetamide;

N-(2,3-difluorophenyl)-2-{4-[(7-{3-[(2S)-2-(hydroxymethyl)pyrrolidin-1-yl]propoxy}quinazolin-4-yl)amino]-1H-pyrazol-1-yl}acetamide;

N-(2,3-difluorophenyl)-2-{4-[(7-{3-[(2R)-2-(hydroxymethyl)pyrrolidin-1-yl]propoxy}quinazolin-4-yl)amino]-1H-pyrazol-1-yl}acetamide;

2-{4-[(7-{3-[cyclopentyl(2-hydroxyethyl)amino]propoxy}quinazolin-4-yl)amino]-1H-pyrazol-1-yl}-N-(2,3-difluorophenyl)acetamide;

N-(2,3-difluorophenyl)-2-{4-[(7-{3-[ethyl(2-hydroxyethyl)amino]propoxy}quinazolin-4-yl)amino]-1H-pyrazol-1-yl}acetamide;

N-(2,3-difluorophenyl)-2-{4-[(7-{3-[4-(2-hydroxyethyl)piperazin-1-yl]propoxy}quinazolin-4-yl)amino]-1H-pyrazol-1-yl}acetamide;

N-(2,3-difluorophenyl)-2-{4-[(7-{3-[4-(hydroxymethyl)piperidin-1-yl]propoxy}quinazolin-4-yl)amino]-1H-pyrazol-1-yl}acetamide;

N-(2,3-difluorophenyl)-2-{4-[(7-{3-[(3-hydroxy-1,1-dimethylpropyl)amino]propoxy}quinazolin-4-yl)amino]-1H-pyrazol-1-yl}acetamide;

2-{4-[(7-{3-[(2-cyanoethyl)(2-hydroxyethyl)amino]propoxy}quinazolin-4-yl)amino]-1H-pyrazol-1-yl}-N-(2,3-difluorophenyl)acetamide;

N-(2,3-difluorophenyl)-2-(4-{[7-(3-morpholin-4-ylpropoxy)quinazolin-4-yl]amino}-1H-pyrazol-1-yl)acetamide;

N-(2,3-difluorophenyl)-2-{4-[(7-{3-[(3-hydroxy-2,2-dimethylpropyl)amino]propoxy)quinazolin-4-yl)amino]-1H-pyrazol-1-yl}acetamide;

N-(2,3-difluorophenyl)-2-{4-[(7-{3-[(3-hydroxypropyl)amino]propoxy}quinazolin-4-yl)amino]-1H-pyrazol-1-yl}acetamide;

N-(2,3-difluorophenyl)-2-{4-[(7-{3-[(3-hydroxypropyl)(propyl)amino]propoxy}quinazolin-4-yl)amino]-1H-pyrazol-1-yl}acetamide;

N-(2,3-difluorophenyl)-2-{4-[(7-{3-[ethyl(3-hydroxypropyl)amino]propoxy}quinazolin-4-yl)amino]-1H-pyrazol-1-yl}acetamide;

N-(2,3-difluorophenyl)-2-{4-[(7-{3-[4-(2-hydroxyethyl)-3-oxopiperazin-1-yl]propoxy}quinazolin-4-yl)amino]-1H-pyrazol-1-yl}acetamide;

N-(2,3-difluorophenyl)-2-[4-({7-[3-(propylamino)propoxy]quinazolin4-yl)amino)-1H-pyrazol-1-yl]acetamide;

N-(2,3-difluorophenyl)-2-(4-{[7-(3-piperazin-1-ylpropoxy)quinazolin-4-yl]amino}-1H-pyrazol-1-yl)acetamide;

N-(2,3-difluorophenyl)-2-{4-[(7-{3-[glycoloyl(propyl)amino]propoxy}quinazolin-4-yl)amino]-1H-pyrazol-1-yl}acetamide;

N-(2,3-difluorophenyl)-2-[4-({7-[3-(4-glycoloylpiperazin-1-yl)propoxy]quinazolin-4-yl}amino)-1H-pyrazol-1-yl]acetamide;

N-(2,3-difluorophenyl)-2-(4-{[7-(3-{[trans-2-(hydroxymethyl)cyclohexyl]amino}propoxy)quinazolin-4-yl]amino}-1H-pyrazol-1-yl)acetamide;

N-(2,3-difluorophenyl)-2-{4-[(7-{3-[(1α,5α,6α)-6-(hydroxymethyl)-3-azabicyclo[3.1.0]hex-3-yl]propoxy}quinazolin-4-yl)amino]-1H-pyrazol-1-yl}acetamide;

N-(2,3-difluorophenyl)-2-(4-{[7-(3-{[(2R)-2-hydroxypropyl]amino}propoxy)quinazolin-4-yl]amino}-1H-pyrazol-1-yl)acetamide;

N-(2,3-difluorophenyl)-2-(4-{[7-(3-{[(1S)-2-hydroxy-1-methylethyl]amino}propoxy)quinazolin-4-yl]amino}-1H-pyrazol-1-yl)acetamide;

N-(2,3-difluorophenyl)-2-{4-[(7-{3-[(2-hydroxy-1,1-dimethylethyl)amino]propoxy}quinazolin-4-yl)amino]-1H-pyrazol-1-yl}acetamide;

N-(2,3-difluorophenyl)-2-{4-[(7-{3-[(2,3-dihydroxypropyl)amino]propoxy}quinazolin-4-yl)amino]-1H-pyrazol-1-yl}acetamide;

N-(2,3-difluorophenyl)-2-(4-{[7-(3-{[2-(2-hydroxyethoxy)ethyl]amino}propoxy)quinazolin-4-yl]amino}-1H-pyrazol-1-yl)acetamide;

2-[4-({7-[3-(4-acetylpiperazin-1-yl)propoxy]quinazolin-4-yl}amino)-1H-pyrazol-1-yl]-N-(2,3-difluorophenyl)acetamide;

N-(2,3-difluorophenyl)-2-{4-[(7-{3-[(tetrahydrofuran-2-ylmethyl)amino]propoxy}quinazolin-4-yl)amino]-1H-pyrazol-1-yl}acetamide;

2-[4-({7-[3-(allylamino)propoxy]quinazolin-4-yl}amino)-1H-pyrazol-1-yl]-N-(2,3-difluorophenyl)acetamide;

N-(2,3-difluorophenyl)-2-(4-{[7-(3-{[1-(hydroxymethyl)-2-methylpropyl]amino}propoxy)quinazolin-4-yl]amino}-1H-pyrazol-1-yl)acetamide;

N-(2,3-difluorophenyl)-2-(4-{[7-(3-{[(5-methylisoxazol-3-yl)methyl]amino}propoxy)quinazolin-4-yl]amino}-1H-pyrazol-1-yl)acetamide;

N-(2,3-difluorophenyl)-2-[4-({7-[3-(tetrahydro-2H-pyran-4-ylamino)propoxy]quinazolin-4-yl}amino)-1H-pyrazol-1-yl]acetamide;

N-(2,3-difluorophenyl)-2-{4-[(7-{3-[(3S)-3-(hydroxymethyl)pyrrolidin-1-yl]propoxy}quinazolin-4-yl)amino]-1H-pyrazol-1-yl}acetamide;

N-(2,3-difluorophenyl)-2-(4-{[7-(3-hydroxypropoxy)quinazolin-4-yl]amino}-1H-pyrazol-1-yl)acetamide;

2-(4-{[7-(3-aminopropoxy)quinazolin-4-yl]amino}-1H-pyrazol-1-yl)-N-(2,3-difluorophenyl)acetamide;

N-(2,3-difluorophenyl)-2-{4-[(7-{3-[(2S,4R)-4-hydroxy-2-(hydroxymethyl)pyrrolidin-1-yl]propoxy}quinazolin-4-yl)amino]-1H-pyrazol-1-yl}acetamide;

N-(2,3-difluorophenyl)-2-{4-[(7-{2-[(3-hydroxy-2,2-dimethylpropyl)amino]ethoxy}quinazolin-4-yl)amino]-1H-pyrazol-1-yl}acetamide;

2-{4-[(7-{2-[cyclohexyl(2-hydroxyethyl)amino]ethoxy}quinazolin-4-yl)amino]-1H-pyrazol-1-yl}-N-(2,3-difluorophenyl)acetamide;

2-[4-({7-[2-(cyclopropylamino)ethoxy]quinazolin-4-yl}amino)-1H-pyrazol-1-yl]-N-(2,3-difluorophenyl)acetamide;

2-[4-({7-[2-(cyclobutylamino)ethoxy]quinazolin-4-yl}amino)-1H-pyrazol-1-yl]-N-(2,3-difluorophenyl)acetamide;

N-(2,3-difluorophenyl)-2-[4-({7-[2-(tetrahydro-2H-pyran-4-ylamino)ethoxy]quinazolin-4-yl}amino)-1H-pyrazol-1-yl]acetamide;

2-[4-({7-[2-(cyclopentylamino)ethoxy]quinazolin-4-yl}amino)-1H-pyrazol-1-yl]-N-(2,3-difluorophenyl)acetamide;

N-(2,3-difluorophenyl)-2-{4-[(7-{2-[(2-hydroxyethyl)(tetrahydro-2H-pyran-4-yl)amino]ethoxy}quinazolin-4-yl)amino]-1H-pyrazol-1-yl}acetamide;

2-{4-[(7-{2-[cyclopentyl(2-hydroxyethyl)amino]ethoxy}quinazolin-4-yl)amino]-1H-pyrazol-1-yl}-N-(2,3-difluorophenyl)acetamide;

N-(2,3-difluorophenyl)-2-{4-[(7-{2-[(2R)-2-(hydroxymethyl)pyrrolidin-1-yl]ethoxy)quinazolin-4-yl)amino]-1H-pyrazol-1-yl}acetamide;

2-{4-[(7-{2-[cyclopropyl(2-hydroxyethyl)amino]ethoxy}quinazolin-4-yl)amino]-1H-pyrazol-1-yl}-N-(2,3-difluorophenyl)acetamide;

2-{4-[(7-{2-[cyclobutyl(2-hydroxyethyl)amino]ethoxy}quinazolin-4-yl)amino]-1H-pyrazol-1-yl}-N-(2,3-difluorophenyl)acetamide;

2-(4-[(7-(2-[cyclopentyl(3-hydroxypropyl)amino]ethoxy}quinazolin-4-yl)amino]-1H-pyrazol-1-yl}-N-(2,3-difluorophenyl)acetamide;

2-{4-[(7-{2-[cyclopentyl(glycoloyl)amino]ethoxy}quinazolin-4-yl)amino]-1H-pyrazol-1-yl}-N-(2,3-difluorophenyl)acetamide;

N-(2,3-difluorophenyl)-2-{4-[(7-{2-[(3S)-3-(hydroxymethyl)-4-methylpiperazin-1-yl]ethoxy}quinazolin-4-yl)amino]-1H-pyrazol-1-yl}acetamide;

N-(2,3-difluorophenyl)-2-{4-[(7-{2-[(2S)-2-(hydroxymethyl)pyrrolidin-1-yl]ethoxy}quinazolin-4-yl)amino]-1H-pyrazol-1-yl}acetamide;

N-(2,3-difluorophenyl)-2-{4-[(7-{2-[(2R)-2-(hydroxymethyl)-4-methylpiperazin-1-yl]ethoxy}quinazolin-4-yl)amino]-1H-pyrazol-1-yl}acetamide;

N-(2,3-difluorophenyl)-2-{4-[(7-{2-[4-(hydroxymethyl)piperidin-1-yl]ethoxy}quinazolin-4-yl)amino]-1H-pyrazol-1-yl}acetamide;

N-(2,3-difluorophenyl)-2-{4-[(7-{2-[4-(2-hydroxyethyl)piperidin-1-yl]ethoxy}quinazolin-4-yl)amino]-1H-pyrazol-1-yl}acetamide;

N-(2,3-difluorophenyl)-2-{4-[(7-{2-[(2-hydroxyethyl)amino]ethoxy}quinazolin-4-yl)amino]-1H-pyrazol-1-yl}acetamide;

N-(2,3-difluorophenyl)-2-(4-{[7-(2-{[trans-2-(hydroxymethyl)cyclohexyl]amino}ethoxy)quinazolin-4-yl]amino}-1H-pyrazol-1-yl)acetamide;

N-(2,3-difluorophenyl)-2-{4-[(7-{3-[(2-hydroxyethyl)amino]propoxy}quinazolin-4-yl)amino]-1H-pyrazol-1-yl}acetamide;

N-(2,3-difluorophenyl)-2-(4-{[7-(3-pyrrolidin-1-ylpropoxy)quinazolin-4-yl]amino}-1H-pyrazol-1-yl)acetamide;

N-(2,3-difluorophenyl)-2-{4-[(7-methoxyquinazolin-4-yl)amino]-1H-pyrazol-1-yl}acetamide;

N-(2,3-difluorophenyl)-2-{4-[(7-{3-[(2-hydroxyethyl)(tetrahydro-2H-pyran-4-yl)amino]propoxy}quinazolinyl-4-yl)amino]-1H-pyrazol-1-yl}acetamide;

N-(2,3-difluorophenyl)-2-{4-[(7-{3-[(2R)-2-(2-hydroxyethyl)piperidin-1-yl]propoxy}quinazolin-4-yl)amino]-1H-pyrazol-1-yl}acetamide;

N-(2,3-difluorophenyl)-2-{4-[(7-{3-[(2S)-2-(2-hydroxyethyl)piperidin-1-yl]propoxy}quinazolin-4-yl)amino]-1H-pyrazol-1-yl}acetamide;

N-(2,3-difluorophenyl)-2-{4-[(7-{3-[(2R)-2-(hydroxymethyl)-4-methylpiperazin-1-yl]propoxy}quinazolin-4-yl)amino]-1H-pyrazol-1-yl}acetamide;

N-(2,3-difluorophenyl)-2-{4-[(7-{3-[(3S)-3-(hydroxymethyl)-4-methylpiperazin-1-yl]propoxy}quinazolin-4-yl)amino]-1H-pyrazol-1-yl}acetamide;

N-(2,3-difluorophenyl)-2-{4-[(7-{3-[(2R)-2-(hydroxymethyl)morpholin-4-yl]propoxy}quinazolin-4-yl)amino]-1H-pyrazol-1-yl}acetamide;

N-(2,3-difluorophenyl)-2-{4-[(7-{3-[(3S)-3-(hydroxymethyl)morpholin-4-yl]propoxy}quinazolin-4-yl)amino]-1H-pyrazol-1-yl}acetamide;

N-(2,3-difluorophenyl)-2-[4-({7-[3-(glycoloylamino)propoxy]quinazolin-4-yl}amino)-1H-pyrazol-1-yl]acetamide;

N-(3-fluorophenyl)-2-{4-[(7-{3-[(2-hydroxyethyl)(propyl)amino]propoxy}quinazolin-4-yl)amino]-1H-pyrazol-1-yl}acetamide;

2-{4-[(7-{3-[ethyl(2-hydroxyethyl)amino]propoxy}quinazolin-4-yl)amino]-1H-pyrazol-1-yl}-N-(3-fluorophenyl)acetamide;

N-(3-fluorophenyl)-2-{4-[(7-{3-[(2R)-2-(hydroxymethyl)pyrrolidin-1-yl]propoxy}quinazolin-4-yl)amino]-1H-pyrazol-1-yl}acetamide;

N-(3-fluorophenyl)-2-{4-[(7-{3-[4-hydroxymethyl)piperidin-1-yl]propoxy}quinazolin-4-yl)amino]-1H-pyrazol-1-yl}acetamide;

N-(3-fluorophenyl)-2-{4-[(7-{3-[(3-hydroxy-1,1-dimethylpropyl)amino]propoxy}quinazolin-4-yl)amino]-1H-pyrazol-1-yl}acetamide;

N-(3-fluorophenyl)-2-{4-[(7-{3-[2-(2-hydroxyethyl)piperidin-1-yl]propoxy}quinazolin-4-yl)amino]-1H-pyrazol-1-yl}acetamide;

N-(3-fluorophenyl)-2-{4-[(7-{3-[4-(2-hydroxyethyl)piperazin-1-yl]propoxy}quinazolin-4-yl)amino]-1H-pyrazol-1-yl}acetamide;

N-(3-fluorophenyl)-2-{4-[(7-{3-[(2-hydroxyethyl)(tetrahydrofuran-3-yl)amino]propoxy}quinazolin-4-yl)amino]-1H-pyrazol-1-yl}acetamide;

N-(3-fluorophenyl)-2-(4-{[7-(3-morpholin-4-ylpropoxy)quinazolin-4-yl]amino}-1H-pyrazol-1-yl)acetamide;

N-(3-fluorophenyl)-2-[4-({7-[(2S)-pyrrolidin-2-ylmethoxy]quinazolin-4-yl}amino)-1H-pyrazol-1-yl]acetamide;

N-(3-fluorophenyl)-2-{4-[(7-{[(2S)-1-(2-hydroxyethyl)pyrrolidin-2-yl]methoxy}quinazolin-4-yl)amino]-1H-pyrazol-1-yl}acetamide;

N-(3-fluorophenyl)-2-{4-[(7-{[(2S)-1-glycoloylpyrrolidin-2-yl]methoxy}quinazolin-4-yl)amino]-1H-pyrazol-1-yl}acetamide;

N-(3-fluorophenyl)-2-(4-{[7-(pyrrolidin-3-ylmethoxy)quinazolin-4-yl]amino}-1H-pyrazol-1-yl)acetamide;

N-(3-fluorophenyl)-2-{4-[(7-{[1-(2-hydroxyethyl)pyrrolidin-3-yl]methoxy}quinazolin-4-yl)amino]-1H-pyrazol-1-yl}acetamide;

N-(3-fluorophenyl)-2-[4-({7-[(1-glycoloylpyrrolidin-3-yl)methoxy]quinazolin-4-yl}amino)-1H-pyrazol-1-yl]acetamide;

N-(3-fluorophenyl)-2-{4-[(7-{3-[(2-hydroxyethyl)(2-methoxyethyl)amino]propoxy}quinazolin-4-yl)amino]-1H-pyrazol-1-yl}acetamide;

N-(3-fluorophenyl)-2-{4-[(7-hydroxyquinazolin-4-yl)amino]-1H-pyrazol-1-yl}acetamide;

N-(2-fluorophenyl)-2-{4-[(7-{3-[(2R)-2-(hydroxymethyl)pyrrolidin-1-yl]propoxy}quinazolin-4-yl)amino]-1H-pyrazol-1-yl}acetamide;

2-{4-[(7-{3-[ethyl(2-hydroxyethyl)amino]propoxy}quinazolin-4-yl)amino]-1H-pyrazol-1-yl}-N-(2-fluorophenyl)acetamide;

2-{4-[(7-{3-[(2R)-2-(hydroxymethyl)pyrrolidin-1-yl]propoxy}quinazolin-4-yl)amino]-1H-pyrazol-1-yl}-N-phenylacetamide;

2-{4-[(7-{3-[ethyl(2-hydroxyethyl)amino]propoxy}quinazolin-4-yl)amino]-1H-pyrazol-1-yl}-N-phenylacetamide;

N-(2,6-difluorophenyl)-2-{4-[(7-{3-[(2R)-2-(hydroxymethyl)pyrrolidin-1-yl]propoxy}quinazolin-4-yl)amino]-1H-pyrazol-1-yl}acetamide;

2-{4-[(7-{3-[ethyl(2-hydroxyethyl)amino]propoxy}-6-fluoroquinazolin-4-yl)amino]-1H-pyrazol-1-yl}-N-(3-fluorophenyl)acetamide;

2-{4-[(7-{3-[(cyclopropylmethyl)(2-hydroxyethyl)amino]propoxy}-6-fluoroquinazolin-4-yl)amino]-1H-pyrazol-1-yl}-N-(2,3-difluorophenyl)acetamide;

N-(2,3-difluorophenyl)-2-{4-[(6-fluoro-7-{3-[(2-hydroxyethyl)(propyl)amino]propoxy}quinazolin-4-yl)amino]-1H-pyrazol-1-yl}acetamide;

N-(2,3-difluorophenyl)-2-{4-[(6-fluoro-7-{3-[(2R)-2-(hydroxymethyl)pyrrolidin-1-yl]propoxy}quinazolin-4-yl)amino]-1H-pyrazol-1-yl}acetamide;

2-{4-[(7-{3-[cyclopentyl(2-hydroxyethyl)amino]propoxy}-6-fluoroquinazolin-4-yl)amino]-1H-pyrazol-1-yl}-N-(2,3-difluorophenyl)acetamide;

2-{4-[(7-{3-[bis(2-hydroxyethyl)amino]propoxy}-5-isopropoxyquinazolin-4-yl)amino]-1H-pyrazol-1-yl}-N-(2,3-difluorophenyl)acetamide;

N-(2,3-difluorophenyl)-2-{4-[(7-{3-[(2R)-2-(hydroxymethyl)pyrrolidin-1-yl]propoxy}-5-isopropoxyquinazolin-4-yl)amino]-1H-pyrazol-1-yl}acetamide;

N-(2,3-difluorophenyl)-2-{4-[(7-{3-[4-(2-hydroxyethyl)piperazin-1-yl]propoxy}-5-isopropoxyquinazolin-4-yl)amino]-1H-pyrazol-1-yl}acetamide;

N-(2,3-difluorophenyl)-2-(4-{[5-isopropoxy-7-(3-piperazin-1-ylpropoxy)quinazolin-4-yl]amino}-1H-pyrazol-1-yl)acetamide;

N-(2,3-difluorophenyl)-2-{4-[(7-{3-[(2S)-2-(hydroxymethyl)pyrrolidin-1-yl]propoxy}-5-isopropoxyquinazolin-4-yl)amino]-1H-pyrazol-1-yl}acetamide;

N-(2,3-difluorophenyl)-2-{4-[(7-{3-[(2-hydroxyethyl)amino]propoxy}-5-isopropoxyquinazolin-4-yl)amino]-1H-pyrazol-1-yl}acetamide;

N-(2,3-difluorophenyl)-2-[4-({7-[3-(4-glycoloylpiperazin-1-yl)propoxy]-5-isopropoxyquinazolin-4-yl}amino)-1H-pyrazol-1-yl]acetamide;

N-(2,3-difluorophenyl)-2-{4-[(7-{3-[(2R)-2-(hydroxymethyl)pyrrolidin-1-yl]propoxy}-5-methoxy-quinazolin-4-yl)amino]-1H-pyrazol-1-yl}acetamide;

N-(2,3-difluorophenyl)-2-{4-[(5,7-dimethoxyquinazolin-4-yl)amino]-1H-pyrazol-1-yl}acetamide;

N-(2,3-difluorophenyl)-2-{4-[(5-hydroxy-7-methoxyquinazolin-4-yl)amino]-1H-pyrazol-1-yl}acetamide;

N-(2,3-difluorophenyl)-2-[4-({7-methoxy-5-[(2R)-pyrrolidin-2-ylmethoxy]quinazolin-4-yl}amino)-1H-pyrazol-1-yl]acetamide;

N-(2,3-difluorophenyl)-2-{4-[(5-{[(2R)-1-glycoloylpyrrolidin-2-yl]methoxy}-7-methoxyquinazolin-4-yl)amino]-1H-pyrazol-1-yl}acetamide;

N-(2,3-difluorophenyl)-2-{4-[(5-{[(2R)-1-(N,N-dimethylglycyl)pyrrolidin-2-yl]methoxy}-7-methoxyquinazolin-4-yl)amino]-1H-pyrazol-1-yl}acetamide;

N-(2,3-difluorophenyl)-2-{4-[(5-{[(2R)-1-(2-hydroxyethyl)pyrrolidin-2-yl]methoxy}-7-methoxyquinazolin-4-yl)amino]-1H-pyrazol-1-yl}acetamide;

N-(2,3-difluorophenyl)-2-{4-[(5-methoxyquinazolin-4-yl)amino]-1H-pyrazol-1-yl}acetamide;

N-(2,3-difluorophenyl)-2-{4-[(5-fluoroquinazolin-4-yl)amino]-1H-pyrazol-1-yl}acetamide;

N-(3-fluorophenyl)-2-(4-{[7-methoxy-6-(3-morpholin-4-ylpropoxy)quinazolin-4-yl]amino}-1H-pyrazol-1-yl)acetamide;

N-(3-fluorophenyl)-2-[4-({7-methoxy-6-[(1-methylpyrrolidin-3-yl)oxy]quinazolin-4-yl}amino)-1H-pyrazol-1-yl]acetamide;

N-(3-fluorophenyl)-2-(4-{[7-methoxy-6-(2-morpholin-4-ylethoxy)quinazolin-4-yl]amino}-1H-pyrazol-1-yl)acetamide;

2-(4-{[6,7-bis(2-methoxyethoxy)quinazolin-4-yl]amino}-1H-pyrazol-1-yl)-N-(2,3-difluorophenyl)acetamide;

N-(3-fluorophenyl)-2-{4-[(6-hydroxy-7-methoxyquinazolin-4-yl)amino]-1H-pyrazol-1-yl}acetamide;

4-((1-(2-((2,3-difluorophenyl)amino)-2-oxoethyl)-1H-pyrazol-4-yl)amino)-7-((1-methylpiperidin-4-yl)methoxy)quinazolin-6-yl benzoate;

N-(2,3-difluorophenyl)-2-(4-((6-hydroxy-7-((1-methylpiperidin-4-yl)methoxy)quinazolin-4-yl)amino)-1H-pyrazol-1-yl)acetamide;

1-{2-[(3-fluorophenyl)amino]-2-oxoethyl}-4-[(7-{3-[(2-hydroxyethyl)(2-methoxyethyl)amino]propoxy}-6-methoxyquinazolin-4-yl)amino]-1H-pyrazole-3-carboxamide;

1-{2-[(3-fluorophenyl)amino]-2-oxoethyl}-4-[(7-{3-[(2S)-2-(hydroxymethyl)pyrrolidin-1-yl]propoxy}-6-methoxyquinazolin-4-yl)amino]-1H-pyrazole-3-carboxamide;

2-{3-(acetylamino)-4-[(7-{3-[(2R)-2-(hydroxymethyl)pyrrolidin-1-yl]propoxy}quinazolin-4-yl)amino]-1H-pyrazol-1-yl}-N-(3-fluorophenyl)acetamide;

ethyl 1-{2-[(3-fluorophenyl)amino]-2-oxoethyl}-4-[(7-{3-[(2R)-2-(hydroxymethyl)pyrrolidin-1-yl]propoxy}quinazolin-4-yl)amino]-1H-pyrazole-3-carboxylate;

1-{2-[(3-fluorophenyl)amino]-2-oxoethyl}-4-[(7-{3-[(2R)-2-(hydroxymethyl)pyrrolidin-1-yl]propoxy}quinazolin-4-yl)amino]-1H-pyrazole-3-carboxylic acid;

or a salt, ester or prodrug thereof, or more particularly a pharmaceutically acceptable salt thereof.

A further particular compound of formula (I) is any one of:

2-(4-{[7-(3-chloropropoxy)-6-methoxyquinazolin-4-yl]amino}-1H-pyrazol-1-yl)-N-(3-fluorophenyl)acetamide;

2-(4-{[7-(3-chloropropoxy)-6-methoxyquinazolin-4-yl]amino}-1H-pyrazol-1-yl)-N-(2,3-difluorophenyl)acetamide;

2-(4-{[7-(2-chloroethoxy)-6-methoxyquinazolin-4-yl]amino}-1H-pyrazol-1-yl)-N-(2,3-difluorophenyl)acetamide;

4-{[7-(3-chloropropoxy)-6-methoxyquinazolin-4-yl]amino}-1-{2-[(3-fluorophenyl)amino]-2-oxoethyl}-1H-pyrazole-3-carboxamide;

2-(4-{[7-(3-chloropropoxy)-6-fluoroquinazolin-4-yl]amino}-1H-pyrazol-1-yl)-N-(2,3-difluorophenyl)acetamide;

2-(4-{[7-(3-chloropropoxy)-6-fluoroquinazolin-4-yl]amino}-1H-pyrazol-1-yl)-N-(3-fluorophenyl)acetamide;

N-(3-fluorophenyl)-2-{4-[(7-{3-[(2S)-2-(hydroxymethyl)pyrrolidin-1-yl]propoxy}-6-methoxyquinazolin-4-yl)amino]-1H-pyrazol-1-yl}acetamide;

N-(3-fluorophenyl)-2-{4-[(7-{3-[(2-hydroxyethyl)(isobutyl)amino]propoxy}-6-methoxyquinazolin-4-yl)amino]-1H-pyrazol-1-yl}acetamide;

N-(3-fluorophenyl)-2-{4-[(7-{3-[(2-hydroxyethyl)(propyl)amino]propoxy}-6-methoxyquinazolin-4-yl)amino]-1H-pyrazol-1-yl}acetamide;

N-(3-fluorophenyl)-2-(4-{[6-methoxy-7-(3-piperidin-1-ylpropoxy)quinazolin-4-yl]amino}-1H-pyrazol-1-yl)acetamide;

N-(3-fluorophenyl)-2-(4-{[6-methoxy-7-(3-pyrrolidin-1-ylpropoxy)quinazolin-4-yl]amino}-1H-pyrazol-1-yl)acetamide;

2-[4-({7-[3-(diethylamino)propoxy]-6-methoxyquinazolin-4-yl}amino)-1H-pyrazol-1-yl]-N-(3-fluorophenyl)acetamide;

N-(3-fluorophenyl)-2-(4-{[6-methoxy-7-(3-piperazin-1-ylpropoxy)quinazolinyl-4-yl]amino}-1H-pyrazol-1-yl)acetamide;

N-(3-fluorophenyl)-2-{4-[(7-{3-[(2-hydroxyethyl)(methyl)amino]propoxy}-6-methoxyquinazolin-4-yl)amino]-1H-pyrazol-1-yl}acetamide;

2-[4-({7-[3-(cyclopropylamino)propoxy]-6-methoxyquinazolin-4-yl}amino)-1H-pyrazol-1-yl]-N-(3-fluorophenyl)acetamide;

2-{4-[(7-{3-[[2-(dimethylamino)ethyl](methyl)amino]propoxy}-6-methoxyquinazolin-4-yl)amino]-1H-pyrazol-1-yl}-N-(3-fluorophenyl)acetamide;

N-(3-fluorophenyl)-2-[4-({6-methoxy-7-[3-(4-methylpiperazin-1-yl)propoxy]quinazolin-4-yl}amino)-1H-pyrazol-1-yl]acetamide;

N-(3-fluorophenyl)-2-{4-[(7-{3-[(2R)-2-(hydroxymethyl)pyrrolidin-1-yl]propoxy}-6-methoxyquinazolin-4-yl)amino]-1H-pyrazol-1-yl}acetamide;

N-(3-fluorophenyl)-2-[4-({7-[3-(4-hydroxypiperidin-1-yl)propoxy]-6-methoxyquinazolin-4-yl}amino)-1H-pyrazol-1-yl]acetamide;

2-{4-[(7-{3-[bis(2-hydroxyethyl)amino]propoxy}-6-methoxyquinazolin-4-yl)amino]-1H-pyrazol-1-yl}-N-(3-fluorophenyl)acetamide;

2-{4-[(7-{3-[ethyl(methyl)amino]propoxy}-6-methoxyquinazolin-4-yl)amino]-1H-pyrazol-1-yl}-N-(3-fluorophenyl)acetamide;

2-{4-[(7-{3-[ethyl(2-hydroxyethyl)amino]propoxy}-6-methoxyquinazolin-4-yl)amino]-1H-pyrazol-1-yl}-N-(3-fluorophenyl)acetamide;

2-{4-[(7-{3-[[2-(dimethylamino)ethyl](ethyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[2-(2-hydroxyethyl)piperidin-1-yl]propoxy}-6-methoxyquinazolin-4-yl)amino]-1H-pyrazol-1-yl}acetamide;

N-(3-fluorophenyl)-2-{4-[(7-{3-[4-(2-hydroxyethyl)piperazin-1-yl]propoxy}-6-methoxyquinazolin-4-yl)amino]-1H-pyrazol-1-yl}acetamide;

2-{4-[(7-{3-[(cyclopropylmethyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[4-(2-hydroxyethyl)piperidin-1-yl]propoxy}-6-methoxyquinazolin-4-yl)amino]-1H-pyrazol-1-yl}acetamide;

N-(3-fluorophenyl)-2-{4-[(6-methoxy-7-{3-[methyl(prop-2-yn-1-yl)amino]propoxy}quinazolin-4-yl)amino]-1H-pyrazol-1-yl}acetamide;

2-{4-[(7-{3-[allyl(methyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[isobutyl(methyl)amino]propoxy}-6-methoxyquinazolin-4-yl)amino]-1H-pyrazol-1-yl}acetamide;

N-(3-fluorophenyl)-2-[4-({7-[3-(3-hydroxypiperidin-1-yl)propoxy]-6-methoxyquinazolin-4-yl}amino)-1H-pyrazol-1-yl]acetamide;

N-(3-fluorophenyl)-2-{4-[(7-{3-[4-(hydroxymethyl)piperidin-1-yl]propoxy}-6-methoxyquinazolin-4-yl)amino]-1H-pyrazol-1-yl}acetamide;

N-(3-fluorophenyl)-2-{4-[(6-methoxy-7-{3-[methyl(propyl)amino]propoxy}quinazolin-4-yl)amino]-1H-pyrazol-1-yl}acetamide;

2-{-[(7-{3-[(cyclopropylmethyl)(propyl)amino]propoxy}-6-methoxyquinazolin-4-yl)amino]-1H-pyrazol-1-yl}-N-(3-fluorophenyl)acetamide;

2-{4-[(7-{3-[[2-(diethylamino)ethyl](methyl)amino]propoxy}-6-methoxyquinazolin-4-yl)amino]-1H-pyrazol-1-yl}-N-(3-fluorophenyl)acetamide;

2-{4-[(7-{3-[[2-(diethylamino)ethyl](ethyl)amino]propoxy}-6-methoxyquinazolin-4-yl)amino]-1H-pyrazol-1-yl}-N-(3-fluorophenyl)acetamide;

N-(3-fluorophenyl)-2-[4-({6-methoxy-7-[3-(4-methyl-1,4-diazepan-1-yl)propoxy]quinazolin-4-yl}amino)-1H-pyrazol-1-yl]acetamide;

N-(3-fluorophenyl)-2-{4-[(7-{3-[(2-hydroxyethyl)(isopropyl)amino]propoxy}-6-methoxyquinazolin-4-yl)amino]-1H-pyrazol-1-yl}acetamide;

2-{4-[(7-{3-[cyclopropyl(2-hydroxyethyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[(2-hydroxyethyl)(2-methoxyethyl)amino]propoxy}-6-methoxyquinazolin-4-yl)amino]-1H-pyrazol-1-yl}acetamide;

2-{4-[(7-{3-[cyclobutyl(2-hydroxyethyl)amino]propoxy}-6-methoxyquinazolin-4-yl)amino]-1H-pyrazol-1-yl}-N-(3-fluorophenyl)acetamide;

2-{4-[(7-{3-[(cyclopropylmethyl)(2-hydroxyethyl)amino]propoxy}-6-methoxyquinazolin-4-yl)amino]-1H-pyrazol-1-yl}-N-(3-fluorophenyl)acetamide;

2-{4-[(7-{3-[(cyclobutylmethyl)(2-hydroxyethyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[(2-hydroxyethyl)(prop-2-yn-1-yl)amino]propoxy}-6-methoxyquinazolin-4-yl)amino]-1H-pyrazol-1-yl}acetamide;

2-{4-[(7-{3-[allyl(2-hydroxyethyl)amino]propoxy}-6-methoxyquinazolin-4-yl)amino]-1H-pyrazol-1-yl}-N-(3-fluorophenyl)acetamide;

2-{4-[(7-{3-[(2,2-dimethylpropyl)(2-hydroxyethyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[(2-hydroxyethyl)(3,3,3-trifluoropropyl)amino]propoxy}-6-methoxyquinazolin-4-yl)amino]-1H-pyrazol-1-yl}acetamide;

2-(4-{[7-(3-azetidin-1-ylpropoxy)-6-methoxyquinazolin-4-yl]amino}-1H-pyrazol-1-yl)-N-(3-fluorophenyl)acetamide;

2-{4-[(6,7-dimethoxyquinazolin-4-yl)amino]-1H-pyrazol-1-yl}-N-(3-fluorophenyl)acetamide;

N-(3-fluorophenyl)-2-{4-[(7-hydroxy-6-methoxyquinazolin-4-yl)amino]-1H-pyrazol-1-yl}acetamide;

N-(2,3-difluorophenyl)-2-{4-[(7-{3-[(2-hydroxyethyl)(isobutyl)amino]propoxy}-6-methoxyquinazolin-4-yl)amino]-1H-pyrazol-1-yl}acetamide;

N-(2,3-difluorophenyl)-2-{4-[(7-{3-[(2S)-2-(hydroxymethyl)pyrrolidin-1-yl]propoxy}-6-methoxyquinazolin-4-yl)amino]-1H-pyrazol-1-yl}acetamide;

N-(2,3-difluorophenyl)-2-{4-[(7-{3-[(2-hydroxyethyl)(propyl)amino]propoxy}-6-methoxyquinazolin-4-yl)amino]-1H-pyrazol-1-yl}acetamide;
N-(2,3-difluorophenyl)-2-[4-({7-[3-(dimethylamino)propoxy]-6-methoxyquinazolin-4-yl}amino)-1H-pyrazol-1-yl]acetamide;
N-(2,3-difluorophenyl)-2-(4-{[6-methoxy-7-(3-piperidin-1-ylpropoxy)quinazolin-4-yl]amino}-1H-pyrazol-1-yl)acetamide;
N-(2,3-difluorophenyl)-2-(4-{[6-methoxy-7-(3-pyrrolidin-1-ylpropoxy)quinazolin-4-yl]amino}-1H-pyrazol-1-yl)acetamide;
N-(2,3-difluorophenyl)-2-(4-{[6-methoxy-7-(3-piperazin-1-ylpropoxy)quinazolin-4-yl]amino}-1H-pyrazol-1-yl)acetamide;
N-(2,3-difluorophenyl)-2-{4-[(7-{3-[(2-hydroxyethyl)(methyl)amino]propoxy}-6-methoxyquinazolin-4-yl)amino]-1H-pyrazol-1-yl}acetamide;
2-[4-({7-[3-(cyclopropylamino)propoxy]-6-methoxyquinazolin-4-yl}amino)-1H-pyrazol-1-yl]-N-(2,3-difluorophenyl)acetamide;
N-(2,3-difluorophenyl)-2-{4-[(7-{3-[[2-(dimethylamino)ethyl](methyl)amino]propoxy}-6-methoxyquinazolin-4-yl)amino]-1H-pyrazol-1-yl}acetamide;
N-(2,3-difluorophenyl)-2-[4-({6-methoxy-7-[3-(4-methylpiperazin-1-yl)propoxy]quinazolin-4-yl}amino)-1H-pyrazol-1-yl]acetamide;
N-(2,3-difluorophenyl)-2-{4-[(7-{3-[(2R)-2-(hydroxymethyl)pyrrolidin-1-yl]propoxy}-6-methoxyquinazolin-4-yl)amino]-1H-pyrazol-1-yl}acetamide;
N-(2,3-difluorophenyl)-2-[4-({7-[3-(4-hydroxypiperidin-1-yl)propoxy]-6-methoxyquinazolin-4-yl}amino)-1H-pyrazol-1-yl]acetamide;
2-{4-[(7-{3-[bis(2-hydroxyethyl)amino]propoxy}-6-methoxyquinazolin-4-yl)amino]-1H-pyrazol-1-yl}-N-(2,3-difluorophenyl)acetamide;
N-(2,3-difluorophenyl)-2-{4-[(7-{3-[ethyl(methyl)amino]propoxy}-6-methoxyquinazolin-4-yl)amino]-1H-pyrazol-1-yl}acetamide;
N-(2,3-difluorophenyl)-2-{4-[(7-{3-[ethyl(2-hydroxyethyl)amino]propoxy}-6-methoxyquinazolin-4-yl)amino]-1H-pyrazol-1-yl}acetamide;
N-(2,3-difluorophenyl)-2-{4-[(7-{3-[[2-(dimethylamino)ethyl](ethyl)amino]propoxy}-6-methoxyquinazolin-4-yl)amino]-1H-pyrazol-1-yl}acetamide;
N-(2,3-difluorophenyl)-2-{4-[(7-{3-[2-(2-hydroxyethyl)piperidin-1-yl]propoxy}-6-methoxyquinazolin-4-yl)amino]-1H-pyrazol-1-yl}acetamide;
N-(2,3-difluorophenyl)-2-{4-[(7-{3-[4-(2-hydroxyethyl)piperazin-1-yl]propoxy}-6-methoxyquinazolin-4-yl)amino]-1H-pyrazol-1-yl}acetamide;
2-{4-[(7-{3-[(cyclopropylmethyl)amino]propoxy}-6-methoxyquinazolin-4-yl)amino]-1H-pyrazol-1-yl}-N-(2,3-difluorophenyl)acetamide;
N-(2,3-difluorophenyl)-2-{4-[(7-{3-[4-(2-hydroxyethyl)piperidin-1-yl]propoxy}-6-methoxyquinazolin-4-yl)amino]-1H-pyrazol-1-yl}acetamide;
N-(2,3-difluorophenyl)-2-{4-[(6-methoxy-7-{3-[methyl(prop-2-yn-1-yl)amino]propoxy}quinazolin-4-yl)amino]-1H-pyrazol-1-yl}acetamide;
N-(2,3-difluorophenyl)-2-{4-[(7-{3-[isobutyl(methyl)amino]propoxy}-6-methoxyquinazolin-4-yl)amino]-1H-pyrazol-1-yl}acetamide;
N-(2,3-difluorophenyl)-2-[4-({7-[3-(3-hydroxypiperidin-1-yl)propoxy]-6-methoxyquinazolin-4-yl}amino)-1H-pyrazol-1-yl]acetamide;
N-(2,3-difluorophenyl)-2-{4-[(7-{3-[4-(hydroxymethyl)piperidin-1-yl]propoxy}-6-methoxyquinazolin-4-yl)amino]-1H-pyrazol-1-yl}acetamide;
N-(2,3-difluorophenyl)-2-{4-[(6-methoxy-7-{3-[methyl(propyl)amino]propoxy}quinazolin-4-yl)amino]-1H-pyrazol-1-yl}acetamide;
2-{4-[(7-{3-[(cyclopropylmethyl)(propyl)amino]propoxy}-6-methoxyquinazolin-4-yl)amino]-1H-pyrazol-1-yl}-N-(2,3-difluorophenyl)acetamide;
2-{4-[(7-{3-[[2-(diethylamino)ethyl](methyl)amino]propoxy}-6-methoxyquinazolin-4-yl)amino]-1H-pyrazol-1-yl}-N-(2,3-difluorophenyl)acetamide;
2-{4-[(7-{3-[[2-(diethylamino)ethyl](ethyl)amino]propoxy}-6-methoxyquinazolin-4-yl)amino]-1H-pyrazol-1-yl}-N-(2,3-difluorophenyl)acetamide;
N-(2,3-difluorophenyl)-2-[4-({6-methoxy-7-[3-(4-methyl-1,4-diazepan-1-yl)propoxy]quinazolin-4-yl}amino)-1H-pyrazol-1-yl]acetamide;
N-(2,3-difluorophenyl)-2-{4-[(7-{3-[(2-hydroxyethyl)(isopropyl)amino]propoxy}-6-methoxyquinazolin-4-yl)amino]-1H-pyrazol-1-yl}acetamide;
2-{4-[(7-{3-[cyclopropyl(2-hydroxyethyl)amino]propoxy}-6-methoxyquinazolin-4-yl)amino]-1H-pyrazol-1-yl}-N-(2,3-difluorophenyl)acetamide;
N-(2,3-difluorophenyl)-2-{4-[(7-{3-[(2-hydroxyethyl)(2-methoxyethyl)amino]propoxy}-6-methoxyquinazolin-4-yl)amino]-1H-pyrazol-1-yl}acetamide;
2-{4-[(7-{3-[cyclobutyl(2-hydroxyethyl)amino]propoxy}-6-methoxyquinazolin-4-yl)amino]-1H-pyrazol-1-yl}-N-(2,3-difluorophenyl)acetamide;
2-{4-[(7-{3-[(cyclopropylmethyl)(2-hydroxyethyl)amino]propoxy}-6-methoxyquinazolin-4-yl)amino]-1H-pyrazol-1-yl}-N-(2,3-difluorophenyl)acetamide;
2-{4-[(7-{3-[(cyclobutylmethyl)(2-hydroxyethyl)amino]propoxy}-6-methoxyquinazolin-4-yl)amino]-1H-pyrazol-1-yl}-N-(2,3-difluorophenyl)acetamide;
N-(2,3-difluorophenyl)-2-{4-[(7-{3-[(2-hydroxyethyl)(prop-2-yn-1-yl)amino]propoxy}-6-methoxyquinazolin-4-yl)amino]-1H-pyrazol-1-yl}acetamide;
2-{4-[(7-{3-[allyl(2-hydroxyethyl)amino]propoxy}-6-methoxyquinazolin-4-yl)amino]-1H-pyrazol-1-yl}-N-(2,3-difluorophenyl)acetamide;
N-(2,3-difluorophenyl)-2-{4-[(7-{3-[(2,2-dimethylpropyl)(2-hydroxyethyl)amino]propoxy}-6-methoxyquinazolin-4-yl)amino]-1H-pyrazol-1-yl}acetamide;
N-(2,3-difluorophenyl)-2-{4-[(7-{3-[(2-hydroxyethyl)(3,3,3-trifluoropropyl)amino]propoxy}-6-methoxyquinazolin-4-yl)amino]-1H-pyrazol-1-yl}acetamide;
N-(2,3-difluorophenyl)-2-{4-[(7-{2-[(2R)-2-(hydroxymethyl)pyrrolidin-1-yl]ethoxy}-6-methoxyquinazolin-4-yl)amino]-1H-pyrazol-1-yl}acetamide;
N-(2,3-difluorophenyl)-2-(4-{[7-(2-{4-[2-(2-hydroxyethoxy)ethyl]piperazin-1-yl}ethoxy)-6-methoxyquinazolin-4-yl]amino}-1H-pyrazol-1-yl)acetamide;
N-(2,3-difluorophenyl)-2-{4-[(7-{2-[2-(hydroxymethyl)piperidin-1-yl]ethoxy}-6-methoxyquinazolin-4-yl)amino]-1H-pyrazol-1-yl}acetamide;
N-(2,3-difluorophenyl)-2-{4-[(7-{2-[(2-hydroxy-1,1-dimethylethyl)amino]ethoxy}-6-methoxyquinazolin-4-yl)amino]-1H-pyrazol-1-yl}acetamide;
N-(2,3-difluorophenyl)-2-{4-[(7-{2-[4-(2-hydroxyethyl)piperazin-1-yl]ethoxy}-6-methoxyquinazolin-4-yl)amino]-1H-pyrazol-1-yl}acetamide;
N-(2,3-difluorophenyl)-2-{4-[(7-{2-[(trans-4-hydroxycyclohexyl)amino]ethoxy}-6-methoxyquinazolin-4-yl)amino]-1H-pyrazol-1-yl}acetamide;

N-(2,3-difluorophenyl)-2-{4-[(7-{2-[3-(hydroxymethyl)piperidin-1-yl]ethoxy}-6-methoxyquinazolin-4-yl)amino]-1H-pyrazol-1-yl}acetamide;

N-(2,3-difluorophenyl)-2-(4-{[7-(2-{[1-(hydroxymethyl)cyclopentyl]amino}ethoxy)-6-methoxyquinazolin-4-yl]amino}-1H-pyrazol-1-yl)acetamide;

N-(2,3-difluorophenyl)-2-{4-[(7-{2-[4-(3-hydroxypropyl)piperazin-1-yl]ethoxy}-6-methoxyquinazolin-4-yl)amino]-1H-pyrazol-1-yl}acetamide;

2-{4-[(7-{2-[cyclohexyl(2-hydroxyethyl)amino]ethoxy}-6-methoxyquinazolin-4-yl)amino]-1H-pyrazol-1-yl}-N-(2,3-difluorophenyl)acetamide;

N-(2,3-difluorophenyl)-2-{4-[(7-{2-[(2-hydroxyethyl)(propyl)amino]ethoxy}-6-methoxyquinazolin-4-yl)amino]-1H-pyrazol-1-yl}acetamide;

N-(2,3-difluorophenyl)-2-{4-[(7-{2-[(3-hydroxy-2,2-dimethylpropyl)amino]ethoxy}-6-methoxyquinazolin-4-yl)amino]-1H-pyrazol-1-yl}acetamide;

N-(2,3-difluorophenyl)-2-[4-({6-methoxy-7-[2-(tetrahydro-2H-pyran-4-ylamino)ethoxy]quinazolin-4-yl}amino)-1H-pyrazol-1-yl]acetamide;

2-{4-[(7-{2-[cyclobutyl(2-hydroxyethyl)amino]ethoxy}-6-methoxyquinazolin-4-yl)amino]-1H-pyrazol-1-yl}-N-(2,3-difluorophenyl)acetamide;

N-(2,3-difluorophenyl)-2-{4-[(7-{2-[(2-hydroxyethyl)(tetrahydro-2H-pyran-4-yl)amino]ethoxy}-6-methoxyquinazolin-4-yl)amino]-1H-pyrazol-1-yl}acetamide;

N-(2,3-difluorophenyl)-2-{4-[(7-{2-[(2S)-2-(hydroxymethyl)pyrrolidin-1-yl]ethoxy}-6-methoxyquinazolin-4-yl)amino]-1H-pyrazol-1-yl}acetamide;

N-(2,3-difluorophenyl)-2-{4-[(7-{2-[(2R)-2-(2-hydroxyethyl)piperidin-1-yl]ethoxy}-6-methoxyquinazolin-4-yl)amino]-1H-pyrazol-1-yl}acetamide;

N-(2,3-difluorophenyl)-2-{4-[(7-{2-[(2S)-2-(2-hydroxyethyl)piperidin-1-yl]ethoxy}-6-methoxyquinazolin-4-yl)amino]-1H-pyrazol-1-yl}acetamide;

2-{4-[(7-{3-[ethyl(2-hydroxyethyl)amino]propoxy}-6-fluoroquinazolin-4-yl)amino]-1H-pyrazol-1-yl}-N-(3-fluorophenyl)acetamide;

2-{4-[(7-{3-[(cyclopropylmethyl)(2-hydroxyethyl)amino]propoxy}-6-fluoroquinazolin-4-yl)amino]-1H-pyrazol-1-yl}-N-(2,3-difluorophenyl)acetamide;

N-(2,3-difluorophenyl)-2-{4-[(6-fluoro-7-{3-[(2-hydroxyethyl)(propyl)amino]propoxy}quinazolin-4-yl)amino]-1H-pyrazol-1-yl}acetamide;

N-(2,3-difluorophenyl)-2-{4-[(6-fluoro-7-{3-[(2R)-2-(hydroxymethyl)pyrrolidin-1-yl]propoxy}quinazolin-4-yl)amino]-1H-pyrazol-1-yl}acetamide;

2-{4-[(7-{3-[cyclopentyl(2-hydroxyethyl)amino]propoxy}-6-fluoroquinazolin-4-yl)amino]-1H-pyrazol-1-yl}-N-(2,3-difluorophenyl)acetamide;

N-(3-fluorophenyl)-2-(4-{[7-methoxy-6-(3-morpholin-4-ylpropoxy)quinazolin-4-yl]amino}-1H-pyrazol-1-yl)acetamide;

N-(3-fluorophenyl)-2-[4-({7-methoxy-6-[(1-methylpyrrolidin-3-yl)oxy]quinazolin-4-yl}amino)-1H-pyrazol-1-yl]acetamide;

N-(3-fluorophenyl)-2-(4-{[7-methoxy-6-(2-morpholin-4-ylethoxy)quinazolin-4-yl]amino}-1H-pyrazol-1-yl)acetamide;

2-(4-{[6,7-bis(2-methoxyethoxy)quinazolin-4-yl]amino}-1H-pyrazol-1-yl)-N-(2,3-difluorophenyl)acetamide;

N-(3-fluorophenyl)-2-{4-[(6-hydroxy-7-methoxyquinazolin-4-yl)amino]-1H-pyrazol-1-yl}acetamide;

4-((1-(2-((2,3-difluorophenyl)amino)-2-oxoethyl)-1H-pyrazol-4-yl)amino)-7-((1-methylpiperidin-4-yl)methoxy)quinazolin-6-yl benzoate;

N-(2,3-difluorophenyl)-2-(4-((6-hydroxy-7-((1-methylpiperidin-4-yl)methoxy)quinazolin-4-yl)amino)-1H-pyrazol-1-yl)acetamide;

1-{2-[(3-fluorophenyl)amino]-2-oxoethyl}-4-[(7-{3-[(2-hydroxyethyl)(2-methoxyethyl)amino]propoxy}-6-methoxyquinazolin-4-yl)amino]-1H-pyrazole-3-carboxamide;

1-{2-[(3-fluorophenyl)amino]-2-oxoethyl}-4-[(7-{3-[(2S)-2-(hydroxymethyl)pyrrolidin-1-yl]propoxy}-6-methoxyquinazolin-4-yl)amino]-1H-pyrazole-3-carboxamide;

or a salt, ester or prodrug thereof, or more particularly a pharmaceutically acceptable salt thereof.

Another particular compound of formula (I) is any one of:

2-(4-{[7-(3-chloropropoxy)quinazolin-4-yl]amino}-1H-pyrazol-1-yl)-N-(2,3-difluorophenyl)acetamide;

2-(4-{[7-(3 -chloropropoxy)quinazolin-4-yl]amino}-1H-pyrazol-1-yl)-N-(3-fluorophenyl)acetamide;

2-(4-{[7-(2-chloroethoxy)quinazolin-4-yl]amino}-1H-pyrazol-1-yl)-N-(2,3-difluorophenyl)acetamide;

N-(2,3-difluorophenyl)-2-(4-{[7-(2,2-dimethoxyethoxy)quinazolin-4-yl]amino}-1H-pyrazol-1-yl)acetamide;

ethyl 4-{[7-(3-chloropropoxy)quinazolin-4-yl]amino}-1-{2-[(3-fluorophenyl)amino]-2-oxoethyl}-1H-pyrazole-3-carboxylate;

2-(3-(acetylamino)-4-{[7-(3-chloropropoxy)quinazolin-4-yl]amino}-1H-pyrazol-1-yl)-N-(3-fluorophenyl)acetamide;

N-(2,3-difluorophenyl)-2-[4-(quinazolin-4-ylamino)-1H-pyrazol-1-yl]acetamide;

2-(4-{[7-(3-chloropropoxy)-5-isopropoxyquinazolin-4-yl]amino}-1H-pyrazol-1-yl)-N-(2,3-difluorophenyl)acetamide;

2-(4-{[7-(3-chloropropoxy)-5-methoxyquinazolin-4-yl]amino}-1H-pyrazol-1-yl)-N-(2,3-difluorophenyl)acetamide;

N-(2,3-difluorophenyl)-2-{4-[(7-{3-[(2-hydroxyethyl)(propyl)amino]propoxy}quinazolin-4-yl)amino]-1H-pyrazol-1-yl}acetamide;

N-(2,3-difluorophenyl)-2-{4-[(7-{3-[(2-hydroxyethyl)(isobutyl)amino]propoxy}quinazolin-4-yl)amino]-1H-pyrazol-1-yl}acetamide;

N-(2,3-difluorophenyl)-2-{4-[(7-{3-[(2S)-2-(hydroxymethyl)pyrrolidin-1-yl]propoxy}quinazolin-4-yl)amino]-1H-pyrazol-1-yl}acetamide;

N-(2,3-difluorophenyl)-2-{4-[(7-{3-[(2R)-2-(hydroxymethyl)pyrrolidin-1-yl]propoxy}quinazolin-4-yl)amino]-1H-pyrazol-1-yl}acetamide;

2-{4-[(7-{3-[cyclopentyl(2-hydroxyethyl)amino]propoxy}quinazolin-4-yl)amino]-1H-pyrazol-1-yl}-N-(2,3-difluorophenyl)acetamide;

N-(2,3-difluorophenyl)-2-{4-[(7-{3-[ethyl(2-hydroxyethyl)amino]propoxy}quinazolin-4-yl)amino]-1H-pyrazol-1-yl}acetamide;

N-(2,3-difluorophenyl)-2-{4-[(7-{3-[4-(2-hydroxyethyl)piperazin-1-yl]propoxy}quinazolin-4-yl)amino]-1H-pyrazol-1-yl}acetamide;

N-(2,3-difluorophenyl)-2-{4-[(7-{3-[4-(hydroxymethyl)piperidin-1-yl]propoxy}quinazolin-4-yl)amino]-1H-pyrazol-1-yl}acetamide;

N-(2,3-difluorophenyl)-2-{4-[(7-{3-[(3-hydroxy-1,1-dimethylpropyl)amino]propoxy}quinazolin-4-yl)amino]-1H-pyrazol-1-yl}acetamide;

2-{4-[(7-{3-[(2-cyanoethyl)(2-hydroxyethyl)amino]propoxy}quinazolin-4-yl)amino]-1H-pyrazol-1-yl}-N-(2,3-difluorophenyl)acetamide;

N-(2,3-difluorophenyl)-2-(4-{[7-(3-morpholin-4-ylpropoxy)quinazolin-4-yl]amino}-1H-pyrazol-1-yl)acetamide;

N-(2,3-difluorophenyl)-2-{4-[(7-{3-[(3-hydroxy-2,2-dimethylpropyl)amino]propoxy}quinazolin-4-yl)amino]-1H-pyrazol-1-yl}acetamide;

N-(2,3-difluorophenyl)-2-{4-[(7-{3-[(3-hydroxypropyl)amino]propoxy}quinazolin-4-yl)amino]-1H-pyrazol-1-yl}acetamide;

N-(2,3-difluorophenyl)-2-{4-[(7-{3-[(3-hydroxypropyl)(propyl)amino]propoxy}quinazolin-4-yl)amino]-1H-pyrazol-1-yl}acetamide;

N-(2,3-difluorophenyl)-2-(4-[(7-{3-[ethyl(3-hydroxypropyl)amino]propoxy}quinazolin-4-yl)amino]-1H-pyrazol-1-yl}acetamide;

N-(2,3-difluorophenyl)-2-{4-[(7-{3-[4(2-hydroxyethyl)-3-oxopiperazin-1-yl]propoxy}quinazolin-4-yl)amino]-1H-pyrazol-1-yl}acetamide;

N-(2,3-difluorophenyl)-2-[4-({7-[3-(propylamino)propoxy]quinazolin-4-yl}amino)-1H-pyrazol-1-yl]acetamide;

N-(2,3-difluorophenyl)-2-(4-{[7-(3-piperazin-1-ylpropoxy)quinazolin-4-yl]amino}-1H-pyrazol-1-yl)acetamide;

N-(2,3-difluorophenyl)-2-{4-[(7-{3-[glycoloyl(propyl)amino]propoxy}quinazolin-4-yl)amino]-1H-pyrazol-1-yl}acetamide;

N-(2,3-difluorophenyl)-2-[4-({7-[3-(4-glycoloylpiperazin-1-yl)propoxy]quinazolin-4-yl}amino)-1H-pyrazol-1-yl]acetamide;

N-(2,3-difluorophenyl)-2-(4-{[7-(3-{[trans-2-(hydroxymethyl)cyclohexyl]amino}propoxy)quinazolin-4-yl]amino}-1H-pyrazol-1-1)acetamide;

N-(2,3-difluorophenyl)-2-{4-[(7-{3-[(1α;5α;6α)-6-(hydroxymethyl)-3-azabicyclo[3.1.0]hex-3-yl]propoxy}quinazolin-4-yl)amino]-1H-pyrazol-1-yl}acetamide;

N-(2,3-difluorophenyl)-2-(4-{[7-(3-{[(2R)-2-hydroxypropyl]amino}propoxy)quinazolin-4-yl]amino)-1H-pyrazol-1-yl)acetamide;

N-(2,3-difluorophenyl)-2-(4-{[7-(3-{[(1S)-2-hydroxy-1-methylethyl]amino}propoxy)quinazolin-4-yl]amino}-1H-pyrazol-1-yl)acetamide;

N-(2,3-difluorophenyl)-2-{4-[(7-{3-[(2-hydroxy-1,1-dimethylethyl)amino]propoxy}quinazolin-4-yl)amino]-1H-pyrazol-1-yl}acetamide;

N-(2,3-difluorophenyl)-2-{4-[(7-{3-[(2,3-dihydroxypropyl)amino]propoxy}quinazolin-4-yl)amino]-1H-pyrazol-1-yl}acetamide;

N-(2,3-difluorophenyl)-2-(4-{[7-(3-{[2-(2-hydroxyethoxy)ethyl]amino}propoxy)quinazolin-4-yl]amino)-1H-pyrazol-1-yl)acetamide;

2-[4-({7-[3-(4-acetylpiperazin-1-yl)propoxy]quinazolin4-yl}amino)-1H-pyrazol-1-yl]-N-(2,3-difluorophenyl)acetamide;

N-(2,3-difluorophenyl)-2-{4-[(7-{3-[(tetrahydrofuran-2-ylmethyl)amino]propoxy}quinazolin-4-yl)amino]-1H-pyrazol-1-yl}acetamide;

2-[4-({7-[3-(allylamino)propoxy]quinazolin-4-yl}amino)-1H-pyrazol-1-yl]-N-(2,3-difluorophenyl)acetamide;

N-(2,3-difluorophenyl)-2-(4-{[7-(3-{[1-(hydroxymethyl)-2-methylpropyl]amino}propoxy)quinazolin-4-yl)amino}-1H-pyrazol-1-yl)acetamide;

N-(2,3-difluorophenyl)-2-(4-{[7-(3-{[(5-methylisoxazol-3-yl)methyl]amino}propoxy)quinazolin-4-ylamino}-1H-pyrazol-1-yl)acetamide;

N-(2,3-difluorophenyl)-2-[4-({7-[3-(tetrahydro-2H-pyran-4-ylamino)propoxy]quinazolin-4-yl}amino)-1H-pyrazol-1-yl]acetamide;

N-(2,3-difluorophenyl)-2-{4-[(7-{3-[(3S)-3-(hydroxymethyl)pyrrolidin-1-yl]propoxy)quinazolin-4-yl)amino]-1H-pyrazol-1-yl}acetamide;

N-(2,3-difluorophenyl)-2-(4-{[7-(3-hydroxypropoxy)quinazolin-4-yl]amino}-1H-pyrazol-1-yl)acetamide;

2-(4-{[7-(3 -aminopropoxy)quinazolin-4-yl]amino}-1H-pyrazol-1-yl)-N-(2,3-difluorophenyl)acetamide;

N-(2,3-difluorophenyl)-2-{4-[(7-{3-[(2S,4R)-4-hydroxy-2-(hydroxymethyl)pyrrolidin-1-yl]propoxy}quinazolin-4-yl)amino]-1H-pyrazol-1-yl}acetamide;

N-(2,3-difluorophenyl)-2-{4-[(7-{2-[(3-hydroxy-2,2-dimethylpropyl)amino]ethoxy}quinazolin-4-yl)amino]-1H-pyrazol-1-yl}acetamide;

2-{4-[(7-{2-[cyclohexyl(2-hydroxyethyl)amino]ethoxy}quinazolin-4-yl)amino]-1H-pyrazol-1-yl}-N-(2,3-difluorophenyl)acetamide;

2-[4-({7-[2-(cyclopropylamino)ethoxy]quinazolin-4-yl}amino)-1H-pyrazol-1-yl]-N-(2,3-difluorophenyl)acetamide;

2-[4-({7-[2-(cyclobutylamino)ethoxy]quinazolin-4-yl amino)-1H-pyrazol-1-yl]-N-(2,3-difluorophenyl)acetamide;

N-(2,3-difluorophenyl)-2-[4-({7-[2-(tetrahydro-2H-pyran4-ylamino)ethoxy]quinazolin-4-yl}amino)-1H-pyrazol-1-yl]acetamide;

2-[4-({7-[2-(cyclopentylamino)ethoxy]quinazolin-4-yl}amino)-1H-pyrazol-1-yl]-N-(2,3-difluorophenyl)acetamide;

N-(2,3-difluorophenyl)-2-{4-[(7-{2-[(2-hydroxyethyl)(tetrahydro-2H-pyran-4-yl)amino]ethoxy}quinazolinyl)amino]-1H-pyrazol-1-yl}acetamide;

2-{4-[(7-{2-[cyclopentyl(2-hydroxyethyl)amino]ethoxy}quinazolin-4-yl)amino]-1H-pyrazol-1-yl}-N-(2,3-difluorophenyl)acetamide;

N-(2,3-difluorophenyl)-2-{4-[(7-{2-[(2R)-2-(hydroxymethyl)pyrrolidin-1-yl]ethoxy}quinazolin-4-yl)amino]-1H-pyrazol-1-yl}acetamide;

2-{4-[(7-{2-[cyclopropyl(2-hydroxyethyl)amino]ethoxy}quinazolin-4-yl)amino]-1H-pyrazol-1-yl}-N-(2,3-difluorophenyl)acetamide;

2-{4-[(7-{2-[cyclobutyl(2-hydroxyethyl)amino]ethoxy}quinazolin-4-yl)amino]-1H-pyrazol-1-yl}-N-(2,3-difluorophenyl)acetamide;

2-{4-[(7-{2-[cyclopentyl(3-hydroxypropyl)amino]ethoxy}quinazolin-4-yl)amino]-1H-pyrazol-1-yl}-N-(2,3-difluorophenyl)acetamide;

2-{4[(7-{2-[cyclopentyl(glycoloyl)amino]ethoxy}quinazolin-4-yl)amino]-1H-pyrazol-1-yl}-N-(2,3-difluorophenyl)acetamide;

N-(2,3-difluorophenyl)-2-{4-[(7-{2-[(3S)-3-(hydroxymethyl)-4-methylpiperazin-1-yl]ethoxy}quinazolin-4-yl)amino]-1H-pyrazol-1-yl}acetamide;

N-(2,3-difluorophenyl)-2-{4-[(7-{2-[(2S)-2-(hydroxymethyl)pyrrolidin-1-yl]ethoxy}quinazolin-4-yl)amino]-1H-pyrazol-1-yl}acetamide;

N-(2,3-difluorophenyl)-2-{4-[(7-{2-[(2R)-2-(hydroxymethyl)-4-methylpiperazin-1-yl]ethoxy}quinazolin-4-yl)amino]-1H-pyrazol-1-yl}acetamide;

N-(2,3-difluorophenyl)-2-{4-[(7-{2-[4-(hydroxymethyl)piperidin-1-yl]ethoxy}quinazolin-4-yl)amino]-1H-pyrazol-1-yl}acetamide;

N-(2,3-difluorophenyl)-2-{4-[(7-{2-[4-(2-hydroxyethyl)piperidin-1-yl]ethoxy}quinazolin-4-yl)amino]-1H-pyrazol-1-yl}acetamide;

N-(2,3-difluorophenyl)-2-{4-[(7-{2-[(2-hydroxyethyl)amino]ethoxy}quinazolin-4-yl)amino]-1H-pyrazol-1-yl}acetamide;

N-(2,3-difluorophenyl)-2-(-{[7-(2-{[trans-2-(hydroxymethyl)cyclohexyl]amino}ethoxy)quinazolin-4-yl]amino}-1H-pyrazol-1-yl)acetamide;

N-(2,3-difluorophenyl)-2-{4-[(7-{3-[(2-hydroxyethyl) amino]propoxy}quinazolin-4-yl)amino]-1H-pyrazol-1-yl}acetamide;

N-(2,3-difluorophenyl)-2-(4-{[7-(3-pyrrolidin-1-ylpropoxy) quinazolin-4-yl]amino}-1H-pyrazol-1-yl)acetamide;

N-(2,3-difluorophenyl)-2-{4-[(7-methoxyquinazolin-4-yl) amino]-1H-pyrazol-1-yl}acetamide;

178-N-(2,3-difluorophenyl)-2-{4-[(7-{3-[(2-hydroxyethyl) (tetrahydro-2H-pyran-4-yl)amino]propoxy}quinazolin-4-yl)amino]-1H-pyrazol-1-yl}acetamide;

N-(2,3-difluorophenyl)-2-{4-[(7-{3-[(2R)-2-(2-hydroxy-ethyl)piperidin-1-yl]propoxy}quinazolin-4-yl)amino]-1H-pyrazol-1-yl}acetamide;

N-(2,3-difluorophenyl)-2-{4-[(7-{3-[(2S)-2-(2-hydroxy-ethyl)piperidin-1-yl]propoxy}quinazolin-4-yl)amino]-1H-pyrazol-1-yl}acetamide;

N-(2,3-difluorophenyl)-2-{4-[(7-{3-[(2R)-2-(hydroxym-ethyl)-4-methylpiperazin-1-yl]propoxy}quinazolin-4-yl) amino)-1H-pyrazol-1-yl}acetamide;

N-(2,3-difluorophenyl)-2-{4-[(7-{3-[(3S)-3-(hydroxym-ethyl)-4-methylpiperazin-1-yl]propoxy}quinazolin-4-yl) amino]-1H-pyrazol-1-yl}acetamide;

N-(2,3-difluorophenyl)-2-{4-[(7-{3-[(2R)-2-(hydroxym-ethyl)morpholin-4-yl]propoxy}quinazolin-4-yl)amino]-1H-pyrazol-1-yl}acetamide;

N-(2,3-difluorophenyl)-2-{4-[(7-{3-[(3S)-3-(hydroxym-ethyl)morpholin-4-yl]propoxy}quinazolin-4-yl)amino]-1H-pyrazol-1-yl}acetamide;

N-(2,3-difluorophenyl)-2-[4-({7-[3-(glycoloylamino)pro-poxy]quinazolin-4-yl}amino)-1H-pyrazol-1-yl]aceta-mide;

N-(3-fluorophenyl)-2-{4-[(7-{3-[(2-hydroxyethyl)(propyl) amino]propoxy}quinazolin-4-yl)amino]-1H-pyrazol-1-yl}acetamide;

2-{4-[(7-{3-[ethyl(2-hydroxyethyl)amino] propoxy}quinazolin-4-yl)amino]-1H-pyrazol-1-yl}-N-(3-fluorophenyl)acetamide;

N-(3-fluorophenyl)-2-{4-[(7-{3-[(2R)-2-(hydroxymethyl) pyrrolidin-1-yl]propoxy}quinazolin-4-yl)amino]-1H-pyrazol-1-yl}acetamide;

N-(3-fluorophenyl)-2-{4-[(7-{3-[4-(hydroxymethyl)piperi-din-1-yl]propoxy}quinazolin-4-yl)amino]-1H-pyrazol-1-yl}acetamide;

N-(3-fluorophenyl)-2-{4-[(7-{3-[(3-hydroxy-1,1-dimethyl-propyl)amino]propoxy}quinazolin-4-yl)amino]-1H-pyra-zol-1-yl}acetamide;

N-(3-fluorophenyl)-2-{4-[(7-{3-[2-(2-hydroxyethyl)piperi-din-1-yl]propoxy}quinazolin-4-yl)amino]-1H-pyrazol-1-yl}acetamide;

N-(3-fluorophenyl)-2-{4-[(7-{3-[4-(2-hydroxyethyl)piper-azin-1-yl]propoxy}quinazolin-4-yl)amino]-1H-pyrazol-1-yl}acetamide;

N-(3-fluorophenyl)-2-{4-[(7-{3-[(2-hydroxyethyl)(tetrahy-drofuran-3-yl)amino]propoxylquinazolin-4-yl)amino]-1H-pyrazol-1-yl}acetamide;

N-(3-fluorophenyl)-2-(4-{[7-(3-morpholin-4-ylpropoxy) quinazolin-4-yl]amino}-1H-pyrazol-1-yl)acetamide;

N-(3-fluorophenyl)-2-[4-({7-[(2S)-pyrrolidin-2-ylmethoxy] quinazolin-4-yl}amino)-1H-pyrazol-1-yl]acetamide;

N-(3-fluorophenyl)-2-{4-[(7-{[(2S)-1-(2-hydroxyethyl)pyr-rolidin-2-yl]methoxy}quinazolin-4-yl)amino]-1H-pyra-zol-1-yl}acetamide;

N-(3-fluorophenyl)-2-{4-[(7-{[(2S)-1-glycoloylpyrrolidin-2-yl]methoxy}quinazolin-4-yl)amino]-1H-pyrazol-1-yl}acetamide;

N-(3-fluorophenyl)-2-(4-{[7-(pyrrolidin-3-ylmethoxy) quinazolin-4-yl]amino)-1H-pyrazol-1-yl)acetamide;

N-(3-fluorophenyl)-2-{4-[(7-{[1-(2-hydroxyethyl)pyrroli-din-3-yl]methoxy}quinazolin-4-yl)amino]-1H-pyrazol-1-yl}acetamide;

N-(3-fluorophenyl)-2-[4-({7-[(1-glycoloylpyrrolidin-3-yl) methoxy]quinazolin-4-yl}amino)-1H-pyrazol-1-yl]aceta-mide;

N-(3-fluorophenyl)-2-{4-[(7-(3-[(2-hydroxyethyl)(2-meth-oxyethyl)amino]propoxy}quinazolin-4-yl)amino]-1H-pyrazol-1-yl}acetamide;

N-(3-fluorophenyl)-2-{4-[(7-hydroxyquinazolin-4-yl) amino]-1H-pyrazol-1-yl}acetamide;

N-(2-Fluorophenyl)-2-{4-[(7-{3-[(2R)-2-(hydroxymethyl) pyrrolidin-1-yl]propoxy}quinazolin-4-yl)amino]-1H-pyrazol-1-yl}acetamide;

2-{4-[(7-{3-[ethyl(2-hydroxyethyl)amino] propoxy}quinazolin-4-yl)amino]-1H-pyrazol-1-yl}-N-(2-fluorophenyl)acetamide;

2-{4-[(7-{3-[(2R)-2-(hydroxymethyl)pyrrolidin-1-yl] propoxy}quinazolin-4-yl)amino]-1H-pyrazol-1-yl}-N-phenylacetamide;

2-{4-[(7-{3-[ethyl(2-hydroxyethyl)amino] propoxy}quinazolin-4-yl)amino]-1H-pyrazol-1-yl}-N-phenylacetamide;

N-(2,6-difluorophenyl)-2-{4-[(7-{3-[(2R)-2-(hydroxym-ethyl)pyrrolidin-1-yl]propoxy}quinazolin-4-yl)amino]-1H-pyrazol-1-yl}acetamide;

2-{4-[(7-{3-[bis(2-hydroxyethyl)amino]propoxy}-5-isopro-poxyquinazolin-4-yl)amino]-1H-pyrazol-1-yl}-N-(2,3-difluorophenyl)acetamide;

N-(2,3-difluorophenyl)-2-{4-[(7-{3-[(2R)-2-(hydroxym-ethyl)pyrrolidin-1-yl]propoxy}-5-isopropoxyquinazolin-4-yl)amino]-1H-pyrazol-1-yl}acetamide;

N-(2,3-difluorophenyl)-2-{4-[(7-{3-[4-(2-hydroxyethyl) piperazin-1-yl]propoxy}-5-isopropoxyquinazolin-4-yl) amino]-1H-pyrazol-1-yl}acetamide;

N-(2,3-difluorophenyl)-2-(4-{[5-isopropoxy-7-(3-piper-azin-1-ylpropoxy)quinazolin-4-]amino}-1H-pyrazol-1-yl)acetamide;

N-(2,3-difluorophenyl)-2-{4-[(7-{3-[(2S)-2-(hydroxym-ethyl)pyrrolidin-1-yl]propoxy}-5-isopropoxyquinazolin-4-yl)amino]-1H-pyrazol-1-yl}acetamide;

N-(2,3-difluorophenyl)-2-{4-[(7-{3-[(2-hydroxyethyl) amino]propoxy}-5-isopropoxyquinazolin-4-yl)amino]-1H-pyrazol-1-yl}acetamide;

N-(2,3-difluorophenyl)-2-[4-({7-[3-(4-glycoloylpiperazin-1-yl)propoxy]-5-isopropoxyquinazolin-4-yl}amino)-1H-pyrazol-1-yl]acetamide;

N-(2,3-difluorophenyl)-2-{4-[(7-{3-[(2R)-2-(hydroxym-ethyl)pyrrolidin-1-yl]propoxy}-5-methoxyquinazolin-4-yl)amino]-1H-pyrazol-1-yl}acetamide;

N-(2,3-difluorophenyl)-2-{4-[(5,7-dimethoxyquinazolin-4-yl)amino]-1H-pyrazol-1-yl}acetamide;

N-(2,3-difluorophenyl)-2-{4-[(5-hydroxy-7-methox-yquinazolin-4-yl)amino]-1H-pyrazol-1-}acetamide;

N-(2,3-difluorophenyl)-2-[4-({7-methoxy-5-[(2R)-pyrroli-din-2-ylmethoxy]quinazolin-4-yl}amino)-1H-pyrazol-1-yl]acetamide;

N-(2,3-difluorophenyl)-2-{4-[(5-{[(2R)-1-glycoloylpyrroli-din-2-yl]methoxy}-7-methoxyquinazolin-4-yl)amino]-1H-pyrazol-1-yl}acetamide;

N-(2,3-difluorophenyl)-2-{4-[(5-{[(2R)-1-(N,N-dimethylg-lycyl)pyrrolidin-2-yl]methoxy}-7-methoxyquinazolin-4-yl)amino]-1H-pyrazol-1-yl}acetamide;

N-(2,3-difluorophenyl)-2-{4-[(5-{[(2R)-1-(2-hydroxyethyl) pyrrolidin-2-yl]methoxy}-7-methoxyquinazolin-4-yl) amino]-1H-pyrazol-1-yl}acetamide;

N-(2,3-difluorophenyl)-2-{4-[(5-methoxyquinazolin-4-yl) amino]-1H-pyrazol-1-yl}acetamide;

N-(2,3-difluorophenyl)-2-{4-[(5-fluoroquinazolin-4-yl) amino]-1H-pyrazol-1-yl}acetamide;

2-{3-(acetylamino)-4[(7-{3-[(2R)-2-(hydroxymethyl)pyrrolidin-1-yl]propoxy}quinazolin-4-yl)amino]-1H-pyrazol-1-yl}-N-(3-fluorophenyl)acetamide;

ethyl 1-{2-[(3-fluorophenyl)amino]-2-oxoethyl}-4-[(7-{3-[(2R)-2-(hydroxymethyl)pyrrolidin-1-yl] propoxy}quinazolin-4-yl)amino]-1H-pyrazole-3-carboxylate;

1-{2-[(3-fluorophenyl)amino]-2-oxoethyl}-4-[(7-{3-[(2R)-2-(hydroxymethyl)pyrrolidin-1-yl]propoxy}quinazolin-4-yl)amino]-1H-pyrazole-3-carboxylic acid;

or a salt, ester or prodrug thereof, or more particularly a pharmaceutically acceptable salt thereof.

In another aspect a particular compound of formula (IA) is any one of:

2-[[3-({4-[(1-{2-[(2,3-difluorophenyl)amino]-2-oxoethyl}-1H-pyrazol-4-yl)amino]-6-methoxyquinazolin-7-yl}oxy) propyl](propyl)amino]ethyl dihydrogen phosphate;

{(2S)-1-[3-({4-[(1-{2-[(2,3-difluorophenyl)amino]-2-oxoethyl}-1H-pyrazol-4-yl)amino]-6-methoxyquinazolin-7-yl}oxy)propyl]pyrrolidin-2-yl}methyl dihydrogen phosphate;

{(2S)-1-[3-({4-[(1-{2-[(3-fluorophenyl)amino]-2-oxoethyl}-1H-pyrazol-4-yl)amino]-5-methoxyquinazolin-7-yl}oxy)propyl]pyrrolidin-2-yl}methyl dihydrogen phosphate;

2-{ethyl[3-({4-[(1-{2-[(3-fluorophenyl)amino]-2-oxoethyl}-1H-pyrazol4-yl)amino]-6-methoxyquinazolin-7-yl}oxy)propyl]amino}ethyl dihydrogen phosphate;

{(2R)-1-[3-({4-[(1-{2-[(3-fluorophenyl)amino]-2-oxoethyl}-1H-pyrazol-4-yl)amino]-6-methoxyquinazolin-7-yl}oxy)propyl]pyrrolidin-2-yl}methyl dihydrogen phosphate;

2-[[3-({4-[(1-{2-[(2,3-difluorophenyl)amino]-2-oxoethyl}-1H-pyrazol-4-yl)amino]-6-methoxyquinazolin-7-yl}oxy) propyl](2-methoxyethyl)amino]ethyl dihydrogen phosphate;

{(2S)-1-[3-({4-[(1-{2-[(2,3-difluorophenyl)amino]-2-oxoethyl}-1H-pyrazol-4-yl)amino]quinazolin-7-yl}oxy)propyl]pyrrolidin-2-yl}methyl dihydrogen phosphate;

{(2R)-1-[3-({4-[(1-{2-[(2,3-difluorophenyl)amino]-2-oxoethyl}-1H-pyrazol-4-yl)amino]quinazolin-7-yl}oxy)propyl]pyrrolidin-2-yl}methyl dihydrogen phosphate;

{(2R)-1-[3-({4-[(1-{2-[(2,3-difluorophenyl)amino]-2-oxoethyl}-1H-pyrazol-4-yl)amino]-6-methoxyquinazolin-7-yl}oxy)propyl]pyrrolidin-2-yl}methyl dihydrogen phosphate;

2-[[3-({4-[(1-{2-[(2,3-difluorophenyl)amino]-2-oxoethyl}-1H-pyrazol-4-yl)amino]-6-methoxyquinazolin-7-yl}oxy) propyl](ethyl)amino]ethyl dihydrogen phosphate;

2-[[3-({4-[(1-{2-[(2,3-difluorophenyl)amino]-2-oxoethyl}-1H-pyrazol-4-yl)amino]quinazolin-7-yl}oxy)propyl] (propyl)amino]ethyl dihydrogen phosphate;

2-{cyclobutyl[3-({4-[(1-{2-[(2,3-difluorophenyl)amino]-2-oxoethyl}-1H-pyrazol-4-yl)amino]-6-methoxyquinazolin-7-yl}oxy)propyl]amino}ethyl dihydrogen phosphate;

2-{cyclobutyl[3-({4-[(1-{2-[(3-fluorophenyl)amino]-2-oxoethyl}-1H-pyrazol]-4-yl)amino]-6-methoxyquinazolin-7-yl}oxy)propyl]amino}ethyl dihydrogen phosphate;

2-[[3-({4-[(1-{2-[(3-fluorophenyl)amino]-2-oxoethyl}-1H-pyrazolyl)amino]-6-methoxyquinazolin-7-yl}oxy)propyl](2-methoxyethyl)amino]ethyl dihydrogen phosphate;

2-[[3-((4-[(1-{2-[(3-fluorophenyl)amino]-2-oxoethyl}-1H-pyrazolyl)amino]quinazolin-7-yl}oxy)propyl)(propyl) amino]ethyl dihydrogen phosphate;

2-{4-[3-({4-[(1-{2-[(2,3-difluorophenyl)amino]-2-oxoethyl}-1H-pyrazol-4-yl)amino]quinazolin-7-yl}oxy)propyl]piperazin-1-yl}ethyl dihydrogen phosphate;

2-{ethyl[3-({4-[(1-{2-[(3-fluorophenyl)amino)-2-oxoethyl}-1H-pyrazol-4-yl)amino]quinazolin-7-yl}oxy)propyl]amino}ethyl dihydrogen phosphate;

2-[[3-({4-[(1-{2-[(2,3-difluorophenyl)amino]-2-oxoethyl}-1H-pyrazol-4-yl)amino]quinazolin-7-yl}oxy)propyl] (ethyl)amino]ethyl dihydrogen phosphate;

3-{[3-({4-[(1-{2-[(3-fluorophenyl)amino]-2-oxoethyl}-1H-pyrazol-4-yl)amino]quinazolin-7-yl}oxy)propyl]amino}-3-methylbutyl dihydrogen phosphate;

3-{[3-({4-[(1-{2-[(2,3-difluorophenyl)amino]-2-oxoethyl}-1H-pyrazol-4-yl)amino]quinazolin-7-yl )oxy)propyl] amino)-3-methylbutyl dihydrogen phosphate;

{(2R)-1-[3-({4-[(1-{2-[(3-fluorophenyl)amino]-2-oxoethyl}-1H-pyrazol-4-yl)amino]quinazolin-7-yl)oxy)propyl] pyrrolidin-2-yl}methyl dihydrogen phosphate;

2-{4-[3-({4-[(1-{2-[(3-fluorophenyl)amino]-2-oxoethyl}-1H-pyrazol-4-yl)amino]quinazolin-7-yl )oxy)propyl]piperazin-1-yl}ethyl dihydrogen phosphate;

3-{[3-({4-[(1-{2-[(2,3-difluorophenyl)amino)-2-oxoethyl}-1H-pyrazol-4-yl)amino]quinazolin-7-yl}oxy)propyl] amino}propyl dihydrogen phosphate;

2-{[3-({4-[(1-{2-[(2,3-difluorophenyl)amino]-2-oxoethyl}-1H-pyrazol-4-yl)amino]quinazolin-7-yl}oxy)propyl] amino}ethyl dihydrogen phosphate;

2-[[3-({4-[(1-{2-[(3-fluorophenyl)amino]-2-oxoethyl)-1H-pyrazolyl)amino]quinazolin-7-yl}oxy)propyl](2-methoxyethyl)amino]ethyl dihydrogen phosphate;

3-[[3-({4-[(1-{2-[(2,3-difluorophenyl)amino]-2-oxoethyl}-1H-pyrazol-4-yl)amino]quinazolin-7-yl}oxy)propyl] (ethyl)amino]propyl dihydrogen phosphate;

3-[[3-((4-[(1-{2-[(2,3-difluorophenyl)amino]-2-oxoethyl}-1H-pyrazol-4-yl)amino]quinazolin-7-yl}oxy)propyl] (propyl)amino]propyl dihydrogen phosphate;

2-[[3-({4-[(1-{2-[(2,3-difluorophenyl)amino)-2-oxoethyl})-1H-pyrazol-4-yl)amino]quinazolin-7-yl}oxy)propyl] (propyl)amino}-2-oxoethyl dihydrogen phosphate;

2-{4-[3-({4-[(1-{2-[(2,3-difluorophenyl)amino]-2-oxoethyl}-1H-pyrazol-4-yl)amino]quinazolin-7-yl)oxy)propyl] piperazin-1-yl}-2-oxoethyl dihydrogen phosphate;

{(2R)-1-[3-({4-[(1-{2-[(2,3-difluorophenyl)amino]-2-oxoethyl}-1H-pyrazol-4-yl)amino]-6-fluoroquinazolin-7-yl}oxy)propyl]pyrrolidin-2-yl}methyl dihydrogen phosphate;

4-((1-(2-((2,3-difluorophenyl)amino)-2-oxoethyl)-1H-pyrazol-4-yl)amino)-7-((1-methylpiperidin-4-yl)methoxy) quinazolin-6-yl dihydrogen phosphate;

{(2R)-1-[3-({4-[(1-{2-[(2,3-difluorophenyl)amino]-2-oxoethyl}-1H-pyrazol-4-yl)amino]-5-isopropoxyquinazolin-7-yl}oxy)propyl]pyrrolidin-2-yl}methyl dihydrogen phosphate;

2-{4-[3-({4-[(1-{2-[(2,3-difluorophenyl)amino]-2-oxoethyl}-1H-pyrazol)-4-yl)amino]-5-isopropoxyquinazolin-7-yl}oxy)propyl]piperazin-1-yl}ethyl dihydrogen phosphate;

2-{[3-({4-[(1-{2-[(2,3-difluorophenyl)amino]-2-oxoethyl}-1H-pyrazol-4-yl)amino]-5-isopropoxyquinazolin-7-yl}oxy)propyl]amino}ethyl dihydrogen phosphate;

{(2R)-1-[3-({4-[(1-{2-[(2,3-difluorophenyl)amino]-2-oxoethyl}-1H-pyrazol-4-yl)amino]-5-methoxyquinazolin-7-yl}oxy)propyl]pyrrolidin-2-yl}methyl dihydrogen phosphate;

{(2R)-1-[2-({4-[(1-{2-[(2,3-difluorophenyl)amino]-2-oxoethyl}-1H-pyrazol-4-yl)amino]-6-methoxyquinazolin-7-yl}oxy)ethyl]pyrrolidin-2-yl )methyl dihydrogen phosphate;

{(2S)-1-[2-({4-[(1-{2-[(2,3-difluorophenyl)amino]-2-oxoethyl}-1H-pyrazol-4-yl)amino]-6-methoxyquinazolin-7-yl}oxy)ethyl]pyrrolidin-2-yl )methyl dihydrogen phosphate;

2-[[2-({4-[(1-{2-[(2,3-difluorophenyl)amino]-2-oxoethyl}-1H-pyrazol-4-yl)amino]-6-methoxyquinazolin-7-yl}oxy)ethyl](tetrahydro-2H-pyran-4-yl)amino]ethyl dihydrogen phosphate;

2-{4-[3-({4-[(1-{2-[(2,3-difluorophenyl)amino]-2-oxoethyl}-1H-pyrazol-4-yl)amino]quinazolin-7-yl}oxy)propyl]-2-oxopiperazin-1-yl}ethyl dihydrogen phosphate;

2-[[2-({4-[(1-{2-[(2,3-difluorophenyl)amino]-2-oxoethyl}-1H-pyrazol-4-yl)amino]quinazolin-7-yl}oxy)ethyl](tetrahydro-2H-pyran-4-yl)amino]ethyl dihydrogen phosphate;

or a salt or ester thereof, or more particularly a pharmaceutically acceptable salt thereof.

A further particular compound of formula (IA) is any one of:

2-[[3-({4-[(1-{2-[(2,3-difluorophenyl)amino]-2-oxoethyl}-1H-pyrazol-4-yl)amino]-6-methoxyquinazolin-7-yl}oxy)propyl](propyl)amino]ethyl dihydrogen phosphate;

{(2S)-1-[3-({4-[(1-{2-[(2,3-difluorophenyl)amino]-2-oxoethyl}-1H-pyrazol-4-yl)amino]-6-methoxyquinazolin-7-yl}oxy)propyl]pyrrolidin-2-yl}methyl dihydrogen phosphate;

{(2S)-1-[3-({4-[(1-{2-[(3-fluorophenyl)amino]-2-oxoethyl}-1H-pyrazol-4-yl)amino]-6-methoxyquinazolin-7-yl}oxy)propyl]pyrrolidin-2-yl}methyl dihydrogen phosphate;

2-{ethyl[3-({4-[(1-{2-[(3-fluorophenyl)amino]-2-oxoethyl}-1H-pyrazol-4-yl)amino]-6-methoxyquinazolin-7-yl}oxy)propyl]amino)ethyl dihydrogen phosphate;

{(2R)-1-[3-({4-[(1-{2-[(3-fluorophenyl)amino]-2-oxoethyl}-1H-pyrazol-4-yl)amino]-6-methoxyquinazolin-7-yl}oxy)propyl]pyrrolidin-2-yl}methyl dihydrogen phosphate;

2-[[3-({4[(1-{2-[(2,3-difluorophenyl)amino]-2-oxoethyl}-1H-pyrazol-4-yl)amino]-6-methoxyquinazolin-7-yl}oxy)propyl](2-methoxyethyl)amino]ethyl dihydrogen phosphate;

{(2R)-1-[3-({4-[(1-{2-[(2,3-difluorophenyl)amino]-2-oxoethyl}-1H-pyrazol-4-yl)amino]-6-methoxyquinazolin-7-yl}oxy)propyl]pyrrolidin-2-yl}methyl dihydrogen phosphate;

2-[[3-({4-[(1-{2-[(2,3-difluorophenyl)amino]-2-oxoethyl}-1H-pyrazol-4-yl)amino]-6-methoxyqunazolin-7-yl}oxy)propyl](ethyl)amino]ethyl dihydrogen phosphate;

2-{cyclobutyl[3-({4-[(1-{2-[(2,3-difluorophenyl)amino]-2-oxoethyl}-1H-pyrazol-4-yl)amino]-6-methoxyquinazolin-7-yl}oxy)propyl]amino}ethyl dihydrogen phosphate;

2-{cyclobutyl[3-({4-[(1-{2-[(3-fluorophenyl)amino]-2-oxoethyl}-1H-pyrazol-4-yl)amino]-6-methoxyquinazolin-7-yl}oxy)propyl]amino}ethyl dihydrogen phosphate;

2-[[3-({4-[(1-{2-[(3-fluorophenyl)amino]-2-oxoethyl}-1H-pyrazol-4-yl)amino]-6-methoxyquinazolin-7-yl}oxy)propyl](2-methoxyethyl)amino]ethyl dihydrogen phosphate;

{(2R)-1-[3-({4-[(1-{2-[(2,3-difluorophenyl)amino]-2-oxoethyl}-1H-pyrazol-4-yl)amino]-6-fluoroquinazolin-7-yl}oxy)propyl]pyrrolidin-2-yl}methyl dihydrogen phosphate;

4-((1-(2-((2,3-difluorophenyl)amino)-2-oxoethyl)-1H-pyrazol-4-yl)amino)-7-((1-methylpiperidin-4-yl)methoxy)quinazolin-6-yl dihydrogen phosphate;

{(2R)-1-[2-({4-[(1-{2-[(2,3-difluorophenyl)amino]-2-oxoethyl}-1H-pyrazol-4-yl)amino]-6-methoxyquinazolin-7-yl}oxy)ethyl]pyrrolidin-2-yl}methyl dihydrogen phosphate;

{(2S)-1-[2-({4-[(1-{2-[(2,3-difluorophenyl)amino]-2-oxoethyl}-1H-pyrazol-4-yl)amino]-6-methoxyquinazolin-7-yl}oxy)ethyl]pyrrolidin-2-yl}methyl dihydrogen phosphate;

2-[[2-({4-[(1-{2-[(2,3-difluorophenyl)amino]-2-oxoethyl}-1H-pyrazol-4-yl)amino]-6-methoxyquinazolin-7-yl}oxy)ethyl](tetrahydro-2H-pyran-4-yl)amino]ethyl dihydrogen phosphate;

or a salt or ester thereof, or more particularly a pharmaceutically acceptable salt thereof.

Another particular compound of formula (IA) is any one of:

{(2S)-1-[3-({4-[(1-{2-[(2,3-difluorophenyl)amino]-2-oxoethyl}-1H-pyrazol-4-yl)amino]quinazolin-7-yl}oxy)propyl]pyrrolidin-2-yl}methyl dihydrogen phosphate;

{(2R)-1-[3-({4-[(1-{2-[(2,3-difluorophenyl)amino]-2-oxoethyl}-1H-pyrazol-4-yl)amino]quinazolin-7-yl}oxy)propyl]pyrrolidin-2-yl}methyl dihydrogen phosphate;

2-[[3-({4-[(1-{2-[(2,3-difluorophenyl)amino]-2-oxoethyl}-1H-pyrazol-4-yl)amino]quinazolin-7-yl}oxy)propyl](propyl)amino]ethyl dihydrogen phosphate;

2-[[3-({4-[(1-{2-[(3-fluorophenyl)amino]-2-oxoethyl}-1H-pyrazol-4-yl)amino]quinazolin-7-yl}oxy)propyl](propyl)amino]ethyl dihydrogen phosphate;

2-{4-[3-({4-[(1-{2-[(2,3-difluorophenyl)amino]-2-oxoethyl}-1H-pyrazol-4-yl)amino]quinazolin-7-yl}oxy)propyl]piperazin-1-yl}ethyl dihydrogen phosphate;

2-{ethyl[3-({4-[(1-{2-[(3-fluorophenyl)amino]-2-oxoethyl}-1H-pyrazol-4-yl)amino]quinazolin-7-yl}oxy)propyl]amino}ethyl dihydrogen phosphate;

2-[[3-({4-[(1-{2-[(2,3-difluorophenyl)amino]-2-oxoethyl}-1H-pyrazol-4-yl)amino]quinazolin-7-yl}oxy)propyl](ethyl)amino]ethyl dihydrogen phosphate;

3-{[3-({4-[(1-{2-[(3-fluorophenyl)amino]-2-oxoethyl}-1H-pyrazol-4-yl)amino]quinazolin-7-yl}oxy)propyl)amino}-3-methylbutyl dihydrogen phosphate;

3-{[3-({4-[(1-{2-[(2,3-difluorophenyl)amino]-2-oxoethyl}-1H-pyrazol-4-yl)amino]quinazolin-7-yl}oxy)propyl]amino}-3-methylbutyl dihydrogen phosphate;

{(2R)-1-[3-({4-[(1-{2-[(3-fluorophenyl)amino]-2-oxoethyl}-1H-pyrazol-4-yl)amino]quinazolin-7-yl}oxy)propyl]pyrrolidin-2-yl}methyl dihydrogen phosphate;

2-{4-[3-({4-[(1-{2-[(3-fluorophenyl)amino]-2-oxoethyl}-1H-pyrazol-4-yl)amino]quinazolin-7-yl}oxy)propyl]piperazin-1-yl}ethyl dihydrogen phosphate;

3-{[3-({4-[(1-{2-[(2,3-difluorophenyl)amino]-2-oxoethyl}-1H-pyrazol-4-yl)amino]quinazolin-7-yl}oxy)propyl]amino}propyl dihydrogen phosphate;

2-{[3-({4-[(1-{2-[(2,3-difluorophenyl)amino]-2-oxoethyl}-1H-pyrazol-4-yl)amino]quinazolin-7-yl}oxy)propyl]amino}ethyl dihydrogen phosphate;

2-[[3-({4-[(1-{2-[(3-fluorophenyl)amino]-2-oxoethyl}-1H-pyrazol-4-yl)amino]quinazolin-7-yl}oxy)propyl](2-methoxyethyl)amino]ethyl dihydrogen phosphate;

3-[[3-({4-[(1-{2-[(2,3-difluorophenyl)amino]-2-oxoethyl}-1H-pyrazol-4-yl)amino]quinazolin-7-yl}oxy)propyl](ethyl)amino]propyl dihydrogen phosphate;

3-[[3-({4-[(1-{2-[(2,3-difluorophenyl)amino]-2-oxoethyl}-1H-pyrazol-4-yl)amino]quinazolin-7-yl}oxy)propyl](propyl)amino]propyl dihydrogen phosphate;

2-[[3-({4-[(1-{2-[(2,3-difluorophenyl)amino]-2-oxoethyl}-1H-pyrazol-4-yl)amino]quinazolin-7-yl}oxy)propyl](propyl)amino]-2-oxoethyl dihydrogen phosphate;

2-{4-[3-({4-[(1-{2-[(2,3-difluorophenyl)amino]-2-oxoethyl}-1H-pyrazol-4-yl)amino]quinazolin-7-yl}oxy)propyl]piperazin-1-yl}-2-oxoethyl dihydrogen phosphate;

{(2R)-1-[3-({-[(1-{2-[(2,3-difluorophenyl)amino]-2-oxoethyl}-1H-pyrazol-4-yl)amino]-5-isopropoxyquinazolin-7-yl}oxy)propyl]pyrrolidin-2-yl}methyl dihydrogen phosphate;

2-{4-[3-({4-[(1-{2-[(2,3-difluorophenyl)amino]-2-oxoethyl}-1H-pyrazol-4-yl)amino]-5-isopropoxyquinazolin-7-yl}oxy)propyl]piperazin-1-yl}ethyl dihydrogen phosphate;

2-{[3-({4-[(1-{2-[(2,3-difluorophenyl)amino]-2-oxoethyl}-1H-pyrazol-4-yl)amino]-5-isopropoxyquinazolin-7-yl}oxy)propyl]amino}ethyl dihydrogen phosphate;

{(2R)-1-[3-({4-[(1-{2-[(2,3-difluorophenyl)amino]-2-oxoethyl}-1H-pyrazol-4-yl)amino]-5-methoxyquinazolin-7-yl}oxy)propyl]pyrrolidin-2-yl}methyl dihydrogen phosphate;

2-{4-[3-({4-[(1-{2-[(2,3-difluorophenyl)amino]-2-oxoethyl}-1H-pyrazol-4-yl)amino]quinazolin-7-yl}oxy)propyl]-2-oxopiperazin-1-yl}ethyl dihydrogen phosphate;

2-[[2-({4-[(1-{2-[(2,3-difluorophenyl)amino]-2-oxoethyl}-1H-pyrazol-4-yl)amino]quinazolin-7-yl}oxy)ethyl](tetrahydro-2H-pyran-4-yl)amino]ethyl dihydrogen phosphate;

or a salt or ester thereof, or more particularly a pharmaceutically acceptable salt thereof.

In another aspect a compound of the invention is N-(3-fluorophenyl)-2-{4-[(7-{2-[(2-hydroxyethyl)(tetrahydro-2H-pyran-4-yl)amino]ethoxy}-6-methoxyquinazolin-4-yl)amino]-1H-pyrazol-1-yl}acetamide or N-(3-fluorophenyl)-2-{4-[(7-{2-[(2-hydroxyethyl)(tetrahydro-2H-pyran-4-yl)amino]ethoxy}quinazolin-4-yl)amino]-1H-pyrazol-1-yl}acetamide or a salt, ester or prodrug thereof, wherein the compounds may be prepared by analogous methods to those described herein.

In a further aspect a compound of the invention is 2-[[2-({4-[(1-{2-[(3-fluorophenyl)amino]-2-oxoethyl}-1H-pyrazol-4-yl)amino]-6-methoxyquinazolin-7-yl}oxy)ethyl](tetrahydro-2H-pyran-4-yl)amino]ethyl dihydrogen phosphate or 2-[[2-({4-[(1-{2-[(3-fluorophenyl)amino]-2-oxoethyl}-1H-pyrazol-4-yl)amino]quinazolin-7-yl}oxy)ethyl](tetrahydro-2H-pyran-4-yl)amino]ethyl dihydrogen phosphate or a salt or ester thereof, wherein the compounds may be prepared by analogous methods to those described herein.

Preferred compounds of formula (I) are those that are stable in mouse, rat, or human serum, preferably those that are stable in human serum.

The present invention also provides a process for the preparation of a compound of formula (I) or a salt, ester or prodrug thereof, which process comprises reacting a compound of formula (II)

(II)

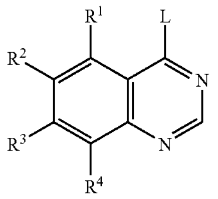

where L is a suitable leaving group such as chloro, bromo, SMe etc. with a compound of formula (III)

(III)

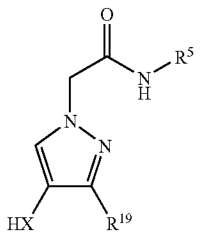

in the presence of hydrochloric acid in dioxane under an inert atmosphere, and thereafter if necessary:

i) converting a compound of the formula (I) into another compound of the formula (I); and/or ii) removing any protecting groups; and/or iii) forming a salt, ester or prodrug thereof.

The reaction is suitably effected in an organic solvent such as dimethyl acetamide or isopropanol at elevated temperatures of from 80° C. to 120° C. for 30 minutes to 2 hours.

The process may further comprise a process for the preparation of a compound of formula (II) when $R^3$ is $—X^3R^{13}$, which process comprises reacting a compound of formula (IV)

(IV)

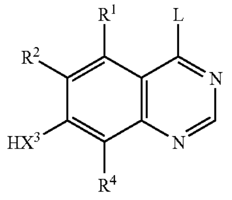

with a compound of formula (V)

$L^1$-$R^{13}$ (V)

where $L^1$ is an appropriate leaving group such as chloro or $L^1$ is —OH which is suitably activated by a reagent such as $PPh_3$.

Compounds of formula (IV) and formula (V) are either known in the art or can be derived from other compounds known in the art by conventional methods which would be apparent from the literature. An analogous process exists for the preparation of a compound of formula (II) when $R^1$ is $—X^1R^{11}$ and/or $R^2$ is $—X^2R^{12}$ and/or $R^4$ is $—X^4R^{14}$.

The process may further comprise a process for the preparation of a compound of formula (III) which process comprises the reaction of a compound of formula (VI)

(VI)

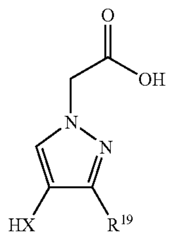

with a compound of formula (VII)

$R^5$—$NH_2$ (VII)

The reaction is suitably effected in an organic solvent such as tetrahydrofuran (THF) or dichloromethane (DCM) at temperatures from 0° C. to 25° C. in the presence of a base such as pyridine under an inert atmosphere for 1 to 3 hours.

Further provided is a process for the preparation of a compound of formula (IA) or a salt or ester thereof, which process comprises phosphorylation of a suitable compound of formula (I) by reacting a compound of formula (I) and tetrazole with di-tert-butyl diethylphosphoramidite in an appropriate organic solvent such as dimethylformamide or dimethylacetamide under an inert atmosphere, followed by (after 1 to 5 hours) the addition of hydrogen peroxide and sodium metabisulphite. Deprotection of the phosphate group then yields a compound of formula (A). Deprotection is suitably effected with hydrochloric acid in dioxane or dichloromethane (DCM) at ambient temperature for 6 to 30 hours.

Suitable reaction conditions are illustrated herein.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

According to a further aspect of the invention there is provided a pharmaceutical composition which comprises a compound formula (I), or a pharmaceutically acceptable salt, ester or prodrug thereof, as defined herein in association with a pharmaceutically acceptable diluent or carrier.

Also provided is a pharmaceutical composition which comprises a compound of formula (IA), or a pharmaceutically acceptable salt or ester thereof, as defined herein in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, soya bean oil, coconut oil, or preferably olive oil, or any other acceptable vehicle.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible or lyophilised powders and granules suitable for preparation of an aqueous suspension or solution by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, solutions, emulsions or particular systems, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in polyethylene glycol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30 μm or much less preferably 5 μm or less and more preferably between 5 μm and 1 μm, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

Therefore in a further aspect of the invention there is provided a compound of formula (I), or a pharmaceutically acceptable salt, ester or prodrug thereof, for use in therapy. In addition a compound of formula (IA) or a pharmaceutically acceptable salt or ester thereof is provided for use in therapy.

Further provided is a compound of formula (I), or a pharmaceutically acceptable salt, ester or prodrug thereof, for use as a medicament and also provided is a compound of formula (IA), or a pharmaceutically acceptable salt or ester thereof, for use as a medicament.

Additionally a compound of formula (I), or a pharmaceutically acceptable salt, ester or prodrug thereof is provided for use in a method of treatment of a warm-blooded animal such as man by therapy. A compound of formula (IA) or a pharmaceutically acceptable salt or ester thereof is also provided for use in a method of treatment of a warm-blooded animal such as man by therapy.

In another aspect of the invention, there is provided a compound of formula (I) or a pharmaceutically acceptable salt, ester or prodrug thereof, in the preparation of a medicament for the treatment of a disease where the inhibition of one or more Aurora kinase(s) is beneficial. A compound of formula (IA) or a pharmaceutically acceptable salt thereof is also provided for use in the preparation of a medicament for the treatment of a disease where the inhibition of one or more Aurora kinase(s) is beneficial is also provided. In particular it is envisaged that inhibition of Aurora-A kinase and/or Aurora-B kinase may be beneficial.

In another aspect of the invention, there is provided a compound of formula (I) or a pharmaceutically acceptable salt, ester or prodrug thereof, for use in the preparation of a medicament for the treatment of hyperproliferative diseases such as cancer and in particular colorectal, breast, lung, prostate, bladder, renal or pancreatic cancer or leukaemia or lymphoma. Also provided is a compound of formula (IA) or a pharmaceutically acceptable salt or ester thereof for use in the preparation of a medicament for the treatment of hyperproliferative diseases such as cancer and in particular colorectal, breast, lung, prostate, bladder, renal or pancreatic cancer or leukaemia or lymphoma.

In another aspect of the invention, there is provided the use of a compound of formula (I) or a pharmaceutically acceptable salt, ester or prodrug thereof, in the preparation of a medicament for the treatment of a disease where the inhibition of one or more Aurora kinase(s) is beneficial. The use of a compound of formula (IA) or a pharmaceutically acceptable salt thereof in the preparation of a medicament for the treatment of a disease where the inhibition of one or more Aurora kinase(s) is beneficial is also provided. In particular it is envisaged that inhibition of Aurora-A kinase and/or Aurora-B kinase may be beneficial.

In another aspect of the invention, there is provided the use of a compound of formula (I) or a pharmaceutically acceptable salt, ester or prodrug thereof, in the preparation of a medicament for the treatment of hyperproliferative diseases such as cancer and in particular colorectal, breast, lung, prostate, bladder, renal or pancreatic cancer or leukaemia or lymphoma. Also provided is the use of a compound of formula (IA) or a pharmaceutically acceptable salt or ester thereof in the preparation of a medicament for the treatment of hyperproliferative diseases such as cancer and in particular colorectal, breast, lung, prostate, bladder, renal or pancreatic cancer or leukaemia or lymphoma.

According to yet another aspect, there is provided a compound of formula (I) or a pharmaceutically acceptable salt ester or prodrug thereof for use in a method of treating a human suffering from a disease in which the inhibition of one or more Aurora kinases is beneficial, comprising the steps of administering to a person in need thereof a therapeutically effective amount of a compound of formula (I) or a pharmaceutically acceptable salt, ester or prodrug thereof. Further provided is a compound of formula (IA) or a pharmaceutically acceptable salt or ester thereof for use in a method of treating a human suffering from a disease in which the inhibition of one or more Aurora kinases is beneficial, comprising the steps of administering to a person in need thereof a therapeutically effective amount of a compound of formula (IA) or a pharmaceutically acceptable salt or ester thereof. In particular it is envisaged that inhibition of Aurora-A kinase and/or Aurora-B kinase may be beneficial.

Further provided is a compound of formula (I) or a pharmaceutically acceptable salt thereof for use in a method of treating a human suffering from a hyperproliferative disease such as cancer and in particular colorectal, breast, lung, prostate, bladder, renal or pancreatic cancer or leukaemia or lymphoma, comprising the steps of administering to a person in need thereof a therapeutically effective amount of a compound of formula (I) or a pharmaceutically acceptable salt, ester or prodrug thereof. A compound of formula (IA) is also provided for use in a method of treating a human suffering from a hyperproliferative disease such as cancer and in particular colorectal, breast, lung, prostate, bladder, renal or pancreatic cancer or leukaemia or lymphoma, comprising the steps of administering to a person in need thereof a therapeutically effective amount of a compound of formula (IA) or a pharmaceutically acceptable salt or ester thereof.

Also provided is a method of treating a human suffering from a disease in which the inhibition of one or more Aurora kinases is beneficial, comprising the steps of administering to a person in need thereof a therapeutically effective amount of a compound of formula (I) or a pharmaceutically acceptable salt, ester or prodrug thereof. Further provided is a method of treating a human suffering from a disease in which the inhibition of one or more Aurora kinases is beneficial, comprising the steps of administering to a person in need thereof a therapeutically effective amount of a compound of formula (IA) or a pharmaceutically acceptable salt or ester thereof. In particular it is envisaged that inhibition of Aurora-A kinase and/or Aurora-B kinase may be beneficial.

Additionally provided is a method of treating a human suffering from a hyperproliferative disease such as cancer and in particular colorectal, breast, lung, prostate, bladder, renal or pancreatic cancer or leukaemia or lymphoma, comprising the steps of administering to a person in need thereof a therapeutically effective amount of a compound of formula (I) or a pharmaceutically acceptable salt, ester or prodrug thereof. Another aspect provides a method of treating a human suffering from a hyperproliferative disease such as cancer and in particular colorectal, breast, lung, prostate, bladder, renal or pancreatic cancer or leukaemia or lymphoma, comprising the steps of administering to a person in need thereof a therapeutically effective amount of a compound of formula (IA) or a pharmaceutically acceptable salt or ester thereof.

For the above mentioned therapeutic uses the dose administered will vary with the compound employed, the mode of administration, the treatment desired, the disorder indicated and the age and sex of the animal or patient. The size of the dose would thus be calculated according to well known principles of medicine.

In using a compound of formula (I) or formula (IA) for therapeutic or prophylactic purposes it will generally be administered so that a daily dose in the range, for example, 0.05 mg/kg to 50 mg/kg body weight is received, given if required in divided doses. In general lower doses will be administered when a parenteral route is employed. Thus, for example, for intravenous administration, a dose in the range, for example, 0.05 mg/kg to 25 mg/kg body weight will generally be used. Similarly, for administration by inhalation, a dose in the range, for example, 0.05 mg/kg to 25 mg/kg body weight will be used.

The treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestratrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine-threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO97/22596, WO97/30035, WO97/32856 and WO98/13354) and compounds that work by other mechanisms (for example linomide, inhibitors of integrin αvμ3 function and angiostatin);

(vi) vascular damaging agents such as Combretastatin A4 and compounds disclosed in International Patent Applications WO99/02166, WO00/40529, WO00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In addition a compound of the invention may be used in combination with one or more cell cycle inhibitors. In particular with cell cycle inhibitors which inhibit bub1, bubR1 or CDK.

Such conjoint treatment may be achieved by way of the simultaneous, sequential or separate dosing of the individual components of the treatment. Such combination products employ the compounds of this invention within the dosage range described herein and the other pharmaceutically-active agent within its approved dosage range.

In addition to their use in therapeutic medicine, a compound of formula (I) or a salt, ester or prodrug thereof or a compound of formula (IA) or a salt or ester thereof are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

The compounds of the invention inhibit the serine-threonine kinase activity of the Aurora kinases, in particular Aurora-A kinase and/or Aurora-B kinase and thus inhibit the cell cycle and cell proliferation. These properties may be assessed for example, using one or more of the procedures set out below.

(a) In Vitro Aurora-A Kinase Inhibition Test

This assay determines the ability of a test compound to inhibit serine-threonine kinase activity. DNA encoding Aurora-A may be obtained by total gene synthesis or by cloning. This DNA may then be expressed in a suitable expression system to obtain polypeptide with serine-threonine kinase activity. In the case of Aurora-A, the coding sequence was isolated from cDNA by polymerase chain reaction (PCR) and cloned into the BamH1 and Not1 restriction endonuclease sites of the baculovirus expression vector pFastBac HTc (GibcoBRL/Life technologies). The 5' PCR primer contained a recognition sequence for the restriction endonuclease BamH15' to the Aurora-A coding sequence.

This allowed the insertion of the Aurora-A gene in frame with the 6 histidine residues, spacer region and rTEV protease cleavage site encoded by the pFastBac HTc vector. The 3' PCR primer replaced the Aurora-A stop codon with additional coding sequence followed by a stop codon and a recognition sequence for the restriction endonuclease Not1. This additional coding sequence (5' TAC CCA TAC GAT GTT CCA GAT TAC GCT TCT TAA 3') encoded for the polypeptide sequence YPYDVPDYAS. This sequence, derived from the influenza hemagglutin protein, is frequently used as a tag epitope sequence that can be identified using specific monoclonal antibodies. The recombinant pFastBac vector therefore encoded for an N-terminally 6 his tagged, C terminally influenza hemagglutin epitope tagged Aurora-A protein. Details of the methods for the assembly of recombinant DNA molecules can be found in standard texts, for example Sambrook et al. 1989, Molecular Cloning—A Laboratory Manual, $2^{nd}$ Edition, Cold Spring Harbor Laboratory press and Ausubel et al. 1999, Current Protocols in Molecular Biology, John Wiley and Sons Inc.

Production of recombinant virus can be performed following manufacturer's protocol from GibcoBRL. Briefly, the pFastBac-1 vector carrying the Aurora-A gene was transformed into *E. coli* DH10Bac cells containing the baculovirus genome (bacmid DNA) and via a transposition event in the cells, a region of the pFastBac vector containing gentamycin resistance gene and the Aurora-A gene including the baculovirus polyhedrin promoter was transposed directly into the bacmid DNA. By selection on gentamycin, kanamycin, tetracycline and X-gal, resultant white colonies should contain recombinant bacmid DNA encoding Aurora-A. Bacmid DNA was extracted from a small scale culture of several BH10Bac white colonies and transfected into Spodoptera frugiperda Sf21 cells grown in TC100 medium (GibcoBRL) containing 10% serum using CellFECTIN reagent (GibcoBRL) following manufacturer's instructions. Virus particles were harvested by collecting cell culture medium 72 hrs post transfection. 0.5 mls of medium was used to infect 100 ml suspension culture of Sf21s containing $1\times10^7$ cells/ml. Cell culture medium was harvested 48 hrs post infection and virus titre determined using a standard plaque assay procedure. Virus stocks were used to infect Sf9 and "High 5" cells at a multiplicity of infection (MOI) of 3 to ascertain expression of recombinant Aurora-A protein.

For the large scale expression of Aurora-A kinase activity, Sf21 insect cells were grown at 28° C. in TC100 medium supplemented with 10% foetal calf serum (Viralex) and 0.2% F68 Pluronic (Sigma) on a Wheaton roller rig at 3 r.p.m. When the cell density reached $1.2\times10^6$ cells $ml^{-1}$ they were infected with plaque-pure Aurora-A recombinant virus at a multiplicity of infection of 1 and harvested 48 hours later. All subsequent purification steps were performed at 4° C. Frozen insect cell pellets containing a total of $2.0\times10^8$ cells were thawed and diluted with lysis buffer (25 mM HEPES (N-[2-hydroxyethyl]piperazine-N'-[2-ethanesulphonic acid]) pH7.4 at 4° C., 100 mM KCl, 25 mM NaF, 1 mM $Na_3VO_4$, 1 mM PMSF (phenylmethylsulphonyl fluoride), 2 mM 2-mercaptoethanol, 2 mM imidazole, 1 μg/ml aprotinin, 1 μg/ml pepstatin, 1 μg/ml leupeptin), using 1.0 ml per $3\times10^7$ cells. Lysis was achieved using a dounce homogeniser, following which the lysate was centrifuged at 41,000 g for 35 minutes. Aspirated supernatant was pumped onto a 5 mm diameter chromatography column containing 500 μl Ni NTA (nitrilo-tri-acetic acid) agarose (Qiagen, product no. 30250) which had been equilibrated in lysis buffer. A baseline level of UV absorbance for the eluent was reached after washing the column with 12 ml of lysis buffer followed by 7 ml of wash buffer (25 mM HEPES pH 7.4 at 4° C., 100 mM KCl, 20 mM imidazole, 2 mM 2-mercaptoethanol). Bound Aurora-A protein was eluted from the column using elution buffer (25 mM HEPES pH7.4 at 4° C., 100 mM KCl, 400 mM imidazole, 2 mM 2-mercaptoethanol). An elution fraction (2.5 ml) corresponding to the peak in UV absorbance was collected. The elution fraction, containing active Aurora-A kinase, was dialysed exhaustively against dialysis buffer (25 mM HEPES pH7.4 at 4° C., 45% glycerol (v/v), 100 mM KCl, 0.25% Nonidet P40 (v/v), 1 mM dithiothreitol).

Each new batch of Aurora-A enzyme was titrated in the assay by dilution with enzyme diluent (25 mM Tris-HCl pH 7.5, 12.5 mM KCl, 0.6 mM DTT). For a typical batch, stock enzyme is diluted 1 in 666 with enzyme diluent & 20 μl of dilute enzyme is used for each assay well. Test compounds (at 10 mM in dimethylsulphoxide (DMSO) were diluted with water & 10 μl of diluted compound was transferred to wells in the assay plates. "Total" & "blank" control wells contained 2.5% DMSO instead of compound. Twenty microliters of freshly diluted enzyme was added to all wells, apart from "blank" wells. Twenty microliters of enzyme diluent was added to "blank" wells. Twenty microliters of reaction mix (25 mM Tris-HCl, 78.4 mM KCl, 2.5 mM NaF, 0.6 mM dithiothreitol, 6.25 mM $MnCl_2$, 6.25 mM ATP, 7.5 μM peptide substrate [biotin-LRRWSLGLRRWSLGLRRWSLGLRRWSLG]) containing 0.2 μCi [$\gamma^{33}P$]ATP (Amersham Pharmacia, specific activity ≧2500 Ci/mmol) was then added to all test wells to start the reaction. The plates were incubated at room temperature for 60 minutes. To stop the reaction 100 μl 20% v/v orthophosphoric acid was added to all wells. The peptide substrate was captured on positively-charged nitrocellulose P30 filtermat (Whatman) using a 96-well plate harvester (TomTek) & then assayed for incorporation of $^{33}P$ with a Beta plate counter. "Blank" (no enzyme) and "total" (no compound) control values were used to determine the dilution range of test compound which gave 50% inhibition of enzyme activity. In this test, the compounds of the invention generally give 50% inhibition of enzyme activity at concentrations of 1 nM to 1000 nM and in particular compound 27 in Table 2 gave 50% inhibition of enzyme activity at a concentration of 34 nM, compound 60 in Table 3 gave 50% inhibition of enzyme activity at a concentration of 10 nM and compound 187 in Table 5 gave 50% inhibition of enzyme activity at a concentration of 0.5 μM (b) In Vitro Aurora-B Kinase Inhibition Test This assay determines the ability of a test compound to inhibit serine-threonine kinase activity. DNA encoding Aurora-B may be obtained by total gene synthesis or by cloning. This DNA may then be expressed in a suitable expression system to obtain polypeptide with serine-threonine kinase activity. In the case of Aurora-B, the coding sequence was isolated from cDNA by polymerase chain reaction (PCR) and cloned into the pFastBac system in a manner similar to that described above for Aurora-A (i.e. to direct expression of a 6-histidine tagged Aurora-B protein).

For the large scale expression of Aurora-B kinase activity, Sf21 insect cells were grown at 28° C. in TC100 medium supplemented with 10% foetal calf serum (Viralex) and 0.2% F68 Pluronic (Sigma) on a Wheaton roller rig at 3 r.p.m. When the cell density reached $1.2\times10^6$ cells $ml^{-1}$ they were infected with plaque-pure Aurora-B recombinant virus at a multiplicity of infection of 1 and harvested 48 hours later. All subsequent purification steps were performed at 4° C. Frozen insect cell pellets containing a total of $2.0\times10^8$ cells were thawed and diluted with lysis buffer (50 mM HEPES (N-[2-hydroxyethyl]piperazine-N'-[2-ethanesulphonic acid]) pH 7.5 at 4° C., 1 mM $Na_3VO_4$, 1 mM PMSF (phenylmethylsulphonyl fluoride), 1 mM dithiothreitol, 1 μg/ml aprotinin, 1 μg/ml pepstatin, 1 μg/ml leupeptin), using 1.0 ml per $2\times10^7$ cells. Lysis was achieved using a sonication homogeniser, following which the lysate was centrifuged at 41,000 g for 35 minutes. Aspirated supernatant was pumped onto a 5 mm diameter chromatography column containing 1.0 ml CM sepharose Fast Flow (Amersham Pharmacia Biotech) which had been equilibrated in lysis buffer. A baseline level of UV absorbance for the eluent was reached after washing the column with 12 ml of lysis buffer followed by 7 ml of wash buffer (50 mM HEPES pH 7.4 at 4° C., 1 mM dithiothreitol). Bound Aurora-B B protein was eluted from the column using a gradient of elution buffer (50 mM HEPES pH 7.4 at 4° C., 0.6 M NaCl, 1 mM dithiothreitol, running from 0% elution buffer to 100% elution buffer over 15 minutes at a flowrate of 0.5 ml/min). Elution fractions (1.0 ml) corresponding to the peak in UV absorbance was collected. Elution fractions were dialysed exhaustively against dialysis buffer (25 mM HEPES pH 7.4 at 4° C., 45% glycerol (v/v), 100 mM KCl, 0.05% (v/v) IGEPAL CA630 (Sigma Aldrich), 1 mM dithiothreitol). Dialysed fractions were assayed for Aurora-B kinase activity.

Each new batch of Aurora-B enzyme was titrated in the assay by dilution with enzyme diluent (25 mM Tris-HCl pH 7.5, 12.5mM KCl, 0.6 mM DTT). For a typical batch, stock enzyme is diluted 1 in 40 with enzyme diluent & 20 μl of dilute enzyme is used for each assay well. Test compounds (at 10 mM in dimethylsulphoxide (DMSO) were diluted with water & 10 μl of diluted compound was transferred to wells in the assay plates. "Total" & "blank" control wells contained 2.5% DMSO instead of compound. Twenty microliters of freshly diluted enzyme was added to all wells, apart from "blank" wells. Twenty microliters of enzyme diluent was added to "blank" wells. Twenty microliters of reaction mix (25 mM Tris-HCl, 78.4 mM KCl, 2.5 mM NaF, 0.6 mM dithiothreitol, 6.25 mM $MnCl_2$, 37.5 mM ATP, 25 μM peptide substrate [biotin-LRRWSLGLRRWSLGLRRWSLGIR-RWSLG]) containing 0.2 μCi [$\gamma^{33}$P]ATP (Amersham Pharmacia, specific activity ≧2500 Ci/mmol) was then added to all test wells to start the reaction. The plates were incubated at room temperature for 60 minutes. To stop the reaction 100 μl 20% v/v orthophosphoric acid was added to all wells. The peptide substrate was captured on positively-charged nitrocellulose P30 filtermat (Whatman) using a 96-well plate harvester (TomTek) & then assayed for incorporation of $^{33}$P with a Beta plate counter. "Blank" (no enzyme) and "total" (no compound) control values were used to determine the dilution range of test compound which gave 50% inhibition of enzyme activity. In this test, the compounds of the invention generally give 50% inhibition of enzyme activity at concentrations of 1 nM to 1000 nM and in particular compound 27 in Table 2 gave 50% inhibition of enzyme activity at a concentration of 5 nM, compound 60 in Table 3 gave 50% inhibition of enzyme activity at a concentration of 8 nM and compound 187 in Table 5 gave 50% inhibition of enzyme activity at a concentration of 9 nM.

(c) In Vitro cell Proliferation Assay

This and other assays can be used to determine the ability of a test compound to inhibit the growth of adherent mammalian cell lines, for example the human tumour cell line SW620 (ATCC CCL-227). This assay determines the ability of at test compound to inhibit the incorporation of the thymidine analogue, 5'-bromo-2'-deoxy-uridine (BrdU) into cellular DNA. SW620 or other adherent cells were typically seeded at $1\times10^5$ cells per well in L-15 media (GIBCO) plus 5% foetal calf serum, 1% L-glutamine (100 μl /well) in 96 well tissue culture treated 96 well plates (Costar) and allowed to adhere overnight. The following day the cells were dosed with compound (diluted from 10 mM stock in DMSO using L-15 (with 5% FCS, 1% L-glutamine). Untreated control wells and wells containing a compound known to give 100% inhibition of BrdU incorporation were included on each plate. After 48 hours in the presence/absence of test compound the ability of the cells to incorporate BrdU over a 2 hour labelling period was determined using a Boehringer (Roche) Cell Proliferation BrdU EUSA kit (cat. No. 1 647 229) according to manufacturers directions. Briefly, 15 μl of BrdU labelling reagent (diluted 1:100 in media—L-15, 5% FCS, 1% L-glutamine) was added to each well and the plate returned to a humidified (+5% $CO_2$) 37° C. incubator for 2 hours. After 2 hours the labelling reagent was removed by decanting and tapping the plate on a paper towel. FixDenat solution (50 μl per well) was added and the plates incubated at room temperature for 45 mins with shaking. The FixDenat solution was removed by decanting and tapping the inverted plate on a paper towel. The plate was then washed once with phosphate buffered saline (PBS) and 100 μl/well of Anti-BrdU-POD antibody solution (diluted 1:100 in antibody dilution buffer) added. The plate was then incubated at room temperature with shaking for 90 min. Unbound Anti-BrdU-POD antibody was removed by decanting and washing the plate 4 times with PBS before being blotted dry. TMB substrate solution was added (100 μl/well) and incubated for approximately 10 minutes at room temperature with shaking until a colour change was apparent. The optical density of the wells was then determined at 690 nm wavelength using a Titertek Multiscan plate reader. The values from compound treated, untreated and 100% inhibition controls were used to determine the dilution range of a test compound that gave 50% inhibition of BrdU incorporation. The compounds of the invention are generally active at 1 nM to 100 μM in this test and in particular compound 27 in Table 2 gave 50% inhibition of enzyme activity at a concentration of 10 nM, compound 60 in Table 3 gave 50% inhibition of enzyme activity at a concentration of 1 nM and compound 187 in Table 5 gave 50% inhibition of enzyme activity at a concentration of 1 nM.

(d) In Vitro Cell Cycle Analysis Assay

This assay determines the ability of a test compound to arrest cells in specific phases of the cell cycle. Many different mammalian cell lines could be used in this assay and SW620 cells are included here as an example. SW620 cells were seeded at $7\times10^5$ cells per T25 flask (Costar) in 5 ml L-15 (5% FCS, 1% L-glutamine). Flasks were then incubated overnight in a humidified 37° C. incubator with 5% $CO_2$. The following day, 5 μl of L-15 (5% FCS, 1% L-glutamine) carrying the appropriate concentration of test compound solubilised in DMSO was added to the flask. A no compound control treatment was also included (0.5% DMSO). The cells were then incubated for a defined time (24 hours) with compound. After this time the media was aspirated from the cells and they were washed with 5 ml of prewarmed (37° C.) sterile PBSA, then detached from the flask by brief incubation with trypsin and followed by resuspension in 5 ml of 1% Bovine Serum Albumin (BSA, Sigma-Aldrich Co.) in sterile PBSA. The samples were then centrifuged at 2200 rpm for 10 min. The supernatant was aspirated to leave 200 μl of the PBS/BSA solution. The pellet was resuspended in this 200 μl of solution by pipetting 10 times to create a single cell suspension. One ml of ice-cold 80% ethanol was slowly added to each cell suspension and the samples stored at −20° C. overnight or until required for staining. Cells were pelleted by centrifugation, ethanol aspirated off and pellets resuspended in 200 µl PBS containing 100 µg/ml RNAse (Sigma Aldrich) & 10 µg/ml Propidium Iodide (Sigma Aldrich). Cell suspensions were incubated at 37° C. for 30 min, a further 200 µl PBS added and samples stored in the dark at 4° C. overnight.

Each sample was then syringed 10 times using 21-guage needle. The samples were then transferred to LPS tubes and DNA content per cell analysed by Fluorescence activated cell sorting (FACS) using a FACScan flow cytometer (Becton Dickinson). Typically 30,000 events were counted and recorded using CellQuest v1.1 software (Verity Software). Cell cycle distribution of the population was calculated using Modfit software (Verity Software) and expressed as percentage of cells with 2N (G0/G1), 2N4N (S phase) and with 4N (G2/M) DNA content.

The compounds of the invention are generally active in this test at 1 nM to 10 µM and in particular compound 27 in Table 2 gave 50% inhibition of enzyme activity at a concentration of 7 nM, compound 60 in Table 3 gave 50% inhibition of enzyme activity at a concentration of 3 nM and compound 187 in Table 5 gave 50% inhibition of enzyme activity at a concentration of 21 nM.

The invention will now be illustrated in the following non limiting examples, in which standard techniques known to the skilled chemist and techniques analogous to those described in these examples may be used where appropriate, and in which, unless otherwise stated:

(i) evaporations were carried out by rotary evaporation in vacuo and work up procedures were carried out after removal of residual solids such as drying agents by filtration;

(ii) operations were carried out at ambient temperature, typically in the range 18-25° C. and in air unless stated, or unless the skilled person would otherwise operate under an atmosphere of an inert gas such as argon;

(iii) column chromatography (by the flash procedure) and medium pressure liquid chromatography (MPLC) were performed on Merck Kieselgel silica (Art. 9385);

(iv) yields are given for illustration only and are not necessarily the maximum attainable;

(v) the structures of the end products of the formula (I) were generally confirmed by nuclear (generally proton) magnetic resonance (NMR) and mass spectral techniques; proton magnetic resonance chemical shift values were measured in deuterated dimethyl sulphoxide (DMSO $d_6$) (unless otherwise stated) on the delta scale (ppm downfield from tetramethylsilane) using one of the following four instruments Varian Gemini 2000 spectrometer operating at a field strength of 300 MHz Bruker DPX300 spectrometer operating at a field strength of 300 MHz JEOL EX 400 spectrometer operating at a field strength of 400 MHz Bruker Avance 500 spectrometer operating at a field strength of 500 MHz Peak multiplicities are shown as follows: s, singlet; d, doublet; dd, double doublet; t, triplet; q, quartet; qu, quintet; m, multiplet; br s, broad singlet;

(vi) robotic synthesis was carried out using a Zymate XP robot, with solution additions via a Zymate Master Laboratory Station and stirred via a Stem RS5000 Reacto-Station at 25° C.;

(vii) work up and purification of reaction mixtures from robotic synthesis was carried out as follows: evaporations were carried out in vacuo using a Genevac HT 4; column chromatography was performed using either an Anachem Sympur MPLC system on silica using 27 mm diameter columns filled with Merck silica (60 µm, 25 g); the structures of the final products were confirmed by LCMS on a Waters 2890/ZMD micromass system using the following and are quoted as retention time (RT) in minutes:

Column: waters symmetry C18 3.5 µm 4.6×50 mm

Solvent A: $H_2O$

Solvent B: $CH_3CN$

Solvent C: MeOH+5% HCOOH

Flow rate: 2.5 ml/min

Run time: 5 minutes with a 4.5 minute gradient from 0-100% C

Wavelength: 254 nm, bandwidth 10 nm

Mass detector: ZMD micromass

Injection volume 0.005 ml (viii) Analytical LCMS for compounds which had not been prepared by robotic synthesis was performed on a Waters Alliance HT system using the following and are quoted as retention time (RT) in minutes:

Column: 2.0 mm×5 cm Phenomenex Max-RP 80A

Solvent A: Water

Solvent B: Acetonitrile

Solvent C: Methanol/1% formic acid or Water/1% formic acid

Flow rate: 1.1 ml/min

Run time: 5 minutes with a 4.5 minute gradient from 0-95% B+constant 5% solvent C Wavelength: 254 nm, bandwidth 10 nm Injection volume 0.005 ml Mass detector: Micromass ZMD (ix) Preparative high performance liquid chromatography (HPLC) was performed on either Waters preparative LCMS instrument, with retention time (RT) measured in minutes:

Column: β-basic Hypercil (21×100 mm) 5 µm

Solvent A: Water/0.1% Ammonium carbonate

Solvent B: Acetonitrile

Flow rate: 25 ml/min

Run time: 10 minutes with a 7.5 minute gradient from 0-100% B

Wavelength: 254 nm, bandwidth 10 nm

Injection volume 1-1.5 ml

Mass detector: Micromass ZMD

Gilson preparative HPLC instrument, with retention time (RT) measured in minutes:

Column: 21 mm×15 cm Phenomenex Luna2 C18

Solvent A: Water+0.1% trifluoracetic acid,

Solvent B: Acetonitrile+0.1% trifluoracetic acid

Flow rate: 21 ml/min

Run time: 20 minutes with various 10 minute gradients from 5-100% B

Wavelength: 254 nm, bandwidth 10 nm

Injection volume 0.1-4.0 ml (x) intermediates were not generally fully characterised and purity was assessed by thin layer chromatography (TLC), HPLC, infra-red (IR), MS or NMR analysis.

TABLE 1

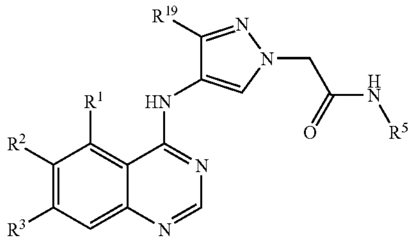

| Compound | $R^1$ | $R^2$ | $R^3$ | $R^5$ | $R^{19}$ |
|---|---|---|---|---|---|
| 1 | H | OMe | 3-chloropropoxy | 3-fluorophenyl | H |
| 2 | H | H | 3-chloropropoxy | 2,3-difluorophenyl | H |
| 3 | H | OMe | 3-chloropropoxy | 2,3-difluorophenyl | H |
| 4 | H | H | 3-chloropropoxy | 3-fluorophenyl | H |
| 5 | H | H | 2-chloroethoxy | 2,3-difluorophenyl | H |
| 6 | H | OMe | 2-chloroethoxy | 2,3-difluorophenyl | H |
| 7 | H | H | 2,2-dimethoxyethoxy | 2,3-difluorophenyl | H |
| 8 | H | OMe | 3-chloropropoxy | 3-fluorophenyl | carboxamide |
| 9 | H | H | 3-chloropropoxy | 3-fluorophenyl | ethyl carboxylate |
| 10 | H | H | 3-chloropropoxy | 3-fluorophenyl | acetylamino |
| 11 | H | H | H | 2,3-difluorophenyl | H |
| 12 | isopropoxy | H | 3-chloropropoxy | 2,3-difluorophenyl | H |
| 13 | OMe | H | 3-chloropropoxy | 2,3-difluorophenyl | H |
| 14 | H | F | 3-chloropropoxy | 2,3-difluorophenyl | H |
| 15 | H | F | 3-chloropropoxy | 3-fluorophenyl | H |

TABLE 2

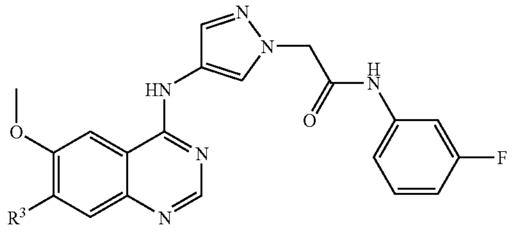

| Compound | $R^3$ |
|---|---|
| 16 | 3-[(2S)-2-(hydroxymethyl)pyrrolidin-1-yl]propoxy |
| 17 | 3-{(2-hydroxyethyl)(isobutyl)amino]propoxy |
| 18 | 3-[(2-hydroxyethyl)(propyl)amino]propoxy |
| 19 | 3-piperidin-1-ylpropoxy |
| 20 | 3-pyrrolidin-1-ylpropoxy |
| 21 | 3-(diethylamino)propoxy |
| 22 | 3-piperazin-1-ylpropoxy |
| 23 | 3-[(2-hydroxyethyl)(methyl)amino]propoxy |
| 24 | 3-(cyclopropylamino)propoxy |
| 25 | 3-[[2-(dimethylamino)ethyl](methyl)amino]propoxy |
| 26 | 3-(4-methylpiperazin-1-yl)propoxy |
| 27 | 3-[(2R)-2-(hydroxymethyl)pyrrolidin-1-yl]propoxy |
| 28 | 3-(4-hydroxypiperidin-1-yl)propoxy |
| 29 | 3-[bis(2-hydroxyethyl)amino]propoxy |

TABLE 2-continued

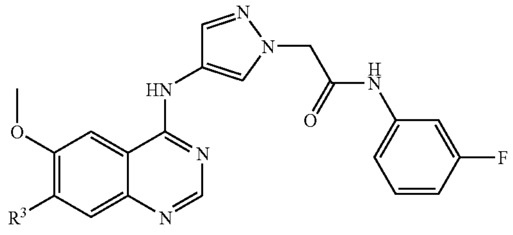

| Compound | $R^3$ |
|---|---|
| 30 | 3-[ethyl(methyl)amino]propoxy |
| 31 | 3-[ethyl(2-hydroxyethyl)amino]propoxy |
| 32 | 3-[[2-(dimethylamino)ethyl]ethyl)amino]propoxy |
| 33 | 3-[2-(2-hydroxyethyl)piperidin-1-yl]propoxy |
| 34 | 3-[4-(2-hydroxyethyl)piperazin-1-yl]propoxy |
| 35 | 3-[(cyclopropylmethyl)amino]propoxy |
| 36 | 3-[4-(2-hydroxyethyl)piperidin-1-yl]propoxy |
| 37 | 3-[methyl(prop-2-yn-1-yl)amino]propoxy |
| 38 | 3-[allyl(methyl)amino]propoxy |
| 39 | 3-[isobutyl(methyl)amino]propoxy |
| 40 | 3-(3-hydroxypiperidin-1-yl)propoxy |
| 41 | 3-[4-(hydroxymethyl)piperidin-1-yl]propoxy |
| 42 | 3-[methyl(propyl)amino]propoxy |
| 43 | 3-[(cyclopropylmethyl)(propyl)amino]propoxy |

TABLE 2-continued

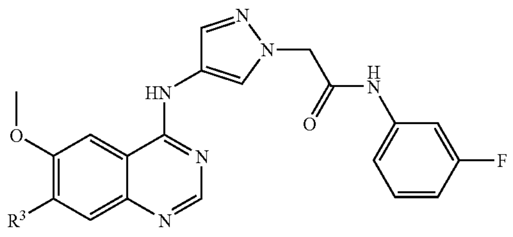

| Compound | $R^3$ |
|---|---|
| 44 | 3-[[(2-(diethylamino)ethyl](methyl)amino]propoxy |
| 45 | 3-[[2-(diethylamino)ethyl](ethyl)amino]propoxy |
| 46 | 3-(4-methyl-1,4-diazepan-1-yl)propoxy |
| 47 | 3-[(2-hydroxyethyl)(isopropyl)amino]propoxy |
| 48 | 3-[cyclopropyl(2-hydroxyethyl)amino]propoxy |
| 49 | 3-[(2-hydroxyethyl)(2-methoxyethyl)amino]propoxy |
| 50 | 3-[cyclobutyl(2-hydroxyethyl)amino]propoxy |
| 51 | 3-[(cyclopropyhnethyl)(2-hydroxyethyl)amino]propoxy |
| 52 | 3-[(cyclobutylmethyl)(2-hydroxyethyl)amino]propoxy |
| 53 | 3-[(2-hydroxyethyl)(prop-2-yn-1-yl)amino]propoxy |
| 54 | 3-[allyl(2-hydroxyethyl)amino]propoxy |
| 55 | 3-[(2,2-dimethylpropyl)(2-hydroxyethyl)amino]propoxy |
| 56 | 3-[(2-hydroxyethyl)(3,3,3-trifluoropropyl)amino]propoxy |
| 57 | 3-azetidin-1-ylpropoxy |
| 58 | methoxy |
| 59 | hydroxy |

TABLE 3

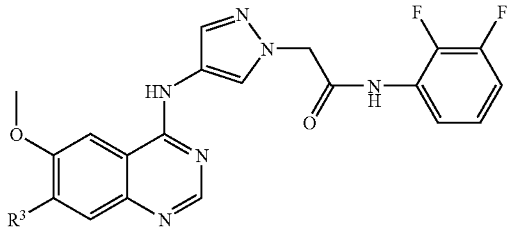

| Compound | $R^3$ |
|---|---|
| 60 | 3-[(2-hydroxyethyl)(isobutyl)amino]propoxy |
| 61 | 3-[(2S)-2-(hydroxymethyl)pyrrolidin-1-yl]propoxy |
| 62 | 3-[(2-hydroxyethyl)(propyl)amino]propoxy |
| 63 | 3-(dimethylamino)propoxy |
| 64 | 3-piperidin-1-ylpropoxy |
| 65 | 3-pyrrolidin-1-ylpropoxy |
| 66 | 3-piperazin-1-ylpropoxy |
| 67 | 3-[(2-hydroxyethyl)(methyl)amino]propoxy |
| 68 | 3-(cyclopropylamino)propoxy |
| 69 | 3-[[2-(dimethylamino)ethyl](methyl)amino]propoxy |
| 70 | 3-(4-methylpiperazin-1-yl)propoxy |
| 71 | 3-[(2R)-2-(hydroxymethyl)pyrrolidin-1-yl]propoxy |
| 72 | 3-(4-hydroxypiperidin-1-yl)propoxy |
| 73 | 3-[bis(2-hydroxyethyl)amino]propoxy |
| 74 | 3-[ethyl(methyl)amino]propoxy |
| 75 | 3-[ethyl(2-hydroxyethyl)amino]propoxy |
| 76 | 3-[[2-(dimethylamino)ethyl](ethyl)amino]propoxy |
| 77 | 3-[2-(2-hydroxyethyl)piperidin-1-yl]propoxy |
| 78 | 3-[4-(2-hydroxyethyl)piperazin-1-yl]propoxy |
| 79 | 3-[(cyclopropylmethyl)amino]propoxy |
| 80 | 3-[4-(2-hydroxyethyl)piperidin-1-yl]propoxy |
| 81 | 3-[methyl(prop-2-yn-1-yl)amino]propoxy |
| 82 | 3-[isobutyl(methyl)amino]propoxy |
| 83 | 3-(3-hydroxypiperidin-1-yl)propoxy |
| 84 | 3-[4-(hydroxymethyl)piperidin-1-yl]propoxy |
| 85 | 3-[methyl(propyl)amino]propoxy |
| 86 | 3-[(cyclopropylmethyl)(propyl)amino]propoxy |
| 87 | 3-[[2-(diethylamino)ethyl](methyl)amino]propoxy |
| 88 | 3-[[2-(diethylamino)ethyl](ethyl)amino]propoxy |

TABLE 3-continued

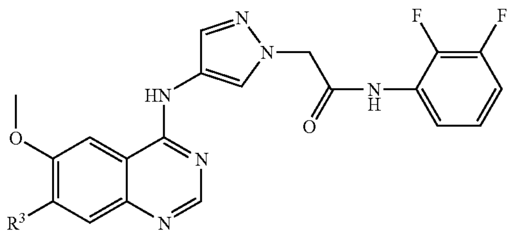

| Compound | $R^3$ |
|---|---|
| 89 | 3-(4-methyl-1,4-diazepan-1-yl)propoxy |
| 90 | 3-[(2-hydroxyethyl)(isopropyl)amino]propoxy |
| 91 | 3-[cyclopropyl(2-hydroxyethyl)amino]propoxy |
| 92 | 3-[(2-hydroxyethyl)(2-methoxyethyl)amino]propoxy |
| 93 | 3-[cyclobutyl(2-hydroxyethyl)amino]propoxy |
| 94 | 3-[(cyclopropylmethyl)(2-hydroxyethyl)amino]propoxy |
| 95 | 3-[(cyclobutylmethyl)(2-hydroxyethyl)amino]propoxy |
| 96 | 3-[(2-hydroxyethyl)(prop-2-yn-1-yl)amino]propoxy |
| 97 | 3-[allyl(2-hydroxyethyl)amino]propoxy |
| 98 | 3-[(2,2-dimethylpropyl)(2-hydroxyethyl)amino]propoxy |
| 99 | 3-[(2-hydroxyethyl)(3,3,3-trifluoropropyl)amino]propoxy |
| 100 | 2-[(2R)-(2-hydroxymethyl)pyrrolidin-1-yl]ethoxy |
| 101 | 2-{4-[2-(2-hydroxyethoxy)ethyl]piperazin-1-yl}ethoxy |
| 102 | 2-[2-(hydroxymethyl)piperidin-1-yl]ethoxy |
| 103 | 2-[(2-hydroxy-1,1-dimethylethyl)amino]ethoxy |
| 104 | 2-[4-(2-hydroxyethyl)piperazin-1-yl]ethoxy |
| 105 | 2-[(trans-4-hydroxycyclohexyl)amino]ethoxy |
| 106 | 2-[3-(hydroxymethyl)piperidin-1-yl]ethoxy |
| 107 | 2-{[1-(hydroxymethyl)cyclopentyl]amino}ethoxy |
| 108 | 2-[4-(3-hydroxypropyl)piperazin-1-yl]ethoxy |
| 109 | 2-[cyclohexyl(2-hydroxyethyl)amino]ethoxy |
| 110 | 2-[(2-hydroxyethyl)(propyl)amino]ethoxy |
| 111 | 2-[(3-hydroxy-2,2-dimethylpropyl)amino]ethoxy |
| 112 | 2-(tetrahydro-2H-pyram-4-ylamino)ethoxy |
| 113 | 2-[cyclobutyl(2-hydroxyethyl)amino]ethoxy |
| 114 | 2-[(2-hydroxyethyl)(tetrahydro-2H-pyran-4-yl)amino]ethoxy |
| 115 | 2-[(2S)-2-(hydroxymethyl)pyrrolidin-1-yl]ethoxy |
| 116 | 2-[(2R)-2-(2-hydroxyethyl)piperidine-1-yl]ethoxy |
| 117 | 2-[(2S)-2-(2-hydroxyethyl)piperidine-1-yl]ethoxy |

TABLE 4

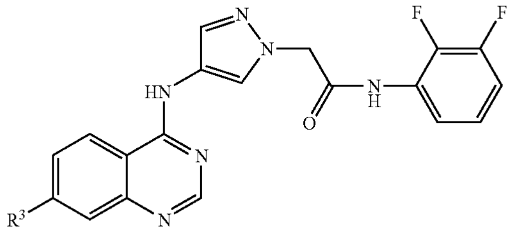

| Compound | $R^3$ |
|---|---|
| 118 | 3-[(2-hydroxyethyl)(propyl)amino]propoxy |
| 119 | 3-[(2-hydroxyethyl)(isobutyl)amino]propoxy |
| 120 | 3-[(2S)-2-(hydroxymethyl)pyrrolidin-1-yl]propoxy |
| 121 | 3-[(2R)-2-(hydroxymethyl)pyrrolidin-1-yl]propoxy |
| 122 | 3-[(2-hydroxyethyl)(cyclopentyl)amino]propoxy |
| 123 | 3-[(2-hydroxyethyl)(ethyl)amino]propoxy |
| 124 | 3-[4-(2-hydroxyethyl)piperazin-1-yl]propoxy |
| 125 | 3-[4-(hydroxymethyl)piperidin-1-yl]propoxy |
| 126 | 3-[(3-hydroxy-1,1 dimethylpropyl)amino]propoxy |
| 127 | 3-[(2-cyanoethyl)(2-hydroxyethyl)amino]propoxy |
| 128 | 3-morpholin-4-ylpropoxy |
| 129 | 3-[(3-hydroxy-2,2-dixnethylpropyl)amino]propoxy |
| 130 | 3-[(3-hydroxypropyl)amino]propoxy |
| 131 | 3-[(3-hydroxypropyl)(propyl)aimno]propoxy |
| 132 | 3-[ethyl(3-hydroxypropyl)amino]propoxy |

TABLE 4-continued

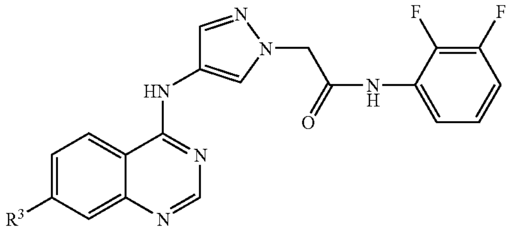

| Compound | $R^3$ |
|---|---|
| 133 | 3-[4-(2-hydroxyethyl)-3-oxopiperazin-1-yl]propoxy |
| 134 | 3-(propylamino)propoxy |
| 135 | 3-piperazin-1-ylpropoxy |
| 136 | 3-[glycoloyl(propyl)amino]propoxy |
| 137 | 3-(4-glycoloylpiperazin-1-yl)propoxy |
| 138 | 3-{[trans-2-(hydroxymethyl)cyclohexyl]amino}propoxy |
| 139 | 3-[(1α,5α,6α)-6-(hydroxymethyl)-3-azabicyclo[3.1.0]hex-3-yl]propoxy |
| 140 | 3-{[(2R)-2-hydroxypropyl]amino}propoxy |
| 141 | 3-{[(1S)-2-hydroxy-1-methylethyl]amino}propoxy |
| 142 | 3-[(2-hydroxy-1,1-dimethylethyl)amino]propoxy |
| 143 | 3-[(2,3-dihydroxypropyl)amino]propoxy |
| 144 | 3-{[2-(2-hydroxyethoxy)ethyl]amino}propoxy |
| 145 | 3-(4-acetylpiperazin-1-yl)propoxy |
| 146 | 3-[(tetrahydrofuran-2-ylmethyl)amino]propoxy |
| 147 | 3-(allylamino)propoxy |
| 148 | 3-{[1-(hydroxymethyl)-2-methylpropyl]amino}propoxy |
| 149 | 3-{[(5-methylisoxazol-3-yl)methyl]amino}propoxy |
| 150 | 3-(tetrahydro-2H-pyran-4-ylamino)propoxy |
| 151 | 3-[(3S)-3-(hydroxymethyl)pyrrolidin-1-yl]propoxy |
| 152 | 3-hydroxypropoxy |
| 153 | 3-aminopropoxy |
| 154 | 3-[(2S,4R)-4-hydroxy-2-(hydroxymethyl)pyrrolidin-1-yl]propoxy |
| 155 | 2-[(3-hydroxy-2,2-dimethylpropyl)amino]ethoxy |
| 156 | 2-[cyclohexyl(2-hydroxyethyl)amino]ethoxy |
| 157 | 2-(cyclopropylamino)ethoxy |
| 158 | 2-(cyclobutylamino)ethoxy |
| 159 | 2-(tetrahydro-2H-pyran-4-ylamino)ethoxy |
| 160 | 2-(cyclopentylamino)ethoxy |
| 161 | 2-[(2-hydroxyethyl)(tetrahydro-2H-pyran-4-yl)amino]ethoxy |
| 162 | 2-[cyclopentyl(2-hydroxyethyl)amino]ethoxy |
| 163 | 2-[(2R)-2-(hydroxymethyl)pyrrolidin-1-yl]ethoxy |
| 164 | 2-[cyclopropyl(2-hydroxyethyl)amino]ethoxy |
| 165 | 2-[cyclobutyl(2-hydroxyethyl)amino]ethoxy |
| 166 | 2-[cyclopentyl(3-hydroxypropyl)amino]ethoxy |
| 167 | 2-[cyclopentyl(glycoloyl)amino]ethoxy |
| 168 | 2-[(3S)-3-(hydroxymethyl)-4-methylpiperazin-1-yl]ethoxy |
| 169 | 2-[(2S)-2-(hydroxymethyl)pyrrolidin-1-yl]ethoxy |
| 170 | 2-[(2R)-2-(hydroxymethyl)-4-methylpiperazin-1-yl]ethoxy |
| 171 | 2-[4-(hydroxymethyl)piperidin-1-yl]ethoxy |
| 172 | 2-[4-(2-hydroxyethyl)piperidin-1-yl]ethoxy |
| 173 | 2-[(2-hydroxyethyl)amino]ethoxy |
| 174 | 2-{[trans-2-(hydroxymethyl)cyclohexyl]amino}ethoxy |
| 175 | 3-[(2-hydroxyethyl)amino]propoxy |
| 176 | 3-pyrrolidin-1-ylpropoxy |
| 177 | methoxy |
| 178 | 3-[(2-hydroxyethyl)(tetrahydro-2H-pyran-4-yl)amino]propoxy |
| 179 | 3-[(2R)-2-(2-hydroxyethyl)piperidin-1-yl]propoxy |
| 180 | 3-[(2S)-2-(2-hydroxyethyl)piperidin-1-yl]propoxy |
| 181 | 3-[(2R)-2-(hydroxymethyl)-4-methylpiperazin-1-yl]propoxy} |
| 182 | 3-[(3S)-3-(hydroxymethyl)-4-methylpiperazin-1-yl]propoxy |
| 183 | 3-[(2R)-2-(hydroxymethyl)morpholin-4-yl]propoxy |
| 184 | 3-[(3S)-3-(hydroxymethyl)morpholin-4-yl]propoxy |
| 185 | 3-(glycoloylamino)propoxy |

TABLE 5

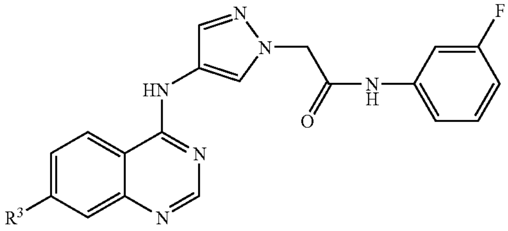

| Compound | $R^3$ |
|---|---|
| 186 | 3-[(2-hydroxyethyl)(propyl)amino]propoxy |
| 187 | 3-[(2-hydroxyethyl)(ethyl)amino]propoxy |
| 188 | 3-[(2R)-2-(hydroxymethyl)pyrrolidin-1-yl]propoxy |
| 189 | 3-[4-(hydroxymethyl)piperidin-1-yl]propoxy |
| 190 | 3-[(3-hydroxy-1,1 dimethylpropyl)amino]propoxy |
| 191 | 3-[2-(2-hydroxyethyl)piperidin-1-yl]propoxy |
| 192 | 3-[4-(2-hydroxyethyl)piperazin-1-yl]propoxy |
| 193 | 3-[(2-hydroxyethyl)(tetrahydrofuran-3-yl)amino]propoxy |
| 194 | 3-morpholin-4-ylpropoxy |
| 195 | (2S)-pyrrolidin-2-ylmethoxy |
| 196 | [(2S)-1-(2-hydroxyethyl)pyrrolidin-2-yl]methoxy |
| 197 | [(2S)-1-glycoloylpyrrolidin-2-yl]methoxy |
| 198 | (pyrrolidin-3-yl)methoxy |
| 199 | [1-(2-hydroxyethyl)pyrrolidin-3-yl]methoxy |
| 200 | (1-glycoloylpyrrolidin-3-yl)methoxy |
| 201 | 3-[(2-hydroxyethyl)(2-methoxyethyl)amino]propoxy |
| 202 | hydroxy |

TABLE 6

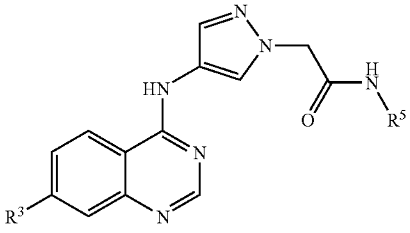

| Compound | $R^3$ | $R^5$ |
|---|---|---|
| 203 | 3-[(2R)-2-(hydroxymethyl)pyrrolidin-1-yl]propoxy | 2-fluorophenyl |
| 204 | 3-[ethyl(2-hydroxyethyl)amino]propoxy | 2-fluorophenyl |
| 205 | 3-[(2R)-2-(hydroxymethyl)pyrrolidin-1-yl]propoxy | phenyl |
| 206 | 3-[ethyl(2-hydroxyethyl)amino]propoxy | phenyl |
| 207 | 3-[(2R)-2-(hydroxymethyl)pyrrolidin-1-yl]propoxy | 2,6-difluorophenyl |

TABLE 7

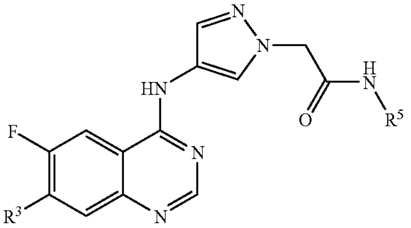

| Compound | $R^3$ | $R^5$ |
|---|---|---|
| 208 | 3-[ethyl(2-hydroxyethyl)amino]propoxy | 3-fluorophenyl |
| 209 | 3-[(cyclopropylmethyl)(2-hydroxyethyl)amino]propoxy | 2,3-difluorophenyl |
| 210 | 3-[(2-hydroxyethyl)(propyl)amino]propoxy | 2,3-difluorophenyl |

TABLE 7-continued

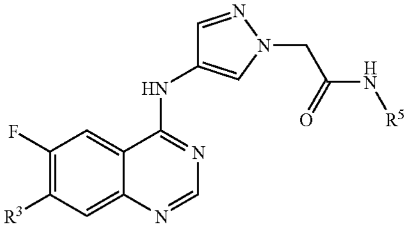

| Compound | $R^3$ | $R^5$ |
|---|---|---|
| 211 | 3-[(2R)-2-(hydroxymethyl)pyrrolidin-1-yl]propoxy | 2,3-difluorophenyl |
| 212 | 3-[cyclopentyl(2-hydroxyethyl)amino]propoxy | 2,3-difluorophenyl |

TABLE 8

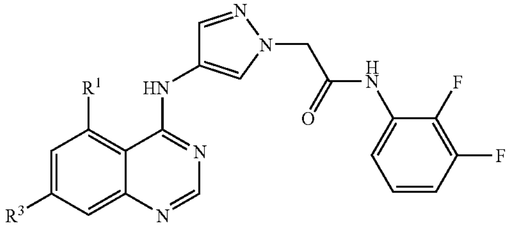

| Compound | $R^1$ | $R^3$ |
|---|---|---|
| 213 | isopropoxy | 3-[bis(2-hydroxyethyl)amino]propoxy |
| 214 | isopropoxy | 3-[(2R)-2-(hydroxymethyl)pyrrolidin-1-yl]propoxy |
| 215 | isopropoxy | 3-[4-(2-hydroxyethyl)piperazin-1-yl]propoxy |
| 216 | isopropoxy | 3-piperazin-1-ylpropoxy |
| 217 | isopropoxy | 3-[(2S)-2-(hydroxymethyl)pyrrolidin-1-yl |
| 218 | isopropoxy | (2-hydroxyethyl)amino]propoxy |
| 219 | isopropoxy | 3-(4-glycoloylpiperazin-1-yl)propoxy |
| 220 | OMe | 3-[(2R)-2-(hydroxymethyl)pyrrolidin-1-yl]propoxy |
| 221 | OMe | OMe |
| 222 | OH | OMe |
| 223 | (2R)-pyrrolidin-2-ylmethoxy | OMe |
| 224 | [(2R)-1-glycoloylpyrrolidin-2-yl]methoxy | OMe |
| 225 | [(2R)-1-(N,N-dimethylglycyl)pyrrolidin-2-yl]methoxy}- | OMe |
| 226 | [(2R)-1-(2-hydroxyethyl)pyrrolidin-2-yl]methoxy | OMe |
| 227 | OMe | H |
| 228 | F | H |

TABLE 9

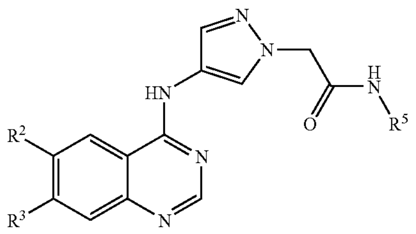

| Compound | $R^2$ | $R^3$ | $R^5$ |
|---|---|---|---|
| 229 | 3-morpholin-4-ylpropoxy | OMe | 3-fluorophenyl |
| 230 | (1-methylpyrrolidin-3-yl)oxy | OMe | 3-fluorophenyl |
| 231 | 2-morpholin-4-ylethoxy | OMe | 3-fluorophenyl |
| 232 | 2-methoxyethoxy | 2-methoxyethoxy | 2,3-difluorophenyl |
| 233 | OH | OMe | 3-fluorophenyl |
| 234 | benzoate | (1-methylpiperidin-4-yl)methoxy | 2,3-difluorophenyl |
| 235 | OH | (1-methylpiperidin-4-yl)methoxy | 2,3-difluorophenyl |

TABLE 10

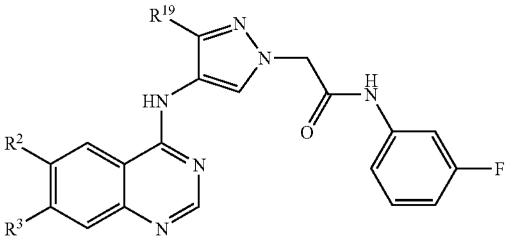

| Compound | $R^2$ | $R^3$ | $R^{19}$ |
|---|---|---|---|
| 236 | OMe | 3-[(2-hydroxyethyl)(2-methoxyethyl)amino]propoxy | carboxamide |
| 237 | OMe | 3-[(2S)-2-(hydroxymethyl)pyrrolidin-1-yl]propoxy | carboxamide |
| 238 | H | 3-[(2R)-2-(hydroxymethyl)pyrrolidin-1-yl]propoxy | acetylamino |

TABLE 10-continued

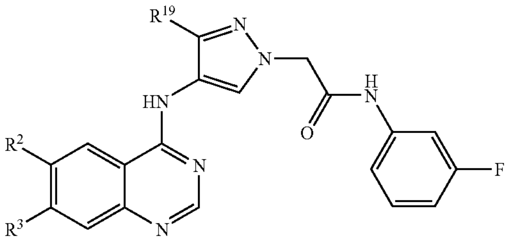

| Compound | $R^2$ | $R^3$ | $R^{19}$ |
|---|---|---|---|
| 239 | H | 3-[(2R)-2-(hydroxymethyl)pyrrolidin-1-yl]propoxy | ethyl carboxylate |
| 240 | H | 3-[(2R)-2-(hydroxymethyl)pyrrolidin-1-yl]propoxy | carboxylic acid |

TABLE 11

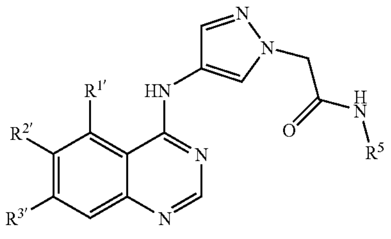

| Compound | $R^{1'}$ | $R^{2'}$ | $R^{3'}$ (* is point of attachment) | $R^5$ |
|---|---|---|---|---|
| 241 | H | OMe | 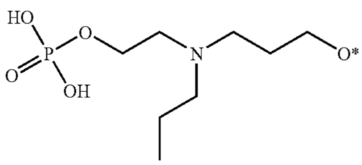 | 2,3-difluorophenyl |

TABLE 11-continued
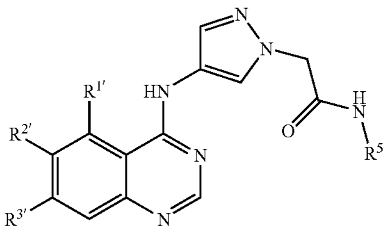
| Compound | $R^{1'}$ | $R^{2'}$ | $R^{3'}$ (* is point of attachment) | $R^5$ |
|---|---|---|---|---|
| 242 | H | OMe | 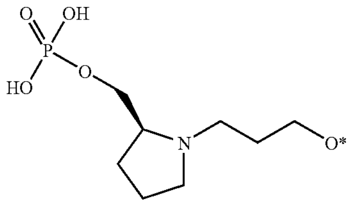 | 2,3-difluorophenyl |
| 243 | H | OMe | 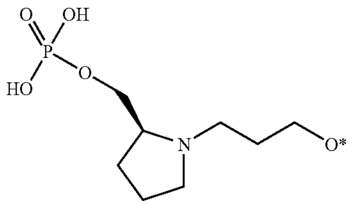 | 3-fluorophenyl |
| 244 | H | OMe | 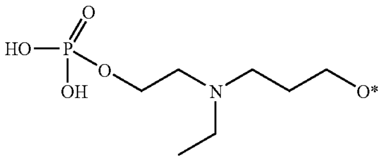 | 3-fluorophenyl |
| 245 | H | OMe | 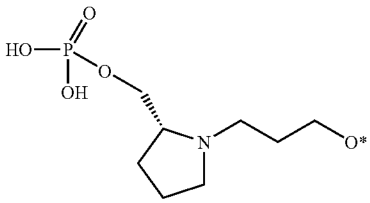 | 3-fluorophenyl |
| 246 | H | OMe | 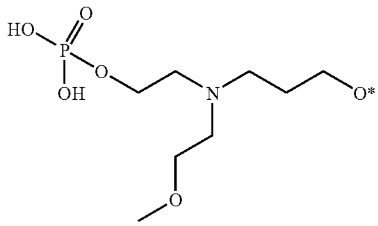 | 2,3-difluorophenyl |
| 247 | H | H | 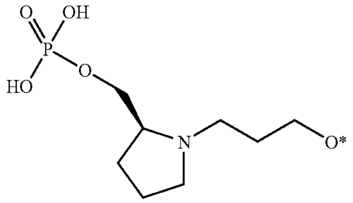 | 2,3-difluorophenyl |

TABLE 11-continued
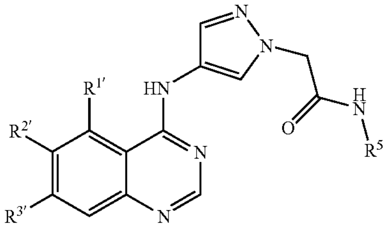
| Compound | $R^{1'}$ | $R^{2'}$ | $R^{3'}$ (* is point of attachment) | $R^5$ |
|---|---|---|---|---|
| 248 | H | H | 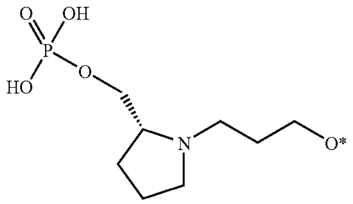 | 2,3-difluorophenyl |
| 249 | H | OMe | 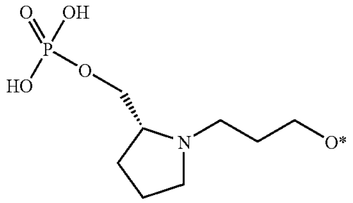 | 2,3-difluorophenyl |
| 250 | H | OMe | 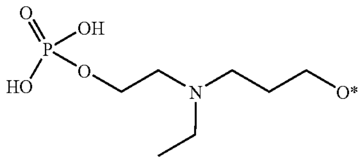 | 2,3-difluorophenyl |
| 251 | H | H | 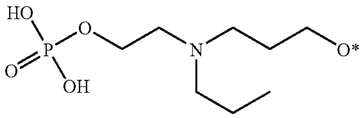 | 2,3-difluorophenyl |
| 252 | H | OMe | 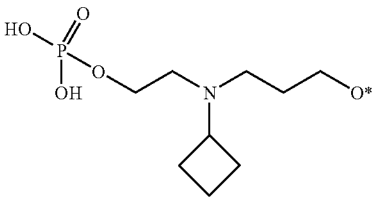 | 2,3-difluorophenyl |
| 253 | H | OMe | 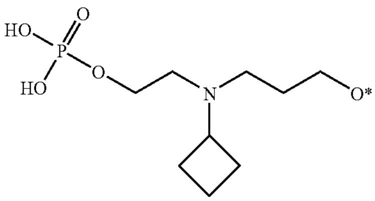 | 3-fluorophenyl |

TABLE 11-continued
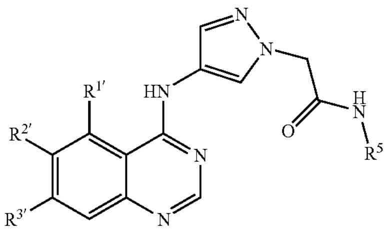
| Compound | $R^{1'}$ | $R^{2'}$ | $R^{3'}$ (* is point of attachment) | $R^5$ |
|---|---|---|---|---|
| 254 | H | OMe | 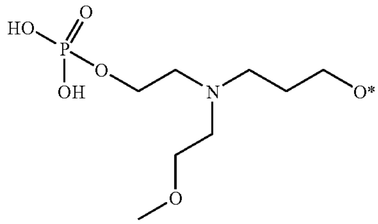 | 3-fluorophenyl |
| 255 | H | H | 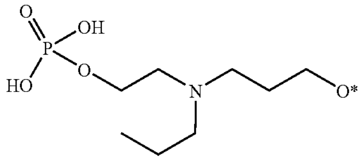 | 3-fluorophenyl |
| 256 | H | H | 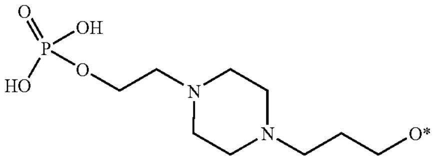 | 2,3-difluorophenyl |
| 257 | H | H | 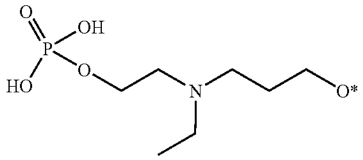 | 3-fluorophenyl |
| 258 | H | H | 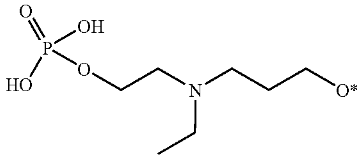 | 2,3-difluorophenyl |
| 259 | H | H | 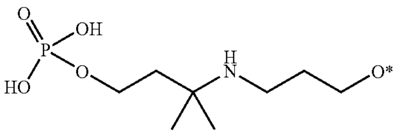 | 3-fluorophenyl |
| 260 | H | H | 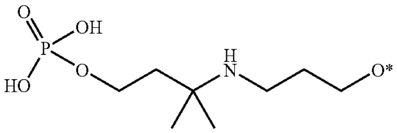 | 2,3-difluorophenyl |

TABLE 11-continued
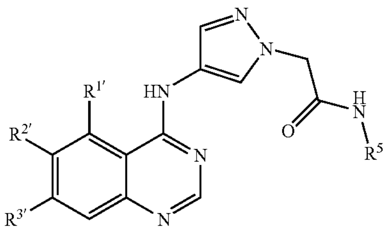
| Compound | $R^{1'}$ | $R^{2'}$ | $R^{3'}$ (* is point of attachment) | $R^5$ |
|---|---|---|---|---|
| 261 | H | H | 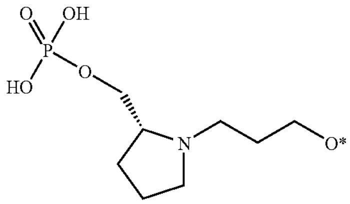 | 3-fluorophenyl |
| 262 | H | H | 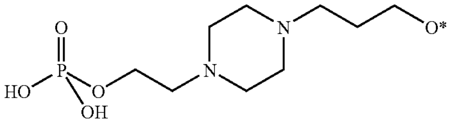 | 3-fluorophenyl |
| 263 | H | H | 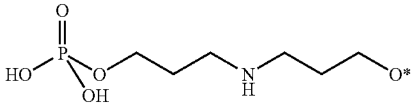 | 2,3-difluorophenyl |
| 264 | H | H | 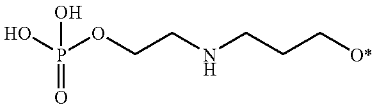 | 2,3-difluorophenyl |
| 265 | H | H | 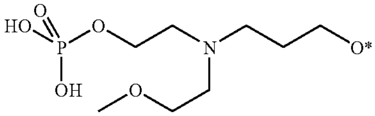 | 3-fluorophenyl |
| 266 | H | H | 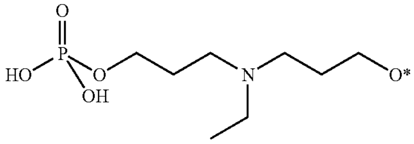 | 2,3-difluorophenyl |
| 267 | H | H | 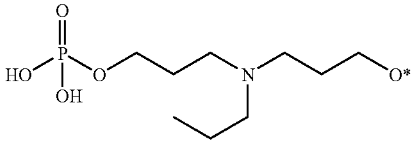 | 2,3-difluorophenyl |
| 268 | H | H | 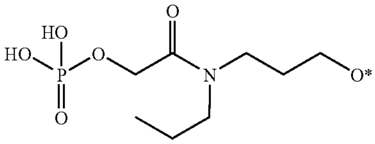 | 2,3-difluorophenyl |
| 269 | H | H | 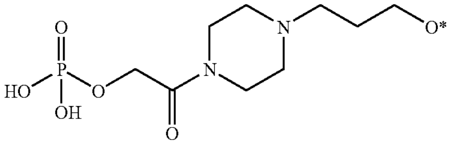 | 2,3-difluorophenyl |

TABLE 11-continued
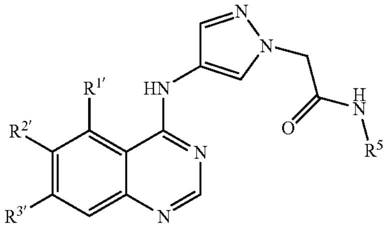
| Compound | $R^{1'}$ | $R^{2'}$ | $R^{3'}$ (* is point of attachment) | $R^5$ |
|---|---|---|---|---|
| 270 | H | F | 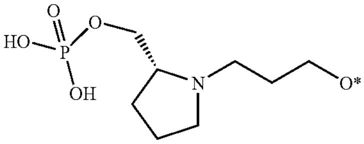 | 2,3-difluorophenyl |
| 271 | H | 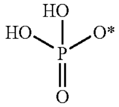 | (1-methylpiperidin-4-yl)methoxy | 2,3-difluorophenyl |
| 272 | isopropoxy | H | 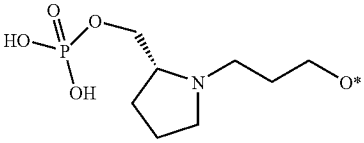 | 2,3-difluorophenyl |
| 273 | isopropoxy | H | 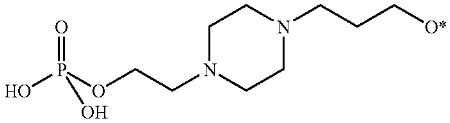 | 2,3-difluorophenyl |
| 274 | isopropoxy | H | 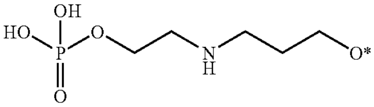 | 2,3-difluorophenyl |
| 275 | OMe | H | 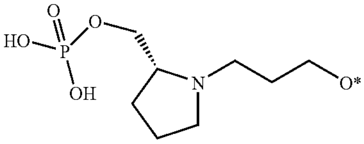 | 2,3-difluorophenyl |
| 276 | H | OMe | 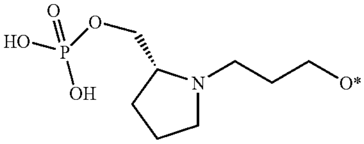 | 2,3-difluorophenyl |
| 277 | H | OMe | 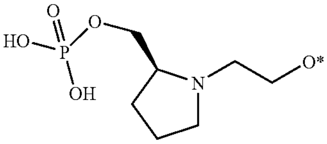 | 2,3-difluorophenyl |

TABLE 11-continued

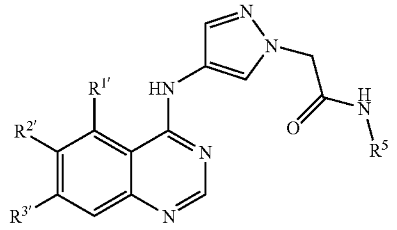

| Compound | $R^{1'}$ | $R^{2'}$ | $R^{3'}$ (* is point of attachment) | $R^5$ |
|---|---|---|---|---|
| 278 | H | OMe | 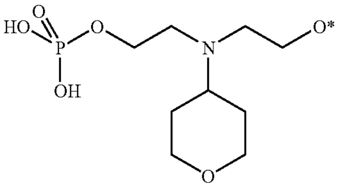 | 2,3-difluorophenyl |
| 279 | H | H | 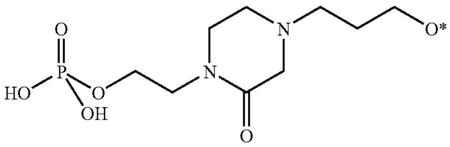 | 2,3-difluorophenyl |
| 280 | H | H | 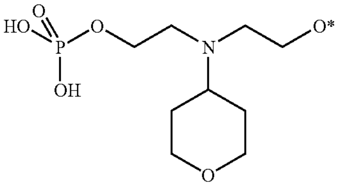 | 2,3-difluorophenyl |

EXAMPLE 1

Preparation of Compound 1 in Table 1—2-(4-{[7-(3-chloropropoxy)-6-methoxyquinazolin-4-yl]amino}-1H-pyrazol-1-yl)-N-(3-fluorophenyl)acetamide A solution of 4.0 N hydrochloric acid in dioxane (250 μl) was added to a suspension of 2-(4-amino-1H-pyrazol-1-yl)-N-(3-fluorophenyl)acetamide (234 mg, 1 mmol) and 4-chloro-7-(3-chloropropoxy)-6-methoxyquinazoline (287 mg, 1 mmol) in dimethylacetamide (5 ml) and reaction mixture heated at 90° C. under argon for 0.5 hours. The mixture was cooled to ambient temperature, diluted with dichloromethane (16 ml) and the resultant precipitate filtered. The solid was washed with dichloromethane, diethyl ether and dried in vacuo to yield compound 1 in table 1 (495 mg, 95% yield):

$^1$H-NMR (DMSO $d_6$, TFA): 8.96 (s, 1H), 8.39 (s, 1H), 8.09 (s, 1H), 7.95 (s, 1H), 7.61 (d, 1H), 7.38 (m, 2H), 7.33 (s, 1H), 6.92 (t, 1H), 5.15 (s, 211), 4.33 (t, 2H), 4.03 (s, 3H), 3.84 (t, 2H), 2.32 (m, 2H). MS (+ve ESI): 485.1, 487.2 $(M+H)^+$

2-(4-amino-1H-pyrazol-1-yl)-N-(3-fluorophenyl)acetamide used as Starting Material, was Obtained as Follows a) A solution of phosphorus oxychloride (668 mg, 4.40 mmol) in tetrahydrofuran (4 ml) was added to a mixture of (4-nitro-1H-pyrazol-1-yl)acetic acid (684 mg, 4.00 mmol), 3-fluoroaniline (500 mg, 4.5 mmol) and pyridine (1.26 g, 16 mmol) in tetrahydrofuran (20 ml) at 0° C. under argon. The resulting mixture was stirred for 1 hour and an aqueous solution of sodium bicarbonate (20 ml) added. The mixture was further diluted with water and extracted with ethyl acetate (3×50 ml). The organic phase was recovered, dried and concentrated to give an oil which was triturated with diethyl ether:petroleum ether (1:1) to yield N-(3-fluorophenyl)-2-(4-nitro-1H-pyrazol-1-yl)acetamide (695 mg, 65% yield):

$^1$H-NMR (DMSO $d_6$): 8.93 (s, 1H), 8.33 (s, 1H), 7.51 (dd, 1H), 7.38 (q, 1H), 7.31 (d, 1H), 6.95 (t, 1H), 5.17 (s, 2H). MS (+ve ESI): 265.2 $(M+H)^+$.

b) A solution of N-(3-fluorophenyl)-2-(4-nitro-1H-pyrazol-1-yl)acetamide (634 mg, 2.40 mmol) and platinum oxide (126 mg) in ethanol:ethyl acetate (1:4, 50 ml) was stirred under an atmosphere of hydrogen (80 psi) for 3 hours. The catalyst was removed by filtration and the residue purified by silica gel chromatography. Elution with dichloromethane: methanol (9:1 to 8:2) followed by dichloromethane:methanolic ammonia (3 N) (9:1) gave an oil which was triturated with diethyl ether to yield 2-(4-amino-1H-pyrazol-1-yl)-N-(3-fluorophenyl)acetamide (350 mg, 62% yield):

$^1$H-NMR (DMSO $d_6$): 7.57 (d, 1H), 7.35 (q, 1H), 7.29 (d, 1H), 7.09 (s, 1H), 6.96 (s, 1H), 6.91 (t, 1H), 5.77 (s, 2H), 4.82 (br s, 2H). MS (+ve ESI): 235.3 $(M+H)^+$.

4-chloro-7-(3-chloropropoxy)-6-methoxyquinazoline used as Starting Material, was Obtained as Follows a) Palladium on carbon (3.3 g of a 10% mixture) was added to a solution of 7-(benzyloxy)-6-methoxyquinazolin-4-(3H)-one (20 g, 71 mmol) (prepared according to *J. Med. Chem.* 1999, 42, 5369-5389) was suspended in dimethylformamide (530 ml). Ammonium formate (45 g, 710 mmol) was then added portion wise over 1.25 hours. The reaction mixture was stirred for an additional 0.5 hours and the catalyst was removed by filtration. The solvent was removed in vacuo to yield 7-hydroxy-6-methoxyquinazolin-4-(3H)-one (8.65 g, 64% yield):

$^1$H-NMR (DMSO $d_6$): 7.91 (s, 1H), 7.45 (s, 1H), 7.01 (s, 1H), 3.90 (s, 3H).

b) A mixture of 7-hydroxy-6-methoxyquinazolin-4-(3H)-one (8.0 g, 41.6 mmol), pyridine (7.5 ml) and acetic anhydride (63 ml) was heated at 100° C. for 4.5 hours and left to cool to ambient temperature 18 hours. The reaction mixture was poured into ice/water (400 ml) and the resultant precipitate collected by filtration and dried in vacuo. Analysis revealed that hydrolysis of the acetate group on the 4 position of the quinazoline was incomplete. The mixture was therefore treated with water (150 ml) and pyridine (0.5 ml) at 90° C. for 15 minutes. The reaction was cooled and the solid was collected by filtration, washed with water and dried in vacuo to yield 7-(acetoxy)-6-methoxyquinazolin-4-(3H)-one (7.4 g, 76% yield):

$^1$H-NMR (DMSO $d_6$): 8.05 (s, 1H), 7.65 (s, 1H), 7.45 (s, 1H), 3.90 (s, 3H), 2.31 (s, 3H).

c) Dimethylformamide (0.5 ml) was added to a solution of 7-(acetoxy)-6-methoxyquinazolin-4-(3H)-one (2.0 g, 8.5 mmol) in thionyl chloride (32 ml) and the reaction mixture was heated at reflux for 1.5 hours. Upon cooling to ambient temperature, the thionyl chloride was removed in vacuo and azeotroped twice with toluene. The residue was diluted with dichloromethane (15 ml), a solution of 10% ammonia in methanol (80 ml) added and the mixture heated at 80° C. for 10 minutes. Upon cooling to ambient temperature, the solvent was evaporated to almost complete dryness, water was added and the pH adjusted to 7 with dilute hydrochloric acid. The resultant precipitate was collected by filtration and dried in vacuo at 35° C. for 18 hours to yield 4-chloro-7-hydroxy-6-methoxyquinazoline (1.65 g, 92% yield):

$^1$H-NMR (DMSO $d_6$): 8.81 (s, 1H), 7.40 (s, 1H), 7.25 (s, 1H), 4.00 (s, 3H).

d) Triphenylphosphine (2.6 g, 10.1 mmol) and 3-chloropropanol (0.69 ml, 8.2 mmol) were added to a suspension of 4-chloro-7-hydroxy-6-methoxyquinazoline (1.65 g, 7.8 mmol) in dichloromethane (100 ml) under argon. The flask was placed in a water bath at 20° C. and di-tertbutyl azodicarboxylate (2.30 g, 10.1 mmol) added portion wise over a few minutes. The reaction mixture was stirred at ambient temperature for 2 hours. The reaction mixture was concentrated and the solution loaded directly onto a silica chromatography column. Elution with ethyl acetate:petroleum ether (3:7), yielded 4-chloro-7-(3-chloropropoxy)-6-methoxyquinazoline (2.0 g, 91% yield):

$^1$H-NMR (DMSO $d_6$): 8.90 (s, 1H), 7.55 (s, 1H), 7.45 (s, 1H), 4.42 (m, 2H), 4.05 (s, 3H), 3.80 (m, 2H), 2.31 (m, 2H).

EXAMPLE 2

Preparation of Compound 2 in Table 1—2-(4-{[7-(3-chloropropoxy)quinazolin-4-yl]amino}-1H-pyrazol-1-yl)-N-(2,3-difluorophenyl)acetamide Di-tertbutyl azodicarboxylate (805 mg, 3.50 mmol) in dichloromethane (5 ml) was slowly added to a mixture of N-(2,3-difluorophenyl)-2-{4-[(7-hydroxyquinazolin-4-yl)amino]-1H-pyrazol-1-yl}acetamide (554 mg, 1.40 mmol), triphenyl phosphine (917 mg, 3.5 mmol) and 3-chloro-1-propanol (172 mg, 1.82 mmol) in dichloromethane (10 ml) and tetrahydrofuran (25 ml) at ambient temperature under argon. The mixture was stirred at ambient temperature for 18 hours and concentrated in vacuo. The residual oil was dissolved in dichloromethane and 4.0 N hydrochloric acid in dioxane (2 ml) added. Diethyl ether (10 ml) was added and the resultant precipitate was recovered by filtration, washed with diethyl ether and dried. The solid was dissolved in dichloromethane and treated with an aqueous solution of sodium bicarbonate. The aqueous phase was extracted with dichloromethane (2×15 ml) and the combined organic phases were dried and concentrated to yield compound 2 in table 1 (400 mg, 60% yield):

$^1$H-NMR (DMSO $d_6$, TFA): 8.98 (s, 1H), 8.62 (d, 1H), 8.41 (s, 1H), 7.98 (s, 1H), 7.75 (t, 1H), 7.56 (d, 1H), 7.28 (s, 1H), 7.21 (m, 2H), 5.26 (s, 2H), 4.32 (t, 2H), 3.85 (t, 2H), 2.30 (t, 2H). MS (+ve ESI): 473 $(M+H)^+$.

N-(2,3-difluorophenyl)-2-{4-[(7-hydroxyquinazolin-4-yl)amino]-1H-pyrazol-1-yl}acetamide used as Starting Material, was Obtained as Follows a) 2-Amino-4-fluorobenzoic acid (7.75 g, 50 mmol) was heated in formamide (50 ml) at 150° C. for 8 hours. Water (50 ml) was added to the reaction mixture and the solid recovered by filtration, washed with water and dried in vacuo (50° C., 0.1 mm Hg) to yield 7-fluoroquinazolin-4-(3H)-one (7.3 g, 89% yield):

$^1$H-NMR (DMSO $d_6$): 8.21 (m, 1H), 8.15 (s, 1H), 7.45 (m, 1H), 7.38 (m, 1H).

b) Sodium (10.3 g, 0.45 mol) was added to benzyl alcohol (200 ml, 1.94 mol) under argon and the mixture heated at 120° C. for 4 hours. 7-Fluoroquinazolin-4-(3H)-one (15 g, 90 mmol) was added to the mixture and the reaction heated at 120° C. for 18 hours. The mixture was cooled, poured into water (800 ml) and the pH adjusted to 4 with hydrochloric acid (2 N, 150 ml). The resultant precipitate was collected by filtration, washed with water, pentane and diethyl ether to yield 7-(benzyloxy)quinazolin-4-(3H)-one (22.3 g, 98% yield):

$^1$H-NMR (DMSO $d_6$): 8.05 (s, 1H), 8.02 (d, 1H), 7.48 (m, 2H), 7.41 (t, 2H), 7.36 (d, 1H), 7.17 (m, 2H), 5.26 (s, 2H).

c) Dimethylformamide (0.5 ml) was added to a suspension of 7-(benzyloxy)quinazolin-4-(3H)-one (5.04 g, 20 mmol) in thionyl chloride (50 ml) and the mixture heated at reflux for 2 hours. The thionyl chloride was removed in vacuo and the residual oil dissolved in dichloromethane (100 ml). This solution was slowly added to an aqueous saturated solution of sodium bicarbonate (100 ml) and the organic phase recovered. The aqueous phase was extracted with dichloromethane (2×50 ml) and the combined organics dried and concentrated to yield 7-(benzyloxy)-4-chloroquinazoline (4.68 g, 86.5% yield):

$^1$H-NMR (DMSO $d_6$, TFA): 9.15 (s, 1H), 8.15 (d, 1H), 7.51 (m, 2H), 7.43 (m, 2H), 7.38 (m, 2H), 7.30 (m, 1H), 5.32 (s, 2H).

d) 2-(4-amino-1H-pyrazol-1-yl)-N-(2,3-difluorophenyl)acetamide (504 mg, 2 mmol) was added to a solution of 7-(benzyloxy)-4-chloroquinazoline (541 mg, 2 mmol) in dimethylacetamide (10 ml) under argon. A solution of 4.0 N hydrochloric acid in dioxane (500 μl, 2 mmol) was added and the mixture was heated at 90° C. for 1.5 hours. The mixture was cooled, diluted with dichloromethane and the resultant precipitate recovered by filtration. The solid was washed with dichloromethane and diethyl ether and dried in vacuo to yield 2-(4-{[7-(benzyloxy)quinazolin-4-yl]amino}-1H-pyrazol-1-yl)-N-(2,3-difluorophenyl)acetamide (850 mg, 81% yield):

$^1$H-NMR (DMSO $d_6$, TFA): 8.97 (s, 1H), 8.68 (d, 1H), 8.41 (s, 1H), 8.00 (s, 1H), 7.75 (t, 1H), 7.61 (d, 1H), 7.53 (m, 2H), 7.45 (m, 2H), 7.42 (d, 1H), 7.36 (m, 1H), 7.20 (m, 2H), 5.38 (s, 2H), 5.25 (s, 2H).

MS (+ve ESI): 487.1 $(M+H)^+$.

e) 2-(4-{[7-(benzyloxy)quinazolin-4-yl]amino}-1H-pyrazol-1-yl)-N-(2,3-difluorophenyl)acetamide (836 mg, 1.60 mmol) was dissolved in trifluoroacetic acid (8 ml) and heated under reflux for 2.5 hours. The solution was concentrated and the residual oil was dissolved in methanol and neutralised with an aqueous solution of sodium bicarbonate. Water was added to the mixture and the solid recovered by filtration and dried in vacuo to yield N-(2,3-difluorophenyl)-2-{4-[(7-hydroxyquinazolin-4-yl)amino]-1H-pyrazol-1-yl}acetamide (633 mg, 100% yield):

$^1$H-NMR (DMSO $d_6$, TFA): 8.92 (s, 1H), 8.51 (d, 1H), 8.36 (s, 1H), 7.92 (s, 1H), 7.70 (t, 1H), 7.32 (d, 1H), 7.21 (m, 2H), 7.13 (s, 1H), 5.22 (s, 2H). MS (+ve ESI): 397 $(M+H)^+$.

2-(4-amino-1H-pyrazol-1-yl)-N-(2,3-difluorophenyl) acetamide, used as Starting Material was Prepared as Follows a) An analogous reaction to that described in example 1a, but starting 2,3-difluoroaniline (1.55 g, 120 mmol) yielded N-(2,3-difluorophenyl)-2-(4-nitro-1H-pyrazol-1-yl)acetamide (1.13 g, 40% yield):

$^1$H-NMR (DMSO $d_6$): 10.43 (br s, 1H), 8.90 (s, 1H), 8.30 (s, 1H), 7.69 (m, 1H), 7.19 (m, 2H), 5.23 (s, 2H).

b) An analogous reaction to that described in example 1b, but starting with N-(2,3-difluorophenyl)-2-(4-nitro-1H-pyrazol-1-yl)acetamide (5.22 g, 185 mmol) yielded 2-(4-amino-1H-pyrazol-1-yl)-N-(2,3-difluorophenyl)acetamide (4.2 g, 90% yield):

$^1$H-NMR (DMSO $d_6$): 7.68 (m, 1H), 7.17 (m, 2H), 7.09 (s, 1H), 6.97 (s, 1H), 4.90 (s, 2H), 3.85 (br s, 2H). MS (+ve ESI): 253 $(M+H)^+$.

EXAMPLE 3

Preparation of Compound 3 in Table 1—2-(4-{[7-(3-chloropropoxy)-6-methoxyquinazolin-4-yl]amino}-1H-pyrazol-1-yl)-N-(2,3-difluorophenyl)acetamide 4 N hydrochloric acid in dioxane (250 μl, 1 mmol) was added to a solution of 2-(4-amino-1H-pyrazol-1-yl)-N-(2,3-difluorophenyl)acetamide (293 mg, 1 mmol) and 4-chloro-7-(3-chloropropoxy)-6-methoxyquinazoline (287 mg, 1 mmol) in dimethylacetamide (8 ml) and the mixture heated under argon at 90° C. for 1 hour. The reaction was cooled, diluted with dichloromethane (20 ml) and the resultant precipitate recovered by filtration. The solid was washed with dichloromethane, diethyl ether and dried in vacuo to yield compound 3 in table 1 (480 mg, 90% yield):

$^1$H-NMR (DMSO $d_6$, TFA): 8.94 (s, 1H), 8.41 (s, 1H), 8.13 (s, 1H), 7.98 (s, 1H), 7.74 (m, 1H), 7.34 (s, 1H), 7.21 (m, 2H), 5.24 (s, 2H), 4.33 (t, 2H), 4.03 (s, 3H), 3.83 (t, 2H), 2.32 (t, 2H). MS (+ve ESI): 503 $(M+H)^+$.

EXAMPLE 4

Preparation of Compound 4 in Table 1—2-(4-{[7-(3-chloropropoxy)quinazolin-4-yl]amino}-1H-pyrazol-1-yl)-N-(3-fluorophenyl)acetamide An analogous reaction to that described in example 3 but starting with 2-(4-amino-1H-pyrazol-1-yl)-N-(3-fluorophenyl)acetamide (312 mg, 1.34 mmol) and 4-chloro-7-(3-chloropropoxy)quinazoline (344 mg, 1.34 mmol) yielded compound 4 in table 1 (624 mg, 95% yield):

$^1$H-NMR (DMSO $d_6$): 11.84 (s, 1H), 10.81 (s, 1H), 8.94 (s, 1H), 8.82 (m, 1H), 8.42 (s, 1H), 8.02 (s, 1H), 7.60 (m, 1H), 7.49 (m, 1H), 7.36 (m, 3H), 6.92 (m, 1H), 5.15 (s, 2H), 4.13 (t, 2H), 3.85 (t, 2H), 2.28 (t, 2H). MS (+ve ESI): 455 $(M+H)^+$.

4-chloro-7-(3-chloropropoxy)quinazoline, used as the Starting Material was Obtained as Follows a) Formamidine acetate (20.13 g, 193.4 mmol) was added to a solution of 2-amino-4-fluorobenzoic acid (15 g, 96.7 mmol) in 2-methoxyethanol (97 ml) and the mixture heated to reflux for 18 hours. The reaction was cooled, concentrated and the residue stirred in aqueous ammonium hydroxide (0.01 M, 250 ml) for 1 hour. The suspension was filtered, washed with water and dried over phosphorus pentoxide to yield 7-fluoroquinazolin-4-ol as an off-white solid (10.35 g, 65% yield):

$^1$H-NMR (DMSO $d_6$): 12.32 (br s, 1H), 8.19 (dd, 1H), 8.14 (s, 1H), 7.45 (m, 1H), 7.39 (m, 1H). $^{19}$F-NMR (DMSO $d_6$): −105 (m) MS (−ve ESI): 163 $(M-H)^-$, MS (+ve ESI): 165 $(M+H)^+$.

b) Sodium hydride (14.6 g, 365 mmol) was added at 0° C. to a solution of 1,3-propanediol (27.8 g, 365 mmol) in dimethylformamide (70 ml). 7-Fluoroquinazolin-4-ol (10 g, 60.9 mmol) was added portion wise and the reaction mixture heated at 60° C., then at 110° C. for 3 hours. The reaction was cooled to 0° C., quenched with water (280 ml) and adjusted to pH 5.9. The resulting suspension was filtered, washed with water then diethyl ether and dried over phosphorus pentoxide to yield 7-(3-hydroxypropoxy)quinazolin-4-ol as a white powder (12.41 g, 92% yield):

$^1$H-NMR (DMSO $d_6$): 11.90 (br s, 1H), 8.04 (s, 1H), 8.00 (d, 1H), 7.10 (m, 2H), 4.17 (t, 2H), 3.58 (t, 2H), 1.92 (m, 2H). MS (+ve ESI): 221 $(M+H)^+$.

c) Dimethylformamide (1 ml) was added to a mixture of 7-(3-hydroxypropoxy)quinazolin-4-ol (10.5 g, 47.7 mmol) and thionyl chloride (100 ml, 137 mmol) and the reaction mixture heated to 85° C. for 1 hour. The mixture was cooled to ambient temperature, diluted with toluene and evaporated to dryness. This was repeated until all thionyl chloride was removed. The residue was dissolved in dichloromethane and washed with a saturated sodium bicarbonate solution. The aqueous layer was extracted with dichloromethane and the combined organics were dried (magnesium sulphate) and concentrated to leave a yellow solid. Trituration with diethyl ether removed a less soluble impurity and the diethyl ether filtrate was concentrated to yield 4-chloro-7-(3-chloropropoxy)quinazoline as an off-white solid (8.5 g, 70% yield):

$^1$H-NMR (DMSO $d_6$): 13.25 (br s, 1H), 8.34 (s, 1H), 8.06 (d, 1H), 7.17 (m, 2H), 4.21 (t, 2H), 3.83 (t, 2H), 2.23 (m, 2H). MS (+ve ESI): 257, 259 $(M+H)^+$.

EXAMPLE 5

Preparation of Compound 5 in Table 1—2-(4-{[7-(2-chloroethoxy)quinazolin-4-yl]amino}-1H-pyrazol-1-yl)-N-(2,3-difluorophenyl)acetamide A mixture of 4-chloro-7-(2-chloroethoxy)quinazoline (1.65 g, 6.8 mmol), 2-(4-amino-1H-pyrazol-1-yl)-N-(2,3-difluorophenyl)acetamide (1.7 g, 6.8 mmol) and hydrogen chloride (1.57 ml of a 4M solution in 1,4-dioxane, 6.3 mmol) in dimethylacetamide (30 ml) was heated at 90° C. for 1 hour and then allowed to cool to room temperature. The mixture was diluted with diethyl ether and the resultant precipitate filtered to give compound 5 in table 1 as the hydrochloride salt (4.3 g, 100% yield):

$^1$H-NMR (DMSO $d_6$): 11.74 (br s, 1H), 10.02 (s, 1H), 8.89 (s, 1H), 8.87 (d, 1H), 8.42 (s, 1H), 8.05 (s, 1H), 7.68 (m, 1H), 7.45 (m, 2H), 7.15 (m, 2H), 5.17 (s, 2H), 4.52 (t, 2H), 4.00 (t, 2H). MS (+ve ESI): 459 $(M+H)^+$ MS (−ve ESI): 457 $(M-H)^-$.

4-chloro-7-(2-chloroethoxy)quinazoline used as Starting Material, was Prepared as Follows a) A mixture of sodium hydride (60% in oil, 7.67 g, 189.6 mmol) and dimethylacetamide (160 ml) were cooled in an ice-bath under a nitrogen atmosphere and then ethylene glycol (18.2 g, 284 mmol) was slowly added. The reaction mixture was warmed to 60° C. for 10 minutes and then 7-fluoroquinazolin-4-ol (7.75 g, 47.3 mmol) was slowly added. The reaction mixture was heated to 110° C. for 16 hours and then the mixture was concentrated to approximately half volume. The mixture was poured into water and the pH of the solution was adjusted to 5 with dilute hydrochloric acid. The resultant precipitate was filtered and then dried in a vacuum oven at 65° C. for 16 hours. The residue was triturated with diethyl ether to give 7-(2-hydroxyethoxy)quinazolin-4-ol (4.4 g) as an off white solid which was used in subsequent steps without further purification: MS (+ve ESI): 207 $(M+H)^+$ MS (−ve ESI): 205 $(M-H)^-$.

b) A mixture of 7-(2-hydroxyethoxy)quinazolin-4-ol (4.4 g, ~21 mmol), thionyl chloride (40 ml) and dimethylformamide (0.4 ml) was heated at reflux for 2 hours. The mixture was evaporated under reduced pressure and then co-evaporated twice with toluene. The residue was partitioned between dichloromethane and aqueous ammonia solution and the organic layer was separated, dried over magnesium sulphate and then evaporated under reduced pressure. The residue was purified by silica gel chromatography eluting with a 0 to 8% mixture of methanol (containing 10% 7N ammonia in methanol) in dichloromethane to give 4-chloro-7-(2-chloroethoxy) quinazoline (4 g, 65% yield):

$^1$H-NMR ($CDCl_3$): 8.95 (s, 1H), 8.17 (d, 1H), 7.37 (dd, 1H), 7.30 (d, 1H), 4.43 (t, 2H), 3.93 (t, 2H). MS (+ve ESI): 243, 244, 246 $(M+H)^+$.

EXAMPLE 6

Preparation of Compound 6 in Table 1—2-(4-{[7-(2-chloroethoxy)-6-methoxyquinazolin-4-yl]amino}-1H-pyrazol-1-yl)-N-(2,3-difluorophenyl)acetamide A mixture of 4-chloro-6-methoxyquinazolin-7-ol (5.0 g, 24 mmol), potassium carbonate (9.94 g, 72 mmol) and 1-bromo-2-chloroethane (7.98 ml, 96 mmol) in dimethyl acetamide (50 ml) was heated at 90° C. for 3 hours. The reaction mixture was allowed to cool to room temperature and then filtered. The filtrate was purified directly by silica gel chromatography eluting with a 20 to 80% mixture of ethyl acetate in iso-hexane. The obtained product was triturated with diethyl ether to give a 3:1 mixture of 4-chloro-7-(2-chloroethoxy)-6-methoxyquinazoline: 4-chloro-7-(2-bromoethoxy)-6-methoxyquinazoline (4.77 g, 73% yield) as a white solid:

$^1$H-NMR (DMSO $d_6$ data for 4-chloro-7-(2-chloroethoxy)-6-methoxyquinazoline): 8.90 (s, 1H), 7.53 (s, 1H), 7.41 (s, 1H), 4.54 (t, 2H), 4.09 (t, 2H), 4.02 (s, 3H). MS (+ve ESI, data for 4-chloro-7-(2-chloroethoxy)-6-methoxyquinazoline): 273, 275, 277 $(M+H)^+$ b) A 3:1 mixture of 4-chloro-7-(2-chloroethoxy)-6-methoxyquinazoline: 4-chloro-7-(2-bromoethoxy)-6-methoxyquinazoline (1.3 g, 4.5 mmol), 2-(4-amino-1H-pyrazol-1-yl)-N-(2,3-difluorophenyl)acetamide (1.4 g, 5.5 mmol) and hydrogen chloride (1.06 ml of a 4M solution in 1,4-dioxane) in dimethyl acetamide (20 ml) was heated at 90° C. for 1 hour. The mixture was allowed to cool to room temperature and then diluted with diethyl ether and filtered to leave compound 6 in table 1 as a 2:1 mixture of 2-(4-{[7-(2-chloroethoxy)-6-methoxyquinazolin-4-yl]amino}-1H-pyrazol-1-yl)-N-(2,3-difluorophenyl)acetamide: 2-(4-{[7-(2-bromoethoxy)-6-methoxyquinazolin-4-yl]amino}-1H-pyrazol-1-yl)-N-(2,3-difluorophenyl)acetamide as the hydrochloride salt (2.5 g):

MS (+ve ESI data for 2-(4-{[7-(2-chloroethoxy)-6-methoxyquinazolin-4-yl]amino}-1H-pyrazol-1-yl)-N-(2,3-difluorophenyl)acetamide): 489, 491 $(M+H)^+$.

EXAMPLE 7

Preparation of Compound 7 in Table 1—N-(2,3-difluorophenyl)-2-(4-{[7-(2,2-dimethoxyethoxy) quinazolin-4-yl]amino}-1H-pyrazol-1-yl)acetamide Bromoacetaldehyde dimethyl acetal (1.3 ml, 11.0 mmol) was added to a solution of N-(2,3-difluorophenyl)-2-{4-[(7-hydroxyquinazolin-4-yl)amino]-1H-pyrazol-1-yl}acetamide trifluoroacetate (4.37 g, 10.5 mmol), cesium carbonate (13.21 g, 40.5 mmol) and potassium iodide (1.86 g, 11.2 mmol) in dimethylacetamide (35 ml) heated at 106° C. and the mixture was stirred at this temperature for 3.5 hours. The mixture was allowed to cool to room temperature and then a dilute solution of hydrochloric acid (2M, 27.5 ml) was added to pH 7. The solution was diluted with water (100 ml) and the resultant precipitate was filtered. The filtered solid was washed with water (2×30 ml) and then with diethylether (2×50 ml) to give compound 7 in table 1 (1.76 g, 34% yield) which was used in subsequent steps without further purification:

$^1$H-NMR (DMSO $d_6$): 10.27 (s, 1H), 9.93 (s, 1H), 8.54 (s, 1H), 8.36 (d, 1H), 8.33 (s, 1H), 7.77 (s, 1H), 7.68-7.74 (m, 1H), 7.25 (dd, 1H), 7.13-7.22 (m, 3H), 5.14 (s, 2H), 4.75 (t, 1H), 4.15 (d, 2H), 3.37 (s, 6H); MS (+ve ESI): 485 $(M+H)^+$.

N-(2,3-difluorophenyl)-2-{4-[(7-hydroxyquinazolin-4-yl)amino]-1H-pyrazol-1-yl}acetamide trifluoroacetate used as Starting Material, was Prepared as Follows a) A solution of 2-(4-{[7-(benzyloxy)quinazolin-4-yl]amino}-1H-pyrazol-1-yl)-N-(2,3-difluorophenyl)acetamide (0.977 g, 1.87 mmol) in trifluoroacetic acid (20 ml) was heated at reflux for 4.5 hours. The mixture was evaporated under reduced pressure and the resultant residue was triturated with diethyl ether to give N-(2,3-difluorophenyl)-2-{4-[(7-hydroxyquinazolin-4-yl)amino]-1H-pyrazol-1-yl}acetamide as the trifluoroacetate salt (0.944 g, 99% yield):

$^1$H-NMR (DMSO $d_6$): 11.43 (br s, 1H), 10.39 (br s, 1H), 8.90 (s, 1H), 8.50 (d, 1H), 8.34 (s, 1H), 7.92 (s, 1H), 7.67-7.73 (m, 1H), 7.29 (dd, 1H), 7.16-7.23 (m, 2H), 7.11 (d, 1H), 5.21 (s, 2H);

MS (+ve ESI): 397 $(M+H)^+$.

EXAMPLE 8

Preparation of Compound 8 in Table 1—4-{[7-(3-chloropropoxy)-6-methoxyquinazolin-4-yl]amino}-1-{2-[(3-fluorophenyl)amino]-2-oxoethyl}-1H-pyrazole-3-carboxamide A solution of 4-chloro-7-(3-chloropropoxy)-6-methoxyquinazoline (327 mg, 1 mmol) and 4-amino-1-{2-[(3-fluorophenyl)amino]-2-oxoethyl}-1H-pyrazole-3-carboxamide (280 mg, 1 mmol) in dimethylacetamide (5 ml) and a solution of hydrogen chloride in dioxane (4M, 0.25 ml) was heated at 85° C. for 1 hour. The mixture was evaporated and the residue was triturated with dichloromethane and diethylether and then dried in vacuo at 50° C. to yield compound 8 in table 1 (580 mg, 100% yield):

$^1$H-NMR (DMSOd$_6$): 11.72 (s, 1H), 10.92 (s, 1H), 8.97 (s, 1H), 8.58 (s, 1H), 8.07 (s, 1H), 7.81 (s, 1H), 7.6 (d, 1H), 7.51 (s, 1H), 7.45 (s, 1H), 7.37 (m, 2H), 6.93 (m, 1H), 5.28 (s, 2H), 4.33 (t, 2H), 4.02 (s, 3H), 3.85 (t, 2H), 2.32 (m, 2H); MS (+ve ESI): 528.06 (M+H)$^+$.

4-amino-1-{2-[(3-fluorophenyl)amino]-2-oxoethyl}-1H-pyrazole-3-carboxamide used as Starting Material, was Prepared as Follows a) Ethyl 4-nitro-1H-pyrazole-3-carboxylate (741 mg, 4 mmol) was heated at 90° C. with a concentrated solution of aqueous ammonia (28%, 20 ml) in a sealed vessel for 3 hours. The mixture was evaporated and the residue was triturated with diethyl ether to give 4-nitro-1H-pyrazole-3-carboxamide (0.54 g, 86% yield) as a white solid:

$^1$H-NMR (DMSO d$_6$): 8.70 (s, 1H), 8.06 (s, 1H), 7.83 (s, 1H); MS (+ve ESI): 157.13 (M+H)$^+$.

b) A mixture of 2-chloro-N-(3-fluorophenyl)acetamide (0.65 g, 3.46 mmol), 4-nitro-1H-pyrazole-3-carboxamide (0.54 g, 3.46 mmol) and potassium carbonate (0.57 g, 4.13 mmol) in dimethylformamide (10 ml) was stirred at room temperature for 48 hours. The mixture was evaporated and the residue partitioned between ethyl acetate and water. The organic phase was separated, washed, dried and then concentrated to yield 1-{2-[(3-fluorophenyl)amino]-2-oxoethyl}-4-nitro-1H-pyrazole-3-carboxamide (730 mg, 69% yield).

$^1$H NMR (DMSO d$_6$): 10.68 (s, 1H), 8.9 (s, 1H), 8.05 (s, 1H), 7.78 (s, 1H), 7.55 (m, 1H), 7.38 (m, 1H), 7.29 (d, 1H), 6.94 (m, 1H), 5.15 (s, 2H); MS (+ve ESI): 308.08 (M+H)$^+$.

c) Hydrazine hydrate (0.4 ml, 8.26 mmol) was slowly added to a mixture of 1-{2-[(3-fluorophenyl)amino]-2-oxoethyl}-4-nitro-1H-pyrazole-3-carboxamide (580 mg, 1.89 mmol) and Raney nickel (0.25 g) in ethanol (40 ml) at 50° C., and the mixture was stirred for 1 hour. Dimethylformamide was added to the mixture to solubilize the precipitated solid. The mixture was filtered, the filtrate was evaporated and the residue triturated with a mixture of dichloromethane and diethyl ether to yield 4-amino-1-{2-[(3-fluorophenyl)amino]-2-oxoethyl}-1H-pyrazole-3-carboxamide (430 mg, 81% yield):

$^1$H-NMR (DMSO d$_6$): 10.49 (s, 1H), 7.55 (d, 1H), 7.37 (q, 1H), 7.29 (d, 1H), 7.16 (s, 1H), 7.14 (s, 1H), 7.0 (s, 1H), 6.91 (m, 1H), 4.92 (s, 2H), 4.68 (s, 2H); MS (+ve ESI): 278.19 (M+H)$^+$.

EXAMPLE 9

Preparation of Compound 9 in Table 1—ethyl 4-{[7-(3-chloropropoxy)quinazolin-4-yl]amino}-1-{2-[(3-fluorophenyl)amino]-2-oxoethyl}-1H-pyrazole-3-carboxylate A mixture of ethyl 4-amino-1-{2-[(3-fluorophenyl)amino]-2-oxoethyl}-1H-pyrazole-3-carboxylate (0.123 g, 0.4 mmol) and 4-chloro-7-(3-chloropropoxy)quinazoline (0.102 g, 0.4 mmol) in dimethyl acetamide (2ml) was heated at 80° C. for 0.5 hour. The reaction mixture was allowed to cool and then diluted with diethyl ether. The precipitated solid was filtered and then washed with a mixture of diethyl ether: dichloromethane 1:1 to give compound 9 in table 1 (0.219 g, 92% yield):

$^1$H-NMR (DMSO d$_6$ TFA): 9.0 (s, 1H), 8.49 (m, 2H), 7.59 (m, 2H), 7.37 (m, 3H), 6.92 (t, 1H), 5.3 (s, 2H), 4.38 (t, 2H), 4.29 (q, 2H), 3.87 (t, 2H), 2.32 (t, 2H), 1.2 (t, 3H). MS (+ve ESI): 527.22 (M+H)$^+$

Ethyl 4-amino-1-{2-[(3-fluorophenyl)amino]-2-oxoethyl}-1H-pyrazole-3-carboxylate used as Starting Material, was Prepared as Follows a) A mixture of ethyl 4-nitro-1H-pyrazole-3-carboxylate (0.685 g, 3.7 mmol) and 2-chloro-N-(3-fluorophenyl) acetamide (0.694 g, 3.7 mmol) and potassium carbonate (0.613 g, 4.44 mmol) in dimethyl formamide (10 ml) was stirred at room temperature for 20 hours. The mixture was evaporated and the residue was purified by silica gel chromatography eluting with a 8 to 10% mixture of ethyl acetate in dichloromethane to give ethyl 1-{2-[(3-fluorophenyl)amino]-2-oxoethyl}-4-nitro-1H-pyrazole-3-carboxylate (0.920 g, 74% yield):

$^1$H-NMR (DMSO d$_6$ TFA): 9.02 (s, 1H), 7.57 (d, 1H), 7.39 (q, 1H), 7.32 (d, 1H), 6.93 (t, 1H), 5.24 (s, 2H), 4.38 (q, 2H), 1.31 (t, 3H); MS (+ve ESI): 337.17 (M+H)$^+$.

b) A mixture of ethyl 1-{2-[(3-fluorophenyl)amino]-2-oxoethyl}-4-nitro-1H-pyrazole-3-carboxylate (0.168 g, 0.5 mmol) was hydrogenated over 10% palladium on carbon (0.034 g) in a mixture of methanol (6 ml) and dichloromethane (3 ml) for 3 hours. The mixture was filtered through Celite and the filtrate was evaporated to leave ethyl 4-amino-1-{2-[(3-fluorophenyl)amino]-2-oxoethyl}-1H-pyrazole-3-carboxylate (0.135 g, 88% yield):

$^1$H-NMR (DMSO d$_6$): 10.57 (s, 1H), 7.56 (d, 1H), 7.37 (q, 1H), 7.29 (d, 1H), 7.23 (s, 1H), 6.91 (t, 1H), 4.96 (s, 2H), 4.71 (s, 2H), 4.23 (q, 2H), 1.27 (t, 3H). MS (+ve ESI): 307.27 (M+H)$^+$

EXAMPLE 10

Preparation of Compound 10 in Table 1—2-(3-(acetylamino)-4-{[7-(3-chloropropoxy)quinazolin-4-yl]amino}-1H-pyrazol-1-yl)-N-(3-fluorophenyl)acetamide 2-[3-(Acetylamino)-4-amino-1H-pyrazol-1-yl]-N-(3-fluorophenyl)acetamide (0.160 g, 0.55 mmol) and 4-chloro-7-(3-chloropropoxy)quinazoline (0.141 g, 0.55 mmol) were dissolved in dimethyl acetamide (2 ml). Dioxane hydrochloric acid (4 M, 0.055 ml) was added and the mixture was heated at 80° C. for 20 minutes. The reaction mixture was allowed to cool and then diluted with diethyl ether. The resultant solid was filtered and then dried in vacuo at 50° C. to leave compound 10 in table 1 (0.280 g, 89% yield):

$^1$H-NMR (DMSO $d_6$): 10.66 (s, 1H), 8.95 (s, 1H), 8.56 (s, 1H), 8.19 (d, 1H), 7.57 (d, 1H), 7.52 (d, 1H), 7.34 (m, 2H), 7.29 (s, 1H), 6.88 (t, 1H), 5.06 (s, 2H), 4.3 (t, 2H), 3.82 (t, 2H), 2.27 (t, 2H), 2.15 (s, 3H); MS (+ve ESI): 512.25, 514.25 $(M+H)^+$.

2-[3-(Acetylamino)-4-amino-1H-pyrazol-1-yl]-N-(3-fluorophenyl)acetamide used as Starting Material, was Prepared as Follows a) A solution of N-1H-pyrazol-3-ylacetamide (*Liebigs annalen der chemie.,* 1967, 707, 147; 0.500 g, 4.0 mmol) was stirred in a mixture of nitric acid (d=1.52, 0.2 ml, 4.8 mmol) and sulphuric acid (d=1.83, 2 ml) at 0° C. for 2.5 hours. The mixture was poured onto ice and the resultant precipitate was filtered, washed with water and then a 2:1 mixture of diethyl ether:methanol and then with diethyl ether. The residue was dried in vacuo to give N-(4-nitro-1H-pyrazol-3-yl)acetamide (0.44 g, 65% yield):

$^1$H-NMR (DMSO $d_6$ TFA): 8.33 (s, 1H), 2.18 (s, 3H); MS (−ve ESI): 169.2 $(M-H)^-$.

b) A mixture of N-(4-nitro-1H-pyrazol-3-yl)acetamide (0.380 g, 2.25 mmol), 2-chloro-N-(3-fluorophenyl)acetamide (0.420 g, 2.25 mmol) and potassium carbonate (00.370 g, 2.7 mmol) in dimethyl formamide (10 ml) was heated at 50° C. for 1 hour. The mixture was filtered and the filtrate was evaporated. The residue was triturated with a mixture of 2% methanol in dichloromethane and then with diethyl ether to give 2-[3-(acetylamino)-4-nitro-1H-pyrazol-1-yl]-N-(3-fluorophenyl)acetamide (0.400 g, 55% yield):

$^1$H-NMR (DMSO $d_6$ TFA): 8.85 (s, 1H), 7.56 (d, 1H), 7.37 (q, 1H), 7.31 (d, 1H), 6.93 (t, 1H), 5.08 (s, 2H), 2.06 (s, 3H); MS (+ve ESI): 322.21 $(M+H)^+$.

c) Hydrazine hydrate (43.6 μl, 0.9 mmol) was slowly added to a solution of 2-[3-(acetylamino)-4-nitro-1H-pyrazol-1-yl]-N-(3-fluorophenyl)acetamide (0.145 g, 0.45 mmol) in a mixture of dimethylacetamide (3 ml) and methanol (3 ml) in the presence of 10% palladium on carbon (0.030 g). The mixture was stirred at 75° C. for 20 minutes and then allowed to cool. The mixture was filtered through Celite and the residue washed with methanol. The filtrate was evaporated and the residue triturated with a 1:2 mixture of dichloromethane: diethyl ether to give 2-[3-(acetylamino)-4-amino-1H-pyrazol-1-yl]-N-(3-fluorophenyl)acetamide (0.125 g, 95% yield):

$^1$H-NMR (DMSO $d_6$ TFA): 7.99 (s, 1H), 7.58 (d, 1H), 7.37 (q, 1H), 7.30 (d, 1H), 6.92 (t, 1H), 5.02 (s, 2H), 2.09 (s, 3H); MS (+ve ESI): 292.27 $(M+H)^+$.

EXAMPLE 11

Preparation of Compound 11 in Table 1—N-(2,3-difluorophenyl)-2-[4-(quinazolin-4-ylamino)-1H-pyrazol-1-yl]acetamide A mixture of quinazolin-4(3H)-one (0.146 g, 1.0 mmol) and 1 drop of dimethylformamide in thionyl chloride (3 ml) was heated at 70° C. for 1 hour. The mixture was evaporated under reduced pressure and the residue suspended in dimethylacetamide (5 ml). 2-(4-Amino-1H-pyrazol-1-yl)-N-(2,3-difluorophenyl)acetamide (0.252 g, 1.0 mmol) was added and the mixture was then heated at 80° C. for 1 hour. The reaction mixture was allowed to cool to room temperature and then acetonitrile (20 ml) was added and the resultant solid filtered to leave compound 11 in table 1 (0.220 g, 58% yield):

$^1$H-NMR (DMSO $d_6$): 11.82 (br s, 1H), 10.39 (br s, 1H), 9.00 (s, 1H), 8.78 (d, 1H), 8.42 (s, 1H), 8.10 (d, 1H), 8.04 (s, 1H), 7.84 (m, 2H), 7.65 (m, 1H), 7.20 (m, 2H), 5.22 (s, 2H); MS (+ve ESI): 381 $(M+H)^+$.

EXAMPLE 12

Preparation of Compound 12 in Table 1—2-(4-{[7-(3-chloropropoxy)-5-isopropoxyquinazolin-4-yl]amino}-1H-pyrazol-1-yl)-N-(2,3-difluorophenyl)acetamide 1-Bromo-3-chloropropane (0.6 ml, 6 mmol) was added to a solution of N-(2,3-difluorophenyl)-2-{4-[(7-hydroxy-5-isopropoxyquinazolin-4-yl)amino]-1H-pyrazol-1-yl}acetamide (2.7 g, 6.0 mmol) and potassium carbonate (0.90 g, 6.0 mmol) in dimethylacetamide (60 ml) and the mixture was heated at 70° C. for 1 hour. The mixture was evaporated under reduced pressure and the residue was purified by silica gel chromatography eluting with a 0 to 10% mixture of methanol (containing 10% 7N ammonia in methanol) in dichloromethane to give compound 12 in table 1 (1.5 g, 46% yield) as a white solid:

$^1$H-NMR (DMSO $d_6$): 10.68 (br s, 1H), 9.8 (s, 1H), 8.42 (s, 1H), 8.34 (s, 1H), 7.70 (s, 2H), 7.19 (m, 2H), 6.78 (d, 1H), 6.70 (d, 1H), 5.15 (s, 2H), 4.96 (septet, 1H), 4.20 (m, 2H), 3.80 (t, 2H), 2.22 (t, 2H), 1.42 (d, 6H); MS (+ve ESI): 532 $(M+H)^+$ MS (−ve ESI): 529 $(M-H)^-$.

N-(2,3-difluorophenyl)-2-{4-[(7-hydroxy-5-isopropoxyquinazolin-4-yl)amino]-1H-pyrazol-1-yl}acetamide used as Starting Material, was Prepared as Follows a) Isopropanol (1.5 ml, 18.7 mmol) was added to a solution of [7-(benzyloxy)-5-hydroxy-4-oxoquinazolin-3(4H)-yl]methyl pivalate (see WO01/094341, 6.5 g, 17.0 mmol) and triphenylphosphine (6.2 g, 23.8 mmol) in dichloromethane (300 ml). The reaction mixture was cooled to 0° C. and then a solution of di-tert-butylazodicarboxylate (4.7 g, 20.4 mmol) in dichloromethane (25 ml) was added dropwise over 30 minutes. The mixture was allowed to warm to room temperature and then stirred for 2 hours. The mixture was evaporated under reduced pressure to afford crude [7-(benzyloxy)-5-isopropoxy-4-oxoquinazolin-3(4H)-yl]methyl pivalate which was used in the next stage without further purification.

b) [7-(benzyloxy)-5-isopropoxy-4-oxoquinazolin-3(4H)-yl]methyl pivalate was stirred in a 7N solution of ammonia in methanol (250 ml) at room temperature for 24 hours. The mixture was evaporated under reduced pressure and the residue purified by silica gel chromatography eluting with a 0 to 10% mixture of methanol in dichloromethane to give 7-(benzyloxy)-5-isopropoxyquinazolin-4(3H)-one (4.6 g, 87% yield over 2 steps) as a white solid:

$^1$H-NMR (DMSO $d_6$): 11.63 (br s, 1H), 7.88 (s, 1H), 7.40 (m, 5H), 6.74 (d, 1H), 6.60 (d, 1H), 5.20 (s, 2H), 4.63 (septet, 1H), 1.26 (d, 6H); MS (+ve ESI): 311 $(M+H)^+$ MS (−ve ESI): 309 $(M-H)^-$.

c) Ammonium formate (9.5 g, 150 mmol) and 10% palladium on carbon (500 mg) were added to a solution of 7-(benzyloxy)-5-isopropoxyquinazolin-4(3H)-one (4.6 g, 15.0 mmol) in dimethylformamide (40 ml) and the mixture stirred at ambient temperature for 4 hours. The mixture was filtered through Celite and then evaporated under reduced pressure. The residue was stirred in water (100 ml) for 30 minutes and then filtered and washed with water (25 ml) and then dried to leave 7-hydroxy-5-isopropoxyquinazolin-4(3H)-one (3.3 g, 100% yield) as a white solid:

$^1$H-NMR (DMSO $d_6$): 11.47 (br s, 1H), 10.29 (br s, 1H), 7.88 (s, 1H), 6.48 (d, 1H), 6.40 (d, 1H), 4.56 (septet, 1H), 1.26 (d, 6H); MS (+ve ESI): 221 $(M+H)^+$ MS (−ve ESI): 219 $(M-H)^-$.

d) Pyridine (0.18 ml, 1.5 mmol) was added to a suspension of 7-hydroxy-5-isopropoxyquinazolin-4(3H)-one (3.3 g, 15 mmol) in acetic anhydride (10 ml, 75 mmol) and the mixture was stirred at 75° C. for 45 minutes. The mixture was evaporated under reduced pressure and the residue obtained was stirred in water (50 ml) at 75° C. for 1 hour and then cooled to ambient temperature and filtered to afford 5-isopropoxy-4-oxo-3,4-dihydroquinazolin-7-yl acetate (2.6 g, 65% yield) as a white solid:

$^1$H-NMR (DMSO $d_6$): 11.85 (br s, 1H), 7.96 (s, 1H), 6.89 (d, 1H), 6.82 (d, 1H), 4.62 (septet, 1H), 2.25 (s, 3H), 1.28 (d, 6H); MS (+ve ESI): 263 $(M+H)^+$ MS (−ve ESI): 261 $(M-H)^-$.

e) Phosphoryl chloride (3.7 ml, 40 mmol) was added to a solution of 5-isopropoxy-4-oxo-3,4-dihydroquinazolin-7-yl acetate (2.6 g, 10 mmol) and di-iso-propylethylamine (14 ml, 80 mmol) in 1,2-dichloroethane (75 ml) and the reaction was heated at 80° C. for 1 hour. The mixture was evaporated under reduced pressure and the residue suspended in dimethylacetamide (30 ml). 2-(4-Amino-1H-pyrazol-1-yl)-N-(2,3-difluorophenyl)acetamide (2.5 g, 10 mmol) was added and the mixture was then heated at 90° C. for 1 hour. The mixture was evaporated under reduced pressure and the residue stirred in a 7N solution of ammonia in methanol (100 ml) at ambient temperature for 2 hours. The mixture was evaporated under reduced pressure to leave a yellow solid which was stirred in water (50 ml) for 1 hour, then filtered and the residue purified by silica gel chromatography eluting with a 0 to 10% mixture of methanol in dichloromethane to give N-(2,3-difluorophenyl)-2-{4-[(7-hydroxy-5-isopropoxyquinazolin-4-yl)amino]-1H-pyrazol-1-yl}acetamide (2.7 g, 60% yield):

$^1$H-NMR (DMSO $d_6$): 10.27 (br s, 1H), 9.8 (s, 1H), 8.38 (s, 1H), 8.34 (s, 1H), 7.70 (s, 2H), 7.19 (m, 2H), 6.60 (s, 1H), 5.12 (s, 2H), 4.84 (septet, 1H), 1.42 (d, 6H); MS (+ve ESI): 455 $(M+H)^+$ MS (−ve ESI): 453 $(M-H)^-$.

EXAMPLE 13

Preparation of Compound 13 in Table 1—2-(4-{[7-(3-chloropropoxy)-5-methoxyquinazolin-4-yl]amino}-1H-pyrazol-1-yl)-N-(2,3-difluorophenyl)acetamide Phosphoryl chloride (0.21 ml, 2.3 mmol) was added to a solution of 7-(3-chloropropoxy)-5-methoxyquinazolin-4(3H)-one (0.180 g, 0.67 mmol) and di-iso-propylethylamine (0.75 ml, 4.3 mmol) in 1,2-dichloroethane (10 ml) and the mixture was heated at 80° C. for 3 hours. The mixture was evaporated under reduced pressure and the residue suspended in dimethylacetamide (10 ml). 2-(4-Amino-1H-pyrazol-1-yl)-N-(2,3-difluorophenyl)acetamide (0.169 g, 0.67 mmol) was added and the mixture was heated at 90° C. for 1 hour. The mixture was evaporated under reduced pressure and the residue triturated with methanol to give compound 13 in table 1 (0.250 g, 74% yield):

$^1$H-NMR (DMSO $d_6$): 8.80 (s, 1H), 8.35 (s, 1H), 7.95 (s, 1H), 7.70 (m, 1H), 7.20 (m, 2H), 6.92 (s, 1H), 6.80 (s, 1H), 5.20 (s, 2H), 4.30 (t, 2H), 4.15 (s, 3H), 3.81 (t, 2H), 2.20 (m, 2H); MS (+ve ESI): 503 $(M+H)^+$.

7-(3-chloropropoxy)-5-methoxyquinazolin-4(3H)-one used as Starting Material, was Prepared as Follows a) Potassium carbonate (5.4 g, 41.6 mmol) was added to a solution of [7-(benzyloxy)-5-hydroxy-4-oxoquinazolin-3(4H)-yl]methyl pivalate (see WO01/094341, 4.0 g, 10.4 mmol) in dimethylformamide (200 ml) and the mixture was stirred at 0° C. for 5 minutes. Dimethyl sulphate (2.0 ml, 20.8 mmol) was added and the reaction mixture stirred at 0° C. for a further 5 minutes and then warmed to room temperature and stirred for 1 hour. The reaction mixture was evaporated under reduced pressure and the residue dissolved in dichloromethane (100 ml) and washed with water (2×50 ml). The organics were dried over magnesium sulphate, filtered and evaporated under reduced pressure to give 7-(benzyloxy)-5-methoxy-4-oxoquinazolin-3(4H)-yl]methyl pivalate which was used in the next stage without further purification.

b) 7-(benzyloxy)-5-methoxy4-oxoquinazolin-3(4H)-yl]methyl pivalate in trifluoroacetic acid (50 ml) was heated at 70° C. for 3 hours. The mixture was evaporated under reduced pressure and purified by reverse phase chromatography eluting with 0.2% aqueous trifluoroacetic acid in acetonitrile using a 5 to 50% gradient over 25 minutes to give 7-hydroxy-5-methoxy-4-oxoquinazolin-3(4H)-yl)methyl pivalate (1.68 g, 53% yield over 2 steps) as a white solid:

$^1$H-NMR (DMSO $d_6$): 10.82 (br s, 1H), 8.20 (s, 1H), 6.50 (s, 1H), 6.45 (s, 1H), 5.78 (s, 2H), 3.78 (s, 3H), 1.15 (s, 9H); MS (+ve ESI): 307 $(M+H)^+$.

c) 1-Bromo-3-chloropropane (0.44 ml, 4.4 mmmol) was added to a solution of 7-hydroxy-5-methoxy-4-oxoquinazolin-3(4H)-yl)methyl pivalate (1.68 g, 4.4 mmol) and potassium carbonate (1.2 g, 8.8 mmol) in dimethylacetamide (40 ml) and the mixture was heated at 70° C. for 3 hours. The mixture was evaporated under reduced pressure and the residue purified by reverse phase chromatography eluting with 0.2% aqueous trifluoroacetic acid in acetonitrile using a 5 to 50% gradient over 25 minutes. The fractions containing product were concentrated under reduced pressure and then basified with aqueous sodium carbonate. The resultant solid was filtered and washed with water to give 7-(3-chloropropoxy)-5-methoxy-4-oxoquinazolin-3(4H)-yl]methyl pivalate (0.380 g, 36% yield):

$^1$H-NMR (DMSO $d_6$): 8.35 (s, 1H), 6.70 (d, 1H), 6.60 (d, 1H), 5.80 (s, 2H), 4.23 (t, 2H), 3.82 (s, 3H), 3.78 (t, 2H), 2.20 (m, 2H), 1.15 (s, 9H); MS (+ve ESI): 383 $(M+H)^+$.

d) 7-(3-chloropropoxy)-5-methoxy-4-oxoquinazolin-3(4H)-yl]methyl pivalate (0.380 g, 1.0 mmol) was stirred in a 7N solution of ammonia in methanol (50 ml) at room temperature for 24 hours. The volatiles were removed by evaporation under reduced pressure and the residue purified by reverse phase chromatography eluting with 0.2% aqueous trifluoroacetic acid in acetonitrile using a 5 to 50% gradient over 25 minutes. The fractions containing product were concentrated under reduced pressure and then basified with aqueous sodium carbonate. The resultant solid was filtered and washed with water to give 7-(3-chloropropoxy)-5-methoxyquinazolin-4(3H)-one (0.180 g, 67% yield):

$^1$H-NMR (DMSO $d_6$): 8.35 (s, 1H), 6.70 (d, 1H), 6.60 (d, 1H), 5.80 (s, 2H), 4.23 (t, 2H), 3.82 (s, 3H), 3.78 (t, 2H), 2.20 (m, 2H), 1.15 (s, 9H); MS (+ve ESI): 383 $(M+H)^+$.

EXAMPLE 14

Preparation of Compound 14 in Table 1—2-(4-{[7-(3-chloropropoxy)-6-fluoroquinazolin-4-yl]amino}-1H-pyrazol-1-yl)-N-(2,3-difluorophenyl)acetamide A mixture of 2-{4-[(6-fluoro-7-hydroxyquinazolin-4-yl)amino]-1H-pyrazol-1-yl}-N-(2,3-difluorophenyl)acetamide trifluoroacetate (1.89 g, 3.58 mmol), 1-bromo-3-chloropropane (0.68 g, 4.32 mmol) and cesium carbonate (2.5 g, 7.67 mmol) in dimethylformamide (20 ml) was heated at 70° C. for 90 minutes. The mixture was allowed to cool to room temperature and then poured into water and the resultant precipitate filtered to give compound 14 in table 1 (1.59 g, 90% yield):

MS (+ve ESI): 491 $(M+H)^+$

2-{4-[(6-fluoro-7-hydroxyquinazolin-4-yl)amino]-1H-pyrazol-1-yl}-N-(2,3-difluorophenyl)acetamide trifluoroacetate used as Starting Material, was Prepared as Follows a) Benzyl alcohol (4.27 g, 39.5 mmol) was added dropwise to a stirred suspension of sodium hydride (1.6 g of a 60% dispersion in mineral oil, 40.0 mmol) in dimethylformamide (50 ml) at 0° C. The reaction was stirred at 0° C. for 1 hour before addition of 6,7-difluoroquinazolin-4(1H)-one (3.60 g, 19.8 mmol) whereupon the reaction was heated to 60° C. for 2 hours. The reaction was cooled to ambient temperature, poured into water (200 ml) and the resultant solid collected by suction filtration. Drying of the solid in vacuo yielded 7-(benzyloxy)-6-fluoroquinazolin-4(1H)-one (4.45 g, 83% yield) as a pale brown solid:

$^1$H-NMR (DMSO $d_6$): 12.24 (br s, 1H), 8.05 (s, 1H), 7.80 (d, 1H), 7.52 (m, 2H), 7.44 (m, 3H), 7.38 (t, 1H), 5.35 (s, 2H).

b) 7-(Benzyloxy)-6-fluoroquinazolin-4(1H)-one (2.00 g, 7.41 mmol) was taken up in phosphorus oxychloride (20 ml) and the reaction heated at reflux for 90 minutes. The reaction was cooled, azeotroped with toluene (2×50 ml) and taken up in dichloromethane (5 ml) The organic phase was washed with saturated aqueous sodium hydrogen carbonate solution and then dried over magnesium sulphate. Solvent evaporation in vacuo followed by drying of the solid in vacuo yielded 7-(benzyloxy)-4-chloro-6-fluoroquinazoline (1.50 g, 71% yield) as a pale yellow solid:

$^1$H-NMR ($CDCl_3$): 8.93 (s, 1H), 7.89 (d, 1H), 7.51 (m, 3H), 7.35-7.46 (m, 3H), 5.32 (s, 2H).

c) A mixture of 7-(benzyloxy)-4-chloro-6-fluoroquinazoline (1.20 g, 4.16 mmol) and 2-(4-amino-1H-pyrazol-1-yl)-N-(2,3-difluorophenyl)acetamide (1.05 g, 4.16 mmol) in isopropanol (20 ml) was heated at 80° C. for 10 minutes and then allowed to cool to room temperature. The mixture was diluted with diethyl ether and then filtered to give 2-(4-{[7-(benzyloxy)-6-fluoroquinazolin-4-yl]amino}-1H-pyrazol-1-yl)-N-(2,3-difluorophenyl)acetamide hydrochloride (1.96 g, 87% yield) as a yellow solid:

$^1$H-NMR (DMSO-$d_6$): 11.80 (s, 1H), 10.40 (s, 1H), 8.94 (s, 1H), 8.90 (d, 1H), 8.42 (s, 1H), 8.03 (s, 1H), 7.71 (m, 1H), 7.61 (m, 1H), 7.55 (m, 2H), 7.45 (m, 3H), 7.20 (m, 2H), 5.41 (s, 2H), 5.22 (s, 2H); MS (+ve ESI): 505 $(M+H)^+$.

d) A solution of 2-(4-{[7-(benzyloxy)-6-fluoroquinazolin-4-yl]amino}-1H-pyrazol-1-yl)-N-(2,3-difluorophenyl)acetamide hydrochloride (1.90 g, 3.51 mmol) in trifluoroacetic acid (20 ml) was heated at 70° C. for 4 hours. The mixture was evaporated and the residue triturated with diethyl ether to give 2-{4-[(6-fluoro-7-hydroxyquinazolin-4-yl)amino]-1H-pyrazol-1-yl}-N-(2,3-difluorophenyl)acetamide as the trifluoroacetic acid salt (1.89 g, 100% yield) as a pale yellow solid:

MS (+ve ESI): 415 $(M+H)^+$.

EXAMPLE 15

Preparation of Compound 15 in Table 1—2-(4-{[7-(3-chloropropoxy)-6-fluoroquinazolin-4-yl]amino}-1H-pyrazol-1-yl)-N-(3-fluorophenyl)acetamide A mixture of 2-{4-[(6-fluoro-7-hydroxyquinazolin-4-yl)amino]-1H-pyrazol-1-yl}-N-(3-fluorophenyl)acetamide trifluoroacetate (0.496 g, 0.97 mmol), 1-bromo-3-chloropropane (0.184 g, 1.17 mmol) and cesium carbonate (0.634 g, 1.94 mmol) in dimethylformamide (5 ml) was heated at 90° C. for 30 minutes. The mixture was allowed to cool to room temperature and then poured into water and the resultant precipitate filtered to give compound 15 in table 1 (0.402 g, 88% yield) as a pale brown solid:

$^1$H-NMR (DMSO-$d_6$): 10.51 (s, 1H), 9.84 (s, 1H), 8.57 (s, 1H), 8.34 (m, 2H), 7.77 (s, 1H), 7.59 (d, 1H), 7.39 (m, 2H), 7.32 (m, 1H), 6.91 (m, 1H), 5.07 (s, 2H),, 4.37 (t, 2H), 3.83 (t, 2H), 2.29 (quintet, 2H).

2-{4-[(6-fluoro-7-hydroxyquinazolin-4-yl)amino]-1H-pyrazol-1-yl}-N-(3-fluorophenyl)acetamide trifluoroacetate used as Starting Material, was Prepared as Follows a) A mixture of 7-(benzyloxy)-4chloro-6-fluoroquinazoline (0.288 g, 1.0 mmol) and 2-(4-amino-1H-pyrazol-1-yl)-N-(3-fluorophenyl)acetamide (0.234 g, 1.0 mmol) in isopropanol (5 ml) was heated at 80° C. for 10 minutes. The mixture was allowed to cool to room temperature and then diluted with diethyl ether. The resultant solid was filtered to give 2-(4-{[7-(benzyloxy)-6-fluoroquinazolin-4-yl]amino}-1H-pyrazol-1-yl)-N-(3-fluorophenyl)acetamide hydrochloride (0.499 g, 95% yield) as a yellow solid:

MS (+ve ESI): 487 $(M+H)^+$.

b) A solution of 2-(4-{[7-(benzyloxy)-6-fluoroquinazolinyl]amino}-1H-pyrazol-1-yl)-N-(3-fluorophenyl)acetamide hydrochloride (0.499 g, 1.18 mmol) in trifluoroacetic acid (5 ml) was heated at 70° C. for 4 hours. The mixture was evaporated and the residue triturated with diethyl ether to give 2-{4-[(6-fluoro-7-hydroxyquinazolin-4-yl)amino]-1H-pyrazol-1-yl}-N-(3-fluorophenyl)acetamide as the trifluoroacetate salt (0.496 g, 97% yield) as a pale yellow solid:

MS (+ve ESI): 397 $(M+H)^+$.

EXAMPLE 16

Preparation of Compound 16 in Table 2—N-(3-fluorophenyl)-2-{4-[(7-{3-[(2S)-2-(hydroxymethyl)pyrrolidin-1-yl]propoxy}-6-methoxyquinazolin-4-yl)amino]-1H-pyrazol-1-yl}acetamide (2S)-Pyrrolidin-2-ylmethanol (80 mg, 0.8 mmol) was added to a solution of 2-(4-{[7-(3-chloropropoxy)-6-methoxyquinazolinyl]amino}-1H-pyrazol-1-yl)-N-(3-fluorophenyl)acetamide (104 mg, 0.2 mmol) and potassium iodide (66 mg, 0.4 mmol) in dimethylacetamide (0.5 ml) and the mixture heated under argon at 90° C. for 3 hours. The solvent was evaporated, and the residue purified by preparative LCMS (Waters symmetry 5 μm column, 19×100 mm) to yield compound 16 in table 2 (100 mg, 91% yield):

$^1$H-NMR (DMSO $d_6$, TFA): 8.97 (s, 1H), 8.41 (s, 1H), 8.09 (s, 1H), 7.96 (s, 1H), 7.61 (d, 1H), 7.34 (m, 3H), 6.91 (t, 1H), 5.15 (s, 2H), 4.30 (t, 2H), 4.03 (s, 3H), 3.78 (m, 1H), 3.62 (m, 4H), 3.25 (m, 2H), 2.38 (m, 2H), 2.14 (m, 1H), 2.05 (m, 1H), 1.91 (m, 1H), 1.81 (m, 1H); MS (+ve ESI): 550.3 $(M+H)^+$.

EXAMPLE 17

Preparation of Compound 17 in Table 2—N-(3-fluorophenyl)-2-{4-[(7-{3-[(2-hydroxyethyl)(isobutyl)amino]propoxy}-6-methoxyquinazolin-4-yl)amino]-1H-pyrazol-1-yl}acetamide An analogous reaction to that described in example 16 but starting with 2-(isobutyl amino)ethanol (94 mg, 0.8 mmol) yielded compound 17 in table 2 (75 mg, 66% yield):

$^1$H-NMR (DMSO $d_6$, TFA): 8.98 (s, 1H), 8.42 (s, 1H), 8.09 (s, 1H), 7.95 (s, 1H), 7.61 (d, 1H), 7.36 (m, 3H), 6.92 (t, 1H), 5.15 (s, 2H), 4.30 (m, 2H), 4.03 (s, 3H), 3.80 (m, 2H), 3.38 (m, 2H), 3.29 (m, 2H), 3.12 (m, 1H), 3.08 (m, 1H), 2.31 (m, 2H), 1.10 (t, 1H), 1.01 (d, 6H); MS (+ve ESI): 566.2 $(M+H)^+$.

EXAMPLE 18

Preparation of Compound 18 in Table 2—N-(3-fluorophenyl)-2-{4-[(7-{3-[(2-hydroxyethyl)(propyl)amino]propoxy}-6-methoxyquinazolin-4-yl)amino]-1H-pyrazol-1-yl}acetamide An analogous reaction to that described in example 16 but starting with 2-(propylamino)ethanol (82 mg, 0.8 mmol) yielded compound 18 in table 2 (85 mg, 77% yield):

$^1$H-NMR (DMSO $d_6$, TFA): 8.97 (s, 1H), 8.39 (s, 1H), 8.08 (s, 1H), 7.95 (s, 1H), 7.60 (m, 1H), 7.38 (m, 1H), 7.32 (m, 2H), 6.92 (m, 1H), 5.15 (s, 2H), 4.29 (t, 2H), 4.02 (s, 3H), 3.77 (t, 2H), 3.39 (m, 2H), 3.28 (t, 2H), 3.15 (m, 2H), 2.28 (m, 2H), 1.71 (m, 2H), 0.95 (t, 3H); MS (+ve ESI): 552.2 $(M+H)^+$.

EXAMPLE 19

Preparation of Compound 19 in Table 2—N-(3-fluorophenyl)-2-(4-{[6-methoxy-7-(3-piperidin-1-ylpropoxy)quinazolin-4-yl]amino}-1H-pyrazol-1-yl)acetamide An analogous reaction to that described in example 16 but starting with piperidine (55 mg, 0.65 mmol) yielded compound 19 in table 2 (78 mg, 73% yield):

$^1$H-NMR (DMSO $d_6$): 9.68 (s, 1H), 8.48 (s, 1H), 8.35 (s, 1H), 7.78 (s, 1H), 7.76 (s, 1H), 7.59 (m, 1H), 7.37 (m, 1H), 7.34 (m, 1H), 7.31 (s, 1H), 6.92 (m, 1H), 5.06 (s, 2H), 4.16 (t, 2H), 3.96 (s, 3H), 2.41 (t, 2H), 2.35 (m, 4H), 1.94 (m, 2H), 1.51 (m, 4H), 1.39 (m, 2H); MS (+ve ESI): 534.2 $(M+H)^+$.

EXAMPLE 20

Preparation of Compound 20 in Table 2—N-(3-fluorophenyl)-2-(4-{[6-methoxy-7-(3-pyrrolidin-1-ylpropoxy)quinazolin-4-yl]amino}-1H-pyrazol-1-yl)acetamide An analogous reaction to that described in example 16 but starting with pyrrolidine (46 mg, 0.65 mmol) yielded compound 20 in table 2 (71 mg, 69% yield):

$^1$H-NMR (DMSO $d_6$): 9.69 (s, 1H), 8.42 (s, 1H), 8.35 (s, 1H), 7.78 (s, 1H), 7.75 (s, 1H), 7.59 (m, 1H), 7.37 (m, 1H), 7.32 (m, 1H), 7.15 (s, 1H), 6.83 (m, 1H), 5.06 (s, 2H), 4.17 (t, 2H), 3.96 (s, 3H), 2.54 (t, 2H), 2.45 (m, 4H), 1.96 (m, 2H), 1.69 (m, 4H); MS (+ve ESI): 520.2 $(M+H)^+$.

EXAMPLE 21

Preparation of Compound 21 in Table 2—2-[4-({7-[3-(diethylamino)propoxy]-6-methoxyquinazolin-4-yl}amino)-1H-pyrazol-1-yl]-N-(3-fluorophenyl)acetamide An analogous reaction to that described in example 16 but starting with diethyl amine (48 mg, 0.65 mmol) yielded compound 21 in table 2 (62 mg, 59% yield):

$^1$H-NMR (DMSO $d_6$): 9.68 (s, 1H), 8.48 (s, 1H), 8.34 (s, 1H), 7.81 (s, 1H), 7.76 (s, 1H), 7.58 (m, 1H), 7.37 (m, 1H), 7.32 (m, 1H), 7.14 (s, 1H), 6.92 (m, 1H), 5.06 (s, 2H), 4.16 (t, 2H), 3.96 (s, 3H), 2.52 (t, 2H), 2.46 (m, 4H), 1.89 (m, 2H), 0.95 (t, 6H); MS (+ve ESI): 522.1 $(M+H)^+$.

EXAMPLE 22

Preparation of Compound 22 in Table 2—N-(3-fluorophenyl)-2-(4-{[6-methoxy-7-(3-piperazin-1-ylpropoxy)quinazolin-4-yl]amino}-1H-pyrazol-1-yl)acetamide An analogous reaction to that described in example 16 but starting with piperazine (56 mg, 0.65 mmol) yielded compound 22 in table 2 (54 mg, 51% yield):

$^1$H-NMR (DMSO $d_6$): 9.68 (s, 1H), 8.48 (s, 1H), 8.34 (s, 1H), 7.78 (s, 1H), 7.75 (s, 1H), 7.58 (m, 1H), 7.39 (m, 1H), 7.32 (m, 1H), 7.15 (s, 1H), 6.92 (m, 1H), 5.06 (s, 2H), 4.16 (t, 2H), 3.96 (s, 3H), 2.69 (m, 4H), 2.41 (t, 2H), 2.31 (m, 4H), 1.94 (m, 2H); MS (+ve ESI): 535.1 $(M+H)^+$.

EXAMPLE 23

Preparation of Compound 23 in Table 2—N-(3-fluorophenyl)-2-{4-[(7-{3-[(2-hydroxyethyl)(methyl)amino]propoxy}-6-methoxyquinazolin-4-yl)amino]-1H-pyrazol-1-yl}acetamide An analogous reaction to that described in example 16 but starting 2-(methylamino)ethanol (49 mg, 0.65 mmol) yielded compound 23 in table 2 (67 mg, 64% yield):

$^1$H-NMR (DMSO $d_6$): 9.18 (s, 1H), 8.42 (s, 1H), 8.35 (s, 1H), 7.81 (s, 1H), 7.76 (s, 1H), 7.58 (m, 1H), 7.37 (m, 1H), 7.32 (m, 1H), 7.16 (s, 1H), 6.92 (m, 1H), 5.06 (s, 2H), 4.36 (t, 1H), 4.17 (t, 2H), 3.96 (s, 3H), 3.47 (m, 2H), 2.5 (m, 2H), 2.42 (t, 2H), 2.2 (s, 3H), 1.92 (m, 2H); MS (+ve ESI): 524.1 $(M+H)^+$.

EXAMPLE 24

Preparation of Compound 24 in Table 2—2-[4-({7-[3-(cyclopropyl}amino)propoxy]-6-methoxyquinazolin-4-ylamino)-1H-pyrazol-1-yl]-N-(3-fluorophenyl)acetamide An analogous reaction to that described in example 16 but starting with cyclopropylamine (37 mg, 0.65 mmol) yielded compound 24 in table 2 (51 mg, 51% yield):

$^1$H-NMR (DMSO $d_6$): 9.71 (s, 1H), 8.50 (s, 1H), 8.37 (s, 1H), 7.80 (s, 1H), 7.78 (s, 1H), 7.61 (m, 1H), 7.39 (m, 1H), 7.34 (m, 1H), 7.18 (s, 1H), 6.95 (m, 1H), 5.09 (s, 2H), 4.19 (t,

2H), 3.98 (s, 3H), 2.77 (t, 2H), 2.09 (m, 1H), 1.94 (m, 2H), 0.37 (m, 2H), 0.23 (m, 2H); MS (+ve ESI): 506.1 $(M+H)^+$.

EXAMPLE 25

Preparation of Compound 25 in Table 2—2-{4-[(7-{3-[[2-(dimethylamino)ethyl](methyl)amino]propoxy}-6-methoxyquinazolin-4-yl)amino]-1H-pyrazol-1-yl}-N-(3-fluorophenyl)acetamide An analogous reaction to that described in example 16 but starting with N,N,N'-trimethylethane-1,2-diamine (66 mg, 0.65 mmol) yielded compound 25 in table 2 (49 mg, 45% yield):

$^1$H-NMR (DMSO $d_6$): 9.68 (s, 1H), 8.48 (s, 1H), 8.35 (s, 1H), 7.78 (s, 1H), 7.76 (s, 1H), 7.59 (m, 1H), 7.37 (m, 1H), 7.31 (m, 1H), 7.14 (s, 1H), 6.93 (m, 1H), 5.06 (s, 2H), 4.15 (t, 2H), 3.96 (s, 3H), 2.50 (m, 2H), 2.41 (m, 2H), 2.29 (m, 2H), 2.19 (s, 3H), 2.11 (s, 6H), 1.91 (m, 2H); MS (+ve ESI): 551.1 $(M+H)^+$.

EXAMPLE 26

Preparation of Compound 26 in Table 2—N-(3-fluorophenyl)-2-[4-({6-methoxy-7-[3-(4-methylpiperazin-1-yl)propoxy]quinazolin-4-yl}amino)-1H-pyrazol-1-yl]acetamide An analogous reaction to that described in example 16 but starting with 1-methylpiperazine (65 mg, 0.65 mmol) yielded compound 26 in table 2 (80 mg, 73% yield):

$^1$H-NMR (DMSO $d_6$): 9.69 (s, 1H), 8.48 (s, 1H), 8.35 (s, 1H), 7.78 (s, 1H), 7.76 (s, 1H), 7.59 (m, 1H), 7.38 (m, 1H), 7.32 (m, 1H), 7.15 (s, 1H), 6.90 (m, 1H), 5.06 (s, 2H), 4.16 (t, 2H), 3.96 (s, 3H), 2.44 (t, 2H), 2.11-2.60 (m, 8H), 2.14 (s, 3H), 1.94 (m, 2H); MS (+ve ESI): 549.1 $(M+H)^+$.

EXAMPLE 27

Preparation of Compound 27 in Table 2—N-(3-fluorophenyl)-2-{4-[(7-{3-[(2R)-2-(hydroxymethyl)pyrrolidin-1-yl]propoxy}-6-methoxyquinazolin-4-yl)amino]-1H-pyrazol-1-yl}acetamide An analogous reaction to that described in example 16 but starting with (2R)-pyrrolidin-2-ylmethanol (66 mg, 0.65 mmol) yielded compound 27 in table 2 (74 mg, 67% yield):

$^1$H-NMR (DMSO $d_6$): 9.68 (s, 1H), 8.48 (s, 1H), 8.35 (s, 1H), 7.78 (s, 1H), 7.76 (s, 1H), 7.58 (m, 1H), 7.37 (m, 1H), 7.31 (m, 1H), 7.16 (s, 1H), 6.92 (m, 1H), 5.06 (s, 2H), 4.34 (t, 1H), 4.17 (t, 2H), 3.96 (s, 3H), 3.17 (m, 1H), 3.07 (m, 1H), 2.96 (m, 1H), 2.41 (m, 3H), 2.15 (m, 1H), 1.94 (m, 2H), 1.80 (m, 1H), 1.65 (m, 2H), 1.56 (m, 1H); MS (+ve ESI): 550.1 $(M+H)^+$.

EXAMPLE 28

Preparation of Compound 28 in Table 2—N-(3-fluorophenyl)-2-[4-({7-[3-(4-hydroxypiperidin-1-yl)propoxy]-6-methoxyquinazolin-4-yl}amino)-1H-pyrazol-1-yl]acetamide An analogous reaction to that described in example 16 but starting with 4-piperidinol (66 mg, 0.65 mmol) yielded compound 28 in table 2 (110 mg, 100% yield):

$^1$H-NMR (DMSO $d_6$, TFA): 8.97 (s, 1H), 8.48 (s, 1H), 8.14 (s, 1H), 7.98 (s, 1H), 7.61 (m, 1H), 7.38 (m, 2H), 7.36 (s, 1H), 6.91 (m, 1H), 5.16 (s, 2H), 4.31 (t, 2H), 4.04 (s, 3H), 3.70 (m, 1H), 3.57 (d, 1H), 3.41 (d, 1H), 3.30 (m, 3H), 3.04 (t, 1H), 2.32 (m, 2H), 2.02 (m, 1H), 1.89 (m, 2H), 1.61 (m, 1H); MS (+ve ESI): 550.1 $(M+H)^+$.

EXAMPLE 29

Preparation of Compound 29 in Table 2—2-{4-[(7-{3-[bis(2-hydroxyethyl)amino]propoxy}-6-methoxyquinazolin-4-yl)amino]-1H-pyrazol-1-yl}-N-(3-fluorophenyl)acetamide An analogous reaction to that described in example 16 but starting with 2,2'-iminodiethanol (68 mg, 0.65 mmol) yielded compound 29 in table 2 (53 mg, 48% yield):

$^1$H-NMR (DMSO $d_6$): 9.68 (s, 1H), 8.48 (s, 1H), 8.34 (s, 1H), 7.78 (s, 1H), 7.76 (s, 1H), 7.58 (m, 1H), 7.38 (m, 1H), 7.32 (m, 1H), 7.17 (s, 1H), 6.92 (m, 1H), 5.06 (s, 2H), 4.35 (t, 2H), 4.18 (t, 2H), 3.96 (s, 3H), 3.42 (m, 4H), 2.64 (m, 2H), 2.54 (m, 4H), 1.90 (m, 2H); MS (+ve ESI): 554.2 $(M+H)^+$.

EXAMPLE 30

Preparation of Compound 30 in Table 2—2-{4-[(7-{3-[ethyl(methyl)amino]propoxy}-6-methoxyquinazolin-4-yl)amino]-1H-pyrazol-1-yl}-N-(3-fluorophenyl)acetamide An analogous reaction to that described in example 16 but starting with ethyl (methyl)amine (38 mg, 0.65 mmol) yielded compound 30 in table 2 (67 mg, 66% yield):

$^1$H-NMR (DMSO $d_6$): 9.69 (s, 1H), 8.48 (s, 1H), 8.35 (s, 1H), 7.78 (s, 1H), 7.76 (s, 1H), 7.58 (m, 1H), 7.37 (m, 1H), 7.31 (m, 1H), 7.15 (s, 1H), 6.92 (m, 1H), 5.06 (s, 2H), 4.16 (t, 2H), 3.96 (s, 3H), 2.46 (t, 2H), 2.36 (q, 2H), 2.16 (s, 3H), 1.92 (m, 2H), 0.98 (t, 3H); MS (+ve ESI): 508.1 $(M+H)^+$.

EXAMPLE 31

Preparation of Compound 31 in Table 2—2-{4-[(7-{3-[ethyl(2-hydroxyethyl)amino]propoxy}-6-methoxyquinazolin-4-yl)amino]-1H-pyrazol-1-yl}-N-(3-fluorophenyl)acetamide An analogous reaction to that described in example 16 but starting with 2-(ethylamino)ethanol (58 mg, 0.65 mmol) yielded compound 31 in table 2 (63 mg, 58% yield):

$^1$H-NMR (DMSO $d_6$): 9.68 (s, 1H), 8.48 (s, 1H), 8.35 (s, 1H), 7.78 (s, 1H), 7.76 (s, 1H), 7.58 (m, 1H), 7.37 (m, 1H), 7.32 (m, 1H), 7.15 (s, 1H), 6.92 (m, 1H), 5.06 (s, 2H), 4.33 (t, 1H), 4.17 (t, 2H), 3.96 (s, 3H), 3.42 (m, 2H), 2.61 (t, 2H), 2.50 (m, 4H), 1.89 (m, 2H), 0.96 (t, 3H); MS (+ve ESI): 538.1 $(M+H)^+$.

EXAMPLE 32

Preparation of Compound 32 in Table 2—2-{4-[(7-{3-[[2-(dimethylamino)ethyl](ethyl)amino]propoxy}-6-methoxyquinazolin-4-yl)amino]-1H-pyrazol-1-yl}-N-(3-fluorophenyl)acetamide An analogous reaction to that described in example 16 but starting with N'-ethyl-N,N-dimethylethane-1,2-diamine (76 mg, 0.65 mmol) yielded compound 32 in table 2 (33 mg, 29% yield):

$^1$H-NMR (DMSO $d_6$): 9.69 (s, 1H), 8.48 (s, 1H), 8.35 (s, 1H), 7.78 (s, 1H), 7.76 (s, 1H), 7.58 (m, 1H), 7.37 (m, 1), 7.32

(m, 1H), 7.14 (s, 1H), 6.92 (m, 1H), 5.06 (s, 1H), 4.17 (t, 2H), 3.96 (s, 3H), 2.57 (t, 2H), 2.48 (m, 4H), 2.27 (t, 2H), 2.09 (s, 6H), 1.88 (m, 2H), 0.95 (t, 3H); MS (+ve ESI): 565.1 $(M+H)^+$.

EXAMPLE 33

Preparation of Compound 33 in Table 2—N-(3-fluorophenyl)-2-{4-[(7-{3-[2-(2-hydroxyethyl)piperidin-1-yl]propoxy}-6-methoxyquinazolin-4-yl)amino]-1H-pyrazol-1-yl}acetamide An analogous reaction to that described in example 16 but starting with 2-piperidin-2-ylethanol (84 mg, 0.65 mmol) yielded compound 33 in table 2 (67 mg, 58% yield):

$^1$H-NMR (DMSO $d_6$): 9.68 (s, 1H), 8.48 (s, 1H), 8.35 (s, 1H), 7.78 (s, 1H), 7.76 (s, 1H), 7.58 (m, 1H), 7.37 (m, 1H), 7.32 (m, 1H), 7.15 (s, 1H), 6.92 (m, 1H), 5.06 (s, 2H), 4.38 (t, 1H), 4.15 (t, 2H), 3.96 (s, 3H), 3.44 (m, 2H), 2.76 (m, 2H), 2.46 (m, 2H), 2.23 (m, 1H), 1.91 (m, 2H), 1.74 (m, 1H), 1.59 (m, 2H), 1.46 (m, 3H), 1.28 (m, 2H); MS (+ve ESI): 578.2 $(M+H)^+$.

EXAMPLE 34

Preparation of Compound 34 in Table 2—N-(3-fluorophenyl)-2-{4-[(7-{3-[4-(2-hydroxyethyl)piperazin-1-yl]propoxy}-6-methoxyquinazolin-4-yl)amino]-1H-pyrazol-1-yl}acetamide An analogous reaction to that described in example 16 but starting with 2-piperazin-1-ylethanol (85 mg, 0.65 mmol) yielded compound 34 in table 2 (85 mg, 74% yield):

$^1$H-NMR (DMSO $d_6$): 9.69 (s, 1H), 8.48 (s, 1H), 8.35 (s, 1H), 7.78 (s, 1H), 7.76 (s, 1H), 7.58 (m, 1H), 7.37 (m, 1H), 7.32 (m, 1H), 7.15 (s, 1H), 6.92 (m, 1H), 5.06 (s, 2H), 4.36 (t, 1H), 4.16 (t, 2H), 3.96 (s, 3H), 3.47 (m, 2H), 2.35-2.45 (m, 12H), 1.94 (m, 2H); MS (+ve ESI): 579.2 $(M+H)^+$.

EXAMPLE 35

Preparation of Compound 35 in Table 2—2-{4-[(7-{3-[(cyclopropylmethyl)amino]propoxy}-6-methoxyquinazolin-4-yl)amino]-1H-pyrazol-1-yl)-N-(3-fluorophenyl)acetamide An analogous reaction to that described in example 16 but starting with (cyclopropylmethyl)amine (46 mg, 0.65 mmol) yielded compound 35 in table 2 (53 mg, 51% yield):

$^1$H-NMR (DMSO $d_6$): 9.68 (s, 1H), 8.48 (s, 1H), 8.35 (s, 1H), 7.78 (s, 1H), 7.76 (s, 1H), 7.59 (m, 1H), 7.37 (m, 1H), 7.32 (m, 1H), 7.16 (s, 1H), 6.92 (m, 1H), 5.06 (s, 2H), 4.19 (t, 2H), 3.96 (s, 3H), 2.71 (t, 2H), 2.39 (d, 2H), 1.93 (m, 2H), 0.88 (m, 1H), 0.39 (m, 2H), 0.11 (m, 2H); MS (+ve ESI): 520.1 $(M+H)^+$.

EXAMPLE 36

Preparation of Compound 36 in Table 2—N-(3-fluorophenyl)-2-{4-[(7-{3-[4-(2-hydroxyethyl)piperidin-1-yl]propoxy}-6-methoxyquinazolin-4-yl)amino]-1H-pyrazol-1-yl}acetamide An analogous reaction to that described in example 16 but starting with 2-piperidin-4-ylethanol (84 mg, 0.65 mmol) yielded compound 36 in table 2 (101 mg, 88% yield):

$^1$H-NMR (DMSO $d_6$): 9.68 (s, 1H), 8.48 (s, 1H), 8.35 (s, 1H), 7.78 (s, 1H), 7.76 (s, 1H), 7.58 (m, 1H), 7.37 (m, 1H), 7.32 (m, 1H), 7.15 (s, 1H), 6.92 (m, 1H), 5.06 (s, 2H), 4.32 (t, 1H), 4.15 (t, 2H), 3.96 (s, 3H), 3.43 (m, 2H), 2.85 (m, 2H), 2.42 (t, 2H), 1.94 (m, 2H), 1.85 (t, 2H), 1.61 (d, 2H), 1.35 (t, 3H), 1.13 (m, 2H); MS (+ve ESI): 578.1 $(M+H)^+$.

EXAMPLE 37

Preparation of Compound 37 in Table 2—N-(3-fluorophenyl)-2-{4-[(6-methoxy-7-{3-[methyl(prop-2-yn-1-yl)amino]propoxy}quinazolin-4-yl)amino]-1H-pyrazol-1-yl}acetamide An analogous reaction to that described in example 16 but starting with N-methylprop-2-yn-1-amine (45 mg, 0.65 mmol) yielded compound 37 in table 2 (58 mg, 56% yield):

$^1$H-NMR (DMSO $d_6$): 8.61 (s, 1H), 8.37 (s, 1H), 7.99 (s, 1H), 7.86 (s, 1H), 7.61 (m, 1H), 7.37 (m, 1H), 7.33 (m, 1H), 7.23 (s, 1H), 6.92 (m, 1H), 5.09 (s, 2H), 4.24 (t, 2H), 3.99 (s, 3H), 3.71 (m, 1H), 3.08 (m, 2H), 2.74 (m, 2H), 2.17 (m, 2H); MS (+ve ESI): 518.1 $(M+H)^+$.

EXAMPLE 38

Preparation of Compound 38 in Table 2—2-{4-[(7-{3-[allyl(methyl)amino]propoxy}-6-methoxyquinazolin-4-yl)amino]-1H-pyrazol-1-yl}-N-(3-fluorophenyl)acetamide An analogous reaction to that described in example 16 but starting with N-methylprop-2-en-1-amine (46 mg, 0.65 mmol) yielded compound 38 in table 2 (79 mg, 76% yield):

$^1$H-NMR (DMSO $d_6$): 9.69 (s, 1H), 8.48 (s, 1H), 8.35 (s, 1H), 7.78 (s, 1H), 7.76 (s, 1H), 7.58 (m, 1H), 7.37 (m, 1H), 7.32 (m, 1H), 7.15 (s, 1H), 6.92 (m, 1H), 5.83 (m, 1H), 5.18 (d, 1H), 5.07 (d, 1H), 5.06 (s, 2H), 4.16 (t, 2H), 3.96 (s, 3H), 2.98 (d, 2H), 2.48 (m, 2H), 2.16 (s, 3H), 1.94 (m, 2H); MS (+ve ESI): 520.1 $(M+H)^+$.

EXAMPLE 39

Preparation of Compound 39 in Table 2—N-(3-fluorophenyl)-2-{4-[(7-{3-(isobutyl(methyl)amino]propoxy}-6-methoxyquinazolin-4-yl)amino]-1H-pyrazol-1-yl}acetamide An analogous reaction to that described in example 16 but starting with isobutyl(methyl)amine (57 mg, 0.65 mmol) yielded compound 39 in table 2 (64 mg, 60% yield):

$^1$H-NMR (DMSO $d_6$): 9.69 (s, 1H), 8.48 (s, 1H), 8.35 (s, 1H), 7.78 (s, 1H), 7.76 (s, 1H), 7.58 (m, 1H), 7.38 (m, 1H), 7.32 (m, 1H), 7.13 (s, 1H), 6.92 (m, 1H), 5.06 (s, 2H), 4.17 (t, 2H), 3.96 (s, 3H), 2.45 (t, 2H), 2.15 (s, 3H), 2.04 (d, 2H), 1.92 (m, 2H), 1.72 (m, 1H), 0.82 (d, 6H); MS (+ve ESI): 536.2 $(M+H)^+$.

EXAMPLE 40

Preparation of Compound 40 in Table 2—N-(3-fluorophenyl)-2-[4-({7-[3-(3-hydroxypiperidin-1-yl)propoxy]-6-methoxyquinazolin-4-yl}amino)-1H-pyrazol-1-yl]acetamide An analogous reaction to that described in example 16 but starting with piperidin-3-ol (66 mg, 0.65 mmol) yielded compound 40 in table 2 (78 mg, 71% yield):

$^1$H-NMR (DMSO $d_6$): 9.69 (s, 1H), 8.48 (s, 1H), 8.35 (s, 1H), 7.78 (s, 1H), 7.76 (s, 1H), 7.58 (m, 1H), 7.37 (m, 1H), 7.32 (m, 1H), 7.16 (s, 1H), 6.92 (m, 1H), 5.06 (s, 2H), 4.59 (d, 1H), 4.16 (t, 2H), 3.96 (s, 3H), 3.48 (m, 2H), 2.83 (m, 1H), 2.67 (m, 1H), 2.46 (m, 2H), 1.94 (m, 2H), 1.85 (m, 1H), 1.76 (m, 2H), 1.61 (m, 1H), 1.42 (m, 1H); MS (+ve ESI): 550.1 $(M+H)^+$.

EXAMPLE 41

Preparation of Compound 41 in Table 2—N-(3-fluorophenyl)-2-{4-[(7-{3-[4-(hydroxymethyl)piperidin-1-yl]propoxy}-6-methoxyquinazolin-4-yl)amino]-1H-pyrazol-1-yl}acetamide An analogous reaction to that described in example 16 but starting with piperidin-4-ylmethanol (75 mg, 0.65 mmol) yielded compound 41 in table 2 (88 mg, 78% yield):

$^1$H-NMR (DMSO $d_6$): 9.69 (s, 1H), 8.48 (s, 1H), 8.35 (s, 1H), 7.78 (s, 1H), 7.76 (s, 1H), 7.58 (m, 1H), 7.37 (m, 1H), 7.32 (m, 1H), 7.15 (s, 1H), 6.92 (m, 1H), 5.06 (s, 2H), 4.40 (t, 1H), 4.15 (t, 2H),3.96 (s, 3H), 3.23 (m, 2H), 2.87 (d, 2H), 2.43 (t, 2H), 1.94 (m, 2H), 1.85 (t, 2H), 1.63 (d, 2H), 1.33 (m, 1H), 1.13 (m, 2H); MS (+ve ESI): 564.2 $(M+H)^+$.

EXAMPLE 42

Preparation of Compound 42 in Table 2—N-(3-fluorophenyl)-2-{4-[(6-methoxy-7-{3-[methyl(propyl)amino]propoxy}quinazolin-4-yl)amino]-1H-pyrazol-1-yl}acetamide An analogous reaction to that described in example 16 but starting with methyl(propyl)amine (48 mg, 0.65 mmol) yielded compound 42 in table 2 (68 mg, 66% yield):

$^1$H-NMR (DMSO $d_6$): 9.69 (s, 1H), 8.48 (s, 1H), 8.35 (s, 1H), 7.78 (s, 1H), 7.76 (s, 1H), 7.58 (m, 1H), 7.37 (m, 1H), 7.32 (m, 1H), 7.14 (s, 1H), 6.92 (m, 1H), 5.06 (s, 2H), 4.16 (t, 2H), 3.96 (s, 3H), 2.46 (t, 2H), 2.26 (t, 2H), 2.16 (s, 3H), 1.92 (m, 2H), 1.42 (m, 2H), 0.83 (t, 3H); MS (+ve ESI): 522.1 $(M+H)^+$.

EXAMPLE 43

Preparation of Compound 43 in Table 2—2-{4-[(7-{3-[(cyclopropylmethyl)(propyl)amino]propoxy}-6-methoxyquinazolin-4-yl)amino]-1H-pyrazol-1-yl}-N-(3-fluorophenyl)acetamide An analogous reaction to that described in example 16 but starting with (cyclopropylmethyl)propylamine (74 mg, 0.65 mmol) yielded compound 43 in table 2 (3 mg, 3% yield):

$^1$H-NMR (DMSO $d_6$): 9.68 (s, 1H), 8.48 (s, 1H), 8.34 (s, 1H), 7.78 (s, 1H), 7.76 (s, 1H), 7.58 (m, 1H), 7.38 (m, 1H), 7.32 (m, 1H), 7.14 (s, 1H), 6.92 (m, 1H), 5.06 (s, 2H), 4.18 (t, 2H), 3.95 (s, 3H), 2.64 (m, 2H), 2.43 (m, 2H), 2.31 (d, 2H), 1.90 (m, 2H), 1.42 (m, 2H), 0.83 (m, 4H), 0.40 (m, 2H), 0.06 (m, 2H); MS (+ve ESI): 562.2 $(M+H)^+$.

EXAMPLE 44

Preparation of Compound 44 in Table 2—2-[4-[(7-{3-[[2-(diethylamino)ethyl](methyl)amino]propoxy}-6-methoxyquinazolin-4-yl)amino]-1H-pyrazol-1-yl}-N-(3-fluorophenyl)acetamide An analogous reaction to that described in example 16 but starting with N,N-diethyl-N'-methylethane-1,2-diamine (85 mg, 0.65 mmol) yielded compound 44 in table 2 (83 mg, 71% yield):

$^1$H-NMR (DMSO $d_6$): 9.68 (s, 1H), 8.48 (s, 1H), 8.35 (s, 1H), 7.78 (s, 1H), 7.76 (s, 1H), 7.58 (m, 1H), 7.37 (m, 1H), 7.32 (m, 1H), 7.14 (s, 1H), 6.92 (m, 1H), 5.06 (s, 2H), 4.16 (t, 2H), 3.96 (s, 3H), 2.41 (m, 10H), 2.19 (s, 3H), 1.91 (m, 2H), 0.90 (t, 6H);

MS (+ve ESI): 579.2 $(M+H)^+$.

EXAMPLE 45

Preparation of Compound 45 in Table 2—2-{4-[(7-{3-[[2-(diethylamino)ethyl](ethyl)amino]propoxy}-6-methoxyquinazolin-4-yl)amino]-1H-pyrazol-1-yl}-N-(3-fluorophenyl)acetamide An analogous reaction to that described in example 16 but starting with N,N,N'-triethylethane-1,2-diamine (94 mg, 0.65 mmol) yielded compound 45 in table 2 (70 mg, 59% yield):

$^1$H-NMR (DMSO $d_6$): 9.68 (s, 1H), 8.48 (s, 1H), 8.35 (s, 1H), 7.78 (s, 1H), 7.76 (s, 1H), 7.58 (m, 1H), 7.37 (m, 1H), 7.32 (m, 1H), 7.14 (s, 1H), 6.92 (m, 1H), 5.06 (s, 2H), 4.17 (t, 2H), 3.96 (s, 3H), 2.58 (m, 2H), 2.42 (m, 10H), 1.88 (m, 2H), 0.96 (t, 3H), 0.91 (t, 6H); MS (+ve ESI): 593.2 $(M+H)^+$.

EXAMPLE 46

Preparation of Compound 46 in Table 2—N-(3-fluorophenyl)-2-[4-({6-methoxy-7-[3-(4-methyl-1,4-diazepan-1-yl)propoxy]quinazolin-4-yl}amino)-1H-pyrazol-1-yl]acetamide An analogous reaction to that described in example 16 but starting with 1-methyl-1,4-diazepane (74 mg, 0.65 mmol) yielded compound 46 in table 2 (55 mg, 49% yield):

$^1$H-NMR (DMSO $d_6$): 9.69 (s, 1H), 8.48 (s, 1H), 8.35 (s, 1H), 7.78 (s, 1H), 7.76 (s, 1H), 7.58 (m, 1H), 7.37 (m, 1H), 7.32 (m, 1H), 7.15 (s, 1H), 6.92 (m, 1H), 5.06 (s, 2H), 4.16 (t, 2H), 3.95 (s, 3H), 2.63 (m, 10H), 2.23 (s, 3H), 1.91 (m, 2H), 1.71 (m, 2H); MS (+ve ESI): 563.2 $(M+H)^+$.

EXAMPLE 47

Preparation of Compound 47 in Table 2—N-(3-fluorophenyl)-2-{4-[(7-{3-[(2-hydroxyethyl)(isopropyl)amino]propoxy}-6-methoxyquinazolin-4-yl)amino]-1H-pyrazol-1-yl}acetamide An analogous reaction to that described in example 16 but starting with 2-(isopropylamino)ethanol (67 mg, 0.65 mmol) yielded compound 47 in table 2 (82 mg, 74% yield):

$^1$H-NMR (DMSO $d_6$): 9.68 (s, 1H), 8.48 (s, 1H), 8.34 (s, 1H), 7.78 (s, 1H), 7.76 (s, 1H), 7.58 (m, 1H), 7.37 (m, 1H), 7.32 (m, 1H), 7.15 (s, 1H), 6.92 (m, 1H), 5.06 (s, 4.27 (t, 1H), 4.16 (t, 2), 3.97 (s, 3H), 3.35 (m, 2H), 2.89 (m, 1H), 2.54 (m, 2H), 2.45 (m, 2H), 1.86 (m, 2H), 0.92 (d, 6H); MS (+ve ESI): 552.2 $(M+H)^+$.

EXAMPLE 48

Preparation of Compound 48 in Table 2—2-{4-[(7-{3-[cyclopropyl(2-hydroxyethyl)amino]propoxy}-6-methoxyquinazolin-4-yl)amino]-1H-pyrazol-1-yl}-N-(3-fluorophenyl)acetamide An analogous reaction to that described in example 16 but starting with 2-(cyclopropylamino)ethanol (66 mg, 0.65 mmol) yielded compound 48 in table 2 (73 mg, 66% yield):

$^1$H-NMR (DMSO $d_6$): 9.69 (s, 1H), 8.48 (s, 1H), 8.35 (s, 1H), 7.78 (s, 1H), 7.76 (s, 1H), 7.58 (m, 1H), 7.37 (m, 1H), 7.32 (m, 1H), 7.15 (s, 1H), 6.92 (m, 1H), 5.06 (s, 2H), 4.32 (m, 1H), 4.15 (t, 2H), 3.96 (s, 3H), 3.5 (m, 2H), 2.76 (t, 2H), 2.65 (t, 2H), 1.95 (m, 2H), 1.82 (m, 1H), 0.43 (m, 2H), 0.31 (m, 2H); MS (+ve ESI): 550.1 $(M+H)^+$.

EXAMPLE 49

Preparation of Compound 49 in Table 2—N-(3-fluorophenyl)-2-{4-[(7-{3-[(2-hydroxyethyl)(2-methoxyethyl)aminopropoxy}-6-methoxyquinazolin-4-yl) amino]-1H-pyrazol-1-yl}acetamide An analogous reaction to that described in example 16 but starting with 2-((2-methoxyethyl)amino)ethanol (77 mg, 0.65 mmol) yielded compound 49 in table 2 (97 mg, 85% yield):

$^1$H-NMR (DMSO $d_6$): 9.68 (s, 1H), 8.48 (s, 1H), 8.35 (s, 1H), 7.78 (s, 1H), 7.76 (s, 1H), 7.59 (m, 1H), 7.38 (m, 1H), 7.32 (m, 1H), 7.15 (s, 1H), 6.92 (m, 1H), 5.06 (s, 2H), 4.31 (t, 1H), 4.17 (t, 2H), 3.96 (s, 3H), 3.43 (m, 2H), 3.37 (m, 2H), 3.20 (s, 3H), 2.64 (m, 4H), 2.53 (t, 2H), 1.91 (m, 2H); MS (+ve ESI): 568.1 $(M+H)^+$.

EXAMPLE 50

Preparation of Compound 50 in Table 2—2-{4-[(7-{3-[cyclobutyl(2-hydroxyethyl)amino]propoxy}-6-methoxyquinazolin-4-yl)amino]-1H-pyrazol-1-yl}-N-(3-fluorophenyl)acetamide An analogous reaction to that described in example 16 but starting with 2-(cyclobutylamino)ethanol (75 mg, 0.65 mmol) yielded compound 50 in table 2 (106 mg, 94% yield):

$^1$H-NMR (DMSO $d_6$): 9.68 (s, 1H), 8.48 (s, 1H), 8.34 (s, 1H), 7.78 (s, 1H), 7.76 (s, 1H), 7.53 (m, 1H), 7.37 (m, 1H), 7.32 (m, 1H), 7.15 (s, 1H), 6.92 (m, 1H), 5.06 (s, 2H), 4.35 (t, 1H), 4.15 (t, 2H), 3.96 (s, 3H), 3.42 (m, 2H), 3.12 (m, 1H), 2.56 (t, 2H), 2.46 (t, 2H), 1.94 (m, 2H), 1.88 (m, 2H), 1.75 (m, 2H), 1.54 (m, 2H); MS (+ve ESI): 564.1 $(M+H)^+$.

EXAMPLE 51

Preparation of Compound 51 in Table 2—2-[4-[(7-{3-[(cyclopropylmethyl)(2-hydroxyethyl)amino] propoxy}-6-methoxyquinazolin-4-yl)amino]-1H-pyrazol-1-yl}-N-(3-fluorophenyl)acetamide An analogous reaction to that described in example 16 but starting with 2-((cyclopropylmethyl)amino)ethanol (75 mg, 0.65 mmol) yielded compound 51 in table 2 (75 mg, 66% yield):

$^1$H-NMR (DMSO $d_6$): 9.68 (s, 3H), 8.48 (s, 1H), 8.35 (s, 1H), 7.78 (s, 1H), 7.76 (s, 1H), 7.58 (m, 1H), 7.38 (m, 1H), 7.32 (m, 1H), 7.15 (s, 1H), 6.92 (m, 1H), 5.06 (s, 2H), 4.32 (t, 1H), 4.18 (t, 2H), 3.96 (s, 3H), 3.46 (m, 2H), 2.69 (t, 2H), 2.58 (t, 2H), 2.35 (d, 2H), 1.91 (m, 2H), 0.83 (m, 1H), 0.41 (m, 2H), 0.08 (m, 2H); MS (+ve ESI): 564.1 $(M+H)^+$.

EXAMPLE 52

Preparation of Compound 52 in Table 2—2-{4-[(7-{3-[(cyclobutylmethyl)(2-hydroxyethyl)amino]propoxy}-6-methoxyquinazolin-4-yl)amino]-1H-pyrazol-1-yl}-N-(3-fluorophenyl)acetamide An analogous reaction to that described in example 16 but starting with 2-((cyclobutylmethyl)amino)ethanol (84 mg, 0.65 mmol) yielded compound 52 in table 2 (90 mg, 78% yield):

$^1$H-NMR (DMSO $d_6$): 9.69 (s, 1H), 8.48 (s, 1H), 8.35 (s, 1H), 7.78 (s, 1H), 7.76 (s, 1H), 7.58 (m, 1H), 7.37 (m, 1H), 7.32 (m, 1H), 7.14 (s, 1H), 6.92 (m, 1H), 5.07 (s, 2H), 4.29 (t, 1H), 4.15 (t, 2H), 3.97 (s, 3H), 3.42 (m, 2H), 2.57 (t, 2H), 2.47 (m, 4H), 1.93 (m, 3H), 1.89 (t, 2H), 1.76 (m, 2H), 1.59 (m, 2H); MS (+ve ESI): 578.2 $(M+H)^+$.

EXAMPLE 53

Preparation of Compound 53 in Table 2—N-(3-fluorophenyl)-2-{4-[(7-{3-[(2-hydroxyethyl)(prop-2-yn-1-yl)amino]propoxy}-6-methoxyquinazolin-4-yl) amino]-1H-pyrazol-1-yl}acetamide An analogous reaction to that described in example 16 but starting with 2-(prop-2-yn-1-ylamino)ethanol (64 mg, 0.65 mmol) yielded compound 53 in table 2 (69 mg, 63% yield):

$^1$H-NMR (DMSO $d_6$): 9.69 (s, 1H), 8.48 (s, 1H), 8.35 (s, 1H), 7.78 (s, 1H), 7.76 (s, 1H), 7.59 (m, 1H), 7.38 (m, 1H), 7.32 (m, 1H), 7.16 (s, 1H), 6.92 (m, 1H), 5.06 (s, 2H), 4.43 (t, 1H), 4.17 (t, 2H), 3.96 (s, 3H), 3.46 (m, 2H), 3.41 (d, 2H), 3.09 (t, 1H), 2.63 (t, 2H), 2.54 (t, 2H), 1.92 (m, 2H); MS (+ve ESI): 548.1 $(M+H)^+$.

EXAMPLE 54

Preparation of Compound 54 in Table 2—2-{4-[(7-{3-[allyl(2-hydroxyethyl)amino]propoxy}-6-methoxyquinazolin-4-yl)amino]-1H-pyrazol-1-yl}-N-(3-fluorophenyl)acetamide An analogous reaction to that described in example 16 but starting with 2-(allylamino)ethanol (66 mg, 0.65 mmol) yielded compound 54 in table 2 (100 mg, 91% yield):

$^1$H-NMR (DMSO $d_6$): 9.68 (s, 1H), 8.48 (s, 1H), 8.35 (s, 1H), 7.78 (s, 1H), 7.76 (s, 1H), 7.58 (m, 1H), 7.37 (m, 1H), 7.32 (m, 1H), 7.15 (s, 1H), 6.92 (m, 1H), 5.83 (m, 1H), 5.18 (dd, 1H), 5.09 (dd, 1H), 5.06 (s, 2H), 4.36 (t, 1H), 4.16 (t, 2H), 3.96 (s, 3H), 3.45 (m, 1H), 3.11 (d, 2H), 2.61 (t, 2H), 1.92 (m, 2H); MS (+ve ESI): 550.1 $(M+H)^+$.

EXAMPLE 55

Preparation of Compound 55 in Table 2—2-{4-[(7-{3-[(2,2-dimethylpropyl)(2-hydroxyethyl)amino] propoxy}-6-methoxyquinazolin-4-yl)amino]-1H-pyrazol-1-yl}-N-(3-fluorophenyl)acetamide An analogous reaction to that described in example 16 but starting with 2-((2,2-dimethylpropyl)amino)ethanol (85 mg, 0.65 mmol) yielded compound 55 in table 2 (85 mg, 66% yield):

$^1$H-NMR (DMSO $d_6$): 9.68 (s, 1H), 8.48 (s, 1H), 8.34 (s, 1H), 7.78 (s, 1H), 7.76 (s, 1H), 7.58 (m, 1H), 7.37 (m, 1H), 7.32 (m, 1H), 7.14 (s, 1H), 6.92 (m, 1H), 5.06 (s, 2H), 4.33 (t,

1H), 4.17 (t, 2H), 3.95 (s, 3H), 3.44 (m, 2H), 2.64 (t, 2H), 2.54 (t, 2H), 2.21 (s, 2H), 1.91 (m, 2H), 0.83 (s, 9H); MS (+ve ESI): 580.2 $(M+H)^+$.

EXAMPLE 56

Preparation of Compound 56 in Table 2—N-(3-fluorophenyl)-2-{4-[(7-{3-[(2-hydroxyethyl)(3,3,3-trifluoropropyl)amino]propoxy}-6-methoxyquinazolin-4-yl)amino]-1H-pyrazol-1-yl}acetamide An analogous reaction to that described in example 16 but starting with 2-((3,3,3-trifluoropropyl)amino)ethanol (102 mg, 0.65 mmol) yielded compound 56 in table 2 (80 mg, 66% yield):

$^1$H-NMR (DMSO $d_6$): 9.69 (s, 1H), 8.48 (s, 1H), 8.35 (s, 1H), 7.78 (s, 1H), 7.76 (s, 1H), 7.58 (m, 1H), 7.37 (m, 1H), 7.32 (m, 1H), 7.16 (s, 1H), 6.92 (m, 1H), 5.07 (s, 2H), 4.41 (m, 1H), 4.17 (t, 2H), 3.96 (s, 3H), 3.45 (t, 2H), 2.72 (t, 2H), 2.63 (t, 2H), 2.53 (m, 2H), 2.40 (m, 2H), 1.92 (m, 2H); MS (+ve ESI): 606.3 $(M+H)^+$.

EXAMPLE 57

Preparation of Compound 57 in Table 2—2-(4-{[7-(3-azetidin-1-ylpropoxy)-6-methoxyquinazolin-4-yl]amino}-1H-pyrazol-1-yl)-N-(3-fluorophenyl)acetamide An analogous reaction to that described in example 16 but starting with azetidine (37 mg, 0.65 mmol) yielded compound 57 in table 2 (13 mg, 13% yield):

$^1$H-NMR (DMSO $d_6$): 9.68 (s, 1H), 8.48 (s, 1H), 8.34 (s, 1H), 7.78 (s, 1H), 7.75 (s, 1H), 7.58 (m, 1H), 7.37 (m, 1H), 7.32 (m, 1H), 7.14 (s, 1H), 6.91 (m, 1H), 5.06 (s, 2H), 4.13 (m, 2H), 3.95 (s, 3H), 3.09 (t, 4H), 2.51 (m, 2H), 1.95 (m, 2H), 1.76 (m, 2H);

MS (+ve ESI): 506.1 $(M+H)^+$.

EXAMPLE 58

Preparation of Compound 58 in Table 2—2-{4-[(6,7-dimethoxyquinazolin-4-yl)amino)-1H-pyrazol-1-yl}-N-(3-fluorophenyl)acetamide A solution of 2-(4-amino-1H-pyrazol-1-yl)-N-(3-fluorophenyl)acetamide (0.246 g, 1.05 mmol) and 4-chloro-6,7-dimethoxyquinazoline (0.224 g, 1.0 mmol) in dimethylacetamide (5 ml) was heated at 90° C. for 2 hours. The mixture was allowed to cool to room temperature and then diluted with diethyl ether and filtered. The solid was washed with diethyl ether and then dried in vacuo. The solid was partitioned between dichloromethane and sodium hydroxide solution (1 M), the organic layer was separated, dried over magnesium sulphate and evaporated to leave compound 58 in table 2 (0.115 g, 27% yield):

$^1$H-NMR (DMSO $d_6$): 10.54 (br s, 1H), 9.74 (br s, 1H), 8.51 (s, 1H), 8.34 (s, 1H), 7.81 (s, 1H), 7.78 (s, 1H), 7.59 (m, 1H), 7.35 (m, 2H), 7.18 (s, 1H), 6.92 (m, 1H), 5.07 (s, 2H), 3.97 (s, 3H), 3.93 (s, 3H); MS (+ve ESI): 423 $(M+H)^+$.

EXAMPLE 59

Preparation of Compound 59 in Table 2—N-(3-fluorophenyl)-2-{4-[(7-hydroxy-6-methoxyquinazolin-4-yl)amino]-1H-pyrazol-1-yl}acetamide A mixture of 4-[(1-{2-[(3-fluorophenyl)amino]-2-oxoethyl}-1H-pyrazol-4-yl)amino]-6-methoxyquinazolin-7-yl acetate (0.358 g, ~0.8 mmol) and potassium carbonate (0.14 g, 1.0 mmol) in methanol (10 ml) was stirred at room temperature for 2 hours. The solvent was evaporated and the residue was partitioned between water (10 ml) and dichloromethane (10 ml). The aqueous layer was separated and made acidic by the addition of concentrated hydrochloric acid and the resultant precipitate filtered. The solid was washed with methanol and finally with diethyl ether and then dried under nitrogen to yield compound 59 in table 2 (0.225 g, 69% yield) as the hydrochloride salt:

$^1$H-NMR (DMSO $d_6$): 14.65 (br s, 1H), 11.61 (s, 1H), 11.53 (br s, 1H), 10.74 (s, 1H), 8.84 (s, 1H), 8.40 (s, 1H), 8.33 (s, 1H), 8.03 (s, 1H), 7.60 (m, 1H), 7.37 (m, 3H), 6.91 (m, 1H), 5.13 (s, 2H), 4.03 (s, 3H); MS (+ve ESI): 409 $(M+H)^+$.

4-[(1-{2-[(3-fluorophenyl)amino]-2-oxoethyl}-1H-pyrazol-4-yl)amino]-6-methoxyquinazolin-7-yl acetate used as Starting Material, was Obtained as Follows a) A solution of 2-(4-amino-1H-pyrazol-1-yl)-N-(3-fluorophenyl)acetamide (0.246 g, 1.05 mmol) and 4-chloro-6-methoxyquinazolin-7-yl acetate (see WO96/15118, 0.252 g, 1.0 mmol) in dimethylacetamide (5 ml) was heated at 90° C. for 2 hours. The mixture was allowed to cool to room temperature and then diluted with diethyl ether and filtered. The solid was washed with diethyl ether and then dried in vacuo to leave 4-[(1-{2-[(3-fluorophenyl)amino]-2-oxoethyl}-1H-pyrazol-4-yl)amino]-6-methoxyquinazolin-7-yl acetate as a mixture with 15% N-(3-fluorophenyl)-2-{4-[(7-hydroxy-6-methoxyquinazolin-4-yl)amino]-1H-pyrazol-1-yl}acetamide (0.358 g, 78% yield):

$^1$H-NMR (DMSO $d_6$): 12.04 (br s, 1H), 10.72 (br s, 1H), 8.94 (s, 1H), 8.63 (s, 1H), 8.48 (s, 1H), 8.10 (s, 1H), 7.73 (s, 1H), 7.60 (m, 1H), 7.36 (m, 2H), 6.91 (m, 1H), 5.15 (s, 2H), 4.05 (s, 3H), 2.38 (s, 3H); MS (+ve ESI): 451 $(M+H)^+$.

EXAMPLE 60

Preparation of Compound 60 in Table 3—N-(2,3-difluorophenyl)-2-{4-[(7-{3-[(2-hydroxyethyl)(isobutyl)amino]propoxy}-6-methoxyquinazolin-4-yl)amino]-1H-pyrazol-1-yl}acetamide An analogous reaction to that described in example 16 but starting with 2-(4-{[7-(3-chloropropoxy)-6-methoxyquinazolin-4-yl]amino}-1H-pyrazol-1-yl)-N-(2,3-difluorophenyl)acetamide (129 mg, 0.23 mmol) and 2-(isobutylamino)ethanol (146 mg, 0.93 mmol) yielded compound 60 in table 3 (95 mg, 70% yield):

$^1$H-NMR (DMSO $d_6$): 9.68 (s, 1H), 8.48 (s, 1H), 8.35 (s, 1H), 7.74 (m, 3H), 7.21 (m, 2H), 7.14 (s, 1H), 5.17 (s, 2H), 4.30 (t, 1H), 4.17 (t, 2H), 3.96 (s, 3H), 3.43 (m, 2H), 2.58 (m, 2H), 2.47 (m, 2H), 2.15 (m, 2H), 1.89 (m, 2H), 1.67 (m, 1H), 0.81 (d, 6H); MS (+ve ESI): 584.2 $(M+H)^+$.

EXAMPLE 61

Preparation of Compound 61 in Table 3—N-(2,3-difluorophenyl)-2-{4-[(7-{3-[(2S)-2-(hydroxymethyl)pyrrolidin-1-yl]propoxy}-6-methoxyquinazolin-4-yl)amino]-1H-pyrazol-1-yl}acetamide An analogous reaction to that described in example 60 but starting with (2S)-pyrrolidin-2-ylmethanol (98 μl, 1 mmol) yielded compound 61 in table 3 (105 mg, 74% yield):

$^1$H-NMR (DMSO $d_6$): 9.68 (s, 1H), 8.48 (s, 1H), 8.35 (s, 1H), 7.74 (m, 3H), 7.21 (m, 2H), 7.16 (s, 1H), 5.16 (s, 2H), 4.33 (t, 1H), 4.17 (t, 2H), 3.95 (s, 3H), 3.39 (m, 1H), 3.18 (m, 1H), 3.08 (m, 1H), 2.97 (m, 1H), 2.42 (m, 2H), 2.15 (m, 1H), 1.95 (m, 2H), 1.79 (m, 1H), 1.65 (m, 2H), 1.55 (m, 1H); MS (+ve ESI): 568.1 $(M+H)^+$.

EXAMPLE 62

Preparation of Compound 62 in Table 3—N-(2,3-difluorophenyl)-2-{4-[(7-{3-[(2-hydroxyethyl)(propyl)amino]propoxy}-6-methoxyquinazolin-4-yl)amino]-1H-pyrazol-1-yl}acetamide An analogous reaction to that described in example 60 but starting with 2-(propylamino)ethanol (82 mg, 0.8 mmol) yielded compound 62 in table 3 (88 mg, 77% yield):

$^1$H-NMR (DMSO $d_6$, TFA): 8.97 (s, 1H), 8.39 (s, 1H), 8.08 (s, 1H), 7.95 (s, 1H), 7.74 (m, 1H), 7.33 (s, 1H), 7.21 (m, 2H), 5.25 (s, 2H), 4.29 (t, 2H), 4.02 (s, 3H), 3.77 (t, 2H), 3.33 (m, 2H), 3.28 (m, 2H), 3.15 (m, 2H), 2.28 (m, 2H), 1.71 (m, 2H), 0.95 (t, 3H); MS (+ve ESI): 570.3 $(M+H)^+$.

EXAMPLE 63

Preparation of Compound 63 in Table 3—N-(2,3-difluorophenyl)-2-[4-({7-[3-(dimethylamino)propoxy]-6-methoxyquinazolin-4-yl}amino)-1H-pyrazol-1-yl]acetamide An analogous reaction to that described in example 60 but starting with dimethylamine (29 mg, 0.65 mmol) yielded compound 63 in table 3 (51 mg, 56% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.21 (m, 2H), 7.14 (s, 1H), 5.16 (s, 2H), 4.15 (t, 2H), 3.96 (s, 3H), 2.38 (t, 2H), 2.16 (s, 6H), 1.93 (m, 2H); MS (+ve ESI): 512.1 $(M+H)^+$.

EXAMPLE 64

Preparation of Compound 64 in Table 3—N-(2,3-difluorophenyl)-2-(4-{[6-methoxy-7-(3-piperidin-1-ylpropoxy)quinazolin-4-yl]amino}-1H-pyrazol-1-yl)acetamide An analogous reaction to that described in example 60 but starting with piperidine (55 mg, 0.65 mmol) yielded compound 64 in table 3 (68 mg, 69% yield):

$^1$H-NMR (DMSO $d_6$): 9.68 (s, 1H), 8.45 (s, 1H), 8.34 (s, 1H), 7.78 (s, 1H), 7.76 (s, 1H), 7.73 (m, 1H), 7.19 (m, 2H), 7.15 (s, 1H), 5.16 (s, 2H), 4.15 (t, 2H), 3.95 (s, 3H), 2.41 (t, 2H), 2.35 (m, 4H), 1.93 (m, 2H), 1.51 (m, 4H), 1.39 (m, 2H);

MS (+ve ESI): 552.2 $(M+H)^+$.

EXAMPLE 65

Preparation of Compound 65 in Table 3—N-(2,3-difluorophenyl)-2-(4-{[6-methoxy-7-(3-pyrrolidin-1-ylpropoxy)quinazolin-4-yl]amino}-1H-pyrazol-1-yl)acetamide An analogous reaction to that described in example 60 but starting with pyrrolidine (46 mg, 0.65 mmol) yielded compound 65 in table 3 (65 mg, 67% yield):

$^1$H-NMR (DMSO $d_6$): 9.68 (s, 1H), 8.49 (s, 1H), 8.35 (s, 1H), 7.78 (s, 1H), 7.76 (s, 1H), 7.73 (m, 1H), 7.21 (m, 2H), 7.15 (s, 1H), 5.16 (s, 2), 4.17 (t, 2H), 3.96 (s, 3H), 2.52 (t, 2H), 2.45 (m, 4H), 1.96 (m, 2H), 1.69 (m, 4H); MS (+ve ESI): 538.1 $(M+H)^+$.

EXAMPLE 66

Preparation of Compound 66 in Table 3—N-(2,3-difluorophenyl)-2-(4-{[6-methoxy-7-(3-piperazin-1-ylpropoxy)quinazolin-4-yl]amino}-1H-pyrazol-1-yl)acetamide An analogous reaction to that described in example 60 but starting with piperazine (56 mg, 0.65 mmol) yielded compound 66 in table 3 (67 mg, 68% yield):

$^1$H-NMR (DMSO $d_6$): 9.67 (s, 1H), 8.48 (s, 1H), 8.35 (s, 1H), 7.78 (s, 1H), 7.77 (s, 1H), 7.73 (m, 1H), 7.21 (m, 2H), 7.15 (s, 1H), 5.16 (s, 2H), 4.16 (t, 2H), 3.95 (s, 3H), 2.69 (m, 4H), 2.41 (t, 2H), 2.31 (m, 4H), 1.94 (m, 2H); MS (+ve ESI): 553.1 $(M+H)^+$.

EXAMPLE 67

Preparation of Compound 67 in Table 3—N-(2,3-difluorophenyl)-2-{4-[(7-{3-[(2-hydroxyethyl)(methyl)amino]propoxy}-6-methoxyquinazolin-4-yl)amino]-1H-pyrazol-1-yl}acetamide An analogous reaction to that described in example 60 but starting with 2-(methylamino)ethanol (49 mg, 0.65 mmol) yielded compound 67 in table 3 (66 mg, 67% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.22 (m, 2H), 7.16 (s, 1H), 5.16 (s, 2H), 4.36 (t, 1H), 4.16 (t, 2H), 3.96 (s, 3H), 3.46 (m, 2H), 2.51 (m, 2H), 2.42 (m, 2H), 2.20 (s, 3H), 1.91 (m, 2H); MS (+ve ESI): 542.1 $(M+H)^+$.

EXAMPLE 68

Preparation of Compound 68 in Table 3—2-[4-({7-[3-(cyclopropylamino)propoxy]-6-methoxyquinazolin-4-yl}amino)-1H-pyrazol-1-yl]-N-(2,3-difluorophenyl)acetamide An analogous reaction to that described in example 60 but starting with cyclopropylamine (37 mg, 0.65 mmol) yielded compound 68 in table 3 (67 mg, 71% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.21 (m, 2H), 7.16 (s, 1H), 5.16 (s, 2H), 4.18 (t, 2H), 3.96 (s, 3H), 2.74 (m, 2H), 2.07 (m, 1H), 1.92 (m, 2H), 0.35 (m, 2H), 0.21 (m, 2H); MS (+ve ESI): 524.1 $(M+H)^+$.

EXAMPLE 69

Preparation of Compound 69 in Table 3—N-(2,3-difluorophenyl)-2-{4-[(7-{3-[[2-(dimethylamino)ethyl](methyl)amino]propoxy}-6-methoxyquinazolin-4-yl)amino]-1H-pyrazol-1-yl}acetamide An analogous reaction to that described in example 60 but starting with N,N,N'-trimethylethane-1,2-diamine (66 mg, 0.65 mmol) yielded compound 69 in table 3 (43 mg, 42% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.21 (m, 2H), 7.14 (s, 1H), 5.16 (s, 2H), 4.16 (t, 2H), 3.96 (s, 3H), 2.49 (m, 2H), 2.40 (m, 2H), 2.29 (m, 2H), 2.19 (s, 3H), 2.11 (s, 6H), 1.91 (m, 2H); MS (+ve ESI): 569.2 $(M+H)^+$.

EXAMPLE 70

Preparation of Compound 70 in Table 3—N-(2,3-difluorophenyl)-2-[4-({6-methoxy-7-[3-(4-methylpiperazin-1-yl)propoxy]quinazolin-4-yl]amino)-1H-pyrazol-1-yl]acetamide An analogous reaction to that described in example 60 but starting with 1-methylpiperazine (65 mg, 0.65 mmol) yielded compound 70 in table 3 (85 mg, 84% yield):

$^1$H-NMR (DMSO $d_6$): 9.67 (s, 1H), 8.48 (s, 1H), 8.35 (s, 1H), 7.78 (s, 1H), 7.77 (s, 1H), 7.73 (m, 1H), 7.21 (m, 2H), 7.14 (s, 1H), 5.16 (s, 2H), 4.15 (t, 2H), 3.95 (s, 3H), 2.44 (t, 2H), 2.32 (m, 8H), 2.14 (s, 3H), 1.94 (m, 2H); MS (+ve ESI): 567.2 $(M+H)^+$.

EXAMPLE 71

Preparation of Compound 71 in Table 3—N-(2,3-difluorophenyl)-2-{4-[(7-{3-[(2R)-2-(hydroxymethyl)pyrrolidin-1-yl]propoxy}-6-methoxyquinazolin-4-yl)amino]-1H-pyrazol-1-yl}acetamide An analogous reaction to that described in example 60 but starting with (2R)pyrrolidin-2-ylmethanol (66 mg, 0.65 mmol) yielded compound 71 in table 3 (80 mg, 78% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.22 (m, 2H), 7.16 (s, 1H), 5.16 (s, 2H), 4.33 (t, 1H), 4.17 (t, 2H), 3.96 (s, 3H), 3.38 (m, 1H), 3.17 (m, 1H), 3.07 (m, 1H), 2.96 (m, 1H), 2.41 (m, 2H), 2.14 (m, 1H), 1.94 (m, 2H), 1.79 (m, 1H), 1.65 (m, 2H), 1.55 (m, 1H); MS (+ve ESI): 568.1 $(M+H)^+$.

EXAMPLE 72

Preparation of Compound 72 in Table 3—N-(2,3-difluorophenyl)-2-[4-({7-[3-(4-hydroxypiperidin-1-yl)propoxy}-6-methoxyquinazolin-4-yl}amino)-1H-pyrazol-1-yl]acetamide An analogous reaction to that described in example 60 but starting with piperidin-4-ol (66 mg, 0.65 mmol) yielded compound 72 in table 3 (102 mg, 100% yield):

$^1$H-NMR (DMSO $d_6$): 9.69 (s, 1H), 8.48 (s, 1H), 8.35 (s, 1H), 7.78 (s, 1H), 7.77 (s, 1H), 7.73 (m, 1H), 7.21 (m, 2H), 7.15 (s, 1H), 5.16 (s, 2H), 4.54 (m, 1H), 4.15 (t, 2H), 3.96 (s, 3H), 3.44 (m, 1H), 2.73 (m, 2H), 2.43 (m, 2H), 2.02 (m, 2H), 1.92 (m, 2H), 1.71 (m, 2H), 1.39 (m, 2H); MS (+ve ESI): 568.2 $(M+H)^+$.

EXAMPLE 73

Preparation of Compound 73 in Table 3—2-{4-[(7-{3-[bis(2-hydroxyethyl)amino]propoxy}-6-methoxyquinazolin-4-yl)amino]-1H-pyrazol-1-yl}-N-(2,3-difluorophenyl)acetamide An analogous reaction to that described in example 60 but starting with 2,2'-iminodiethanol (68 mg, 0.65 mmol) yielded compound 73 in table 3 (95 mg, 93% yield):

$^1$H-NMR (DMSO $d_6$): 9.68 (s, 1H), 8.48 (s, 1H), 8.35 (s, 1H), 7.78 (s, 1H), 7.77 (s, 1H), 7.72 (m, 1H), 7.21 (m, 2H), 7.17 (s, 1H), 5.16 (s, 2H), 4.34 (t, 2H), 4.18 (t, 2H), 3.96 (s, 3H), 3.41 (m, 4H), 2.52 (m, 4H), 2.63 (m, 2H), 1.91 (m, 2H); MS (+ve ESI): 572.1 $(M+H)^+$.

EXAMPLE 74

Preparation of Compound 74 in Table 3—N-(2,3-difluorophenyl)-2-{4-[(7-{3-[ethyl(methyl)amino]propoxy}-6-methoxyquinazolin-4-yl)amino]-1H-pyrazol-1-yl}acetamide An analogous reaction to that described in example 60 but starting with ethyl(methyl)amine (38 mg, 0.65 mmol) yielded compound 74 in table 3 (58 mg, 61% yield):

$^1$H-NMR (DMSO $d_6$): 9.68 (s, 1H), 8.48 (s, 1H), 8.35 (s, 1H), 7.78 (s, 1H), 7.77 (s, 1H), 7.72 (m, 1H), 7.21 (m, 2H), 7.15 (s, 1H), 5.16 (s, 2H), 4.16 (t, 2H), 3.96 (s, 3H), 2.46 (m, 2H), 2.36 (q, 2H), 2.16 (s, 3H), 1.92 (m, 2H), 0.98 (t, 3H); MS (+ve ESI): 526.1 $(M+H)^+$.

EXAMPLE 75

Preparation of Compound 75 in Table 3—N-(2,3-difluorophenyl)-2-{4-[(7-{3-[ethyl(2-hydroxyethyl)amino]propoxy}-6-methoxyquinazolin-4-yl)amino]-1H-pyrazol-1-yl]acetamide An analogous reaction to that described in example 60 but starting with 2-(ethylamino)ethanol (58 mg, 0.65 mmol) yielded compound 75 in table 3 (91 mg, 91% yield):

$^1$H-NMR (DMSO $d_6$): 9.68 (s, 1H), 8.48 (s, 1H), 8.35 (s, 1H), 7.78 (s, 1H), 7.77 (s, 1H), 7.72 (m, 1H), 7.21 (m, 2H), 7.15 (s, 1H), 5.16 (s, 2H), 4.32 (t, 1H), 4.17 (t, 2H), 3.96 (s, 3H), 3.43 (m, 2H), 2.59 (t, 2H), 2.50 (m, 2H), 1.89 (m, 2H), 0.95 (t, 3H); MS (+ve ESI): 556.1 $(M+H)^+$.

EXAMPLE 76

Preparation of Compound 76 in Table 3—N-(2,3-difluorophenyl)-2-{4-[(7-{3-[[2-(dimethylamino)ethyl](ethyl)amino]propoxy}-6-methoxyquinazolin-4-yl)amino]-1H-pyrazol-1-yl}acetamide An analogous reaction to that described in example 60 but starting with N'-ethyl-N,N-dimethylethane-1,2-diamine (76 mg, 0.65 mmol) yielded compound 76 in table 3 (29 mg, 27% yield):

$^1$H-NMR (DMSO $d_6$, TFA): 8.96 (s, 1H), 8.42 (s, 1H), 8.12 (s, 1H), 7.98 (s, 1H), 7.77 (m, 1H), 7.40 (s, 1H), 7.21 (m, 2H), 5.27 (s, 2H), 4.31 (m, 2H), 4.04 (s, 3H), 3.66 (m, 2H), 3.60 (m, 2H), 3.51 (m, 2H), 3.23 (s, 6H), 3.08 (m, 2H), 2.42 (m, 2H), 1.26 (t, 3H); MS (+ve ESI): 583.2 $(M+H)^+$.

EXAMPLE 77

Preparation of Compound 77 in Table 3—N-(2,3-difluorophenyl)-2-{4-[(7-{3-[2-(2-hydroxyethyl)piperidin-1-yl]propoxy}-6-methoxyquinazolin-4-yl)amino]-1H-pyrazol-1-yl}acetamide An analogous reaction to that described in example 60 but starting with 2-piperidin-2-ylethanol (84 mg, 0.65 mmol) yielded compound 77 in table 3 (86 mg, 80% yield):

$^1$H-NMR (DMSO $d_6$): 9.68 (s, 1H), 8.49 (s, 1H), 8.35 (s, 1H), 7.78 (s, 1H), 7.77 (s, 1H), 7.73 (m, 1H), 7.21 (m, 2H), 7.15 (s, 1H), 5.16 (s, 2H), 4.38 (t, 1H), 4.15 (t, 2H), 3.96 (s, 3H), 3.44 (m, 2H), 2.76 (m, 2H), 2.44 (m, 2H), 2.23 (m, 1H), 1.91 (m, 2H), 1.73 (m, 1H), 1.58 (m, 2H), 1.46 (m, 3H), 1.28 (m, 2H); MS (+ve ESI): 596.2 $(M+H)^+$.

EXAMPLE 78

Preparation of Compound 78 in Table 3—N-(2,3-difluorophenyl)-2-{4-[(7-{3-[4-(2-hydroxyethyl)piperazin-1-yl]propoxy}-6-methoxyquinazolin-4-yl)amino]-1H-pyrazol-1-yl}acetamide An analogous reaction to that described in example 60 but starting with 2-piperazine-1-ylethanol (85 mg, 0.65 mmol) yielded compound 78 in table 3 (75 mg, 70% yield):

$^1$H-NMR (DMSO $d_6$): 9.68 (s, 1H), 8.48 (s, 1H), 8.35 (s, 1H), 7.77 (s, 1H), 7.76 (s, 1H), 7.73 (m, 1H), 7.22 (m, 2H), 7.14 (s, 1H), 5.16 (s, 2H), 4.37 (t, 1H), 4.15 (t, 2H), 3.95 (s, 3H), 3.47 (m, 2H), 2.43 (m, 2H), 2.41 (m, 8H), 2.36 (m, 2H), 1.94 (m, 2H); MS (+ve ESI): 597.2 $(M+H)^+$.

EXAMPLE 79

Preparation of Compound 79 in Table 3—2-{4-[(7-{3-[(cyclopropylmethyl)amino]propoxy}-6-methoxyquinazolin-4-yl)amino]-1H-pyrazol-1-yl}-N-(2,3-difluorophenyl)acetamide An analogous reaction to that described in example 60 but starting with (cyclopropylmethyl)amine (46 mg, 0.65 mmol) yielded compound 79 in table 3 (66 mg, 68% yield):

$^1$H-NMR (DMSO $d_6$): 10.31 (s, 1H), 9.68 (s, 1H), 8.48 (s, 1H), 8.35 (s, 1H), 7.78 (s, 1H), 7.77 (s, 1H), 7.73 (m, 1H), 7.22 (m, 2H), 7.16 (s, 1H), 5.16 (s, 2H), 4.19 (t, 2H), 3.96 (s, 3H), 2.71 (t, 2H), 2.39 (d, 2H), 1.92 (m, 2H), 0.88 (m, 1H), 0.39 (m, 2H), 0.09 (m, 2H); MS (+ve ESI): 538.1 $(M+H)^+$.

EXAMPLE 80

Preparation of Compound 80 in Table 3—N-(2,3-difluorophenyl)-2-{4-[(7-{3-[4-(2-hydroxyethyl)piperidin-1-yl]propoxy}-6-methoxyquinazolin-4-yl)amino]-1H-pyrazol-1-yl}acetamide An analogous reaction to that described in example 60 but starting with 2-piperidin-4-ylethanol (84 mg, 0.65 mmol) yielded compound 80 in table 3 (102 mg, 95% yield):

$^1$H-NMR (DMSO $d_6$): 9.41 (s, 1H), 8.20 (s, 1H), 8.07 (s, 1H), 7.51 (s, 1H), 7.49 (s, 1H), 7.45 (m, 1H), 6.91 (m, 2H), 6.86 (s, 1H), 4.88 (s, 2H), 4.03 (t, 1H), 3.87 (t, 2H), 3.67 (s, 3H), 3.14 (m, 2H), 2.57 (m, 2H), 2.14 (t, 2H), 1.65 (m, 2H), 1.56 (t, 2H), 1.33 (d, 2H), 1.06 (m, 3H), 0.86 (m, 2H); MS (+ve ESI): 596.2 $(M+H)^+$.

EXAMPLE 81

Preparation of Compound 81 in Table 3—N-(2,3-difluorophenyl)-2-{4-[(6-methoxy-7-{3-[methyl(prop-2-yn-1-yl)amino]propoxy}quinazolin-4-yl)amino]-1H-pyrazol-1-yl}acetamide An analogous reaction to that described in example 60 but starting with N-methylprop-2-yn-1-amine (45 mg, 0.65 mmol) yielded compound 81 in table 3 (55 mg, 57% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.21 (m, 2H), 7.14 (s, 1H), 5.16 (s, 2H), 4.15 (t, 2H), 3.96 (s, 3H), 3.13 (m, 1H), 2.51 (m, 4H), 2.23 (s, 3H), 1.93 (m, 2H);

MS (+ve ESI): 536.1 $(M+H)^+$.

EXAMPLE 82

Preparation of Compound 82 in Table 3—N-(2,3-difluorophenyl)-2-{4-[(7-{3-[isobutyl(methyl)amino]propoxy}-6-methoxyquinazolin-4-yl)amino]-1H-pyrazol-1-yl}acetamide An analogous reaction to that described in example 60 but starting with N,2-dimethylpropan-1-amine (57 mg, 0.65 mmol) yielded compound 82 in table 3 (29 mg, 29% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.21 (m, 2H), 7.13 (s, 1H), 5.16 (s, 2H), 4.15 (t, 2H), 3.95 (s, 3H), 2.45 (m, 2H), 2.15 (s, 3H), 2.04 (d, 2H), 1.92 (m, 2H), 1.71 (m, 1H), 0.82 (d, 6H); MS (+ve ESI): 554.2 $(M+H)^+$.

EXAMPLE 83

Preparation of Compound 83 in Table 3—N-(2,3-difluorophenyl)-2-[4-({7-[3-(3-hydroxypiperidin-1-yl)propoxy]-6-methoxyquinazolin-4-yl}amino)-1H-pyrazol-1-yl]acetamide An analogous reaction to that described in example 60 but starting with piperidin-3-ol (66 mg, 0.65 mmol) yielded compound 83 in table 3 (102 mg, 100% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.22 (m, 2H), 7.15 (s, 1H), 5.16 (s, 2H), 4.61 (d, 1H), 4.16 (t, 2H), 3.96 (s, 3H), 3.47 (m, 1H), 2.83 (m, 1H), 2.66 (m, 1H), 2.44 (m, 2H), 1.93 (m, 2H), 1.85 (m, 1H), 1.75 (m, 2H), 1.61 (m, 1H), 1.41 (m, 1H), 1.07 (m, 1H); MS (+ve ESI): 568.2 $(M+H)^+$.

EXAMPLE 84

Preparation of Compound 84 in Table 3—N-(2,3-difluorophenyl)-2-{4-[(7-{3-[4-(hydroxymethyl)piperidin-1-yl]propoxy}-6-methoxyquinazolin-4-yl)amino]-1H-pyrazol-1-yl}acetamide An analogous reaction to that described in example 60 but starting with piperidin-4-ylmethanol (75 mg, 0.65 mmol) yielded compound 84 in table 3 (85 mg, 81% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.21 (m, 2H), 7.14 (s, 1H), 5.16 (s, 2H), 4.41 (t, 1H), 4.15 (t, 2H), 3.96 (s,

3H), 3.24 (t, 2H), 2.87 (m, 2H), 2.43 (t, 2H), 1.95 (m, 2H), 1.85 (t, 2H), 1.63 (d, 2H), 1.33 (m, 1H), 1.13 (m, 2H); MS (+ve ESI): 582.2 $(M+H)^+$.

EXAMPLE 85

Preparation of Compound 85 in Table 3—N-(2,3-difluorophenyl)-2-{4-[(6-methoxy-7-{3-[methyl(propyl)amino]propoxy}quinazolin-4-yl)amino]-1H-pyrazol-1-yl}acetamide An analogous reaction to that described in example 60 but starting methyl(propyl)amine (48 mg, 0.65 mmol) yielded compound 85 in table 3 (71 mg, 74% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.22 (m, 2H), 7.14 (s, 1H), 5.16 (s, 2H), 4.16 (t, 2H), 3.96 (s, 3H), 2.46 (t, 2H), 2.26 (t, 2H), 2.16 (s, 3H), 1.92 (m, 2H), 1.41 (m, 2H), 0.83 (t, 3H);

MS (+ve ESI): 540.2 $(M+H)^+$.

EXAMPLE 86

Preparation of Compound 86 in Table 3—2-{4-[(7-{3-[(cyclopropylmethyl)(propyl)amino]propoxy}-6-methoxyquinazolin-4-yl)amino]-1H-pyrazol-1-yl}-N-(2,3-difluorophenyl)acetamide An analogous reaction to that described in example 60 but starting with (cyclopropylmethyl)propylamine (74 mg, 0.65 mmol) yielded compound 86 in table 3 (85 mg, 82% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.22 (m, 2H), 7.13 (s, 1H), 5.16 (s, 2H), 4.18 (t, 2H), 3.95 (s, 3H), 2.64 (m, 2H), 2.43 (t, 2H), 2.29 (d, 2H), 1.90 (m, 2H), 1.41 (m, 2H), 0.83 (t, 3H), 0.81 (m, 1H), 0.41 (m, 2H), 0.06 (m, 2H); MS (+ve ESI): 580.2 $(M+H)^+$.

EXAMPLE 87

Preparation of Compound 87 in Table 3—2-{4-[(7-{3-[[2-(diethylamino)ethyl](methyl)amino]propoxy}-6-methoxyquinazolin-4-yl)amino]-1H-pyrazol-1-yl}-N-(2,3-difluorophenyl)acetamide An analogous reaction to that described in example 60 but starting with N,N-diethyl-N'-methylethane-1,2-diamine (85 mg, 0.65 mmol) yielded compound 87 in table 3 (55 mg, 51% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.21 (m, 2H), 7.14 (s, 1H), 5.16 (s, 2H), 4.16 (t, 2H), 3.95 (s, 3H), 2.41 (m, 10H), 2.19 (s, 3H), 1.91 (m, 2H), 0.90 (t, 6H);

MS (+ve ESI): 597.3 $(M+H)^+$.

EXAMPLE 88

Preparation of Compound 88 in Table 3—2-{4-[(7-{3-[[2-(diethylamino)ethyl](ethyl)amino]propoxy}-6-methoxyquinazolin-4-yl)amino]-1H-pyrazol-1-yl}-N-(2,3-difluorophenyl)acetamide An analogous reaction to that described in example 60 but starting with N,N,N'-triethylethane-1,2-diamine (94 mg, 0.65 mmol) yielded compound 88 in table 3 (9 mg, 8% yield):

$^1$H-NMR (DMSO $d_6$): 9.68 (s, 1H), 8.48 (s, 1H), 8.34 (s, 1H), 7.77 (s, 1H), 7.76 (s, 1H), 7.72 (m, 1H), 7.20 (m, 2H), 7.14 (s, 1H), 5.15 (s, 2H), 4.17 (t, 2H), 3.95 (s, 3H), 2.57 (t, 2H), 2.43 (m, 10H), 1.89 (m, 2H), 0.95 (t, 3H), 0.91 (t, 6H); MS (+ve ESI): 611.2 $(M+H)^+$.

EXAMPLE 89

Preparation of Compound 89 in Table 3—N-(2,3-difluorophenyl)-2-[4-({6-methoxy-7-[3-(4-methyl-1,4-diazepan-1-yl)propoxy]quinazolin-4-yl]amino)-1H-pyrazol-1-yl]acetamide An analogous reaction to that described in example 60 but starting with 1-methyl-1,4-diazepane (74 mg, 0.65 mmol) yielded compound 89 in table 3 (52 mg, 50% yield):

$^1$H-NMR (DMSO $d_6$): 9.69 (s, 1H), 8.48 (s, 1H), 8.35 (s, 1H), 7.78 (s, 1H), 7.77 (s, 1H), 7.73 (m, 1H), 7.21 (m, 2H), 7.15 (s, 1H), 5.16 (s, 2H), 4.16 (t, 2H), 3.95 (s, 3H), 2.63 (m, 10H), 2.23 (s, 3H), 1.91 (m, 2H), 1.71 (m, 2H); MS (+ve ESI): 581.2 $(M+H)^+$.

EXAMPLE 90

Preparation of Compound 90 in Table 3—N-(2,3-difluorophenyl)-2-{4-[(7-{3-[(2-hydroxyethyl)(isopropyl)amino]propoxy}-6-methoxyquinazolin-4-yl)amino]-1H-pyrazol-1-yl}acetamide An analogous reaction to that described in example 60 but starting with 2-(isopropylamino)ethanol (67 mg, 0.65 mmol) yielded compound 90 in table 3 (59 mg, 58% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.22 (m, 2H), 7.15 (s, 1H), 5.16 (s, 2H), 4.27 (t, 1H), 4.17 (t, 2H), 3.96 (s, 3H), 3.36 (m, 2H), 2.87 (m, 1H), 2.26 (t, 2H), 2.44 (t, 2H), 1.86 (m, 2H), 0.92 (d, 6H);

MS (+ve ESI): 570.3 $(M+H)^+$.

EXAMPLE 91

Preparation of Compound 91 in Table 3—2-{4-[(7-{3-[cyclopropyl(2-hydroxyethyl)amino]propoxy}-6-methoxyquinazolin-4-yl)amino]-1H-pyrazol-1-yl}-N-(2,3-difluorophenyl)acetamide An analogous reaction to that described in example 60 but starting with 2-(cyclopropylamino)ethanol (66 mg, 0.65 mmol) yielded compound 91 in table 3 (58 mg, 56% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.22 (m, 2H), 7.15 (s, 1H), 5.16 (s, 2H), 4.31 (m, 1H), 4.13 (t, 2H), 3.96 (s, 3H), 3.51 (m, 2H), 2.77 (m, 2H), 2.64 (m, 2H), 1.97 (m, 2H), 1.83 (m, 1H), 0.43 (m, 2H), 0.31 (m, 2H); MS (+ve ESI): 568.2 $(M+H)^+$.

EXAMPLE 92

Preparation of Compound 92 in Table 3—N-(2,3-difluorophenyl)-2-{4-[(7-{3-[(2-hydroxyethyl)(2-methoxyethyl)amino]propoxy}-6-methoxyquinazolin-4-yl)amino]-1H-pyrazol-1-yl}acetamide An analogous reaction to that described in example 60 but starting with 2-((2-methoxyethyl)amino)ethanol (77 mg, 0.65 mmol) yielded compound 92 in table 3 (75 mg, 71% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.22 (m, 2H), 7.15 (s, 1H), 5.16 (s, 2H), 4.31 (t, 1H), 4.17 (t, 2H), 3.96 (s, 3H), 3.43 (m, 2H), 3.37 (m, 2H), 3.21 (s, 3H), 2.64 (m, 4H), 2.53 (m, 2H), 1.89 (m, 2H); MS (+ve ESI): 586.2 $(M+H)^+$.

EXAMPLE 93

Preparation of Compound 93 in Table 3—2-{4-[(7-{3-[cyclobutyl(2-hydroxyethyl)amino]propoxy}-6-methoxyquinazolin-4-yl)amino]-1H-pyrazol-1-yl}-N-(2,3-difluorophenyl)acetamide An analogous reaction to that described in example 60 but starting with 2-(cyclobutylamino)ethanol (75 mg, 0.65 mmol) yielded compound 93 in table 3 (49 mg, 47% yield):

$^1$H-NMR (DMSO $d_6$): 9.68 (s, 1H), 8.49 (s, 1H), 8.48 (s, 1H), 7.81 (s, 1H), 7.78 (s, 1H), 7.73 (m, 1H), 7.22 (m, 2H), 7.15 (s, 1H), 5.16 (s, 2H), 4.35 (m, 1H), 4.15 (t, 2H), 3.95 (s, 3H), 3.40 (m, 2H), 3.12 (m, 1H), 2.56 (m, 2H), 2.46 (m, 2H), 1.95 (m, 2H), 1.89 (m, 2H), 1.76 (m, 2H), 1.54 (m, 2H); MS (+ve ESI): 582.2 $(M+H)^+$.

EXAMPLE 94

Preparation of Compound 94 in Table 3—2-{4-[(7-{3-[(cyclopropylmethyl)(2-hydroxyethyl)amino]propoxy}-6-methoxyquinazolin-4-yl)amino]-1H-pyrazol-1-yl}-N-(2,3-difluorophenyl)acetamide An analogous reaction to that described in example 60 but starting with 2-((cyclopropylmethyl)amino)ethanol (75 mg, 0.65 mmol) yielded compound 94 in table 3 (66 mg, 63% yield):

$^1$H-NMR (DMSO $d_6$, TFA): 9.05 (s, 1H), 8.41 (s, 1H), 8.09 (s, 1H), 7.97 (s, 1H), 7.75 (m, 1H), 7.34 (s, 1H), 7.21 (m, 2H), 5.27 (s, 2H), 4.32 (m, 2H), 4.03 (s, 3H), 3.82 (m, 2H), 3.45 (m, 2H), 3.40 (m, 1H), 3.34 (m, 1H), 3.18 (m, 2H), 2.31 (m, 2H), 1.17 (m, 1H), 0.69 (m, 2H), 0.45 (m, 2H); MS (+ve ESI): 582.2 $(M+H)^+$.

EXAMPLE 95

Preparation of Compound 95 in Table 3—2-{4-[(7-{3-[(cyclobutylmethyl)(2-hydroxyethyl)amino]propoxy}-6-methoxyquinazolin-4-yl)amino]-1H-pyrazol-1-yl}-N-(2,3-difluorophenyl)acetamide An analogous reaction to that described in example 60 but starting with 2-((cyclobutylmethyl)amino)ethanol (84 mg, 0.65 mmol) yielded compound 95 in table 3 (70 mg, 66% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.22 (m, 2H), 7.14 (s, 1H), 5.16 (s, 2H), 4.28 (m, 1H), 4.16 (t, 2H), 3.96 (s, 3H), 3.43 (m, 2H), 2.57 (m, 2H), 2.45 (m, 4H), 1.91 (m, 5H), 1.76 (m, 2H), 1.59 (m, 2H); MS (+ve ESI): 596.2 $(M+H)^+$.

EXAMPLE 96

Preparation of Compound 96 in Table 3—N-(2,3-difluorophenyl)-2-{4-[(7-{3-[(2-hydroxyethyl)(prop-2-yn-1-yl)amino]propoxy}-6-methoxyquinazolin-4-yl)amino]-1H-pyrazol-1-yl}acetamide An analogous reaction to that described in example 60 but starting with 2-(prop-2-yn-1-ylamino)ethanol (64 mg, 0.65 mmol) yielded compound 96 in table 3 (68 mg, 67% yield):

$^1$H-NMR (DMSO $d_6$): 9.68 (s, 1H), 8.48 (s, 1H), 8.35 (s, 1H), 7.78 (s, 1H), 7.77 (s, 1H), 7.73 (m, 1H), 7.22 (m, 2H), 7.16 (s, 1H), 5.16 (s, 2H), 4.43 (t, 1H), 4.15 (t, 2H), 3.96 (s, 3H), 3.44 (m, 2H), 3.38 (m, 2H), 3.09 (m, 1H), 2.63 (t, 2H), 2.54 (m, 2H), 1.92 (m, 2H); MS (+ve ESI): 566.2 $(M+H)^+$.

EXAMPLE 97

Preparation of Compound 97 in Table 3—2-{4-[(7-{3-[allyl(2-hydroxyethyl)amino]propoxy}-6-methoxyquinazolin-4-yl)amino]-1H-pyrazol-1-yl}-N-(2,3-difluorophenyl)acetamide An analogous reaction to that described in example 60 but starting with 2-(allylamino)ethanol (66 mg, 0.65 mmol) yielded compound 97 in table 3 (73 mg, 71% yield):

$^1$H-NMR (DMSO $d_6$): 9.68 (s, 1H), 8.49 (s, 1H), 8.35 (s, 1H), 7.78 (s, 1H), 7.77 (s, 1H), 7.72 (m, 1H), 7.22 (m, 2H), 7.15 (s, 1H), 5.82 (m, 1H), 5.17 (m, 1H), 5.16 (s, 2H), 5.09 (m, 1H), 4.35 (t, 1H), 4.16 (t, 2H), 3.95 (s, 3H), 3.44 (m, 2H), 3.32 (m, 2H), 3.1 (d, 2H), 2.62 (t, 2H), 1.91 (m, 2H); MS (+ve ESI): 568.2 $(M+H)^+$.

EXAMPLE 98

Preparation of Compound 98 in Table 3—N-(2,3-difluorophenyl)-2-{4-[(7-{3-[(2,2-dimethylpropyl)(2-hydroxyethyl)amino]propoxy}-6-methoxyquinazolin-4-yl)amino]-1H-pyrazol-1-yl}acetamide An analogous reaction to that described in example 60 but starting with 2-((2,2-dimethylpropyl)amino)ethanol (85 mg, 0.65 mmol) yielded compound 98 in table 3 (67 mg, 62% yield):

$^1$H-NMR (DMSO $d_6$): 9.68 (s, 1H), 8.48 (s, 1H), 8.35 (s, 1H), 7.77 (s, 1H), 7.76 (s, 1H), 7.74 (m, 1H), 7.21 (m, 2H), 7.14 (s, 1H), 5.17 (s, 2H), 4.33 (t, 1H), 4.17 (t, 2H), 3.95 (s, 3H), 3.44 (m, 2H), 2.65 (m, 2H), 2.54 (m, 2H), 2.21 (s, 2H), 1.91 (m, 2H), 0.83 (s, 9H); MS (+ve ESI): 598.2 $(M+H)^+$.

EXAMPLE 99

Preparation of Compound 99 in Table 3—N-(2,3-difluorophenyl)-2-{4-[(7-{3-[(2-hydroxyethyl)(3,3,3-trifluoropropyl)amino]propoxy}-6-methoxyquinazolin-4-yl)amino]-1H-pyrazol-1-yl}acetamide An analogous reaction to that described in example 60 but starting with 2-((3,3,3-trifluoropropyl)amino)ethanol (102 mg, 0.65 mmol) yielded compound 99 in table 3 (80 mg, 72% yield):

$^1$H-NMR (DMSO $d_6$): 9.73 (s, 1H), 8.49 (s, 1H), 8.35 (s, 1H), 7.79 (s, 1H), 7.77 (s, 1H), 7.73 (m, 1H), 7.23 (m, 2H), 7.16 (s, 1H), 5.17 (s, 2H), 4.18 (t, 2H), 3.96 (s, 3H), 3.49 (m, 2H), 2.67 (m, 6H), 1.94 (m, 2H); MS (+ve ESI): 624.2 $(M+H)^+$.

EXAMPLE 100

Preparation of Compound 100 in Table 3—N-(2,3-difluorophenyl)-2-{4-[(7-{2-[(2R)-2-(hydroxymethyl)pyrrolidin-1-yl]ethoxy}-6-methoxyquinazolin-4-yl)amino]-1H-pyrazol-1-yl}acetamide A 2:1 mixture of 2-(4-{[7-(2-chloroethoxy)-6-methoxyquinazolin-4-yl]amino}-1H-pyrazol-1-yl)-N-(2,3-difluorophenyl)acetamide: 2-(4-{[7-(2-bromoethoxy)-6-methoxyquinazolin-4-yl]amino]-1H-pyrazol-1-yl)-N-(2,3-difluorophenyl)acetamide as the di-hydrochloride salt (0.15 g, ~0.3 mmol), triethylamine (0.11 ml, 0.8 mmol), (2R)-pyrrolidin-2-ylmethanol (0.081 g, 0.8 mmol) and sodium iodide (0.08 g, 0.53 mmol) in dimethylacetamide (2 ml) was heated at 90° C. for 6 hours. The reaction mixture was diluted with dichloromethane and a few drops of methanol and then filtered. The filtrate was purified directly by silica gel chromatography, eluting with a 1 to 12% mixture of methanol (containing 10% 7N ammonia in methanol) in dichloromethane. The obtained product was triturated with acetonitrile and then diethyl ether to give compound 100 in table 3 (0.08 g, 54% yield) as a fawn coloured solid:

$^1$H-NMR (DMSO $d_6$ at 373K): 10.18 (br s, 1H), 9.97 (s, 1H), 8.70 (s, 1H), 8.31 (s, 1H), 7.99 (s, 1H), 7.91 (s, 1H), 7.71 (m, 1H), 7.32 (s, 1H), 7.18 (m, 2H), 7.03 (br s, 1H), 5.20 (s, 2H), 4.62 (t, 2H), 4.07 (s, 3H), 3.60 (m, 7H), 1.95 (m, 4H); MS (+ve ESI): 554 $(M+H)^+$.

EXAMPLE 101

Preparation of Compound 101 in Table 3—N-(2,3-difluorophenyl)-2-(4-{[7-(2-{4-[2-(2-hydroxy-ethoxy)ethyl]piperazin-1-yl}ethoxy)-6-methoxyquinazolin-4-yl]amino}-1H-pyrazol-1-yl)acetamide An analogous reaction to that described in example 100 but starting with 2-(2-piperazin-1-ylethoxy)ethanol (0.09 ml, 0.53 mmol) yielded compound 101 in table 3 (0.035 g, 31% yield):

$^1$H-NMR (DMSO $d_6$ at 373K): 9.85 (s, 1H), 9.38 (br s, 1H), 8.47 (s, 1H), 8.27 (s, 1H), 7.84 (s, 1H), 7.80 (s, 1H), 7.75 (m, 1H), 7.19 (m, 3H), 5.21 (s, 2H), 4.28 (t, 2H), 3.98 (s, 3H), 3.52 (m, 6H), 2.80 (m, 12H); MS (+ve ESI): 627 $(M+H)^+$ MS (−ve ESI): 625 $(M—H)^-$.

EXAMPLE 102

Preparation of Compound 102 in Table 3—N-(2,3-difluorophenyl)-2-{4-[(7-{2-[2-(hydroxymethyl)piperidin-1-yl]ethoxy}-6-methoxyquinazolin-4-yl)amino]-1H-pyrazol-1-yl}acetamide An analogous reaction to that described in example 100 but starting with piperidin-2-ylmethanol (0.08 g, 0.07 mmol) yielded compound 102 in table 3 (0.04 g, 31% yield):

$^1$H-NMR (DMSO $d_6$ at 373K): 9.85 (s, 1H), 9.36 (s, 1H), 8.45 (s, 1H), 8.28 (s, 1H), 7.83 (s, 1H), 7.78 (s, 1H), 7.69 (m, 1H), 7.18 (m, 3H), 5.12 (s, 2H), 4.22 (t, 2H), 3.96 (s, 3H), 3.59 (m, 2H), 3.25 (br s, 1H), 2.50 (m, 5H, under DMSO), 1.42 (m, 6H); MS (+ve ESI): 568 $(M+H)^+$ MS (−ve ESI): 566 $(M-H)^-$.

EXAMPLE 103

Preparation of Compound 103 in Table 3—N-(2,3-difluorophenyl)-2-{4-[(7-{2-[(2-hydroxy-1,1-dimethylethyl)amino]ethoxy}-6-methoxyquinazolin-4-yl)amino]-1H-pyrazol-1-yl}acetamide An analogous reaction to that described in example 100 but starting with 2-amino-2-methylpropan-1-ol (0.062 g, 0.7 mmol) yielded compound 103 in table 3 (0.075 g, 60% yield): MS (+ve ESI): 542 $(M+H)^+$ MS (−ve ESI): 540 $(M-H)^-$.

EXAMPLE 104

Preparation of Compound 104 in Table 3—N-(2,3-difluorophenyl)-2-{4-[(7-{2-[4-(2-hydroxyethyl)piperazin-1-yl]ethoxy}-6-methoxyquinazolin-4-yl)amino]-1H-pyrazol-1-yl}acetamide An analogous reaction to that described in example 100 but starting with 2-piperazin-1-ylethanol (0.091 g, 0.7 mmol) yielded compound 104 in table 3 (0.112 g, 83% yield): MS (+ve ESI): 583 $(M+H)^+$.

EXAMPLE 105

Preparation of Compound 105 in Table 3—N-(2,3-difluorophenyl)-2-{4-[(7-{2-[(trans-4-hydroxycyclohexyl)amino]ethoxy}-6-methoxyquinazolin-4-yl)amino]-1H-pyrazol-1-yl}acetamide An analogous reaction to that described in example 100 but starting with trans-4-hydroxycyclohexyl amine (0.08 g, 0.7 mmol) yielded compound 105 in table 3 (0.06 g, 46% yield): MS (+ve ESI): 568 $(M+)^+$ MS (−ve ESI): 566 $(M-H)^-$.

EXAMPLE 106

Preparation of Compound 106 in Table 3—N-(2,3-difluorophenyl)-2-{4-[(7-{2-[3-(hydroxymethyl)piperidin-1-yl]ethoxy}-6-methoxyquinazolin-4-yl)amino]-1H-pyrazol-1-yl}acetamide An analogous reaction to that described in example 100 but starting with piperidin-3-ylmethanol (0.08 g, 0.7 mmol) yielded compound 106 in table 3 (0.073 g, 56% yield): MS (+ve ESI): 568 $(M+H)^+$ MS (−ve ESI): 566 $(M-H)^-$.

EXAMPLE 107

Preparation of Compound 107 in Table 3—N-(2,3-difluorophenyl)-2-(4-{[7-(2-{[1-(hydroxymethyl)cyclopentyl]amino]ethoxy)-6-methoxyqlinazolin-4-yl]amino}-1H-pyrazol-1-yl)acetamide An analogous reaction to that described in example 100 but starting with (1-aminocyclopentyl)methanol (0.08 g, 0.7 mmol) yielded compound 107 in table 3 (0.069 g, 53% yield): MS (+ve ESI): 568 $(M+H)^+$ MS (−ve ESI): 566 $(M-H)^-$.

EXAMPLE 108

Preparation of Compound 108 in Table 3—N-(2,3-difluorophenyl)-2-{4-[(7-{2-[4-(3-hydroxypropyl)piperazin-1-yl]ethoxy}-6-methoxyquinazolin-4-yl)amino]-1H-pyrazol-1-yl}acetamide An analogous reaction to that described in example 100 but starting with 3-piperazin-1-ylpropan-1-ol (0.101 g, 0.7 mmol) yielded compound 108 in table 3 (0.101 g, 74% yield): MS (+ve ESI): 597 $(M+H)^+$ MS (−ve ESI): 595 $(M-H)^-$.

EXAMPLE 109

Preparation of Compound 109 in Table 3—2-{4-[(7-{2-[cyclohexyl(2-hydroxyethyl)amino]ethoxy}-6-methoxyquinazolin-4-yl)amino]-1H-pyrazol-1-yl)-N-(2,3-difluorophenyl)acetamide An analogous reaction to that described in example 100 but starting with 2-(cyclohexylamino)ethanol (0.1 g, 0.7 mmol) yielded compound 109 in table 3 (0.02 g, 15% yield):

MS (+ve ESI): 596 $(M+H)^+$.

EXAMPLE 110

Preparation of Compound 110 in Table 3—N-(2,3-difluorophenyl)-2-{4-[(7-{2-[(2-hydroxyethyl)(propyl)amino]ethoxy}-6-methoxyquinazolin-4-yl)amino]-1H-pyrazol-1-yl}acetamide An analogous reaction to that described in example 100 but starting with 2-(propylamino)ethanol (0.072 g, 0.7 mmol) yielded compound 110 in table 3 (0.032 g, 25% yield): MS (+ve ESI): 556 $(M+H)^+$ MS (−ve ESI): 554 $(M-H)^-$.

EXAMPLE 111

Preparation of Compound 111 in Table 3—N-(2,3-difluorophenyl)-2-{4-[(7-{2-[(3-hydroxy-2,2-dimethylpropyl)amino]ethoxy}-6-methoxyquinazolin-4-yl)amino]-1H-pyrazol-1-yl}acetamide An analogous reaction to that described in example 100 but starting with 3-amino-2,2-dimethylpropan-1-ol (0.072 g, 0.7 mmol) yielded compound 111 in table 3 (0.11 g, 86% yield): MS (+ve ESI): 556 $(M+H)^+$ MS (−ve ESI): 554 $(M-H)^-$.

EXAMPLE 112

Preparation of Compound 112 in Table 3—N-(2,3-difluorophenyl)-2-[4-({6-methoxy-7-[2-(tetrahydro-2H-pyran-4-ylamino)ethoxy]quinazolin-4-yl}amino)-1H-pyrazol-1-yl]acetamide An analogous reaction to that described in example 100 but starting with tetrahydro-2H-pyran-4-amine (0.069 g, 0.7 mmol) yielded compound 112 in table 3 (0.107 g, 84% yield): MS (+ve ESI): 554 $(M+H)^+$ MS (−ve ESI): 552 $(M-H)^-$.

EXAMPLE 113

Preparation of Compound 113 in Table 3—2-{4-[(7-{2-[cyclobutyl(2-hydroxyethyl)amino]ethoxy}-6-methoxyquinazolin-4-yl)amino]-1H-pyrazol-1-yl}-N-(2,3-difluorophenyl)acetamide An analogous reaction to that described in example 100 but starting with 2-(cyclobutylamino)ethanol (0.15 g, 1.3 mmol) yielded compound 113 in table 3 (0.086 g, 37% yield):

$^1$H-NMR (DMSO $d_6$): 10.26 (br s, 1H), 9.66 (s, 1H), 8.47 (s, 1H), 8.33 (s, 1H), 7.74 (m, 3H), 7.18 (m, 3H), 5.15 (s, 2H), 4.34 (br s, 1H), 4.13 (t, 2H), 3.96 (s, 3H), 3.48 (q, 2H), 2.90 (t, 2H), 2.85 (t, 1H), 2.59 (t, 2H), 2.04 (m, 2H), 1.82 (m, 2H), 1.58 (m, 2H). MS (+ve ESI): 568 $(M+H)^+$ MS (−ve ESI): 566 $(M-H)^-$.

EXAMPLE 114

Preparation of Compound 114 in Table 3—N-(2,3-difluorophenyl)-2-{4-[(7-{2-[(2-hydroxyethyl)(tetrahydro-2H-pyran-4-yl)amino]ethoxy}-6-methoxyquinazolin-4-yl)amino]-1H-pyrazol-1-yl}acetamide A mixture of N-(2,3-difluorophenyl)-2-[4-({6-methoxy-7-[2-(tetrahydro-2H-pyran-4-ylamino)ethoxy]quinazolin-4-yl}amino)-1H-pyrazol-1-yl]acetamide (0.17 g, 0.31 mmol), glycolaldehyde (0.028 g, 0.46 mmol) and MP-triacetoxyborohydride (2 mmol/g, 0.39 g, 0.78 mmol) in dimethylformamide (1.5 ml) was stirred at ambient temperature for 2 hours. The resin was removed by filtration and the filtrate evaporated under reduced pressure. The residue was purified by silica gel chromatography eluting with a 0 to 10% mixture of methanol (containing 10% 7N ammonia in methanol) in dichloromethane. The obtained product was triturated with diethyl ether to give compound 114 in table 3 (0.045 g, 24% yield) as a white solid:

$^1$H-NMR (DMSO $d_6$): 10.28 (br s, 1H), 9.68 (s, 1H), 8.48 (s, 1H), 8.35 (s, 1H), 7.72 (m, 3H), 7.18 (m, 3H), 5.16 (s, 2H), 4.30 (t, 1H), 4.15 (t, 2), 3.97 (s, 3H), 3.88 (q, 2H), 3.39 (m, 4H), under $H_2O$), 2.97 (t, 2H), 2.80 (m, 1H), 2.63 (t, 2H), 1.68 (m, 2H), 1.43 (m, 2H); MS (+ve ESI): 598 $(M+H)^+$ MS (−ve ESI): 596 $(M-H)^-$.

EXAMPLE 115

Preparation of Compound 115 in Table 3—N-(2,3-difluorophenyl)-2-{4-[(7-{2-[(2S)-2-(hydroxymethyl)pyrrolidin-1-yl]ethoxy}-6-methoxyquinazolin-4-yl)amino]-1H-pyrazol-1-yl}acetamide An analogous reaction to that described in example 100 but starting with (2S)-pyrrolidin-2-ylmethanol (616 mg, 6.10 mmol) and purification by reverse phase chromatography on C-18 silica using a water/acetonitrile/trifluoroacetic acid gradient as eluent gave compound 115 in table 3 (637 mg, 75% yield) as a pale brown solid:

$^1$H-NMR (DMSO $d_6$): 9.68 (s(br.), 1H), 8.50 (s, 1H), 8.34 (s, 1H), 7.79 (d, 1H), 7.78 (s, 1H), 7.72 (m, 1H), 7.18 (m, 3H), 5.13 (s, 2H), 4.32 (s (br.), 1H), 4.22 (t, 2H), 3.95 (s, 3H), 3.41 (m, 1H), 3.30 (m, (partially obscured by $H_2O$), 2H), 3.17 (m, 1H), 2.80 (m, 1H), 2.60 (m, 1H); 2.35 (q, 1H), 1.82 (m, 1H), 1.67 (m, 2H), 1.52 (m, 1H); MS (+ve ESI): 554 $(M+H)^+$.

EXAMPLE 116

Preparation of Compound 116 in Table 3—N-(2,3-difluorophenyl)-2-{4-[(7-{2-[(2R)-2-(2-hydroxyethyl)piperidin-1-yl]ethoxy}-6-methoxyquinazolin-4-yl)amino]-1H-pyrazol-1-yl}acetamide An analogous reaction to that described in example 115 but starting with 2-[(2R)-piperidin-2-yl]ethanol (6.0 mmol) gave compound 116 in table 3 (604 mg, 68% yield) as a pale yellow solid:

$^1$H-NMR (DMSO $d_6$): 10.28 (s, 1H), 9.67 (s, 1H), 8.50 (s, 1H), 8.34 (s, 1H), 7.80 (d, 1H), 7.79 (s, 1H), 7.73 (m, 1H), 7.20 (m, 3H), 5.17 (s, 2H), 4.39 (s (br.), 1H), 4.21 (t, 2H), 3.96 (s, 3H), 3.52 (m, 1H), 3.45 (m, 1H), 3.05 (m, 1H), 2.90 (m,

1H), 2.83 (m, 1H), 2.58 (m, 1H), 2.45 (m, 1H), 1.80 (m, 1H), 1.61 (m, 2H), 1.50 (m, 3H), 1.32 (m, 2H); MS (+ve ESI): 582 $(M+H)^+$.

EXAMPLE 117

Preparation of Compound 117 in Table 3—N-(2,3-Difluorophenyl)-2-{4-[(7-{2-[(2S)-2-(2-hydroxy-ethyl)piperidin-1-yl]ethoxy}-6-methoxyquinazolin-4-yl)amino]-1H-pyrazol-1-yl}acetamide An analogous reaction to that described in example 115 but starting with 2-[(2S)-piperidin-2-yl]ethanol (6.0 mmol) gave compound 117 in table 3 (564 mg, 64% yield):

$^1$H-NMR (DMSO $d_6$): 10.28 (s, 1H), 9.67 (s, 1H), 8.50 (s, 1H), 8.34 (s, 1H), 7.80 (d, 1H), 7.79 (s, 1H), 7.73 (m, 1H), 7.20 (m, 3H), 5.17 (s, 2H), 4.39 (s(br.), 1H), 4.21 (t, 2H), 3.96 (s, 3H), 3.52 (m, 1H), 3.45 (m, 1H), 3.05 (m, 1H), 2.90 (m, 1H), 2.83 (m, 1H), 2.58 (m, 1H), 2.45 (m, 1H), 1.80 (m, 1H), 1.61 (m, 2H), 1.50 (m, 3H), 1.32 (m, 2H); MS (+ve ESI): 582 $(M+H)^+$.

EXAMPLE 118

Preparation of Compound 118 in Table 4—N-(2,3-difluorophenyl)-2-{4-[(7-{3-[(2-hydroxyethyl)(propyl)amino5propoxy}quinazolin-4-yl)amino]-1H-pyrazol-1-yl}acetamide 2-(Propylamino)ethanol (95 mg, 0.92 mmol) was added to a solution of 2-(4-{[7-(3-chloropropoxy)quinazolin-4-yl]amino}-1H-pyrazol-1-yl)-N-(2,3-difluorophenyl)acetamide (103 mg, 0.23 mmol) and potassium iodide (76 mg, 0.46 mmol) in dimethylacetamide (0.5 ml) and the mixture heated at 90° C. for 2 hours under argon. The reaction mixture was cooled and water (1 ml) was added resulting in precipitation. The solid was recovered by filtration, dissolved in dichloromethane:methanol (1:1) and the solution filtered through a teflon filter. The solvent was evaporated and the residual oil triturated in dichloromethane:diethyl ether (1:1) to yield compound 118 in table 4 (70 mg, 56% yield):

$^1$H-NMR (DMSO $d_6$, TFA): 9.01 (s, 1H), 8.62 (d, 1H), 8.41 (s, 1H), 7.98 (s, 1H), 7.72 (m, 1H), 7.51 (d, 1H), 7.27 (s, 1H), 7.20 (m, 2H), 5.25 (s, 2H), 4.30 (m, 2H), 3.78 (m, 2H), 3.34 (m, 2H), 3.27 (m, 2H), 3.15 (m, 2H), 2.25 (m, 2H), 1.71 (m, 2H), 0.94 (t, 3H); MS (+ve ESI): 540.1 $(M+H)^+$.

EXAMPLE 119

Preparation of Compound 119 in Table 4—N-(2,3-difluorophenyl)-2-{4-[(7-{3-[(2-hydroxyethyl)(isobutyl)amino]propoxy}quinazolin-4-yl)amino]-1H pyrazol-1-yl}acetamide An analogous reaction to that described in example 118 but starting with 2-(isobutylamino)ethanol (107 mg, 0.92 mmol) yielded compound 119 in table 4 (85 mg, 67% yield):

$^1$H-NMR (DMSO $d_6$, TFA): 9.01 (s, 1H), 8.63 (d, 1H), 8.41 (s, 1H), 7.98 (s, 1H), 7.73 (m, 1H), 7.51 (d, 1H), 7.28 (s, 1H), 7.20 (m, 2H), 5.25 (s, 2H), 4.31 (m, 2H), 3.82 (m, 2H), 3.38 (m, 2H), 3.29 (m, 2H), 3.10 (m, 1H), 3.04 (m, 1H), 2.27 (m, 2H), 2.16 (m, 1H), 1.01 (d, 6H); MS (+ve ESI): 554.2 $(M+H)^+$.

EXAMPLE 120

Preparation of Compound 120 in Table 4—N-(2,3-difluorophenyl)-2-{4-[(7-{3-[(2S)-2-(ydroxymethyl)pyrrolidin-1-yl]propoxy}quinazolin-4-yl)amino]-1H-pyrazol-1-yl}acetamide An analogous reaction to that described in example 118, but starting with (2S)-pyrrolidin-2-ylmethanol (93 mg, 0.92 mmol) yielded compound 120 in table 4 (83 mg, 67% yield):

$^1$H-NMR (DMSO $d_6$, TFA): 9.01 (s, 1H), 8.63 (d, 1H), 8.41 (s, 1H), 7.98 (s, 1H), 7.73 (m, 1H), 7.50 (d, 1H), 7.27 (s, 1H), 7.21 (m, 2H), 5.25 (s, 2H), 4.31 (t, 2H), 3.78 (m, 1H), 3.62 (m, 4H), 3.26 (m, 1H), 3.18 (m, 1H), 2.26 (m, 2H), 2.13 (m, 1H), 2.03 (m, 1H), 1.89 (m, 1H), 1.79 (m, 1H); MS (+ve ESI): 538.2 $(M+H)^+$.

EXAMPLE 121

Preparation of Compound 121 in Table 4—N-(2,3-difluorophenyl)-2-{4-[(7-{3-[(2R)-2-(hydroxymethyl)pyrrolidin-1-yl]propoxy}quinazolin-4-yl)amino]-1H-pyrazol-1-yl}acetamide An analogous reaction to that described in example 118, but starting with (2R)-pyrrolidin-2-ylmethanol (73 mg, 0.72 mmol) yielded compound 121 in table 4 (58 mg, 59% yield):

$^1$H-NMR (DMSO $d_6$, TFA): 8.99 (s, 1H), 8.61 (d, 1H), 8.40 (s, 1H), 7.96 (s, 1H), 7.72 (m, 1H), 7.51 (d, 1H), 7.26 (s, 1H), 7.17 (m, 2H), 5.23 (s, 2H), 4.29 (t, 2H), 3.76 (m, 1H), 3.61 (m, 4H), 3.26 (m, 1H), 3.15 (m, 1H), 2.24 (m, 2H), 2.12 (m, 1H), 2.02 (m, 1H), 1.89 (m, 1H), 1.77 (m, 1H); MS (+ve ESI): 538.2 $(M+H)^+$.

EXAMPLE 122

Preparation of Compound 122 in Table 4—2-{4-[(7-{3-[cyclopentyl(2-hydroxyethyl)amino]propoxy}quinazolin-4-yl)amino]-1H-pyrazol-1-yl}-N-(2,3-difluorophenyl)acetamide The reaction was carried out in an analogous manner to that described in example 118, but starting with 2-(cyclopentylamino)ethanol (136 mg, 1.06 mmol). On completion of reaction, the reaction mixture was diluted with dichloromethane (10 ml) and loaded directly onto a silica gel chromatography column. Elution with dichloromethane followed by increased polarity to dichloromethane:methanol (20:1) then dichloromethane:methanol:ammonia (20:1:0.1) yielded compound 122 in table 4 (75 mg, 63% yield):

$^1$H-NMR (DMSO $d_6$): 10.27 (br s, 1H), 9.91 (br s, 1H), 8.54 (s, 1H), 8.34 (m, 2H), 7.79 (s, 1H), 7.72 (m, 1H), 7.20 (m, 3H), 7.13 (s, 1H), 5.16 (s, 2H), 4.29 (s, 1H), 4.17 (t, 2H), 3.43 (m, 2H), 3.06 (m, 1H), 2.67 (t, 2H), 2.56 (s, 2H), 1.88 (m, 2H), 1.71 (m, 2H), 1.56 (m, 2H), 1.45 (m, 2H), 1.31 (m, 2H); MS (+ve ESI): 566 $(M+H)^+$.

EXAMPLE 123

Preparation of Compound 123 in Table 4—N-(2,3-difluorophenyl)-2-{4-[(7-{3-[ethyl(2-hydroxyethyl)amino]propoxy}quinazolin-4-yl)amino]-1H-pyrazol-1-yl}acetamide An analogous reaction to that described in example 122, but starting with 2-(ethylamino)ethanol (178 mg, 2 mmol) yielded compound 123 in table 4 (141 mg, 67% yield):

$^1$H-NMR (DMSO $d_6$): 8.66 (s, 1H), 8.46 (m, 2H), 7.91 (s, 1H), 7.83 (m, 1H), 7.30 (m, 3H), 7.25 (m, 1H), 5.26 (s, 2H), 4.24 (s, 1H), 4.28 (t, 2H), 3.55 (m, 2H), 2.71 (t, 2H), 2.52 (m, 4H), 1.99 (m, 2H), 1.07 (t, 3H); MS (+ve ESI): 526 $(M+H)^+$.

EXAMPLE 124

Preparation of Compound 124 in Table 4—N-(2,3-difluorophenyl)-2-{4-[(7-{3-[4-(2-hydroxyethyl)piperazin-1-yl]propoxy}quinazolin-4-yl)amino]-1H-pyrazol-1-yl}acetamide An analogous reaction to that described in example 122, but starting with 2-piperazin-1-ylethanol (138 mg, 1.06 mmol) yielded compound 124 in table 4 (78 mg, 65% yield):

$^1$H-NMR (DMSO $d_6$): 10.26 (br s, 1H), 9.90 (br s, 1H), 8.54 (s, 1H), 8.33 (m, 2H), 7.78 (s, 1H), 7.70 (m, 1H), 7.18 (m, 3H), 7.13 (s, 1H), 5.16 (s, 2H), 4.31 (m, 1H), 4.16 (t, 2H), 3.46 (m, 2H), 2.38 (m, 12H), 1.92 (m, 2H); MS (+ve ESI): 567 $(M+H)^+$.

EXAMPLE 125

Preparation of Compound 125 in Table 4—N-(2,3-difluorophenyl)-2-{4-[(7-{3-[4-(hydroxymethyl)piperidin-1-yl]propoxy}quinazolin-4-yl)amino]-1H-pyrazol-1-yl}acetamide An analogous reaction to that described in example 122, but starting with piperidin-4-ylmethanol (230 mg, 2 mmol) yielded compound 125 in table 4 (111 mg, 50% yield):

$^1$H-NMR (DMSO $d_6$): 9.95 (br s, 1H), 8.56 (s, 1H), 8.39 (m, 1H), 8.34 (s, 1H), 7.79 (s, 1H), 7.70 (t, 1H), 7.19 (m, 4H), 5.16 (s, 2H), 4.60 (m, 1H), 4.24 (t, 2H), 3.55 (m, 2H), 3.25 (m, 4H), 2.92 (m, 2H), 2.17 (m, 2H), 1.95 (m, 2H), 1.63 (m, 1H), 1.39 (m, 2H); MS (+ve ESI): 552 $(M+H)^+$.

EXAMPLE 126

Preparation of Compound 126 in Table 4—N-(2,3-difluorophenyl)-2-{4-[(7-{3-[(3-hydroxy-1,1-dimethylpropyl)amino]propoxy}quinazolin-4-yl)amino]-1H-pyrazol-1-yl}acetamide An analogous reaction to that described in example 122, but starting with 3-amino-3-methylbutan-1-ol (206 mg, 2 mmol) yielded compound 126 in table 4 (89 mg, 41% yield):

$^1$H-NMR (DMSO $d_6$): 8.65 (s, 1H), 8.45 (m, 2H), 7.90 (s, 1H), 7.82 (m, 1H), 7.30 (m, 4H), 5.25 (s, 2H), 4.33 (t, 2H), 3.67 (t, 2H), 2.97 (t, 2H), 2.09 (m, 2H), 1.76 (t, 2H), 1.26 (s, 6H); MS (+ve ESI): 540 $(M+H)^+$.

EXAMPLE 127

Preparation of Compound 127 in Table 4—2-{4-[(7-{3-[(2-cyanoethyl)(2-hydroxyethyl)amino]propoxy}quinazolin-4-yl)amino]-1H-pyrazol-1-yl}-N-(2,3-difluorophenyl)acetamide An analogous reaction to that described in example 122, but starting with 3-[(2-hydroxyethyl)amino]propanenitrile (see Bell, J. A.; Kenworthy, C. *Synthesis,* 1971, 12, 650-652, 0.258 g, 2.00 mmol) yielded compound 127 in table 4 (0.076 g, 48% yield):

$^1$H-NMR (DMSO $d_6$): 10.28 (1H, s), 9.89 (1H, s), 8.54 (1H, s), 8.33 (2H, d), 7.77 (1H, s), 7.70 (1H, m), 7.19 (3H, m), 7.14 (1H, s), 5.13 (2H, s), 4.37 (1H, t), 4.19 (2H, t), 3.48 (1H, m), 2.79 (2H, t), 2.69 (2H, t), 2.58 (3H, m), 1.90 (2H, m); MS (+ve ESI): 551 $(M+H)^+$ MS (−ve ESI): 549 $(M-H)^-$.

EXAMPLE 128

Preparation of Compound 128 in Table 4—N-(2,3-difluorophenyl)-2-(4-{[7-(3-morpholin-4-ylpropoxy)quinazolin-4-yl]amino}-1H-pyrazol-1-yl)acetamide A solution of 2-(4-{[7-(3-chloropropoxy)quinazolin-4-yl]amino}-1H-pyrazol-1-yl)-N-(2,3-difluorophenyl)acetamide (0.060 g, 0.13 mmol) in morpholine (20 ml) was heated at 80° C. for 2 hours and then allowed to cool to room temperature. The mixture was evaporated under reduced pressure to leave a brown solid which was purified by silica gel chromatography eluting with a 0 to 10% mixture methanol (containing 10% 7N ammonia in methanol) in dichloromethane to give compound 128 in table 4 (0.055 g, 81% yield) as a white solid:

$^1$H-NMR (DMSO $d_6$): 10.27 (br s, 1H), 8.55 (s, 1H), 8.38 (d, 1H), 8.32 (s, 1H), 7.79 (s, 1H), 7.68 (m, 2H), 7.18 (m, 3H), 5.15 (s, 2H), 4.20 (t, 2H), 3.65 (m, 4H), 3.30 (m, 4H), 2.75 (m, 4H); MS (+ve ESI): 524 $(M+H)^+$.

EXAMPLE 129

Preparation of Compound 129 in Table 4—N-(2,3-difluorophenyl)-2-{4-[(7-{3-[(3-hydroxy-2,2-dimethylpropyl)amino]propoxy}quinazolin-4-yl)amino]-1H-pyrazol-1-yl}acetamide An analogous reaction to that described in example 122, but starting with 3-amino-2,2-dimethylpropan-1-ol (438 mg, 4.25 mmol) yielded compound 129 in table 4 (290 mg, 63% yield) as a white solid:

$^1$H-NMR (DMSO $d_6$): 10.28 (br s, 1H), 9.90 (s, 1H), 8.50 (s, 1H), 8.38 (d, 1H), 8.30 (s, 1H), 7.79 (s, 1H), 7.68 (t, 1H), 7.16 (m, 4H), 5.25 (s, 2H), 4.20 (t, 2H), 3.30 (br s, 2H), 3.20 (s, 2H), 2.80 (t, 2H), 2.42 (s, 6H), 2.00 (m, 2H); MS (+ve ESI): 540 $(M+H)^+$ MS (−ve ESI): 538 $(M-H)^-$.

EXAMPLE 130

Preparation of Compound 130 in Table 4—N-(2,3-difluorophenyl)-2-{4-[(7-{3-[(3-hydroxypropyl)amino]propoxy}quinazolin-4-yl)amino]-1H-pyrazol-1-yl}acetamide An analogous reaction to that described in example 122, but starting with 3-aminopropan-1-ol (0.33 ml, 4.25 mmol) yielded compound 130 in table 4 (320 mg, 74% yield):

$^1$H-NMR (DMSO $d_6$): 9.90 (s, 1H), 8.50 (s, 1H), 8.38 (d, 1H), 8.30 (s, 1H), 7.79 (s, 1H), 7.68 (t, 1H), 7.20 (m, 4H), 5.19 (s, 2H), 4.20 (t, 2H), 3.42 (t, 2H), 2.90 (t, 2H), 2.78 (t, 2H), 2.02 (quintet, 2H), 1.65 (quintet, 2H); MS (+ve ESI): 512 $(M+H)^+$ MS (−ve ESI): 510 $(M-H)^-$.

EXAMPLE 131

Preparation of Compound 131 in Table 4—N-(2,3-difluorophenyl)-2-{4-[(7-{3-[(3-hydroxypropyl)(propyl)amino]propoxy}quinazolin-4-yl)amino]-1H-pyrazol-1-yl}acetamide A mixture of propionaldehyde (0.020 ml, 0.31 mmol), N-(2,3-difluorophenyl)-2-{4-[(7-{3-[(3-hydroxypropyl)amino]propoxy}quinazolin-4-yl)amino]-1H-pyrazol-1-yl}acetamide (0.160 g, 0.31 mmol), acetic acid (0.020 ml, 0.31 mmol) and MP-cyanoborohydride (2 mmol/g, 0.024 g, 0.47 mmol) in methanol (4 ml) was stirred at room temperature for 2 hours. The reaction mixture was filtered and the filtrate evaporated under reduced pressure and the residue was then purified by silica gel chromatography eluting with a 0 to 10% mixture of methanol (containing 10% 7N ammonia in methanol) in dichloromethane to give compound 131 in table 4 (0.085 g, 49% yield):

$^1$H-NMR (DMSO $d_6$): 10.32 (br s, 1H), 10.00 (s, 1H), 8.54 (s, 1H), 8.38 (d, 1H), 8.30 (s, 1H), 7.78 (s, 1H), 7.65 (t, 1H), 7.18 (m, 4H), 5.18 (s, 2H), 4.18 (t, 2H), 3.40 (t, 2H), 2.60 (m, 6H), 2.20 (m, 2H), 1.58 (m, 4H), 0.84 (t, 3H); MS (+ve ESI): 554 $(M+H)^+$.

EXAMPLE 132

Preparation of Compound 132 in Table 4—N-(2,3-difluorophenyl)-2-{4-[(7-{3-[ethyl(3-hydroxypropyl)amino]propoxy}quinazolin-4-yl)amino]-1H-pyrazol-1-yl}acetamide A mixture of acetaldehyde (0.034 g, 0.78 mmol), N-(2,3-difluorophenyl)-2-{4-[(7-{3-[(3-hydroxypropyl)amino]propoxy}quinazolin-4-yl)amino]-1H-pyrazol-1-yl}acetamide (0.400 g, 0.78 mmol), acetic acid (0.040 ml, 0.78 mmol) and MP-cyanoborohydride (2 mmol/g, 0.586 g, 1.17 mmol) in methanol (8 ml) was stirred at room temperature for 2 hours. The reaction mixture was filtered and then evaporated to leave a brown oil which was purified by silica gel chromatography eluting with a 0 to 10% mixture of methanol (containing 10% 7N ammonia in methanol) in dichloromethane to give compound 132 in table 4 (0.250 g, 60% yield):

$^1$H-NMR (DMSO $d_6$): 10.29 (br s, 1H), 9.98 (s, 1H), 8.50 (s, 1H), 8.35 (d, 1H), 8.30 (s, 1H), 7.78 (s, 1H), 7.70 (m, 1H), 7.18 (m, 4H), 5.18 (s, 2H), 4.18 (t, 2H), 3.42 (t, 2H), 2.62 (m, 6H), 1.95 (t, 2H), 1.60 (quintet, 2H), 1.02 (t, 3H); MS (+ve ESI): 540 $(M+H)^+$ MS (−ve ESI): 538 $(M-H)^-$.

EXAMPLE 133

Preparation of Compound 133 in Table 4—N-(2,3-difluorophenyl)-2-{4-[(7-{3-[4-(2-hydroxyethyl)-3-oxopiperazin-1-yl]propoxy}quinazolin-4-yl)amino]-1H-pyrazol-1-yl}acetamide An analogous reaction to that described in example 122 but starting with 1-(2-hydroxyethyl)piperazin-2-one (0.226 g, 1.5 7 mmol) yielded compound 133 in table 4 (0.186 g, 82% yield) as a pale orange solid:

$^1$H-NMR (DMSO $d_6$): 10.29 (s, 1H), 10.18 (s, 1H), 8.61 (s, 1H), 8.40 (d, 1H), 8.34 (s, 1H), 7.81 (s, 1H), 7.72 (m, 1H), 7.27 (m, 1H), 7.20 (m, 3H), 5.17 (s, 2H), 4.70 (m, 1H), 4.21 (t, 2H), 3.52 (t, 2H), 3.42 (m, 2H), 3.30 (m, 2H, partially obscured by $H_2O$), 3.17 (m, 2H), 2.80 (m, 2H), 2.65 (m, 2H), 2.00 (quintet, 2H); MS (+ve ESI): 581 $(M+H)^+$.

1-(2-Hydroxyethyl)piperazin-2-one used as Starting Material, was Prepared as Follows a) A solution of (2-bromoethoxy)-tert-butyldimethylsilane (4.71 g, 19.7 mmol) in tetrahydrofuran (20 ml) was added dropwise at room temperature to a stirred solution of tert-butyl 3-oxopiperazine-1-carboxylate (3.94 g, 19.7 mmol), powdered potassium hydroxide (1.32 g, 23.6 mmol) and tetrabutylammonium bromide (1.27 g, 3.94 mmol) in tetrahydrofuran (30 ml) and the resulting mixture was stirred for 4 hours. The mixture was filtered and then evaporated to leave a colourless viscous oil which was purified by silica gel chromatography eluting with methyl tert-butyl ether as eluent to give tert-butyl 4-(2-{[tert-butyl(dimethyl)silyl]oxy}ethyl)-3-oxopiperazine-1-carboxylate (3.42 g, 45% yield) as a colourless oil:

$^1$H-NMR ($CDCl_3$): 4.08 (s, 2H), 3.80 (t, 2H), 3.61 (m, 2H), 3.50 (m, 4H), 1.46 (s, 9H), 0.87 (s, 9H), 0.05 (s, 6H).

b) A mixture of tert-butyl 4-(2-{[tert-butyl(dimethyl)silyl]oxy}ethyl)-3-oxopiperazine-1-carboxylate (3.4 g, 9.50 mmol) and hydrogen chloride (15 ml of a 4M solution in 1,4-dioxane) in 1,4-dioxane (10 ml) was stirred at room temperature for 4 hour and then the mixture was evaporated. The residue was dissolved in a mixture of 5% methanol in dichloromethane (30 ml), basified with a 7N solution of ammonia in methanol and then filtered. The filtrate was evaporated and the residue was purified by silica gel chromatography eluting with 10% methanol in dichloromethane containing 0-5% 7M ammonia in methanol to give 1-(2-hydroxyethyl)piperazin-2-one (0.708 g, 57% yield) as a pale yellow oil.

$^1$H-NMR ($CDCl_3$): 3.80 (t, 2H), 3.53 (t, 2H), 3.52 (s, 2H), 3.42 (t, 2H), 3.10 (t, 2H), 2.52 (br s, 2H).

EXAMPLE 134

Preparation of Compound 134 in Table 4—N-(2,3-difluorophenyl)-2-[4-({7-[3-(propylamino)propoxy]quinazolin-4-yl}amino)-1H-pyrazol-1-yl]acetamide An analogous reaction to that described in example 122 but starting with propylamine (0.73 ml, 8.85 mmol) yielded compound 134 in table 4 (0.54 g, 62% yield):

$^1$H-NMR (DMSO $d_6$): 10.28 (br s, 1H), 9.98 (s, 1H), 8.57 (s, 1H), 8.38 (d, 1H), 8.36 (s, 1H), 7.78 (s, 1H), 7.71 (m, 1H), 7.18 (m, 4H), 5.15 (s, 2H), 4.20 (t, 2H), 3.82 (t, 2H), 2.70 (t, 2H), 1.98 (m, 2H), 1.52 (m, 2H), 0.89 (t, 3H); MS (+ve ESI): 496 $(M+H)^+$ MS (−ve ESI): 494 $(M-H)^-$.

EXAMPLE 135

Preparation of Compound 135 in Table 4—N-(2,3-difluorophenyl)-2-(4-{[7-(3-piperazin-1-ylpropoxy)quinazolin-4-yl]amino}-1H-pyrazol-1-yl)acetamide An analogous reaction to that described in example 122 but starting piperazine (0.761 g, 8.85 mmol) yielded compound 135 in table 4 (0.68 g, 74% yield) as a white solid:

$^1$H-NMR (DMSO $d_6$): 9.94 (s, 1H), 8.55 (s, 1H), 8.36 (d, 1H), 8.34 (s, 1H), 7.78 (s, 1H), 7.71 (m, 1H), 7.18 (m, 4H), 5.15 (s, 2H), 4.18 (t, 2H), 2.80 (s, 8H), 2.42 (m, 2H), 1.95 (m, 2H); MS (+ve ESI): 523 $(M+H)^+$ MS (−ve ESI): 521 $(M-H)^-$.

EXAMPLE 136

Preparation of Compound 136 in Table 4—N-(2,3-difluorophenyl)-2-{4-[(7-{3-[glycoloyl(propyl)amino]propoxy}quinazolin-4-yl)amino]-1H-pyrazol-1-yl}acetamide A mixture of N-(2,3-difluorophenyl)-2-[4-({7-[3-(propylamino)propoxy]quinazolin-4-yl}amino)-1H-pyrazol-1-yl]acetamide (0.52 g, 1.05 mmol), glycolic acid (0.08 g, 1.05 mmol), O-(7-azabenzotriazol-1-yl)-N,N,N',N'-tetramethyluronium hexafluorophosphate (0.6 g, 1.58 mmol) and diisopropylethylamine (0.55 ml, 3.15 mmol) in dimethyl acetamide (8 ml) was stirred at ambient temperature for 16 hours.

The mixture was partitioned between water and dichloromethane, the organic layer was separated, dried over magnesium sulphate and evaporated under reduced pressure. The residue was purified by silica gel chromatography eluting with a 3 to 10% mixture of methanol (containing 10% 7N ammonia in methanol) in dichloromethane. The obtained product was triturated with diethyl ether to give compound 136 in table 4 (0.29 g, 50% yield) as a white solid:

$^1$H-NMR (DMSO $d_6$): 10.22 (br s, 1H), 10.00 (s, 1H), 8.57 (s, 1H), 8.36 (d, 1H), 8.34 (s, 1H), 7.78 (s, 1H), 7.71 (m, 1H), 7.18 (m, 4H), 5.15 (s, 2H), 4.39 (br s, 1H), 4.15 (m, 4H), 3.30 (m, 4H), 2.02 (m, 2H), 1.52 (m, 2H), 0.82 (t, 3H); MS (+ve ESI): 554 $(M+H)^+$ MS (−ve ESI): 552 $(M-H)^-$.

EXAMPLE 137

Preparation of Compound 137 in Table 4—N-(2,3-difluorophenyl)-2-[4-({7-[3-(4-glycoloylpiperazin-1-yl)propoxy]quinazolin-4-yl]amino)-1H-pyrazol-1-yl]acetamide An analogous reaction to that described in example 136 but starting with N-(2,3-difluorophenyl)-2-(4-{[7-(3-piperazin-1-ylpropoxy)quinazolin-4-yl]amino}-1H-pyrazol-1-yl)acetamide (0.68 g, 1.3 mmol) yielded compound 137 in table 4 (0.232 g, 31% yield) as a white solid:

$^1$H-NMR (DMSO $d_6$): 10.28 (s, 1H), 9.95 (s, 1H), 8.57 (s, 1H), 8.36 (d, 1H), 8.34 (s, 1H), 7.78 (s, 1H), 7.71 (m, 1H), 7.21 (m, 4H), 5.15 (s, 2H), 4.50 (t, 1H), 4.22 (t, 2H), 4.09 (d, 2H), 3.45 (br s, 2H), 3.34 (br s, 2H), 2.50 (t, 2H under DMSO), 2.38 (br s, 4H), 1.95 (m, 2H); MS (−ve ESI): 579 $(M-H)^-$.

EXAMPLE 138

Preparation of Compound 138 in Table 4—N-(2,3-difluorophenyl)-2-(4-{[7-(3-{[trans-2-(hydroxymethyl)cyclohexyl]amino}propoxy)quinazolin-4-yl]amino}-1H-pyrazol-1-yl)acetamide A mixture of 2-(4-{[7-(3-chloropropoxy)quinazolin-4-yl]amino}-1H-pyrazol-1-yl)-N-(2,3-difluorophenyl)acetamide hydrochloride (0.25 g, 0.49 mmol), trans-2-(hydroxymethyl)cyclohexylamine hydrochloride (0.242 g, 1.5 mmol) diisopropylethylamine (0.44 ml, 2.5 mmol) and potassium iodide (0.249 g, 1.5 mmol) in dimethylacetamide (5 ml) was heated at 80° C. for 1 hour and then at 125° C. overnight. The solvent was evaporated and the residue was purified directly by reverse phase chromatography eluting with a mixture of 5 to 95% acetonitrile (containing 0.2% trifluoroacetic acid) in water (containing 0.2% trifluoroacetic acid). The fractions containing product were combined and then evaporated to approximately quarter volume and the aqueous solution was made basic by the dropwise addition of concentrated sodium hydroxide. The resultant precipitate was filtered, washed with water and allowed to dry in air to give compound 138 in table 4 (0.142 g, 51% yield):

$^1$H-NMR (DMSO $d_6$): 10.26 (s, 1H), 9.90 (s, 1H), 8.53 (s, 1H), 8.34 (d, 1H), 8.33 (s, 1H), 7.77 (s, 1H), 7.68-7.75 (m, 1H), 7.15-7.24 (m, 3H), 7.12 (d, 1H), 5.14 (s, 2H), 4.18 (t, 2H), 3.47 (dd, 1H), 3.36 (dd, 1H), 2.82-2.92 (m, 1H), 2.53-2.63 (m, 1H), 2.15-2.28 (m, 1H), 1.97-2.06 (m, 1H), 1.82-1.93 (m, 2H), 1.54-1.70 (m, 3H), 0.80-1.35 (m, 5H); MS (+ve ESI): 566 $(M+H)^+$.

EXAMPLE 139

Preparation of Compound 139 in Table 4—N-(2,3-difluorophenyl)-2-{4-[(7-{3-[(1α,5α,6α)-6-(hydroxymethyl)-3-azabicyclo[3.1.0]hex-3-yl]propoxy}quinazolin-4-yl)amino]-1H-pyrazol-1-yl}acetamide A mixture of 2-(4-{[7-(3-chloropropoxy)quinazolin-4-yl]amino}-1H-pyrazol-1-yl)-N-(2,3-difluorophenyl)acetamide hydrochloride (0.738 g, 1.45 mmol), (1α,5α,6α)-3-azabicyclo[3.1.0]hexane-6-methanol (see *Synlett,* 1996, 11, 1097-1099, 0.149 g, 1.32 mmol), diisopropylethylamine (0.51 ml, 2.9 mmol) and potassium iodide (0.241 g, 1.45 mmol) in dimethylacetamide (5 ml) was heated at 80° C. for 4 hours. A further portion of diisopropylethylamine (0.25 ml) was added and the mixture heated at 80° C. for a further 2 hours. The mixture was allowed to cool to room temperature and then diluted with dichloromethane and purified directly by silica gel chromatography eluting with a 0 to 10% mixture of methanol (containing 10% 7M ammonia in methanol) in dichloromethane to give compound 139 in table 4 (0.320 g, 44% yield):

$^1$H-NMR (DMSO $d_6$): 10.27 (s, 1H), 9.91 (s, 1H), 8.55 (s, 1H), 8.36 (d, 1H), 8.35 (s, 1H), 7.79 (s, 1H), 7.70-7.75 (m, 1H), 7.17-7.24 (m, 3H), 7.12 (d, 1H), 5.16 (s, 2H), 4.34 (t, 1H), 4.15 (t, 2H), 3.22 (t, 2H), 2.98 (d, 2H), 2.55 (t, 2H), 2.26 (d, 2H), 1.85-1.93 (m, 2H), 1.22-1.27 (m, 3H); MS (+ve ESI): 550 $(M+H)^+$.

EXAMPLE 140

Preparation of Compound 140 in Table 4—N-(2,3-difluorophenyl)-2-(4-{[7-(3-{[(2R)-2-hydroxypropyl]amino}propoxy)quinazolin-4-yl]amino}-1H-pyrazol-1-yl)acetamide An analogous reaction to that described in example 122 but starting with (2R)-1-aminopropan-2-ol (0.150 g, 2.0 mmol). After chromatography the obtained solids were triturated with hot acetonitrile and then with diethyl ether to yield compound 140 in table 4 (0.035 g, 14% yield):

$^1$H-NMR (DMSO $d_6$+acetic acid $d_4$): 8.54 (s, 1H), 8.30-8.40 (m, 2H), 7.78 (s, 1H), 7.65-7.77 (m, 1H), 7.10-7.25 (m, 4H), 5.14 (s, 2H), 4.17-4.27 (m, 2H), 3.85-3.98 (m, 1H), 3.03-3.14 (t, 2H), 2.92-3.01 (m, 1H), 2.71-2.81 (m, 1H), 2.08-2.21 (m, 2H), 1.11 (d, 3H); MS (+ve ESI): 512 $(M+H)^+$.

EXAMPLE 141

Preparation of Compound 141 in Table 4—N-(2,3-difluorophenyl)-2-(4-{[7-(3-{[(1S)-2-hydroxy-1-methylethyl]amino}propoxy)quinazolin-4-yl]amino}-1H-pyrazol-1-yl)acetamide An analogous reaction to that described in example 140 but starting with (2S)-2-aminopropan-1-ol (0.150 g, 2.0 mmol) yielded compound 141 in table 4 (0.090 g, 35% yield):

$^1$H-NMR (DMSO $d_6$+acetic acid $d_4$): 8.55 (s, 1H), 8.37 (d, 1H), 8.33 (s, 1H), 7.79 (s, 1H), 7.67-7.75 (m, 1H), 7.11-7.25 (m, 4H), 5.14 (s, 2H), 4.24 (t, 2H), 3.66 (dd, 1H), 3.46 (dd, 1H), 3.23-3.35 (m, 1H), 3.14 (t, 2H), 2.09-2.21 (m, 2H), 1.20 (d, 3H); MS (+ve ESI): 512 $(M+H)^+$.

EXAMPLE 142

Preparation of Compound 142 in Table 4—N-(2,3-difluorophenyl)-2-{4-[(7-{3-[(2-hydroxy-1,1-dimethylethyl)amino]propoxy}quinazolin-4-yl)amino]-1H-pyrazol-1-yl}acetamide A mixture of 2-(4-{[7-(3-chloropropoxy)quinazolin-4-yl]amino}-1H-pyrazol-1-yl)-N-(2,3-difluorophenyl)acetamide hydrochloride (0.25 g, 0.49 mmol), diisopropylethylamine (0.171 ml, 0.98 mmol), 2-amino-2-methylpropanol (0.13 g, 1.47 mmol) and potassium iodide (0.16 g, 0.98 mmol) in dimethylacetamide (3 ml) was heated at 75° C. for 16 hours. The reaction mixture was diluted with a mixture of dimethylsulphoxide:acetonitrile:water (7:2:1, 3 ml) and purified by reverse phase chromatography eluting with 0.2% aqueous trifluoroacetic acid in acetonitrile using a 5 to 50% gradient over 25 minutes. The appropriate fractions were concentrated under reduced pressure and then basified with aqueous sodium carbonate. The product was extracted into ethyl acetate, dried over magnesium sulphate, filtered and evaporated under reduced pressure to give compound 142 in table 4 (0.23 g, 90% yield) as a cream coloured solid.

$^1$H-NMR (DMSO $d_6$): 10.35 (br s, 1H), 9.98 (s, 1H), 8.55 (s, 1H), 8.35 (m, 2H), 7.85 (s, 1H), 7.65 (m, 1H), 7.15 (m, 4H), 5.15 (s, 2H), 4.20 (t, 2H), 2.70 (m, 2H), 2.50 (m, 4H) under DMSO, 1.95 (m, 2H), 1.0 (m, 6H); MS (+ve ESI): 526 $(M+H)^+$ MS (−ve ESI): 524 $(M-H)^-$.

EXAMPLE 143

Preparation of Compound 143 in Table 4—N-(2,3-difluorophenyl)-2-{4-[(7-{3-[(2,3-dihydroxypropyl)amino]propoxy}quinazolin-4-yl)amino]-1H-pyrazol-1-yl}acetamide An analogous reaction to that described in example 142 but starting with (±)-3-amino-1,2-propanediol (0.16 g, 1.47 mmol) yielded compound 143 in table 4 (0.05 g, 19% yield):

$^1$H-NMR (DMSO $d_6$): 10.35 (br s, 1H), 9.90 (s, 1H), 8.50 (s, 1H), 8.40 (m, 2H), 7.80 (s, 1H), 7.70 (m, 1H), 7.20 (m, 4H), 5.20 (s, 2H), 4.25 (t, 2H), 3.50 (m, 4H), 2.75 (t, 2H), 2.6 (m, 1H), 1.90 (m, 2H); MS (+ve ESI): 528 $(M+H)^+$ MS (−ve ESI): 526 $(M-H)^-$.

EXAMPLE 144

Preparation of Compound 144 in Table 4—N-(2,3-difluorophenyl)-2-(4-{[7-(3-{[2-(2-hydroxyethoxy)ethyl]amino}propoxy)quinazolin-4-yl]amino}-1H-pyrazol-1-yl)acetamide A mixture of 2-(4-{[7-(3-chloropropoxy)quinazolin-4-yl]amino}-1H-pyrazol-1-yl)-N-(2,3-difluorophenyl)acetamide hydrochloride (0.25 g, 0.49 mmol), diisopropylethylamine (0.171 ml, 0.98 mmol), 2-(2-aminoethoxy)-ethanol (0.155 g, 1.47 mmol) and potassium iodide (0.16 g, 0.98 mmol) in dimethylacetamide (3 ml) was heated at 75° C. for 16 hours. The reaction mixture was diluted with dimethylsulphoxide:acetonitrile:water (7:2:1, 3 ml) and purified by reverse phase chromatography eluting with 0.2% aqueous trifluoroacetic acid in acetonitrile using a 5 to 50% gradient over 25 minutes. The appropriate fractions were concentrated under reduced pressure and then basified with aqueous sodium carbonate. The resultant precipitate was filtered, washed with water and then dried under vacuum at 60° C. to give compound 144 in table 4 (0.195 g, 73% yield) as a white solid:

$^1$H-NMR (DMSO $d_6$): 10.35 (br s, 1H), 9.90 (br s, 1H), 8.50 (s, 1H), 8.40 (m, 2H), 7.80 (s, 1H), 7.70 (m, 1H), 7.20 (m, 4H), 5.20 (s, 2H), 4.60 (br s, 1H), 4.25 (t, 2H), 3.50 (m, 4H), 3.30 (m, 2H), 2.65 (m, 4H), 1.90 (m, 2H); MS (+ve ESI): 542 $(M+H)^+$ MS (−ve ESI): 540 $(M-H)^-$.

EXAMPLE 145

Preparation of Compound 145 in Table 4—2-[4-({7-[3-(4-acetylpiperazin-1-yl)propoxy]quinazolin-4-yl}amino)-1H-pyrazol-1-yl]-N-(2,3-difluorophenyl)acetamide An analogous reaction to that described in example 144 but starting with 1-acetylpiperazine (0.188 g, 1.47 mmol) yielded compound 145 in table 4 (0.25 g, 91% yield):

$^1$H-NMR (DMSO $d_6$): 10.35 (br s, 1H), 9.90 (s, 1H), 8.50 (s, 1H), 8.40 (m, 2H), 7.80 (s, 1H), 7.70 (m, 1H), 7.20 (m, 4H), 5.20 (s, 2H), 4.25 (t, 2H), 3.50 (m, 4H), 3.30 (m, 2H), 2.40 (m, 2H), 2.30 (m, 2H), 1.98 (s, 3H), 1.90 (m, 2H); MS (+ve ESI): 565 $(M+H)^+$ MS (−ve ESI): 563 $(M-H)^-$.

EXAMPLE 146

Preparation of Compound 146 in Table 4—N-(2,3-difluorophenyl)-2-{4-[(7-{3-[(tetrahydrofuran-2-ylmethyl)amino]propoxy}quinazolin-4-yl)amino]-1H-pyrazol-1-yl}acetamide An analogous reaction to that described in example 144 but starting with (tetrahydrofuran-2-ylmethyl)amine (0.152 g, 1.47 mmol) yielded compound 146 in table 4 (0.19 g, 73% yield):

$^1$H-NMR (DMSO $d_6$): 10.0 (br s, 1H), 8.50 (s, 1H), 8.40 (m, 2H), 7.80 (s, 1H), 7.70 (m, 1H), 7.20 (m, 4H), 5.20 (s, 2H), 4.25 (t, 2H), 3.90 (m, 1H), 3.70 (m, 1H), 3.60 (m, 1H), 2.80 (t, 2H), 2.55 (m, 2H), 1.80 (m, 3H), 1.70 (m, 2H), 1.65 (m, 1H), 1.50 (m, 1H); MS (+ve ESI): 538 $(M+H)^+$ MS (−ve ESI): 536 $(M-H)^-$.

EXAMPLE 147

Preparation of Compound 147 in Table 4—2-[4-({7-[3-(allylamino)propoxy]quinazolin-4-yl}amino)-1H-pyrazol-1-yl]-N-(2,3-difluorophenyl)acetamide An analogous reaction to that described in example 142 but starting with allylamine (0.084 g, 1.47 mmol) yielded compound 147 in table 4 (0.117 g, 48% yield):

$^1$H-NMR (DMSO $d_6$): 11.0 (br s, 1H), 10.40 (br s, 1H), 8.90 (s, 1H), 8.60 (m, 1H), 8.40 (s, 1H), 7.90 (s, 1H), 7.70 (m, 1H), 7.40 (m, 1H), 7.20 (m, 3H), 5.95 (m, 1H), 5.50 (m, 2H), 5.20 (s, 2H), 4.25 (t, 2H), 3.80 (m, 2H), 3.15 (m, 2H), 2.15 (m, 2H); MS (+ve ESI): 494 $(M+H)^+$ MS (−ve ESI): 492 $(M-H)^-$.

EXAMPLE 148

Preparation of Compound 148 in Table 4—N-(2,3-difluorophenyl)-2-(4-{[7-(3-{[1-(hydroxymethyl)-2-methylpropyl]amino}propoxy)quinazolin-4-yl]amino}-1H-pyrazol-1-yl)acetamide An analogous reaction to that described in example 144 but starting with (±) valinol (0.152 g, 1.47 mmol) yielded compound 148 in table 4 (0.137 g, 52% yield):

$^1$H-NMR (DMSO $d_6$): 10.35 (br s, 1H), 9.90 (s, 1H), 8.55 (s, 1H), 8.30 (m, 2H), 7.80 (s, 1H), 7.70 (m, 1H), 7.20 (m, 4H), 5.20 (s, 2H), 4.35 (br s, 1H), 4.25 (t, 2H), 3.40 (m, 1H), 3.30 (m, 1H), 2.70 (m, 2H), 2.30 (m, 1H), 1.90 (m, 2H), 1.85 (m, 1H), 1.50 (br s, 1H), 0.85 (m, 6H); MS (+ve ESI): 540(M+H)$^+$.

EXAMPLE 149

Preparation of Compound 149 in Table 4 N-(2,3-difluorophenyl)-2-(4-{[7-(3-{[(5-methylisoxazol-3-yl)methyl]amino}propoxy)quinazolin-4-yl]amino}-1H-pyrazol-1-yl)acetamide An analogous reaction to that described in example 144 but starting with [(5-methylisoxazol-3-yl)methyl]amine (0.166 g, 1.47 mmol) yielded compound 149 in table 4 (0.124 g, 46% yield):

$^1$H-NMR (DMSO $d_6$): 10.35 (br s, 1H), 9.90 (br s, 1H), 8.55 (s, 1H), 8.30 (m, 2H), 7.80 (s, 1H), 7.70 (m, 1H), 7.20 (m, 4H), 6.20 (s, 1H), 5.20 (s, 2H), 4.25 (t, 2H), 3.60 (s, 2H), 2.70 (m, 2H), 2.30 (s, 3H), 2.20 (br s, 1H), 1.90 (m, 2H); MS (+ve ESI): 549 (M+H)$^+$ MS (−ve ESI): 547 (M−H)$^-$.

EXAMPLE 150

Preparation of Compound 150 in Table 4 N-(2,3-difluorophenyl)-2-[4-({7-[3-(tetrahydro-2H-pyran-4-ylamino)propoxy]quinazolin-4-yl}amino)-1H-pyrazol-1-yl]acetamide An analogous reaction to that described in example 144 but starting with tetrahydro-2H-pyran-4-amine (0.150 g, 1.47 mmol) yielded compound 150 in table 4 (0.149 g, 56% yield):

$^1$H-NMR (DMSO $d_6$): 10.35 (br s, 1H), 9.90 (br s, 1H), 8.55 (s, 1H), 8.30 (m, 2H), 7.80 (s, 1H), 7.70 (m, 1H), 7.20 (m, 4H), 5.20 (s, 2H), 4.25 (t, 2H), 3.80 (m, 2H), 2.70 (m, 2H), 2.60 (m, 1H), 1.90 (m, 2H), 1.70 (m, 2H), 1.60 (br s, 1H), 1.20 (m, 2H); MS (+ve ESI): 538 (M+H)$^+$ MS (−ve ESI): 536 (M−H)$^-$.

EXAMPLE 151 AND 152

Preparation of Compound 151 in Table 4—N-(2,3-difluorophenyl)-2-{4-[(7-{3-[(3S)-3-(hydroxymethyl)pyrrolidin-1-yl]propoxy}quinazolin-4-yl)amino]-1H-pyrazol-1-yl}acetamide and compound 152 in table 4—N-(2,3-difluorophenyl)-2-(4-{[7-(3-hydroxypropoxy)quinazolin-4-yl]amino}-1H-pyrazol-1-yl)acetamide An analogous reaction to that described in example 144 but starting with (3S)-pyrrolidin-3-ylmethanol (0.150 g, 1.47 mmol) yielded compound 151 in table 4 eluted first (0.075 g, 28% yield):

$^1$H-NMR (DMSO $d_6$): 10.30 (br s, 1H), 9.90 (br s, 1H), 8.55 (s, 1H), 8.30 (m, 2H), 7.80 (s, 1H), 7.70 (m, 1H), 7.20 (m, 4H), 5.20 (s, 2H), 4.25 (t, 2H), 3.80 (m, 2H), 2.50 (m, 5H), 2.30 (m, 1H), 2.20 (m, 1H), 1.90 (m, 2H), 1.80 (m, 1H), 1.40 (m, 1H); MS (+ve ESI): 538 (M+H)$^+$ MS (−ve ESI): 536 (M−H)$^-$.

and compound 152 in table 4 eluted second (0.027 g, 12% yield):

$^1$H-NMR (DMSO $d_6$): 8.55 (s, 1H), 8.35 (m, 2H), 7.80 (s, 1H), 7.70 (m, 1H), 7.20 (m, 4H), 5.20 (s, 2H), 4.25 (t, 2H), 3.60 (t, 2H), 1.95 (m, 2H); MS (+ve ESI): 455 (M+H)$^+$ MS (−ve ESI): 453 (M−H)$^-$.

(3S)-pyrrolidin-3-ylmethanol used as Starting Material, was Prepared as Follows a) tert-Butyl (3S)-3-(hydroxymethyl)pyrrolidine-1-carboxylate (0.9 g, 4.48 mmol), was dissolved in dichloromethane (10 ml) and trifluoroacetic acid (2 ml) was added. The reaction mixture was stirred for 16 hours at ambient temperature. The reaction mixture was concentrated under reduced pressure and then co-evaporated with toluene. The residue was dissolved in methanol (20 ml) and then macroporous carbonate (3 g) was added and the heterogeneous mixture was stirred for 16 hours at ambient temperature to give a pH 9 mixture. The mixture was filtered and the filtrate was concentrated under reduced pressure to give (3S)-pyrrolidin-3-ylmethanol as an oil which was used without further purification:

$^1$H-NMR (DMSO $d_6$): 3.25 (m, 2H), 3.10 (m, 3H), 2.85 (m, 1H), 2.30 (m, 1H), 1.90 (m, 1H), 1.60 (m, 1H); MS (+ve ESI): 101 (M+H)$^+$.

EXAMPLE 153

Preparation of Compound 153 in Table 4—2-(4-{[7-(3-aminopropoxy)quinazolin-4-yl]amino}-1H-pyrazol-1-yl)-N-(2,3-difluorophenyl)acetamide N-(2,3-difluorophenyl)-2-[4-({7-[3-(1,3-dioxo-1,3-dihydro-2H-isoindol-2-yl)propoxy]quinazolin-4-yl}amino)-1H-pyrazol-1-yl]acetamide (0.214 g, 0.37 mmol) was dissolved in ethanol (10 ml). Hydrazine hydrate (2.2 mmol) was added and the mixture was heated at 80° C. for 16 hours. The reaction mixture was concentrated, diluted with a mixture of dimethylsulphoxide:acetonitrile:water (7:2:1, 3 ml) and then purified by reverse phase chromatography eluting with 0.2% aqueous trifluoroacetic acid in acetonitrile using a 5 to 50% gradient over 25 minutes. The fractions containing product were concentrated under reduced pressure and then basified with aqueous sodium carbonate. The resultant precipitate was filtered, washed with water and dried under vacuum at 60° C. to give compound 153 in table 4 (0.086 g, 52% yield) as a white solid:

$^1$H-NMR (DMSO $d_6$): 10.0 (br s, 1H), 8.55 (s, 1H), 8.30 (m, 2H), 7.80 (s, 1H), 7.70 (m, 1H), 7.20 (m, 4H), 5.20 (s, 2H), 4.20 (t, 2H), 2.70 (t, 2H), 1.80 (m, 2H); MS (+ve ESI): 454 (M+H)$^+$ MS (−ve ESI): 452 (M−H)$^-$.

N-(2,3-difluorophenyl)-2-[4-({7-[3-(1,3-dioxo-1,3-dihydro-2H-isoindol-2-yl)propoxy]quinazolin-4-yl}amino)-1H-pyrazol-1-yl]acetamide used as Starting Material, was Prepared as Follows a) A mixture of 2-(4-{[7-(3-chloropropoxy)quinazolin-4-yl]amino}-1H-pyrazol-1-yl)-N-(2,3-difluorophenyl)acetamide hydrochloride (0.25 g, 0.49 mmol), potassium phthalimide (0.109 g, 0.59 mmol), potassium carbonate (0.081 g, 0.59 mmol) and potassium iodide (0.098 g, 0.59 mmol) in dimethylacetamide (2 ml) was heated at 75° C. for 16 hours. The reaction mixture was allowed to cool to room temperature. Aqueous sodium hydrogen carbonate was added to the mixture and the resultant precipitate was filtered and washed with water, acetonitrile then diethyl ether to give N-(2,3-difluorophenyl)-2-[4-({7-[3-(1,3-dioxo-1,3-dihydro-2H-isoindol-2-yl)propoxy]quinazolin-4-yl}amino)-1H-pyrazol-1-yl]acetamide (0.214 g, 75% yield):

$^1$H-NMR (DMSO $d_6$): 10.0 (br s, 1H), 8.55 (s, 1H), 8.30 (m, 2H), 7.85 (m, 3H), 7.80 (s, 1H), 7.70 (m, 1H), 7.20 (m,

2H), 7.05 (m, 1H), 6.95 (m, 1H), 5.20 (s, 2H), 4.20 (t, 2H), 3.80 (t, 2H), 2.15 (m, 2H); MS (+ve ESI): 584 $(M+H)^+$ MS (−ve ESI): 582 $(M-H)^-$.

EXAMPLE 154

Preparation of Compound 154 in Table 4—N-(2,3-difluorophenyl)-2-{4-[(7-{3-[(2S,4R)-4-hydroxy-2-(hydroxymethyl)pyrrolidin-1-yl]propoxy}quinazolin-4-yl)amino]-1H-pyrazol-1-yl}acetamide An analogous reaction to that described in example 144 but starting with (3R, 5S)-5-(hydroxymethyl)pyrrolidin-3-ol (0.150 g, 1.0 mmol) yielded compound 154 in table 4 (0.138 g, 50% yield):

$^1$H-NMR (DMSO $d_6$): 10.0 (br s, 1H), 8.55 (s, 1H), 8.30 (m, 2H), 7.80 (s, 1H), 7.70 (m, 1H), 7.20 (m, 4H), 5.20 (s, 2H), 4.70 (br s, 1H), 4.30 (br s, 1H), 4.20 (m, 4H), 3.10 (m, 2H), 2.95 (m, 1H), 2.60 (m, 1H), 2.40 (m, 1H), 2.10 (m, 1H), 1.90 (m, 2H), 1.70 (m, 2H); MS (+ve ESI): 554 $(M+H)^+$ MS (−ve ESI): 552 $(M-H)^-$.

EXAMPLE 155

Preparation of Compound 155 in Table 4—N-(2,3-difluorophenyl)-2-{4-[(7-{2-[(3-hydroxy-2,2-dimethylpropyl)amino]ethoxy}quinazolin-4-yl)amino]-1H-pyrazol-1-yl}acetamide A mixture of 2-(4-{[7-(2-chloroethoxy)quinazolin-4-yl]amino}-1H-pyrazol-1-yl)-N-(2,3-difluorophenyl)acetamide hydrochloride (0.20 g, 0.38 mmmol), triethylamine (0.15 ml, 1.13 mmol), 3-amino-2,2-dimethylpropan-1-ol (0.117 g, 1.13 mmol) and potassium iodide (0.126 g, 0.76 mmol) in dimethylacetamide (3 ml) was heated at 90° C. for 1 hour. The mixture was diluted with dichloromethane and then filtered. The filtrate was purified directly by silica gel chromatography eluting with a 0 to 10% mixture of methanol (containing 10% 7N ammonia in methanol) in dichloromethane. The obtained product was triturated with acetonitrile and then with diethyl ether to give compound 155 in table 4 (0.089 g, 65% yield) as a cream coloured solid:

$^1$H-NMR (DMSO $d_6$): 10.28 (br s, 1H), 9.98 (s, 1H), 8.57 (s, 1H), 8.39 (d, 1H), 8.35 (s, 1H), 7.79 (s, 1H), 7.70 (t, 1H), 7.22 (m, 4H), 5.15 (s, 2H), 4.43 (t, 2H), 3.43 (t, 2H), 3.33 (s, 1H), 3.00 (s, 2H), 2.50 (s, 2H under DMSO), 0.97 (s, 6H); MS (+ve ESI): 526 $(M+H)^+$ MS (−ve ESI): 524 $(M-H)^-$.

EXAMPLE 156

Preparation of Compound 156 in Table 4—2-{4-[(7-{2-[cyclohexyl(2-hydroxyethyl)amino]ethoxy}quinazolin-4-yl)amino]-1H-pyrazol-1-yl}-N-(2,3-difluorophenyl)acetamide An analogous reaction to that described in example 155 but starting with 2-(cyclohexylamino)ethanol (0.162 g, 1.13 mmol) yielded compound 156 in table 4 (0.045 g, 21% yield):

$^1$H-NMR (DMSO $d_6$ at 373K): 9.89 (s, 1H), 9.68 (s, 1H), 8.57 (s, 1H), 8.35 (d, 1H), 8.31 (s, 1H), 7.79 (s, 1H), 7.72 (m, 1H), 7.22 (m, 4H), 5.15 (s, 2H), 4.23 (t, 2H), 3.53 (t, 2H), 3.08 (t, 2H under water), 2.82 (s, 2H), 1.87 (m, 4H), 1.65 (d, 1H), 1.32 (m, 6H); MS (+ve ESI): 566 $(M+H)^+$ MS (−ve ESI): 564 $(M-H)^-$.

EXAMPLE 157

Preparation of Compound 157 in Table 4—2-[4-({7-[2-(cyclopropylamino)ethoxy]quinazolin-4-yl}amino)-1H-pyrazol-1-yl]-N-(2,3-difluorophenyl)acetamide An analogous reaction to that described in example 155 but starting with cyclopropyl amine (0.4 g, 6.8 mmol) yielded compound 157 in table 4 (0.18 g, 44% yield):

$^1$H-NMR (DMSO $d_6$): 10.27 (br s, 1H), 9.95 (s, 1H), 8.57 (s, 1H), 8.39 (d, 1H), 8.31 (s, 1H), 7.79 (s, 1H), 7.72 (m, 1H), 7.22 (m, 3H), 5.15 (s, 2H), 4.36 (t, 2H), 3.42 (t, 2H), 2.70 (m, 1H), 0.70 (d, 4H); MS (+ve ESI) 480 $(M+H)^+$ MS (−ve ESI): 478 $(M-H)^-$.

EXAMPLE 158

Preparation of Compound 158 in Table 4—2-[4-({7-[2-(cyclobutylamino)ethoxy]quinazolin-4-yl}amino)-1H-pyrazol-1-yl]-N-(2,3-difluorophenyl)acetamide An analogous reaction to that described in example 155 but starting with cyclobutyl amine (0.5 g, 6.8 mmol) yielded compound 158 in table 4 (0.225 g, 54% yield):

$^1$H-NMR (DMSO $d_6$): 10.27 (br s, 1H), 9.95 (s, 1H), 8.57 (s, 1H), 8.39 (d, 1H), 8.31 (s, 1H), 7.79 (s, 1H), 7.72 (m, 1H), 7.22 (m, 3H), 5.15 (s, 2H), 4.33 (t, 2H), 3.66 (m, 1H), 3.17 (t, 2H), 2.20 (m, 2H), 2.02 (m, 2H), 1.77 (m, 2H); MS (+ve ESI) 494 $(M+H)^+$ MS (−ve ESI): 492 $(M-H)^-$.

EXAMPLE 159

Preparation of Compound 159 in Table 4—N-(2,3-difluorophenyl)-2-[4-({7-[2-(tetrahydro-2H-pyran-4-ylamino)ethoxy]quinazolin-4-yl}amino)-1H-pyrazol-1-yl]acetamide An analogous reaction to that described in example 155 but starting with 4-aminoterahydro-2H-pyran (0.68 g, 6.8 mmol) yielded compound 159 in table 4 (0.078 g, 18% yield):

$^1$H-NMR (DMSO $d_6$): 10.27 (br s, 1H), 9.95 (s, 1H), 8.57 (s, 1H), 8.39 (d, 1H), 8.33 (s, 1H), 7.79 (s, 1H), 7.72 (m, 1H), 7.22 (m, 4H), 5.15 (s, 2H), 4.39 (t, 2H), 3.88 (m, 2H), 3.34 (2H under water), 3.00 (t, 2H), 2.71 (m, 1H), 1.80 (m, 2H), 1.28 (m, 2H); MS (+ve ESI) 524 $(M+H)^+$ MS (−ve ESI): 522 $(M-H)^-$.

EXAMPLE 160

Preparation of Compound 160 in Table 4—2-[4-({7-[2-(cyclopentylamino)ethoxy]quinazolin-4-yl}amino)-1H-pyrazol-1-yl]-N-(2,3-difluorophenyl)acetamide An analogous reaction to that described in example 155 but starting with cyclopentyl amine (1.9 g, 22.4 mmol) yielded compound 160 in table 4 (0.640 g, 45% yield):

$^1$H-NMR (DMSO $d_6$): 10.27 (br s, 1H), 9.95 (s, 1H), 8.57 (s, 1H), 8.38 (d, 1H), 8.33 (s, 1H), 7.79 (s, 1H), 7.72 (m, 1H), 7.22 (m, 4H), 5.15 (s, 2H), 4.29 (t, 2H), 3.34 (1H under water), 3.13 (s, 2H), 1.87 (m, 2H), 1.69 (m, 2H), 1.50 (m, 4H); MS (+ve ESI) 508 $(M+H)^+$ MS (−ve ESI): 506 $(M-H)^-$.

EXAMPLE 161

Preparation of Compound 161 in Table 4—N-(2,3-difluorophenyl)-2-{4-[(7-{2-[(2-hydroxyethyl)(tetrahydro-2H-pyran-4-yl)amino]ethoxy}quinazolin-4-yl)amino]-1H-pyrazol-1-yl}acetamide An analogous reaction to that described in example 155 but starting with 2-(tetrahydro-2H-pyran-4-ylamino)ethanol (0.569 g, 3.93 mmol) yielded compound 161 in table 4 (0.391 g, 53% yield):

$^1$H-NMR (DMSO $d_6$): 10.28 (s, 1H), 9.91 (s, 1H), 8.54 (s, 1H), 8.36 (d, 1H), 8.35 (s, 1H), 7.78 (s, 1H), 7.72 (m, 1H), 7.20 (m, 4H), 5.16 (s, 2H), 4.29 (t, 1H), 4.14 (t, 2H), 3.89 (m, 2H), 3.42 (m, 2H), 3.25 (m, 2H), 2.94 (t, 2H), 2.76 (m, 1H), 2.65 (t, 2H), 1.65 (m, 2H), 1.45 (m, 2H); MS (+ve ESI): 568 $(M+H)^+$.

2-(tetrahydro-2H-pyran-4-ylamino)ethanol used as a Starting Material, was Prepared as Follows a) A mixture of ethanolamine (1.76 ml, 0.029 mmol) and tetrahydro-4H-pyran-4-one (3.5 g, 0.035 mmol) in ethanol (30 ml) was stirred at ambient temperature for 30 minutes. The reaction mixture was cooled in ice and then sodium borohydride (1.33 g, 0.035 mmol) was added slowly over 20 minutes. The mixture was stirred for a further 15 minutes and then water (10 ml) was added. The mixture was evaporated under reduced pressure and the residue dissolved in dichloromethane and dried over magnesium sulphate and then evaporated under reduced pressure. The residue was purified by silica gel chromatography eluting with a 0 to 15% mixture of methanol (containing 10% 7N ammonia in methanol) in dichloromethane to give 2-(tetrahydro-2H-pyran-4-ylamino) ethanol (1.25 g, 30% yield) as a clear oil:

$^1$H-NMR ($CDCl_3$): 4.00 (m, 2H), 3.66 (t, 2H), 3.42 (m, 2H), 2.83 (t, 2H), 2.70 (m, 1H), 1.88 (m, 2H), 1.43 (m, 2H); MS (+ve ESI) 146 $(M+H)^+$.

EXAMPLE 162

Preparation of Compound 162 in Table 4—2-{4-[(7-{2-[cyclopentyl(2-hydroxyethyl)amino]ethoxy}quinazolin-4-yl)amino]-1H-pyrazol-1-yl}-N-(2,3-difluorophenyl)acetamide A mixture of 2-(4-{[7-(2-chloroethoxy)quinazolin-4-yl]amino}-1H-pyrazol-1-yl)-N-(2,3-difluorophenyl)acetamide hydrochloride (0.25 g, 0.47 mmol), triethylamine (0.2 ml, 1.41 mmol), 2-(cyclopentylamino)ethanol (0.121 g, 0.094 mmol) and potassium iodide (0.156 g, 0.94 mmol) in dimethylacetamide (3 ml) was heated at 90° C. for 1 hour. The mixture was diluted with dimethylacetamide and then filtered. The filtrate was purified directly by reverse phase chromatography eluting with a 5 to 95% mixture of acetonitrile (containing 0.2% trifluoroacetic acid) in water (containing 0.2% trifluoroacetic acid). The fractions containing product were concentrated to half volume and then sodium carbonate (1.5 g) was added. The resultant precipitate was filtered and dried to give compound 162 in table 4 (0.027 g, 10% yield) as a off white solid:

$^1$H-NMR (DMSO $d_6$): 8.54 (s, 1H), 8.36 (d, 1H), 8.33 (s, 1H), 7.77 (s, 1H), 7.70 (m, 1H), 7.17 (m, 4H), 5.13 (s, 2H), 4.16 (t, 2H), 3.45 (t, 2H), 3.14 (m, 1H under water), 2.91 (t, 2H), 2.64 (t, 2H), 1.78 (m, 2H), 1.61 (m, 2H), 1.50 (m, 2H), 1.34 (m, 2H); MS (+ve ESI): 552$(M+H)^+$ MS (−ve ESI): 550 $(M-H)^-$.

2-(cyclopentylamino)ethanol used as a Starting Material, was Prepared as Follows a) A mixture of ethanolamine (4 ml, 0.066 mmol) and cyclopentanone (6.85 ml, 0.08 mmol) in ethanol (60 ml) was stirred at ambient temperature for 30 minutes. The mixture was cooled in ice and then sodium borohydide (3.04 g, 0.08 mmol) was added slowly over 20 minutes. The mixture was stirred for 15 minutes before water (10 ml) was added. The mixture was evaporated under reduced pressure and the residue dissolved in dichloromethane and dried over magnesium sulphate and then evaporated under reduced pressure. The crude product was purified by vacuum distillation to give 2-(cyclopentylamino)ethanol (3 g, 35% yield) as a clear oil:

$^1$H-NMR ($CDCl_3$): 3.63 (t, 2H), 3.07 (quintet, 1H), 2.77 (t, 2H), 1.83 (m, 2H), 1.68 (m, 2H), 1.56 (m, 2H), 1.34 (m, 2H).

EXAMPLE 163

Preparation of Compound 163 in Table 4—N-(2,3-difluorophenyl)-2-{4-[(7-{2-[(2R)-2-(hydroxymethyl)pyrrolidin-1-yl]ethoxy}quinazolin-4-yl)amino]-1H-pyrazol-1-yl}acetamide An analogous reaction to that described in example 162 but starting with (2R)-pyrrolidin-2ylmethanol (0.16 g, 1.6 mmol) to give compound 163 in table 4 (0.105 g, 37% yield):

$^1$H-NMR (DMSO $d_6$+$CD_3COOH$): 8.90 (s, 1H), 8.57 (d, 1H), 8.37 (s, 1H), 7.93 (s, 1H), 7.70 (m, 1H), 7.48 (d, 1H), 7.28 (s, 1H), 7.18 (m, 2H), 5.20 (s, 2H), 4.58 (s, 2H), 3.66 (m, 7H), 1.92 (m, 4H); MS (+ve ESI) 524 $(M+H)^+$ MS (−ve ESI): 522 $(M-H)^-$.

EXAMPLE 164

Preparation of Compound 164 in Table 4—2-{4-[(7-{2-[cyclopropyl(2-hydroxyethyl)amino]ethoxy}quinazolin-4-yl)amino]-1H-pyrazol-1-yl}-N-(2,3-difluorophenyl)acetamide A mixture of 2-[4-({7-[2-(cyclopropylamino)ethoxy]quinazolin-4-yl}amino)-1H-pyrazol-1-yl]-N-(2,3-difluorophenyl)acetamide (0.15 g, 0.31 mmol), glycolaldehyde (0.028 g, 0.46 mmol) and MP-triacetoxyborohydride (2 mmol/g, 0.39 g, 0.78 mmol) in dimethylformamide (1.5 ml) was stirred at ambient temperature for 1 hour. The mixture was filtered and the filtrate evaporated under reduced pressure. The residue was purified by silica gel chromatography eluting with a mixture of 0 to 10% methanol (containing 10% 7N ammonia in methanol) in dichloromethane. The obtained product was triturated with diethyl ether to give compound 164 in table 4 (0.065 g, 40% yield) as a yellow solid:

$^1$H-NMR (DMSO $d_6$): 10.27 (s, 1H), 9.95 (s, 1H), 8.57 (s, 1H), 8.39 (d, 1H), 8.38 (s, 1H), 7.79 (s, 1), 7.72 (m, 1H), 7.22 (m, 4H), 5.15 (s, 2H), 4.39 (t, 1H), 4.29 (t, 2H), 3.57 (q, 2H), 3.02 (t, 2H), 2.82 (t, 2H), 2.00 (m, 1H), 0.49 (m, 2H), 0.37 (m, 2H); MS (+ve ESI) 524 $(M+H)^+$.

EXAMPLE 165

Preparation of Compound 165 in Table 4—2-{4-[(7-{2-[cyclobutyl(2-hydroxyethyl)amino]ethoxy}quinazolin-4-yl)amino]-1H-pyrazol-1-yl}-N-(2,3-difluorophenyl)acetamide An analogous reaction to that described in example 164 but starting with 2-[4-({7-[2-(cyclobutylamino)ethoxy]quinazolin-4-yl}amino)-1H-pyrazol-1-yl]-N-(2,3-difluorophenyl)acetamide (0.13 g, 0.26 mmol) yielded compound 165 in table 4 (0.072 g, 52% yield):

$^1$H-NMR (DMSO $d_6$): 10.27 (br s, 1H), 9.95 (s, 1H), 8.57 (s, 1H), 8.35 (d, 1H), 8.33 (s, 1H), 7.79 (s, 1H), 7.72 (m, 1H), 7.22 (m, 4H), 5.15 (s, 2H), 4.35 (t, 1H), 4.16 (t, 2H), 3.46 (m, 2H), 3.23 (1H under water), 2.88 (t, 2H), 2.55 (t, 2H), 2.01 (m, 2H), 1.82 (m, 2H), 1.58 (m, 2H); MS (+ve ESI) 538 $(M+H)^+$.

EXAMPLE 166

Preparation of Compound 166 in Table 4—2-{4-[(7-{2-[cyclopentyl(3-hydroxypropyl)amino]ethoxy}quinazolin-4-yl)amino]-1H-pyrazol-1-yl}-N-(2,3-difluorophenyl)acetamide A mixture of 2-[4({7-[2-(cyclopentylamino)ethoxy]quinazolin-4-yl}amino)-1H-pyrazol-1-yl]-N-(2,3-difluorophenyl)acetamide (0.15 g, 0.296 mmol), potassium carbonate (0.121 g, 0.88 mmol), 3-chloropropanol (0.075 ml, 0.088 mmol) and potassium iodide (0.098 g, 0.59 mmol) in dimethylacetamide (2 ml) was heated at 90° C. for 1 hour. The mixture was diluted with dichloromethane and a few drops of methanol and then filtered. The filtrate was purified directly by silica gel chromatography eluting with a mixture of 0 to 10% methanol (containing 10% 7N ammonia) in dichloromethane. The obtained product was triturated with diethyl ether to give compound 166 in table 4 (0.022 g, 13% yield) as a yellow coloured solid:

$^1$H-NMR (DMSO $d_6$): 10.26 (br s, 1H), 9.93 (s, 1H), 8.54 (s, 1H), 8.44 (d, 1H), 8.42 (s, 1H), 7.80 (s, 1H), 7.68 (m, 1H), 7.18 (m, 4H), 5.15 (s, 2H), 4.37 (br s, 1H), 4.13 (t, 2H), 3.45 (t, 2H), 3.14 (m, 1H), 2.91 (t, 2H), 2.64 (t, 2H), 1.80 (m, 2H), 1.61 (m, 4H), 1.50 (m, 2H), 1.34 (m, 2H); MS (+ve ESI): 566$(M+H)^+$ MS (−ve ESI): 564 $(M-H)^-$.

EXAMPLE 167

Preparation of Compound 167 in Table 4—2-{4-[(7-{2-[cyclopentyl(glycoloyl)amino]ethoxy}quinazolin-4-yl)amino]-1H-pyrazol-1-yl}-N-(2,3-difluorophenyl)acetamide A mixture of 2-[4-({7-[2-(cyclopentylamino)ethoxy]quinazolin-4-yl}amino)-1H-pyrazol-1-yl]-N-(2,3-difluorophenyl)acetamide (0.15 g, 0.3 mmol), glycolic acid (0.023 g, 0.3 mmol), O-(7-azabenzotriazol-1-yl)-N,N,N',N'-tetramethyluronium hexafluorophosphate (0.171 g, 0.45 mmol) and diisopropylethylamine (0.156 ml, 0.9 mmol) in dimethylacetamide (2 ml) was stirred at ambient temperature for 16 hour. The mixture was diluted with dichloromethane and then purified first by silica gel chromatography eluting with a 0 to 10% mixture of methanol (containing 10% 7N ammona) in dichloromethane and then by reverse phase chromatography eluting with a 5 to 95% mixture of acetonitrile (containing 0.2% trifluoroacetic acid) water (containing 0.2% trifluoroacetic acid) to give compound 167 in table 4 (0.038 g, 22% yield) as a white solid:

$^1$H-NMR (DMSO $d_6$ at 373K): 9.86 (br s, 1H), 9.72 (s, 1H), 8.57 (s, 1H), 8.38 (d, 1H), 8.33 (s, 1H), 7.98 (s, 1H), 7.81 (s, 1H), 7.70 (m, 1H), 7.18 (m, 4H), 5.15 (s, 2H), 4.32 (t, 2H), 4.20 (m, 3H), 3.70 (t, 2H), 3.20 (1H under water), 1.87 (m, 2H), 1.74 (m, 4H), 1.56 (m, 2H); MS (+ve ESI) 566 $(M+H)^+$ MS (−ve ESI): 564 $(M-H)^-$.

EXAMPLE 168

Preparation of Example 168 in Table 4—N-(2,3-difluorophenyl)-2-{4-[(7-{2-[(3S)-3-(hydroxymethyl)-4-methylpiperazin-1-yl]ethoxy}quinazolin-4-yl)amino]-1H-pyrazol-1-yl}acetamide MP-sodium cyanoborohydride (2.0 mmol/g, 0.363 g, 0.726 mmol) was added to a mixture of N-(2,3-difluorophenyl)-2-(4-{[7-(2-oxoethoxy)quinazolin-4-yl]amino}-1H-pyrazol-1-yl)acetamide (0.202 g, 0.46 mmol), acetic acid (0.039 ml, 0.68 mmol), [(2S)-1-methylpiperazin-2-yl]methanol (0.089 g, 0.68 mmol) in methanol (5 ml) and the mixture was stirred at room temperature for 5 hours. Sodium bicarbonate (0.049 g, 0.58 mmol) was added and the mixture stirred at room temperature overnight. The mixture was filtered and the residue polymer washed exhaustively with methanol. The filtrate was evaporated and the residue was purified by silica gel chromatography eluting with a 3 to 10% mixture of 7N ammonia in methanol in dichloromethane to give compound 168 in table 4 (0.086 g, 34% yield):

$^1$H-NMR (DMSO $d_6$): 10.28 (s, 1H), 9.93 (s, 1H), 8.54 (s, 1H), 8.36 (d, 1H), 8.34 (s, 1H), 7.79 (s, 1H), 7.69-7.75 (m, 1H), 7.12-7.24 (m, 4H), 5.15 (s, 2H), 4.45 (br s, 1H), 4.22 (t, 2H), 3.51-3.60 (m, 1H), 3.25-3.43 (m, 1H), 2.95 (d, 1H), 2.65-2.80 (m, 4H), 2.20 (s, 3H), 2.15-2.22 (m, 2H), 2.06-2.09 (m, 1H), 1.96 (t, 1H);

MS (+ve ESI): 553 $(M+H)^+$.

[(2S)-1-methylpiperazin-2-yl]methanol used as Starting Material, was Prepared as Follows a) A solution of lithium aluminium hydride in tetrahydrofuran (1M, 22.0 ml, 22.0 mmol) was added dropwise to a solution of (2S)-1-(tert-butoxycarbonyl)piperazine-2-carboxylic acid (see U.S. Pat. No. 5,348,955, 1.007 g, 4.38 mmol) in tetrahydrofuran (20 ml) cooled to −15° C. The mixture was allowed to warm to 15° C. over 1.5 hours and then heated at reflux for 3 hours. The mixture was cooled in an ice bath and then water (0.4 ml) was added dropwise followed by a dilute solution of sodium hydroxide (1M, 0.4 ml) and a further portion of water (1.2 ml). The mixture was stirred at room temperature for 0.5 hours and then allowed to stand overnight. The resultant precipitate was filtered and the residue was washed with diethyl ether. The filtrate was evaporated and the residue purified by silica gel chromatography eluting with a 10% mixture of methanol (containing 10% 7M ammonia in methanol) in dichloromethane to give [(2S)-1-methylpiperazin-2-yl]methanol (0.3802 g, 67% yield):

$^1$H-NMR ($CDCl_3$): 3.88 (dd, 1H), 3.46 (dd, 1H), 2.79-2.96 (m, 4H), 2.25-2.35 (m, 1H), 2.33 (s, 3H), 2.00-2.15 (m, 4H);

$^{13}$C-NMR ($CDCl_3$): 43.1, 46.3, 49.0, 56.2, 61.6, 63.6.

N-(2,3-difluorophenyl)-2-(4-{[7-(2-oxoethoxy)quinazolin-4-yl]amino}-1H-pyrazol-1-yl)acetamide used as Starting Material, was Prepared as Follows a) A solution of N-(2,3-difluorophenyl)-2-(4-{[7-(2,2-dimethoxyethoxy)quinazolin-4-yl]amino}-1H-pyrazol-1-yl)acetamide (0.104 g, 0.21 mmol) in a dilute solution of hydrochloric acid (1M, 1 ml) and tetrahydrofuran (5 ml) was heated at reflux for 10 hours. The mixture was allowed to cool to room temperature and was then filtered. The filtered solid was triturated with tetrahydrofuran and then dried under vaccum to give N-(2,3-difluorophenyl)-2-(4-{[7-(2-oxoethoxy)quinazolin-4-yl]amino}-1H-pyrazol-1-yl)acetamide as an approximate 1:1 mixture of aldehyde:hemiacetal (0.080 g, 87% yield) which was used in the next step without further purification:

MS (+ve ESI): 457 $(M+H_2O+H)^+$.

EXAMPLE 169

Preparation of Example 169 in Table 4—N-(2,3-difluorophenyl)-2-{4-[(7-{2-[(2S)-2-(hydroxymethyl)pyrroldin-1-yl]ethoxy}quinazolin-4-yl)amino]-1H-pyrazol-1-yl}acetamide An analogous reaction to that described in example 168 but starting with (2S)-2-(hydroxymethyl)pyrrolidine (0.016 g, 0.158 mmol) yielded compound 169 in table 4 (0.0395 g, 48% yield):

$^1$H-NMR (DMSO $d_6$): 10.27 (s, 1H), 9.91 (s, 1H), 8.53 (s, 1H), 8.34 (d, 1H), 8.33 (s, 1H), 7.77 (s, 1H), 7.68-7.74 (m, 1H), 7.14-7.23 (m, 4H), 5.14 (s, 2H), 4.37 (br s, 1H), 4.21 (t, 2H), 3.36-3.44 (m, 1H), 3.19-3.33 (m, 2H), 3.10-3.17 (m, 1H), 2.70-2.79 (m, 1H), 2.55-2.59 (m, 1H), 2.26-2.38 (m, 1H), 1.75-1.84 (m, 1H), 1.61-1.70 (m, 2H), 1.48-1.55 (m, 1H); MS (+ve ESI): 524 $(M+H)^+$.

EXAMPLE 170

Preparation of Example 170 in Table 4—N-(2,3-difluorophenyl)-2-{4-[(7-{2-[(2R)-2-(hydroxymethyl)-4-methylpiperazin-1 -yl]ethoxy}quinazolin-4-yl)amino]-1H-pyrazol-1-yl}acetamide An analogous reaction to that described in example 168 but starting with [(2R)-4-methylpiperazin-2-yl]methanol (*Synlett.,* 1996, 143-144, 0.089 g, 0.68 mmol) yielded compound 170 in table 4 (0.050 g, 20% yield):

$^1$H-NMR (DMSO $d_6$): 10.27 (s, 1H), 9.92 (s, 1H), 8.53 (s, 1H), 8.35 (d, 1H), 8.33 (s, 1H), 7.78 (s, 1H), 7.68-7.73 (m, 1H), 7.15-7.21 (m, 4H), 5.14 (s, 2H), 4.20 (m, 2H), 3.61 (dd, 1H), 3.20-3.45 (under $H_2O$), 3.12-3.16 (m, 2H), 2.72-2.87 (m, 2H), 2.60 (d, 1H), 2.20-2.49 (under DMSO), 2.13 (s, 3H), 2.05-2.18 (m, 1H), 1.92-1.99 (m, 1H); MS (+ve ESI): 553 $(M+H)^+$.

EXAMPLE 171

Preparation of Example 171 in Table 4—N-(2,3-difluorophenyl)-2-{4-[(7-{2-[4-(hydroxymethyl)piperidin-1-yl]ethoxy}quinazolin-4-yl)amino]-1H-pyrazol-1-yl}acetamide An analogous reaction to that described in example 168 but starting with piperidin-4-ylmethanol (0.079 g, 0.69 mmol) yielded compound 171 in table 4 (0.040 g, 16% yield):

$^1$H-NMR (DMSO $d_6$): 10.27 (s, 1H), 9.91 (s, 1H), 8.53 (s, 1H), 8.35 (d, 1H), 8.33 (s, 1H), 7.77 (s, 1H), 7.68-7.74 (m, 1H), 7.14-7.24 (m, 4H), 5.14 (s, 2H), 4.37 (t, 1H), 4.22 (t, 2H), 3.23 (t, 2H), 2.95 (d, 2H), 2.73 (t, 2H), 2.00 (t, 2H), 1.63 (d, 2H), 1.26-1.38 (m, 1H), 1.06-1.19 (m, 2H); MS (+ve ESI): 538 $(M+H)^+$.

EXAMPLE 172

Preparation of Example 172 in Table 4—N-(2,3-difluorophenyl)-2-{4-[(7-{2-[4-(2-hydroxyethyl)piperidin-1-yl]ethoxy}quinazolin-4-yl)amino]-1H-pyrazol-1-yl}acetamide An analogous reaction to that described in example 168 but starting with 2-piperidin-4-ylethanol (0.088 g, 0.68 mmol) yielded compound 172 in table 4 (0.098 g, 39% yield):

$^1$H-NMR (DMSO $d_6$): 10.27 (s, 1H), 9.91 (s, 1H), 8.53 (s, 1H), 8.35 (d, 1H), 8.33 (s, 1H), 7.77 (s, 1H), 7.68-7.75 (m, 1H), 7.13-7.27 (m, 4H), 5.15 (s, 2H), 4.29 (t, 1H), 4.22 (t, 2H), 3.39-3.45 (m, 2H), 2.88-2.96 (m, 2H), 2.72 (t, 2H), 2.01 (t, 2H), 1.56-1.65 (m, 2H), 1.30-1.39 (m, 3H), 1.07-1.21 (m, 2H); MS (+ve ESI): 552 $(M+H)^+$.

EXAMPLE 173

Preparation of Example 173 in Table 4—N-(2,3-difluorophenyl)-2-{4-[(7-{2-[(2-hydroxyethyl)amino]ethoxy}quinazolin-4-yl)amino]-1H-pyrazol-1-yl}acetamide An analogous reaction to that described in example 168 but starting with 2-aminoethanol (0.042 g, 0.69 mmol) yielded compound 173 in table 4 (0.011 g, 5% yield):

$^1$H-NMR (DMSO $d_6$): 10.27 (br s, 1H), 9.92 (s, 1H), 8.53 (s, 1H), 8.35 (d, 1H), 8.33 (s, 1H), 7.78 (s, 1H), 7.66-7.75 (m, 1H), 7.12-7.25 (m, 4H), 5.14 (s, 2H), 4.52 (m, 1H), 4.19 (t, 2H), 3.48 (m, 2H), 2.98 (t, 2H), 2.68 (t, 2H); MS (+ve ESI): 484 $(M+H)^+$.

EXAMPLE 174

Preparation of Example 174 in Table 4—N-(2,3-difluorophenyl)-2-(4-{[7-(2-{[trans-2-(hydroxymethyl)cyclohexyl]amino}ethoxy)quinazolin-4-yl]amino}-1H-pyrazol-1-yl)acetamide An analogous reaction to that described in example 168 but starting with trans-2-(hydroxymethyl)cyclohexylamine hydrochloride (0.113 g, 0.68 mmol) yielded compound 174 in table 4 (0.041 g, 16% yield):

$^1$H-NMR (DMSO $d_6$): 10.27 (br s, 1H), 9.91 (s, 1H), 8.54 (s, 1H), 8.34 (d, 1H), 8.34 (s, 1H), 7.78 (s, 1H), 7.68-7.75 (m, 1H), 7.10-7.24 (m, 4H), 5.15 (s, 2H), 4.14 (t, 2H), 3.48 (dd, 1H), 3.37 (dd, 1H), 3.04-3.13 (m, 1H), 2.79-2.89 (m, 1H), 2.28 (td, 1H), 1.96-2.05 (m, 1H), 1.55-1.75 (m, 3H), 0.80-1.38 (m, 5H); MS (+ve ESI): 552 $(M+H)^+$.

EXAMPLE 175

Preparation of Compound 175 in Table 4—N-(2,3-difluorophenyl)-2-{4-[(7-{3-[(2-hydroxyethyl)amino]propoxy}quinazolin-4-yl)amino]-1H-pyrazol-1-yl}acetamide An analogous reaction to that described in example 122, but starting with ethanolamine (0.15 ml, 1.90 mmol) yielded compound 175 in table 4 (0.125 g, 66% yield):

$^1$H-NMR (DMSO $d_6$): 9.62 (br s, 1H), 8.52 (s, 1H), 8.32 (d, 1H), 8.28 (s, 1H), 7.82 (s, 1H), 7.70 (m, 1H), 7.15 (m, 4H), 5.09 (s, 2H), 4.25 (t, 2H), 4.00 (br s, 1H), 3.50 (t, 2H), 2.70 (t, 2H), 2.60 (t, 2H), 1.98 (quintet, 2H); MS (+ve ESI): 498 $(M+H)^+$.

EXAMPLE 176

Preparation of Compound 176 in Table 4—N-(2,3-difluorophenyl)-2-(4-{[7-(3-pyrrolidin-1-ylpropoxy) quinazolin-4-yl]amino}-1H-pyrazol-1-yl)acetamide An analogous reaction to that described in example 122, but starting with pyrrolidine (0.059 g, 0.39 mmol) yielded compound 176 in table 4 (0.110 g, 56% yield):

$^1$H-NMR (DMSO $d_6$): 10.30 (br s, 1H), 9.89 (br s, 1H), 8.59 (s, 1H), 8.38 (d, 1H), 8.32 (s, 1H), 7.80 (s, 1H), 7.65 (m, 1H), 7.20 (m, 3H), 7.15 (s, 1H), 5.18 (s, 2H), 4.20 (t, 2H), 3.15 (m, 10H), 2.08 (m, 2H); MS (+ve ESI): 507 $(M+H)^+$.

EXAMPLE 177

Preparation of Compound 177 in Table 4—N-(2,3-difluorophenyl)-2-{4-[(7-methoxyquinazolin-4-yl) amino]-1H-pyrazol-1-yl}acetamide A mixture of caesium carbonate (0.122 g, 0.38 mmol), N-(2,3-difluorophenyl)-2-{4-[(7-hydroxyquinazolin-4-yl) amino]-1H-pyrazol-1-yl}acetamide (0.150 g, 0.38 mmol) and methyl iodide (0.054 g, 0.38 mmol) in dimethylacetamide (5 ml) was stirred at room temperature for 1 hour. The reaction mixture was evaporated under reduced pressure and the residue was then triturated with acetonitrile to give a yellow solid which was purified by reverse phase chromatography eluting with 0.2% aqueous trifluoroacetic acid in acetonitrile using a 5 to 50% gradient over 25 minutes. The fractions containing product were concentrated under reduced pressure and then basified with aqueous sodium carbonate. The resultant solid was filtered and washed with water to give compound 177 in table 4 (0.026 g, 17% yield):

$^1$H-NMR (DMSO $d_6$): 10.27 (br s, 1H), 8.40 (s, 1H), 8.25 (d, 1H), 8.18 (s, 1H), 7.75 (s, 1H), 7.65 (m, 1H), 7.20 (m, 4H), 6.75 (s, 1H), 5.15 (s, 2H), 3.64 (s, 3H); MS (+ve ESI): 412 $(M+H)^+$.

EXAMPLE 178

Preparation of Compound 178 in Table 4—N-(2,3-difluorophenyl)-2-{4-[(7-{3-[(2-hydroxyethyl)(tetrahydro-2H-pyran-4-yl)amino]propoxy}quinazolin-4-yl)amino]-1H-pyrazol-1-yl}acetamide A mixture of 2-(4-{[7-(3-chloropropoxy)quinazolin-4-yl] amino}-1H-pyrazol-1-yl)-N-(2,3-difluorophenyl)acetamide hydrochloride salt (0.5 g 0.98 mmol), N-N-diisopropylethylamine (0.342 ml, 1.97 mmol), 2-(tetrahydro-2H-pyran-4-ylamino)ethanol (0.285 g, 1.97 mmol) and potassium iodide (0.326 g, 1.97 mmol) in dimethylacetamide (4 ml) was heated at 70° C. for 16 hours. The reaction mixture was diluted with dimethylsulphoxide:acetonitrile:water (7:2:1, 3 ml) and purified by reverse phase chromatography eluting with 0.2% aqueous trifluoroacetic acid in acetonitrile using a 5 to 50% gradient over 25 minutes. The eluent was concentrated under reduced pressure and basified with aqueous sodium carbonate. The product was filtered, washed with water then triturated with diethylether to give compound 178 in table 4 (0.308 g, 54% yield) as a cream coloured solid.

$^1$H-NMR (DMSO $d_6$): 10.35 (br s, 1H), 9.90 (s, 1H), 8.55 (s, 1H), 8.35 (m, 2H), 7.80 (s, 1H), 7.65 (m, 1H), 7.25 (m, 3H), 7.10 (s, 1H), 5.20 (s, 2H), 4.30 (t, 1H), 4.20 (t, 2H), 3.90-3.80 (m, 2H), 3.45-3.35 (m, 4H), 3.30 (t, 2H), 2.75-2.60 (m, 3H), 1.90-1.80 (m, 2H), 1.65-1.55 (m, 2H), 1.50-1.40 (m, 2H); MS (+VE ESI): 582 $(M+H)^+$ MS (−VE ESI): 580 $(M-H)^-$.

EXAMPLE 179

Preparation of Compound 179 in Table 4—N-(2,3-difluorophenyl)-2-{4-[(7-{3-[(2R)-2-(2-hydroxyethyl)piperidin-1-yl]propoxy}quinazolin-4-yl) amino]-1H-pyrazol-1-yl}acetamide A mixture of 2-(4-{[7-(3-chloropropoxy)quinazolin-4-yl] amino}-1H-pyrazol-1-yl)-N-(2,3-difluorophenyl)acetamide hydrochloride salt (0.5 g 0.98 mmol), N-N-diisopropylethylamine (1.37 ml, 7.86 mmol), 2-[(2R)-piperidin-2-yl]ethanol hydrochloride (0.57 g, 3.94 mmol) and potassium iodide (0.652 g, 3.94 mmol) in dimethylacetamide (4 ml) was heated at 80° C. for 32 hours. The reaction mixture was diluted with dimethylsulphoxide:acetonitrile:water (7:2:1, 6 ml) and purified by reverse phase chromatography eluting with 0.2% aqueous trifluoroacetic acid in acetonitrile using a 5 to 50% gradient over 25 minutes. The eluent was concentrated under reduced pressure and basified with aqueous sodium carbonate. The product was filtered, washed with water and dried in vacuum oven at 40° C. for 16 hours to give compound 179 in table 4 (0.228 g, 41% yield) as a cream coloured solid.

$^1$H-NMR (DMSO $d_6$): 10.30 (br s, 1H), 9.90 (s, 1H), 8.52 (s, 1H), 8.30 (m, 2H), 7.80 (s, 1H), 7.70 (m, 1H), 7.30 (m, 3H), 7.20 (s, 1H), 5.20 (s, 2H), 4.50 (m, 1H), 4.20 (t, 2H), 3.50 (m, 2H), 2.70 (m, 2H), 2.40 (m, 2H), 2.20 (m, 1H), 1.90 (m, 2H), 1.80 (m, 1H), 1.70 (m, 2H), 1.50 (m, 3H), 1.30 (m, 2H); MS (+VE ESI): 566 $(M+H)^+$.

EXAMPLE 180

Preparation of Compound 180 in Table 4—N-(2,3-difluorophenyl)-2-{4-[(7-{3-[(2S)-2-(2-hydroxyethyl)piperidin-1-yl]propoxy}quinazolin-4-yl) amino]-1H-pyrazol-1-yl}acetamide An analogous reaction to that described in example 179 but starting with 2-[(2S)-piperidin-2-yl]ethanol hydrochloride (0.0.57 g, 3.94 mmol) gave compound 180 in table 4 (0.280 g, 50% yield) as a cream coloured solid.

$^1$H-NMR (DMSO $d_6$): 10.30 (br s, 1H), 9.90 (s, 1H), 8.52 (s, 1H), 8.30 (m, 2H), 7.80 (s, 1H), 7.70 (m, 1H), 7.30 (m, 3H), 7.20 (s, 1H), 5.20 (s, 2H), 4.50 (m, 1H), 4.20 (t, 2H), 3.50 (m, 2H), 2.70 (m, 2H), 2.40 (m, 2H), 2.20 (m, 1H), 1.90 (m, 2H), 1.80 (m, 1H), 1.70 (m, 2H), 1.50 (m, 3H), 1.30 (m, 2H); MS (+VE ESI): 566 $(M+H)^+$.

EXAMPLE 181

Preparation of Compound 181 in Table 4—N-(2,3-difluorophenyl)-2-{4-[(7-{3-[(2R)-2-(hydroxymethyl)-4-methylpiperazin-1-yl]propoxy}quinazolin-4-yl)amino]-1H-pyrazol-1-yl}acetamide An analogous reaction to that described in example 179 but starting with [(2R)-4-methylpiperazin-2-yl]methanol (0.216 g, 1.66 mmol) gave compound 181 in table 4 (0.161 g, 34% yield) as a cream coloured solid.

$^1$H-NMR (DMSO $d_6$): 10.35 (bs, 1H), 9.90 (s, 1H), 8.55 (s, 1H), 8.35 (m, 2H), 7.80 (s, 1H), 7.70 (m, 1H), 7.20 (m, 3H), 7.10 (s, 1H), 5.15 (s, 2H), 4.50 (bs, 1H), 4.20 (t, 2H), 3.60 (m, 1H), 2.95 (m, 1H), 2.80 (m, 1H), 2.60 (m, 1H), 2.50 (m, 2H), 2.30 (m, 4H), 2.15 (m, 3H), 1.80 (m, 3H); MS (+VE ESI): 567 $(M+H)^+$ MS (−VE ESI): 565 $(M-H)^-$.

EXAMPLE 182

Preparation of Compound 182 in Table 4—N-(2,3-difluorophenyl)-2-{4-[(7-{3-[(3S)-3-(hydroxymethyl)-4-methylpiperazin-1-yl]propoxy}quinazolin-4-yl)amino]-1H-pyrazol-1-yl}acetamide A mixture of 2-(4-{[7-(3-chloropropoxy)quinazolin-4-yl]amino}-1H-pyrazol-1-yl)-N-(2,3-difluorophenyl)acetamide hydrochloride salt (0.550 g, 1.08 mmol), N-N-diispropylethylamine (0.376 ml, 2.16 mmol), [(2S)-1-methylpiperazin-2-yl]methanol (0.281 g, 2.16 mmol) and potassium iodide (0.356 g, 2.16 mmol) in dimethylacetamide (4 ml) was heated at 80° C. for 16 hours. The reaction mixture was diluted with dimethylsulphoxide:acetonitrile:water (7:2:1, 6 ml) and purified by reverse phase chromatography eluting with 0.2% aqueous trifluoroacetic acid in acetonitrile using a 5 to 50% gradient over 25 minutes. The eluent was concentrated under reduced pressure and basified with aqueous sodium carbonate. The product was extracted into 10% methanol in dichloromethane, dried over magnesium sulphate and concentrated under reduced pressure to give compound 182 in table 4 (0.466 g, 76% yield) as a white solid.

$^1$H-NMR (DMSO $d_6$): 10.10 (bs, 2H), 8.55 (s, 1H), 8.35 (m, 2H), 7.75 (s, 1H), 7.70 (m, 1H), 7.20 (m, 3H), 7.10 (s, 1H), 5.10 (s, 2H), 4.40 (bs, 1H), 4.20 (t, 2H), 3.60 (m, 1H), 2.90 (m, 1H), 2.70 (m, 2H), 2.40 (t, 2H), 2.20 (s, 3H), 2.0 (m, 2H), 1.90 (m, 2H), 1.80 (m, 1H); MS (−VE ESI): 565 $(M-H)^-$.

EXAMPLE 183

Preparation of Compound 183 in Table 4—N-(2,3-difluorophenyl)-2-{4-[(7-{3-[(2R)-2-(hydroxymethyl)morpholin-4-yl]propoxy}quinazolin-4-yl)amino]-1H-pyrazol-1-yl}acetamide An analogous reaction to that described in example 179 but starting with (2R)-morpholin-2-ylmethanol (0.200 g, 1.71 mmol) gave compound 183 in table 4 (0.161 g, 34% yield) as a cream coloured solid.

$^1$H-NMR (DMSO $d_6$): 10.30 (bs, 1H), 9.90 (s, 1H), 8.55 (s, 1H), 8.40 (m, 2H), 7.75 (s, 1H), 7.70 (m, 1H), 7.20 (m, 3H), 7.10 (s, 1H), 5.10 (s, 2H), 4.60 (t, 1H), 4.20 (t, 2H), 3.75 (m, 1H), 3.50 (m, 1H), 3.40 (m, 2H), 2.80 (m, 1H), 2.70 (m, 1H), 2.40 (m, 2H), 2.0 (m, 3H), 1.75 (m, 1H); MS (−VE ESI): 552 $(M-H)^-$.

EXAMPLE 184

Preparation of Compound 184 in Table 4—N-(2,3-difluorophenyl)-2-{4-[(7-{3-[(3S)-3-(hydroxymethyl)morpholin-4-yl]propoxy}quinazolin-4-yl)amino]-1H-pyrazol-1-yl}acetamide An analogous reaction to that described in example 179 but starting with (3S)-morpholin-3-ylmethanol (0.567 g, 4.84 mmol) gave compound 184 in table 4 (0.292 g, 27% yield) as a white solid.

$^1$H-NMR (DMSO $d_6$): 8.55 (s, 1H), 8.35 (m, 2H), 7.80 (s, 1H), 7.65 (m, 1H), 7.25-7.04 (m, 4H), 5.10 (s, 2H), 4.20 (t, 2H), 3.75-3.55 (m, 3H), 3.50-3.40 (m, 1H), 3.0-2.85 (m, 1H), 2.80-2.65 (m, 1H), 2.50 (4H, m under DMSO), 2.40-2.20 (m, 4H), 2.0-1.80 (m, 2H); MS (+VE ESI): 554 $(M+H)^+$ MS (−VE ESI): 552 $(M-E)^-$.

EXAMPLE 185

Preparation of Compound 185 in Table 4—N-(2,3-difluorophenyl)-2-[4-({7-[3-(glycoloylamino)propoxy]quinazolin-4-yl}amino)-1H-pyrazol-1-yl]acetamide A mixture of 2-(4-{[7-(3-aminopropoxy)quinazolin-4-yl]amino}-1H-pyrazol-1-yl)-N-(2,3-difluorophenyl)acetamide (0.15 g 0.33 mmol), hydroxyacetic acid (0.033 g, 0.43 mmol), N-N-diisopropylethylamine (0.115 ml, 0.66 mmol) and O-(7-Azabenzotriazole-1-yl)-N,N,N',N'-tetramethyluronium hexafluorophospahte (0.164 g, 1.97 mmol) in dimethylacetamide (4 ml) was stirred at ambient temperature for 16 hours. The reaction mixture was diluted with dimethylsulphoxide:acetonitrile:water (7:2:1, 3 ml) and purified by reverse phase chromatography eluting with 0.2% aqueous trifluoroacetic acid in acetonitrile using a 5 to 70% gradient over 25 minutes. The eluent was concentrated under reduced pressure and basified with aqueous sodium carbonate. The product was filtered, washed with water and then triturated with diethylether to give compound 185 in table 4 (0.055 g, 32% yield) as a cream coloured solid.

$^1$H-NMR (DMSO $d_6$): 10.35 (br s, 1H), 8.55 (s, 1H), 8.35 (m, 1H), 8.30 (m, 2H), 7.90 (m, 1H), 7.75 (m, 1H), 7.70 (m, 1H), 7.30-7.05 (m, 4H), 5.50 (br s, 1H), 5.10 (s, 2H), 4.15 (t, 2H), 3.70 (s, 2H), 2.70 (s, 2H), 2.0 (m, 2H); MS (+VE ESI): 512 $(M+H)^+$ MS (−VE ESI): 510 $(M-H\ )^-$.

EXAMPLE 186

Preparation of Compound 186 in Table 5—N-(3-fluorophenyl)-2-{4-[(7-{3-[(2-hydroxyethyl)(propyl)amino]propoxy}quinazolin-4-yl)amino]-1H-pyrazol-1-yl}acetamide An analogous reaction to that described in example 122, but starting with 2-(propylamino)ethanol (129 mg, 1.25 mmol) and 2-(4-{[7-(3-chloropropoxy)quinazolin-4-yl]amino}-1H-pyrazol-1-yl)-N-(3-fluorophenyl)acetamide (113 mg, 0.25 mmol) yielded compound 186 in table 5 (60 mg, 46% yield):

$^1$H-NMR (DMSO $d_6$): 10.50 (s, 1H), 9.90 (s, 1H), 8.45 (s, 1H), 8.32 (m, 2H), 7.78 (s, 1H), 7.56 (m, 1H), 7.34 (m, 1H), 7.31 (m, 1H), 7.20 (m, 1H), 7.11 (s, 1H), 6.90 (m, 1H), 5.04 (s, 2H), 4.26 (t, 1H), 4.16 (t, 2H), 2.60 (t, 2H), 2.48 (m, 2H), 2.38 (m, 2H), 1.87 (m, 2H), 1.38 (m, 2H), 0.81 (t, 3H); MS (+ve ESI): 522 $(M+H)^+$.

EXAMPLE 187

Preparation of Compound 187 in Table 5—2-{4-[(7-{3-[ethyl(2-hydroxyethyl)amino]propoxy}quinazolin-4-yl)amino]-1H-pyrazol-1-yl}-N-(3-fluorophenyl)acetamide An analogous reaction to that described in example 186, but starting with 2-(ethylamino)ethanol (111 mg, 1.25 mmol) yielded compound 187 in table 5 (40 mg, 32% yield):

$^1$H-NMR (DMSO $d_6$): 10.58 (s, 1H), 9.96 (s, 1H), 8.56 (s, 1H), 8.36 (m, 2H), 7.79 (s, 1H), 7.60 (m, 1H), 7.33 (m, 2H), 7.23 (m, 1H), 7.14 (s, 1H), 6.91 (m, 1H), 5.08 (s, 2H), 4.36 (br s, 1H), 4.19 (m, 2H), 3.46 (m, 2H), 2.61 (m, 2H), 2.51 (m, 4H), 1.90 (m, 2H), 0.98 (t, 3H); MS (+ve ESI): 508 $(M+H)^+$.

EXAMPLE 188

Preparation of Compound 188 in Table 5—N-(3-fluorophenyl)-2-{4-[(7-{3-[(2R)-2-(hydroxymethyl)pyrrolidin-1-yl]propoxy}quinazolin-4-yl)amino]-1H-pyrazol-1-yl}acetamide An analogous reaction to that described in example 186, but starting with (2R)-pyrrolidin-2-ylmethanol (126 mg, 1.25 mmol) yielded compound 188 in table 5 (101 mg, 78% yield): $^1$H-NMR (DMSO $d_6$): 9.92 (br s, 1H), 8.55 (s, 1H), 8.35 (m, 2H), 7.77 (s, 1H), 7.59 (m, 1H), 7.33 (m, 2H), 7.22 (m, 1H), 7.15 (s, 1H), 6.90 (m, 1H), 5.05 (s, 2H), 4.40 (br s, 1H), 4.20 (t, 2H), 3.40 (m, 1H), 3.30 (m, 1H), 2.50 (m, 2H), 2.28 (m, 1H), 1.96 (m, 2H), 1.82 (m, 1H), 1.67 (m, 2H), 1.58 (m, 1H); MS (+ve ESI): 520 $(M+H)^+$.

EXAMPLE 189

Preparation of Compound 189 in Table 5—N-(3-fluorophenyl)-2-{4-[(7-{3-[4-(hydroxymethyl)piperidin-1-yl]propoxy}quinazolin-4-yl)amino]-1H-pyrazol-1-yl}acetamide An analogous reaction to that described in example 186, but starting with piperidin-4-ylmethanol (144 mg, 1.25 mmol) yielded compound 189 in table 5 (122 mg, 92% yield): $^1$H-NMR (DMSO $d_6$): 10.50 (br s, 1H), 9.92 (br s, 11H), 8.57 (s, 1H), 8.34 (m, 2H), 7.79 (s, 1H), 7.57 (m, 1H), 7.30 (m, 2H), 7.21 (m, 1H), 7.17 (s, 1H), 6.90 (m, 1H), 5.06 (s, 2H), 4.54 (br s, 1H), 4.21 (t, 2H), 3.31 (m, 2H), 2.98 (m, 2H), 2.50 (m, 4H), 2.10 (m, 2H), 1.79 (m, 2H), 1.53 (m, 1H), 1.30 (m, 2H); MS (+ve ESI): 534 $(M+H)^+$.

EXAMPLE 190

Preparation of Compound 190 in Table 5-N-(3-fluorophenyl)-2-{4-[(7-{3-[(3-hydroxy-1,1-dimethylpropyl)amino]propoxy}quinazolin-4-yl)amino]-1H-pyrazol-1-yl}acetamide An analogous reaction to that described in example 186, but starting with 3-amino-3methylbutan-1-ol (129 mg, 1.25 mmol) yielded compound 190 in table 5 (105 mg, 81% yield): $^1$H-NMR (DMSO $d_6$): 10.51 (s, 1H), 9.91 (s, 1H), 8.56 (s, 1H), 8.36 (m, 1H), 8.33 (s, 1H), 7.77 (s, 1H), 7.58 (m, 1H), 7.37 (m, 1H), 7.32 (m, 1H), 7.23 (m, 1H), 7.16 (s, 1H), 6.91 (m, 1H), 5.05 (s, 2H), 4.24 (t, 2H), 3.58 (t, 2H), 2.97 (t, 2H), 2.03 (m, 2H), 1.70 (t, 2H), 1.22 (s, 6H); MS (+ve ESI): 522 $(M+H)^+$.

EXAMPLE 191

Preparation of Compound 191 in Table 5—N-(3-fluorophenyl)-2-{4-[(7-{3-[2-(2-hydroxyethyl)piperidin-1-yl]propoxy}quinazolin-4-yl)amino]-1H-pyrazol-1-yl}acetamide An analogous reaction to that described in example 186, but starting with 2-(2-hydroxyethyl)piperidine (0.258 g, 2.00 mmol) yielded compound 191 in table 5 (0.150 g, 77% yield): $^1$H-NMR (DMSO $d_6$, 373K): 10.19 (1H, s), 9.63 (1H, s), 8.53 (1H, s), 8.33 (1H, d), 8.27 (1H, s), 7.79 (1H, s), 7.52 (1H, d), 7.33 (2H, m), 7.18 (2H, m), 6.86 (1H, m), 5.02 (2H, s), 4.21 (2H, t), 3.50 (2H, m), 2.74 (2H, m), 2.54 (1H, m), 2.01 (3H, m), 1.84 (1H, m), 1.72 (1H, m), 1.59 (5H, m), 1.39 (2H, m); MS (+ve ESI): 548 $(4+H)^+$ MS (−ve ESI): 546 $(M-H)^-$.

EXAMPLE 192

Preparation of Compound 192 in Table 5—N-(3-fluorophenyl)-2-{4-[(7-{3-[4-(2-hydroxyethyl)piperazin-1-yl]propoxy}quinazolin-4-yl)amino]-1H-pyrazol-1-yl}acetamide An analogous reaction to that described in example 186, but starting with 2-piperazin-1-ylethanol (0.26 ml, 2.15 mmol) yielded compound 192 in table 5 (0.214 g, 91% yield): $^1$H-NMR (DMSO $d_6$): 10.27 (br s, 1H), 9.20 (br s, 1H), 8.62 (s, 1H), 8.43 (d, 1H), 8.38 (s, 1H), 7.82 (s, 1H), 7.62 (d, 1H), 7.30 (m, 3H), 7.15 (s, 1H), 6.92 (t, 1H), 5.28 (br s, 1H), 5.15 (s, 2H), 4.20 (s, 2H), 3.35 (m, 16H); MS (+ve ESI): 549 $(M+H)^+$.

EXAMPLE 193

Preparation of Compound 193 in Table 5—N-(3-fluorophenyl)-2-{4-[(7-{3-[(2-hydroxyethyl)(tetrahydrofuran-3-yl)amino]propoxy}quinazolin-4-yl)amino]-1H-pyrazol-1-yl}acetamide 2-{4-[(7-{3-[(2-{[tert-butyl(dimethyl)silyl]oxy}ethyl)(tetrahydrofuran-3-yl)amino]propoxy}quinazolin-4-yl)amino]-1H-pyrazol-1-yl}-N-(3-fluorophenyl)acetamide (0.110 g, 0.16 mmol) was dissolved in anhydrous tetrahydrofuran (10 ml) under a nitrogen atmosphere and then a solution of tetra-N-butylammonium fluoride in tetrahydrofuran (1M solution, 0.8 ml, 0.8 mmol) was added. After stirring for 1 hour a further portion of tetra-N-butylammonium fluoride in tetrahydrofuran (1M solution, 0.64 ml, 0.64 mmol) was added and the reaction mixture was left to stir overnight at room temperature. The solvent was evaporated under reduced pressure and the residue purified by silica gel chromatography eluting with a gradient of 0 to 10% methanol in dichloromethane containing 2% 7N ammonia in methanol. The obtained product was triturated with acetonitrile to give compound 193 in table 5 (0.028 g, 32% yield): $^1$H-NMR (DMSO $d_6$): 10.51 (1H, s), 9.90 (1H, s), 8.53 (1H, s), 8.33 (2H, d), 7.78 (1H, s), 7.58 (1H, d), 7.34 (2H, m), 7.21 (1H, d), 7.16 (1H, s), 6.90 (1H, t), 5.05 (2H, s), 4.37 (1H, t), 4.18 (2H, t), 3.81 (1H, m), 3.69 (1H, m), 3.57 (1H, m), 3.45 (4H, m), 2.62 (3H, m), 1.92 (3H, m), 1.72 (1H, m); MS (+ve ESI): 550 $(M+H)^+$ MS (−ve ESI): 548 $(M-H)^-$.

2-{4-[(7-{3-[(2-{[tert-butyl(dimethyl)silyl]oxy}ethyl)(tetrahydrofuran-3-yl)amino]propoxy}quinazolin-4-yl)amino]-1H-pyrazol-1-yl}-N-(3-fluorophenyl)acetamide used as starting material, was prepared as follows a) A solution of tetrahydrofuran-3-amine (see WO98/08855, 0.500 g, 4.04 mmol) and sodium acetate (0.331 g, 4.04 mmol) in a 1:3 mixture of methanol and tetrahydrofuran (60 ml) was stirred at room temperature. To this was added (tert-butyl-dimethylsilanyloxy)acetaldehyde (2.112 g, 12.12 mmol) followed by glacial acetic acid (1.456 g, 24.24 mmol) and then sodium triacetoxyborohydride (2.568 g, 12.12 mmol) was then added in 5 portions over 3 minutes (CAUTION: vigorous effervescence) and the resulting suspension was left to stir at room temperature for 4 hours. The mixture was evaporated under reduced pressure to leave a thick brown paste which was dissolved in dichloromethane (20 ml) and to this was added a solution of ammonia in methanol (7M solution, 25 ml). The mixture was stirred for 10 minutes and then evaporated under reduced pressure to leave an orange paste which was triturated with dichloromethane (50 ml) and filtered through Celite. The mixture was evaporated under reduced pressure to leave a brown gum which was dissolved in methyl tert-butyl ether (3 ml) and then purified by silica gel chromatography using methyl tert-butyl ether as eluent to give N-(2-{[tert-butyl(dimethyl)silyl]oxy}ethyl)tetrahydrofuran-3-amine (0.446 g, 48% yield) as a brown oil:

$^1$H-NMR ($CDCl_3$): 3.68 (8H, m), 2.68 (2H, m), 2.04 (1H, m), 1.73 (1H, m), 0.82 (9H, s), 0.00 (6H, s).

b) An analogous reaction to that described in example 186, but starting with N-(2-{[tert-butyl(dimethyl)silyl]oxy}ethyl) tetrahydrofuran-3-amine (0.446 g, 1.81 mmol) yielded 2-{4-[(7-{3-[(2-{[tert-butyl(dimethyl)silyl]oxy}ethyl)(tetrahydrofuran-3-yl)amino]propoxy}quinazolin-4-yl)amino]-1H-pyrazol-1-yl}-N-(3-fluorophenyl)acetamide (0.112 g, 39% yield):

$^1$H-NMR ($CDCl_3$): 11.01 (1H, br s), 9.79 (1H, br s), 8.70 (1H, d), 8.63 (1H, s), 8.48 (1H, s), 8.09 (1H, s), 7.58 (1H, d), 7.51 (1H, s), 7.30 (2H, d), 7.24 (1H, m), 6.78 (1H, m), 5.09 (2H, s), 4.33 (1H, m), 4.14 (2H, m), 3.96 (2H, t), 3.88 (2H, m), 3.72 (2H, m), 3.34 (1H, br s), 3.13 (2H, m), 2.32 (5H, m), 0.92 (9H, s), 0.11 (6H, s); MS (+ve ESI): 664 $(M+H)^+$ MS (−ve ESI): 662 $(M-H)^-$.

EXAMPLE 194

Preparation of Compound 194 in Table 5—N-(3-fluorophenyl)-2-(4-{[7-(3-morpholin-4-ylpropoxy)quinazolin-4-yl]amino}-1H-pyrazol-1-yl)acetamide A solution of 2-(4-{[7-(3-chloropropoxy)quinazolin-4-yl]amino}-1H-pyrazol-1-yl)-N-(3-fluorophenyl)acetamide (0.060 g, 0.13 mmol) in morpholine (20 ml) was heated at 80° C. for 2 hours and then allowed to cool to room temperature. The mixture was evaporated under reduced pressure to leave a brown solid, which was washed with water, dried and triturated with diethyl ether to give compound 194 in table 5 (0.052 g, 76% yield) as a white solid:

$^1$H-NMR (DMSO $d_6$): 10.72 (br s, 1H), 8.55 (s, 1H), 8.40 (d, 1H), 8.35 (s, 1H), 7.79 (s, 1H), 7.58 (d, 1H), 7.35 (m, 2H), 7.20 (dd, 1H), 7.15 (d, 1H), 6.85 (m, 1H), 5.05 (s, 2H), 4.16 (t, 2H), 3.65 (m, 6H), 3.35 (quintet, 2H), 2.35 (m, 2H), 1.98 (quintet, 2H); MS (+ve ESI): 506 $(M+H)^+$ MS (−ve ESI): 504 $(M-H)^-$.

EXAMPLE 195

Preparation of Compound 195 in Table 5—N-(3-fluorophenyl)-2-[4-({7-[(2S)-pyrrolidin-2-ylmethoxy]quinazolin-4-yl}amino)-1H-pyrazol-1-yl]acetamide A solution of tert-butyl (2S)-2-[({4-[(1-(2-[(3-fluorophenyl)amino]-2-oxoethyl}-1H-pyrazol-4-yl)amino]quinazolin-7-yl}oxy)methyl]pyrrolidine-1-carboxylate (0.332 g, 0.59 mmol) in trifluoroacetic acid (5 ml) was stirred at room temperature for 1 hour. The solvent was evaporated and the residue triturated with diethyl ether to yield compound 195 in table 5 (0.355 g, 87% yield) as the di-trifluoroacetate salt:

$^1$H-NMR (DMSO $d_6$): 11.17 (br s, 1H), 10.60 (s, 1H), 9.37 (br s, 1H), 8.91 (m, 2H), 8.59 (d, 1H), 8.38 (s, 1H), 7.92 (s, 1H), 7.59 (m, 1H), 7.47 (dd, 1H), 7.39 (m, 1H), 7.31 (m, 2H), 6.92 (m, 1H), 5.12 (s, 2H), 4.50 (m, 1H), 4.33 (m, 1H), 4.03 (br m, 1H), 3.28 (br m, 2H), 2.19 (m, 1H), 2.01 (m, 2H), 1.83 (m, 1H); MS (+ve ESI): 462 $(M+H)^+$.

tert-butyl (2S)-2-[({4-[(1-{2-[(3-fluorophenyl)amino]-2-oxoethyl}-1H-pyrazol-4-yl)amino]quinazolin-7-yl}oxy)methyl]pyrrolidine-1-carboxylate used as Starting Material, was Obtained as Follows a) Methane sulphonyl chloride (0.11 ml, 1.4 mmol) was added to a solution of tert-butyl (2S)-2-(hydroxymethyl)pyrrolidine-1-carboxylate (0.25 g, 1.24 mmol) and 4-(dimethylamino)pyridine (0.167 g, 1.4 mmol) in dichloromethane (5 ml). The mixture was stirred at room temperature for 1 hour and then 4-(dimethylamino)pyridine (0.051 g, 0.42 mmol) and methane sulphonyl chloride (0.033 ml, 0.42 mmol) were added and the mixture stirred at room temperature for a further 1 hour. The mixture was purified directly by silica gel chromatography, eluting with a 3:1 to 1:1 mixture of isohexane:ethyl acetate to yield tert-butyl (2S)-2-{[(methylsulphonyl)oxy]methyl}pyrrolidine-1-carboxylate (0.325 g, 94% yield):

$^1$H-NMR ($CDCl_3$): 4.28 (m, 2H), 4.03 (m, 1H), 3.36 (m, 2H), 3.00 (s, 3H), 1.92 (m, 4H).

b) A solution of N-(3-fluorophenyl)-2-{4-[(7-hydroxyquinazolin-4-yl)amino]-1H-pyrazol-1-yl}acetamide (0.590 g, 0.97 mmol), cesium carbonate (1.95 g, 5.98 mmol) and tert-butyl (2S)-2-{[(methylsulphonyl)oxy]methyl}pyrrolidine-1-carboxylate (0.325 g, 1.16 mmol) in dimethylacetamide (10 ml) was heated at 80° C. for 18 hours. The mixture was poured into water and extracted with ethyl acetate. The organic layer was separated, dried over magnesium sulphate and evaporated in vacuo to leave a brown oil which was purified by silica gel chromatography. Elution with 5 to 7% methanol in dichloromethane gave tert-butyl (2S)-2-[({4-[(1-{2-[(3-fluorophenyl)amino]-2-oxoethyl}-1H-pyrazol-4-yl)amino]quinazolin-7-yl}oxy)methyl]pyrrolidine-1-carboxylate (0.332 g, 61% yield) as a light brown solid.

$^1$H-NMR (DMSO $d_6$): 10.51 (s, 1H), 9.94 (s, 1H), 8.55 (s, 1H), 8.38 (d, 1H), 8.35 (s, 1H), 7.78 (s, 1H), 7.58 (m, 1H), 7.35 (m, 2H), 7.26 (m, 1H), 7.20 (m, 1H), 6.91 (m, 1H), 5.06 (s, 2H), 4.23 (m, 1H), 4.10 (m, 2H), 3.30 (m, 2H under water), 1.97 (m, 3H), 1.82 (m, 1H), 1.42 (s, 9H); MS (+ve ESI): 562 $(M+H)^+$.

EXAMPLE 196

Preparation of Compound 196 in Table 5—N-(3-fluorophenyl)-2-{4-[(7-{[(2S)-1-(2-hydroxyethyl)pyrrolidin-2-yl]methoxy}quinazolin-4-yl)amino]-1H-pyrazol-1-yl}acetamide A solution of tetra-butylammonium fluoride (1 M in tetrahydrofuran, 0.5 ml, 0.5 mmol) was added to a solution of 2-{4-[(7-{[(2S)-1-(2-{[tert-butyl(dimethyl)silyl]oxy}ethyl)pyrrolidin-2-yl]methoxy}quinazolin-4-yl)amino]-1H-pyrazol-1-yl}-N-(3-fluorophenyl)acetamide (0.055 g, 0.09 mmol) in tetrahydrofuran (5 ml) and the mixture was stirred at room temperature for 15 minutes. The mixture was poured into water and extracted with dichloromethane. The organic layer was separated, dried over magnesium sulphate and then evaporated to leave a yellow film which was purified by silica gel chromatography. Elution with 5 to 10% methanol and then 10% methanol containing 7M ammonia, gave the title compound as a colourless film which was dissolved in methanol (5 ml) and a solution of hydrogen chloride in diethyl ether (1M, 0.5 ml, 0.5 mmol) was added. The solvent was evaporated and the residue triturated with diethyl ether to yield compound 196 in table 5 as the dihydrochloride salt (0.027 g, 52% yield):

$^1$H-NMR (DMSO $d_6$): 12.06 (s, 1H), 10.82 (s, 1H), 10.53 (br s, 1H), 8.96 (m, 2H), 8.45 (s, 1H), 8.07 (s, 1H), 7.58 (m, 2H), 7.39 (m, 3H), 6.92 (m, 1H), 5.15 (s, 2H), 4.64 (m, 1H), 4.56 (m, 1H), 4.09 (m, 1H), 3.81 (m, 2H), 3.71 (m, 1H), 3.59 (m, 1H), 3.29 (m, 2H), 2.30 (m, 1H), 2.05 (m, 2H), 1.89 (m, 1H); MS (+ve ESI): 506 (M+H)$^+$.

2-{4-[(7-{[(2S)-1-(2-{[tert-butyl(dimethyl)silyl]oxy}ethyl)pyrrolidin-2-yl]methoxy}quinazolin-4-yl)amino]-1H-pyrazol-1-yl}-N-(3-fluorophenyl)acetamide used as Starting Material, was Obtained as Follows a) Sodium triacetoxyborohydride (0.11 g, 0.52 mmol) was added to a mixture of N-(3-fluorophenyl)-2-[4-({7-[(2S)-pyrrolidin-2-ylmethoxy]quinazolin-4-yl}amino)-1H-pyrazol-1-yl]acetamide bis(trifluoroacetate) (0.20 g, 0.29 mmol) and (tert-butyldimethylsilyloxy)acetaldehyde (0.10 ml, 0.52 mmol) in tetrahydrofuran (9 ml) and methanol (3 ml) containing a catalytic amount of acetic acid. The mixture was stirred at room temperature for 1 hour. A further portion of sodium triacetoxyborohydride (0.22 g, 1.04 mmol) was added and the mixture stirred at room temperature for 1 hour. A further portion of sodium triacetoxyborohydride (0.22 g, 1.04 mmol) was added and the mixture stirred at room temperature overnight. The mixture was poured into sodium hydroxide solution (1M, 50 ml) and extracted with dichloromethane. The organic layer was separated, washed with brine, dried over magnesium sulphate and then evaporated to leave a yellow film which was purified by silica gel chromatography. Elution with 5 to 10% methanol in dichloromethane gave 2-{4-[(7-{[(2S)-1-(2-{[tert-butyl(dimethyl)silyl]oxy}ethyl)pyrrolidin-2-yl]methoxy}quinazolin-4-yl)amino]-1H-pyrazol-1-yl}-N-(3-fluorophenyl)acetamide (0.055 g, 31% yield): MS (+ve ESI): 620 (M+H)$^+$.

EXAMPLE 197

Preparation of Compound 197 in Table 5—N-(3-fluorophenyl)-2-{4-[(7-{[(2S)-1-glycoloylpyrrolidin-2-yl]methoxy}quinazolin-4-yl)amino]-1H-pyrazol-1-yl}acetamide Acetoxyacetyl chloride (0.017 ml, 0.16 mmol) was added to a solution of N-(3-fluorophenyl)-2-[4-({7-[(2S)-pyrrolidin-2-ylmethoxy]quinazolin-4-yl}amino)-1H-pyrazol-1-yl]acetamide bis(trifluoroacetate) (0.112 g, 0.16 mmol) and triethylamine (0.1 ml, 0.7 mmol) in tetrahydrofuran (5 ml) and the mixture was stirred at room temperature for 30 minutes. The mixture was evaporated and the residue was dissolved in methanol (5 ml). A solution of sodium hydroxide (2M, 0.5 ml) was added and the mixture stirred at room temperature for 2.5 hours. The mixture was evaporated and the residue sonicated in water (5 ml) and then filtered. The solid was purified by reverse phase chromatography to yield compound 197 in table 5 (0.029 g, 35% yield):

$^1$H-NMR (DMSO $d_6$): 10.55 (br s, 1H), 9.94 (br s, 1H), 8.55 (s, 1H), 8.38 (d, 1H), 8.35 (s, 1H), 7.78 (s, 1H), 7.58 (m, 1H), 7.36 (m, 2H), 7.24 (m, 2H), 6.91 (m, 1H), 5.06 (s, 2H), 4.56 and 4.37 (m, 2H), 4.29 (m, 1H), 4.11 (m, 1H), 4.04 (m, 1H), 3.40 (m, 2H under water), 1.98 (m, 4H); MS (+ve ESI): 520 (M+H)$^+$.

EXAMPLE 198

Preparation of Compound 198 in Table 5—N-(3-fluorophenyl)-2-(4-{[7-(pyrrolidin-3-ylmethoxy)quinazolin-4-yl]amino}-1H-pyrazol-1-yl)acetamide A solution of tert-butyl 3-[({4-[(1-{2-[(3-fluorophenyl)amino]-2-oxoethyl}-1H-pyrazol-4-yl)amino]quinazolin-7-yl]oxy)methyl]pyrrolidine-1-carboxylate (0.435 g, 0.78 mmol) in trifluoroacetic acid (10 ml) was stirred at room temperature for 30 minutes. The mixture was evaporated and the residue was stirred in diethyl ether (25 ml) and then filtered and dried under nitrogen to yield compound 198 in table 5 (0.537 g, 100% yield):

$^1$H-NMR (DMSO $d_6$): 11.43 (s, 1H), 10.63 (s, 1H), 8.97 (br s, 2H), 8.94 (s, 1H), 8.60 (d, 1H), 8.39 (s, 1H), 7.94 (s, 1H), 7.59 (m, 1H), 7.50 (m, 1H), 7.38 (m, 1H), 7.31 (m, 2H), 6.92 (m, 1H), 5.13 (s, 2H), 4.25 (m, 2H), 3.43 (m, 1H), 3.33 (m, 1H), 3.25 (m, 1H), 3.11 (m, 1H), 2.84 (m, 1H), 2.17 (m, 1H), 1.83 (m, 1H); MS (+ve ESI): 462 (M+H)$^+$.

tert-butyl 3-[({4-[(1-{2-[(3-fluorophenyl)amino]-2-oxoethyl}-1H-pyrazol-4-yl)amino]quinazolin-7-yl}oxy)methyl]pyrrolidine-1-carboxylate used as Starting Material, was Obtained as Follows a) Methane sulphonyl chloride (0.39 ml, 5.0 mmol) was added dropwise to a solution of tert-butyl 3-(hydroxymethyl)pyrrolidine-1-carboxylate (0.51 g, 2.5 mmol) and 4-(dimethylamino)pyridine (0.61 g, 5.0 mmol) in dichloromethane (15 ml). The mixture was stirred at room temperature for 30 minutes and then concentrated to approximately half volume and purified by silica gel chromatography. Elution with a mixture of 3:1 to 1:1 iso-hexane:ethyl acetate yielded tert-butyl 3-{[(methylsulphonyl)oxy]methyl}pyrrolidine-1-carboxylate.

$^1$H-NMR ($CDCl_3$): 4.16 (m, 2H), 3.28-3.61 (m, 3H), 3.15 (m, 1H), 3.03 (s, 3H), 2.63 (m, 1H), 2.05 (m, 1H), 1.74 (m, 1H), 1.47 (s, 9H).

b) A mixture of N-(3-fluorophenyl)-2-{4-[(7-hydroxyquinazolin-4-yl)amino]-1H-pyrazol-1-yl}acetamide (0.59 g, 1.2 mmol), cesium carbonate (1.95 g, 6.0 mmol) and tert-butyl 3-{[(methylsulphonyl)oxy]methyl}pyrrolidine-1-carboxylate (assumed 1.3 mmol) in dimethyl acetamide (10 ml) was heated at 80° C. for 6 hours. The mixture was poured into water and extracted with ethyl acetate. The organic layer was separated, washed with brine, dried over magnesium sulphate and evaporated in vacuo. The residue was purified by silica gel chromatography eluting with 4 to 7% methanol in dichloromethane to yield tert-butyl 3-[({4-[(1-{2-[(3-fluorophenyl)amino]-2-oxoethyl}-1H-pyrazol-4-yl)amino]quinazolin-7-yl}oxy)methyl]pyrrolidine-1-carboxylate (0.435 g, 65% yield): MS (+ve ESI): 562 (M+H)$^+$.

EXAMPLE 199

Preparation of Compound 199 in Table 5—N-(3-fluorophenyl)-2-{4-[(7-{[1-(2-hydroxyethyl)pyrrolidin-3-yl]methoxy}quinazolin-4-yl)amino]-1H-pyrazol-1-yl}acetamide Sodium triacetoxyborohydride (0.23 g, 1.1 mmol) was added to a mixture of N-(3-fluorophenyl)-2-(4-{[7-(pyrrolidin-3-ylmethoxy)quinazolin-4-yl]amino}-1H-pyrazol-1-yl)acetamide bis(trifluoroacetate) (0.30 g, 0.44 mmol) and (tert-butyldimethylsilyloxy)acetaldehyde (0.20 ml, 1.0 mmol) in tetrahydrofuran (9 ml) and methanol (3 ml) containing a catalytic amount of acetic acid. The mixture was stirred at room temperature for 1 hour. The mixture was poured into sodium hydroxide solution (1M) and extracted with dichloromethane. The organic layer was separated, washed with brine, dried over magnesium sulphate and then evaporated to leave a brown oil which was purified by silica gel chromatography. Elution with 3 to 6% methanol in dichloromethane gave 2-{4-[(7-{[1-(2-{[tert-butyl(dimethyl)silyl]oxy}ethyl) pyrrolidin-3-yl]methoxy}quinazolin-4-yl)amino]-1H-pyrazol-1-yl}-N-(3-fluorophenyl)acetamide. MS (+ve ESI): 620 $(M+H)^+$.

A solution of tetra-butylammonium fluoride (1 M in tetrahydrofuran, 0.6 ml, 0.6 mmol) was added to a solution of the 2-{4-[(7-{[1-(2-{[tert-butyl(dimethyl)silyl]oxy}ethyl) pyrrolidin-3-yl]methoxy}quinazolin-4-yl)amino]-1H-pyrazol-1-yl}-N-(3-fluorophenyl)acetamide in tetrahydrofuran (5 ml) and the mixture was stirred at room temperature for 4 hours. The solution was made acidic by the addition of acetic acid and then a solution of ammonia in methanol (7M, 1 ml) was added and the mixture was concentrated in vacuo. The residue was purified by silica gel chromatography, elution with 5 to 10% methanol and then 10% methanol containing 7M ammonia, gave the tide compound as a colourless film which was dissolved in methanol (5 ml) and a solution of hydrogen chloride in diethyl ether (4M, 0.5 ml, 2.0 mmol) was added. The solvent was evaporated and the residue triturated with diethyl ether to leave a bright yellow solid which was purified by reverse phase chromatography to yield compound 199 in table 5 (0.041 g, 19% yield over 2 steps):

$^1$H-NMR (DMSO $d_6$): 10.52 (s, 1H), 9.92 (s, 1H), 8.55 (s, 1H), 8.36 (d, 1H), 8.34 (s, 1H), 7.78 (s, 1H), 7.58 (m, 1H), 7.35 (m, 2H), 7.23 (dd, 1H), 7.15 (d, 1H), 6.91 (m, 1H), 5.06 (s, 2H), 4.39 (m, 1H), 4.04 (m, 2H), 3.49 (m, 2H), 2.70 (m, 1H), 2.58 (m, 3H), 2.44 (m, 1H), 1.96 (m, 1H), 1.55 (m, 1H); MS (+ve ESI): 506 $(M+H)^+$.

EXAMPLE 200

Preparation of Compound 200 in Table 5—N-(3-fluorophenyl)-2-[4-({7-[(1-glycoloylpyrrolidin-3-yl) methoxy]quinazolin-4-yl}amino)-1H-pyrazol-1-yl] acetamide Acetoxyacetyl chloride (0.025 ml, 0.23 mmol) was added to a solution of N-(3-fluorophenyl)-2-(4-{[7-(pyrrolidin-3-ylmethoxy)quinazolin-4-yl]amino}-1H-pyrazol-1-yl)acetamide bis(trifluoroacetate) (0.161 g, 0.23 mmol) and triethylamine (0.11 ml, 0.79 mmol) in tetrahydrofuran (5 ml) and the mixture was stirred at room temperature for 30 minutes. The mixture was evaporated and the residue was dissolved in methanol (5 ml). A solution of sodium hydroxide (2M, 0.5 ml) was added and the mixture stirred at room temperature for 2.5 hours. The mixture was evaporated and the residue sonicated in water (5 ml) and then filtered. The solid was purified by reverse phase chromatography eluting with a mixture of 5 to 95% acetonitrile (containing 0.2% trifluoroacetic acid) in water (containing 0.2% trifluoroacetic acid) to yield compound 200 in table 5 (0.026 g, 22% yield): MS (+ve ESI): 520 $(M+H)^+$.

EXAMPLE 201

Preparation of Compound 201 in Table 5—N-(3-fluorophenyl)-2-{4-[(7-{3-[(2-hydroxyethyl)(2-methoxyethyl)amino]propoxy}quinazolin-4-yl) amino]-1H-pyrazol-1-yl}acetamide An analogous reaction to that described in example 186, but starting with 2-((2-methoxyethyl)amino)ethanol (0.931 g, 2 mmol) yielded compound 201 in table 5 (0.533 g, 49% yield) as a pale yellow solid:

$^1$H-NMR ($DMSOd_6$): 10.55 (s, 1H), 9.94 (s, 1H), 8.54 (s, 1H), 8.37 (d, 1H), 8.35 (s, 1H), 7.77 (s, 1H), 7.58 (d, 1H), 7.37 (m, 1H), 7.31 (d, 1H), 7.22 (m, 1H), 7.14 (m, 1H), 6.91 (m, 1H), 5.06 (s, 2H), 4.31 (m, 1H), 4.17 (t, 2H), 3.43 (m, 2H), 3.38 (m, 2H), 3.2 (s, 3H), 2.64 (m, 4H), 2.55 (m, 2H), 1.88 (t, 2H); MS (+ve ESI): 538.19 $(M+H)^+$.

EXAMPLE 202

Preparation of Compound 202 in Table 5—N-(3-fluorophenyl)-2-{4-[(7-hydroxyquinazolin-4-yl) amino]-1H-pyrazol-1-yl}acetamide A solution of 2-(4-{[7-(benzyloxy)quinazolin-4-yl] amino}-1H-pyrazol-1-yl)-N-(3-fluorophenyl)acetamide hydrochloride (0.30 g, 0.59 mmol) in trifluoroacetic acid (4 ml) was heated at reflux for 2 hours. The solvent was evaporated in vacuo and the residue triturated with diethyl ether to yield compound 202 in table 5 (0.295 g, 100% yield) as the trirluoroacetate salt:

$^1$H-NMR (DMSO $d_6$): 11.57 (br s, 1H), 11.38 (br s, 1H), 10.59 (br s, 1H), 8.89 (s, 1H), 8.50 (d, 1H), 8.34 (s, 1H), 7.91 (s, 1H), 7.57 (dt, 1H), 7.33 (m, 3H), 7.11 (m, 1H), 6.91 (m, 1H), 5.11 (s, 2H); MS (+ve ESI): 379 $(M+H)^+$.

2-(4-{[7-(benzyloxy)quinazolin-4-yl]amino}-1H-pyrazol-1-yl)-N-(3-fluorophenyl)acetamide used as Starting Material, was Obtained as Follows a) Benzyl alcohol (12.6 ml, 122 mmol) was added dropwise over 15 minutes to a slurry of sodium hydride (60% dispersion in mineral oil, 7.6 g, 190 mmol) in dimethylacetamide (100 ml) cooled in an ice-bath. The mixture was stirred at 0° C. for 15 minutes and then 7-fluoroquinazolin-4(3H)-one (prepared as described in WO03/055491) (10.0 g, 61 mmol) was added portionwise over 15 minutes. The mixture was warmed to room temperature and then heated at 60° C. for 15 hours and then at 80° C. for 3 hours. The mixture was poured into water (600 ml) and made acidic (pH~6) by the addition of concentrated hydrochloric acid. The resultant precipitate was filtered and washed with water to yield 7-(benzyloxy)quinazolin-4(3H)-one as a colourless solid (11.5 g, 75% yield):

$^1$H-NMR (DMSO $d_6$): 12.07 (br s, 1H), 8.03 (m, 2H), 7.49 (m, 2H), 7.38 (m, 3H), 7.18 (m, 2H), 5.27 (s, 2H); MS (+ve ESI): 253 $(M+H)^+$.

b) A solution of 7-(benzyloxy)quinazolin-4(3H)-one (5.0 g, 19.8 mmol) in thionyl chloride (40 ml) containing a catalytic amount of dimethylformamide was heated at 90° C. for 2 hours. The solvent was concentrated in vacuo and the oily residue co-evaporated with toluene (2×100 ml) to leave a yellow solid which was triturated with diethyl ether to yield 7-(benzyloxy)4-chloroquinazoline (4.79 g, 90% yield) as a pale yellow solid:

$^1$H-NMR (DMSO $d_6$): 8.96 (s, 1H), 8.17 (d, 1H), 7.53 (m, 4H), 7.39 (m, 3H), 5.36 (s, 2H);

MS (+ve ESI): 271 $(M+H)^+$.

c) A mixture of 7-(benzyloxy)-4-chloroquinazoline (1.94 g, 7.17 mmol) and 2-(4-amino-1H-pyrazol-1-yl)-N-(3-fluorophenyl)acetamide (1.66 g, 7.09 mmol) in dimethylacetamide (25 ml) was heated at 90° C. for 1 hour. The mixture was cooled to room temperature and then diluted with diethyl ether (75 ml) and filtered. The solid was washed with diethyl ether and dried to yield 2-(4-{[7-(benzyloxy)quinazolin-4-yl]amino}-1H-pyrazol-1-yl)-N-(3-fluorophenyl)acetamide hydrochloride (2.92 g, 82% yield) as a yellow solid:

$^1$H-NMR (DMSO $d_6$): 11.76 (br s, 1H), 10.74 (br s, 1H), 8.93 (s, 1H), 8.76 (d, 1H), 8.40 (s, 1H), 7.99 (s, 1H), 7.53 (m, 4H), 7.39 (m, 7H), 6.90 (m, 1H), 5.34 (s, 2H), 5.13 (s, 2H).

MS (+ve ESI): 469 $(M+H)^+$

EXAMPLE 203

Preparation of compound 203 in table 6-N-(2-Fluorophenyl)-2-{4-[(7-{3-[(2R)-2-(hydroxymethyl)pyrrolidin-1-yl]propoxy}quinazolin-4-yl)amino]-1H-pyrazol-1-yl}acetamide An analogous reaction to that described in example 186, but starting with 2-(4-{[7-(3-chloropropoxy)quinazolin-4-yl]amino}-1H-pyrazol-1-yl)-N-(2-fluorophenyl)acetamide (0.240 g, 0.53 mmol) and (2R)-pyrrolidin-2-ylmethanol (0.201 g, 1.99 mmol) yielded compound 203 in table 6 (0.193 g, 70% yield):

$^1$H-NMR (DMSO $d_6$): 10.04 (s, 1H), 9.91 (s, 1H), 8.55 (s, 1H), 8.36 (d, 1H), 8.35 (s, 1H), 7.94 (m, 1H), 7.80 (s, 1H), 7.30 (m, 1H), 7.20 (m, 4H), 5.14 (s, 2H), 4.38 (s(br.), 1H), 4.21 (t, 2H), 3.42 (m, 2H), 3.15 (m, 3H), 2.25 (m, 1H), 2.55 (m partially obscured by DMSO, 1H), 2.00 (m, 2H), 1.86 (m, 1H), 1.72 (m, 2H), 1.62 (m, 1H);

MS (+ve ESI): 520 $(M+H)^+$.

2-(4-{[7-(3-chloropropoxy)quinazolin-4-yl]amino}-1H-pyrazol-1-yl)-N-(2-fluorophenyl)acetamide used as starting material, was prepared as follows a) A solution of (4-nitro-1H-pyrazol-1-yl)acetic acid (2.0 g, 11.7 mmol) in toluene (40 ml) was heated to 80° C. and then N,N-dimethylformamide di-tert-butyl acetal (7.0 g, 34.5 mmol) was added dropwise over 1 hour. The reaction mixture was heated at 80° C. for a further 20 minutes and then allowed to cool to room temperature. The mixture was concentrated and the residue purified by silica gel chromatography eluting with 50% methyl tert-butyl ether in iso-hexane to give tert-butyl (4-nitro-1H-pyrazol-1-yl)acetate (2.21 g, 83% yield) as a colourless solid:

$^1$H-NMR ($CDCl_3$): 8.25 (s, 1H), 8.10 (s, 1H), 4.83 (s, 2H), 1.52 (s, 9H).

b) Tert-butyl (4-nitro-1H-pyrazol-1-yl)acetate (1.0 g, 4.40 mmol) and 10% palladium on carbon (0.100 g) in methanol (20 ml) were stirred under an atmosphere of hydrogen for 2 hours and then the mixture was filtered through Celite and the filtrate evaporated to give tert-butyl (4-amino-1H-pyrazol-1-yl)acetate (0.860 g, 99% yield) as a dark orange, viscous oil:

$^1$H-NMR ($CDCl_3$): 7.20 (s, 1H), 7.06 (s, 1H), 4.67 (s, 2H), 2.92 (s, 2H), 1.48 (s, 9H).

c) A mixture of tert-butyl (4-amino-1H-pyrazol-1-yl)acetate (0.305 g, 1.55 mmol) and 4-chloro-7-(3-chloropropoxy)quinazoline (0.398 g, 1.55 mmol) in isopropanol (8 ml) was heated at 90° C. for 5 minutes and then allowed to cool to room temperature. The mixture was diluted with diethyl ether and then filtered to give tert-butyl (4-{[7-(3-chloropropoxy)quinazolin-4-yl]amino}-1H-pyrazol-1-yl)acetate as the hydrochloride salt (0.674 g, 96% yield):

$^1$H-NMR (DMSO $d_6$): 11.85 (s, 1H), 8.93 (s, 1H), 8.82 (d, 1H), 8.36 (s, 1H), 8.01 (s, 1), 7.49 (dd, 1H), 7.37 (d, 1H), 5.03 (s, 2H), 4.33 (t, 2H), 3.86 (t, 2H), 2.28 (quintet, 2H); MS (+ve ESI): 418 $(M+H)^+$.

d) A solution of tert-butyl (4-{[7-(3-chloropropoxy)quinazolin-4-yl]amino}-1H-pyrazol-1-yl)acetate hydrochloride (7.33 g, 16.1 mmol) in trifluoroacetic acid (60 ml) was stirred at room temperature for 30 minutes. The mixture was concentrated and the residue was suspended in water (120 ml), basified to pH 12 with 40% aqueous sodium hydroxide solution and then re-acidified to pH 4.8 with 2N aqueous hydrochloric acid to give (4-{[7-(3-chloropropoxy)quinazolin-4-yl]amino}-1H-pyrazol-1-yl)acetic acid (5.74 g, 98% yield) as a cream coloured solid:

$^1$H-NMR (DMSO $d_6$): 11.10 (s, 1H), 8.70 (s, 1H), 8.50 (d, 1H), 8.31 (s, 1H), 7.83 (s, 1H), 7.34 (dd, 1H), 7.22 (d, 1H), 5.00 (s, 2H), 4.30 (t, 2H), 3.85 (t, 2H), 2.26 (quintet, 2H); MS (+ve ESI): 362 $(M+H)^+$.

e) Pentafluorophenyl trifluoroacetate (0.325 g, 1.16 mmol) was added dropwise, at room temperature, to a stirred suspension of (4-{[7-(3-chloropropoxy)quinazolin-4-yl]amino}-1H-pyrazol-1-yl)acetic acid (0.300 g, 0.83 mmol) and pyridine (0.092 g, 1.16 mmol) in dimethylformamide (3 ml). After stirring for 5 minutes 2-fluoroaniline (0.184 g, 1.66 mmol) was added and the reaction stirred for 5 hours. The mixture was poured into 0.2N aqueous hydrochloric acid (25 ml) to give 2-(4-{[7-(3-chloropropoxy)quinazolin-4-yl]amino}-1H-pyrazol-1-yl)-N-(2-fluorophenyl)acetamide as a cream coloured solid: MS (+ve ESI): 455 $(M+H)^+$.

EXAMPLE 204

Preparation of Compound 204 in Table 6—2-{4-[(7-{3-[ethyl(2-hydroxyethyl)amino]propoxy}quinazolin-4-yl)amino]-1H-pyrazol-1-yl}-N-(2-fluorophenyl)acetamide An analogous reaction to that described in example 203, but starting with 2-(ethylamino)ethanol (0.177 g, 1.99 mmol) yielded compound 204 in table 6 (0.178 g, 66% yield):

$^1$H-NMR (DMSO $d_6$): 10.05 (s, 1H), 9.90 (s, 1H), 8.55 (s, 1H), 8.37 (d, 1H), 8.35 (s, 1H), 7.94 (m, 1H), 7.79 (s, 1H), 7.28 (m, 1H), 7.20 (m, 4H), 5.15 (s, 2H), 4.35 (s(br.), 1H), 4.20 (t, 2H), 3.47 (m, 2H), 2.67 (m, 2H), 2.58 (m, 4H), 1.92 (m, 2H), 1.00 9t, 3H); MS (+ve ESI): 508 $(M+H)^+$.

EXAMPLE 205

Preparation of Compound 205 in Table 6—2-{4-[(7-{3-[(2R)-2-(hydroxymethyl)pyrrolidin-1-yl]propoxy}quinazolin-4-yl)amino]-1H-pyrazol-1-yl}-N-phenylacetamide An analogous reaction to that described in example 203, but starting with 2-(4-{[7-(3-chloropropoxy)quinazolin-4-yl]amino}-1H-pyrazol-1-yl)-N-phenylacetamide (0.240 g, 0.55 mmol) and (2R)-pyrrolidin-2-ylmethanol (0.166 g, 1.64 mmol) yielded compound 205 in table 6 (0.201 g, 73% yield):

$^1$H-NMR (DMSO-$d_6$): 10.28 (s, 1H), 9.91 (s, 1H), 8.55 (s, 1H), 8.36 (d, 1H), 8.35 (s, 1H), 7.78 (s, 1H), 7.61 (d, 2H), 7.34 (t, 2H), 7.23 (dd, 1H), 7.17 (d, 1H), 7.09 (t, 1H), 5.05 (s, 2H), 4.20 (t, 2H), 3.45 (m, 2H), 3.20 (m partially obscured by $H_2O$, 5H), 2.03 (m, 2H), 1.90 (m, 1H), 1.72 (m, 2H), 1.63 (m, 1H); MS (+ve ESI): 502 $(M+H)^+$.

2-(4-{[7-(3-chloropropoxy)quinazolin-4-yl]amino}-1H-pyrazol-1-yl)-N-phenylacetamide used as Starting Material, was Prepared as Follows Pentafluorophenyl trifluoroacetate (0.867 g, 3.10 mmol) was added dropwise, at room temperature, to a stirred suspension of (4-{[7-(3-chloropropoxy)quinazolin-4-yl]amino}-1H-pyrazol-1-yl)acetic acid (0.800 g, 2.21 mmol) and pyridine (0.245 g, 3.10 mmol) in dimethylformamide (8 ml). After stirring for 5 minutes, aniline (0.412 g, 4.43 mmol) was added and the reaction mixture was stirred for 2 hours. The mixture was poured into dilute hydrochloric acid (0.2N, 25 ml) and the resultant solid filtered and then washed with water. The residue was stirred in dilute aqueous sodium hydroxide solution and filtered and the residue washed successively with water, methanol and diethylether to give 2-(4-{[7-(3-chloropropoxy)quinazolin-4-yl]amino}-1H-pyrazol-1-yl)-N-phenylacetamide (0.520 g, 54% yield): MS (+ve ESI): 437 $(M+H)^+$.

EXAMPLE 206

Preparation of Example 206 in Table 6—2-{4-[(7-{3-[ethyl(2-hydroxyethyl)amino]propoxy}quinazolin-4-yl)amino]-1H-pyrazol-1-yl}-N-phenylacetamide An analogous reaction to that described in example 205, but starting with 2-(ethylamino)ethanol (0.147 g, 1.65 mmol) yielded compound 206 in table 6 (0.184 g, 68% yield):

$^1$H-NMR (DMSO $d_6$): 10.28 (s, 1H), 9.91 (s, 1H), 8.54 (s, 1H), 8.36 (d, 1H), 8.35 (s, 1H), 7.78 (s, 1H), 7.60 (d, 2H), 7.33 (t, 2H), 7.23 (dd, 1H), 7.16 (d, 1H), 7.09 (t, 1H), 5.05 (s, 2H), 4.40 (s(br.), 1H), 4.20 (t, 2H), 3.52 (m, 2H), 2.65 (m, 6H), 1.94 (m, 2H), 1.03 T, 3H); MS (+ve ESI): 490 $(M+H)^+$.

EXAMPLE 207

Preparation of Compound 207 in Table 6—N-(2,6-difluorophenyl)-2-{4-[(7-{3-[(2R)-2-(hydroxymethyl)pyrrolidin-1-yl]propoxy}quinazolin-4-yl)amino]-1H-pyrazol-1-yl}acetamide An analogous reaction to that described in example 203, but starting with 2-(4-{[7-(3-chloropropoxy)quinazolin-4-yl]amino}-1H-pyrazol-1-yl)-N-(2,6-difluorophenyl)acetamide (0.280 g, 0.59 mmol) and (2R)-pyrrolidin-2-ylmethanol (0.180 g, 1.78 mmol) yielded compound 207 in table 6 (0.208 g, 65% yield):

$^1$H-NMR (DMSO $d_6$): 10.01 (s, 1H), 9.90 (s, 1H), 8.54 (s, 1H), 8.36 (d, 1H), 8.35 (s, 1H), 7.79 (s, 1H), 7.37 (m, 1H), 7.20 (m, 4H), 5.13 (s, 2H),4.33 (s(br.), 1H), 4.20 (t,2H), 3.42 (m, 1H), 3.24 (m, 1H), 3.11 (m, 1H), 3.02 (m, 1H), 2.50 (m partially obscured by DMSO, 2H), 2.22 (m, 1H), 1.97 (m, 2H), 1.82 (m, 1H), 1.68 (m, 2H), 1.57 (m, 1H); MS (+ve ES]): 538 $(M+H)^+$.

2-(4-{[7-(3-chloropropoxy)quinazolin-4-yl]amino}-1H-pyrazol-1-yl)-N-(2,6-difluorophenyl)acetamide used as Starting Material, was Prepared as Follows a) 4-(4,6-dimethoxytriazin-2-yl)-4-methylmorpholinium chloride (0.391 g, 1.32 mmol) was added in one go, at room temperature, to a stirred suspension of (4-{[7-(3-chloropropoxy)quinazolin-4-yl]amino}-1H-pyrazol-1-yl)acetic acid (0.400 g, 1.11 mmol) and 2,6-difluoroaniline (0.171 g, 1.32 mmol) in dimethylformamide (7 ml). The mixture was stirred for 2 hours and then poured into water (30 ml) the resultant solid was filtered to give 2-(4-{[7-(3-chloropropoxy)quinazolin-4-yl]amino}-1H-pyrazol-1-yl)-N-(2,6-difluorophenyl)acetamide (0.403 g, 77% yield) as a pale brown solid:

MS (+ve ESI): 473 (M+H).

EXAMPLE 208

Preparation of Compound 208 in Table 7—2-{4-[(7-{3-[ethyl(2-hydroxyethyl)amino]propoxy}-6-fluoroquinazolin-4-yl)amino]-1H-pyrazol-1-yl}-N-(3-fluorophenyl)acetamide A mixture of 2-(4-{[7-(3-chloropropoxy)-6-fluoroquinazolin-4-yl]amino}-1H-pyrazol-1-yl)-N-(3-fluorophenyl)acetamide (0.300 g, 0.63 mmol), 2-(ethylamino)ethanol (0.169 g, 1.90 mmol) and potassium iodide (0.211 g, 1.27 mmol) in dimethylacetamide (2 ml) was heated at 90° C. for 90 minutes and then allowed to cool to room temperature. The resulting solution was diluted with dichloromethane and then purified directly by silica gel chromatography eluting with a mixture of 10% methanol in dichloromethane containing 0-4% 7N ammonia in methanol to give compound 208 in table 7 (0.203 g, 61% yield) as a pale yellow solid:

$^1$H-NMR (DMSO $d_6$): 10.52 (s, 1H), 9.85 (s, 1H), 8.58 (s, 1H), 8.34 (m, 2H), 7.77 (s, 1H), 7.59 (d, 1H), 7.40 (m, 2H), 7.33 (m, 1H), 6.92 (m, 1H), 5.33 (m, 1H), 5.08 (s, 2H), 4.35 (m, 2H), 3.74 (m, 2H), 3.25 (m (partially obscured by $H_2O$), 6H), 2.22 (m, 2H), 1.23 (m, 3H); MS (+ve ESI): 526 $(M+H)^+$.

EXAMPLE 209

Preparation of Compound 209 in Table 7—2-{4-[(7-{3-[(cyclopropylmethyl)(2-hydroxyethyl)amino]propoxy}-6-fluoroquinazolin-4-yl)amino]-1H-pyrazol-1-yl}-N-(2,3-difluorophenyl)acetamide An analogous reaction to example 208, but starting with 2-(4-{[7-(3-chloropropoxy)-6-fluoroquinazolin-4-yl]amino}-1H-pyrazol-1-yl)-N-(2,3-difluorophenyl)acetamide (0.300 g, 0.61 mmol) and 2-[(cyclopropylmethyl)amino]ethanol (0.211 g, 1.83 mmol) yielded compound 209 in table 7 (0.210 g, 60% yield):

$^1$H-NMR (DMSO $d_6$): 10.28 (s, 1H), 9.83 (s, 1H), 8.58 (s, 1H), 8.35 (s, 1H), 8.32 (d, 1H), 7.78 (s, 1H), 7.73 (m, 1H), 7.36 (d, 1H), 7.21 (m, 2H), 5.17 (s, 2H), 4.30 (m, 3H), 3.49 (m, 2H), 2.71 (t,2H), 2.61 (t, 2H), 2.37 (d, 2H), 1.94 (quintet, 2H), 0.85 (m, 1H), 0.42 (m, 2H), 0.09 (m, 2H); MS (+ve ESI): 570 $(M+H)^+$.

EXAMPLE 210

Preparation of Compound 210 in Table 7—N-(2,3-difluorophenyl)-2-{4-[(6-fluoro-7-{3-[(2-hydroxyethyl)(propyl)amino]propoxy}quinazolin-4-yl)amino]-1H-pyrazol-1-yl}acetamide An analogous reaction to example 209, but starting with 2-(propylamino)ethanol (0.189 g, 1.83 mmol) yielded compound 210 in table 7 (0.195 g, 57% yield):

$^1$H-NMR (DMSO $d_6$): 10.27 (s, 1H), 9.81 (s, 1H), 8.56 (s, 1H), 8.33 (s, 1H), 8.31 (d, 1H), 7.78 (s, 1H), 7.72 (m, 1H), 7.34 (d, 1H), 7.20 (m, 2H), 5.15 (s, 2H), 4.28 (m, 3H), 3.43 (m, 2H), 2.61 (t, 2H), 2.50 (m (partially obscured by DMSO), 2H), 2.40 (t, 2H), 1.91 (quintet, 2H), 1.41 (m, 2H), 0.81 (t, 3H); MS (+ve ESI): 558 $(M+H)^+$.

EXAMPLE 211

Preparation of Compound 211 in Table 7—N-(2,3-difluorophenyl)-2-{4-[(6-fluoro-7-{3-[(2R)-2-(hydroxymethyl)pyrrolidin-1-yl]propoxy}quinazolin-4-yl)amino]-1H-pyrazol-1-yl}acetamide An analogous reaction to example 209, but starting with (2R)-pyrrolidin-2ylmethanol (0.310 g, 3.06 mmol) yielded compound 211 in table 7 (0.324 g, 57% yield):

$^1$H-NMR (DMSO $d_6$): 10.28 (s, 1H), 9.82 (s, 1H), 8.56 (s, 1H), 8.33 (s, 1H), 8.30 (d, 1H), 7.78 (s, 1H), 7.72 (m, 1H), 7.35 (d, 1H), 7.20 (m, 2H), 5.16 (s, 2H), 4.28 (m, 3H), 3.40 (m, 1H), 3.20 (m, 1H), 3.10 (m, 1H), 2.99 (m, 1H), 2.43 (m, 2H), 2.18 (m, 1H), 1.97 (m, 2H), 1.81 (m, 1H), 1.63 (m, 2H), 1.55 (m, 1H); MS (+ve ESI): 556 $(M+H)^+$.

EXAMPLE 212

Preparation of Compound 212 in Table 7—2-{4-[(7-{3-[cyclopentyl(2-hydroxyethyl)amino]propoxy}-6-fluoroquinazolin-4-yl)amino]-1H-pyrazol-1-yl}-N-(2,3-difluorophenyl)acetamide An analogous reaction to example 209, but starting with 2-(cyclopentylamino)ethanol (0.237 g, 1.83 mmol) yielded compound 212 in table 7 (0.241 g, 67% yield):

$^1$H-NMR (DMSO $d_6$): 10.28 (s, 1H), 9.81 (s, 1H), 8.56 (s, 1H), 8.33 (s, 1H), 8.31 (d, 1H), 7.78 (s, 1H), 7.72 (m, 1H), 7.35 (d, 1H), 7.20 (m, 2H), 5.16 (s, 2H), 4.28 (m, 3H), 3.42 (m, 2H), 3.06 (quintet, 1H), 2.67 (t, 2H), 2.55 (m, 2H), 1.92 (quintet, 2H), 1.72 (m, 2H), 1.56 (m, 2H), 1.48 (m, 2H), 1.33 (m, 2H); MS (+ve ESI): 584 $(M+H)^+$.

EXAMPLE 213

Preparation of Compound 213 in Table 8—2-{4-[(7-{3-[bis(2-hydroxyethyl)amino]propoxy}-5-isopropoxyquinazolin-4-yl)amino]-1H-pyrazol-1-yl}-N-(2,3-difluorophenyl)acetamide A mixture of sodium iodide (9.9 mg, 0.66 mmol), 2,2'-iminodiethanol (60 µl, 0.66 mmol) and 2-(4-{[7-(3-chloropropoxy)-5-isopropoxyquinazolin-4-yl]amino}-1H-pyrazol-1-yl)-N-(2,3-difluorophenyl)acetamide (117 mg, 0.22 mmol) in dimethylacetamide (5 ml) was heated at 90° C. for 1 hour. The mixture was evaporated under reduced pressure and the residue purified by silica gel chromatography eluting with a 0 to 10% mixture of methanol (containing 10% 7N ammonia in methanol) in dichloromethane to give compound 213 in table 8 (28 mg, 21% yield) as a white solid:

$^1$H-NMR ($CDCl_3$): 9.82 (s, 1H), 8.80 (br s, 1H), 8.54 (s, 1H), 8.42 (s, 1H), 8.04 (t, 1H), 7.70 (s, 1H), 7.08 (m, 1H), 6.98 (d, 1H), 6.85 (m, 1H), 6.44 (s, 1H), 5.01 (s, 2H), 4.86 (septet, 1H), 4.22 (t, 2H), 3.70 (m, 2H), 2.67 (m, 8H), 2.00 (t, 2H), 1.60 (d, 6H); MS (+ve ESI): 600 $(M+H)^+$ MS (−ve ESI): 598 $(M-H)^-$.

EXAMPLE 214

Preparation of Compound 214 in Table 8—N-(2,3-difluorophenyl)-2-{4-[(7-{3-[(2R)-2-(hydroxymethyl)pyrrolidin-1-yl]propoxy}-5-isopropoxyquinazolin-4-yl)amino]-1H-pyrazol-1-yl}acetamide An analogous reaction to that described in example 213, but starting with (2R)-pyrrolin-2-ylmethanol (30 µl, 0.30 mmol) yielded compound 214 in table 8 (135 mg, 76% yield):

$^1$H-NMR (DMSO $d_6$): 10.01 (s, 1H), 9.85 (s, 1H), 8.62 (s, 1H), 8.35 (s, 1H), 7.78 (s, 1H), 7.68 (m, 1H), 7.20 (m, 2H), 6.78 (s, 1H), 6.64 (s, 1H), 5.12 (s, 2H), 4.96 (septet, 1H), 4.22 (t, 2H), 3.80 (dd, 1H), 3.62 (m, 4H), 3.25 (m, 2H), 2.10 (m, 6H), 1.50 (d, 6H); MS (+ve ESI): 596 $(M+H)^+$ MS (−ve ESI): 594 $(M-H)^-$.

EXAMPLE 215

Preparation of Compound 215 in Table 8—N-(2,3-difluorophenyl)-2-{4-[(7-{3-[4(2-hydroxyethyl)piperazin-1-yl]propoxy}-5-isopropoxyquinazolin-4-yl)amino]-1H-pyrazol-1-yl}acetamide An analogous reaction to that described in example 213, but starting with N-(2-hydroxyethyl)piperazine (0.17 ml, 1.41 mmol) yielded compound 215 in table 8 (40 mg, 23% yield):

$^1$H-NMR (DMSO $d_6$): 10.20 (s, 1H), 9.98 (s, 1H), 8.62 (s, 1H), 8.35 (s, 1H), 7.82 (s, 1H), 7.65 (m, 1H), 7.18 (m, 2H), 6.85 (s, 1H), 6.80 (s, 1H), 5.18 (s, 2H), 4.99 (septet, 1H), 4.22 (t, 2H), 3.70 (m, 2H), 3.18 (m, 4H), 3.05 (m, 2H), 2.90 (m, 2H), 2.82 (m, 2H), 2.10 (m, 2H), 2.05 (quintet, 2H), 1.50 (d, 6H); MS (+ve ESI): 625 $(M+H)^+$ MS (−ve ESI): 623 $(M-H)^-$.

EXAMPLE 216

Preparation of Compound 216 in Table 8—N-(2,3-difluorophenyl)-2-(4-{[5-isopropoxy-7-(3-piperazin-1-ylpropoxy)quinazolin-4-yl]amino}-1H-pyrazol-1-yl)acetamide An analogous reaction to that described in example 213, but starting with piperazine (97 mg, 1.13 mmol) yielded compound 216 in table 8 (60 mg, 27% yield):

$^1$H-NMR (DMSO $d_6$): 9.98 (br s, 1H), 9.70 (s, 1H), 8.45 (s, 1H), 8.30 (s, 1H), 7.75 (s, 1H), 7.70 (t, 1H), 7.88 (m, 2H), 6.80 (s, 1H), 6.65 (s, 1H), 5.18 (s, 2H), 4.90 (septet, 1H), 4.18 (t, 2H), 3.00 (m, 10H), 2.60 (t, 2H), 1.50 (d, 6H); MS (+ve ESI): 581 $(M+H)^+$ MS (−ve ESI): 579 $(M-H)^-$.

EXAMPLE 217

Preparation of Compound 217 in Table 8—N-(2,3-difluorophenyl)-2-{4-[(7-{3-[(2S)-2-(hydroxymethyl)pyrrolidin-1-yl]propoxy}-5-isopropoxyquinazolin-4-yl)amino]-1H-pyrazol-1-yl}acetamide An analogous reaction to that described in example 213, but starting with (2S)-pyrrolin-2-ylmethanol (0.17 ml, 1.9 mmol) yielded compound 217 in table 8 (150 mg, 66% yield):

$^1$H-NMR (DMSO-$_6$): 10.01 (s, 1H), 9.85 (s, 1H), 8.62 (s, 1H), 8.35 (s, 1H), 7.78 (s, 1H), 7.68 (m, 1H), 7.20 (m, 2H), 6.78 (s, 1H), 6.64 (s, 1H), 5.12 (s, 2H), 4.96 (septet, 1H), 4.22

(t, 2H), 3.80 (dd, 1H), 3.62 (m, 4H), 3.25 (m, 2H), 2.10 (m, 6H), 1.50 (d, 6H); MS (+ve ESI): 596 $(M+H)^+$ MS (−ve ESI): 594 $(M-H)^-$.

EXAMPLE 218

Preparation of Compound 218 in Table 8—N-(2,3-difluorophenyl)-2-{4-[(7-{3-[(2-hydroxyethyl)amino]propoxy}-5-isopropoxyquinazolin-4-yl)amino]-1H-pyrazol-1-yl}acetamide An analogous reaction to that described in example 213, but starting with ethanolamine (0.11 ml, 1.9 mmol) yielded compound 218 in table 8 (282 mg, 80% yield):

$^1$H-NMR (DMSO $d_6$): 9.72 (s, 1H), 8.42 (s, 1H), 8.30 (s, 1H), 7.72 (s, 1H), 7.62 (m, 1H), 7.10 (m, 2H), 6.78 (s, 1H), 6.70 (s, 1H), 5.12 (s, 2H), 4.93 (septet, 1H), 4.20 (t, 2H), 3.45 (t, 2H), 2.90 (t, 2H), 2.78 (t, 2H), 2.02 (quintet, 2H), 1.52 (d, 6H); MS(+ve ESI): 556 $(M+E)^+$ MS(−ve ESI): 554 $(M-H)^-$.

EXAMPLE 219

Preparation of Compound 219 in Table 8—N-(2,3-difluorophenyl)-2-[4-({7-[3-(4-glycoloylpiperazin-1-yl)propoxy]-5-isopropoxyquinazolin-4-yl}amino)-1H-pyrazol-1-yl]acetamide A mixture of glycolic acid (5 mg, 0.07 mmol), di-iso-propylethylamine (0.02 ml, 0.14 mmol) and N-(2,3-difluorophenyl)-2-(4-{[5-isopropoxy-7-(3-piperazin-1-ylpropoxy)quinazolin-4-yl]amino}-1H-pyrazol-1-yl)acetamide (40 mg, 0.07 mmol) in dichloromethane (5 ml) was stirred at room temperature for 10 minutes. O-(7-azabenzotriazol-1-yl)-N,N,N',N'-tetramethyluronium hexafluorophosphate (30 mg, 0.08 mmol) was added and the reaction mixture was stirred at room temperature for 1 hour. The volatiles were removed by evaporation under reduced pressure and the residue purified by silica gel chromatography eluting with a 0 to 10% mixture of methanol (containing 10% 7N ammonia in methanol) in dichloromethane to give compound 219 in table 8 (30 mg, 67% yield):

$^1$H-NMR (DMSO $d_6$): 9.98 (br s, 1H), 9.70 (s, 1H), 8.42 (s, 1H), 8.22 (s, 1H), 7.75 (s, 1H), 7.70 (m, 1H), 7.20 (m, 2H), 6.75 (s, 1H), 6.62 (s, 1H), 5.05 (s, 2H), 4.98 (septet, 1H), 4.15 (t, 2H), 4.04 (s, 1H), 3.35 (app.s, 2H), 3.02 (m, 8H), 2.40 (m, 2H), 1.98 (m, 2H), 1.50 (d, 6H); MS (+ve ESI): 639 $(M+H)^+$ MS (−ve ESI): 638 $(M-H)^-$.

EXAMPLE 220

Preparation of Compound 220 in Table 8—N-(2,3-difluorophenyl)-2-{4-[(7-{3-[(2R)-2-(hydroxymethyl)pyrrolidin-1-yl]propoxy}-5-methoxyquinazolin-4-yl)amino]-1H-pyrazol-1-yl}acetamide A mixture of potassium iodide (0.120 g, 0.8 mmol), (2R)-pyrrolidin-2-ylmethanol (0.080 ml, 0.8 mmol) and 2-(4-{[7-(3-chloropropoxy)-5-methoxyquinazolin-4-yl]amino}-1H-pyrazol-1-yl)-N-(2,3-difluorophenyl)acetamide (0.200 g, 0.4 mmol) in dimethylacetamide (5 ml) was heated at 90° C. for 1 hour. The mixture was evaporated under reduced pressure and the residue purified by silica gel chromatography eluting with a 0 to 10% mixture methanol (containing 10% 7N ammonia in methanol) in dichloromethane to give compound 220 in table 8 (0.070 g, 31% yield) as a white solid:

$^1$H-NMR DMSO $d_6$): 10.20 (s, 1H), 9.98 (s, 1H), 8.65 (s, 1H), 8.25 (s, 1H), 7.88 (s, 1H), 7.68 (m, 1H), 7.18 (m, 2H), 6.78 (s, 1H), 6.72 (s, 1H), 5.05 (s, 2H), 4.25 (t, 2H), 4.15 (s, 3H), 3.80 (m, 1H), 3.52 (m, 2H), 2.15 (m, 10H); MS (+ve ESI): 568 $(M+H)^+$.

EXAMPLE 221

Preparation of Compound 221 in Table 8—N-(2,3-difluorophenyl)-2-{4-[(5,7-dimethoxyquiazolin-4-yl)amino]-1H-pyrazol-1-yl}acetamide Phosphoryl chloride (1 ml, 10.8 mmol) was added to a solution of 5,7-dimethoxyquinazolin-4-ol (0.653 g, 3.17 mmol) and di-iso-propylethylamine (3.75 ml, 21.6 mmol) in 1,2-dichloroethane (40 ml) and the reaction was heated at 80° C. for 4 hours. The mixture was evaporated under reduced pressure and the residue suspended in dimethylacetamide (20 ml) and then 2-(4-amino-1H-pyrazol-1-yl)-N-(2,3-difluorophenyl)acetamide (0.799 g, 3.17 mmol) was added and the mixture was heated at 90° C. for 1 hour. The mixture was evaporated under reduced pressure and the residue triturated with diethyl ether to give compound 221 in table 8 (1.1 g, 79% yield):

$^1$H-NMR (DMSO $d_6$): 8.80 (s, 1H), 8.38 (s, 1H), 7.98 (s, 1H), 7.68 (m, 1H), 7.18 (m, 2H), 6.98 (s, 2H), 5.20 (s, 2H), 4.18 (s, 3H), 3.98 (s, 3H); MS (+ve ESI): 441 $(M+H)^+$.

EXAMPLE 222

Preparation of Compound 222 in Table 8—N-(2,3-difluorophenyl)-2-{4-[(5-hydroxy-7-methoxyquinazolin-4-yl)amino]-1H-pyrazol-1-yl}acetamide Pyridine hydrochloride (0.027 g, 0.23 mmol) was added to a solution of N-(2,3-difluorophenyl)-2-{4-[(5,7-dimethoxyquinazolin-4-yl)amino]-1H-pyrazol-1-yl}acetamide (0.100 g, 0.23 mmol) in pyridine (2 ml) and the reaction was heated at 120° C. for 24 hours. The mixture was evaporated under reduced pressure and the residue purified by reverse phase chromatography eluting with 0.2% aqueous trifluoroacetic acid in acetonitrile using a 5 to 50% gradient over 25 minutes. The fractions containing product were concentrated under reduced pressure and then basified with aqueous sodium carbonate. The resultant solid was filtered and washed with water to give compound 222 in table 8 (0.050 g, 32% yield):

$^1$H-NMR (DMSO $d_6$): 9.95 (s, 1H), 8.50 (s, 1H), 8.20 (s, 1H), 7.80 (s, 1H), 7.68 (m, 1H), 7.18 (m, 2H), 6.65 (s, 1H), 6.62 (s, 1H), 5.10 (s, 2H), 3.92 (s, 3H); MS (+ve ESI): 427 $(M+H)^+$.

EXAMPLE 223

Preparation of Compound 223 in Table 8—N-(2,3-difluorophenyl)-2-[4-({7-methoxy-5-[(2R)-pyrrolidin-2-ylmethoxy]quinazolin-4-yl}amino)-1H-pyrazol-1-yl]acetamide A mixture of tert-butyl (2R)-2-[({4-[(1-{2-[(2,3-difluorophenyl)amino]-2-oxoethyl}-1H-pyrazol-4-yl)amino]-7-methoxyquinazolin-5-yl}oxy)methyl]pyrrolidine-1-carboxylate (0.430 g, 0.70 mmol) and trifluoroacetic acid (3 ml) in dichloromethane (15 ml) was stirred at room temperature for 1 hour. The reaction mixture was evaporated under reduced pressure and the residue was then triturated with diethyl ether to give compound 223 in table 8 (0.370 g, 100% yield) as the di-trifluoroacetic acid salt:

$^1$H-NMR (DMSO $d_6$): 9.95 (br s, 1H), 8.59 (s, 1H), 8.32 (s, 1H), 7.80 (s, 1H), 7.65 (m, 1H), 7.20 (m, 2H), 6.88 (s, 1H), 6.82 (s, 1H), 5.15 (s, 2H), 4.60 (m, 2H), 4.20 (m, 1H), 4.00 (s, 3H), 3.35 (t, 2H), 2.05 (m, 4H); MS (+ve ESI): 510 $(M+H)^+$.

tert-butyl (2R)-2-[({4-[(1-{2-[(2,3-difluorophenyl) amino]-2-oxoethyl}-1H-pyrazol-4-yl)amino]-7-methoxyquinazolin-5-yl}oxy)methyl]pyrrolidine-1-carboxylate used as Starting Material, was Prepared as Follows a) tert-butyl (2R)-2-(hydroxymethyl)pyrrolidine-1-carboxylate (1.70 g, 8.6 mmol) was added to a solution of [7-(benzyloxy)-5-hydroxy-4-oxoquinazolin-3(4H)-yl]methyl pivalate (see WO01/094341, 3.0 g, 7.8 mmol) and PS-triphenylphosphine (1.5 mmol/g, 7.2 g, 4.2 mmol) in dichloromethane (120 ml). The reaction mixture was cooled to 0° C. and then a solution of di-tert-butylazodicarboxylate (2.1 g, 9.3 mmol) in dichloromethane (15 ml) was added dropwise over 30 minutes. The mixture was allowed to warn to room temperature and then stirred for 2 hours. The mixture was evaporated under reduced pressure and the residue was purified by silica gel chromatography eluting with a 0 to 10% mixture methanol in dichloromethane to give tert-butyl (2R)-2-{[(7-(benzyloxy)-3-{[(2,2-dimethylpropanoyl)oxy]methyl}-4-oxo-3,4-dihydroquinazolin-5-yl)oxy] methyl}pyrrolidine-1-carboxylate (1.58 g, 36% yield):

$^1$H-NMR (DMSO $d_6$): 8.60 (s, 1H), 8.35 (s, 1H), 7.40 (m, 5H), 6.78 (s, 1H), 5.80 (s, 2H), 5.22 (s, 2H), 4.88 (m, 1H), 4.15 (m, 4H), 2.05 (m, 4H), 1.38 (s, 9H); MS (+ve ESI): 566 $(M+H)^+$.

b) Ammonium formate (1.80 g, 28 mmol) and 10% palladium on carbon (0.180 g) were added to a solution of tert-butyl (2R)-2-{[(7-(benzyloxy)-3-{[(2,2-dimethylpropanoyl) oxy]methyl}-4-oxo-3,4-dihydroquinazolin-5-yl)oxy] methyl}pyrrolidine-1-carboxylate (1.58 g, 2.8 mmol) in ethyl acetate (30 ml) and the mixture stirred at 70° C. for 24 hours. The mixture was filtered through Celite and then evaporated under reduced pressure. The residue was purified by silica gel chromatography eluting with a 0 to 10% mixture methanol in dichloromethane to give tert-butyl (2R)-2-{[(3-{[(2,2-dimethylpropanoyl)oxy]methyl}-7-hydroxy-4-oxo-3,4-dihydroquinazolin-5-yl)oxy]methyl}pyrrolidine-1-carboxylate (0.750 g, 52% yield):

$^1$H-NMR DMSO $d_6$): 10.35 (s, 1H), 9.92 (s, 1H), 8.59 (s, 1H), 8.25 (s, 1H), 7.90 (s, 1H), 7.75 (m, 1H), 7.15 (m, 2H), 6.85 (m, 2H), 5.12 (s, 2H), 4.48 (m, 2H), 4.20 (m, 1H), 3.97 (s, 3H), 3.35 (m, 2H), 2.05 (m, 4H), 1.40 (s, 9H); MS (+ve ESI): 476 $(M+H)^+$.

c) Potassium carbonate (1.60 g, 12.6 mmol) was added to a solution of tert-butyl (2R)-2-{[(3-{[(2,2-dimethylpropanoyl) oxy]methyl}-7-hydroxy-4-oxo-3,4-dihydroquinazolin-5-yl) oxy]methyl}pyrrolidine-1-carboxylate (1.50 g, 3.2 mmol) in dimethylformamide (10 ml) and the mixture stirred at 0° C. for 5 minutes. Dimethyl sulphate (0.6 ml, 6.3 mmol) was added and the reaction stirred at 0° C. for a further 5 minutes and then warmed to room temperature and stirred for 1 hour. The reaction mixture was evaporated under reduced pressure and the residue dissolved in dichloromethane (20 ml) and washed with water (2×20 ml). The organics were dried over magnesium sulphate, filtered and evaporated under reduced pressure to give tert-butyl (2R)-2-{[(3-{[(2,2-dimethylpropanoyl)oxy]methyl}-7-methoxy-4-oxo-3,4-dihydroquinazolin-5-yl)oxy]methyl}pyrrolidine-1-carboxylate (0.750 g, 48% yield) which was used in the next stage without further purification.

d) tert-butyl (2R)-2-{[(3-{[(2,2-dimethylpropanoyl)oxy] methyl}-7-methoxy-4-oxo-3,4-dihydroquinazolin-5-yl)oxy] methyl}pyrrolidine-1-carboxylate (0.750 g, 1.5 mmol) was stirred in a 7N solution of ammonia in methanol (250 ml) at room temperature for 24 hours. The mixture was evaporated under reduced pressure to give tert-butyl (2R)-2-{[(7-methoxy-4-oxo-3,4-dihydroquinazolin-5-yl)oxy] methyl}pyrrolidine-1-carboxylate (0.560 g, 100% yield) which was used in the next stage without further purification.

e) Phosphoryl chloride (0.27 ml, 2.94 mmol) was added to a solution of tert-butyl (2R)-2-{[(7-methoxy-4-oxo-3,4-dihydroquinazolin-5-yl)oxy]methyl}pyrrolidine-1-carboxylate (0.550 g, 1.47 mmol) and di-iso-propylethylamine (1.02 ml, 5.88 mmol) in 1,2-dichloroethane (20 ml) and the reaction was heated at 80° C. for 1 hour. The mixture was evaporated under reduced pressure and the residue suspended in dimethylacetamide (10 ml) and then 2-(4-amino-1H-pyrazol-1-yl)-N-(2,3-difluorophenyl)acetamide (0.370 g, 1.47 mmol) was added and the mixture was heated at 90° C. for 1 hour. The mixture was evaporated under reduced pressure and the residue stirred in a 7N solution of ammonia in methanol (100 ml) at ambient temperature for 2 hours. The mixture was evaporated under reduced pressure to leave a yellow solid which was stirred in water (50 ml) for 1 hour and then filtered and the residue purified by silica gel chromatography eluting with a 0 to 10% mixture methanol in dichloromethane to give tert-butyl (2R)-2-[({4-[(1-{2-[(2,3-difluorophenyl)amino]-2-oxoethyl}-1H-pyrazol-4-yl)amino]-7-methoxy-3,4-dihydroquinazolin-5-yl}oxy)methyl]pyrrolidine-1-carboxylate (0.400 g, 44% yield over 3 steps):

$^1$H-NMR (DMSO $d_6$): 10.35 (s, 1H), 9.92 (s, 1H), 8.59 (s, 1H), 8.25 (s, 1H), 7.90 (s, 1H), 7.75 (m, 1H), 7.15 (m, 2H), 6.85 (m, 2H), 5.12 (s, 2H), 4.48 (m, 2H), 4.20 (m, 1H), 3.97 (s, 3H), 3.35 (m, 2H), 2.05 (m, 4H), 1.40 (s, 9H); MS (+ve ESI): 610 $(M+H)^+$.

EXAMPLE 224

Preparation of Compound 224 in Table 8—N-(2,3-difluorophenyl)-2-{4-[(5-{[(2R)-1-glycoloylpyrrolidin-2-yl]methoxy}-7-methoxyquinazolin-4-yl) amino]-1H-pyrazol-1-yl}acetamide A mixture of glycolic acid (0.049 g, 0.16 mmol), di-iso-propylethylamine (0.08 ml, 0.48 mmol) and N-(2,3-difluorophenyl)-2-[4-({7-methoxy-5-[(2R)-pyrrolidin-2-yl-methoxy]quinazolin-4-yl}amino}-1H-pyrazol-1-yl] acetamide (example 223 in table 8, 0.100 g, 0.16 mmol) in dichloromethane (5 ml) was stirred at room temperature for 10 minutes. O-(7-azabenzotriazol-1-yl)-N,N,N',N'-tetramethyluronium hexafluorophosphate (0.068 g, 0.18 mmol) was added and the reaction mixture was stirred at room temperature for 1 hour. The volatiles were removed by evaporation under reduced pressure and the residue purified by silica gel chromatography eluting with a 0 to 10% mixture methanol (containing 10% 7N ammonia in methanol) in dichloromethane to give compound 224 in table 8 (0.030 g, 33% yield):

$^1$H-NMR (DMSO $d_6$): 9.65 (br s, 1H), 8.40 (s, 1H), 8.28 (s, 1H), 7.85 (s, 1H), 7.70 (m, 1H), 7.15 (m, 2H), 6.78 (s, 2H), 5.02 (s, 2H), 4.60 (m, 1H), 4.45 (m, 1H), 4.25 (m, 1H), 4.10 (m, 2H), 3.88 (s, 3H), 3.45 (m, 2H), 2.05 (m, 4H); MS (+ve ESI): 568 $(M+H)^+$.

EXAMPLE 225

Preparation of Compound 225 in Table 8—N-(2,3-difluorophenyl)-2-{4-[(5-{[(2R)-1-(N,N-dimethylglycyl)pyrrolidin-2-yl]methoxy}-7-methoxyquinazolin-4-yl)amino]-1H-pyrazol-1-yl}acetamide A mixture of N,N-dimethylglycine (0.019 g, 0.18 mmol), di-iso-propylethylamine (0.08 ml, 0.48 mmol) and N-(2,3-difluorophenyl)-2-[4-({7-methoxy-5-[(2R)-pyrrolidin-2-ylmethoxy]quinazolin-4-yl}amino}-1H-pyrazol-1-yl]acetamide (example 223 in table 8, 0.100 g, 0.16 mmol) in dichloromethane (5 ml) was stirred at room temperature for 10 minutes. O-(7-azabenzotriazol-1-yl)-N,N,N',N'-tetramethyluronium hexafluorophosphate (0.068 g, 0.18 mmol) was added and the reaction mixture was stirred at room temperature for 1 hour. The volatiles were removed by evaporation under reduced pressure and the residue purified by silica gel chromatography eluting with a 0 to 10% mixture methanol (containing 10% 7N ammonia in methanol) in dichloromethane to give compound 225 in table 8 (0.040 g, 42% yield):

$^1$H-NMR (DMSO $d_6$): 8.42 (s, 1H), 8.32 (s, 1H), 7.85 (s, 1H), 7.68 (m, 1H), 7.15 (m, 2H), 6.78 (s, 1H), 6.72 (s, 1H), 5.02 (s, 2H), 4.60 (m, 1H), 4.45 (m, 1H), 4.25 (m, 1H), 3.85 (s, 3H), 3.52 (m, 2H), 2.64 (s, 2H), 2.58 (s, 6H), 2.05 (m, 4H); MS (+ve ESI): 595 $(M+H)^+$.

EXAMPLE 226

Preparation of Compound 226 in Table 8—N-(2,3-difluorophenyl)-2-{4-[(5-{[(2R)-1-(2-hydroxyethyl)pyrrolidin-2-yl]methoxy}-7-methoxyquinazolin-4-yl)amino]-1H-pyrazol-1-yl}acetamide A mixture of hydroxyacetaldehyde (0.009 g, 0.14 mmol), N-(2,3-difluorophenyl)-2-[4-({7-methoxy-5-[(2R)-pyrrolidin-2-ylmethoxy]quinazolin-4-yl}amino}-1H-pyrazol-1-yl] acetamide (example 223 in table 8, 0.070 g, 0.14 mmol), acetic acid (0.010 ml, 0.14 mmol) and MP-cyanoborohydride (2 mmol/g, 0.100 g, 0.21 mmol) in methanol (10 ml) was stirred at room temperature for 2 hour. The reaction mixture was filtered and evaporated under reduced pressure and the residue was then purified by reverse phase chromatography eluting with 0.2% aqueous trifluoroacetic acid in acetonitrile using a 5 to 50% gradient over 25 minutes. The fractions containing product were concentrated under reduced pressure and then basified with aqueous sodium carbonate. The resultant solid was filtered and washed with water to give compound 226 in table 8 (0.024 g, 31% yield):

$^1$H-NMR (DMSO $d_6$): 10.00 (s, 1H), 9.78 (s, 1H) 8.58 (s, 1H), 8.30 (s, 1H), 7.75 (s, 1H), 7.65 (m, 1H), 7.15 (m, 2H), 6.82 (m, 2H), 5.12 (s, 2H), 4.30 (d, 2H), 3.98 (s, 3H), 3.80 (t, 2H), 3.52 (m, 2H), 3.42 (q, 2H), 3.15 (m, 4H), 1.85 (m, 2H); MS (+ve ESI): 554 $(M+H)^+$.

EXAMPLE 227

Preparation of Compound 227 in Table 8—N-(2,3-difluorophenyl)-2-{4-[(5-methoxyquinazolin-4-yl)amino]-1H-pyrazol-1-yl}acetamide Phosphoryl chloride (0.5 ml, 5.3 mmol) was added to a solution of 5-methoxyquinazolin-4-ol (see WO96/09294, 0.300 g, 1.7 mmol) and di-iso-propylethylamine (2.20 ml, 12.9 mmol) in 1,2-dichloroethane (20 ml) and the reaction was heated at 80° C. for 4 hours. The mixture was evaporated under reduced pressure and the residue suspended in dimethylacetamide (20 ml) and then 2-(4-amino-1H-pyrazol-1-yl)-N-(2,3-difluorophenyl)acetamide (0.428 g, 1.7 mmol) was added and the mixture was heated at 90° C. for 1 hour. The mixture was evaporated under reduced pressure and the residue was purified by silica gel chromatography eluting with a 0 to 10% mixture methanol in dichloromethane to give compound 227 in table 8 (0.080 g, 11% yield):

$^1$H-NMR (DMSO $d_6$): 10.40 (s, 1H), 9.98 (s, 1H), 8.75 (s, 1H), 8.25 (s, 1H), 7.90 (s, 1H), 7.80 (t, 1H), 7.65 (m, 1H), 7.35 (d, 1H), 7.20 (d, 1H), 7.08 (m, 2H), 5.20 (s, 2H), 4.15 (s, 3H); MS (+ve ESI): 411 $(M+H)^+$.

EXAMPLE 228

Preparation of Compound 228 in Table 8 N-(2,3-difluorophenyl)-2-{4-[(5-fluoroquinazolin-4-yl)amino]-1H-pyrazol-1-yl}acetamide 2-(4-Amino-1H-pyrazol-1-yl)-N-(2,3-difluorophenyl)acetamide (1.5 g, 6 mmol) was added to a solution of 4-chloro-5-fluoroquinazoline (see WO01/094341, 1.0 g, 5.5 mmol) in isopropanol (40 ml) and the mixture was then heated at 80° C. for 1 hour. The resultant solid was filtered and then washed with isopropanol to give compound 228 in table 8 (1.95 g, 89% yield):

$^1$H-NMR (DMSO $d_6$): 10.70 (br s, 1H), 10.48 (br s, 1H) 8.98 (s, 1H), 8.40 (s, 1H), 8.05 (m, 2H), 7.80 (d, 1H), 7.62 (m, 2H), 7.18 (m, 2H), 5.22 (s, 2H); MS (+ve ESI): 399 $(M+H)^+$.

EXAMPLE 229

Preparation of Compound 229 in Table 9—N-(3-fluorophenyl)-2-(4-{[7-methoxy-6-(3-morpholin-4-ylpropoxy)quinazolin-4-yl]amino}-1H-pyrazol-1-yl) acetamide A mixture of 4-chloro-7-methoxy-6-(3-morpholin-4-ylpropoxy)quinazoline (120 mg, 0.35 mmol), 2-(4-amino-1H-pyrazol-1-yl)-N-(3-fluorophenyl)acetamide (83 mg, 0.35 mmol) and hydrogen chloride (100 ul of a 4M solution in 1,4-dioxane) in dimethylacetamide (2.0 ml) was heated at 90° C. for 2 hours and then allowed to cool to room temperature. The mixture was diluted with diethyl ether, filtered and washed with diethyl ether to give compound 229 in table 9 as the hydrochloride salt (222 mg) as a pale yellow solid:

$^1$H-NMR (DMSO $d_6$): 12.07 (s, 1H), 10.84 (br s), 1H), 10.76 (s, 1H), 8.91 (s, 1H), 8.63 (s, 1H), 8.46 (s, 1H), 8.13 (s, 1H), 7.60 (m, 1H), 7.36 (m, 3H), 6.92 (m, 1H), 5.15 (s, 2H), 4.41 (t, 2H), 4.00 (s, 3H), 3.98 (m, 2H), 3.83 (m, 2H), 3.52 (m, 2H), 3.34 (m, 2H partially obscured by $H_2O$), 3.16 (m, 2H), 2.33 (quintet, 2H); MS (+ve ESI): 536 $(M+H)^+$.

4-Chloro-7-methoxy-6-(3-morpholin-4-ylpropoxy)quinazoline used as Starting Material, was Prepared as Follows a) Di-tert-butyl azodicarboxylate (1.44 g, 6.26 mmol) was added portionwise at room temperature to a stirred suspension of 4-chloro-7-methoxyquinazolin-6-ol (1.20 g, 5.70 mmol), 3-morpholin-4-ylpropan-1-ol (0.91 g, 6.27 mmol) and triphenylphosphine (1.8 g, 6.87 mmol) in dichloromethane (25 ml). The reaction mixture was stirred for 2 hours and then the resulting orange solution was purified directly by silica gel chromatography eluting with a mixture of 5% methanol in dichloromethane to give 4-chloro-7-methoxy-6-(3-morpholin-4-ylpropoxy)quinazoline (1.28 g, 67% yield) as a pale yellow solid:

$^1$H-NMR ($CDCl_3$): 8.86 (s, 1H), 7.40 (s, 1H), 7.31 (s, 1H), 4.28 (t, 2H), 4.05 (s, 3H), 3.73 (m, 4H), 2.60 (t, 2H), 2.50 (m, 4H), 2.13 (quintet, 2H); MS (+ve ESI): 338 $(M+H)^+$.

EXAMPLE 230

Preparation of Compound 230 in Table 9—N-(3-fluorophenyl)-2-[4-({7-methoxy-6-[(1-methylpyrrolidin-3-yl)oxy]quinazolin-4-yl}amino)-1H-pyrazol-1-yl]acetamide An analogous reaction to that described in example 229 but starting with 4chloro-7-methoxy-6-[(1-methylpyrrolidin-3-yl)oxy]quinazoline (120 mg, 0.41 mmol) yielded compound 230 in table 9 as the hydrochloride salt (221 mg) as a pale yellow solid:

$^1$H-NMR (DMSO $d_6$): 12.52(s) & 12.28(s) (1H), 11.10(s) & 10.55(s) (1H), 10.75 (s, 1H), 8.90 (s, 1H), 8.89(s) & 8.74(s) (1H), 8.51(s) & 8.49(s) (1H), 8.22(s) & 8.16(s) (1H), 7.60 (m, 1m), 7.41 (s, 1H), 7.36 (m, 2H), 6.91 (m, 1H), 6.58(m) & 6.50(m) (1H), 5.14 (s, 2H), 4.24(m) & 3.84(m) (1H), 4.00 (s, 3H), 3.74 (m, 2H), 3.25 (m, 2H), 2.92 (s, 3H), 2.32 (m) and 2.16(m) (1H); MS (+ve ESI): 492 $(M+H)^+$.

4-Chloro-7-methoxy-6-[(1-methylpyrrolidin-3-yl) oxy}quinazoline used as Starting Material, was Prepared as Follows a) Diethyl azodicarboxylate (793 mg, 4.56 mmol) was added portionwise at room temperature to a stirred suspension of 4-chloro-7-methoxyquinazolin-6-ol (800 mg, 3.80 mmol), 1-methylpyrrolidin-3-ol (422 mg, 4.18 mmol) and triphenylphosphine (1.3 g, 4.96 mmol) in dichloromethane (16 ml). The reaction mixture was stirred for 1 hour and then a further portion of diethyl azodicarboxylate (360 ul) and triphenylphosphine (0.65 mg) were added. The mixture was stirred for 1 hour and the resulting orange solution was purified directly by silica gel chromatography eluting with a 0-10% mixture of methanol in dichloromethane to 4-chloro-7-methoxy-6-[(1-methylpyrrolidin-3-yl)oxy]quinazoline (330 mg, 28% yield) as a tan coloured solid:

$^1$H-NMR (DMSO $d_6$): 8.87 (s, 1H), 7.45 (s, 1H), 7.30 (s, 1H), 5.14 (m, 1H), 4.01 (s, 3H), 2.80 (m, 3H), 2.40 (m, 2H), 2.29 (s, 3H), 1.88 (m, 1H); MS (+ve ESI): 294 $(M+H)^+$.

EXAMPLE 231

Preparation of Compound 231 in Table 9—N-(3-fluorophenyl)-2-(4-{[7-methoxy-6-(2-morpholin-4-ylethoxy)quinazolin-4-yl]amino}-1H-pyrazol-1-yl) acetamide An analogous reaction to that described in example 229 but starting with 4-chloro-7-methoxy-6-(2-morpholin-4-ylethoxy)quinazoline (120 mg, 0.37 mmol) yielded compound 231 in table 9 as the hydrochloride salt (211 mg) as a pale yellow coloured solid:

$^1$H-NMR (DMSO-$d_6$): 12.13 (s, 1H), 10.75 (s, 1H), 8.91 (s, 1H), 8.78 (s, 1H), 8.48 (s, 1H), 8.14 (s, 1H), 7.60 (m, 1H), 7.40 (s, 1H), 7.38 (m, 2H), 6.92 (m, 1H), 5.14 (s, 2H), 4.78 (t, 2H), 4.00 (s, 3H), 3.92 (m, 4H), 3.70 (t, 2H), 3.35 (m, 4H, partially obscured by $H_2O$); MS (+ve ESI): 522 $(M+H)^+$.

4-Chloro-7-methoxy-6-(2-morpholin-4-ylethoxy) quinazoline used as Starting Material, was Prepared as Follows a) Di-tert-butyl azodicarboxylate (1.44 g, 6.26 mmol) was added portionwise at room temperature to a stirred suspension of 4-chloro-7-methoxyquinazolin-6-ol (1.20 g, 5.70 mmol), 2-morpholin-4-ylethanol (0.82 g, 6.26 mmol) and triphenylphosphine (1.8 g, 6.87 mmol) in dichloromethane (25 ml). The reaction mixture was stirred for 2 hour and then the resulting orange solution was purified directly by silica gel chromatography eluting with a mixture of 3% methanol in dichloromethane and then purified further by chromatography on neutral alumina eluting with a 3% mixture of methanol in dichloromethane to give 4-chloro-7-methoxy-6-(2-morpholin-4-ylethoxy)quinazoline (1.40 g, 76% yield) as a pale yellow solid:

$^1$H-NMR ($CDCl_3$): 8.86 (s, 1H), 7.42 (s, 1H), 7.33 (s, 1H), 4.34 (t, 2H), 4.04 (s, 3H), 3.75 (m, 4H), 2.94 (t, 2H), 2.64 (m, 4H).

EXAMPLE 232

Preparation of Compound 232 in Table 9—2-(4-{[6,7-bis(2-methoxyethoxy)quinazolin-4-yl]amino}-1H-pyrazol-1-yl)-N-(2,3-difluorophenyl)acetamide A mixture of 2-(4-amino-1H-pyrazol-1-yl)-N-(2,3-difluorophenyl)acetamide (152 mg, 0.6 mmol) and 4-chloro-6,7-bis(2-methoxyethoxy)quinazoline (see WO96/15118, 180 mg, 0.6 mmol) in dimethylacetamide (5 ml) was heated at 80° C. for 15 minutes and then allowed to cool to room temperature. The resulting solid was filtered and washed with methanol to give compound 232 in table 9 (248 mg, 78% yield):

$^1$H-NMR (DMSO $d_6$): 11.54 (br s, 1H), 10.39 (br s, 1H), 8.85 (s, 1H), 8.40 (s, 1H), 8.30 (s, 1H), 8.00 (s, 1H), 7.65 (m, 1H), 7.30 (s, 1H), 7.18 (m, 2H), 5.20 (s, 2H), 4.30 (m, 4), 3.78 (m, 4H), 3.28 (s, 3H), 3.27 (s, 3H); MS (+ve ESI): 529 $(M+H)^+$ MS (−ve ESI): 527 $(M-H)^-$.

EXAMPLE 233

Preparation of Compound 233 in Table 9—N-(3-fluorophenyl)-2-{4-[(6-hydroxy-7-methoxyquinazolin-4-yl)amino]-1H-pyrazol-1-yl}acetamide A solution of 4-chloro-7-methoxyquinazolin-6-ol (see WO03/064413, 0.119 g, 0.57 mmol) and 2-(4-amino-1H-pyrazol-1-yl)-N-(3-fluorophenyl)acetamide (0.132 g, 0.56 mmol) in dimethylacetamide (5 ml) was heated at 90° C. for 2 hours and then at 120° C. for 3 hours. The mixture was cooled to room temperature and diluted with diethyl ether (25 ml) and then filtered to yield compound 233 in table 9 as the hydrochloride salt (0.119 g, 48% yield) as a yellow solid.

$^1$H-NMR (DMSO $d_6$): 11.27 (br s, 1H), 10.74 (br s, 1H), 8.86 (s, 1H), 8.36 (s, 1H), 8.00 (s, 1H), 7.95 (s, 1H), 7.58 (m, 1H), 7.34 (m, 3H), 6.93 (m, 1H), 5.12 (s, 2H), 4.01 (s, 3H); MS (+ve ESI): 409 $(M+H)^+$.

EXAMPLE 234

Preparation of Compound 234 in Table 9—4-((1-(2-((2,3-difluorophenyl)amino)-2-oxoethyl)-1H-pyrazol-4-yl)amino)-7-((1-methylpiperidin-4-yl)methoxy)quinazolin-6-yl benzoate A solution of 4-chloro-7-((1-methylpiperidin-4-yl)methoxy)quinazolin-6-yl benzoate (0.250 g, 0.55 mmol) and 2-(4-amino-1H-pyrazol-1-yl)-N-(2,3-difluorophenyl)acetamide (0.140 g, 0.55 mmol) in dimethylacetamide (2 ml) was stirred at 35° C. for 3 hours. The precipitate was collected by filtration, washed with dimethylacetamide and then dried in vacuo (25° C., 0.1 mm Hg) to yield compound 234 in table 9 (0.323 g, 67% yield) as the hydrochloride salt:

$^1$H-NMR (DMSO $d_6$): 11.90 (br s, 1H), 10.50 (br s, 1H), 10.42 (s, 1H), 8.99 (m, 2H), 8.45 (s, 1H), 8.18 (d, 2H), 8.05 (s, 1H), 7.82 (m, 1H), 7.69 (m, 4H), 7.19 (m, 2H), 5.20 (s, 2H), 4.29 (d, 0.2H), and 4.07 (d, 0.8H), 3.31 (d, 2H), 2.81 (m, 1H), 2.65 (s, 3H), 2.55 (m, 1H), 1.95 (m, 1H), 1.79 (m, 2H), 1.55 (m, 2H); MS (+ve ESI): 628 $(M+H)^+$.

4-chloro-7-((1-methylpiperidin-4-yl)methoxy)quinazolin-6-yl benzoate used as Starting Material, was Prepared as Follows a) A mixture of 4-chloro-6-methoxy-7-[(1-methylpiperidin-4-yl)methoxy]quinazoline (see *Journal of Medicinal Chemistry,* 2002, 45, 1300-12, 9.8 g, 30 mmol), D,L-methionine (7.15 g, 48 mmol) and methanesulphonic acid (50 ml) was heated at 150° C. for 32 hours. The reaction mixture was allowed to cool to room temperature. The pH was adjusted to 8 with aqueous sodium hydroxide then, aqueous sodium hydrogen carbonate and concentrated to half the original volume. The resultant solid was filtered and washed with water and then dried for 16 hours at 60° C. to give 7-[(1-methylpiperidin-4-yl)methoxy]quinazoline-4,6-diol (6.16 g, 71% yield).

$^1$H-NMR (DMSO $d_6$): 7.85 (s, 1H), 7.40 (s, 1H), 7.0 (s, 1H), 4.0 (d, 2H), 2.80-2.75 (m, 2H), 2.20 (s, 3H), 2.0-1.65 (m, 5H), 1.45-1.30 (m, 2H); MS (+VE ESI): 290 $(M+H)^+$ MS (−VE ESI): 288 $(M-H)^-$.

b) A mixture of 7-[(1-methylpiperidin-4-yl)methoxy}quinazoline-4,6-diol (6.16 g, 21.3 mmol), benzoic anhydride (6.24 g, 27.7 mmol) and diphenyl ether (60 ml) was heated at 100° C. for 2 hours. The reaction mixture was allowed to cool to 50° C. and then diethyl ether and hexane were added to give a solid which was filtered and washed with diethyl ether and hexane. The product was absorbed on to alumina and purified by flash chromatography on alumina eluting with a gradient of 5-20% methanol in dichloromethane to give 4-hydroxy-7-[(1-methylpiperidin-4-yl)methoxy]quinazolin-6-yl benzoate (7.16 g, 86% yield).

$^1$H-NMR (DMSO $d_6$): 8.10 (d, 2H), 8.05 (s, 1H), 7.85 (s, 1H), 7.80-7.70 (m, 1H), 7.65-7.55 (m, 2H), 7.30 (s, 1H), 4.0 (d, 2H), 2.65-2.55 (m, 2H), 2.0 (s, 3H), 1.70-1.60 (m, 2H), 1.60-1.50 (m, 3H), 1.30-1.10 (m, 2H); MS (+VE ESI): 394 $(M+H)^+$. MS (−VE ESI): 392 $(M-H)^-$.

c) A mixture of 4-hydroxy-7-((1-methylpiperidin-4-yl)methoxy)quinazolin-6-yl benzoate (0.215 g, 0.55 mmol), thionyl chloride (2 ml) and dimethylformamide (0.05 ml) were refluxed for 15 minutes. The solvent was evaporated in vacuo to yield 4-chloro-7-((1-methylpiperidin-4-yl)methoxy)quinazolin-6-yl benzoate (0.250 g, 94% yield) as the hydrochloride salt:

MS (+ve ES]): 412 $(M+H)^+$.

EXAMPLE 235

Preparation of Compound 235 in Table 9—N-(2,3-difluorophenyl)-2-(4-((6-hydroxy-7-((1-methylpiperidin-4-yl)methoxy)quinazolin-4-yl)amino)-1H-pyrazol-1-yl)acetamide 4-((1-(2-((2,3-difluorophenyl)amino)-2-oxoethyl)-1H-pyrazol-4-yl)amino)-7-((1-methylpiperidin-4-yl)methoxy)quinazolin-6-yl benzoate (0.220 g, 0.33 mmol) was dissolved in methanol (25 ml) and 7M ammonia in methanol (5 ml) added and the solution heated at 50° C. for 1 hour. The solvent was evaporated and the residue was dissolved in methanol (5 ml) and applied to an SCX column and the product eluted with 0.5M to 2.0M ammonia in methanol. The fractions containing product were combined and evaporated to yield compound 235 in table 9 (0.146 g, 80% yield):

$^1$H-NMR (DMSO $d_6$): 10.25 (s, 1H), 9.60 (s, 1H), 9.34 (br s, 1H), 8.45 (s, 1H), 8.32 (s, 1H), 7.78 (s, 1H), 7.71 (s, 1H), 7.71 (m, 1H), 7.20 (m, 1H), 7.13 (s, 1H), 5.15 (s, 2H), 4.00 (d, 2R), 3.18 (s, 1H), 2.80 (d, 2H), 2.16 (s, 3H), 1.85 (m, 5H), 1.35 (m, 2H); MS (+ve ESI): 524 $(M+H)^+$.

EXAMPLE 236

Preparation of Compound 236 in Table 10—1-{2-[(3-fluorophenyl)amino]-2-oxoethyl}-4-[(7-{3-[(2-hydroxyethyl)(2-methoxyethyl)amino]propoxy}-6-methoxyquinazolin-4-yl)amino]-1H-pyrazole-3-carboxamide A mixture of 4-{[7-(3-chloropropoxy)-6-methoxyquinazolin-4-yl]amino}-1-{2-[(3-fluorophenyl)amino]-2-oxoethyl}-1H-pyrazole-3-carboxamide (152 mg, 0.25 mmol), 2-((2-methoxyethyl)amino)ethanol (90 mg, 0.75 mmol) and potassium iodide (83 mg) in 1-methyl-2-pyrrolidinone (1 ml) was heated at 80° C. for 6 hours. The mixture was purified directly by silica gel chromatography. Elution first with a 4% solution of methanol in dichloromethane and then a 4 to 7% mixture of methanol (containing 7N ammonia) in dichloromethane yielded compound 236 in table 10 (54 mg, 35% yield) as an off white solid:

$^1$H-NMR (DMSO$d_6$, TFA): 9.04 (s, 1H), 8.61 (s, 1H), 7.60 (d, 1H), 7.55 (s, 1H), 7.41 (s, 1H), 7.38 (m, 1H), 7.33 (m, 1H), 6.93 (t, 1H), 5.28 (s, 2H), 4.32 (t, 2H), 4.05 (s, 3H), 3.80 (t, 2H), 3.73 (t, 2H), 3.46 (m, 6H), 3.34 (s, 3H), 2.29 (m, 2H); MS (+ve ESI): 611.26 $(M+H)^+$.

EXAMPLE 237

Preparation of Compound 237 in Table 10—1-{2-[(3-fluorophenyl)amino]-2-oxoethyl}-4-[(7-{3-[(2S)-2-(hydroxymethyl)pyrrolidin-1-yl]propoxy}-6-methoxyquinazolin-4-yl)amino]-1N-pyrazole-3-carboxamide An analogous reaction to that described in example 236 but starting with (2S)-pyrrolidin-2-yl methanol (74 μl, 0.75 mmol) yielded compound 237 in table 10 (75 mg, 50% yield):

$^1$H-NMR (DMSO$d_6$, TFA): 9.04 (s, 1H), 8.61 (s, 1H), 7.6 (d, 1H), 7.56 (s, 1H), 7.41 (s, 1H), 7.39 (m, 1H), 7.33 (m, 1H), 6.93 (m, 1H), 5.28 (s, 2H), 4.33 (s, 2H), 4.05 (s, 3H), 3.78 (m,

1H), 3.63 (m, 4H), 3.22 (m, 2H), 2.31 (m, 2H), 2.13 (m, 1H), 2.05 (m, 1H), 1.91 (m, 1H), 1.79 (m, 1H); MS (+ve ESI): 593.24 $(M+H)^+$.

EXAMPLE 238

Preparation of Compound 238 in Table 10—2-{3-(acetylamino)-4-[(7-{3-[(2R)-2-(hydroxymethyl)pyrrolidin-1-yl]propoxy}quinazolin-4-yl)amino]-1H-pyrazol-1-yl}-N-(3-fluorophenyl)acetamide An analogous reaction to that described in example 236 but starting 2-(3-(acetylamino)-4-{[7-(3-chloropropoxy)quinazolin-4-yl]amino}-1H-pyrazol-1-yl)-N-(3-fluorophenyl)acetamide (0.12 g, 0.25 mmol) and (2R)-2-(hydroxymethyl) pyrrolidine (0.074 ml, 0.75 mmol) yielded compound 238 in table 10 (0.095 g, 66% yield):

$^1$H-NMR (DMSO $d_6$ TFA): 8.98 (s, 1H), 8.58 (s, 1H), 8.22 (d, 1H), 7.59 (d, 1H), 7.52 (d, 1H), 8.32 (m, 2H), 7.27 (s, 1H), 6.87 (t, 1H), 5.08 (s, 2H), 4.29 (m, 2H), 3.77 (d, 1H), 3.58 (m, 4H), 3.25 (m, 1H), 3.17 (m, 1H), 2.23 (m, 2H), 2.15 (s, 3H), 2.1 (m, 1H), 2.0 (m, 1H), 1.88 (m, 1H), 1.77 (m, 1H); MS (+ve ESI): 577.28 $(M+H)^+$.

EXAMPLE 239

Preparation of Compound 239 in Table 10—ethyl 1-{2-[(3-fluorophenyl)amino]-2-oxoethyl}-4-[(7-{3-[(2R)-2-(hydroxymethyl)pyrrolidin-1-yl]propoxy}quinazolin-4-yl)amino]-1H-pyrazole-3-carboxylate A mixture of ethyl 4-{[7-(3-chloropropoxy)quinazolin-4-yl]amino}-1-{2-[(3-fluorophenyl)amino]-2-oxoethyl}-1H-pyrazole-3-carboxylate (0.179 g, 0.3 mmol) and (2R)-pyrrolidin-2-ylmethanol (0.0910 g, 0.9 mmol) and potassium iodide (0.0996 g, 0.6 mmol) in 1-methyl-2-pyrrolidinone (2 ml) was heated at 80° C. for 3 hours under an argon atmosphere. The crude reaction mixture was purified directly by silica gel chromatography eluting with a mixture of 0 to 6% methanol in dichloromethane to yield compound 239 in table 10 (0.133 g, 75% yield):

$^1$H-NMR (DMSO$d_6$ TFA): 8.99 (s, 1H), 8.49 (d, 1H), 8.44 (s, 1H), 7.58 (m, 2H), 7.39 (q, 1H), 7.33 (m, 2H), 6.93 (t, 1H), 5.28 (s, 2H), 4.33 (t, 2H), 4.26 (q, 2H), 3.8 (m, 1H), 3.63 (m, 4H), 3.27 (m, 1H), 3.19 (m, 1H), 2.28 (m, 2H), 2.14 (m, 1H), 2.05 (m, 1H), 1.91 (m, 1H), 1.79 (m, 1H), 1.17 (t, 3H); MS (+ve ESI): 592.28 $(M+H)^+$.

EXAMPLE 240

Preparation of Compound 240 in Table 10—1-{2-[(3-fluorophenyl)amino]-2-oxoethyl}-4-[(7-{3-[(2R)-2-(hydroxymethyl)pyrrolidin-1-yl]propoxy}quinazolin-4-yl)amino]-1H-pyrazole-3-carboxylic acid A solution of lithium hydroxide (0.0164 g, 0.068 mmol) in water (0.39 ml) was added to a mixture of ethyl 1-{2-[(3-fluorophenyl)amino]-2-oxoethyl}-4-[(7-{3-[(2R)-2-(hydroxymethyl)pyrrolidin-1-yl]propoxy}quinazolin-4-yl)amino]-1H-pyrazole-3-carboxylate (0.0769 g, 0.13 mmol) in methanol (10 ml) and water (2 ml) and the mixture was heated at 50° C. for 1.5 hours. The mixture was evaporated and the residue was purified directly by preperative LCMS on a Thermo Hyersil Beta Basic-18 column eluting with a gradient of water in acetonitrile to give compound 240 in table 10 (0.058 g, 79% yield):

$^1$H-NMR (DMSO$d_6$ TFA): 9.04 (s, 1H), 8.52 (s, 1H), 8.4 (d, 1H), 7.6 (m, 2H), 7.39 (m, 1H), 7.34 (m, 2H), 6.93 (t, 1H), 5.28 (s, 2H), 4.34 (t, 2H), 3.79 (d, 1H), 3.64 (m, 4H), 3.28 (m, 1H), 3.2 (m, 1H), 2.28 (m, 2H), 2.13 (m, 1H), 2.04 (m, 1H), 1.92 (m, 1H), 1.81 (m, 1H); MS (+ve ESI): 564.29 $(M+H)^+$.

EXAMPLE 241

Preparation of Compound 241 in Table 11—2-[[3-({4-[(1-{2-[(2,3-difluorophenyl)amino]-2-oxoethy}-1H-pyrazol-4-yl)amino]-6-methoxyquinazolin-7-yl}oxy)propyl](propyl)amino]ethyl dihydrogen phosphate A solution of 4.0 N hydrochloric acid in dioxane (1.42 ml, 5.7 mmol) was added to a solution of di-tert-butyl 2-[[3-({4-[(1-{2-[(2,3-difluorophenyl)amino]-2-oxoethyl}-1H-pyrazol-4-yl)amino]-6-methoxyquinazolin-7-yl}oxy)propyl](propyl)amino]ethyl phosphate (720 mg, 0.95 mmol) in dichloromethane (7 ml) and dioxane (20 ml) and the mixture was stirred at ambient temperature for 23 hours. The precipitate was filtered, washed with dichloromethane and diethyl ether and dried in vacuo (50° C., 0.1 mm Hg) to yield compound 241 in table 11 (720 mg, 99.5% yield):

$^1$H-NMR (DMSO $d_6$ TFA): 8.96 (s, 1H), 8.43 (s, 1H), 8.22 (s, 1H), 8.02 (s, 1H), 7.75 (m, 1H), 7.37 (s, 1H), 7.21 (m, 2H), 5.26 (s, 2H), 4.28 (m, 4H), 4.04 (s, 3H), 3.51 (m, 2H), 3.39 (m, 2H), 3.21 (m, 2H), 2.31 (m, 2H), 1.74 (m, 2H), 0.96 (t, 3H); MS (+ve ESI): 650.5 $(M+H)^+$.

Di-tert-butyl 2-[[3-({4-[(1-{2-[(2,3-difluorophenyl)amino]-2-oxoethyl}-1H-pyrazol-4-yl)amino]-6-methoxyquinazolin-7-yl}oxy)propyl](propyl)amino]ethyl phosphate used as Starting Material, was Obtained as Follows a) Di-tert-butyl diethylphosphoramidite (486 mg, 1.95 mmol) was added slowly to a solution of N-(2,3-difluorophenyl)-2-{4-[(7-{3-[(2-hydroxyethyl)(propyl)amino]propoxy}-6-methoxyquinazolin-4-yl)amino]-1H-pyrazol-1-yl}acetamide (740 mg, 1.3 mmol) and tetrazole (228 mg, 3.25 mmol) in dimethylformamide (7.4 ml) under argon. The mixture was stirred at ambient temperature for 45 minutes. Hydrogen peroxide (9 N, 288 μl, 2.6 mmol) was added at 0° C. and the reaction stirred for 1.5 hours at ambient temperature. An additional quantity of hydrogen peroxide (72 μl, 0.65 mmol) was added to the solution to complete the oxidation. The mixture was cooled to 0° C. and a saturated solution of sodium metabisulphite (388 mg, 2 ml) was added slowly with vigorous stirring. The mixture was stirred at ambient temperature for 20 minutes, diluted with water and the pH adjusted to 7 with an aqueous solution of sodium bicarbonate. The mixture was extracted with ethyl acetate (3×10 ml), dried and concentrated. Purification by silica gel chromatography, eluting with dichloromethane:methanol (98:2) followed by dichloromethane:methanolic ammonia (3 N) (9:1) yielded di-tert-butyl 2-[[3-({4-[(1-{2-[(2,3-difluorophenyl)amino]-2-oxoethyl}-1H-pyrazol-4-yl)amino]-6-methoxyquinazolin-7-yl}oxy)propyl](propyl)amino]ethyl phosphate (720 mg, 67% yield):

$^1$H-NMR (DMSO $d_6$, TFA): 8.97 (s, 1H), 8.41 (s, 1H), 8.08 (s, 1H), 7.96 (s, 1H), 7.74 (m, 1H), 7.35 (s, 1H), 7.20 (m, 2H), 5.25 (s, 2H), 4.27 (m, 4H), 4.02 (s, 3H), 3.52 (m, 2H), 3.37 (m,

2H), 3.21 (m, 2H), 2.29 (m, 2H), 1.72 (m, 2H), 1.44 (s, 18H), 0.95 (t, 3H), 1.44 (s, 18H); MS (+ve ESI): 762.8 $(M+H)^+$.

EXAMPLE 242

Preparation of Compound 242 in T8able 11—{(2S)-1-[3-({4-[(1-{2-[(2,3-difluorophenyl)amino]-2-oxoethyl}-1H-pyrazol-4-yl)amino]-6-methoxyquinazolin-7-yl}oxy)propyl]pyrrolidin-2-yl}methyl dihydrogen phosphate An analogous reaction to that described in example 241, but starting with di-tert-butyl {(2S)-1-[3-({4-[(1-{2-[(2,3-difluorophenyl)amino]-2-oxoethyl}-1H-pyrazol-4-yl)amino]-6-methoxyquinazolin-7-yl}oxy)propyl]pyrrolidin-2-yl}methyl phosphate (502 mg, 0.66 mmol) yielded compound 242 in table 11 (462 mg, 88% yield):

$^1$H-NMR (DMSO $d_6$, TFA): 8.96 (s, 1H), 8.43 (s, 1H), 8.23 (m, 1H), 8.02 (s, 1H), 7.74 (m, 1H), 7.37 (s, 1H), 7.21 (m, 2H), 5.25 (s, 2H), 4.31 (m, 2H), 4.20 (m, 2H), 4.04 (s, 3H), 3.83 (m, 1H), 3.71 (m, 1H), 3.61 (m, 1H), 3.24 (m, 2H), 2.32 (m, 2H), 2.22 (m, 1H), 2.05 (m, 1H), 1.95 (m, 1H), 1.86 (m, 1H); MS (+ve ESI): 648.0 $(M+H)^+$.

di-tert-butyl {(2)-1-[3-({4-[(1-{2-[(2,3-difluorophenyl)amino]-2-oxoethyl}-1H-pyrazol-4-yl)amino]-6-methoxyquinazolin-7-yl}oxy)propyl]pyrrolidin-2-yl}methyl phosphate used as Starting Material was Obtained as Follows a) An analogous reaction to that described in example 241a, but starting with N-(2,3-difluorophenyl)-2-{4-[(7-{3-[(2S)-2-(hydroxymethyl)pyrrolidin-1-yl]propoxy}-6-methoxyquinazolin-4-yl)amino]-1H-pyrazol-1-yl}acetamide (1.08 g, 1.9 mmol) yielded di-tert-butyl {(2S)-1-[3-({4-[(1-{2-[(2,3-difluorophenyl)amino]-2-oxoethyl}-1H-pyrazol-4-yl)amino]-6-methoxyquinazolin-7-yl}oxy)propyl]pyrrolidin-2-yl}methyl phosphate (512 mg, 35% yield):

$^1$H-NMR (DMSO $d_6$): 10.32 (s, 1H), 9.68 (s, 1H), 8.48 (s, 1H), 8.35 (s, 1H), 7.77 (m, 2H), 7.73 (m, 1H), 7.21 (m, 2H), 7.15 (s, 1H), 5.16 (s, 2H), 4.16 (m, 2H), 3.95 (s, 3H), 3.77 (m, 1H), 3.57 (m, 1H), 3.08 (m, 1H), 2.93 (m, 1H), 2.67 (m, 1H), 2.47 (m, 1H), 2.21 (m, 1H), 1.95 (m, 2H), 1.86 (m, 1H), 1.69 (m, 2H), 1.6 (m, 1H), 1.36 (s, 18H); MS (+ve ESI): 760.4 $(M+H)^+$.

EXAMPLE 243

Preparation of Compound 243 in Table 11—{(2S)-1-[3-({4-[(1-{2-[(3-fluorophenyl)amino]-2-oxoethyl}-1H-pyrazol-4-yl)amino]-6-methoxyquinazolin-7-yl}oxy)propyl]pyrrolidin-2-yl}methyl dihydrogen phosphate An analogous reaction to that described in example 241, but starting with di-tert-butyl {(2S)-1-[3-({4-[(1-{2-[(3-fluorophenyl)amino]-2-oxoethyl}-1H-pyrazolyl)amino]-6-methoxyquinazolin-7-yl}oxy)propyl]pyrrolidin-2-yl}methyl phosphate (605 mg, 0.96 mmol) yielded compound 243 in table 11 (595 mg, 76% yield):

$^1$H-NMR (DMSO $d_6$, $CD_3COOD$): 8.93 (s, 1H), 8.45 (s, 1H), 8.30 (m, 1H), 8.05 (s, 1H), 7.62 (m, 1H), 7.39 (s, 1H), 7.36 (m, 2H), 6.91 (m, 1H), 5.17 (s, 2H), 4.31 (m, 2H), 4.24 (m, 2H), 4.05 (s, 3H), 3.84 (m, 1H), 3.71 (m, 1H), 3.61 (m, 1H), 3.33 (m, 1H), 3.25 (m, 1H), 2.34 (m, 2H), 2.23 (m, 1H), 2.06 (m, 1H), 1.97 (m, 1H), 1.89 (m, 1H);

MS (+ve ESI): 530.2 $(M+H)^+$. cl di-tert-butyl{(2S)-1-[3-({4-[(1-{2-[(3-fluorophenyl)amino]-2-oxoethyl}-1H-pyrazol-4-yl)amino]-6-methoxyquinazolin-7-yl}oxy)propyl]pyrrolidin-2-yl}methyl phosphate used as Starting Material was Obtained as Follows:

a) An analogous reaction to that described in example 241a, but starting with N-(3-fluorophenyl)-2-{4-[(7-{3-[(2S)-2-(hydroxymethyl)pyrrolidin-1-yl]propoxy}-6-methoxyquinazolin-4-yl)amino]-1H-pyrazol-1-yl}acetamide (1.12 g, 2.04 mmol) yielded di-tert-butyl {(2S)-1-[3-({4-[(1-{2-[(3-fluorophenyl)amino]-2-oxoethyl}-1H-pyrazol-4-yl)amino]-6-methoxyquinazolin-7-yl}oxy)propyl]pyrrolidin-2-yl}methyl phosphate (618 mg, 41% yield):

$^1$H-NMR (DMSO $d_6$): 10.56 (s, 1H), 9.68 (s, 1H), 8.48 (s, 1H), 8.35 (s, 1H), 7.78 (s, 1H), 7.76 (s, 1H), 7.59 (m, 1H), 7.36 (m, 1H), 7.32 (m, 1H), 7.15 (s, 1H), 6.92 (m, 1H), 5.06 (s, 2H), 4.16 (m, 2H), 3.96 (s, 3H), 3.78 (m, 1H), 3.56 (m, 1H), 3.08 (m, 1H), 2.93 (m, 1H), 2.67 (m, 1H), 2.49 (m, 1H), 2.21 (m, 1H), 1.95 (m, 2H), 1.86 (m, 1H), 1.69 (m, 2H), 1.62 (m, 1H), 1.37 (s, 18H); MS (+ve ESI): 742.4 $(M+H)^+$.

EXAMPLE 244

Preparation of Compound 244 in Table 11—2-{ethyl[3-({4-[(1-{2-[(3-fluorophenyl)amino]-2-oxoethyl}-1H-pyrazol-4-yl)amino]-6-methoxyquinazolin-7-yl}oxy)propyl]amino}ethyl dihydrogen phosphate An analogous reaction to that described in example 241, but starting with di-tert-butyl 2-{ethyl[3-({4-[(1-{2-[(3-fluorophenyl)amino]-2-oxoethyl}-1H-pyrazol-4-yl)amino]-6-methoxyquinazolin-7-yl}oxy)propyl]amino}ethyl phosphate (610 mg, 0.84 mmol) yielded compound 244 in table 11 (589 mg, 89% yield):

$^1$H-NMR (DMSO $d_6$, TFA): 8.95 (s, 1H), 8.44 (s, 1H), 8.32 (m, 1H), 8.04 (s, 1H), 7.61 (m, 1H), 7.36 (m, 3H), 6.92 (m, 1H), 5.16 (s, 2H), 4.31 (m, 2H), 4.25 (m, 2H), 4.04 (s, 3H), 3.48 (m, 2H), 3.37 (m, 4H), 2.30 (m, 2H), 1.28 (t, 3H); MS (+ve ESI): 618.1 $(M+H)^+$.

di-tert-butyl 2-{ethyl[3-({4-[(1-{2-[(3-fluorophenyl)amino]-2-oxoethyl}-1H-pyrazol-4-yl)amino]-6-methoxyquinazolin-7-yl}oxy)propyl]amino}ethyl phosphate used as Starting Material was Obtained as Follows a) An analogous reaction to that described in example 241a, but starting with 2-{4-[(7-{3-[ethyl(2-hydroxyethyl)amino]propoxy}-6-methoxyquinazolin-4-yl)amino]-1H-pyrazol-1-yl}-N-(3-fluorophenyl)acetamide (645 mg, 1.2 mmol) yielded di-tert-butyl 2-{ethyl[3-({4-[(1-{2-[(3-fluorophenyl)amino]-2-oxoethyl}-1H-pyrazol-4-yl)amino]-6-methoxyquinazolin-7-yl}oxy)propyl]amino}ethyl phosphate (620 mg, 71% yield):

$^1$H-NMR (DMSO $d_6$): 9.67 (s, 1H), 8.48 (s, 1H), 8.35 (s, 1H), 7.78 (s, 1H), 7.76 (s, 1H), 7.59 (d, 1H), 7.38 (q, 1H), 7.32 (d, 1H), 7.14 (s, 1H), 6.91 (t, 1H), 5.06 (s, 2H), 4.16 (t, 2H), 3.96 (s, 3H), 3.86 (m, 2H), 2.67 (t, 2H), 2.62 (t, 2H), 2.54 (m, 2H), 1.90 (m, 2H), 0.97 (t, 3H), 1.38 (s, 18H); MS (+ve ESI): 730.2 $(M+H)^+$.

EXAMPLE 245

Preparation of Compound 245 in Table 11—{(2R)-1-[3-({4-[(1-{2-[(3-fluorophenyl)amino]-2-oxoethyl}-1H-pyrazol-4-yl)amino]-6-methoxyquinazolin-7-yl}oxy)propyl]pyrrolidin-2-yl}methyl dihydrogen phosphate An analogous reaction to that described in example 241, but starting with di-tert-butyl {(2R)-1-[3-({4-[(1-{2-[(3-fluorophenyl)amino]-2-oxoethyl}-1H-pyrazol-4-yl)amino]-6-methoxyquinazolin-7-yl}oxy)propyl]pyrrolidin-2-yl}methyl phosphate (477 mg, 0.64 mmol) yielded compound 245 in table 11 (430 mg, 90% yield):

$^1$H-NMR (DMSO $d_6$, TFA): 8.96 (s, 1H), 8.43 (s, 1H), 8.27 (m, 1H), 8.02 (s, 1H), 7.62 (m, 1H), 7.37 (m, 3H), 6.92 (m, 1H), 5.16 (s, 2H), 4.31 (m, 2H), 4.21 (m, 2H), 4.04 (s, 3H), 3.83 (m, 1H), 3.71 (m, 1H), 3.61 (m, 1H), 3.31 (m, 1H), 3.24 (m, 1H), 2.32 (m, 2H), 2.21 (m, 1H), 2.05 (m, 1H), 1.94 (m, 1H), 1.85 (m, 1H); MS (+ve ESI): 630.2 (M+H)$^+$.

di-tert-butyl {(2R)-1-[3-({4-[(1-{2-[(3-fluorophenyl)amino]-2-oxoethyl}-1H-pyrazol-4-yl)amino]-6-methoxyquinazolin-7-yl}oxy)propyl]pyrrolidin-2-yl}methyl phosphate Used as Starting Material was Obtained as Follows a) An analogous reaction to that described in example 241a, but starting with N-(3-fluorophenyl)-2-{4-[(7-{3-[(2R)-2-(hydroxymethyl)pyrrolidin-1-yl]propoxy}-6-methoxyquinazolin-4-yl)amino]-1H-pyrazol-1-yl}acetamide (588 mg, 1.07 mmol) yielded di-tert-butyl {(2R)-1-[3-({4-[(1-{2-[(3-fluorophenyl)amino]-2-oxoethyl}-1H-pyrazol-4-yl)amino]-6-methoxyquinazolin-7-yl}oxy)propyl]pyrrolidin-2-yl}methyl phosphate (367 mg, 46% yield):

$^1$H-NMR (DMSO $d_6$): 10.56 (s, 1H), 9.67 (s, 1H), 8.48 (s, 1H), 8.35 (s, 1H), 7.78 (s, 1H), 7.76 (s, 1H), 7.59 (d, 1H), 7.37 (q, 1H), 7.32 (d, 1H), 7.15 (s, 1H), 6.91 (t, 1H), 5.06 (s, 1H), 4.17 (m, 2H), 3.96 (s, 3H), 3.56 (m, 1H), 3.08 (m, 1H), 2.94 (m, 1H), 2.67 (m, 1H), 2.21 (m, 1H), 1.95 (m, 2H), 1.86 (m, 1H), 1.69 (m, 2H), 1.62 (m, 1H), 1.37 (s, 18H); MS (+ve ESI): 742.4 (M+H)$^+$.

EXAMPLE 246

Preparation of Compound 246 in table 11—2-[[3-({4-[(1-{2-[(2,3-difluorophenyl)amino]-2-oxoethyl}-1H-pyrazol-4-yl)amino]-6-methoxyquinazolin-7-yl}oxy)propyl](2-methoxyethyl)amino]ethyl dihydrogen phosphate An analogous reaction to that described in example 241, but starting with di-tert-butyl 2-[[3-({4-[(1-{2-[(2,3-difluorophenyl)amino]-2-oxoethyl}-1H-pyrazol-4-yl)amino]-6-methoxyquinazolin-7-yl}oxy)propyl](2-methoxyethyl)amino]ethyl phosphate (540 mg, 0.69 mmol) yielded compound 246 in table 11 (462 mg, 90% yield):

$^1$H-NMR (DMSO $d_6$, $CD_3COOD$): 8.87 (s, 1H), 8.44 (s, 1H), 8.31 (s, 1H), 8.07 (s, 1H), 7.74 (m, 1H), 7.48 (s, 1H), 7.18 (m, 2H), 5.25 (s, 2H), 4.34 (m, 2H), 4.25 (m, 2H), 3.77 (s, 3H), 3.76 (m, 2H), 3.52 (m, 2H), 3.46 (m, 2H), 3.42 (m, 2H), 3.34 (s, 3H), 2.30 (m, 2H); MS (+ve ES]): 666.0 (M+H)$^+$.

di-tert-butyl 2-[[3-({4-[(1-{2-[(2,3-difluorophenyl)amino]-2-oxoethyl}-1H-pyrazol-4-yl)amino]-6-methoxyquinazolin-7-yl}oxy)propyl](2-methoxyethyl)amino]ethyl phosphate used as Starting Material was Obtained as Follows a) An analogous reaction to that described in example 241a, but starting with N-(2,3-difluorophenyl)-2-{4-[(7-{3-[(2-hydroxyethyl)(2-methoxyethyl)amino]propoxy}-6-methoxyquinazolin-4-yl)amino]-1H-pyrazol-1-yl) acetamide (640 mg, 1.09 mmol) yielded di-tert-butyl 2-[[3-({4-[(1-{2-[(2,3-difluorophenyl)amino]-2-oxoethyl}-1H-pyrazol-4-yl)amino]-6-methoxyquinazolin-7-yl}oxy) propyl](2-methoxyethyl)amino]ethyl phosphate (550 mg, 65% yield):

$^1$H-NMR (DMSO $d_6$): 9.67 (s, 1H), 8.48 (s, 1H), 8.35 (s, 1H), 7.78 (s, 1H), 7.76 (s, 1H), 7.73 (m, 1H), 7.21 (m, 2H), 7.14 (s, 1H), 5.15 (s, 2H), 4.16 (t, 2H), 3.96 (s, 3H), 3.85 (m, 2H), 3.38 (t, 2H), 2.73 (t, 2H), 2.68 (m, 4H), 1.90 (m, 2H), 1.38 (s, 18H); MS (+ve ESI): 778.4 (M+H)$^+$.

EXAMPLE 247

Preparation of Compound 247 in Table 11—{(2S)-1-[3-({4[(1-{2-[(2,3-difluorophenyl)amino]-2-oxoethyl}-1H-pyrazol-4-yl)amino]quinazolin-7-yl}oxy)propyl]pyrrolidin-2-yl}methyl dihydrogen phosphate An analogous reaction to that described in example 241, but starting with di-tert-butyl [(2S)-1-[3-({4-[(1-{2-[(2,3-difluorophenyl)amino]-2-oxoethyl}-1H-pyrazol-4-yl)amino] quinazolin-7-yl}oxy)propyl]pyrrolidin-2-yl}methyl phosphate (593 mg, 0.81 mmol) yielded compound 247 in table 11 (559 mg, 100% yield):

$^1$H-NMR (DMSO $d_6$, TFA): 9.00 (s, 1H), 8.71 (d, 1H), 8.42 (s, 1H), 8.01 (s, 1H), 7.74 (m, 1H), 7.51 (dd, 1H), 7.31 (d, 1H), 7.21 (m, 2H), 5.25 (s, 2H), 4.31 (m, 2H), 4.21 (m, 2H), 3.81 (m, 1H), 3.69 (m, 1H), 3.61 (m, 1H), 3.33 (m, 1H), 3.23 (m, 1H), 2.28 (m, 2H), 2.20 (m, 1H), 2.05 (m, 1H), 1.95 (m, 1H), 1.84 (m, 1H); MS (+ve ESI): 618.2 (M+H)$^+$.

di-tert-butyl {(2S)-1-[3-({4-[(1-{2-[(2,3-difluorophenyl)amino]-2-oxoethyl}-1H-pyrazol-4-yl)amino] quinazolin-7-yl}oxy)propyl]pyrrolidin-2-yl}methyl phosphate used as Starting Material was Obtained as Follows a) An analogous reaction to that described in example 241a, but starting with N-(2,3-difluorophenyl)-2-{4-[(7-{3-[(2S)-2-(hydroxymethyl)pyrrolidin-1-yl] propoxy}quinazolin-4-yl)amino]-1H-pyrazol-1-yl}acetamide (698 mg, 1.3 mmol) yielded di-tert-butyl {(2S)-1-[3-({4-[(1-{2-[(2,3-difluorophenyl)amino]-2-oxoethyl}-1H-pyrazol-4-yl)amino]quinazolin-7-yl}oxy)propyl] pyrrolidin-2-yl}methyl phosphate (665 mg, 70% yield):

$^1$H-NMR (DMSO $d_6$, TFA): 9.02 (s, 1H), 8.64 (d, 1H), 8.41 (s, 1H), 7.98 (s, 1H), 7.74 (m, 1H), 7.51 (m, 1H), 7.27 (m, 1H), 7.21 (m, 2H), 5.25 (s, 2H), 4.31 (m, 2H), 4.20 (m, 2H), 3.82 (m, 1H), 3.71 (m, 1H), 3.61 (m, 1H), 3.32 (m, 1H), 3.26 (m, 1H), 2.26 (m, 3H), 2.08 (m, 1H), 1.94 (m, 1H), 1.83 (m, 1H), 1.45 (s, 18H); MS (+ve ESI): 730.6 (M+H)$^+$.

EXAMPLE 248

Preparation of Compound 248 in Table 11—{(2R)-1-[3-({4-[(1-{2-[(2,3-difluorophenyl)amino]-2-oxoethyl}-1H-pyrazol-4-yl)amino]quinazolin-7-yl}oxy)propyl]pyrrolidin-2-yl}methyl dihydrogen phosphate An analogous reaction to that described in example 241, but starting with di-tert-butyl {(2R)-1-[3-({4-[(1-{2-[(2,3-difluorophenyl)amino]-2-oxoethyl}-1H-pyrazol-4-yl)amino]quinazolin-7-yl}oxy)propyl]pyrrolidin-2-yl}methyl phosphate (651 mg, 0.89 mmol) yielded compound 248 in table 11 (608 mg, 97% yield):

$^1$H-NMR (DMSO $d_6$, TFA): 9.01 (s, 1H), 8.72 (d, 1H), 8.43 (s, 1H), 8.02 (s, 1H), 7.74 (s, 1H), 7.51 (m, 1H), 7.32 (m, 1H), 7.21 (m, 2H), 5.25 (s, 2H), 4.32 (m, 2H), 4.21 (m, 2H), 3.82 (m, 1H), 3.68 (m, 1H), 3.62 (m, 1H), 3.32 (m, 1H), 3.23 (m, 1H), 2.29 (m, 2H), 2.21 (m, 1H), 2.06 (m, 1H), 1.94 (m, 1H), 1.84 (m, 1H); MS (+ve ESI): 618.3 $(M+H)^+$.

di-tert-butyl {(2R)-1-[3-({4-[(1-{2-[(2,3-difluorophenyl)amino]-2-oxoethyl}-1H-pyrazol-4-yl)amino]quinazolin-7-yl}oxy)propyl]pyrrolidin-2-yl}methyl phosphate used as Starting Material was Obtained as Follows a) An analogous reaction to that described in example 241 a), but starting with N-(2,3-difluorophenyl)-2-{4-[(7-{3-[(2R)-2-(hydroxymethyl)pyrrolidin-1-yl]propoxy}quinazolin-4-yl)amino]-1H-pyrazol-1-yl}acetamide (688 mg, 1.3 mmol) yielded di-tert-butyl {(2R)-1-[3-({4-[(1-{2-[(2,3-difluorophenyl)amino]-2-oxoethyl}-1H-pyrazol-4-yl)amino]quinazolin-7-yl}oxy)propyl]pyrrolidin-2-yl}methyl phosphate (665 mg, 70% yield):

$^1$H-NMR (DMSO $d_6$, TFA): 9.02 (s, 1H), 8.64 (d, 1H), 8.41 (s, 1H), 7.99 (s, 1H), 7.74 (m, 1H), 7.51 (m, 1H), 7.27 (m, 1H), 7.21 (m, 2H), 5.25 (s, 2H), 4.31 (m, 2H), 4.20 (m, 2H), 3.83 (m, 1H), 3.71 (m, 1H), 3.61 (m, 1H), 3.32 (m, 1H), 3.26 (m, 1H), 2.26 (m, 3H), 2.09 (m, 1H), 1.94 (m, 1H), 1.83 (m, 1H), 1.45 (s, 18H); MS (+ve ESI): 730.6 $(M+H)^+$.

EXAMPLE 249

Preparation of Compound 249 in Table 11—{(2R)-1-[3-({4-[(1-{2-[(2,3-difluorophenyl)amino]-2-oxoethyl}-1H-pyrazol-4-yl)amino]-6-methoxyquinazolin-7-yl}oxy)propyl]pyrrolidin-2-yl}methyl dihydrogen phosphate An analogous reaction to that described in example 241, but starting with di-tert-butyl {(2R)-1-[3-({4-[(1-{2-[(2,3-difluorophenyl)amino]-2-oxoethyl{-1H-pyrazol-4-yl)amino]-6-methoxyquinazolin-7-yl}oxy)propyl]pyrrolidin-2-yl}methyl phosphate (840 mg, 1.1 mmol) yielded compound 249 in table 11 (742 mg, 90% yield):

$^1$H-NMR (DMSO $d_6$, TFA): 8.96 (s, 1H), 8.42 (s, 1H), 8.22 (m, 1H), 8.01 (s, 1H), 7.74 (m, 1H), 7.37 (s, 1H), 7.21 (m, 2H), 5.25 (s, 2H), 4.30 (m, 2H), 4.21 (m, 2H), 4.04 (s, 3H), 3.83 (m, 1H), 3.70 (m, 1H), 3.62 (m, 1H), 3.31 (m, 1H), 3.24 (m, 1H), 2.32 (m, 2H), 2.21 (m, 1H), 2.05 (m, 1H), 1.93 (m, 1H), 1.60 (m, 1H); MS (+ve ESI): 648.3 $(M+H)^+$.

di-tert-butyl {(2R)-1-[3-({4-[(1-{2-[(2,3-difluorophenyl)amino]-2-oxoethyl}-1H-pyrazol-4-yl)amino]-6-methoxyquinazolin-7-yl}oxy)propyl]pyrrolidin-2-yl}methyl phosphate used as Starting Material was Obtained as Follows a) An analogous reaction to that described in example 241a, but starting with N-(2,3-difluorophenyl)-2-{4-[(7-{3-[(2R)-2-(hydroxymethyl)pyrrolidin-1-yl]propoxy}-6-methoxyquinazolin-4-yl)amino]-1H-pyrazol-1-yl}acetamide (777 mg, 1.37 mmol) yielded di-tert-butyl {(2R)-1-[3-({4-[(1-{2-[(2,3-difluorophenyl)amino]-2-oxoethyl}-1H-pyrazol-4-yl)amino]-6-methoxyquinazolin-7-yl}oxy)propyl]pyrrolidin-2-yl}methyl phosphate (0.84 g, 76% yield):

$^1$H-NMR (DMSO $d_6$): 9.67 (s, 1H), 8.48 (s, 1H), 8.35 (s, 1H), 7.77 (s, 1H), 7.76 (s, 1H), 7.31 (m, 1H), 7.21 (m, 2H), 7.15 (s, 1H), 5.16 (s, 2H), 4.16 (m, 2H), 3.95 (s, 3H), 3.76 (m, 1H), 3.55 (m, 1H), 3.08 (m, 1H), 2.94 (m, 1H), 2.67 (m, 1H), 2.50 (m, 1H), 2.21 (m, 1H), 1.95 (m, 2H), 1.86 (m, 1H), 1.69 (m, 2H), 1.62 (m, 1H), 1.36 (s, 18H); MS (+ve ESI): 760.6 $(M+H)^+$.

EXAMPLE 250

Preparation of Compound 250 in Table 11—2-[[3-({4-[(1-{2-[(2,3-difluorophenyl)amino]-2-oxoethyl}-1H-pyrazol-4-yl)amino]-6-methoxyquinazolin-7-yl}oxy)propyl](ethyl)amino]ethyl dihydrogen phosphate An analogous reaction to that described in example 241, but starting with di-tert-butyl 2-[[3-({4-[(1-{2-[(2,3-difluorophenyl)amino]-2-oxoethyl}-1H-pyrazol-4-yl)amino]-6-methoxyquinazolin-7-yl}oxy)propyl](ethyl)amino]ethyl phosphate (773 mg, 0.97 mmol) yielded compound 250 in table 11 (693 mg, 98% yield):

$^1$H-NMR (DMSO $d_6$, TFA): 8.96 (s, 1H), 8.42 (s, 1H), 8.23 (m, 1H), 8.01 (s, 1H), 7.74 (m, 1H), 7.36 (s, 1H), 7.21 (m, 2H), 5.25 (s, 2H), 4.29 (m, 2H), 4.23 (m, 2H), 4.04 (s, 3H), 3.49 (m, 2H), 3.35 (m, 4H), 2.31 (m, 2H), 1.28 (t, 3H); MS (+ve ESI): 636.3 $(M+H)^+$.

di-tert-butyl 2-[[3-({4-[(1-{2-[(2,3-difluorophenyl)amino]-2-oxoethyl}-1H-pyrazol-4-yl)amino]-6-methoxyquinazolin-7-yl}oxy)propyl](ethyl)amino]ethyl phosphate used as Starting Material was Obtained as Follows a) An analogous reaction to that described in example 241a, but starting with N-(2,3-difluorophenyl)-2-{4-[(7-{3-[ethyl(2-hydroxyethyl)amino]propoxy}-6-methoxyquinazolin-4-yl)amino]-1H-pyrazol-1-yl}acetamide (790 mg, 1.42 mmol) yielded di-tert-butyl 2-[[3-({4-[(1-{2-[(2,3-difluorophenyl)amino]-2-oxoethyl}-1H-pyrazol-4-yl)amino]-6-methoxyquinazolin-7-yl}oxy)propyl](ethyl)amino]ethyl phosphate (780 mg, 78% yield):

$^1$H-NMR (DMSO $d_6$): 9.67 (s, 1H), 8.48 (s, 1H), 8.35 (s, 1H), 7.78 (s, 1H), 7.76 (s, 1H), 7.73 (m, 1H), 7.21 (m, 2H), 7.14 (s, 1H), 5.16 (s, 2H), 4.16 (t, 2H), 3.95 (s, 3H), 3.85 (m, 2H), 2.66 (t, 2H), 2.62 (t, 2H), 2.53 (t, 2H), 1.91 (m, 2H), 1.38 (s, 18H), 0.97 (t, 3H), 1.50 (s, 18H); MS (+ve ESI): 748.5 $(M+H)^+$.

EXAMPLE 251

Preparation of Compound 251 in Table 11—2-[[3-({4-[(1-{2-[(2,3-difluorophenyl)amino]-2-oxoethyl}-1H-pyrazol-4-yl)amino]quinazolin-7-yl}oxy)propyl](propyl)amino]ethyl dihydrogen phosphate An analogous reaction to that described in example 241, but starting with di-tert-butyl 2-[[3-({4-[(1-{2-[(2,3-difluorophenyl)amino]-2-oxoethyl}-1H-pyrazol-4-yl)amino]quinazolin-7-yl}oxy)propyl](propyl)amino]ethyl phosphate (510 mg, 0.7 mmol) yielded compound 251 in table 11 (460 mg, 95% yield):

$^1$H-NMR (DMSO $d_6$, TFA): 8.98 (s, 1H), 8.67 (d, 1H), 8.39 (s, 1H), 7.98 (s, 1H), 7.71 (m, 1H), 7.49 (d, 1H), 7.28 (s, 1H), 7.17 (m, 2H), 5.22 (s, 2H), 4.29 (m, 2H), 4.22 (m, 2H), 3.47 (m, 2H), 3.36 (m, 2H), 3.14 (m, 2H), 2.25 (m, 2H), 1.71 (m, 2H), 0.92 (t, 3H); MS (+ve ESI): 620.2 $(M+H)^+$.

di-tert-butyl 2-[[3-({4-[(1-{2-[(2,3-difluorophenyl)amino]-2-oxoethyl}-1H-pyrazol-4-yl)amino]quinazolin-7-yl}oxy)propyl](propyl)amino]ethyl phosphate used as Starting Material was Obtained as Follows a) An analogous reaction to that described in example 241a, but starting with N-(2,3-difluorophenyl)-2-{4-[(7-{3-[(2 hydroxyethyl)(propyl)amino]propoxy)quinazolin-4-yl)amino]-1H-pyrazol-1-yl}acetamide (377 mg, 0.7 mmol) yielded di-tert-butyl 2-[[3-({4-[(1-{2-[(2,3-difluorophenyl)amino]-2-oxoethyl}-1H-pyrazol-4-yl)amino]quinazolin-7-yl)oxy)propyl](propyl)amino]ethyl phosphate (310 mg, 61% yield):

$^1$H-NMR (DMSO $d_6$, TFA): 9.02 (s, 1H), 8.63 (d, 1H), 8.41 (s, 1H), 7.99 (s, 1H), 7.74 (m, 1H), 7.51 (d, 1H), 7.27 (s, 1H), 7.21 (m, 2H), 5.25 (s, 2H), 4.31 (m, 2H), 4.25 (m, 2H), 3.51 (m, 2H), 3.38 (m, 2H), 3.18 (m, 2H), 2.25 (m, 2H), 1.70 (m, 2H), 0.95 (t, 3H), 1.45 (s, 18H); MS (+ve ESI): 732.5 $(M+H)^+$.

EXAMPLE 252

Preparation of Compound 252 in Table 11—2-{cyclobutyl[3-({4-[(1-{2-[(2,3-difluorophenyl)amino]-2-oxoethyl}-1H-pyrazol-4-yl)amino]-6-methoxyquinazolin-7-yl}oxy)propyl]amino}ethyl dihydrogen phosphate An analogous reaction to that described in example 241, but starting with di-tert-butyl 2-{cyclobutyl[3-({4-[(1-{2-[(2,3-difluorophenyl)amino]-2-oxoethyl}-1H-pyrazol-4-yl)amino]-6-methoxyquinazolin-7-yl}oxy)propyl]amino}ethyl phosphate (500 mg, 0.65 mmol) yielded compound 252 in table 11 (450 mg, 95% yield):

$^1$H-NMR (DMSO $d_6$, TFA): 8.92 (s, 1H), 8.42 (s, 1H), 8.31 (m, 1H), 8.03 (s, 1H), 7.72 (m, 1), 7.35 (s, 1H), 7.19 (m, 1H), 5.23 (s, 2H), 4.27 (m, 2H), 4.21 (m, 2H), 4.02 (s, 3H), 3.92 (m, 1H), 3.37 (m, 2H), 3.25 (m, 2H), 2.34 (m, 2H), 2.24 (m, 4H), 1.74 (m, 1H), 1.65 (m, 1H); MS (+ve ES]): 662.4 $(M+H)^+$.

di-tert-butyl 2-{cyclobutyl[3-({4-[(1-{2-[(2,3-difluorophenyl)amino]-2-oxoethyl}-1H-pyrazol-4-yl)amino]-6-methoxyquinazolin-7-yl}oxy)propyl]amino}ethyl phosphate used as Starting Material was Obtained as Follows a) An analogous reaction to that described in example 241a, but starting with 2-{4-[(7-{3-[cyclobutyl(2-hydroxyethyl)amino]propoxy}-6-methoxyquinazolin-4-yl)amino]-1H-pyrazol-1-yl}-N-(2,3-difluorophenyl)acetamide (740 mg, 1.27 mmol) yielded di-tert-butyl 2-{cyclobutyl[3-({4-[(1-{2-[(2,3-difluorophenyl)amino]-2-oxoethyl}-1H-pyrazol-4-yl)amino]-6-methoxyquinazolin-7-yl}oxy)propyl]amino}ethyl phosphate (657 mg, 67% yield):

$^1$H-NMR (DMSO $d_6$): 9.68 (s, 1H), 8.48 (s, 1H), 8.35 (s, 1H), 7.78 (s, 1H), 7.76 (s, 1H), 7.73 (m, 1H), 7.21 (m, 2H), 7.15 (s, 1H), 5.16 (s, 2H), 4.15 (t, 2H), 3.95 (s, 3H), 3.84 (m, 2H), 3.16 (m, 1H), 2.65 (t, 2H), 2.59 (t, 2H), 1.96 (m, 2H), 1.88 (m, 2H), 1.77 (m, 2H), 1.55 (m, 2H), 1.39 (s, 18H); MS (+ve ESI): 774.6 $(M+H)^+$.

EXAMPLE 253

Preparation of Compound 253 in Table 11—2-{cyclobutyl[3-({4-[(1-{2-[(3-fluorophenyl)amino]-2-oxoethyl}-1H-pyrazol-4-yl)amino]-6-methoxyquinazolin-7-yl}oxy)propyl]amino}ethyl dihydrogen phosphate An analogous reaction to that described in example 241, but starting with di-tert-butyl 2-{cyclobutyl[3-({4-[(1-{2-[(3-fluorophenyl)amino]-2-oxoethyl}-1H-pyrazol-4-yl)amino]-6-methoxyquinazolin-7-yl}oxy)propyl]amino}ethyl phosphate (530 mg, 0.7 mmol) yielded compound 253 in table 11 (540 mg, 100% yield):

$^1$H-NMR (DMSO $d_6$, TFA): 8.93 (s, 1H), 8.42 (s, 1H), 8.21 (m, 1H), 7.98 (s, 1H), 7.58 (d, 1H), 7.34 (m, 3H), 6.89 (m, 1H), 5.13 (s, 2H), 4.27 (m, 2H), 4.19 (m, 2H), 4.01 (s, 3H), 3.93 (m, 1H), 3.36 (m, 2H), 3.25 (m, 2H), 2.35 (m, 2H), 2.25 (m, 4H), 1.75 (m, 1H), 1.68 (m, 1H); MS (+ve ESI): 644.3 $(M+H)^+$.

di-tert-butyl 2-{cyclobutyl[3-({4-[(1-{2-[(3-fluorophenyl)amino]-2-oxoethyl}-1H-pyrazol-4-yl)amino]-6-methoxyquinazolin-7-yl}oxy)propyl]amino}ethyl phosphate used as Starting Material was Obtained as Follows a) An analogous reaction to that described in example 241a, but starting with 2-{4-[(7-{3-[cyclobutyl(2-hydroxyethyl)amino]propoxy}-6-methoxyquinazolin-4-yl)amino]-1H-pyrazol-1-yl}-N-(3-fluorophenyl)acetamide (524 mg, 0.93 mmol) yielded di-tert-butyl 2-{cyclobutyl[3-({4-[(1-{2-[(3-fluorophenyl)amino]-2-oxoethyl}-1H-pyrazol-4-yl)amino]-6-methoxyquinazolin-7-yl}oxy)propyl]amino}ethyl phosphate (535 mg, 76% yield):

$^1$H-NMR (DMSO $d_6$): 10.55 (s, 1H), 9.67 (s, 1H), 8.48 (s, 1H), 8.34 (s, 1H), 7.78 (s, 1H), 7.75 (s, 1H), 7.59 (d, 1H), 7.38 (q, 1H), 7.31 (d, 1H), 7.14 (s, 1H), 6.91 (m, 1H), 5.06 (s, 2H), 4.15 (t, 2H), 3.95 (s, 3H), 3.85 (m, 2H), 3.16 (m, 1H), 2.64 (t, 2H), 2.59 (t, 2H), 1.96 (m, 2H), 1.88 (m, 2H), 1.77 (m, 2H), 1.56 (m, 2H), 1.38 (s, 18H); MS (+ve ES]): 756.1 $(M+H)^+$.

EXAMPLE 254

Preparation of Compound 254 in Table 11—2-[[3-({4-[(1-{2-[(3-fluorophenyl)amino]-2-oxoethyl}-1H-pyrazol-4-yl)amino]-6-methoxyquinazolin-7-yl}oxy)propyl](2-methoxyethyl)amino]ethyl dihydrogen phosphate An analogous reaction to that described in example 241, but starting with (325 mg, 0.43 mmol) yielded compound 254 in table 11 (329 mg, 100% yield):

$^1$H-NMR (DMSO $d_6$, TFA): 8.96 (s, 1H), 8.42 (s, 1H), 8.22 (m, 1H), 8.00 (s, 1H), 7.61 (m, 1H), 7.36 (m, 3H), 6.92 (m, 1H), 5.15 (s, 2H), 4.30 (m, 2H), 4.25 (m, 2H), 4.04 (s, 3H), 3.74 (m, 2H), 3.56 (m, 2H), 3.49 (m, 2H), 3.42 (m, 2H), 3.34 (s, 3H), 2.37 (m, 2H); MS (+ve ESI): 648.7(M+H)$^+$.

di-tert-butyl 2-[[3-({4-[(1-{2-[(3-fluorophenyl)amino]-2-oxoethyl}-1H-pyrazol-4-yl)amino]-6-methoxyquinazolin-7-yl}oxy)propyl](2-methoxyethyl)amino]ethyl phosphate used as Starting Material was Obtained as Follows a) An analogous reaction to that described in example 241a, but starting with N-(3-fluorophenyl)-2-{4-[(7-{3-[(2-hydroxyethyl)(2-methoxyethyl)amino]propoxy}-6-methoxyquinazolin-4-yl)amino]-1H-pyrazol-1-yl}acetamide (444 mg, 0.78 mmol) yielded di-tert-butyl 2-[[3-({4-[(1-{2-[(3-fluorophenyl)amino]-2-oxoethyl}-1H-pyrazol-4-yl)amino]-6-methoxyquinazolin-7-yl]oxy)propyl](2-methoxyethyl)amino]ethyl phosphate (325 mg, 55% yield):

$^1$H-NMR (DMSO $d_6$): 10.55 (s, 1H), 9.67 (s, 1H), 8.47 (s, 1H), 8.34 (s, 1H), 7.77 (s, 1H), 7.75 (s, 1H), 7.58 (d, 1H), 7.37 (q, 1H), 7.31 (d, 1H), 7.14 (s, 1H), 6.91 (m, 1H), 5.06 (s, 2H), 4.16 (m, 2H), 3.95 (s, 3H), 3.85 (m, 2H), 3.38 (m, 2H), 3.2 (s, 3H), 2.73 (m, 2H), 2.67 (m, 4H), 1.91 (m, 2H), 1.37 (s, 18H); MS (+ve ESI): 760.6 (M+H)$^+$.

EXAMPLE 255

Preparation of Compound 255 in table 11—2-[[3-({4-[(1-{2-[(3-fluorophenyl)amino]-2-oxoethyl}-1H-pyrazol-4-yl)amino]quinazolin-7-yl}oxy)propyl](propyl)amino]ethyl dihydrogen phosphate Di-tert-butyl diethylphosphoramidite (747 mg, 3 mmol) was added slowly to a solution of N-(3-fluorophenyl)-2-{4-[(7-{3-[(2 hydroxyethyl)(propyl)amino]propoxy}quinazolin-4-yl)amino]-1H-pyrazol-1-yl}acetamide (390 mg, 0.75 mmol) and tetrazole (158 mg, 2.25 mmol) in dimethylacetamide (4 ml) under nitrogen. The mixture was stirred at ambient temperature for 1 hour. Hydrogen peroxide (383 µl, 3.38 mmol, 30% aqueous solution) was added slowly at 0° C. and the reaction mixture stirred for 1.5 hours at ambient temperature. An additional portion of hydrogen peroxide (42 µl, 0.37 mmol) was added to the solution to complete the oxidation. The mixture was cooled to 0° C. and a saturated solution of sodium metabisulphite (7 ml of 0.53 M solution) added slowly with vigorous stirring. The mixture was stirred at ambient temperature for 20 minutes, diluted with water and the pH adjusted to 7 with an aqueous solution of potassium hydrogen carbonate. The reaction mixture was extracted with dichloromethane (3×25 ml) and the combined organics dried and concentrated in vacuo. Purification by silica gel chromatography, eluting with dichloromethane followed by increased polarity to dichloromethane:methanol:ammonia (20:1:0.1 to 20:3:0.2) gave di-tert-butyl 2-[[3-({4-[(1-{2-[(3-fluorophenyl)amino]-2-oxoethyl}-1H-pyrazol-4-yl)amino]quinazolin-7-yl}oxy)propyl](propyl)amino]ethyl phosphite as a pale yellow oil. This intermediate was dissolved in dioxane (10 ml) and a solution of 4.0 N hydrochloric acid in dioxane (1.12 ml, 4.5 mmol) added. The mixture was stirred at ambient temperature for 18 hours. The solid was filtered, washed with dichloromethane and diethyl ether and dried in vacuo for 18 hours (50° C., 0.1 mm Hg) to yield compound 255 in table 11 as the dihydrochloride salt (375 mg, 70% yield):

$^1$H-NMR (DMSO $d_6$, $CD_3CO_2D$): 8.93 (s, 1H), 8.80 (m, 1H), 8.41 (s, 1H), 8.01 (s, 1H), 7.58 (m, 1H), 7.45 (m, 1H), 7.32 (m, 3H), 6.88 (m, 1H), 5.12 (s, 2H), 4.29 (m, 4H), 3.46 (m, 2H), 3.35 (m, 2H), 3.14 (m, 2H), 2.28 (m, 2H), 1.73 (m, 2H), 0.93 (t, 3H); MS (+ve ESI): 602 (M+H)$^+$.

EXAMPLE 256

Preparation of Compound 256 in Table 11—2-{4-[3-({4-[(1-{2-[(2,3-difluorophenyl)amino]-2-oxoethyl}-1H-pyrazol-4-yl)amino]quinazolin-7-yl}oxy)propyl]piperazin-1-yl}ethyl dihydrogen phosphate An analogous reaction to that described in example 255 but starting with N-(2,3-difluorophenyl)-2-{4-[(7-{3-[4-(2-hydroxyethyl)piperazin-1-yl]propoxy}quinazolin-4-yl)amino]-1H-pyrazol-1-yl}acetamide (363 mg, 0.64 mmol) yielded compound 256 in table 11 (442 mg, 91% yield):

$^1$H-NMR (DMSO $d_6$, $CD_3CO_2D$): 8.94 (s, 1E), 8.84 (m, 1H), 8.42 (s, 1H), 8.04 (s, 1H), 7.70 (m, 1H), 7.47 (m, 1H), 7.36 (m, 1H), 7.17 (m, 2H), 5.22 (s, 2H), 4.33 (m, 2H), 4.27 (m, 2H), 3.72 (m, 8H), 3.51 (m, 2H), 3.41 (m, 2H), 2.33 (m, 2H); MS (+ve ESI): 647 (M+H)$^+$.

EXAMPLE 257

Preparation of Compound 257 in Table 11—2-{ethyl [3-({4-[(1-{2-[(3-fluorophenyl)amino]-2-oxoethyl}-1H-pyrazol-4-yl)amino]quinazolin-7-yl}oxy)propyl]amino}ethyl dihydrogen phosphate An analogous reaction to that described in example 255 but starting with 2-{4-[(7-{3-[ethyl(2-hydroxyethyl)amino]propoxy}quinazolin-4-yl)amino]-1H-pyrazol-1-yl}-N-(3-fluorophenyl)acetamide (362 mg, 0.71 mmol) yielded compound 257 in table 11 (246 mg, 50% yield):

$^1$H-NMR (DMSO $d_6$, $CD_3CO_2D$): 8.92 (s, 1H), 8.80 (m, 1H), 8.40 (s, 1H), 8.01 (s, 1H), 7.58 (m, 1H), 7.47 (m, 1H), 7.33 (m, 3H), 6.88 (m, 1H), 5.13 (s, 2H), 4.28 (m, 4H), 3.45 (m, 2H), 3.36 (m, 2H), 3.28 (m, 2H), 2.28 (m, 2H), 1.28 (t, 3H); MS (+ve ESI): 588 (M+H)$^+$.

EXAMPLE 258

Preparation of Compound 258 in Table 11—2-[[3-({4-[(1-{2-[(2,3-difluorophenyl)amino]-2-oxoethyl}-1H-pyrazol-4-yl)amino]quinazolin-7-yl}oxy)propyl](ethyl)amino]ethyl dihydrogen phosphate An analogous reaction to that described in example 255 but starting with N-(2,3-difluorophenyl)-2-{4-[(7-{3-[ethyl(2-hydroxyethyl)amino]propoxy}quinazolin-4-yl)amino]-1H-pyrazol-1-yl}acetamide (368 mg, 0.70 mmol) yielded compound 258 in table 11 (313 mg, 63% yield):

$^1$H-N (DMSO $d_6$, $CD_3CO_2D$): 8.91 (s, 1H), 8.77 (m, 1H), 8.40 (s, 1H), 8.01 (s, 1H), 7.68 (m, 1H), 7.45 (m, 1H), 7.34 (s, 1H), 7.16 (m, 2H), 5.20 (s, 2H), 4.28 (m, 2H), 4.25 (m, 2H), 3.43 (m, 2H), 3.34 (m, 2H), 3.25 (m, 2H), 2.25 (m, 2H), 1.27 (t, 3H); MS (+ve ESI): 606 $(M+H)^+$.

EXAMPLE 259

Preparation of Compound 259 in Table 11—3-{[3-({4-[(1-{2-[(3-fluorophenyl)amino]-2-oxoethyl}-1H-pyrazol-4-yl)amino]quinazolin-7-yl}oxy)propyl]amino}-3-methylbutyl dihydrogen phosphate An analogous reaction to that described in example 255 but starting with N-(3-fluorophenyl)-2-{4-[(7-{3-[(3-hydroxy-1,1-dimethylpropyl)amino]propoxy}quinazolin-4-yl)amino]-1H-pyrazol-1-yl}acetamide (379 mg, 0.72 mmol) yielded compound 259 in table 11 (365 mg, 71% yield):

$^1$H-NMR (DMSO $d_6$, $CD_3CO_2D$): 8.91 (s, 1H), 8.74 (d, 1H), 8.39 (s, 1H), 8.00 (s, 1H), 7.55 (m, 1H), 7.47 (m, 1H), 7.31 (m, 3H), 6.85 (m, 1H), 5.10 (s, 2H), 4.31 (m, 2H), 4.00 (m, 2H), 3.10 (m, 2H), 2.23 (m, 2H), 2.02 (m, 2H), 1.34 (s, 6H); MS (+ve ESI): 602 $(M+H)^+$.

EXAMPLE 260

Preparation of Compound 260 in Table 11—3-{[3-({4-[(1-{2-[(2,3-difluorophenyl)amino]-2-oxoethyl}-1H-pyrazol-4-yl)amino]quinazolin-7-yl}oxy)propyl]amino}-3-methylbutyl dihydrogen phosphate An analogous reaction to that described in example 255 but starting with N-(2,3-difluorophenyl)-2-{4-[(7-(3-[(3-hydroxy-1,1 dimethylpropyl)amino]propoxy}quinazolin-4-yl)amino]-1H-pyrazol-1-yl}acetamide (353 mg, 0.65 mmol) yielded compound 260 in table 11 (310 mg, 65% yield):

$^1$H-NMR (DMSO $d_6$, $CD_3CO_2D$): 9.14 (m, 1H), 8.95 (m, 1H), 8.42 (s, 1H), 8.04 (s, 1H), 7.71 (m, 1H), 7.50 (m, 1H), 7.37 (m, 1H), 7.19 (m, 2H), 5.23 (m, 2H), 4.34 (m, 2H), 4.00 (m, 2H), 3.11 (m, 2H), 2.26 (m, 2H), 2.04 (m, 2H), 1.36 (s, 6H); MS (+ve ESI): 620 $(M+H)^+$.

EXAMPLE 261

Preparation of Compound 261 in Table 11—{(2R)-1-[3-({4-[(1-{2-[(3-fluorophenyl)amino]-2-oxoethyl}-1H-pyrazol-4-yl)amino]quinazolin-7-yl}oxy)propyl]pyrrolidin-2-yl}methyl dihydrogen phosphate An analogous reaction to that described in example 255 but starting with N-(3-fluorophenyl)-2-{4-[(7-{3-[(2R)-2-(hydroxymethyl)pyrrolidin-1-yl]propoxy}quinazolin-4-yl)amino]-1H-pyrazol-1-yl}acetamide (397 mg, 0.76 mmol) yielded compound 261 in table 11 (429 mg, 79% yield):

$^1$H-NMR DMSO $d_6$, $CD_3CO_2D$): 8.92 (m, 1H), 8.76 (m, 1H), 8.40 (s, 1H), 8.00 (s, 1H), 7.56 (m, 1H), 7.46 (m, 1H), 7.31 (m, 2H), 6.85 (m, 1H), 5.10 (s, 2H), 4.29 (m, 2H), 4.20 (m, 2H), 3.78 (m, 1H), 3.64 (m, 1H), 3.59 (m, 1H), 3.29 (m, 1H), 3.18 (m, 1H), 2.27 (m, 2H), 2.18 (m, 1H), 2.01 (m, 1H), 1.94 (m, 1H), 1.80 (m, 1H); MS (+ve ESI): 600 $(M+H)^+$.

EXAMPLE 262

Preparation of Compound 262 in Table 11—2-{4-[3-({4-[(1-{2-[(3-fluorophenyl)amino]-2-oxoethyl}-1H-pyrazol-4-yl)amino]quinazolin-7-yl}oxy)propyl]piperazin-1-yl}ethyl dihydrogen phosphate An analogous reaction to that described in example 255, but starting with N-(3-fluorophenyl)-2-{4-[(7-{3-[4-(2-hydroxyethyl)piperazin-1-yl]propoxy}quinazolin-4-yl)amino]-1H-pyrazol-1-yl}acetamide (430 mg, 0.79 mmol) yielded compound 262 in table 11 (352 mg, 61% yield):

$^1$H-NMR (DMSO $d_6$): 10.83 (br s, 1H), 8.92 (s, 1H), 8.84 (d, 1H), 8.40 (s, 1H), 8.04 (s, 1H), 7.60 (dd, 1H), 7.45 (dd, 1H), 7.30 (m, 3H), 6.90 (m, 1H), 5.15 (s, 2H), 4.30 (t, 2H), 4.20 (m, 2H), 3.35 (m, 12H), 2.25 (m, 2H); MS (+ve ESI): 629 $(M+H)^+$.

EXAMPLE 263

Preparation of Compound 263 in Table 11—3-{[3-({4-[(1-{2-[(2,3-difluorophenyl)amino]-2-oxoethyl}-1H-pyrazol-4-yl)amino]quinazolin-7-yl}oxy)propyl]amino}propyl dihydrogen phosphate An analogous reaction to that described in example 255, but starting with N-(2,3-difluorophenyl)-2-{4-[(7-{3-[(3-hydroxypropyl)amino]propoxy}quinazolin-4-yl)amino]-1H-pyrazol-1-yl)acetamide (270 mg, 0.53 mmol) yielded compound 263 in table 11 (140 mg, 38% yield):

$^1$H-NMR (DMSO $d_6$): 11.98 (br s, 1H), 10.40 (s, 1H), 9.15 (br s, 1H), 8.90 (s, 1H), 8.85 (d, 1H), 8.40 (s, 1H), 8.05 (s, 1H), 7.68 (t, 1H), 7.50 (d, 1H), 7.30 (s, 1H), 7.18 (m, 2H), 5.25 (s, 2H), 4.35 (t, 2H), 4.00 (q, 2H), 3.15 (app. s, 2H), 3.05 (app. s, 2H), 2.30 (quintet, 2H), 2.05 (quintet, 2H);

MS (+ve ESI): 592 $(M+H)^+$.

EXAMPLE 264

Preparation of Compound 264 in Table 11—2-{[3-({4-[(1-{2-[(2,3-difluorophenyl)amino]-2-oxoethyl}-1H-pyrazol-4-yl)amino]quinazolin-7-yl}oxy)propyl]amino}ethyl dihydrogen phosphate An analogous reaction to that described in example 255, but starting with N-(2,3-difluorophenyl)-2-{4-[(7-{3-[(2-hydroxyethyl)amino]propoxy}quinazolin-4-yl)amino]-1H-pyrazol-1-yl}acetamide (280 mg, 0.5 mmol) yielded compound 264 in table 11 (180 mg, 47% yield):

$^1$H-NMR (DMSO $d_6$): 11.96 (br s, 1H), 10.41 (br s, 1H), 8.94 (s, 1H), 8.84 (d, 1H), 8.40 (s, 1H), 8.02 (s, 1H), 7.62 (t, 1H), 7.45 (d, 1H), 7.35 (s, 1H), 7.20 (m, 2H), 5.20 (s, 2H), 4.30 (t, 2H), 4.15 (br q, 2H), 3.20 (m, 4H), 2.20 (br quintet, 2H); MS (+ve ESI): 578 $(M+H)^+$.

EXAMPLE 265

Preparation of Compound 265 in Table 11—2-[[3-({4-[(1-{2-[(3-fluorophenyl)amino]-2-oxoethyl}-1H-pyrazol-4-yl)amino]quinazolin-7-yl}oxy)propyl](2-methoxyethyl)amino]ethyl dihydrogen phosphate An analogous reaction to that described in example 255, but starting with N-(3-fluorophenyl)-2-{4-[(7-{3-[(2-hydroxyethyl)(2-methoxyethyl)amino]propoxy}quinazolin-4-yl)amino]-1H-pyrazol-1-yl}acetamide (483 mg, 0.9 mmol) yielded compound 265 in table 11 (520 mg, 82% yield):

$^1$H-NMR (DMSOd$_6$, TFA): 9.01 (s, 1H), 8.69 (d, 1H), 8.42 (s, 1H), 8.0 (s, 1H), 7.6 (d, 1H), 7.52 (d, 1H), 7.38 (m, 1H), 7.33 (m, 2H), 6.92 (m, 1H), 5.15 (s, 2H), 4.31 (t, 2H), 4.26 (m, 2H), 3.73 (m, 2H), 3.54 (m, 2H), 3.48 (m, 2H), 3.41 (m, 2H), 2.28 (m, 2H); MS (+ve ESI): 618.22 (M+H)$^+$.

EXAMPLE 266

Preparation of Compound 266 in Table 11—3-[[3-({4-[(1-{2-[(2,3-difluorophenyl)amino]-2-oxoethyl}-1H-pyrazol-4-yl)amino]quinazolin-7-yl}oxy)propyl](ethyl)amino]propyl dihydrogen phosphate An analogous reaction to that described in example 255, but starting with N-(2,3-difluorophenyl)-2-{4-[(7-{3-[ethyl(3-hydroxypropyl)amino]propoxy}quinazolin-4-yl)amino]-1H-pyrazol-1-yl}acetamide (200 mg, 0.37 mmol) yielded compound 266 in table 11 (155 mg, 57% yield):

$^1$H-NMR (DMSO d$_6$): 11.75 (br s, 1H), 9.98 (s, 1H), 8.92 (d, 1H), 8.84 (s, 1H), 8.42 (s, 1H), 8.05 (s, 1H), 7.70 (m, 1H), 7.45 (m, 2H), 7.10 (m, 2H), 5.15 (s, 2H), 4.42 (t, 2H), 4.05 (m, 2H), 3.25 (m, 6H), 2.30 (m, 2H), 2.05 (m, 2H), 1.25 (t, 3H); MS (+ve ESI): 620 (M+H)$^+$.

EXAMPLE 267

Preparation of Compound 267 in Table 11—3-[[3-({4-[(1-{2-[(2,3-difluorophenyl)amino]-2-oxoethyl}-1H-pyrazol-4-yl)amino]quinazolin-7-yl}oxy)propyl](propyl)amino]propyl dihydrogen phosphate An analogous reaction to that described in example 255, but starting with N-(2,3-difluorophenyl)-2-{4-[(7-{3-[(3-hydroxypropyl)(propyl)amino]propoxy}quinazolin-4-yl)amino]-1H-pyrazol-1-yl}acetamide (150 mg, 0.27 mmol) yielded compound 267 in table 11 (60 mg; 30% yield):

$^1$H-NMR (DMSO d$_6$): 11.75 (br s, 1H), 10.01 (s, 1H), 8.84 (m, 2H), 8.42 (s, 1H), 8.05 (s, 1H), 7.70 (m, 1H), 7.45 (m, 2H), 7.10 (m, 2H), 5.15 (s, 2H), 4.42 (t, 2H), 4.05 (m, 2H), 3.25 (m, 6H), 2.30 (m, 2H), 2.05 (m, 4H), 1.01 (t, 3H); MS (+ve ESI): 634 (M+H)$^+$.

EXAMPLE 268

Preparation of Compound 268 in Table 11—2-[[3-({4-[(1-{2-[(2,3-difluorophenyl)amino]-2-oxoethyl}-1H-pyrazol-4-yl)amino]quinazolin-7-yl}oxy)propyl](propyl)amino]-2-oxoethyl dihydrogen phosphate An analogous reaction to that described in example 255 but starting with N-(2,3-difluorophenyl)-2-{4-[(7-{3-[glycoloyl(propyl)amino]propoxy}quinazolin-4-yl)amino]-1H-pyrazol-1-yl}acetamide (0.23 g, 0.416 mmol) yielded compound 268 in table 11 (0.141 g, 46% yield):

$^1$H-NMR (DMSO d$_6$): 11.90 (br s, 1H), 10.43 (br s, 1H), 8.95 (s, 1H), 8.84 (m, 1H), 8.42 (s, 1H), 8.03 (s, 1H), 7.70 (t, 1H), 7.48 (t, 1H), 7.27 (m, 3H), 5.22 (s, 2H), 4.52 (t, 2H), 4.22 (d, 2H), 3.45 (m, 2H), 3.22 (m, 2H), 2.06 (m, 2H), 1.55 (m, 2H), 0.83 (t, 3H); MS (+ve ESI): 634 (M+H)$^+$.

EXAMPLE 269

Preparation of Compound 269 in Table 11—2-{4-[3-({4-[(1-{2-[(2,3-difluorophenyl)amino]-2-oxoethyl}-1H-pyrazol-4-yl)amino]quinazolin-7-yl}oxy)propyl]piperazin-1-yl}-2-oxoethyl dihydrogen phosphate An analogous reaction to that described in example 255 but starting with N-(2,3-difluorophenyl)-2-[4-({7-[3-(4-glycoloylpiperazin-1-yl)propoxy]quinazolin-4-yl}amino)-1H-pyrazol-1-yl]acetamide (0.18 g, 0.30 mmol) yielded compound 269 in table 11 (0.125 g, 52% yield):

$^1$H-NMR (DMSO d$_6$): 11.71 (br s, 1H), 10.07 (s, 1H), 8.87 (s, 1H), 8.85 (s, 1H), 8.40 (s, 1H), 8.08 (s, 1H), 7.62 (m, 1H), 7.42 (m, 2H), 7.15 (m, 2H), 5.20 (s, 2H), 4.57 (d, 2H), 4.41 (t, 2H), 3.95 (br s, 2H), 3.65 (s, 2H), 3.31 (m, 6H), 2.37 (m, 2H); MS (+ve ESI): 661 (M+H)$^+$ MS (−ve ESI): 659 (M−H)$^-$.

EXAMPLE 270

Preparation of Compound 270 in Table 11—{(2R)-1-[3-({4-[(1-{2-[(2,3-difluorophenyl)amino]-2-oxoethyl}-1H-pyrazol-4-yl)amino]-6-fluoroquinazolin-7-yl}oxy)propyl]pyrrolidin-2-yl}methyl dihydrogen phosphate An analogous reaction to that described in example 255 but starting with N-(2,3-Difluorophenyl)-2-{4-[(6-fluoro-7-{3-[(2R)-2-(hydroxymethyl)pyrrolidin-1-yl]propoxy}quinazolin-4-yl)amino]-1H-pyrazol-1-yl}acetamide (0.205 g, 0.37 mmol) yielded compound 270 in table 11 (0.183 g, 66% yield):

$^1$H-NMR (DMSO d$_6$): 11.74 (s, 1H), 10.40 (s, 1H), 8.95 (d, 1H), 8.91 (s, 1H), 8.43 (s, 1H), 8.05 (s, 1H), 7.72 (m, 1H), 7.63 (m, 1H), 7.21 (m, 2H), 5.22 (s, 2H), 4.40 (m, 2H), 4.20 (m, 2H), 3.80 (m, 1H), 3.66 (m, 1H), 3.57 (m, 1H), 3.31 (m, 1H), 3.21 (m, 1H), 2.32 (m, 2H), 2.20 (m, 1H), 2.04 (m, 1H), 1.95 (m, 1H), 1.5 (m, 1H).

EXAMPLE 271

Preparation of Compound 271 in Table 11—4-((1-(2-((2,3-difluorophenyl)amino)-2-oxoethyl)-1H-pyrazol-4-yl)amino)-7-((1-methylpiperidin-4-yl)methoxy)quinazolin-6-yl dihydrogen phosphate An analogous reaction to that described in example 255 but starting with N-(2,3-difluorophenyl)-2-(4-((6-hydroxy-7-((1-methylpiperidin-4-yl)methoxy)quinazolin-4-yl)amino)-1H-pyrazol-1-yl)acetamide (0.075 g, 0.14 mmol) yielded compound 271 in table 11 (0.045 g, 46% yield):

$^1$H-NMR (DMSO d$_6$+acetic acid d$_4$): 8.70 (s, 1H), 8.47 (s, 1H), 8.29 (s, 1H), 7.85 (s, 1H), 7.68 (m, 1H), 7.07 (m, 3H), 5.16 (s, 2H), 3.78 (d, 2H), 3.40 (m, 2H), 2.91 (t, 2H), 2.72 (s, 3H), 2.05 (m, 3H), 1.60 (m, 2H); MS (+ve ESI): 604 (M+H)$^+$.

EXAMPLE 272

Preparation of Compound 272 in Table 11—{(2R)-1-[3-({4-[(1-{2-[(2,3-difluorophenyl)amino]-2-oxoethyl}-1H-pyrazol-4-yl)amino]-5-isopropoxyquinazolin-7-yl}oxy)propyl]pyrrolidin-2-yl}methyl dihydrogen phosphate An analogous reaction to that described in example 255, but starting with N-(2,3-difluorophenyl)-2-{4-[(7-{3-[(2R)-2-(hydroxymethyl)pyrrolidin-1-yl]propoxy}-5-isopropoxyquinazolin-4-yl)amino]-1H-pyrazol-1-yl}acetamide (0.200 g, 0.34 mmol) yielded compound 272 in table 11 (0.150 g, 57% yield):

$^1$H-NMR (DMSO $d_6$): 10.55 (s, 1H), 10.00 (s, 1H), 8.80 (s, 1H) 8.40 (s, 1H), 7.85 (s, 1H), 7.70 (s, 1H), 7.20 (m, 2H), 7.00 (s, 1H), 6.95 (s, 1H), 5.18 (s, 2H), 5.01 (m, 1H), 4.30 (m, 2H), 4.15 (m, 1H), 3.52 (m, 4H), 3.35 (m, 2H), 2.08 (m, 6H), 1.55 (d, 6H); MS (+ve ESI): 676 $(M+H)^+$.

EXAMPLE 273

Preparation of Compound 273 in Table 11—2-{4-[3-({4-[(1-{2-[(2,3-difluorophenyl)amino]-2-oxoethyl}-1H-pyrazol-4-yl)amino]-5-isopropoxyquinazolin-7-yl}oxy)propyl]piperazin-1-yl}ethyl dihydrogen phosphate An analogous reaction to that described in example 255, but starting with N-(2,3-difluorophenyl)-2-{4-[(7-{3-[4-(2-hydroxyethyl)piperazin-1-yl]propoxy}-5-isopropoxyquinazolin-4-yl)amino]-1H-pyrazol-1-yl}acetamide (0.086 g, 0.14 mmol) yielded compound 273 in table 11 (0.075 g, 67% yield):

$^1$H-NMR (DMSO $d_6$): 10.70 (s, 1H), 10.00 (s, 1H), 8.75 (s, 1H), 8.30 (s, 1H), 7.82 (s, 1H), 7.65 (m, 1H), 7.15 (m, 2H), 6.95 (s, 1H), 6.85 (s, 1H), 5.18 (s, 2H), 5.03 (septet, 1H), 4.35 (t, 2H), 4.20 (m, 2H), 3.15 (m, 4H), 3.20 (m, 4H), 2.35 (m, 4H), 2.20 (m, 2H), 1.52 (d, 6H); MS (+ve ESI): 705 $(M+H)^+$.

EXAMPLE 274

Preparation of Compound 274 in Table 11—2-([3-({4-[(1-{2-[(2,3-difluorophenyl)amino]-2-oxoethyl}-1H-pyrazol-4-yl)amino]-5-isopropoxyquinazolin-7-yl}oxy)propyl]amino}ethyl dihydrogen phosphate An analogous reaction to that described in example 255, but starting with N-(2,3-difluorophenyl)-2-{4-[(7-{3-[(2-hydroxyethyl)amino]propoxy}-5-isopropoxyquinazolin-4-yl)amino]-1H-pyrazol-1-yl}acetamide (0.181 g, 0.33 mmol) yielded compound 274 in table 11 (0.170 g, 70% yield):

$^1$H-NMR (DMSO $d_6$): 10.60 (s, 1H), 10.00 (s, 1H), 8.75 (s, 1H), 8.30 (s, 1H), 7.82 (s, 1H), 7.65 (m, 1H), 7.15 (m, 2H), 6.95 (s, 1H), 6.85 (s, 1H), 5.15 (s, 2H), 4.99 (septet, 1H), 4.35 (t, 2H), 4.20 (m, 2H), 3.23 (t, 2H), 3.20 (t, 2H), 2.20 (m, 2H), 1.52 (d, 6H); MS (+ve ESI): 636 $(M+H)^+$.

EXAMPLE 275

Preparation of Compound 275 in Table 11—{(2R)-1-[3-({4-[(1-{2-[(2,3-difluorophenyl)amino]-2-oxoethyl}-1H-pyrazol-4-yl)amino]-5-methoxyquinazolin-7-yl}oxy)propyl]pyrrolidin-2-yl}methyl dihydrogen phosphate An analogous reaction to that described in example 255, but starting with N-(2,3-difluorophenyl)-2-{4-[(7-{3-[(2R)-2-(hydroxymethyl)pyrrolidin-1-yl]propoxy}-5-methoxyquinazolin-4-yl)amino]-1H-pyrazol-1-yl}acetamide (0.120 g, 0.21 mmol) yielded compound 275 in table 11 (0.100 g, 66% yield):

$^1$H-NMR (DMSO $d_6$): 10.40 (s, 1H), 9.98 (s, 1H), 8.65 (s, 1H), 8.25 (s, 1H), 7.88 (s, 1H), 7.68 (m, 1H), 7.18 (m, 2H), 6.92 (s, 1H), 6.82 (s, 1H), 5.15 (s, 2H), 4.30 (m, 2H), 4.18 (dd, 2H), 4.15 (s, 3H), 3.45 (m, 5H), 2.15 (m, 6H); MS (+ve ESI): 648 $(M+H)^+$.

EXAMPLE 276

Preparation of Compound 276 in Table 11—{(2R)-1-[2-({4-[(1-{2-[(2,3-Difluorophenyl)amino]-2-oxoethyl}-1H-pyrazol-4-yl)amino]-6-methoxyquinazolin-7-yl}oxy)ethyl]pyrrolidin-2-yl}methyl dihydrogen phosphate An analogous reaction to that described in example 255, but starting with N-(2,3-difluorophenyl)-2-{4-[(7-{2-[(2R)-2-(hydroxymethyl)pyrrolidin-1-yl]ethoxy}-6-methoxyquinazolin-4-yl)amino]-1H-pyrazol-1-yl}acetamide gave compound 276 in table 11 (83% yield):

$^1$H-NMR (DMSO-$d_6$): 12.12 (s, 1H), 10.45 (s, 1H), 8.92 (s, 1H), 8.58 (s, 1H), 8.48 (s, 1H), 8.13 (s, 1H), 7.71 (m, 1H), 7.44 (s, 1H), 7.20 (m, 2H), 5.23 (s, 2H), 4.63 (m, 2H), 4.25 (t, 2H), 4.06 (s, 3H), 3.92 (m, 2H), 3.73 (m, 2H), 3.37 (m, 1H), 2.20 (m, 1H), 2.07 (m, 1H), 1.93 (m, 1H), 1.80 (m, 1H); MS (+ve ESI): 634 $(M+H)^+$.

EXAMPLE 277

Preparation of Compound 277 in Table 11—{(2S)-1-[2-({4-[(1-{2-[(2,3-Difluorophenyl)amino]-2-oxoethyl}-1H-pyrazol-4-yl)amino]-6-methoxyquinazolin-7-yl}oxy)ethyl]pyrrolidin-2-yl}methyl dihydrogen phosphate An analogous reaction to that described in example 255, but starting with N-(2,3-difluorophenyl)-2-{4-[(7-{2-[(2S)-2-(hydroxymethyl)pyrrolidin-1-yl]ethoxy}-6-methoxyquinazolin-4-yl)amino]-1H-pyrazol-1-yl}acetamide gave compound 277 in table 11 (66% yield):

$^1$H-NMR (DMSO-$d_6$): 12.12 (s, 1H), 10.45 (s, 1H), 8.92 (s, 1H), 8.58 (s, 1H), 8.48 (s, 1H), 8.13 (s, 1H), 7.71 (m, 1H), 7.44 (s, 1H), 7.20 (m, 2H), 5.23 (s, 2H), 4.63 (m, 2H), 4.25 (t, 2H), 4.06 (s, 3H), 3.92 (m, 2H), 3.73 (m, 2H), 3.37 (m, 1H), 2.20 (m, 1H), 2.07 (m, 1H), 1.93 (m, 1H), 1.80 (m, 1H); MS (+ve ESI): 634 $(M+H)^+$.

EXAMPLE 278

Preparation of Compound 278 in table 11—2-[[2-({4-[(1-{2-[(2,3-Difluorophenyl)amino]-2-oxoethyl}-1H-pyrazol-4-yl)amino]-6-methoxyquinazolin-7-yl}oxy)ethyl](tetrahydro-2H-pyran-4-yl)amino]ethyl dihydrogen phosphate An analogous reaction to that described in example 255, but starting with N-(2,3-difluorophenyl)-2-{4-[(7-{2-[(2-hydroxyethyl)(tetrahydro-2H-pyran-4-yl)amino]ethoxy}-6-methoxyquinazolin-4-yl)amino]-1H-pyrazol-1-yl}acetamide gave compound 278 in table 11 (81% yield):

$^1$H-NMR (DMSO-$d_6$): 12.10 (s, 1H), 10.47 (s, 1H), 8.91 (s, 1H), 8.57 (s, 1H), 8.47 (s, 1H), 8.12 (s, 1H), 7.71 (m, 1H), 7.40 (s, 1H), 7.21 (m, 2H), 5.24 (s, 2H), 4.65 (m, 2H), 4.34 (m, 2H), 4.01 (m, 2H), 3.78 (m, 3H), 3.58 (m, 2H), 3.33 (t, 2H), 2.10 (m, 2H), 1.80 (m, 2H); MS (+ve ESI): 678 $(M+H)^+$.

EXAMPLE 279

Preparation of Compound 279 in Table 11—2-{4-[3-({4-[(1-{2-[(2,3-Difluorophenyl)amino]-2-oxoethyl}-1H-pyrazol-4-yl)amino]quinazolin-7-yl}oxy)propyl]-2-oxopiperazin-1-yl}ethyl dihydrogen phosphate Di-tert-butyl 2-{4-[3-({4-[(1-{2-[(2,3-difluorophenyl)amino]-2-oxoethyl}-1H-pyrazol-4-yl)amino]quinazolin-7-yl}oxy)propyl]-2-oxopiperazin-1-yl}ethyl phosphate (210 mg, 0.27 mmol) and hydrogen chloride (0.5 ml of a 4M solution in 1,4-dioxane) in 1,4-dioxane (3.0 ml) were stirred at room temperature for 6 hours. The mixture was diluted with diethyl ether and then filtered to give compound 279 in table 11 (206 mg, 98%) as a colourless solid:

$^1$H-NMR (DMSO-d$_6$): 12.00 (s, 1H), 10.44 (s, 1H), 8.96 (s, 1H), 8.91 (d, 1H), 8.44 (s, 1H), 8.06 (s, 1H), 7.70 (m, 1H), 7.47 (dd, 1H), 7.38 (d, 1H), 7.20 (m, 2H), 5.22 (s, 2H), 4.32 (t, 2H), 3.95 (m, 4H), 3.75 (m, 2H), 3.58 (m, 2H), 3.56 (s, 2H), 3.38 (m, 2H), 2.32 (quintet, 2H); MS (+ve ESI): 661 (M+H)$^+$.

di-tert-butyl 2-{4-[3-({4-[(1-{2-[(2,3-difluorophenyl)amino]-2-oxoethyl}-1H-pyrazol-4-yl)amino]quinazolin-7-yl}oxy)propyl]-2-oxopiperazin-1-yl}ethyl phosphate used as Starting Material was Prepared as Follows a) Tetra-n-butylammonium di-tert-butyl phosphate (4.0 g, 8.87 mmol) and 1,2-dibromoethane (5.0 g, 26.7 mmol) in dimethoxyethane (20 ml) were stirred and refluxed for 4 hr. then cooled to room temperature and filtered. The filtrate was concentrated, diluted with diethyl ether, washed with 20% aqueous potassium carbonate solution, dried over magnesium sulphate and evaporated to leave a colourless oil. The crude product was purified by silica gel chromatography eluting with a 20-50% mixture of ethyl acetate in iso-hexane to give 2-bromoethyl di-tert-butyl phosphate (1.3 g, 46% yield) as a colourless oil:

$^1$H-NMR (CDCl$_3$): 4.22 (q, 2H), 3.53 (t, 2H), 1.49 (s, 18H).

b) 2-Bromoethyl di-tert-butyl phosphate (298 mg, 0.94 mmol) in tetrahydrofuran (1.0 ml) was added at room temperature to a stirred suspension of benzyl 3-oxopiperazine-1-carboxylate (200 mg, 0.85 mmol), powdered potassium hydroxide (57 mg, 1.0 mmol) and tetra-n-butylammonium bromide (55 mg, 0.17 mmol) in THF (2.0 ml). The reaction mixture was stirred for 90 minutes and then filtered through Celite and the filtrate evaporated to leave a colourless oil. The crude product was purified by silica gel chromatography eluting with a 2-5% mixture of methanol in dichloromethane to give benzyl 4-{2-[(di-tert-butoxyphosphoryl)oxy]ethyl}-3-oxopiperazine-1-carboxylate (220 mg, 55% yield) as a colourless oil:

$^1$H-NMR (CDCl$_3$): 7.34 (m, 5H), 5.16 (s, 2H), 4.15 (s, 2H), 4.11 (m, 2H), 3.71 (m, 2H), 3.65 (m, 2H), 3.53 (m, 2H), 1.47 (s, 18H).

c) Benzyl 4-{2-[(di-tert-butoxyphosphoryl)oxy]ethyl}-3-oxopiperazine-1-carboxylate (1.20 g, 2.55 mmol) and 10% palladium on carbon (100 mg) in methanol (25 ml) were stirred at room temperature under an atmosphere of hydrogen for 2 hours and then filtered through Celite. The filtrate was evaporated to give di-tert-butyl 2-(2-oxopiperazin-1-yl)ethyl phosphate as a colourless oil which was dissolved in dimethylacetamide(4.0 ml) containing 2-(4-{[7-(3-chloropropoxy)quinazolin-4-yl]amino}-1H-pyrazol-1-yl)-N-(2,3-difluorophenyl)acetamide hydrochloride (326 mg, 0.64 mmol) and potassium iodide (213 mg, 1.28 mmol) and the mixture was then heated at 90° C. for 3 hours. The mixture was cooled to room temperature, poured into dilute aqueous sodium hydrogen carbonate solution and then extracted with a solution of 10% isopropanol in dichloromethane. The organic layer was dried over magnesium sulphate and then evaporated to leave an orange oil. The crude product was purified by silica gel chromatography eluting with 5% methanol in dichloromethane containing 0-4% 7N ammonia in methanol to give di-tert-butyl 2-{4-[3-({4-[(1-{2-[(2,3-difluorophenyl)amino]-2-oxoethyl}-1H-pyrazol-4-yl)amino]quinazolin-7-yl}oxy)propyl]-2-oxopiperazin-1-yl}ethyl phosphate (211 mg, 43% yield) as a pale yellow solid: MS (+ve ESI): 773 (M+H)$^+$.

EXAMPLE 280

Preparation of Compound 280 in Table 11—2-[[2-({4-[(1-{2-[(2,3-Difluorophenyl)amino]-2-oxoethyl}-1H-pyrazol-4-yl)amino]quinazolin-7-yl}oxy)ethyl](tetrahydro-2H-pyran-4-yl)amino]ethyl dihydrogen phosphate An analogous reaction to that described in example 255, but starting with N-(2,3-difluorophenyl)-2-{4-[(7-{2-[(2-hydroxyethyl)(tetrahydro-2H-pyran-4-yl)amino]ethoxy}quinazolin-4-yl)amino]-1H-pyrazol-1-yl}acetamide gave compound 280 in table 11 (2% yield):

$^1$H-NMR (DMSO-d$_6$): 12.08 (s, 1H), 10.44 (s, 1H), 8.98 (d, 1H), 8.97 (s, 1H), 8.44 (s, 1H), 8.07 (s, 1H), 7.69 (m, 1H), 7.52 (dd, 1H), 7.41 (d, 1H), 7.20 (m, 2H), 5.22 (s, 2H), 4.65 (m, 2H), 4.32 (m, 2H), 4.00 (m, 2H), 3.74 (m, 2H), 3.57 (m, 2H), 3.34 (m, 3H), 2.07 (m, 2H), 1.80 (m, 2H); MS (+ve ESI): 648 (M+H)$^+$.

What we claim is:

1. A compound of formula (I)

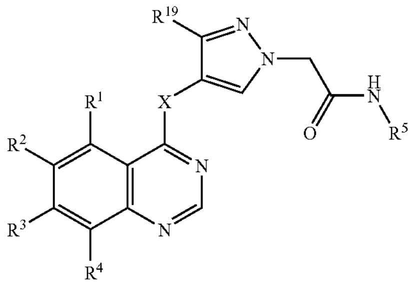

or a salt, ester or prodrug thereof;

where:

X is O or NR$^6$;

R$^6$ is hydrogen or C$_{1-4}$alkyl;

R$^1$ is hydrogen, halo, or —X$^1$R$^{11}$;

X$^1$ is a direct bond, —CH$_2$═CH$_2$—, —O—, —NH—, —N(C$_{1-6}$alkyl)-, —C(O)O—, —C(O)O—, —OC(O)O—, —NHC(O)—, —N(C$_{1-6}$alkyl)C(O)—, —C(O)NH— or —C(O)N(C$_{1-6}$alkyl)-;

R$^{11}$ is hydrogen, or a group selected from C$_{1-6}$alkyl, C$_{2-6}$alkenyl, C$_{2-6}$alkynyl, C$_{3-6}$cycloalkyl, C$_{3-6}$cycloalkenyl, heterocyclyl, heterocyclylC$_{1-4}$alkyl, heterocyclylC$_{2-4}$alkenyl and heterocyclylC$_{2-4}$alkynyl which group is optionally substituted by 1 or 2 substituents independently selected from halo, hydroxy, C$_{1-4}$alkoxy, hydroxyC$_{1-4}$alkyl, —NR$^9$R$^{10}$, —C(O)R$^9$, —C(O)NR$^9$R$^{10}$ and —C(O)OR$^9$;

$R^2$ is hydrogen, halo, nitro, cyano or —$X^2R^{12}$;

$X^2$ is a direct bond, —O—, —NH—, —N($C_{1-6}$alkyl)-, —OC(O)— or —C(O)O—;

$R^{12}$ is hydrogen, or a group selected from $C_{1-6}$alkyl, $C_{2-6}$alkenyl, $C_{2-6}$alkynyl, $C_{3-6}$cycloalkyl, $C_{3-6}$cycloalkenyl, aryl, aryl$C_{1-4}$alkyl, aryl$C_{2-4}$alkenyl, aryl$C_{2-4}$alkynyl, heterocyclyl, heterocyclyl$C_{1-4}$alkyl, heterocyclyl$C_{2-4}$alkenyl and heterocyclyl$C_{2-4}$alkynyl, which group is optionally substituted by 1, 2 or 3 substituents selected from halo, hydroxy, $C_{1-4}$alkyl, $C_{1-4}$alkoxy, —$NR^{15}R^{16}$, —NHC(O)$NR^{15}R^{16}$, —C(O)$R^{15}$ and —C(O)$OR^{15}$;

$R^3$ is hydrogen, halo or —$X^3R^{13}$;

$X^3$ is a direct bond, —$CH_2$=$CH_2$—, —O—, —NH—,—N($C_{1-6}$alkyl)-, —C(O)—, —C(O)O—, —OC(O)—, —NHC(O)O—, —N($C_{1-6}$alkyl)C(O)—, —C(O)NH— or —C(O)N($C_{1-6}$alkyl)-;

$R^{13}$ is hydrogen or a group selected from $C_{1-6}$alkyl, $C_{2-6}$alkenyl, $C_{2-6}$alkynyl, $C_{3-6}$cycloalkyl, $C_{3-6}$cycloalkenyl, aryl, aryl$C_{1-4}$alkyl, aryl$C_{2-4}$alkenyl, aryl$C_{2-4}$alkynyl, heterocyclyl, heterocyclyl$C_{1-4}$alkyl, heterocyclyl$C_{2-4}$alkenyl and heterocyclyl$C_{2-4}$alkynyl which group is optionally substituted by 1 or 2 substituents independently selected from —$NR^7R^8$, —C(O)$NR^7R^8$, halo, hydroxy, $C_{1-4}$alkyl, $C_{1-4}$alkoxy, hydroxy$C_{1-4}$alkyl, hydroxy$C_{1-4}$alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$alkylcarbonyl;

$R^7$ and $R^8$ are independently selected from hydrogen, heterocyclyl, heterocyclyl$C_{1-4}$alkyl, $C_{1-4}$alkylheterocyclyl$C_{1-4}$alkyl, $C_{1-6}$alkyl, hydroxy$C_{1-6}$alkyl, $C_{1-4}$alkoxy$C_{1-6}$alkyl, $C_{3-6}$cycloalkyl, $C_{3-6}$cycloalkyl$C_{1-4}$ alkyl, hydroxy$C_{3-6}$cycloalkyl, hydroxy$C_{1-4}$ alkyl$C_{3-6}$ cycloalkyl, hydroxy$C_{3-6}$cycloalkyl$C_{1-4}$alkyl, hydroxy$C_{1-4}$alkyl$C_{3-6}$cycloalkyl$C_{1-4}$ alkyl, $C_{1-4}$alkoxy$C_{3-6}$cycloalkyl, $C_{1-4}$alkoxy$C_{3-6}$cycloalkyl$C_{1-4}$alkyl, halo$C_{1-6}$alkyl, halo$C_{3-6}$cycloalkyl, halo$C_{3-6}$cycloalkyl$C_{1-4}$alkyl, $C_{2-6}$alkenyl, $C_{2-6}$alkynyl, cyano$C_{1-4}$alkyl, amino$C_{1-6}$alkyl, $C_{1-4}$alkylamino$C_{1-6}$ alkyl, bis($C_{1-4}$alkyl)amino$C_{1-6}$alkyl, hydroxy$C_{1-4}$ alkoxy$C_{1-4}$alkyl, hydroxy$C_{1-4}$alkylcarbonyl, $C_{1-4}$alkylcarbonyl, amino$C_{1-4}$alkylcarbonyl, $C_{1-4}$alkylamino$C_{1-4}$ alkylcarbonyl and bis($C_{1-4}$alkyl)amino$C_{1-4}$ alkylcarbonyl;

or $R^7$ and $R^8$ together with the nitrogen to which they are attached form a heterocyclic ring which ring is monocyclic or bicyclic and comprises 4 to 7 ring atoms of which one is nitrogen and of which another is optionally selected from N, NH, O, S, SO and $SO_2$, and which ring is optionally substituted on carbon or nitrogen by 1 or 2 substituents independently selected from $C_{1-4}$alkyl, hydroxy, $C_{1-4}$alkoxy, hydroxy$C_{1-4}$alkyl, $C_{1-4}$alkoxy$C_{1-4}$ alkyl, hydroxy$C_{1-4}$alkoxy$C_{1-4}$alkyl, $C_{1-4}$alkoxy$C_{1-4}$ alkoxy, hydroxy$C_{1-4}$alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$alkylcarbonyl, and where a ring —$CH_2$— is optionally replaced with —C(O)—;

$R^4$ is selected from hydrogen, halo or —$X^4R^{14}$;

$X^4$ is a direct bond, —O—, —NH— or —N($C_{1-6}$alkyl)-;

$R^{14}$ is selected from hydrogen, $C_{1-6}$alkyl, $C_{2-6}$alkenyl and $C_{2-6}$alkynyl;

$R^5$ is aryl or heteroaryl optionally substituted by 1, 2 or 3 substituents independently selected from halo, hydroxy, cyano, nitro, amino, $C_{1-4}$alkylamino, bis($C_{1-4}$alkyl) amino, $C_{1-4}$alkyl, $C_{2-4}$alkenyl, $C_{2-4}$alkynyl, $C_{1-4}$alkoxy, —CONH$R^{17}$, —NHCO$R^{18}$—S$R^{17}$, —S(O)$R^{17}$ and —S(O)O$R^{17}$;

$R^9$, $R^{10}$, $R^{15}$ and $R^{16}$ are independently selected from hydrogen, $C_{1-6}$alkyl, $C_{3-6}$cycloalkyl, $C_{3-6}$cycloalkyl$C_{1-4}$ alkyl, hydroxy$C_{1-6}$alkyl, halo$C_{1-6}$alkyl, amino$C_{1-6}$ alkyl, $C_{1-4}$alkylamino$C_{1-6}$alkyl and bis($C_{1-4}$ alkyl)amino$C_{1-6}$alkyl;

or $R^9$ and $R^{10}$ together with the nitrogen to which they are attached form a heterocyclic ring which ring is monocyclic or bicyclic and comprises 4 to 7 ring atoms of which one is nitrogen and of which another is optionally selected from N, NH, O, S, SO and $SO_2$, and which ring is optionally substituted on carbon or nitrogen by 1 or 2 substituents independently selected from $C_{1-4}$alkyl, hydroxy, $C_{1-4}$alkoxy, hydroxy$C_{1-4}$alkyl, $C_{1-4}$alkoxy$C_{1-4}$ alkyl, hydroxy$C_{1-4}$alkoxy$C_{1-4}$alkyl, $C_{1-4}$alkoxy$C_{1-4}$ alkoxy, hydroxy$C_{1-4}$alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$alkylcarbonyl, and where a ring —$CH_2$— is optionally replaced with —C(O)—;

$R^{17}$ and $R^{18}$ are independently selected from hydrogen, $C_{1-4}$alkyl, $C_{3-6}$cycloalkyl, $C_{2-4}$alkenyl and $C_{2-4}$alkynyl;

$R^{19}$ is hydrogen, hydroxy$C_{1-4}$alkyl, —C(O)$R^{20}$, —C(O)O$R^{20}$, —CON$R^{20}R^{21}$, —NHC(O)$R^{20}$ or —NHC(O)O$R^{20}$;

$R^{20}$ are $R^{21}$ are independently selected from hydrogen, $C_{1-4}$alkyl and aryl.

2. A compound of formula (IA)

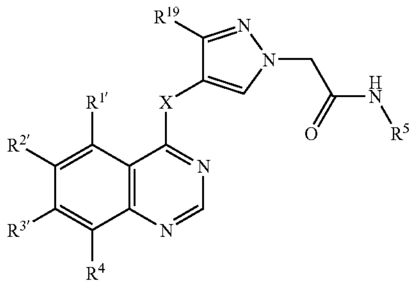

or salt or ester thereof where X, $X^1$, $X^2$, $X^3$, $R^4$, $R^5$ and $R^{19}$ are as defined in relation to formula (I) and $R^{1'}$ is hydrogen, halo, or —$X^1R^{11'}$;

$R^{11'}$ is hydrogen, phosphonooxy or a group selected from $C_{1-6}$alkyl, $C_{2-6}$alkenyl, $C_{2-6}$alkynyl, $C_{3-6}$cycloalkyl, $C_{3-6}$cycloalkenyl, heterocyclyl, heterocyclyl$C_{1-4}$alkyl, heterocyclyl$C_{2-4}$alkenyl and heterocyclyl$C_{2-4}$alkynyl which group is optionally substituted by a substituent selected from halo, hydroxy, phosphonooxy, $C_{1-4}$alkoxy, hydroxy$C_{1-4}$alkyl, phosphonooxy$C_{1-4}$alkyl, —$NR^{9'}R^{10'}$, —C(O)$R^{9'}$, —C(O)$NR^{9'}R^{10'}$ and —C(O)$OR^{9'}$;

$R^{2'}$ is hydrogen, halo, nitro, cyano or —$X^2R^{12'}$;

$R^{12'}$ is hydrogen, phosphonooxy or a group selected from $C_{1-6}$alkyl, $C_{2-6}$alkenyl, $C_{2-6}$alkynyl, $C_{3-6}$cycloalkyl, $C_{3-6}$cycloalkenyl, aryl, aryl$C_{1-4}$alkyl, aryl$C_{2-4}$alkenyl, aryl$C_{2-4}$alkynyl, heterocyclyl, heterocyclyl$C_{1-4}$alkyl, heterocyclyl$C_{2-4}$alkenyl and heterocyclyl$C_{2-4}$alkynyl, which group is optionally substituted by 1, 2 or 3 substituents selected from halo, hydroxy, phosphonooxy, $C_{1-4}$alkyl, $C_{1-4}$alkoxy, —$NR^{15'}R^{16'}$, —NHC(O)$NR^{15'}R^{16'}$—, —C(O)$R^{15'}$— and —C(O)$OR^{15'}$—;

$R^{3'}$ is hydrogen, halo or —$X^3R^{13'}$;

$R^{13'}$ is hydrogen, phosphonooxy or a group selected from $C_{1-6}$alkyl, $C_{2-6}$alkenyl, $C_{2-6}$alkynyl, $C_{3-6}$cycloalkyl, $C_{3-6}$cycloalkenyl, aryl, aryl$C_{1-4}$alkyl, aryl$C_{2-4}$alkenyl, aryl$C_{2-4}$alkynyl, heterocyclyl, heterocyclyl$C_{1-4}$alkyl, heterocyclyl$C_{2-4}$alkenyl and heterocyclyl$C_{2-4}$alkynyl which group is optionally substituted by 1 or 2 substituents independently selected from —$NR^{7'}R^{8'}$, —C(O)$NR^{7'}R^{8'}$, halo, hydroxy, phosphonooxy, $C_{1-4}$alkyl, $C_{1-4}$alkoxy, hydroxy$C_{1-4}$alkyl, phosponooxy$C_{1-4}$alkyl, hydroxy$C_{1-4}$alkylcarbonyl, phosphonooxy$C_{1-4}$alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$alkylcarbonyl;

$R^{7'}$ and $R^{8'}$ are independently selected from hydrogen, heterocyclyl, heterocyclyl$C_{1-4}$alkyl, $C_{1-4}$alkylheterocyclyl$C_{1-4}$alkyl, $C_{1-6}$alkyl, hydroxy$C_{1-6}$alkyl, phosphonooxy$C_{1-6}$alkyl, $C_{1-4}$alkoxy$C_{1-6}$alkyl, $C_{3-6}$cycloalkyl, $C_{3-6}$cycloalkyl$C_{1-4}$alkyl, hydroxy$C_{3-6}$cycloalkyl, phosphonooxy$C_{3-6}$cycloalkyl, hydroxy$C_{1-4}$alkyl$C_{3-6}$ cycloalkyl, phosphonooxy$C_{1-4}$alkyl$C_{3-6}$cycloalkyl, hydroxy$C_{3-6}$cycloalkyl$C_{1-4}$alkyl, phosphonooxy$C_{3-6}$ cycloalkyl$C_{1-4}$alkyl, hydroxy$C_{1-4}$alkyl$C_{3-6}$cycloalkyl$C_{1-4}$alkyl, phosphonooxy$C_{1-4}$alkyl$C_{3-6}$cycloalkyl$C_{1-4}$alkyl, $C_{1-4}$alkoxy$C_{3-6}$cycloalkyl, $C_{1-4}$alkoxy$C_{3-6}$cycloalkyl$C_{1-4}$alkyl, halo$C_{1-6}$alkyl, halo$C_{3-6}$cycloalkyl, halo$C_{3-6}$cycloalkyl$C_{1-4}$alkyl, $C_{2-6}$alkenyl, $C_{2-6}$alkynyl, cyano$C_{1-4}$alkyl, amino$C_{1-6}$ alkyl, $C_{1-4}$alkylamino$C_{1-6}$alkyl, bis($C_{1-4}$alkyl)amino$C_{1-6}$ alkyl, hydroxy$C_{1-4}$alkoxy$C_{1-4}$alkyl, phosphonooxy$C_{1-4}$ alkoxy$C_{1-4}$alkyl, hydroxy$C_{1-4}$alkylcarbonyl, phosphonooxy$C_{1-4}$alkylcarbonyl, $C_{1-4}$alkylcarbonyl, amino$C_{1-4}$ alkylcarbonyl, $C_{1-4}$alkylamino$C_{1-4}$alkylcarbonyl and bis($C_{1-4}$alkyl)amino$C_{1-4}$alkylcarbonyl;

or $R^{7'}$ and $R^{8'}$ together with the nitrogen to which they are attached form a heterocyclic ring which ring is monocyclic or bicyclic and comprises 4 to 7 ring atoms of one is nitrogen and of which another is optionally selected from N, NH, O, S, SO and $SO_2$, and which ring is optionally substituted on carbon or nitrogen by 1 or 2 substituents independently selected from $C_{1-4}$alkyl, hydroxy, phosphonooxy, $C_{1-4}$alkoxy, hydroxy$C_{1-4}$alkyl, phosphonooxy$C_{1-4}$alkyl, $C_{1-4}$alkoxy$C_{1-4}$alkyl, hydroxy$C_{1-4}$alkoxy$C_{1-4}$alkyl, phosphonooxy$C_{1-4}$ alkoxy$C_{1-4}$alkyl, $C_{1-4}$alkoxy$C_{1-4}$alkoxy, hydroxy$C_{1-4}$ alkylcarbonyl, phosphonooxy$C_{1-4}$alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$ alkylcarbonyl, and where a ring —$CH_2$— is optionally replaced with —C(O)—;

$R^{9'}$, $R^{10'}$, $R^{15'}$ and $R^{16'}$ are independently selected from hydrogen, $C_1$-alkyl, $C_{3-6}$cycloalkyl, $C_{3-6}$cycloalkyl$C_{1-3}$ alkyl, hydroxy$C_{1-6}$alkyl, phosphonooxy$C_{1-6}$alkyl, halo$C_{1-6}$alkyl, amino$C_{1-6}$alkyl, $C_{1-6}$alkylamino$C_{1-6}$ alkyl and bis($C_{1-6}$alkyl)amino$C_{1-6}$alkyl;

or $R^{9'}$ and $R^{10'}$ together with the nitrogen to which they are attached form a heterocyclic ring which ring is monocyclic or bicyclic and comprises 4 to 7 ring atoms of which one is nitrogen and of which another is optionally selected from N, NH, O, S, SO and $SO_2$, and which ring is optionally substituted on carbon or nitrogen by 1 or 2 substituents independently selected from $C_{1-4}$alkyl, hydroxy, phosphonooxy, $C_{1-4}$alkoxy, hydroxy$C_{1-4}$alkyl, phosphonooxy$C_{1-4}$alkyl, $C_{1-4}$alkoxy$C_{1-4}$alkyl, hydroxy$C_{1-4}$alkoxy$C_{1-4}$alkyl, phosphonooxy$C_{1-4}$ alkoxy$C_{1-4}$alkyl, $C_{1-4}$alkoxy$C_{1-4}$alkoxy, hydroxy$C_{1-4}$ alkylcarbonyl, phosphonooxy$C_{1-4}$alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$ alkylcarbonyl, and where a ring —$CH_2$— is optionally replaced with —C(O)—;

provided that a compound of formula (IA) contains at least one phosphonooxy group.

3. A compound or a salt or ester thereof according to claim 2 containing only one phosphonooxy group.

4. A compound or a salt or ester thereof according to claim 1 wherein $R^1$ is hydrogen, halo or —$OR^{11}$ and $R^{11}$ is hydrogen or a group selected from $C_{1-6}$alkyl, heterocyclyl and heterocyclyl$C_{1-4}$alkyl, which group is optionally substituted by a substituent selected from hydroxy, $C_{1-4}$alkoxy, hydroxy$C_{1-4}$alkyl, hydroxy$C_{1-4}$alkylcarbonyl, amino$C_{1-4}$ alkylcarbonyl, $C_{1-4}$alkylamino$C_{1-4}$alkylcarbonyl and bis ($C_{1-4}$ alkyl)amino$C_{1-4}$alkylcarbonyl.

5. A compound or a salt or ester thereof according to claim 1 wherein $R^2$ is hydrogen, halo, —$OR^{12}$ or —OC(O)$R^{12}$ and $R^{12}$ is hydrogen or a group selected from $C_{1-4}$alkyl, aryl, heterocyclyl and heterocyclyl$C_{1-4}$alkyl which group is optionally substituted by a substituent selected from $C_{1-4}$alkyl and $C_{1-4}$alkoxy.

6. A compound or a salt or ester thereof according to claim 1 wherein $R^3$ is hydrogen or —$X^3R^{13}$ and $R^{13}$ is hydrogen, methyl, ethyl, propyl, heterocyclyl, heterocyclylmethyl, heterocyclylethyl or heterocyclylpropyl which methyl, ethyl or propyl are optionally substituted by —$NR^7R^8$, —C(O)$NR^7R^8$ or 1 or 2 halo, hydroxy or $C_{1-4}$alkoxy substituents and which heterocyclylmethyl, heterocyclylethyl or heterocyclylpropyl are optionally substituted on heterocyclyl by hydroxy, $C_{1-4}$alkyl, hydroxy$C_{1-4}$alkyl or hydroxy$C_{1-4}$alkylcarbonyl.

7. A compound or a salt or ester thereof according to claim 6 wherein $R^7$ and $R^8$ are independently selected from hydrogen, heterocyclyl, heterocyclyl$C_{1-4}$alkyl, $C_{1-4}$alkylheterocyclyl$C_{1-4}$alkyl, $C_{1-6}$alkyl, hydroxy$C_{1-6}$alkyl, $C_{1-4}$alkoxy$C_{1-4}$ alkyl, $C_{3-6}$cycloalkyl, $C_{3-6}$cycloalkyl$C_{1-4}$alkyl, hydroxy$C_{3-6}$ cycloalkyl, hydroxy$C_{1-4}$alkyl$C_{3-6}$cycloalkyl, halo$C_{1-6}$alkyl, $C_{2-4}$alkenyl, $C_{2-4}$alkynyl, cyano$C_{1-4}$alkyl, amino$C_{1-4}$alkyl, $C_{1-4}$alkylamino$C_{1-4}$alkyl, bis($C_{1-4}$alkyl)amino$C_{1-4}$alkyl, hydroxy$C_{1-4}$alkoxy$C_{1-4}$alkyl and hydroxy$C_{1-4}$alkylcarbonyl; or $R^7$ and $R^8$ together with the nitrogen to which they are attached form a heterocyclic ring selected from azetidine, pyrrolidine, piperidine, morpholine, piperazine, diazepane, 1,4-diazepane and azabicyclo[3.1.0]hexane which ring is optionally substituted on carbon or nitrogen by 1 or 2 substituents independently selected from $C_{1-4}$alkyl, hydroxy, hydroxy$C_{1-4}$alkyl, $C_{1-4}$alkoxy$C_{1-4}$alkyl, hydroxy$C_{1-4}$ alkoxy$C_{1-4}$alkyl, $C_{1-4}$alkylcarbonyl and hydroxy$C_{1-4}$alkylcarbonyl, and where a ring —$CH_2$— is optionally replaced with —C(O)—.

8. A compound or a salt or ester thereof according to claim 2 wherein $R^{1'}$ is hydrogen, halo or —$OR^{11'}$ and $R^{11'}$ is hydrogen, phosphonooxy or a group selected from $C_{1-6}$alkyl, heterocyclyl and heterocyclyl$C_{1-4}$alkyl, which group is optionally substituted by a substituent selected from hydroxy, phosphonooxy, $C_{1-4}$alkoxy, hydroxy$C_{1-4}$alkyl, phosphonooxy$C_{1-4}$alkyl, hydroxy$C_1$ $_4$alkylcarbonyl, phosphonooxy$C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$ alkylcarbonyl.

9. A compound or a salt or ester thereof according to claim 2 wherein $R^{2'}$ is hydrogen, halo, —$OR^{12'}$ or —OC(O)$R^{12'}$ and $R^{12'}$ is hydrogen, phosphonooxy or a group selected from $C_{1-4}$alkyl, aryl, heterocyclyl and heterocyclyl$C_{1-4}$alkyl which group is optionally substituted by a substituent selected from $C_{1-4}$alkyl and $C_{1-4}$alkoxy.

10. A compound or a salt or ester thereof according to claim 2 wherein $R^{3'}$ is hydrogen, phosphonooxy or —$X^3R^{13'}$ and $R^{13'}$ is hydrogen or a group selected from $C_{1-6}$alkyl, aryl, aryl$C_{1-4}$alkyl, heterocyclyl and heterocyclyl$C_{1-4}$alkyl, which group is optionally substituted by 1 or 2 substituents independently selected from —$NR^{7'}R^{8'}$, —C(O)$NR^{7'}R^{8'}$, halo, hydroxy, phosphonooxy, $C_{1-4}$alkyl, $C_{1-4}$alkoxy, hydroxy$C_{1-4}$alkyl, phosphonooxy$C_{1-4}$alkyl, hydroxy$C_{1-4}$alkylcarbonyl, phosphonooxy$C_{1-4}$alkylcarbonyl and $C_{1-4}$alkylcarbonyl.

11. A compound or a salt or ester thereof according to claim 10 wherein $R^{7'}$ and $R^{8'}$ are independently selected from hydrogen, heterocyclyl, heterocyclyl$C_{1-4}$alkyl, $C_{1-4}$alkylheterocyclyl$C_{1-4}$alkyl, $C_{1-6}$alkyl, hydroxy$C_{1-6}$alkyl, phosphonooxy$C_{1-6}$alkyl, $C_{1-4}$alkoxy$C_{1-4}$alkyl, $C_{3-6}$cycloalkyl, $C_{3-6}$cycloalkyl$C_{1-4}$alkyl, hydroxy$C_{3-6}$cycloalkyl, phosphonooxy$C_{3-6}$cycloalkyl, hydroxy$C_{1-4}$alkyl$C_{3-6}$cycloalkyl, phosphonooxy$C_{1-4}$alkyl$C_{3-6}$cycloalkyl, halo$C_{1-6}$alkyl, $C_{2-4}$alkenyl, $C_{2-4}$alkynyl, cyano$C_{1-4}$alkyl, amino$C_{1-4}$alkyl, bis($C_{1-4}$alkyl)amino$C_{1-4}$alkyl, hydroxy$C_{1-4}$alkoxy$C_{1-4}$alkyl, phosphonooxy$C_{1-4}$alkoxy$C_{1-4}$alkyl, hydroxy$C_{1-4}$alkylcarbonyl and phosphonooxy$C_{1-4}$alkylcarbonyl; or $R^{7'}$ and $R^{8'}$ together with the nitrogen to which they are attached form a heterocyclic ring selected from azetidine, pyrrolidine, piperidine, morpholine, piperazine, diazepane, 1,4-diazepane and azabicyclo[3.1.0]hexane which ring is optionally substituted on carbon or nitrogen by 1 or 2 substituents independently selected from $C_{1-4}$alkyl, hydroxy, phosphonooxy, hydroxy$C_{1-4}$alkyl, phosphonooxy$C_{1-4}$alkyl, $C_{1-4}$alkoxy$C_{1-4}$alkyl, hydroxy$C_{1-4}$alkoxy$C_{1-4}$alkyl, phosphonooxy$C_{1-4}$alkoxy$C_{1-4}$alkyl, $C_{1-4}$alkylcarbonyl, hydroxy$C_{1-4}$alkylcarbonyl and phosphonooxy$C_{1-4}$alkylcarbonyl, and where a ring —$CH_2$— is optionally replaced with —C(O)—.

12. A compounds or a salt or ester thereof according to claim 1 wherein X is NH.

13. A compound or a salt or ester thereof according to claim 1 wherein $R^4$ is hydrogen.

14. A compound or a salt or ester thereof according to claim 1 wherein $R^5$ is aryl optionally substituted by 1 or 2 halo.

15. A compound or a salt or ester thereof according to claim 1 wherein $R^{19}$ is hydrogen, hydroxycarbonyl, ethoxycarbonyl, aminocarbonyl and acetylamino.

16. A compound of formula (I) selected from:

2-(4-{[7-(3-chloropropoxy)-6-methoxyquinazolin-4-yl]amino}-1H-pyrazol-1-yl)-N-(3-fluorophenyl)acetamide;

2-(4-{[7-(3-chloropropoxy)quinazolin-4-yl]amino}-1H-pyrazol-1-yl)-N-(2,3-difluorophenyl)acetamide;

2-(4-{[7-(3-chloropropoxy)-6-methoxyquinazolin-4-yl]amino}-1H-pyrazol-1-yl)-N-(2,3-difluorophenyl)acetamide;

2-(4-{[7-(3-chloropropoxy)quinazolin-4-yl]amino}-1H-pyrazol-1-yl)-N-(3-fluorophenyl)acetamide;

2-(4-{[7-(2-chloroethoxy)quinazolin-4-yl]amino}-1H-pyrazol-1-yl)-N-(2,3-difluorophenyl)acetamide;

2-(4-{[7-(2-chloroethoxy)-6-methoxyquinazolin-4-yl]amino}-1H-pyrazol-1-yl)-N-(2,3-difluorophenyl)acetamide;

N-(2,3-difluorophenyl)-2-(4-([7-(2,2-dimethoxyethoxy)quinazolin-4-yl]amino)-1H-pyrazol-1-yl)acetamide;

4-{[7-(3-chloropropoxy)-6-methoxyquinazolin-4-yl]amino}-1-{2-[(3-fluorophenyl)amino]-2-oxoethyl}-1H-pyrazole-3-carboxamide;

ethyl 4-{[7-(3-chloropropoxy)quinazolin-4-yl]amino}-1-{2-[(3-fluorophenyl)amino]-2-oxoethyl}-1H-pyrazole-3-carboxylate;

2-(3-(acetylamino)-4-{[7-(3-chloropropoxy)quinazolin-4-yl]amino}-1H-pyrazol-1-yl)-N-(3-fluorophenyl)acetamide;

N-(2,3-difluorophenyl)-2-[4-(quinazolin-4-ylamino)-1H-pyrazol-1-yl]acetamide;

2-(4-{[7-(3-chloropropoxy)-5-isopropoxyquinazolin-4-yl]amino}-1H-pyrazol-1-yl)-N-(2,3-difluorophenyl)acetamide;

2-(4-{[7-(3-chloropropoxy)-5-methoxyquinazolin-4-yl]amino}-1H-pyrazol-1-yl)-N-(2,3-difluorophenyl)acetamide;

2-(4-{[7-(3-chloropropoxy)-6-fluoroquinazolin-4-yl]amino}-1H-pyrazol-1-yl)-N-(2,3-difluorophenyl)acetamide;

2-(4-{[7-(3-chloropropoxy)-6-fluoroquinazolin-4-yl]amino}-1H-pyrazol-1-yl)-N-(3-fluorophenyl)acetamide;

N-(3-fluorophenyl)-2-{4-[(7-{3-[(2S)-2-(hydroxymethyl)pyrrolidin-1-yl]propoxy}-6-methoxyquinazolin-4-yl)amino]-1H-pyrazol-1-yl}acetamide;

N-(3-fluorophenyl)-2-{4-[(7-{3-[(2-hydroxyethyl)(isobutyl)amino]propoxy}-6-methoxyquinazolin-4-yl)amino]-1H-pyrazol-1-yl}acetamide;

N-(3-fluorophenyl)-2-{4-[(7-{3-[(2-hydroxyethyl)(propyl)amino]propoxy}-6-methoxyquinazolin-4-yl)amino]-1H-pyrazol-1-yl}acetamide;

N-(3-fluorophenyl)-2-(4-{[6-methoxy-7-(3-piperidin-1-ylpropoxy)quinazolin-4-yl]amino}-1H-pyrazol-1-yl)acetamide;

N-(3-fluorophenyl)-2-(4-{[6-methoxy-7-(3-pyrrolidin-1-ylpropoxy)quinazolin-4-yl]amino}-1H-pyrazol-1-yl)acetamide;

2-[4-({7-[3-(diethylamino)propoxy]-6-methoxyquinazolin-4-yl}amino)-1H-pyrazol-1-yl]-N-(3-fluorophenyl)acetamide;

N-(3-fluorophenyl)-2-(4-{[6-methoxy-7-(3-piperazin-1-ylpropoxy)quinazolin-4-yl]amino}-1H-pyrazol-1-yl)acetamide;

N-(3-fluorophenyl)-2-{4-[(7-{3-[(2-hydroxyethyl)(methyl)amino]propoxy}-6-methoxyquinazolin-4-yl)amino]-1H-pyrazol-1-yl}acetamide;

2-[4-({7-[3-(cyclopropylamino)propoxy]-6-methoxyquinazolin-4-yl}amino)-1H-pyrazol-1-yl]-N-(3-fluorophenyl)acetamide;

2-{4-[(7-{3-[[2-(dimethylamino)ethyl](methyl)amino]propoxy}-6-methoxyquinazolin-4-yl)amino]-1H-pyrazol-1-yl}-N-(3-fluorophenyl)acetamide;

N-(3-fluorophenyl)-2-[4-({6-methoxy-7-[3-(4-methylpiperazin-1-yl)propoxy]quinazolin-4-yl}amino)-1H-pyrazol-1-yl]acetamide;

N-(3-fluorophenyl)-2-{4-[(7-{3-[(2R)-2-(hydroxymethyl)pyrrolidin-1-yl]propoxy}-6-methoxyquinazolin-4-yl)amino]-1H-pyrazol-1-yl}acetamide;

N-(3-fluorophenyl)-2-[4-({7-[3-(4-hydroxypiperidin-1-yl)propoxy]-6-methoxyquinazolin-4-yl}amino)-1H-pyrazol-1-yl]acetamide;

2-{4-[(7-{3-[bis(2-hydroxyethyl)amino]propoxy}-6-methoxyquinazolin-4-yl)amino]-1H-pyrazol-1-yl}-N-(3-fluorophenyl)acetamide;

2-{4-[(7-{3-[ethyl(methyl)amino]propoxy}-6-methoxyquinazolin-4-yl)amino]-1H-pyrazol-1-yl}-N-(3-fluorophenyl)acetamide;

2-{4-[(7-{3-[ethyl(2-hydroxyethyl)amino]propoxy}-6-methoxyquinazolin-4-yl)amino]-1H-pyrazol-1-yl}-N-(3-fluorophenyl)acetamide;

2-{4-[(7-{3-[[2-(dimethylamino)ethyl](ethyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[2-(2-hydroxyethyl)piperidin-1-yl]propoxy}-6-methoxyquinazolin-4-yl)amino]-1H-pyrazol-1-yl}acetamide;

N-(3-fluorophenyl)-2-{4-[(7-{3-[4-(2-hydroxyethyl)piperazin-1-yl]propoxy}-6-methoxyquinazolin-4-yl)amino]-1H-pyrazol-1-yl}acetamide;

2-{4-[(7-{3-[(cyclopropylmethyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[4-(2-hydroxyethyl)piperidin-1-yl]propoxy}-6-methoxyquinazolin-4-yl)amino]-1H-pyrazol-1-yl}acetamide;

N-(3-fluorophenyl)-2-{4-[(6-methoxy-7-{3-[methyl(prop-2-yn-1-yl)amino]propoxy}quinazolin-4-yl)amino]-1H-pyrazol-1-yl}acetamide;

2-{4-[(7-{3-[allyl(methyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[isobutyl(methyl)amino]propoxy}-6-methoxyquinazolin-4-yl)amino]-1H-pyrazol-1-yl}acetamide;

N-(3-fluorophenyl)-2-[4-({7-[3-(3-hydroxypiperidin-1-yl)propoxy]-6-methoxyquinazolin-4-yl}amino)-1H-pyrazol-1-yl]acetamide;

N-(3-fluorophenyl)-2-{4-[(7-{3-[4-(hydroxymethyl)piperidin-1-yl]propoxy}-6-methoxyquinazolin-4-yl)amino]-1H-pyrazol-1-yl}acetamide;

N-(3-fluorophenyl)-2-(4-[(6-methoxy-7-{3-[methyl(propyl)amino]propoxy}quinazolin-4-yl)amino]-1H-pyrazol-1-yl}acetamide;

2-{4-[(7-{3-[(cyclopropylmethyl)(propyl)amino]propoxy}-6-methoxyquinazolin-4-yl)amino]-1H-pyrazol-1-yl}-N-(3-fluorophenyl)acetamide;

2-{4-[(7-{3-[[2-(diethylamino)ethyl](methyl)amino]propoxy}-6-methoxyquinazolin-4-yl)amino]-1H-pyrazol-1-yl}-N-(3-fluorophenyl)acetamide;

2-{4-[(7-{3-[[2-(diethylamino)ethyl](ethyl)amino]propoxy}-6-methoxyquinazolin-4-yl)amino]-1H-pyrazol-1-yl}-N-(3-fluorophenyl)acetamide;

N-(3-fluorophenyl)-2-[4-({6-methoxy-7-[3-(4-methyl-1,4-diazepan-1-yl)propoxy]quinazolin-4-yl}amino)-1H-pyrazol-1-yl]acetamide;

N-(3-fluorophenyl)-2-{4-[(7-{3-[(2-hydroxyethyl)(isopropyl)amino]propoxy}-6-methoxyquinazolin-4-yl)amino]-1H-pyrazol-1-yl}acetamide;

2-{4-[(7-{3-[cyclopropyl(2-hydroxyethyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[(2-hydroxyethyl)(2-methoxyethyl)amino]propoxy}-6-methoxyquinazolin-4-yl)amino]-1H-pyrazol-1-yl}acetamide;

2-{4-[(7-{3-[cyclobutyl(2-hydroxyethyl)amino]propoxy}-6-methoxyquinazolin-4-yl)amino]-1H-pyrazol-1-yl}-N-(3-fluorophenyl)acetamide;

2-{4-[(7-{3-[(cyclopropylmethyl)(2-hydroxyethyl)amino]propoxy}-6-methoxyquinazolin-4-yl)amino]-1H-pyrazol-1-yl}-N-(3-fluorophenyl)acetamide;

2-{4-[(7-{3-[(cyclobutylmethyl)(2-hydroxyethyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[(2-hydroxyethyl)(prop-2-yn-1-yl)amino]propoxy}-6-methoxyquinazolin-4-yl)amino]-1H-pyrazol-1-yl}acetamide;

2-{4-[(7-{3-[allyl(2-hydroxyethyl)amino]propoxy}-6-methoxyquinazolin-4-yl)amino]-1H-pyrazol-1-yl}-N-(3-fluorophenyl)acetamide;

2-{4-[(7-{3-[(2,2-dimethylpropyl)(2-hydroxyethyl)amino]propoxy}-6-methoxyquinazolin-4-yl)amino]-1H-pyrazol-1-yl}-N-(3-fluorophenyl)acetamide;

N-(3-fluorophenyl)-2-{4-[(7-{3-[(2-hydroxyethyl)(3,3,3-trifluoropropyl)amino]propoxy}-6-methoxyquinazolin-4-yl)amino]-1H-pyrazol-1-yl}acetamide;

2-(4-{[7-(3-azetidin-1-ylpropoxy)-6-methoxyquinazolin-4-yl]amino}-1H-pyrazol-1-yl)-N-(3-fluorophenyl)acetamide;

2-{4-[(6,7-dimethoxyquinazolin-4-yl)amino]-1H-pyrazol-1-yl}-N-(3-fluorophenyl)acetamide;

N-(3-fluorophenyl)-2-{4-[(7-hydroxy-6-methoxyquinazolin-4-yl)amino]-1H-pyrazol-1-yl}acetamide;

N-(2,3-difluorophenyl)-2-{4-[(7-{3-[(2-hydroxyethyl)(isobutyl)amino]propoxy}-6-methoxyquinazolin-4-yl)amino]-1H-pyrazol-1-yl}acetamide;

N-(2,3-difluorophenyl)-2-{4-[(7-{3-[(2S)-2-(hydroxymethyl)pyrrolidin-1-yl]propoxy}-6-methoxyquinazolin-4-yl)amino]-1H-pyrazol-1-yl}acetamide;

N-(2,3-difluorophenyl)-2-{4-[(7-{3-[(2-hydroxyethyl)(propyl)amino]propoxy}-6-methoxyquinazolin-4-yl)amino]-1H-pyrazol-1-yl}acetamide;

N-(2,3-difluorophenyl)-2-[4-({7-[3-(dimethylamino)propoxy]-6-methoxyquinazolin-4-yl}amino)-1H-pyrazol-1-yl]acetamide;

N-(2,3-difluorophenyl)-2-(4-{[6-methoxy-7-(3-piperidin-1-ylpropoxy)quinazolin-4-yl]amino}-1H-pyrazol-1-yl)acetamide;

N-(2,3-difluorophenyl)-2-(4-{[6-methoxy-7-(3-pyrrolidin-1-ylpropoxy)quinazolin-4-yl]amino}-1H-pyrazol-1-yl)acetamide;

N-(2,3-difluorophenyl)-2-(4-{[6-methoxy-7-(3-piperazin-1-ylpropoxy)quinazolin-4-yl]amino}-1H-pyrazol-1-yl)acetamide;

N-(2,3-difluorophenyl)-2-{4-[(7-{3-[(2-hydroxyethyl)(methyl)amino]propoxy}-6-methoxyquinazolin-4-yl)amino]-1H-pyrazol-1-yl}acetamide 2-[4-({7-[3-(cyclopropylamino)propoxy]-6-methoxyquinazolin-4-yl}amino)-1H-pyrazol-1-yl]-N-(2,3-difluorophenyl)acetamide;

N-(2,3-difluorophenyl)-2-{4-[(7-{3-[[2-(dimethylamino)ethyl](methyl)amino]propoxy}-6-methoxyquinazolin-4-yl)amino]-1H-pyrazol-1-yl}acetamide;

N-(2,3-difluorophenyl)-2-[4-({6-methoxy-7-[3-(4-methylpiperazin-1-yl)propoxy]quinazolin-4-yl}amino)-1H-pyrazol-1-yl]acetamide;

N-(2,3-difluorophenyl)-2-{4-[(7-{3-[(2R)-2-(hydroxymethyl)pyrrolidin-1-yl]propoxy}-6-methoxyquinazolin-4-yl)amino]-1H-pyrazol-1-yl}acetamide;

N-(2,3-difluorophenyl)-2-[4-({7-[3-(4-hydroxypiperidin-1-yl)propoxy]-6-methoxyquinazolin-4-yl}amino)-1H-pyrazol-1-yl]acetamide;

2-{4-[(7-{3-[bis(2-hydroxyethyl)amino]propoxy}-6-methoxyquinazolin-4-yl)amino]-1H-pyrazol-1-yl}-N-(2,3-difluorophenyl)acetamide;

N-(2,3-difluorophenyl)-2-{4-[(7-{3-[ethyl(methyl)amino]propoxy}-6-methoxyquinazolin-4-yl)amino]-1H-pyrazol-1-yl}acetamide;

N-(2,3-difluorophenyl)-2-{4-[(7-{3-[ethyl(2-hydroxyethyl)amino]propoxy}-6-methoxyquinazolin-4-yl)amino]-1H-pyrazol-1-yl}acetamide;

N-(2,3-difluorophenyl)-2-{4-[(7-{3-[[2-(dimethylamino)ethyl](ethyl)amino]propoxy}-6-methoxyquinazolin-4-yl)amino]-1H-pyrazol-1-yl}acetamide;

N-(2,3-difluorophenyl)-2-{4-[(7-{3-[2-(2-hydroxyethyl)piperidin-1-yl]propoxy}-6-methoxyquinazolin-4-yl)amino]-1H-pyrazol-1-yl}acetamide;

N-(2,3-difluorophenyl)-2-{4-[(7-{3-[4-(2-hydroxyethyl)piperazin-1-yl]propoxy}-6-methoxyquinazolin-4-yl)amino]-1H-pyrazol-1-yl}acetamide;

2-{4-[(7-{3-[(cyclopropylmethyl)amino]propoxy}-6-methoxyquinazolin-4-yl)amino]-1H-pyrazol-1-yl}-N-(2,3-difluorophenyl)acetamide;

N-(2,3-difluorophenyl)-2-{4-[(7-{3-[4-(2-hydroxyethyl)piperidin-1-yl]propoxy}-6-methoxyquinazolin-4-yl)amino]-1H-pyrazol-1-yl}acetamide;

N-(2,3-difluorophenyl)-2-{4-[(6-methoxy-7-{3-[methyl(prop-2-yn-1-yl)amino]propoxy}quinazolin-4-yl)amino]-1H-pyrazol-1-yl}acetamide;

N-(2,3-difluorophenyl)-2-{4-[(7-{3-[isobutyl(methyl)amino]propoxy}-6-methoxyquinazolin-4-yl)amino]-1H-pyrazol-1-yl}acetamide;

N-(2,3-difluorophenyl)-2-[4-({7-[3-(3-hydroxypiperidin-1-yl)propoxy]-6-methoxyquinazolin-4-yl}amino)-1H-pyrazol-1-yl]acetamide;

N-(2,3-difluorophenyl)-2-{4-[(7-{3-[4-(hydroxymethyl)piperidin-1-yl]propoxy}-6-methoxyquinazolin-4-yl)amino]-1H-pyrazol-1-yl}acetamide;

N-(2,3-difluorophenyl)-2-{4-[(6-methoxy-7-{3-[methyl(propyl)amino]propoxy}quinazolin-4-yl)amino]-1H-pyrazol-1-yl}acetamide;

2-{4-[(7-{3-[(cyclopropylmethyl)(propyl)amino]propoxy}-6-methoxyquinazolin-4-yl)amino]-1H-pyrazol-1-yl}-N-(2,3-difluorophenyl)acetamide;

2-{4-[(7-{3-[[2-(diethylamino)ethyl](methyl)amino]propoxy}-6-methoxyquinazolin-4-yl)amino]-1H-pyrazol-1-yl}-N-(2,3-difluorophenyl)acetamide;

2-{4-[(7-{3-[[2-(diethylamino)ethyl](ethyl)amino]propoxy}-6-methoxyquinazolin-4-yl)amino]-1H-pyrazol-1-yl}-N-(2,3-difluorophenyl)acetamide;

N-(2,3-difluorophenyl)-2-[4-({6-methoxy-7-[3-(4-methyl-1,4-diazepan-1-yl)propoxy]quinazolin-4-yl}amino)-1H-pyrazol-1-yl]acetamide;

N-(2,3-difluorophenyl)-2-{4-[(7-{3-[(2-hydroxyethyl)(isopropyl)amino]propoxy}-6-methoxyquinazolin-4-yl)amino]-1H-pyrazol-1-yl}acetamide;

2-{4-[(7-{3-[cyclopropyl(2-hydroxyethyl)amino]propoxy}-6-methoxyquinazolin-4-yl)amino]-1H-pyrazol-1-yl}-N-(2,3-difluorophenyl)acetamide;

N-(2,3-difluorophenyl)-2-{4-[(7-{3-[(2-hydroxyethyl)(2-methoxyethyl)amino]propoxy}-6-methoxyquinazolin-4-yl)amino]-1H-pyrazol-1-yl}acetamide;

2-{4-[(7-{3-[cyclobutyl(2-hydroxyethyl)amino]propoxy}-6-methoxyquinazolin-4-yl)amino]-1H-pyrazol-1-yl}-N-(2,3-difluorophenyl)acetamide;

2-{4-[(7-{3-[(cyclopropylmethyl)(2-hydroxyethyl)amino]propoxy}-6-methoxyquinazolin-4-yl)amino]-1H-pyrazol-1-yl}-N-(2,3-difluorophenyl)acetamide;

2-{4-[(7-{3-[(cyclobutylmethyl)(2-hydroxyethyl)amino]propoxy}-6-methoxyquinazolin-4-yl)amino]-1H-pyrazol-1-yl}-N-(2,3-difluorophenyl)acetamide;

N-(2,3-difluorophenyl)-2-{4-[(7-{3-[(2-hydroxyethyl)(prop-2-yn-1-yl)amino]propoxy}-6-methoxyquinazolin-4-yl)amino]-1H-pyrazol-1-yl}acetamide;

2-{4-[(7-{3-[allyl(2-hydroxyethyl)amino]propoxy}-6-methoxyquinazolin-4-yl)amino]-1H-pyrazol-1-yl}-N-(2,3-difluorophenyl)acetamide;

N-(2,3-difluorophenyl)-2-{4-[(7-{3-[(2,2-dimethylpropyl)(2-hydroxyethyl)amino]propoxy}-6-methoxyquinazolin-4-yl)amino]-1H-pyrazol-1-yl}acetamide;

N-(2,3-difluorophenyl)-2-{4-[(7-{3-[(2-hydroxyethyl)(3,3,3-trifluoropropyl)amino]propoxy}-6-methoxyquinazolin-4-yl)amino]-1H-pyrazol-1-yl}acetamide;

N-(2,3-difluorophenyl)-2-{4-[(7-{2-[(2R)-2-(hydroxymethyl)pyrrolidin-1-yl]ethoxy}-6-methoxyquinazolin-4-yl)amino]-1H-pyrazol-1-yl}acetamide;

N-(2,3-difluorophenyl)-2-(4-{[7-(2-{4-[2-(2-hydroxyethoxy)ethyl]piperazin-1-yl}ethoxy)-6-methoxyquinazolin-4-yl]amino}-1H-pyrazol-1-yl)acetamide;

N-(2,3-difluorophenyl)-2-{4-[(7-{2-[2-(hydroxymethyl)piperidin-1-yl]ethoxy}-6-methoxyquinazolin-4-yl)amino]-1H-pyrazol-1-yl}acetamide;

N-(2,3-difluorophenyl)-2-{4-[(7-{2-[(2-hydroxy-1,1-dimethylethyl)amino]ethoxy}-6-methoxyquinazolin-4-yl)amino]-1H-pyrazol-1-yl}acetamide;

N-(2,3-difluorophenyl)-2-{4-[(7-{2-[4-(2-hydroxyethyl)piperazin-1-yl]ethoxy}-6-methoxyquinazolin-4-yl)amino]-1H-pyrazol-1-yl}acetamide;

N-(2,3-difluorophenyl)-2-{4-[(7-{2-[(trans-4-hydroxycyclohexyl)amino]ethoxy}-6-methoxyquinazolin-4-yl)amino]-1H-pyrazol-1-yl}acetamide;

N-(2,3-difluorophenyl)-2-{4-[(7-{2-[3-(hydroxymethyl)piperidin-1-yl]ethoxy}-6-methoxyquinazolin-4-yl)amino]-1H-pyrazol-1-yl}acetamide;

N-(2,3-difluorophenyl)-2-(4-{[7-(2-{[1-(hydroxymethyl)cyclopentyl]amino}ethoxy)-6-methoxyquinazolin-4-yl]amino}-1H-pyrazol-1-yl)acetamide;

N-(2,3-difluorophenyl)-2-{4-[(7-{2-[4-(3-hydroxypropyl)piperazin-1-yl]ethoxy}-6-methoxyquinazolin-4-yl)amino]-1H-pyrazol-1-yl}acetamide;

2-{4-[(7-{2-[cyclohexyl(2-hydroxyethyl)amino]ethoxy}-6-methoxyquinazolin-4-yl)amino]-1H-pyrazol-1-yl}-N-(2,3-difluorophenyl)acetamide;

N-(2,3-difluorophenyl)-2-{4-[(7-{2-[(2-hydroxyethyl)(propyl)amino]ethoxy}-6-methoxyquinazolin-4-yl)amino]-1H-pyrazol-1-yl}acetamide;

N-(2,3-difluorophenyl)-2-{4-[(7-{2-[(3-hydroxy-2,2-dimethylpropyl)amino]ethoxy}-6-methoxyquinazolin-4-yl)amino]-1H-pyrazol-1-yl}acetamide;

N-(2,3-difluorophenyl)-2-[4-({6-methoxy-7-[2-(tetrahydro-2H-pyran-4-ylamino)ethoxy]quinazolin-4-yl}amino)-1H-pyrazol-1-yl]acetamide;

2-{4-[(7-{2-[cyclobutyl(2-hydroxyethyl)amino]ethoxy}-6-methoxyquinazolin-4-yl)amino]-1H-pyrazol-1-yl}-N-(2,3-difluorophenyl)acetamide;

N-(2,3-difluorophenyl)-2-{4-[(7-{2-[(2-hydroxyethyl)(tetrahydro-2H-pyran-4-yl)amino]ethoxy}-6-methoxyquinazolin-4-yl)amino]-1H-pyrazol-1-yl}acetamide;

N-(2,3-difluorophenyl)-2-{4-[(7-{2-[(2S)-2-(hydroxymethyl)pyrrolidin-1-yl]ethoxy}-6-methoxyquinazolin-4-yl)amino]-1H-pyrazol-1-yl}acetamide;

N-(2,3-difluorophenyl)-2-{4-[(7-{2-[(2R)-2-(2-hydroxyethyl)piperidin-1-yl]ethoxy}-6-methoxyquinazolin-4-yl)amino]-1H-pyrazol-1-yl}acetamide;

N-(2,3-difluorophenyl)-2-{4-[(7-{2-[(2S)-2-(2-hydroxyethyl)piperidin-1-yl]ethoxy}-6-methoxyquinazolin-4-yl)amino]-1H-pyrazol-1-yl}acetamide;

N-(2,3-difluorophenyl)-2-{4-[(7-{3-[(2-hydroxyethyl)(propyl)amino]propoxy}quinazolin-4-yl)amino]-1H-pyrazol-1-yl}acetamide;

N-(2,3-difluorophenyl)-2-{4-[(7-{3-[(2-hydroxyethyl)(isobutyl)amino]propoxy}quinazolin-4-yl)amino]-1H-pyrazol-1-yl}acetamide;

N-(2,3-difluorophenyl)-2-{4-[(7-{3-[(2S)-2-(hydroxymethyl)pyrrolidin-1-yl]propoxy}quinazolin-4-yl)amino]-1H-pyrazol-1-yl}acetamide;

N-(2,3-difluorophenyl)-2-{4-[(7-{3-[(2R)-2-(hydroxymethyl)pyrrolidin-1-yl]propoxy}quinazolin-4-yl)amino]-1H-pyrazol-1-yl}acetamide;

2-{4-[(7-{3-[cyclopentyl(2-hydroxyethyl)amino]propoxy}quinazolin-4-yl)amino]-1H-pyrazol-1-yl}-N-(2,3-difluorophenyl)acetamide;

N-(2,3-difluorophenyl)-2-{4-[(7-{3-[ethyl(2-hydroxyethyl)amino]propoxy}quinazolin-4-yl)amino]-1H-pyrazol-1-yl}acetamide;

N-(2,3-difluorophenyl)-2-{4-[(7-{3-[4-(2-hydroxyethyl) piperazin-1-yl]propoxy}quinazolin-4-yl)amino]-1H-pyrazol-1-yl}acetamide;

N-(2,3-difluorophenyl)-2-{4-[(7-{3-[4-(hydroxymethyl) piperidin-1-yl]propoxy}quinazolin-4-yl)amino]-1H-pyrazol-1-yl}acetamide;

N-(2,3-difluorophenyl)-2-{4-[(7-{3-[(3-hydroxy-1,1-dimethylpropyl)amino]propoxy}quinazolin-4-yl)amino]-1H-pyrazol-1-yl}acetamide;

2-{4-[(7-{3-[(2-cyanoethyl)(2-hydroxyethyl)amino] propoxy}quinazolin-4-yl)amino]-1H-pyrazol-1-yl}-N-(2,3-difluorophenyl)acetamide;

N-(2,3-difluorophenyl)-2-(4-{[7-(3-morpholin-4-ylpropoxy)quinazolin-4-yl]amino}-1H-pyrazol-1-yl)acetamide;

N-(2,3-difluorophenyl)-2-{4-[(7-{3-[(3-hydroxy-2,2-dimethylpropyl)amino]propoxy}quinazolin-4-yl)amino]-1H-pyrazol-1-yl}acetamide;

N-(2,3-difluorophenyl)-2-{4-[(7-{3-[(3-hydroxypropyl) amino]propoxy}quinazolin-4-yl)amino]-1H-pyrazol-1-yl}acetamide;

N-(2,3-difluorophenyl)-2-{4-[(7-{3-[(3-hydroxypropyl) (propyl)amino]propoxy}quinazolin-4-yl)amino]-1H-pyrazol-1-yl}acetamide;

N-(2,3-difluorophenyl)-2-{4-[(7-{3-[ethyl(3-hydroxypropyl)amino]propoxy}quinazolin-4-yl)amino]-1H-pyrazol-1-yl}acetamide;

N-(2,3-difluorophenyl)-2-{4-[(7-{3-[4-(2-hydroxyethyl)-3-oxopiperazin-1-yl]propoxy}quinazolin-4-yl)amino]-1H-pyrazol-1-yl}acetamide;

N-(2,3-difluorophenyl)-2-[4-({7-[3-(propylamino)propoxy]quinazolin-4-yl}amino)-1H-pyrazol-1-yl]acetamide;

N-(2,3-difluorophenyl)-2-(4-{[7-(3-piperazin-1-ylpropoxy)quinazolin-4-yl]amino}-1H-pyrazol-1-yl)acetamide;

N-(2,3-difluorophenyl)-2-{4-[(7-{3-[glycoloyl(propyl) amino]propoxy}quinazolin-4-yl)amino]-1H-pyrazol-1-yl}acetamide;

N-(2,3-difluorophenyl)-2-[4-({7-[3-(4-glycoloylpiperazin-1-yl)propoxy]quinazolin-4-yl}amino)-1H-pyrazol-1-yl]acetamide;

N-(2,3-difluorophenyl)-2-(4-{[7-(3-{[trans-2-(hydroxymethyl)cyclohexyl]amino}propoxy)quinazolin-4-yl] amino}-1H-pyrazol-1-yl)acetamide;

N-(2,3-difluorophenyl)-2-{4-[(7-{3-[(1α, 5α, 6α)-6-(hydroxymethyl)-3-azabicyclo[3.1.0]hex-3-yl] propoxy}quinazolin-4-yl)amino]-1H-pyrazol-1-yl}acetamide;

N-(2,3-difluorophenyl)-2-(4-{[7-(3-{[(2R)-2-hydroxypropyl]amino}propoxy)quinazolin-4-yl]amino}-1H-pyrazol-1-yl)acetamide;

N-(2,3-difluorophenyl)-2-(4-{[7-(3-{[(1S)-2-hydroxy-1-methylethyl]amino}propoxy)quinazolin-4-yl]amino}-1H-pyrazol-1-yl)acetamide;

N-(2,3-difluorophenyl)-2-{4-[(7-{3-[(2-hydroxy-1,1-dimethylethyl)amino]propoxy}quinazolin-4-yl)amino]-1H-pyrazol-1-yl}acetamide;

N-(2,3-difluorophenyl)-2-{4-[(7-{3-[(2,3-dihydroxypropyl)amino]propoxy}quinazolin-4-yl)amino]-1H-pyrazol-1-yl}acetamide;

N-(2,3-difluorophenyl)-2-(4-{[7-(3-{[2-(2-hydroxyethoxy)ethyl]amino}propoxy)quinazolin-4-yl]amino}-1H-pyrazol-1-yl)acetamide;

2-[4-({7-[3-(4-acetylpiperazin-1-yl)propoxy]quinazolin-4-yl}amino)-1H-pyrazol-1-yl]-N-(2,3-difluorophenyl)acetamide;

N-(2,3-difluorophenyl)-2-{4-[(7-{3-[(tetrahydrofuran-2-ylmethyl)amino]propoxy}quinazolin-4-yl)amino]-1H-pyrazol-1-yl}acetamide;

2-[4-({7-[3-(allylamino)propoxy]quinazolin-4-yl}amino)-1H-pyrazol-1-yl]-N-(2,3-difluorophenyl)acetamide;

N-(2,3-difluorophenyl)-2-(4-{[7-(3-{[1-(hydroxymethyl)-2-methylpropyl]amino}propoxy)quinazolin-4-yl] amino}-1H-pyrazol-1-yl)acetamide;

N-(2,3-difluorophenyl)-2-(4-{[7-(3-{[(5-methylisoxazol-3-yl)methyl]amino}propoxy)quinazolin-4-yl]amino}-1H-pyrazol-1-yl)acetamide;

N-(2,3-difluorophenyl)-2-[4-({7-[3-(tetrahydro-2H-pyran-4-ylamino)propoxy]quinazolin-4-yl}amino)-1H-pyrazol-1-yl]acetamide;

N-(2,3-difluorophenyl)-2-{4-[(7-{3-[(3S)-3-(hydroxymethyl)pyrrolidin-1-yl]propoxy}quinazolin-4-yl)amino]-1H-pyrazol-1-yl}acetamide;

N-(2,3-difluorophenyl)-2-(4-{[7-(3-hydroxypropoxy) quinazolin-4-yl]amino}-1H-pyrazol-1-yl)acetamide;

2-(4-{[7-(3-aminopropoxy)quinazolin-4-yl]amino}-1H-pyrazol-1-yl)-N-(2,3-difluorophenyl)acetamide;

N-(2,3-difluorophenyl)-2-{4-[(7-{3-[(2S,4R)-4-hydroxy-2-(hydroxymethyl)pyrrolidin-1-yl]propoxy}quinazolin-4-yl)amino]-1H-pyrazol-1-yl}acetamide;

N-(2,3-difluorophenyl)-2-{4-[(7-{2-[(3-hydroxy-2,2-dimethylpropyl)amino]ethoxy}quinazolin-4-yl)amino]-1H-pyrazol-1-yl}acetamide;

2-{4-[(7-{2-[cyclohexyl(2-hydroxyethyl)amino] ethoxy}quinazolin-4-yl)amino]-1H-pyrazol-1-yl}-N-(2,3-difluorophenyl)acetamide;

2-[4-({7-[2-(cyclopropylamino)ethoxy]quinazolin-4-yl}amino)-1H-pyrazol-1-yl]-N-(2,3-difluorophenyl)acetamide;

2-[4-({7-[2-(cyclobutylamino)ethoxy]quinazolin-4-yl}amino)-1H-pyrazol-1-yl]-N-(2,3-difluorophenyl)acetamide;

N-(2,3-difluorophenyl)-2-[4-({7-[2-(tetrahydro-2H-pyran-4-ylamino)ethoxy]quinazolin-4-yl}amino)-1H-pyrazol-1-yl]acetamide;

2-[4-({7-[2-(cyclopentylamino)ethoxy]quinazolin-4-yl}amino)-1H-pyrazol-1-yl]-N-(2,3-difluorophenyl)acetamide;

N-(2,3-difluorophenyl)-2-{4-[(7-{2-[(2-hydroxyethyl) (tetrahydro-2H-pyran-4-yl)amino]ethoxy}quinazolin-4-yl) amino]-1H-pyrazol-1-yl}acetamide;

2-{4-[(7-{2-[cyclopentyl(2-hydroxyethyl)amino] ethoxy}quinazolin-4-yl)amino]-1H-pyrazol-1-yl}-N-(2,3-difluorophenyl)acetamide;

N-(2,3-difluorophenyl)-2-{4-[(7-{2-[(2R)-2-(hydroxymethyl)pyrrolidin-1-yl]ethoxy}quinazolin-4-yl)amino]-1H-pyrazol-1-yl}acetamide;

2-{4-[(7-{2-[cyclopropyl(2-hydroxyethyl)amino] ethoxy}quinazolin-4-yl)amino]-1H-pyrazol-1-yl}-N-(2,3-difluorophenyl)acetamide;

2-{4-[(7-{2-[cyclobutyl(2-hydroxyethyl)amino] ethoxy}quinazolin-4-yl)amino]-1H-pyrazol-1-yl}-N-(2,3-difluorophenyl)acetamide;

2-{4-[(7-{2-[cyclopentyl(3-hydroxypropyl)amino] ethoxy}quinazolin-4-yl)amino]-1H-pyrazol-1-yl}-N-(2,3-difluorophenyl)acetamide;

2-{4-[(7-{2-[cyclopentyl(glycoloyl)amino] ethoxy}quinazolin-4-yl)amino]-1H-pyrazol-1-yl}-N-(2,3-difluorophenyl)acetamide;

N-(2,3-difluorophenyl)-2-{4-[(7-{2-[(3S)-3-(hydroxymethyl)-4-methylpiperazin-1-yl]ethoxy}quinazolin-4-yl) amino]-1H-pyrazol-1-yl}acetamide;

N-(2,3-difluorophenyl)-2-{4-[(7-{2-[(2S)-2-(hydroxymethyl)pyrrolidin-1-yl]ethoxy}quinazolin-4-yl)amino]-1H-pyrazol-1-yl}acetamide;

N-(2,3-difluorophenyl)-2-{4-[(7-{2-[(2R)-2-(hydroxymethyl)-4-methylpiperazin-1-yl]ethoxy}quinazolin-4-yl)amino]-1H-pyrazol-1-yl}acetamide;

N-(2,3-difluorophenyl)-2-{4-[(7-{2-[4-(hydroxymethyl)piperidin-1-yl]ethoxy}quinazolin-4-yl)amino]-1H-pyrazol-1-yl}acetamide;

N-(2,3-difluorophenyl)-2-{4-[(7-{2-[4-(2-hydroxyethyl)piperidin-1-yl]ethoxy}quinazolin-4-yl)amino]-1H-pyrazol-1-yl}acetamide;

N-(2,3-difluorophenyl)-2-{4-[(7-{2-[(2-hydroxyethyl)amino]ethoxy}quinazolin-4-yl)amino]-1H-pyrazol-1-yl}acetamide;

N-(2,3-difluorophenyl)-2-(4-{[7-(2-{[trans-2-(hydroxymethyl)cyclohexyl]amino}ethoxy)quinazolin-4-yl]amino}-1H-pyrazol-1-yl)acetamide;

N-(2,3-difluorophenyl)-2-{4-[(7-{3-[(2-hydroxyethyl)amino]propoxy}quinazolin-4-yl)amino]-1H-pyrazol-1-yl}acetamide;

N-(2,3-difluorophenyl)-2-(4-{[7-(3-pyrrolidin-1-ylpropoxy)quinazolin-4-yl]amino}-1H-pyrazol-1-yl)acetamide;

N-(2,3-difluorophenyl)-2-{4-[(7-methoxyquinazolin-4-yl)amino]-1H-pyrazol-1-yl}acetamide;

N-(2,3-difluorophenyl)-2-{4-[(7-{3-[(2-hydroxyethyl)(tetrahydro-2H-pyran-4-yl)amino]propoxy}quinazolin-4-yl)amino]-1H-pyrazol-1-yl}acetamide;

N-(2,3-difluorophenyl)-2-{4-[(7-{3-[(2R)-2-(2-hydroxyethyl)piperidin-1-yl]propoxy}quinazolin-4-yl)amino]-1H-pyrazol-1-yl}acetamide;

N-(2,3-difluorophenyl)-2-{4-[(7-{3-[(2S)-2-(2-hydroxyethyl)piperidin-1-yl]propoxy}quinazolin-4-yl)amino]-1H-pyrazol-1-yl}acetamide;

N-(2,3-difluorophenyl)-2-{4-[(7-{3-[(2R)-2-(hydroxymethyl)-4-methylpiperazin-1-yl]propoxy}quinazolin-4-yl)amino]-1H-pyrazol-1-yl}acetamide;

N-(2,3-difluorophenyl)-2-{4-[(7-{3-[(3S)-3-(hydroxymethyl)-4-methylpiperazin-1-yl]propoxy}quinazolin-4-yl)amino]-1H-pyrazol-1-yl}acetamide;

N-(2,3-difluorophenyl)-2-{4-[(7-{3-[(2R)-2-(hydroxymethyl)morpholin-4-yl]propoxy}quinazolin-4-yl)amino]-1H-pyrazol-1-yl}acetamide;

N-(2,3-difluorophenyl)-2-{4-[(7-{3-[(3S)-3-(hydroxymethyl)morpholin-4-yl]propoxy}quinazolin-4-yl)amino]-1H-pyrazol-1-yl}acetamide;

N-(2,3-difluorophenyl)-2-[4-({7-[3-(glycoloylamino)propoxy]quinazolin-4-yl}amino)-1H-pyrazol-1-yl]acetamide;

N-(3-fluorophenyl)-2-{4-[(7-{3-[(2-hydroxyethyl)(propyl)amino]propoxy}quinazolin-4-yl)amino]-1H-pyrazol-1-yl}acetamide;

2-{4-[(7-{3-[ethyl(2-hydroxyethyl)amino]propoxy}quinazolin-4-yl)amino]-1H-pyrazol-1-yl}-N-(3-fluorophenyl)acetamide;

N-(3-fluorophenyl)-2-{4-[(7-{3-[(2R)-2-(hydroxymethyl)pyrrolidin-1-yl]propoxy}quinazolin-4-yl)amino]-1H-pyrazol-1-yl}acetamide;

N-(3-fluorophenyl)-2-{4-[(7-{3-[4-(hydroxymethyl)piperidin-1-yl]propoxy}quinazolin-4-yl)amino]-1H-pyrazol-1-yl}acetamide;

N-(3-fluorophenyl)-2-{4-[(7-{3-[(3-hydroxy-1,1-dimethylpropyl)amino]propoxy}quinazolin-4-yl)amino]-1H-pyrazol-1-yl}acetamide;

N-(3-fluorophenyl)-2-{4-[(7-{3-[2-(2-hydroxyethyl)piperidin-1-yl]propoxy}quinazolin-4-yl)amino]-1H-pyrazol-1-yl}acetamide;

N-(3-fluorophenyl)-2-{4-[(7-{3-[4-(2-hydroxyethyl)piperazin-1-yl]propoxy}quinazolin-4-yl)amino]-1H-pyrazol-1-yl}acetamide;

N-(3-fluorophenyl)-2-{4-[(7-{3-[(2-hydroxyethyl)(tetrahydrofuran-3-yl)amino]propoxy}quinazolin-4-yl)amino]-1H-pyrazol-1-yl}acetamide;

N-(3-fluorophenyl)-2-(4-{[7-(3-morpholin-4-ylpropoxy)quinazolin-4-yl]amino}-1H-pyrazol-1-yl)acetamide;

N-(3-fluorophenyl)-2-[4-({7-[(2S)-pyrrolidin-2-ylmethoxy]quinazolin-4-yl}amino)-1H-pyrazol-1-yl]acetamide;

N-(3-fluorophenyl)-2-{4-[(7-{[(2S)-1-(2-hydroxyethyl)pyrrolidin-2-yl]methoxy}quinazolin-4-yl)amino]-1H-pyrazol-1-yl}acetamide;

N-(3-fluorophenyl)-2-{4-[(7-{[(2S)-1-glycoloylpyrrolidin-2-yl]methoxy}quinazolin-4-yl)amino]-1H-pyrazol-1-yl}acetamide;

N-(3-fluorophenyl)-2-(4-{[7-(pyrrolidin-3-ylmethoxy)quinazolin-4-yl]amino}-1H-pyrazol-1-yl)acetamide;

N-(3-fluorophenyl)-2-{4-[(7-{[1-(2-hydroxyethyl)pyrrolidin-3-yl]methoxy}quinazolin-4-yl)amino]-1H-pyrazol-1-yl}acetamide;

N-(3-fluorophenyl)-2-[4-({7-[(1-glycoloylpyrrolidin-3-yl)methoxy]quinazolin-4-yl}amino)-1H-pyrazol-1-yl]acetamide;

N-(3-fluorophenyl)-2-{4-[(7-{3-[(2-hydroxyethyl)(2-methoxyethyl)amino]propoxy}quinazolin-4-yl)amino]-1H-pyrazol-1-yl}acetamide;

N-(3-fluorophenyl)-2-{4-[(7-hydroxyquinazolin-4-yl)amino]-1H-pyrazol-1-yl}acetamide;

N-(2-fluorophenyl)-2-{4-[(7-{3-[(2R)-2-(hydroxymethyl)pyrrolidin-1-yl]propoxy}quinazolin-4-yl)amino]-1H-pyrazol-1-yl}acetamide

2-{4-[(7-{3-[ethyl(2-hydroxyethyl)amino]propoxy}quinazolin-4-yl)amino]-1H-pyrazol-1-yl}-N-(2-fluorophenyl)acetamide;

2-{4-[(7-{3-[(2R)-2-(hydroxymethyl)pyrrolidin-1-yl]propoxy}quinazolin-4-yl)amino]-1H-pyrazol-1-yl}-N-phenylacetamide;

2-{4-[(7-{3-[ethyl(2-hydroxyethyl)amino]propoxy}quinazolin-4-yl)amino]-1H-pyrazol-1-yl)-N-phenylacetamide;

N-(2,6-difluorophenyl)-2-{4-[(7-{3-[(2R)-2-(hydroxymethyl)pyrrolidin-1-yl]propoxy}quinazolin-4-yl)amino]-1H-pyrazol-1-yl}acetamide;

2-{4-[(7-{3-[ethyl(2-hydroxyethyl)amino]propoxy}-6-fluoroquinazolin-4-yl)amino]-1H-pyrazol-1-yl}-N-(3-fluorophenyl)acetamide;

2-{4-[(7-{3-[(cyclopropylmethyl)(2-hydroxyethyl)amino]propoxy}-6-fluoroquinazolin-4-yl)amino]-1H-pyrazol-1-yl}-N-(2,3-difluorophenyl)acetamide;

N-(2,3-difluorophenyl)-2-{4-[(6-fluoro-7-{3-[(2-hydroxyethyl)(propyl)amino]propoxy}quinazolin-4-yl)amino]-1H-pyrazol-1-yl)acetamide;

N-(2,3-difluorophenyl)-2-{4-[(6-fluoro-7-{3-[(2R)-2-(hydroxymethyl)pyrrolidin-1-yl]propoxy}quinazolin-4-yl)amino]-1H-pyrazol-1-yl}acetamide;

2-{4-[(7-{3-[cyclopentyl(2-hydroxyethyl)amino]propoxy}-6-fluoroquinazolin-4-yl)amino]-1H-pyrazol-1-yl}-N-(2,3-difluorophenyl)acetamide;

2-{4-[(7-{3-[bis(2-hydroxyethyl)amino]propoxy}-5-isopropoxyquinazolin-4-yl)amino]-1H-pyrazol-1-yl}-N-(2,3-difluorophenyl)acetamide;

N-(2,3-difluorophenyl)-2-{4-[(7-{3-[(2R)-2-(hydroxymethyl)pyrrolidin-1-yl]propoxy}-5-isopropoxyquinazolin-4-yl)amino]-1H-pyrazol-1-yl}acetamide;

N-(2,3-difluorophenyl)-2-{4-[(7-{3-[4-(2-hydroxyethyl)piperazin-1-yl]propoxy}-5-isopropoxyquinazolin-4-yl)amino]-1H-pyrazol-1-yl}acetamide;

N-(2,3-difluorophenyl)-2-(4-{[5-isopropoxy-7-(3-piperazin-1-ylpropoxy)quinazolin-4-yl]amino}-1H-pyrazol-1-yl)acetamide;

N-(2,3-difluorophenyl)-2-{4-[(7-{3-[(2S)-2-(hydroxymethyl)pyrrolidin-1-yl]propoxy}-5-isopropoxyquinazolin-4-yl)amino]-1H-pyrazol-1-yl}acetamide;

N-(2,3-difluorophenyl)-2-{4-[(7-{3-[(2-hydroxyethyl)amino]propoxy}-5-isopropoxyquinazolin-4-yl)amino]-1H-pyrazol-1-yl}acetamide;

N-(2,3-difluorophenyl)-2-[4-({7-[3-(4-glycoloylpiperazin-1-yl)propoxy]-5-isopropoxyquinazolin-4-yl}amino)-1H-pyrazol-1-yl]acetamide;

N-(2,3-difluorophenyl)-2-{4-[(7-{3-[(2R)-2-(hydroxymethyl)pyrrolidin-1-yl]propoxy}-5-methoxyquinazolin-4-yl)amino]-1H-pyrazol-1-yl}acetamide;

N-(2,3-difluorophenyl)-2-{4-[(5,7-dimethoxyquinazolin-4-yl)amino]-1H-pyrazol-1-yl}acetamide;

N-(2,3-difluorophenyl)-2-{4-[(5-hydroxy-7-methoxyquinazolin-4-yl)amino]-1H-pyrazol-1-yl}acetamide;

N-(2,3-difluorophenyl)-2-[4-({7-methoxy-5-[(2R)-pyrrolidin-2-ylmethoxy]quinazolin-4-yl}amino)-1H-pyrazol-1-yl]acetamide;

N-(2,3-difluorophenyl)-2-{4-[(5-{[(2R)-1-glycoloylpyrrolidin-2-yl]methoxy}-7-methoxyquinazolin-4-yl)amino]-1H-pyrazol-1-yl)acetamide;

N-(2,3-difluorophenyl)-2-{4-[(5-{[(2R)-1-(N,N-dimethylglycyl)pyrrolidin-2-yl]methoxy}-7-methoxyquinazolin-4-yl)amino]-1H-pyrazol-1-yl}acetamide;

N-(2,3-difluorophenyl)-2-{4-[(5-{[(2R)-1-(2-hydroxyethyl)pyrrolidin-2-yl]methoxy}-7-methoxyquinazolin-4-yl)amino]-1H-pyrazol-1-yl}acetamide;

N-(2,3-difluorophenyl)-2-{4-[(5-methoxyquinazolin-4-yl)amino]-1H-pyrazol-1-yl}acetamide;

N-(2,3-difluorophenyl)-2-{4-[(5-fluoroquinazolin-4-yl)amino]-1H-pyrazol-1-yl}acetamide;

N-(3-fluorophenyl)-2-(4-{[7-methoxy-6-(3-morpholin-4-ylpropoxy)quinazolin-4-yl]amino}-1H-pyrazol-1-yl)acetamide;

N-(3-fluorophenyl)-2-[4-({7-methoxy-6-[(1-methylpyrrolidin-3-yl)oxy]quinazolin-4-yl}amino)-1H-pyrazol-1-yl]acetamide;

N-(3-fluorophenyl)-2-(4-{[7-methoxy-6-(2-morpholin-4-ylethoxy)quinazolin-4-yl]amino}-1H-pyrazol-1-yl)acetamide;

2-(4-{[6,7-bis(2-methoxyethoxy)quinazolin-4-yl]amino}-1H-pyrazol-1-yl)-N-(2,3-difluorophenyl)acetamide;

N-(3-fluorophenyl)-2-{4-[(6-hydroxy-7-methoxyquinazolin-4-yl)amino]-1H-pyrazol-1-yl}acetamide;

4-((1-(2-((2,3-difluorophenyl)amino)-2-oxoethyl)-1H-pyrazol-4-yl)amino)-7-((1-methylpiperidin-4-yl)methoxy)quinazolin-6-yl benzoate;

N-(2,3-difluorophenyl)-2-(4-((6-hydroxy-7-((1-methylpiperidin-4-yl)methoxy)quinazolin-4-yl)amino)-1H-pyrazol-1-yl)acetamide;

1-{2-[(3-fluorophenyl)amino]-2-oxoethyl}-4-[(7-{3-[(2-hydroxyethyl)(2-methoxyethyl)amino]propoxy}-6-methoxyquinazolin-4-yl)amino]-1H-pyrazole-3-carboxamide;

1-{2-[(3-fluorophenyl)amino]-2-oxoethyl-4-[(7-{3-[(2S)-2-(hydroxymethyl)pyrrolidin-1-yl]propoxy}-6-methoxyquinazolin-4-yl)amino]-1H-pyrazole-3-carboxamide;

2-{3-(acetylamino)-4-[(7-{3-[(2R)-2-(hydroxymethyl)pyrrolidin-1-yl]propoxy}quinazolin-4-yl)amino]-1H-pyrazol-1-yl}-N-(3-fluorophenyl)acetamide;

ethyl 1-{2-[(3-fluorophenyl)amino]-2-oxoethyl)-4-[(7-{3-[(2R)-2-(hydroxymethyl)pyrrolidin-1-yl]propoxy}quinazolin-4-yl)amino]-1H-pyrazole-3-carboxylate; and

1-{2-[(3-fluorophenyl)amino]-2-oxoethyl}-4-[(7-3-[(2R)-2-(hydroxymethyl)pyrrolidin-1-yl]propoxy}quinazolin-4-yl)amino]-1H-pyrazole-3-carboxylic acid;

or a salt, ester or prodrug thereof.

17. A compound of formula (IA) selected from:

2-[[3-({4-[(1-{2-[(2,3-difluorophenyl)amino]-2-oxoethyl}-1H-pyrazol-4-yl)amino]-6-methoxyquinazolin-7-yl}oxy)propyl](propyl)amino]ethyl dihydrogen phosphate;

{(2S)-1-[3-({4-[(1-{2-[(2,3-difluorophenyl)amino]-2-oxoethyl}-1H-pyrazol-4-yl)amino]-6-methoxyquinazolin-7-yl}oxy)propyl]pyrrolidin-2-yl}methyl dihydrogen phosphate;

{(2S)-1-[3-({4-[(1-{2-[(3-fluorophenyl)amino]-2-oxoethyl}-1H-pyrazol-4-yl)amino]-6-methoxyquinazolin-7-yl}oxy)propyl]pyrrolidin-2-yl}methyl dihydrogen phosphate;

2-{ethyl[3-({4-[(1-{2-[(3-fluorophenyl)amino]-2-oxoethyl}-1H-pyrazol-4-yl)amino]-6-methoxyquinazolin-7-yl}oxy)propyl]amino}ethyl dihydrogen phosphate;

{(2R)-1-[3-({4-[(1-{2-[(3-fluorophenyl)amino]-2-oxoethyl}-1H-pyrazol-4-yl)amino]-6-methoxyquinazolin-7-yl}oxy)propyl]pyrrolidin-2-yl)methyl dihydrogen phosphate;

2-[[3-({4-[(1-{2-[(2,3-difluorophenyl)amino]-2-oxoethyl}-1H-pyrazol-4-yl)amino]-6-methoxyquinazolin-7-yl}oxy)propyl](2-methoxyethyl)amino]ethyl dihydrogen phosphate;

{(2S)-1-[3-({4-[(1-{2-[(2,3-difluorophenyl)amino]-2-oxoethyl}-1H-pyrazol-4-yl)amino]quinazolin-7-yl}oxy)propyl]pyrrolidin-2-yl)methyl dihydrogen phosphate;

{(2R)-1-[3-({4-[(1-{2-[(2,3-difluorophenyl)amino]-2-oxoethyl)-1H-pyrazol-4-yl)amino]quinazolin-7-yl}oxy)propyl]pyrrolidin-2-yl)methyl dihydrogen phosphate;

{(2R)-1-[3-({4-[(1-{2-[(2,3-difluorophenyl)amino]-2-oxoethyl}-1H-pyrazol-4-yl)amino]-6-methoxyquinazolin-7-yl}oxy)propyl]pyrrolidin-2-yl}methyl dihydrogen phosphate;

2-[[3-({4-[(1-{2-[(2,3-difluorophenyl)amino]-2-oxoethyl}-1H-pyrazol-4-yl)amino]-6-methoxyquinazolin-7-yl}oxy)propyl](ethyl)amino]ethyl dihydrogen phosphate;

2-[[3-({4-[(1-{2-[(2,3-difluorophenyl)amino]-2-oxoethyl}-1H-pyrazol-4-yl)amino]quinazolin-7-yl}oxy)propyl](propyl)amino]ethyl dihydrogen phosphate;

2-{cyclobutyl[3-({4-[(1-{2-[(2,3-difluorophenyl)amino]-2-oxoethyl}-1H-pyrazol-4-yl)amino]-6-methoxyquinazolin-7-yl}oxy)propyl]amino}ethyl dihydrogen phosphate;

2-{cyclobutyl[3-({4-[(1-{2-[(3-fluorophenyl)amino]-2-oxoethyl}-1H-pyrazol-4-yl)amino]-6-methoxyquinazolin-7-yl}oxy)propyl]amino}ethyl dihydrogen phosphate;

2-[[3-({4-[(1-{2-[(3-fluorophenyl)amino]-2-oxoethyl}-1H-pyrazol-4-yl)amino]-6-methoxyquinazolin-7-yl}oxy)propyl](2-methoxyethyl)amino]ethyl dihydrogen phosphate;

2-[[3-({4-[(1-{2-[(3-fluorophenyl)amino]-2-oxoethyl}-1H-pyrazol-4-yl)amino]quinazolin-7-yl}oxy)propyl](propyl)amino]ethyl dihydrogen phosphate;

2-{4-[3-({4-[(1-{2-[(2,3-difluorophenyl)amino]-2-oxoethyl}-1H-pyrazol-4-yl)amino]quinazolin-7-yl}oxy)propyl]piperazin-1-yl}ethyl dihydrogen phosphate;

2-{ethyl[3-({4-[(1-{2-[(3-fluorophenyl)amino]-2-oxoethyl}-1H-pyrazol-4-yl)amino]quinazolin-7-yl}oxy)propyl]amino}ethyl dihydrogen phosphate;

2-[[3-({4-[(1-{2-[(2,3-difluorophenyl)amino]-2-oxoethyl}-1H-pyrazol-4-yl)amino]quinazolin-7-yl}oxy)propyl](ethyl)amino]ethyl dihydrogen phosphate;

3-{[3-({4-[(1-{2-[(3-fluorophenyl)amino]-2-oxoethyl}-1H-pyrazol-4-yl)amino]quinazolin-7-yl}oxy)propyl]amino}-3-methylbutyl dihydrogen phosphate;

3-{[3-({4-[(1-{2-[(2,3-difluorophenyl)amino]-2-oxoethyl}-1H-pyrazol-4-yl)amino]quinazolin-7-yl}oxy)propyl]amino}-3-methylbutyl dihydrogen phosphate;

{(2R)-1-[3-({4-[(1-{2-[(3-fluorophenyl)amino]-2-oxoethyl}-1H-pyrazol-4-yl)amino]quinazolin-7-yl}oxy)propyl]pyrrolidin-2-yl}methyl dihydrogen phosphate;

2-{4-[3-({4-[(1-{2-[(3-fluorophenyl)amino]-2-oxoethyl}-1H-pyrazol-4-yl)amino]quinazolin-7-yl}oxy)propyl]piperazin-1-yl}ethyl dihydrogen phosphate

3-{[3-({4-[(1-{2-[(2,3-difluorophenyl)amino]-2-oxoethyl}-1H-pyrazol-4-yl)amino]quinazolin-7-yl}oxy)propyl]amino}propyl dihydrogen phosphate;

2-{[3-({4-[(1-{2-[(2,3-difluorophenyl)amino]-2-oxoethyl}-1H-pyrazol-4-yl)amino]quinazolin-7-yl}oxy)propyl]amino}ethyl dihydrogen phosphate;

2-[[3-((4-[(1-{$^{2}$-[(3-fluorophenyl)amino]-2-oxoethyl}-1H-pyrazol-4-yl)amino]quinazolin-7-yl}oxy)propyl](2-methoxyethyl)amino]ethyl dihydrogen phosphate;

3-[[3-({4-[(1-{2-[(2,3-difluorophenyl)amino]-2-oxoethyl}-1H-pyrazol-4-yl)amino]quinazolin-7-yl}oxy)propyl](ethyl)amino]propyl dihydrogen phosphate;

3-[[3-({4-[(1-{2-[(2,3-difluorophenyl)amino]-2-oxoethyl}-1H-pyrazol-4-yl)amino]quinazolin-7-yl}oxy)propyl](propyl)amino]propyl dihydrogen phosphate;

2-[[3-({4-[(1-{$^{2}$-[(2,3-difluorophenyl)amino]-2-oxoethyl}-1H-pyrazol-4-yl)amino]quinazolin-7-yl}oxy)propyl](propyl)amino]-2-oxoethyl dihydrogen phosphate;

2-{4-[3-({4-[(1-{2-[(2,3-difluorophenyl)amino]-2-oxoethyl}-1H-pyrazol-4-yl)amino]quinazolin-7-yl}oxy)propyl]piperazin-1-yl}-2-oxoethyl dihydrogen phosphate;

{(2R)-1-[3-({4-[(1-{2-[(2,3-difluorophenyl)amino]-2-oxoethyl}-1H-pyrazol-4-yl)amino]-6-fluoroquinazolin-7-yl}oxy)propyl]pyrrolidin-2-yl}methyl dihydrogen phosphate;

4-((1-(2-((2,3-difluorophenyl)amino)-2-oxoethyl)-1H-pyrazol-4-yl)amino)-7-((1-methylpiperidin-4-yl)methoxy)quinazolin-6-yl dihydrogen phosphate;

{(2R)-1-[3-({4-[(1-{2-[(2,3-difluorophenyl)amino]-2-oxoethyl)-1H-pyrazol-4-yl)amino]-5-isopropoxyquinazolin-7-yl}oxy)propyl]pyrrolidin-2-yl}methyl dihydrogen phosphate;

2-{4-[3-({4-[(1-{2-[(2,3-difluorophenyl)amino]-2-oxoethyl}-1H-pyrazol-4-yl)amino]-5-isopropoxyquinazolin-7-yl)oxy)propyl]piperazin-1-yl}ethyl dihydrogen phosphate;

2-{[3-({4-[(1-{2-[(2,3-difluorophenyl)amino]-2-oxoethyl)-1H-pyrazol-4-yl)amino]-5-isopropoxyquinazolin-7-yl}oxy)propyl]amino}ethyl dihydrogen phosphate;

{(2R)-1-[3-({4-[(1-{2-[(2,3-difluorophenyl)amino]-2-oxoethyl}-1H-pyrazol-4-yl)amino]-5-methoxyquinazolin-7-yl}oxy)propyl]pyrrolidin-2-yl}methyl dihydrogen phosphate;

{(2R)-1-[2-({4-[(1-{2-[(2,3-difluorophenyl)amino]-2-oxoethyl}-1H-pyrazol-4-yl)amino]-6-methoxyquinazolin-7-yl}oxy)ethyl]pyrrolidin-2-yl}methyl dihydrogen phosphate;

{(2S)-1-[2-({4-[(1-{2-[(2,3-difluorophenyl)amino]-2-oxoethyl}-1H-pyrazol-4-yl)amino]-6-methoxyquinazolin-7-yl)oxy)ethyl]pyrrolidin-2-yl}methyl dihydrogen phosphate;

2-[[2-({4-[(1-{2-[(2,3-difluorophenyl)amino]-2-oxoethyl)-1H-pyrazol-4-yl)amino]-6-methoxyquinazolin-7-yl}oxy)ethyl](tetrahydro-2H-pyran-4-yl)amino]ethyl dihydrogen phosphate;

2-{4-[3-({4-[(1-{2-[(2,3-difluorophenyl)amino]-2-oxoethyl}-1H-pyrazol-4-yl)amino]quinazolin-7-yl}oxy)propyl]-2-oxopiperazin-1-yl}ethyl dihydrogen phosphate; and

2-[[2-({4-[(1-{2-[(2,3-difluorophenyl)amino]-2-oxoethyl}-1H-pyrazol-4-yl)amino]quinazolin-7-yl}oxy)ethyl](tetrahydro-2H-pyran-4-yl)amino]ethyl dihydrogen phosphate;

or a salt or ester thereof.

18. A pharmaceutical composition comprising a compound according to claim 1, or a pharmaceutically acceptable salt or ester thereof, in association with a pharmaceutically acceptable diluent or carrier.

19. A process for the preparation of a compound according to claim 1 or a pharmaceutically acceptable salt or ester thereof, which process comprises reacting a compound of formula (II)

(II)

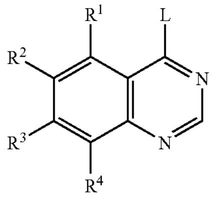

where L is a suitable leaving group and $R^1$, $R^2$, $R^3$, $R^4$ are as defined in claim 1 with a compound of formula (III)

(III)

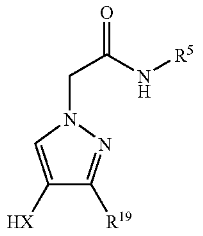

wherein $R^5$ and $R^{19}$ are as defined in claim 1 in the presence of hydrochloric acid in dioxane under an inert atmosphere, and thereafter if necessary:

i) removing any protecting groups; and/or ii) forming a salt, ester or prodrug thereof.

20. A process for the preparation of a compound according to formula (IA) or a pharmaceutically acceptable salt thereof, which process comprises phosphorylation of a compound of formula (I)

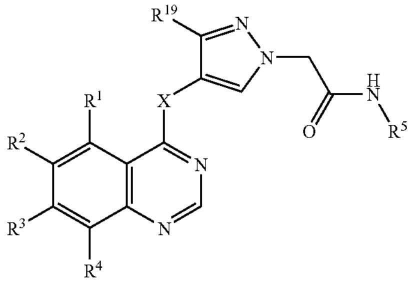

or a salt or ester thereof;

where

X is O or $NR^6$;

$R^6$ is hydrogen or $C_{1-4}$alkyl;

$R^1$ is hydrogen, halo, or —$X^1R^{11}$;

$X^1$ is a direct bond, —$CH_2$=$CH_2$—, —O—, —NH—, —N($C_{1-6}$alkyl)-, —C(O)O—, —C(O)O—, —OC(O)O—, —NHC(O)—, —N($C_{1-6}$alkyl)C(O)—, —C(O)NH— or —C(O)N($C_{1-6}$alkyl)-;

$R^{11}$ is hydrogen, or a group selected from $C_{1-6}$alkyl, $C_{2-6}$alkenyl, $C_{2-6}$alkynyl, $C_{3-6}$cycloalkyl, $C_{3-6}$cycloalkenyl, heterocyclyl, heterocyclyl$C_{1-4}$alkyl, heterocyclyl$C_{2-4}$alkenyl and heterocyclyl$C_{2-4}$alkynyl which group is optionally substituted by 1 or 2 substituents independently selected from halo, hydroxy, $C_{1-4}$alkoxy, hydroxy$C_{1-4}$alkyl, —$NR^9R^{10}$, —C(O)$R^9$, —C(O)$NR^9R^{10}$ and —C(O)O$R^9$;

$R^2$ is hydrogen, halo, nitro, cyano or —$X^2R^{12}$;

$X^2$ is a direct bond, —O—, —NH—, —N($C_{1-6}$alkyl)-, —OC(O)— or —C(O)O—;

$R^{12}$ is hydrogen, or a group selected from $C_{1-6}$alkyl, $C_{2-6}$alkenyl, $C_{2-6}$alkynyl, $C_{3-6}$cycloalkyl, $C_{3-6}$cycloalkenyl, aryl, aryl$C_{1-4}$alkyl, aryl$C_{2-4}$alkenyl, aryl$C_{2-4}$alkynyl, heterocyclyl, heterocyclyl$C_{1-4}$alkyl, heterocyclyl$C_{2-4}$alkenyl and heterocyclyl$C_{2-4}$alkynyl, which group is optionally substituted by 1, 2 or 3 substituents selected from halo, hydroxy, $C_{1-4}$alkyl, $C_{1-4}$alkoxy, —$NR^{15}R^{16}$, —NHC(O)$NR^{15}R^{16}$, —C(O)$R^{15}$ and —C(O)O$R^{15}$;

$R^3$ is hydrogen, halo or —$X^3R^{13}$;

$X^3$ is a direct bond, —$CH_2$=$CH_2$—, —O—, —NH—,—N($C_{1-6}$alkyl)-, —C(O)—, —C(O)O—, —OC(O)—, —NHC(O)O—, —N($C_{1-6}$alkyl)C(O)—, —C(O)NH— or —C(O)N($C_{1-6}$alkyl)-;

$R^{13}$ is hydrogen or a group selected from $C_{1-6}$alkyl, $C_{2-6}$alkenyl, $C_{2-6}$alkynyl, $C_{3-6}$cycloalkyl, $C_{3-6}$cycloalkenyl, aryl, aryl$C_{1-4}$alkyl, aryl$C_{2-4}$alkenyl, aryl$C_{2-4}$alkynyl, heterocyclyl, heterocyclyl$C_{1-4}$alkyl, heterocyclyl$C_{2-4}$alkenyl and heterocyclyl$C_{2-4}$alkynyl which group is optionally substituted by 1 or 2 substituents independently selected from —$NR^7R^8$, —C(O)$NR^7R^8$, halo, hydroxy, $C_{1-4}$alkyl, $C_{1-4}$alkoxy, hydroxy$C_{1-4}$alkyl, hydroxy$C_{1-4}$alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$alkylcarbonyl;

$R^7$ and $R^8$ are independently selected from hydrogen, heterocyclyl, heterocyclyl$C_{1-4}$alkyl, $C_{1-4}$alkylheterocyclyl$C_{1-4}$alkyl, $C_{1-6}$alkyl, hydroxy$C_{1-6}$alkyl, $C_{1-4}$alkoxy$C_{1-6}$alkyl, $C_{3-6}$cycloalkyl, $C_{3-6}$cycloalkyl$C_{1-4}$ alkyl, hydroxy$C_{3-6}$cycloalkyl, hydroxy$C_{1-4}$ alkyl$C_{3-6}$ cycloalkyl, hydroxy$C_{3-6}$cycloalkyl$C_{1-4}$alkyl, hydroxy$C_{1-4}$alkyl$C_{3-6}$cycloalkyl$C_{1-4}$ alkyl, $C_{1-4}$alkoxy$C_{3-6}$cycloalkyl, $C_{1-4}$alkoxy$C_{3-6}$cycloalkyl$C_{1-4}$alkyl, halo$C_{1-6}$alkyl, halo$C_{3-6}$cycloalkyl, halo$C_{3-6}$cycloalkyl$C_{1-4}$alkyl, $C_{2-6}$alkenyl, $C_{2-6}$alkynyl, cyano$C_{1-4}$alkyl, amino$C_{1-6}$alkyl, $C_{1-4}$alkylamino$C_{1-6}$ alkyl, bis($C_{1-4}$alkyl)amino$C_{1-6}$alkyl, hydroxy$C_{1-4}$alkoxy$C_{1-4}$alkyl, hydroxy$C_{1-4}$alkylcarbonyl, $C_{1-4}$alkylcarbonyl, amino$C_{1-4}$alkylcarbonyl, $C_{1-4}$alkylamino$C_{1-4}$ alkylcarbonyl and bis($C_{1-4}$alkyl)amino$C_{1-4}$ alkylcarbonyl;

or $R^7$ and $R^8$ together with the nitrogen to which they are attached form a heterocyclic ring which ring is monocyclic or bicyclic and comprises 4 to 7 ring atoms of which one is nitrogen and of which another is optionally selected from N, NH, O, S, SO and $SO_2$, and which ring is optionally substituted on carbon or nitrogen by 1 or 2 substituents independently selected from $C_{1-4}$alkyl, hydroxy, $C_{1-4}$alkoxy, hydroxy$C_{1-4}$alkyl, $C_{1-4}$alkoxy$C_{1-4}$ alkyl, hydroxy$C_{1-4}$alkoxy$C_{1-4}$alkyl, $C_{1-4}$alkoxy$C_{1-4}$ alkoxy, hydroxy$C_{1-4}$alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$alkylcarbonyl, and where a ring —$CH_2$— is optionally replaced with —C(O)—;

$R^4$ is selected from hydrogen, halo or —$X^4R^{14}$;

$X^4$ is a direct bond, —O—, —NH— or —N($C_{1-6}$alkyl)-;

$R^{14}$ is selected from hydrogen, $C_{1-6}$alkyl, $C_{2-6}$alkenyl and $C_{2-6}$alkynyl;

$R^5$ is aryl or heteroaryl optionally substituted by 1, 2 or 3 substituents independently selected from halo, hydroxy, cyano, nitro, amino, $C_{1-4}$alkylamino, bis($C_{1-4}$alkyl)amino, $C_{1-4}$alkyl, $C_{2-4}$alkenyl, $C_{2-4}$alkynyl, $C_{1-4}$alkoxy, —CONH$R^{17}$, —NHCO$R^{18}$—S$R^{17}$, —S(O)$R^{17}$ and —S(O)O$R^{17}$;

$R^9$, $R^{10}$, $R^{15}$ and $R^{16}$ are independently selected from hydrogen, $C_{1-6}$alkyl, $C_{3-6}$cycloalkyl, $C_{3-6}$cycloalkyl$C_{1-4}$ alkyl, hydroxy$C_{1-6}$alkyl, halo$C_{1-6}$alkyl, amino$C_{1-6}$ alkyl, $C_{1-4}$alkylamino$C_{1-6}$alkyl and bis($C_{1-4}$ alkyl)amino$C_{1-6}$alkyl;

or $R^9$ and $R^{10}$ together with the nitrogen to which they are attached form a heterocyclic ring which ring is monocyclic or bicyclic and comprises 4 to 7 ring atoms of which one is nitrogen and of which another is optionally selected from N, NH, O, S, SO and $SO_2$, and which ring is optionally substituted on carbon or nitrogen by 1 or 2 substituents independently selected from $C_{1-4}$alkyl, hydroxy, $C_{1-4}$alkoxy, hydroxy$C_{1-4}$alkyl, $C_{1-4}$alkoxy$C_{1-4}$ alkyl, hydroxy$C_{1-4}$alkoxy$C_{1-4}$alkyl, $C_{1-4}$alkoxy$C_{1-4}$ alkoxy, hydroxy$C_{1-4}$alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$alkylcarbonyl, and where a ring —$CH_2$— is optionally replaced with —C(O)—;

$R^{17}$ and $R^{18}$ are independently selected from hydrogen, $C_{1-4}$alkyl, $C_{3-6}$cycloalkyl, $C_{2-4}$alkenyl and $C_{2-4}$alkynyl;

$R^{19}$ is hydrogen, hydroxy$C_{1-4}$alkyl, —C(O)$R^{20}$, —C(O)O$R^{20}$, —CON$R^{20}R^{21}$, —NHC(O)$R^{20}$ or —NHC(O)O$R^{20}$;

$R^{20}$ are $R^{21}$ are independently selected from hydrogen, $C_{1-4}$alkyl and aryl followed by deprotection of the phosphate group to yield a compound of formula (IA)

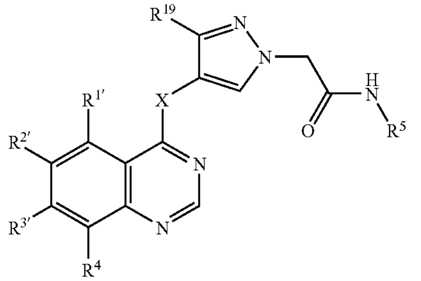

or salt or ester thereof where X, $X^1$, $X^2$, $X^3$, $R^4$, $R^5$ and $R^{19}$ are as defined in relation to formula (I) and $R^{1'}$ is hydrogen, halo, or —$X^1R^{11'}$;

$R^{11'}$ is hydrogen, phosphonooxy or a group selected from $C_{1-6}$alkyl, $C_{2-6}$alkenyl, $C_{2-6}$alkynyl, $C_{3-6}$cycloalkyl, $C_{3-6}$cycloalkenyl, heterocyclyl, heterocyclyl$C_{1-4}$alkyl, heterocyclyl$C_{2-4}$alkenyl and heterocyclyl$C_{2-4}$alkynyl which group is optionally substituted by a substituent selected from halo, hydroxy, phosphonooxy, $C_{1-4}$alkoxy, hydroxy$C_{1-4}$alkyl, phosphonooxy$C_{1-4}$alkyl, —$NR^{9'}R^{10'}$, —$C(O)R^{9'}$, —$C(O)NR^{9'}R^{10'}$ and —C(O)$OR^{9'}$;

$R^{2'}$ is hydrogen, halo, nitro, cyano or —$X^2R^{12'}$;

$R^{12'}$ is hydrogen, phosphonooxy or a group selected from $C_{1-6}$alkyl, $C_{2-6}$alkenyl, $C_{2-6}$alkynyl, $C_{3-6}$cycloalkyl, $C_{3-6}$cycloalkenyl, aryl, aryl$C_{1-4}$alkyl, aryl$C_{2-4}$alkenyl, aryl$C_{2-4}$alkynyl, heterocyclyl, heterocyclyl$C_{1-4}$alkyl, heterocyclyl$C_{2-4}$alkenyl and heterocyclyl$C_{2-4}$alkynyl, which group is optionally substituted by 1, 2 or 3 substituents selected from halo, hydroxy, phosphonooxy, $C_{1-4}$alkyl, $C_{1-4}$alkoxy, —$NR^{15'}R^{16'}$, —NHC(O)$NR^{15'}R^{16'}$—, —$C(O)R^{15'}$— and —$C(O)OR^{15'}$—;

$R^{3'}$ is hydrogen, halo or —$X^3R^{13'}$;

$R^{13'}$ is hydrogen, phosphonooxy or a group selected from $C_{1-6}$alkyl, $C_{2-6}$alkenyl, $C_{2-6}$alkynyl, $C_{3-6}$cycloalkyl, $C_{3-6}$cycloalkenyl, aryl, aryl$C_{1-4}$alkyl, aryl$C_{2-4}$alkenyl, aryl$C_{2-4}$alkynyl, heterocyclyl, heterocyclyl$C_{1-4}$alkyl, heterocyclyl$C_{2-4}$alkenyl and heterocyclyl$C_{2-4}$alkynyl which group is optionally substituted by 1 or 2 substituents independently selected from —$NR^{7'}R^{8'}$, —C(O)$NR^{7'}R^{8'}$, halo, hydroxy, phosphonooxy, $C_{1-4}$alkyl, $C_{1-4}$alkoxy, hydroxy$C_{1-4}$alkyl, posponooxy$C_{1-4}$alkyl, hydroxy$C_{1-4}$alkylcarbonyl, phosphonooxy$C_{1-4}$alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$alkylcarbonyl;

$R^{7'}$ and $R^{8'}$ are independently selected from hydrogen, heterocyclyl, heterocyclyl$C_{1-4}$alkyl, $C_{1-4}$alkylheterocyclyl$C_{1-4}$alkyl, $C_{1-6}$alkyl, hydroxy$C_{1-6}$alkyl, phosphonooxy$C_{1-6}$alkyl, $C_{1-4}$alkoxy$C_{1-6}$alkyl, $C_{3-6}$cycloalkyl, $C_{3-6}$cycloalkyl$C_{1-4}$alkyl, hydroxy$C_{3-6}$cycloalkyl, phosphonooxy$C_{3-6}$cycloalkyl, hydroxy$C_{1-4}$alkyl$C_{3-6}$cycloalkyl, phosphonooxy$C_{1-4}$alkyl$C_{3-6}$cycloalkyl, hydroxy$C_{3-6}$cycloalkyl$C_{1-4}$alkyl, phosphonooxy$C_{3-6}$cycloalkyl$C_{1-4}$alkyl, hydroxy$C_{1-4}$alkyl$C_{3-6}$cycloalkyl$C_{1-4}$alkyl, phosphonooxy$C_{1-4}$alkyl$C_{3-6}$cycloalkyl$C_{1-4}$alkyl, $C_{1-4}$alkoxy$C_{3-6}$cycloalkyl, $C_{1-4}$alkoxy$C_{3-6}$cycloalkyl$C_{1-4}$alkyl, halo$C_{1-6}$alkyl, halo$C_{3-6}$cycloalkyl, halo$C_{3-6}$cycloalkyl$C_{1-4}$alkyl, $C_{2-6}$alkenyl, $C_{2-6}$alkynyl, cyano$C_{1-4}$alkyl, amino$C_{1-6}$ alkyl, $C_{1-4}$alkylamino$C_{1-6}$alkyl, bis($C_{1-4}$alkyl)amino$C_{1-6}$ alkyl, hydroxy$C_{1-4}$alkoxy$C_{1-4}$alkyl, phosphonooxy$C_{1-4}$ alkoxy$C_{1-4}$alkyl, hydroxy$C_{1-4}$alkylcarbonyl, phosphonooxy$C_{1-4}$alkylcarbonyl, $C_{1-4}$alkylcarbonyl, amino$C_{1-4}$ alkylcarbonyl, $C_{1-4}$alkylamino$C_{1-4}$alkylcarbonyl and bis($C_{1-4}$alkyl)amino$C_{1-4}$alkylcarbonyl;

or $R^{7'}$ and $R^{8'}$ together with the nitrogen to which they are attached form a heterocyclic ring which ring is monocyclic or bicyclic and comprises 4 to 7 ring atoms of one is nitrogen and of which another is optionally selected from N, NH, O, S, SO and $SO_2$, and which ring is optionally substituted on carbon or nitrogen by 1 or 2 substituents independently selected from $C_{1-4}$alkyl, hydroxy, phosphonooxy, $C_{1-4}$alkoxy, hydroxy$C_{1-4}$alkyl, phosphonooxy$C_{1-4}$alkyl, $C_{1-4}$alkoxy$C_{1-4}$alkyl, hydroxy$C_{1-4}$alkoxy$C_{1-4}$alkyl, phosphonooxy$C_{1-4}$ alkoxy$C_{1-4}$alkyl, $C_{1-4}$alkoxy$C_{1-4}$alkoxy, hydroxy$C_{1-4}$ alkylcarbonyl, phosphonooxy$C_{1-4}$alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$ alkylcarbonyl, and where a ring —$CH_2$— is optionally replaced with —C(O)—;

$R^{9'}$, $R^{10'}$, $R^{15'}$ and $R^{16'}$ are independently selected from hydrogen, $C_1$-alkyl, $C_{3-6}$cycloalkyl, $C_{3-6}$cycloalkyl$C_{1-3}$ alkyl, hydroxy$C_{1-6}$alkyl, phosphonooxy$C_{1-6}$alkyl, halo$C_{1-6}$alkyl, amino$C_{1-6}$alkyl, $C_{1-6}$alkylamino$C_{1-6}$ alkyl and bis($C_{1-6}$alkyl)amino$C_{1-6}$alkyl;

or $R^{9'}$ and $R^{10'}$ together with the nitrogen to which they are attached form a heterocyclic ring which ring is monocyclic or bicyclic and comprises 4 to 7 ring atoms of which one is nitrogen and of which another is optionally selected from N, NH, O, S, SO and $SO_2$, and which ring is optionally substituted on carbon or nitrogen by 1 or 2 substituents independently selected from $C_{1-4}$alkyl, hydroxy, phosphonooxy, $C_{1-4}$alkoxy, hydroxy$C_{1-4}$alkyl, phosphonooxy$C_{1-4}$alkyl, $C_{1-4}$alkoxy$C_{1-4}$alkyl, hydroxy$C_{1-4}$alkoxy$C_{1-4}$alkyl, phosphonooxy$C_{1-4}$ alkoxy$C_{1-4}$alkyl, $C_{1-4}$alkoxy$C_{1-4}$alkoxy, hydroxy$C_{1-4}$ alkylcarbonyl, phosphonooxy$C_{1-4}$alkylcarbonyl, $C_{1-4}$alkylcarbonyl, amino$C_{1-4}$alkylcarbonyl, $C_{1-4}$alkylamino$C_{1-4}$alkylcarbonyl and bis($C_{1-4}$alkyl)amino$C_{1-4}$ alkylcarbonyl, and where a ring —$CH_2$— is optionally replaced with —C(O)—;

provided that a compound of formula (IA) contains at least one phosphonooxy group.

21. A method of treating a human suffering from colorectal cancer, comprising the steps of administering to a person in need thereof a therapeutically effective amount of a compound according to claim 1 or a pharmaceutically acceptable salt or ester thereof.

* * * * *